(12) United States Patent
Busser et al.

(10) Patent No.: US 12,209,125 B2
(45) Date of Patent: Jan. 28, 2025

(54) TARGETED GENE INTEGRATION OF NK INHIBITORS GENES FOR IMPROVED IMMUNE CELLS THERAPY

(71) Applicant: CELLECTIS, Paris (FR)

(72) Inventors: Brian Busser, New York, NY (US);
Philippe Duchateau, Draveil (FR);
Alexandre Juillerat, New York, NY (US); Laurent Poirot, Paris (FR);
Julien Valton, New York, NY (US)

(73) Assignee: CELLECTIS, Paris (FR)

( * ) Notice: Subject to any disclaimer, the term of this patent is extended or adjusted under 35 U.S.C. 154(b) by 716 days.

(21) Appl. No.: 16/755,082

(22) PCT Filed: Mar. 9, 2018

(86) PCT No.: PCT/EP2018/055957
§ 371 (c)(1),
(2) Date: Apr. 9, 2020

(87) PCT Pub. No.: WO2019/076486
PCT Pub. Date: Apr. 25, 2019

(65) Prior Publication Data
US 2020/0237823 A1 Jul. 30, 2020

(30) Foreign Application Priority Data

Oct. 19, 2017 (WO) ................. PCT/EP2017/076798
Feb. 9, 2018 (WO) ................. PCT/EP2018/053343

(51) Int. Cl.
| | | |
|---|---|---|
| A61K 35/00 | (2006.01) | |
| A61K 39/00 | (2006.01) | |
| C07K 16/28 | (2006.01) | |
| C07K 16/30 | (2006.01) | |
| C12N 5/0783 | (2010.01) | |
| C12N 5/10 | (2006.01) | |

(52) U.S. Cl.
CPC ...... *C07K 16/2803* (2013.01); *A61K 39/4611* (2023.05); *A61K 39/4631* (2023.05); *A61K 39/4636* (2023.05); *A61K 39/464413* (2023.05); *A61K 39/464419* (2023.05); *C07K 16/30* (2013.01); *C12N 5/0636* (2013.01); *C12N 5/0638* (2013.01); *C12N 5/0646* (2013.01); *C12N 5/10* (2013.01); *C07K 2317/622* (2013.01); *C07K 2319/03* (2013.01); *C07K 2319/33* (2013.01)

(58) Field of Classification Search
CPC .... A61K 35/17; C07K 16/2803; C07K 16/30; C07K 2317/622; C07K 2319/03; C07K 2319/33
See application file for complete search history.

(56) References Cited

U.S. PATENT DOCUMENTS

2019/0233797 A1* 8/2019 Navarro ............. A61K 39/4613

FOREIGN PATENT DOCUMENTS

| WO | WO2012145384 | * | 10/2012 |
|---|---|---|---|
| WO | 2016142532 A1 | | 9/2016 |
| WO | WO2016142532 | * | 9/2016 |
| WO | 2017079673 A1 | | 5/2017 |
| WO | 2019076489 A1 | | 4/2019 |

OTHER PUBLICATIONS

Eyquem et al (Nature 543 113-117, published Feb. 2017). (Year: 2017).*
Gornalusse et al (Nat Biotechnol. 35: 765-772, Aug. 2017) (Year: 2017).*
Pietra et al, PNAS 100: 10896-10901, 2003 (Year: 2003).*
Ren et al: "Multiplex Genome Editing to Generate Universal CAR T Cells Resistant to PD1 Inhibition", Clinical Cancer Research, vol. 23, No. 9, Nov. 4, 2016 (Nov. 4, 2016), pp. 2255-2266.
Vivier et al: "Inhibitory NK-cell receptors on T cells: Witness of the past, actors of the future." Nature Reviews Immunology, vol. 4, No. 3, Mar. 2004 (Mar. 2004), pp. 190-198.
Pardoll: "The blockade of immune checkpoints in cancer immunotherapy", Nature Reviews. Cancer, vol. 12, No. 4, Apr. 1, 2012 (Apr. 1, 2012), pp. 252-264.
Poirot et al: "Multiplex Genome-Edited T-cell Manufacturing Platform for "Off-the-Shelf" Adoptive T-cell Immunotherapies", Cancer Research, vol. 75, No. 18, Jul. 16, 2015 (Jul. 16, 2015), pp. 3853-3864.
Fedorov et al: "PD-1- and CTLA-4-Based Inhibitory Chimeric Antigen Receptors (iCARs) Divert Off-Target Immunotherapy Responses", Science Translational Medicine, vol. 5, No. 215, Dec. 11, 2013 (Dec. 11, 2013), pp. 215ra172.
Speiser et al: "In vivo expression of natural killer cell inhibitory receptors by human melanoma-specific cytolytic T lymphocytes", Journal of Experimental Medicine, vol. 190, No. 6, Sep. 20, 1999 (Sep. 20, 1999), pp. 775-782.

* cited by examiner

*Primary Examiner* — Lei Yao
(74) *Attorney, Agent, or Firm* — Arrigo, Lee, Guttman & Mouta-Bellum LLP

(57) ABSTRACT

The invention pertains to the field of adaptive cell immunotherapy. It provides with the genetic insertion of exogenous coding sequence(s) that help the immune cells to direct their immune response against infected or malignant cells. These exogenous coding sequences are more particularly inserted under the transcriptional control of endogenous gene promoters that are sensitive to immune cells activation. Such method allows the production of safer immune primary cells of higher therapeutic potential.

Figure 1:
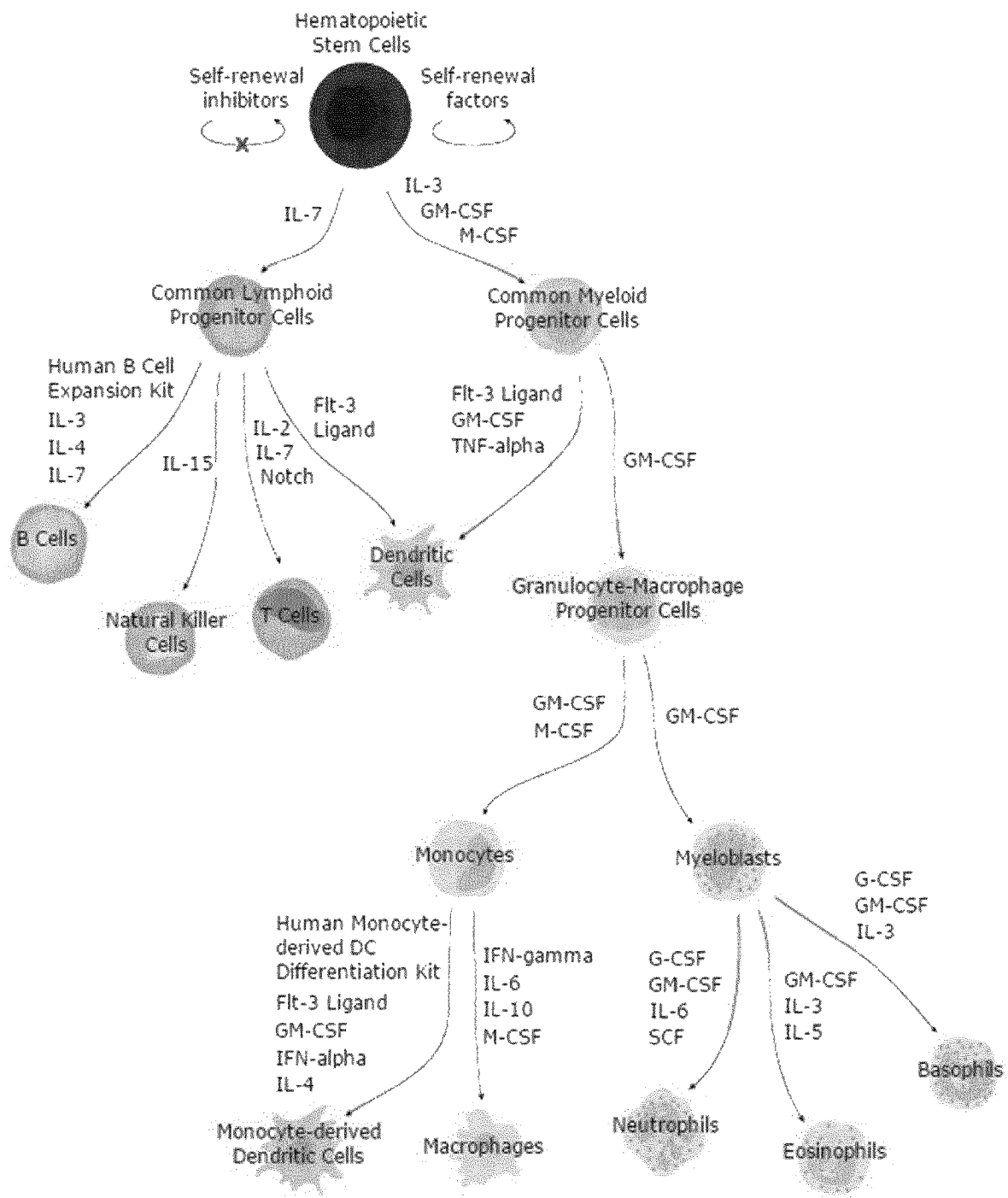

20 Claims, 39 Drawing Sheets
Specification includes a Sequence Listing.

A

B

A

B

TARGETED GENE INTEGRATION OF NK INHIBITORS GENES FOR IMPROVED IMMUNE CELLS THERAPY

CROSS REFERENCE TO RELATED APPLICATIONS

This application is a U.S. National Stage Application of International Application No. PCT/EP2018/055957 under 37 C.F.R. § 371, with an international filing date of Mar. 9, 2018, which claims the benefit of International Application No. PCT/EP2018/053343, filed Feb. 9, 2018 and International Application No. PCT/EP2017/076798, filed Oct. 19, 2017, all of which are herein incorporated by reference in their entirety.

SEQUENCE LISTING

The instant application contains a Sequence Listing, which has been submitted electronically in ASCII format and is hereby incorporated by reference in its entirety. Said ASCII copy, created on May 17, 2024, is named 16755082_SL2.txt and is 296,327 bytes in size.

FIELD OF THE INVENTION

The invention pertains to the field of adaptive cell immunotherapy. It aims to enhance the functionality of primary immune cells against pathologies that develop immune resistance, such as tumors, thereby improving the therapeutic potential of these immune cells. In particular, the method of the invention provides with the genetic insertion of exogenous coding sequence(s) encoding NK inhibitors to prevent allogeneic T-cells rejection from patient's NK cell attack and favor the engraftment of said T-cells, especially when they originate from donors. These exogenous coding sequences are more particularly inserted into the cell's genome under the transcriptional control of endogenous gene promoters that are upregulated upon immune cells activation, upon tumor microenvironment or life threatening inflammatory conditions or promoters that are insensitive to immune cells activation, more particularly at the β2m locus. The invention further provides with sequence-specific endonuclease reagents and donor DNA vectors, such as AAV vectors, to perform such targeted insertions at said particular loci. The method of the invention contributes to improving the therapeutic potential and safety of engineered primary immune cells for their efficient use in cell therapy.

BACKGROUND OF THE INVENTION

Effective clinical application of primary immune cell populations including hematopoietic cell lineages has been established by a number of clinical trials over a decade against a range of pathologies, in particular HIV infection and Leukemia (Tristen S. J. et al. (2011) Treating cancer with genetically engineered T cells. *Trends in Biotechnology.* 29(11):550-557).

However, most of these clinical trials have used immune cells, mainly NK and T-cells, obtained from the patients themselves or from compatible donors, bringing some limitations with respect to the number of available immune cells, their fitness, and their efficiency to overcome diseases that have already developed strategies to get around or reduce patient's immune system.

As a primary advance into the procurement of allogeneic immune cells, universal immune cells, available as "off-the-shelf" therapeutic products, have been produced by gene editing (Poirot et al. (2015) Multiplex Genome-Edited T-cell Manufacturing Platform for "Off-the-Shelf" Adoptive T-cell Immunotherapies *Cancer Res.* 75: 3853-64). These universal immune cells are obtainable by expressing specific rare-cutting endonuclease into immune cells originating from donors, with the effect of disrupting, by double strand-break, their self-recognition genetic determinants.

Since the emergence of the first programmable sequence-specific reagents by the turn of the century, initially referred to as Meganucleases (Smith et al. (2006) A combinatorial approach to create artificial homing endonucleases cleaving chosen sequences. *Nucl. Acids Res.* 34 (22):e149), different types of sequence-specific endonucleases reagents have been developed offering improved specificity, safety and reliability.

TALE-nucleases (WO2011072246), which are fusions of a TALE binding domain with a cleavage catalytic domain have been successfully applied to primary immune cells, in particular T-cells from peripheral blood mononuclear cell (PBMC). Such TALE-nucleases, marketed under the name TALEN®, are those currently used to simultaneously inactivate gene sequences in T-cells originating from donors, in particular to produce allogeneic therapeutic T-Cells in which the genes encoding TCR (T-cell receptor) and CD52 are disrupted. These cells can be endowed with chimeric antigen receptors (CAR) for treating cancer patients (US2013/0315884). TALE-nucleases are very specific reagents because they need to bind DNA by pairs under obligatory heterodimeric form to obtain dimerization of the cleavage domain Fok-1. Left and right heterodimer members each recognizes a different nucleic sequences of about 14 to 20 bp, together spanning target sequences of 30 to 50 bp overall specificity.

Other endonucleases reagents have been developed based on the components of the type II prokaryotic CRISPR (Clustered Regularly Interspaced Short palindromic Repeats) adaptive immune system of the bacteria *S. pyogenes*. This multi-component system referred to as RNA-guided nuclease system (Gasiunas, Barrangou et al. 2012; Jinek, Chylinski et al. 2012), involves members of Cas9 or Cpf1 endonuclease families coupled with a guide RNA molecules that have the ability to drive said nuclease to some specific genome sequences (Zetsche et al. (2015). Cpf1 is a single RNA-guided endonuclease that provides immunity in bacteria and can be adapted for genome editing in mammalian cells. Cell 163:759-771). Such programmable RNA-guided endonucleases are easy to produce because the cleavage specificity is determined by the sequence of the RNA guide, which can be easily designed and cheaply produced. The specificity of CRISPR/Cas9 although stands on shorter sequences than TAL-nucleases of about 10 pb, which must be located near a particular motif (PAM) in the targeted genetic sequence. Similar systems have been described using a DNA single strand oligonucleotide (DNA guide) in combination with Argonaute proteins (Gao, F. et al. DNA-guided genome editing using the *Natronobacterium gregoryi* Argonaute (2016) doi:10.1038/nbt.3547).

Other endonuclease systems derived from homing endonucleases (ex: I-Onul, or I-CreI), combined or not with TAL-nuclease (ex: MegaTAL) or zing-finger nucleases have also proven specificity, but to a lesser extend so far.

In parallel, novel specificities can be conferred to immune cells through the genetic transfer of transgenic T-cell receptors or so-called chimeric antigen receptors (CARs) (Jena et al. (2010) Redirecting T-cell specificity by introducing a tumor-specific chimeric antigen receptor. *Blood.* 116:1035-

1044). CARs are recombinant receptors comprising a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors.

Recently engineered T-cells disrupted in their T-cell receptor (TCR) using TALE-nucleases, endowed with chimeric antigen receptor (CAR) targeting CD19 malignant antigen, referred to as "UCART19" product, have shown therapeutic potential in at least two infants who had refractory leukemia (Leukaemia success heralds wave of gene-editing therapies (2015) Nature 527:146-147). To obtain such UCART19 cells, the TALE-nuclease was transiently expressed into the cells upon electroporation of capped mRNA to operate TCR gene disruption, whereas a cassette encoding the chimeric antigen receptor (CAR CD19) was introduced randomly into the genome using a retroviral vector.

In this later approach, the steps of gene inactivation and of expressing the chimeric antigen receptor are independently performed after inducing activation of the T-Cell "ex-vivo".

However, engineering primary immune cells is not without any consequences on the growth/physiology of such cells. In particular one major challenge is to ovoid cells exhaustion/anergy that significantly reduces their immune reaction and life span. This is more likely to happen when the cells are artificially activated ahead of their infusion into the patient. It is also the case when a cell is endowed with a CAR that is too reactive.

To avoid these pitfalls, the inventors have thought about taking advantage of the transcriptional regulation of some key genes during T-cell activation to express exogenous genetic sequences increasing the therapeutic potential of the immune cells. The exogenous genetic sequences to be expressed or co-expressed upon immune cell activation are introduced by gene targeted insertion using sequence-specific endonuclease reagents, so that their coding sequences are transcribed under the control of the endogenous promoters present at said loci. Alternatively, loci that are not expressed during immune cell activation can be used as "safe-harbor loci" for the integration of expression cassettes without any adverse consequences on the genome.

These cell engineering strategies, as per the present invention, tend to reinforce the therapeutic potential of primary immune cells in general, in particular by increasing their life span, persistence and immune activity, as well as by limiting cell exhaustion. The invention may be carried out on primary cells originating from patients as part of autologous treatment strategies, as well as from donors, as part of allogeneic treatment strategies.

SUMMARY OF THE INVENTION

Non-homologous end-joining (NHEJ) and homology-directed repair (HDR) are the two major pathways used to repair in vivo DNA breaks. The latter pathway repairs the break in a template-dependent manner (HDR naturally utilizes the sister chromatid as a DNA repair template). Homologous recombination has been used for decades to precisely edit genomes with targeted DNA modifications using exogenously supplied donor template. The artificial generation of a double strand break (DSB) at the target location using rare-cutting endonucleases considerably enhances the efficiency of homologous recombination (e.g. U.S. Pat. No. 8,921,332). Also the co-delivery of a rare-cutting endonuclease along with a donor template containing DNA sequences homologous to the break site enables HDR-based gene editing such as gene correction or gene insertion. However, such techniques have not been widely used in primary immune cells, especially CAR T-cells, due to several technical limitations: difficulty of transfecting DNA into such types of cells leading to apoptosis, immune cells have a limited life span and number of generations, homologous recombination occurs at a low frequency in general.

So far, sequence specific endonuclease reagents have been mainly used in primary immune cells for gene inactivation (e.g. WO2013176915) using the NHEJ pathway.

The adoptive transfer of CAR T-cells represents a highly promising strategy to fight against multiple cancers. The clinical outcome of such therapies is intimately linked to the ability of effector cells to engraft, proliferate and specifically kill tumor cells within patients.

When allogeneic CAR T-cell infusion is considered, host versus graft and graft versus host reactions must be avoided to prevent rejection of adoptively transferred cells, to minimize host tissue damages and to elicit significant antitumoral outcomes.

The present invention provides with a novel cell-engineering strategy to address the aforementioned considerations by successfully generating β2m deficient CAR T-cells, in which an exogenous sequence encoding NK inhibitor has been inserted by site directed gene editing for its expression during T-cell activation.

One major advantage of the present invention is to place such exogenous sequences encoding NK inhibitor under control of endogenous promoters, which transcriptional activity is not reduced by the effects of the immune cells activation.

In a preferred aspect, the present invention relies on performing site directed gene editing at the β2m locus, in particular gene insertion (or multi gene insertions) in a target cell in order to have said integrated gene transcription preferentially be under the control of an endogenous promoter of said β2m locus, preferably to be expressed in lieu of β2m Alternatively, the invention can rely on performing gene editing in primary immune cells to have integrated genes transcription be under the control of an endogenous promoter while maintaining the expression of the native gene through the use of cis-regulatory elements (e.g. 2A cis-acting hydrolase elements) or of internal ribosome entry site (IRES) in the donor template.

In further aspects, the invention relies on expressing a chimeric antigen receptor (CAR) at the TCR locus or at selected gene loci that are upregulated upon immune cells activation. The exogenous sequence(s) encoding the CAR and the endogenous gene coding sequence (s) may be co-transcribed, for instance by being separated by cis-regulatory elements (e.g. 2A cis-acting hydrolase elements)

or by an internal ribosome entry site (IRES), which are also introduced. For instance, the exogenous sequences encoding a CAR can be placed under transcriptional control of the promoter of endogenous genes that are activated by the tumor microenvironment, such as HIF1a, transcription factor hypoxia-inducible factor, or the aryl hydrocarbon receptor (AhR), which are gene sensors respectively induced by hypoxia and xenobiotics in the close environment of tumors.

In preferred embodiments, the method of the invention comprises the step of generating a double-strand break at a locus highly transcribed under tumor microenvironment, by expressing sequence-specific nuclease reagents, such as TALEN, ZFN or RNA-guided endonucleases as non-limiting examples, in the presence of a DNA repair matrix preferably set into an AAV6 based vector. This DNA donor template generally includes two homology arms embedding unique or multiple Open Reading Frames and regulatory genetic elements (stop codon and polyA sequences).

The exogenous sequences encoding NK inhibitors preferably comprise sequences encoding non polymorphic class I molecules or viral evasins such as UL18 [Uniprot #F5HFB4] and UL16 [also called ULBP1—Uniprot #Q9BZM6], fragments or fusions thereof.

According to a preferred embodiment said exogenous sequence encodes a polypeptide displaying at least 80% amino acid sequence identity with HLA-G or HLA-E or a functional variant thereof.

These exogenous sequences can be introduced into the genome by deleting or modifying the endogenous coding sequence(s) present at said locus (knock-out by knock-in), so that a gene inactivation can be combined with transgenesis.

Depending on the locus targeted and its involvement in immune cells activity, the targeted endogenous gene may be inactivated or maintained in its original function. Should the targeted gene be essential for immune cells activity, this insertion procedure can generate a single knock-in (KI) without gene inactivation. In the opposite, if the targeted gene is deemed involved in immune cells inhibition/exhaustion, the insertion procedure is designed to prevent expression of the endogenous gene, preferably by knocking-out the endogenous sequence, while enabling expression of the introduced exogenous coding sequence(s).

In more specific aspects, the invention relies on up-regulating, with various kinetics, the target gene expression upon activation of the CAR signalling pathway by targeted integration (with or without the native gene disruption) at the specific loci such as, as non-limiting example, PD1, PDL1, CTLA-4, TIM3, LAG3, TNFa or IFNg.

In an even more specific aspect, it is herein described engineered immune cells, and preferably primary immune cells for infusion into patients, comprising exogenous sequences encoding IL-15 or IL-12 polypeptide(s), which are integrated at the PD1, CD25 or CD69 endogenous locus for their expression under the control of the endogenous promoters present at these loci.

The immune cells according to the present invention can be [CAR]$^{positive}$, [CAR]$^{negative}$, [TCR]$^{positive}$, or [TCR]$^{negative}$, depending on the therapeutic indications and recipient patients. In one preferred aspect, the immune cells are further made [TCR]$^{negative}$ for allogeneic transplantation. This can be achieved especially by genetic disruption of at least one endogenous sequence encoding at least one component of TCR, such as TRAC (locus encoding TCRalpha), preferably by integration of an exogenous sequence encoding a chimeric antigen receptor (CAR) or a recombinant TCR, or component(s) thereof.

According to a further aspect of the invention, the immune cells are transfected with further exogenous sequence, in addition to that coding for a NK inhibitor, encoding polypeptide which can associate and preferably interfere with a cytokine receptor of the IL-6 receptor family, such as a mutated GP130, In particular, the invention provides immune cells, preferably T-cells, which secrete soluble mutated GP130, aiming at reducing cytokine release syndrome (CRS) by interfering, and ideally block, interleukine-6 (IL-6) signal transduction. CRS is a well-known complication of cell immunotherapy leading to auto immunity that appears when the transduced immune cells start to be active in-vivo. Following binding of IL-6 to its receptor IL-6R, the complex associate with the GP130 subunit, initiating signal transduction and a cascade of inflammatory responses. According to a particular aspect, a dimeric protein comprising the extracellular domain of GP130 fused to the Fc portion of an IgG1 antibody (sgp130Fc) is expressed in the engineered immune cells to bind specifically soluble IL-R/IL-6 complex to achieve partial or complete blockade of IL-6 trans signaling.

According to a further aspect of the invention, cytokine release syndrome (CRS) can be mitigated by acting on other pathways, especially by inhibiting the macrophage activated syndrome (MAS) which is a amplifying component of CRS. To achieve this goal, the invention comprises integrating exogenous sequences encoding antagonists of the IL1 and IL18 activating pathways, such as IL1RA and/or IL18BP. Accordingly, the present invention provides methods for generating therapeutic cells, according to which exogenous sequences encoding IL1RA and/or IL18BP are integrated at selected loci, such as one selected loci presented herein.

The present invention thus refers to various methods for limiting CRS in immunotherapy, in combination or without NK inhibitors, wherein immune cells are genetically modified to express a soluble polypeptide which can associate and preferably interfere with IL1 or 1L18, such as IL1RA, IL18BP, orcytokine receptor of the IL-6 receptor family, such as sgp130Fc. According to a preferred aspect, this sequence encoding said soluble polypeptide which can associate and preferably interfere with IL1, IL18 or a cytokine receptor of the IL-6 receptor family, is integrated under control of an endogenous promoter, preferably at one locus responsive to T-cells activation, such as one selected from Tables 6, 8 or 9, more especially PD1, CD25 or CD69 loci. Polynucleotide sequences of the vectors, donor templates comprising the exogenous coding sequences and/or sequences homologous to the endogenous loci, the sequences pertaining to the resulting engineered cells, as well as those permitting the detection of said engineered cells are all part of the present disclosure.

The gene editing step of integrating an exogenous sequence encoding NK inhibitor as per the present invention can be combined with any other step contributing to enhance the potency or the safety of the engineered immune cells, As non-limiting examples, genetic sequences can be introduced for the expression of components of biological "logic gates" ("AND" or "OR" or "NOT" or any combination of these) by targeted integration. Similar to the electronic logic gates, such cellular components expressed at different loci can exchange negative and positive signals that rule, for instance, the conditions of activation of an immune cell. Such component encompasses as non-limiting examples positive and negative chimeric antigen receptors that may be used to control T-cell activation and the resulting cytotoxicity of the engineered T-cells in which they are expressed.

According to a preferred embodiment, the invention relies on introducing the sequence specific endonuclease reagent and/or the donor template containing the gene of interest and sequences homologous to the target gene by transfecting ssDNA (oligonucleotides as non-limiting example), dsDNA (plasmid DNA as non-limiting example), and more particularly adeno-associated virus (AAV) as non-limiting example.

The invention also relates to the vectors, donor templates, reagents, screening methods for identifying new NK inhibitors, and to the resulting engineered cells pertaining to the above methods, as well as their use thereof in therapy.

BRIEF DESCRIPTION OF THE FIGURES AND TABLES

FIG. 1: Strategies for engineering hematopoietic stem cells (HSCs) by introducing exogenous sequences at specific loci under transcriptional control of endogenous promoters specifically activated in specific immune cell types. The figure lists examples of specific endogenous genes, at which loci the exogenous coding sequence(s) can be inserted for expression in the desired hematopoietic lineages as per the present invention. The goal is to produce ex-vivo engineered HSCs to be engrafted into patients, in order for them to produce immune cells in-vivo, which will express selected transgenes while they get differentiated into a desired lineage.

Figure 2:
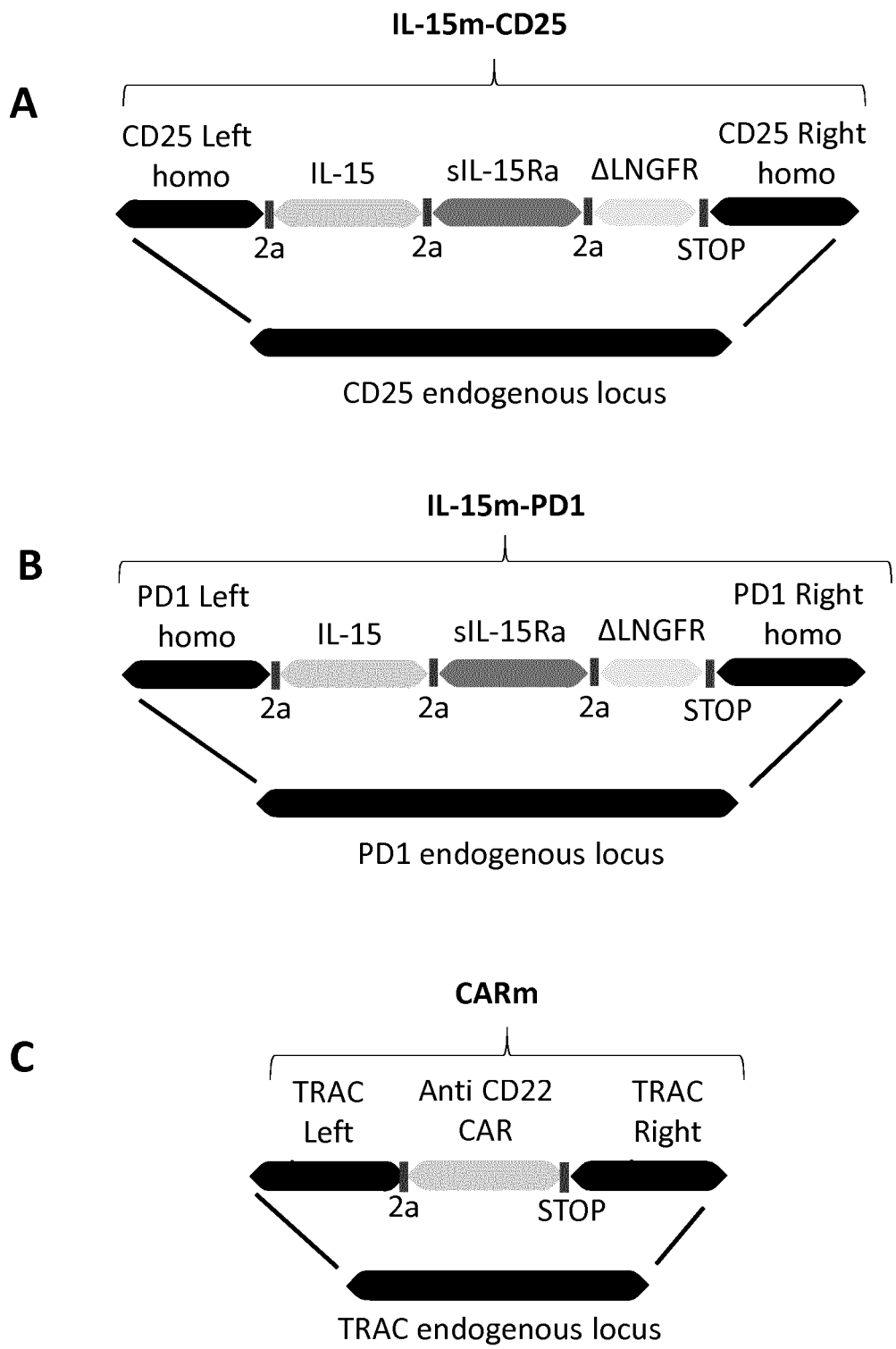

FIG. 2: Schematic representation of the donor sequences used in the experimental section to insert IL-15 exogenous coding sequence at the CD25 and PD1 loci and also the anti-CD22 CAR exogenous coding sequence at the TRAC locus. A: donor template (designated IL-15m-CD25) designed for site directed insertion of IL-15 at the CD25 locus for obtaining co-transcription of CD25 and IL-15 polypeptides by the immune cell. Sequences are detailed in the examples. B: donor template (designated IL-15m-PD1) designed for site directed insertion of IL-15 at the PD1 locus for obtaining transcription of IL-15 under the transcriptional activity of the promoter of PD1 endogenous gene. The PD1 right and Left border sequences can be selected so as to keep the PD1 endogenous coding sequence intact or disrupted. In this later case, PD1 is knocked-out while IL-15 is Knocked-in and transcribed. C: donor template designed for site directed insertion of a chimeric antigen receptor (ex: anti-CD22 CAR) into the TCR locus (ex: TRAC). In general, the left and right borders are chosen so as to disrupt the TCR in order to obtain $[TCR]^{neg}[CAR]^{pos}$ engineered immune cells suitable for allogeneic transplant into patients.

Figure 3A:
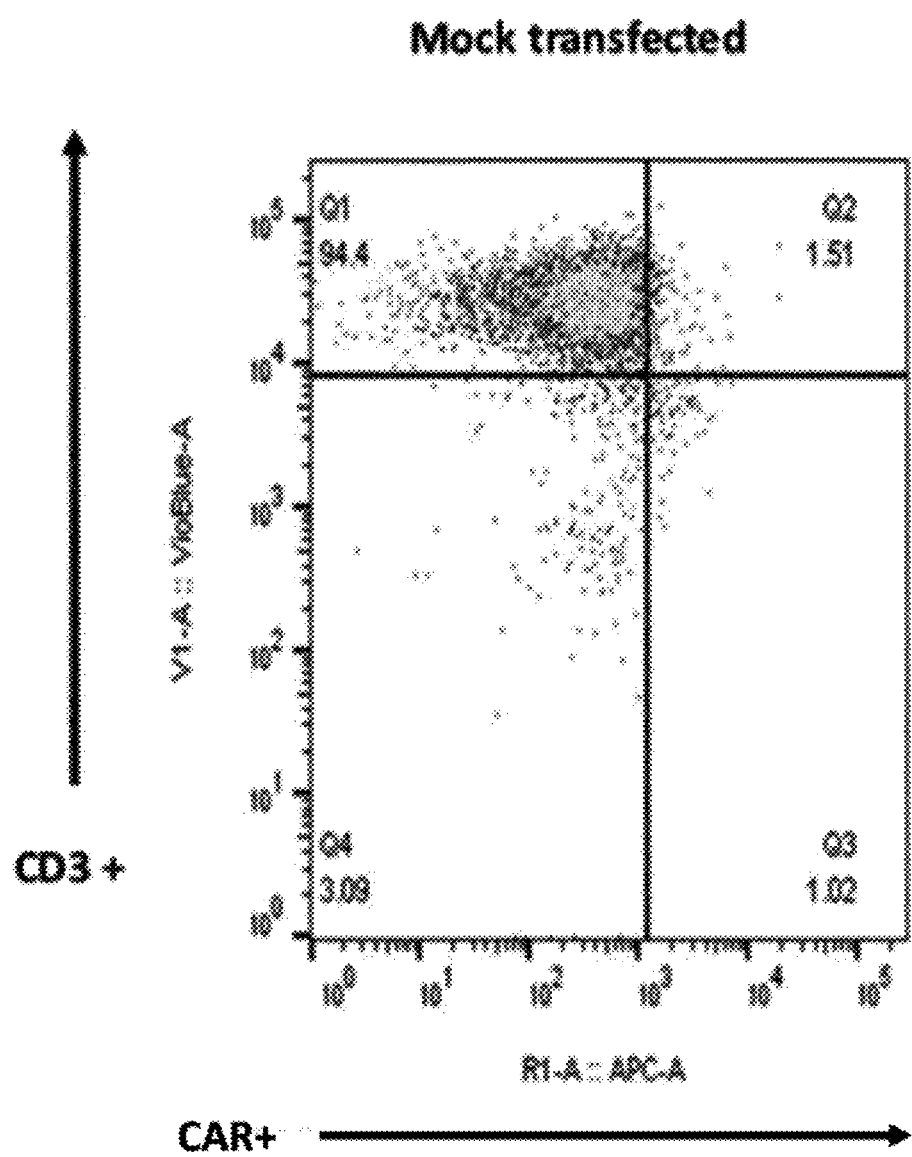
Figure 3B:
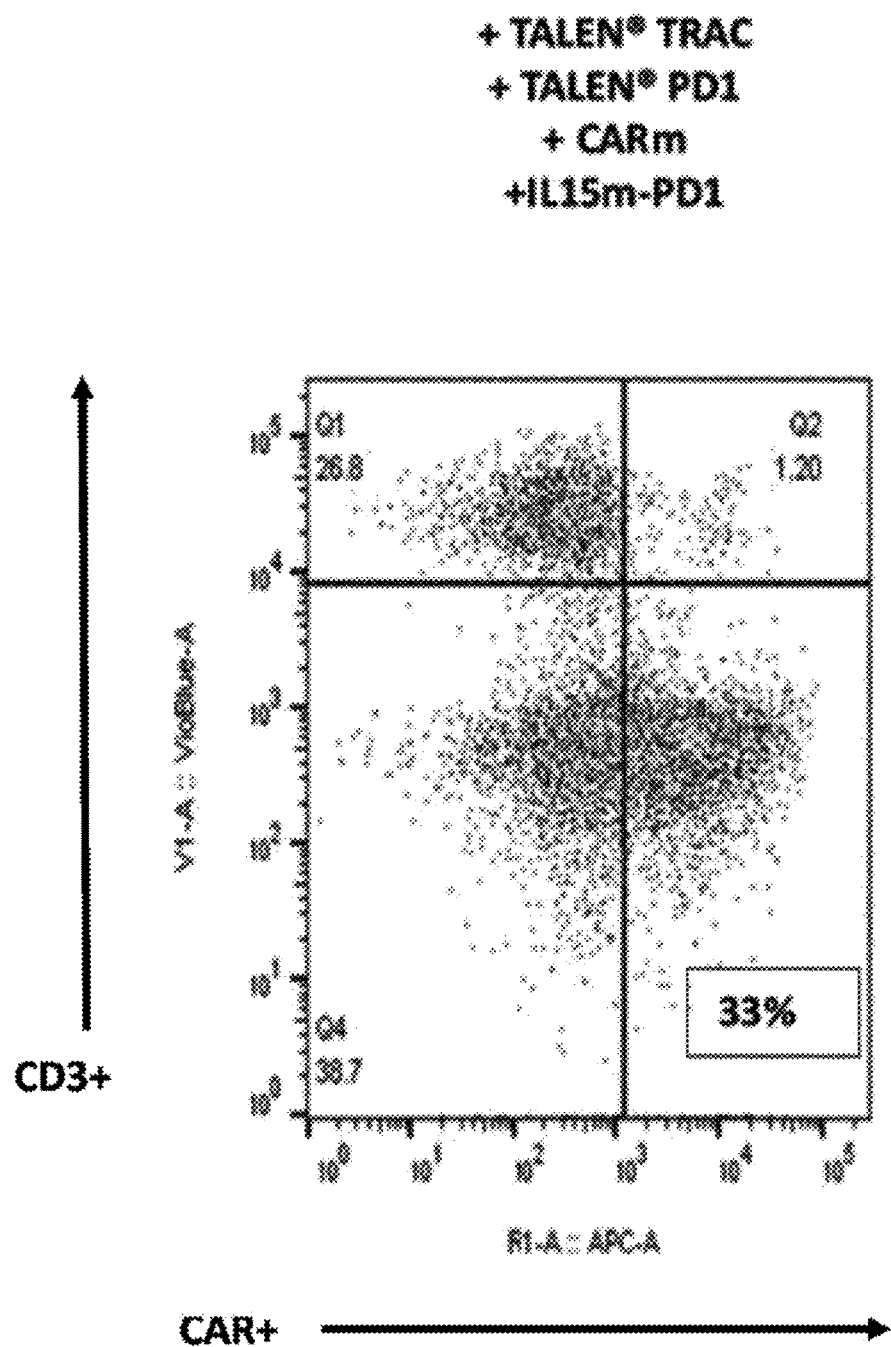
Figure 3C:
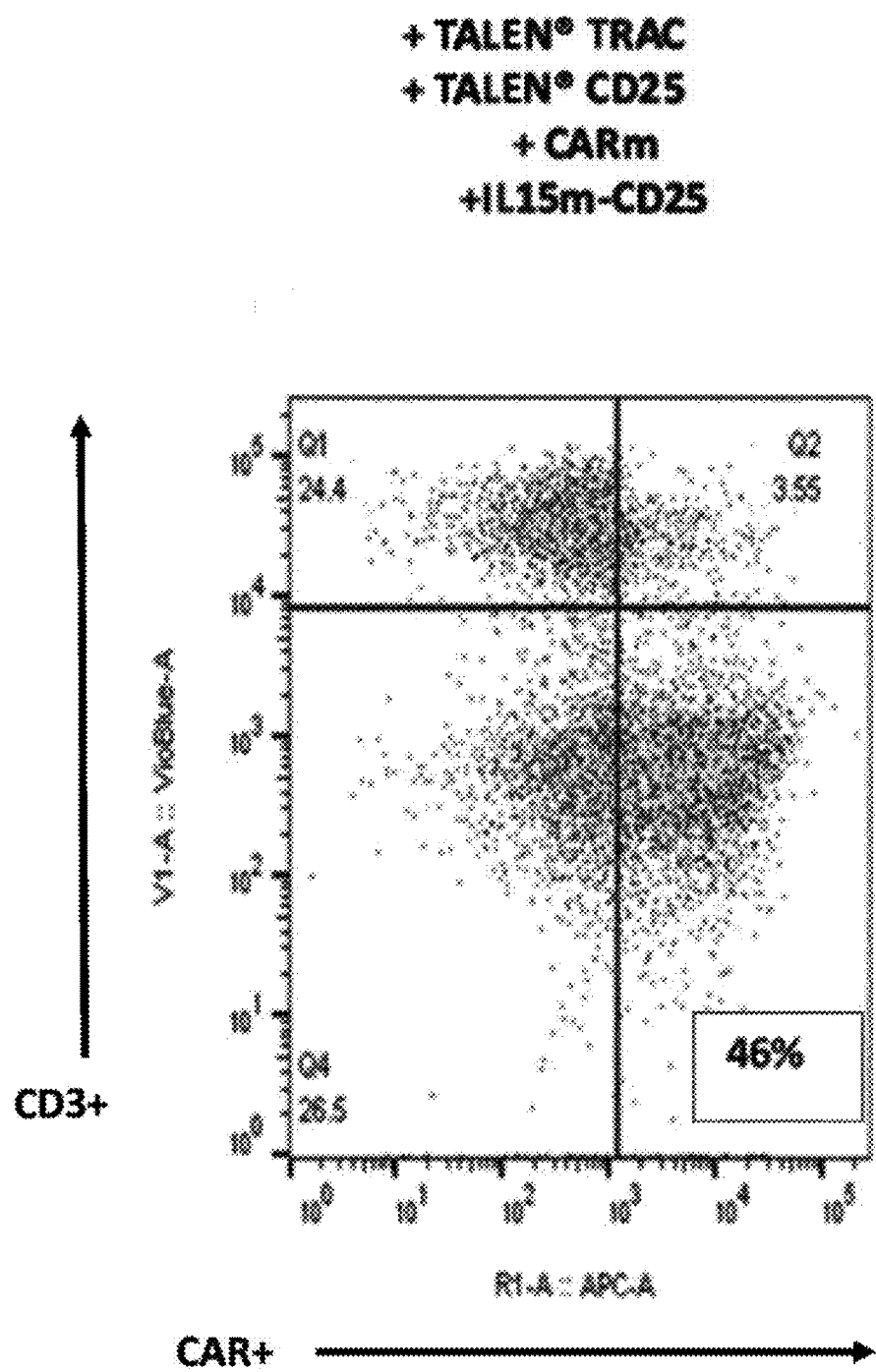

FIG. 3A-C: Flow cytometry measures of the frequency of targeted integration of IL-15m at either the PD1 or CD25 locus by using respectively PD1 or CD25 TALEN®, in a context where an anti-CD22 CAR is also integrated at the TRAC locus using TRAC TALEN®. These results show efficient targeted integration of both the CAR anti-CD22 at the TRAC locus together and the IL-15 coding sequence at the PD1 or CD25 loci. A: mock transfected primary T-cells. B: primary T-cells transfected with the donor sequences described in FIG. 1 (B and C) and specific TALEN® for the double integration at the TCR and PDI loci. C: primary T-cells transfected with the donor sequences described in FIG. 1 (A and C) and specific TALEN® for the double integration at the TCR and CD25 loci.

Figure 4:
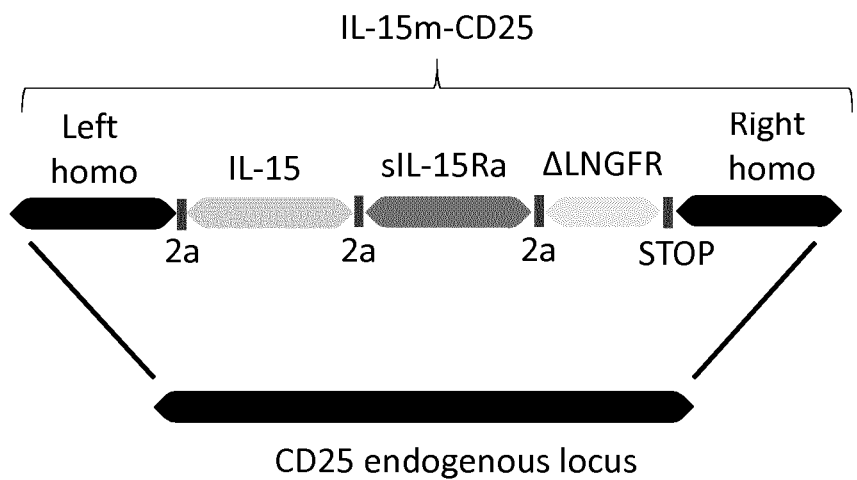
Figure 4:
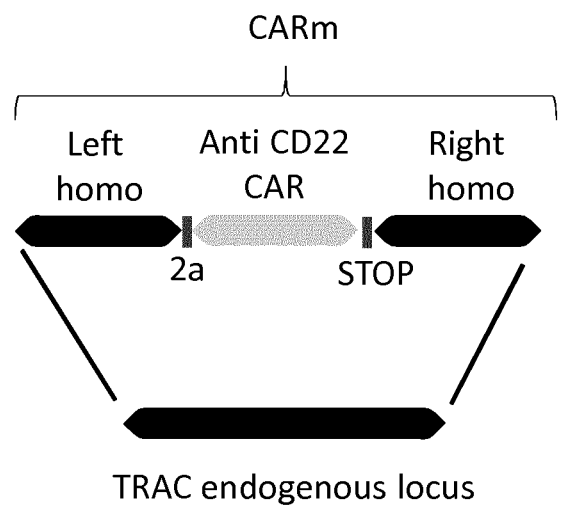
Figure 5A:
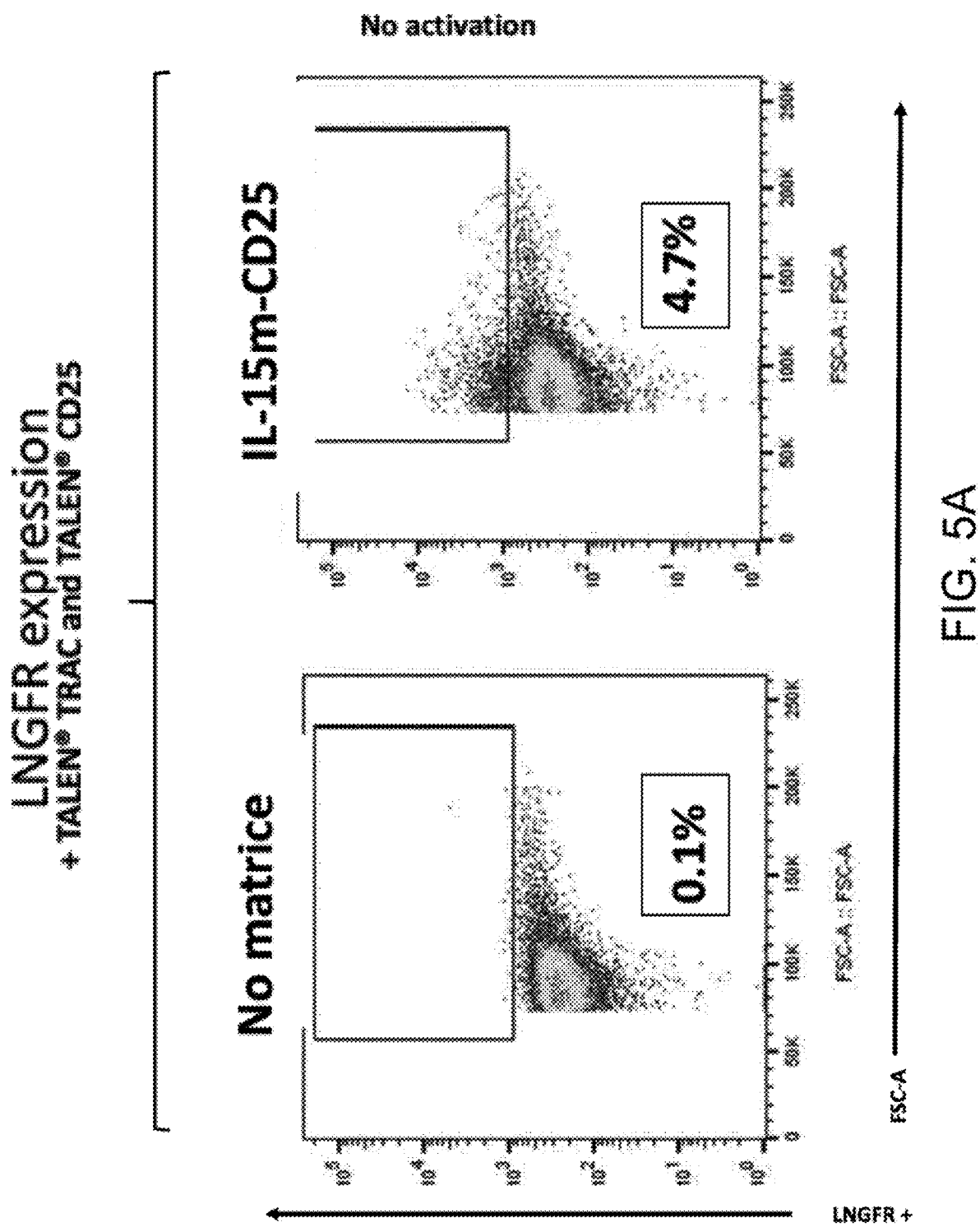
Figure 5B:
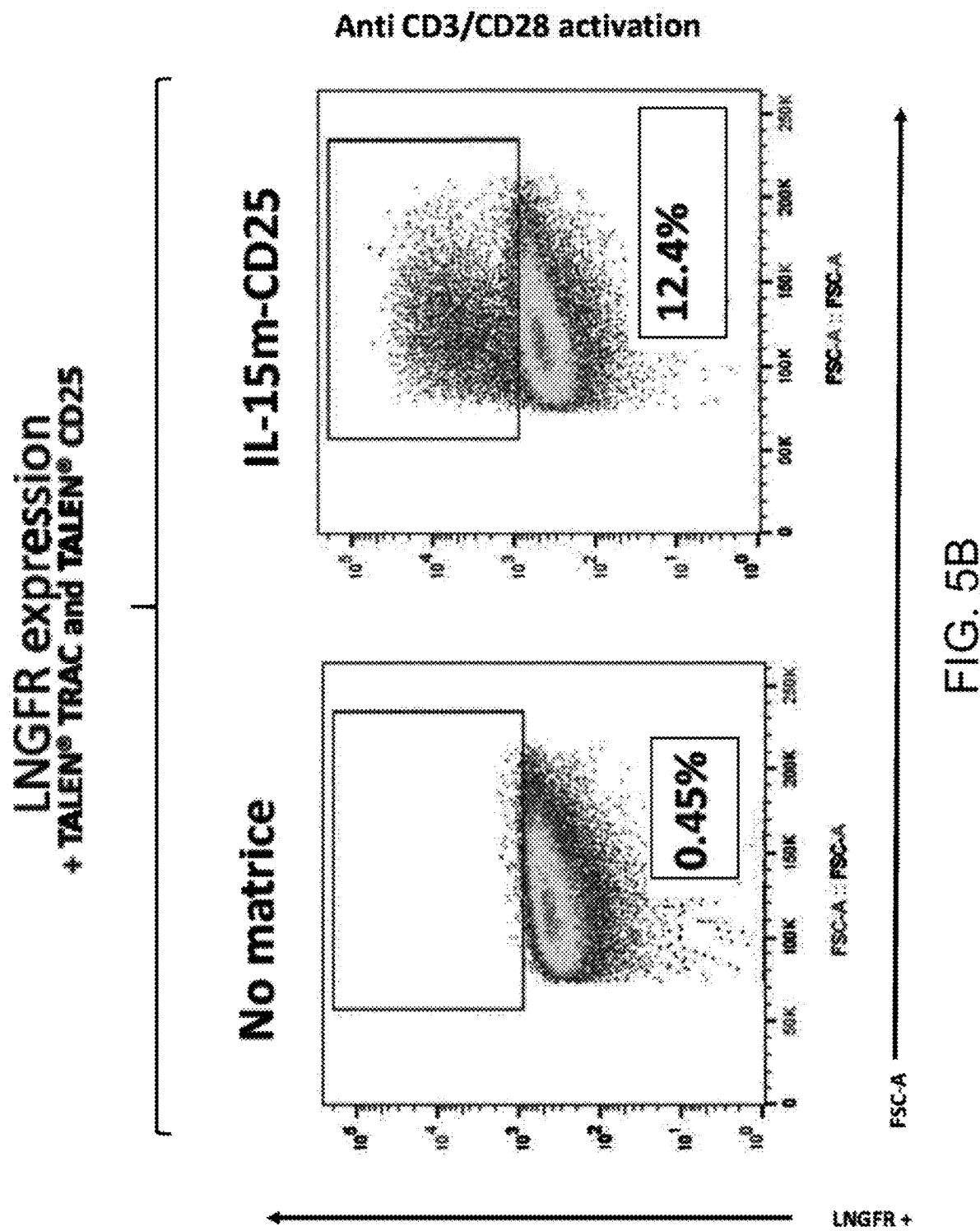
Figure 5C:
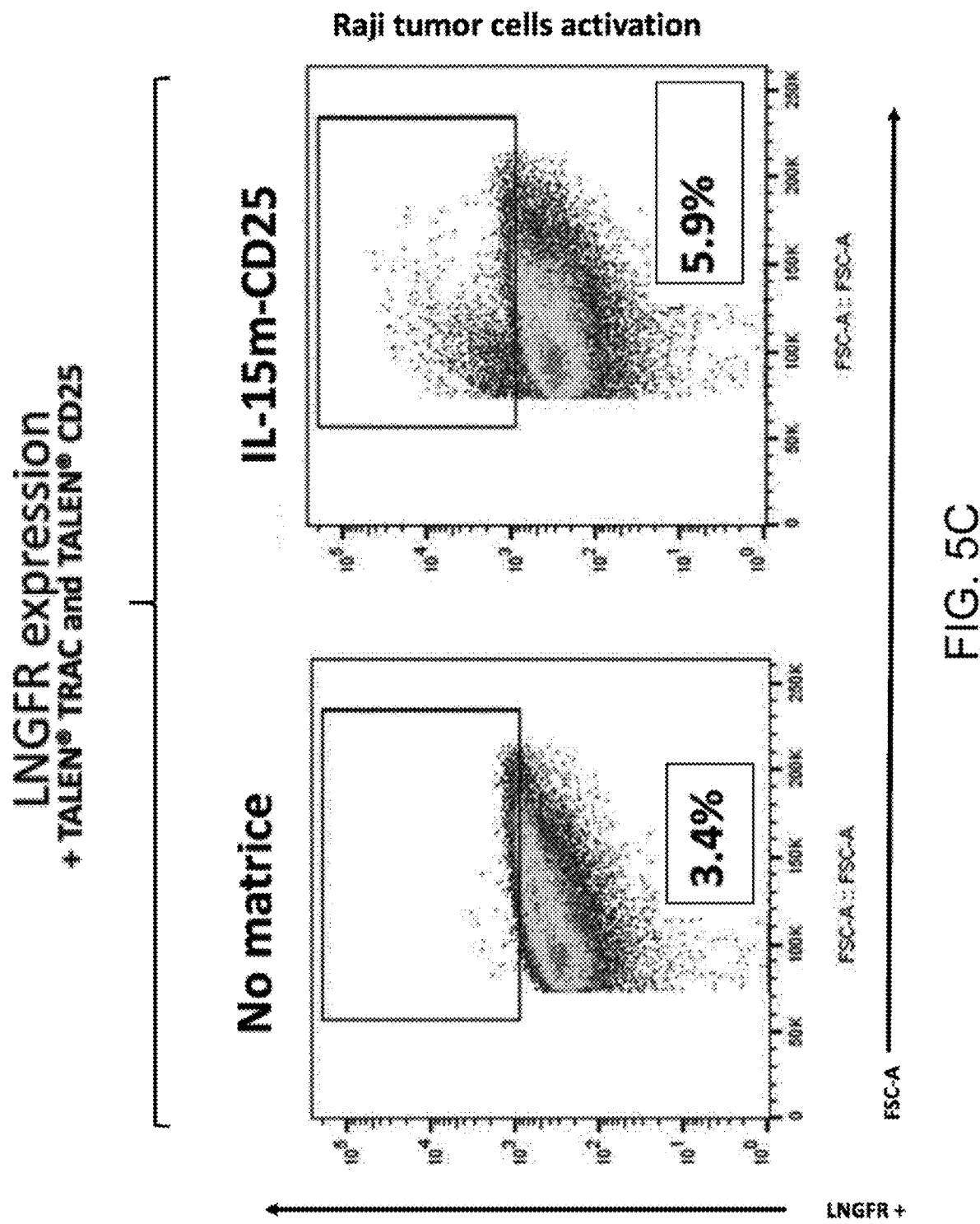
Figure 6A:
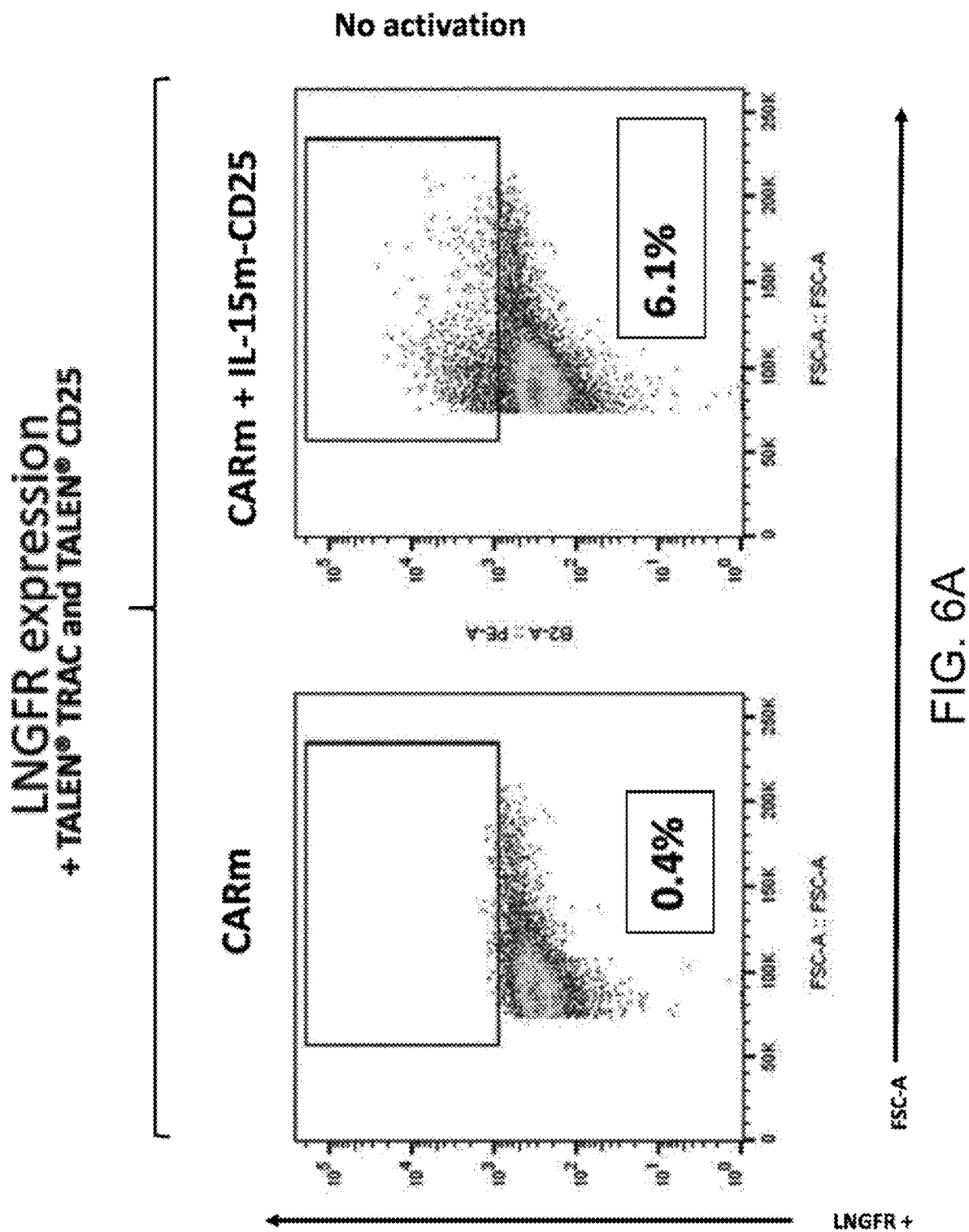
Figure 6B:
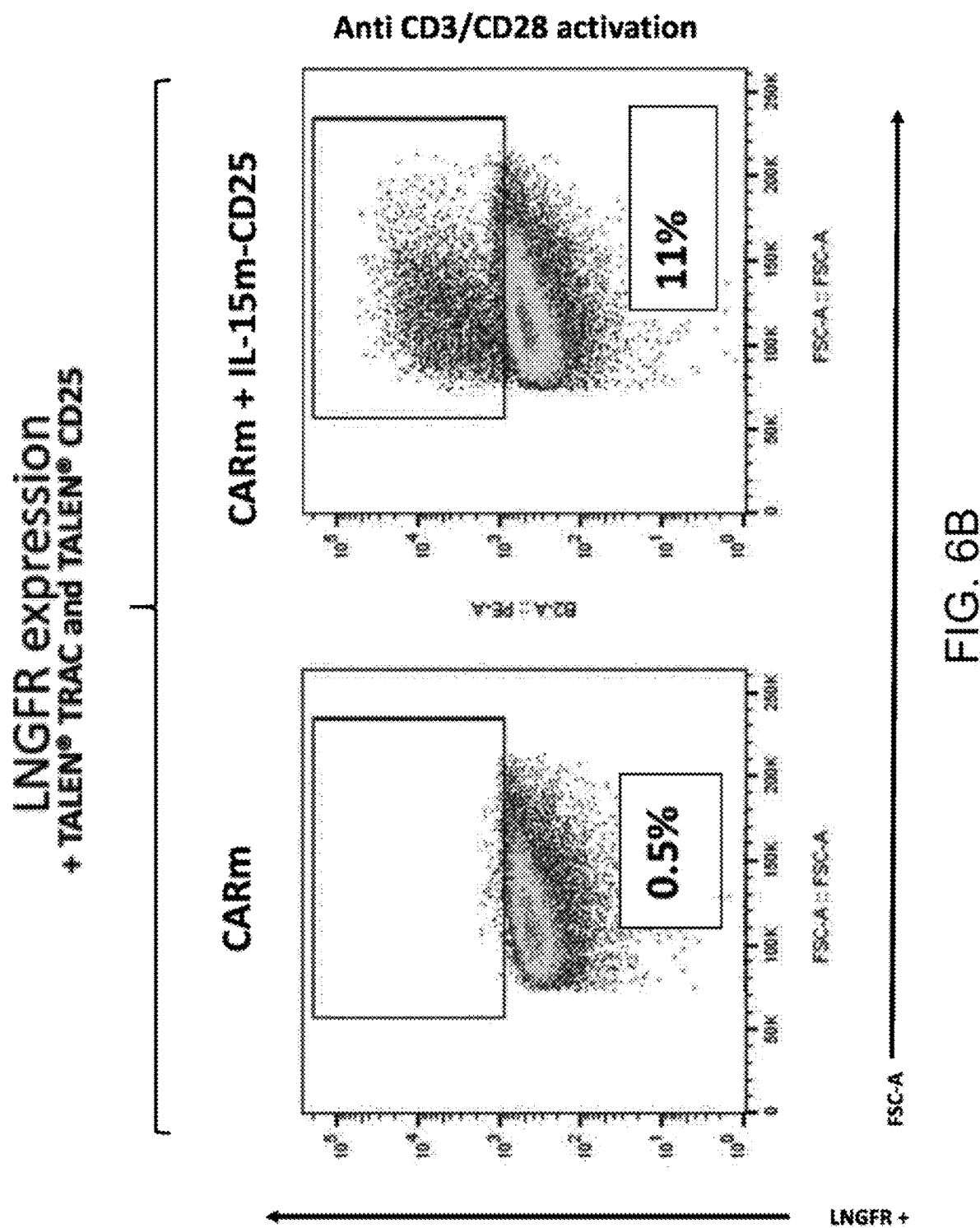
Figure 6C:
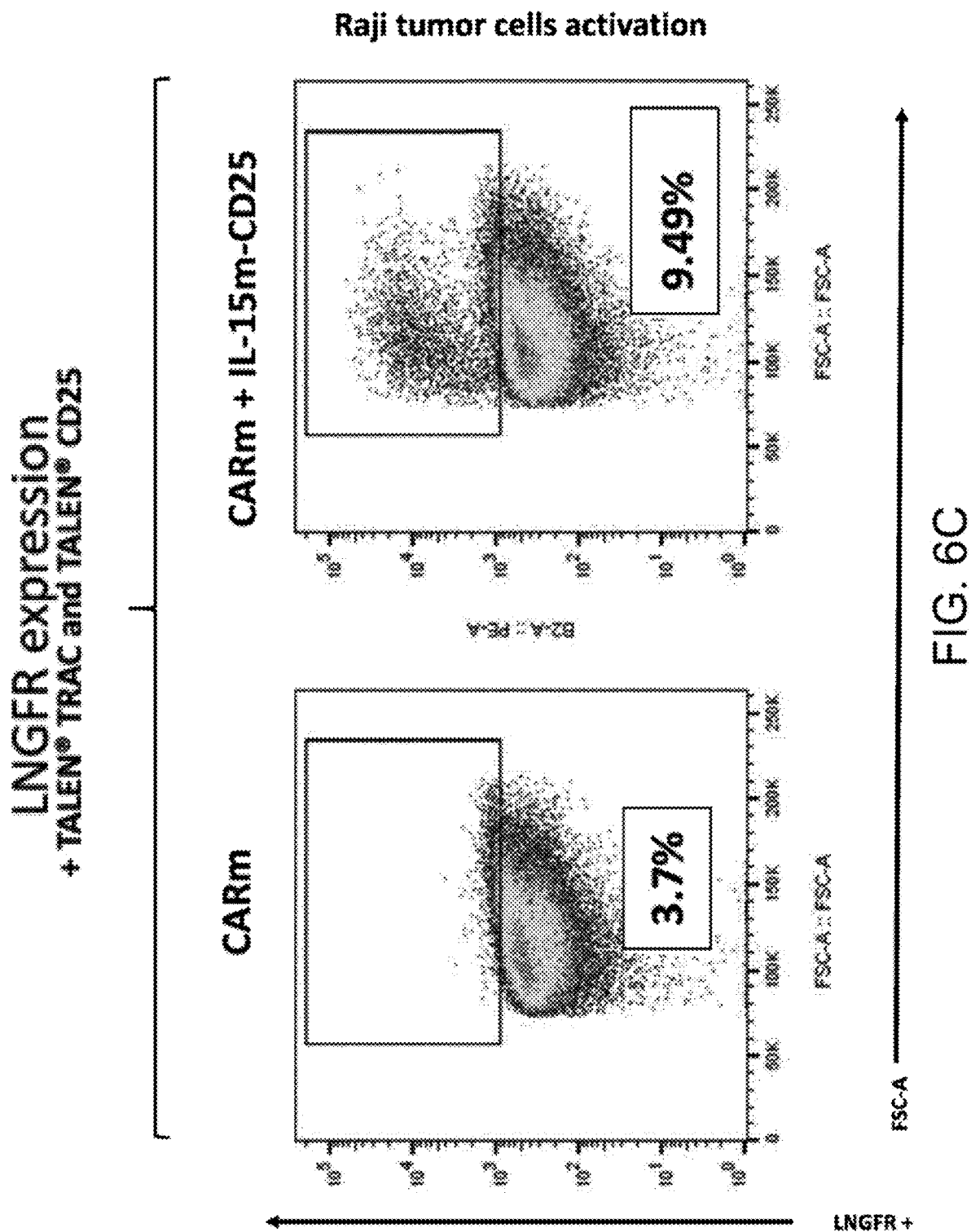
Figure 7A:
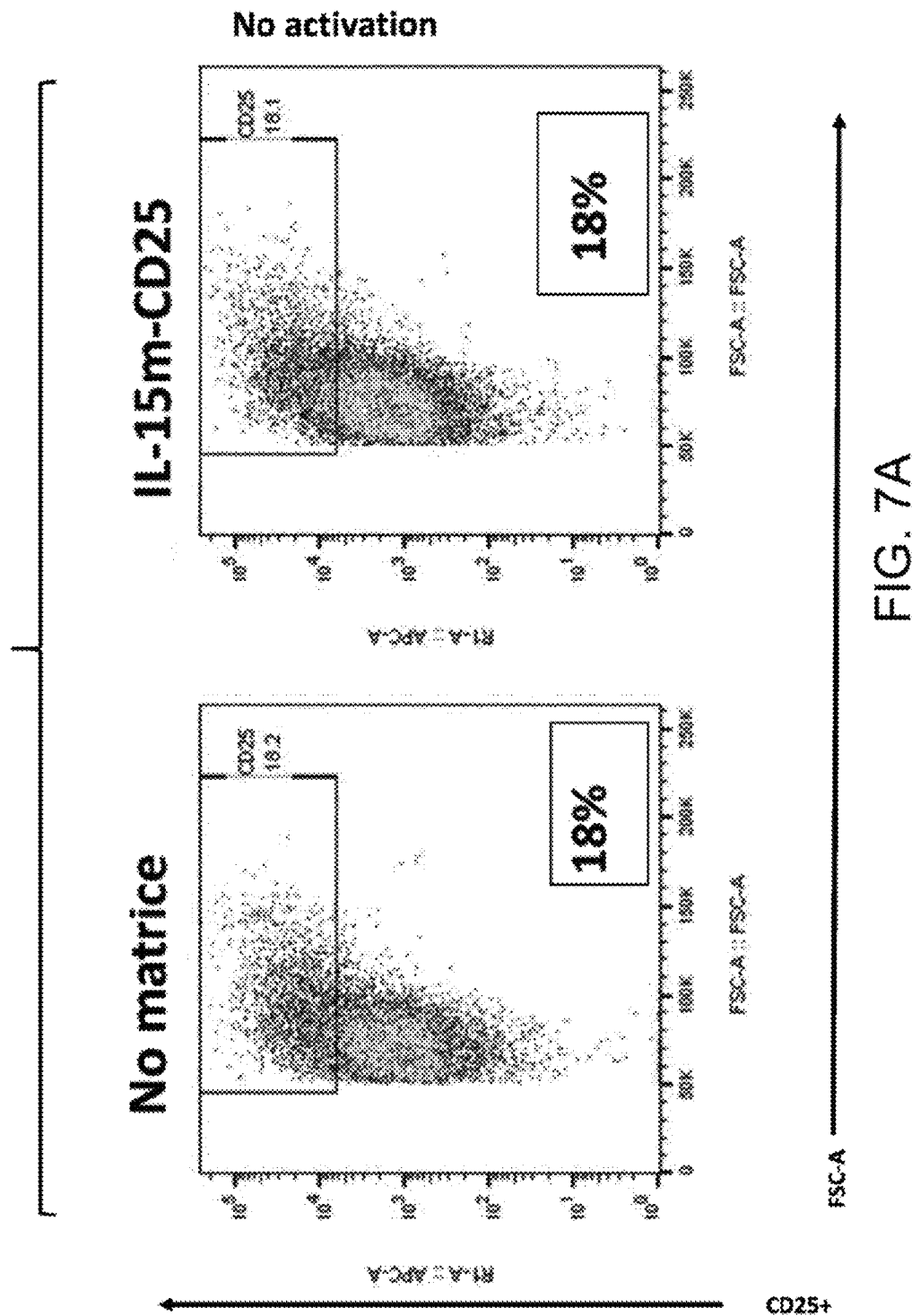
Figure 7B:
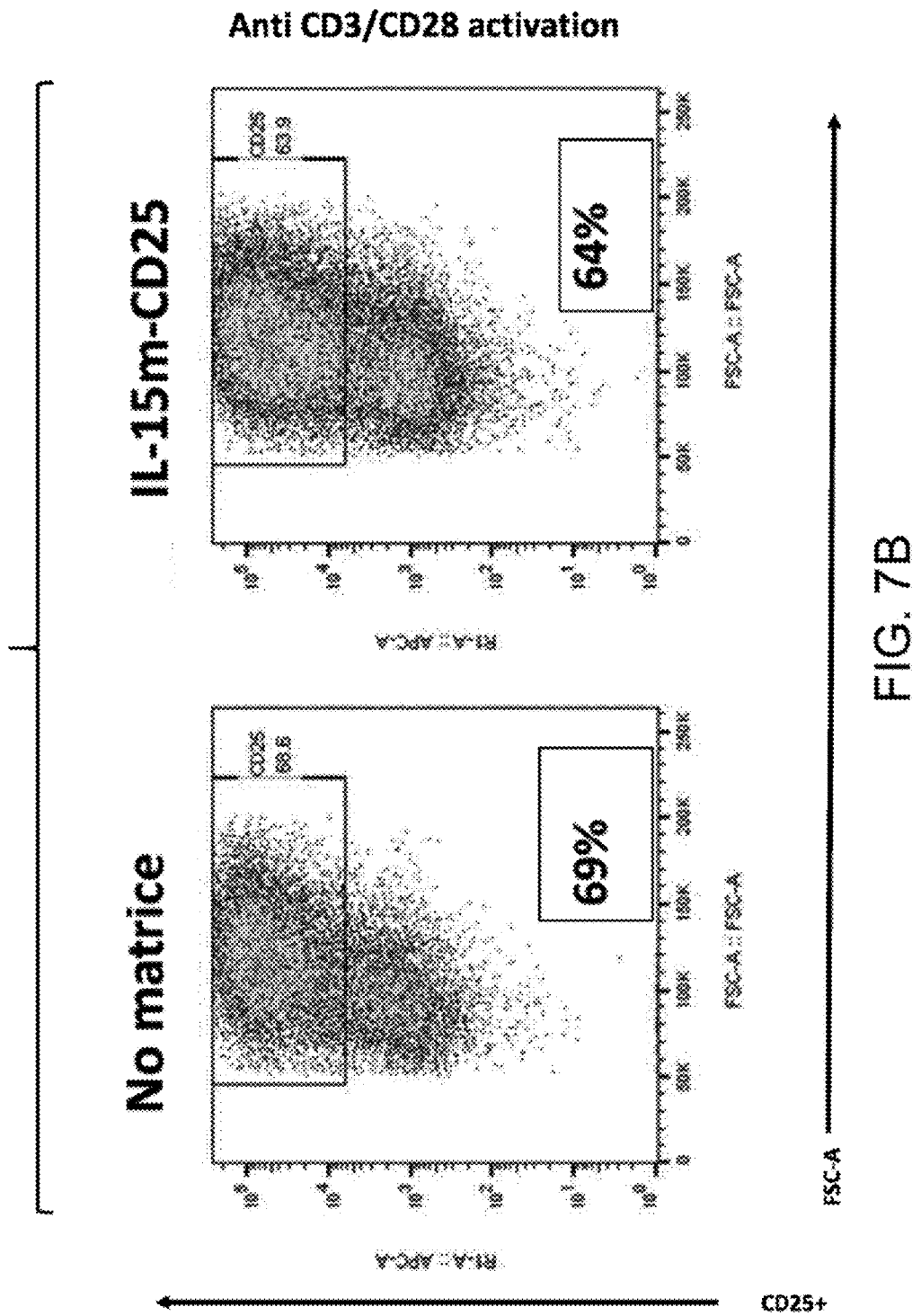
Figure 7C:
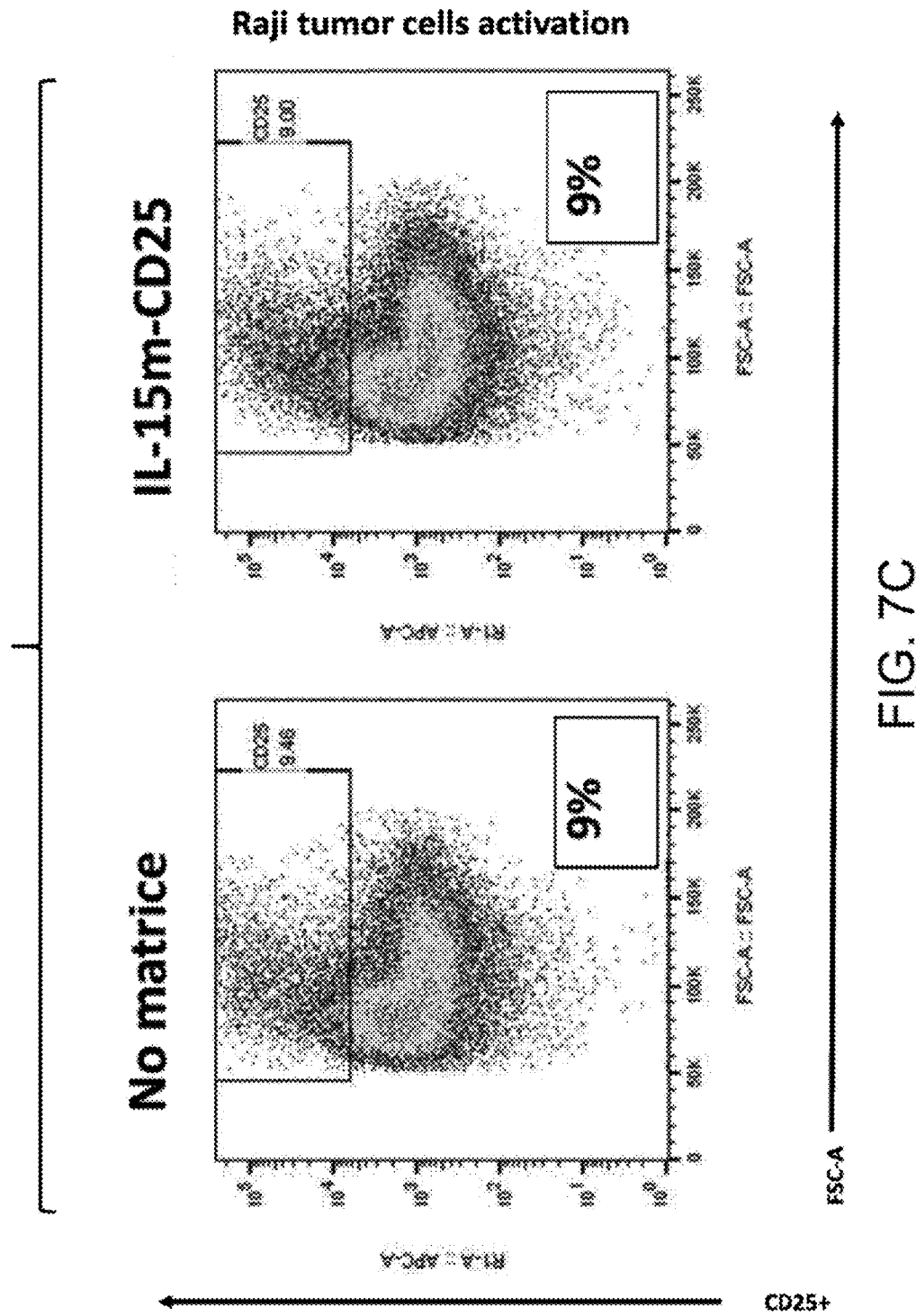
Figure 8A:
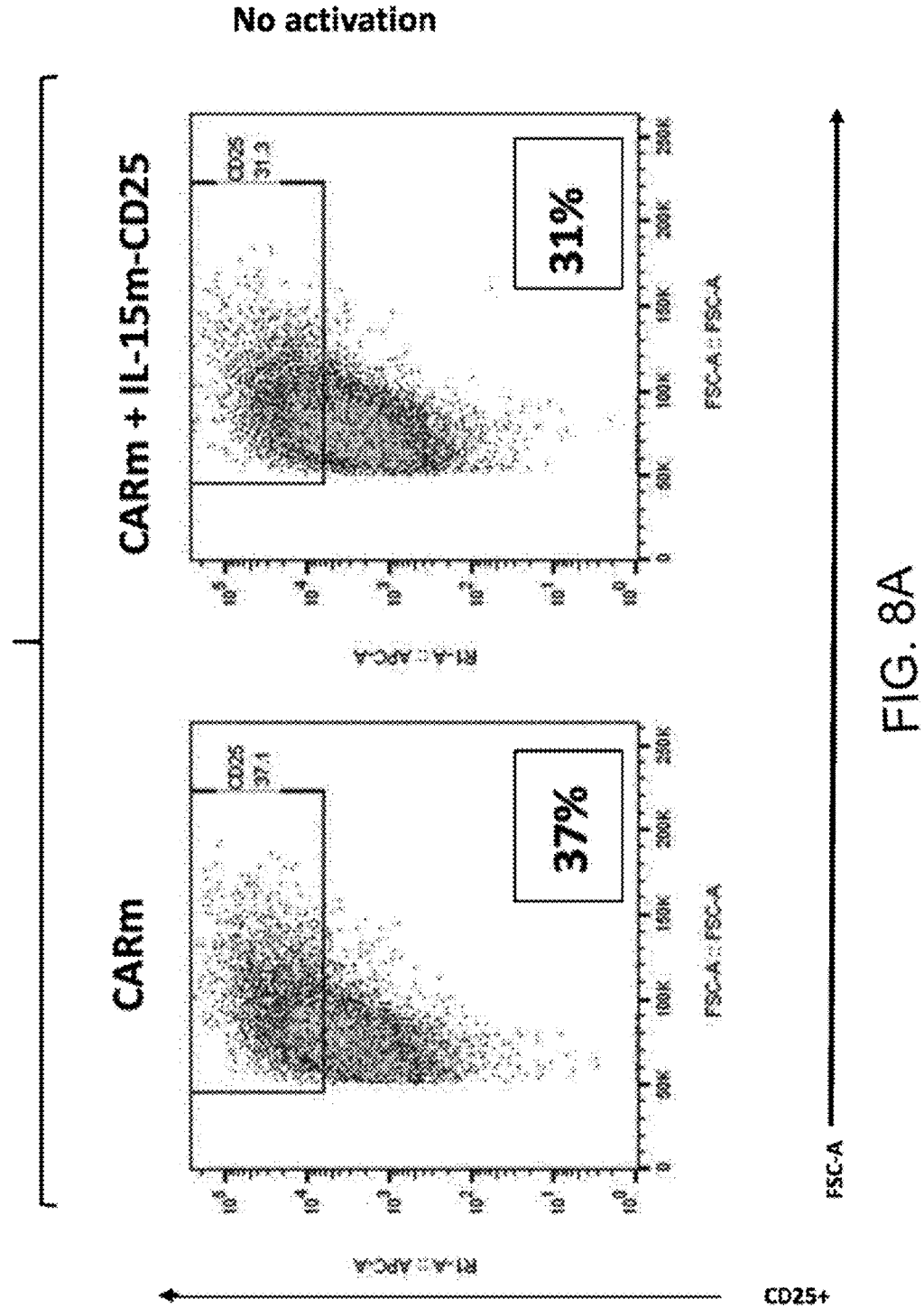
Figure 8B:
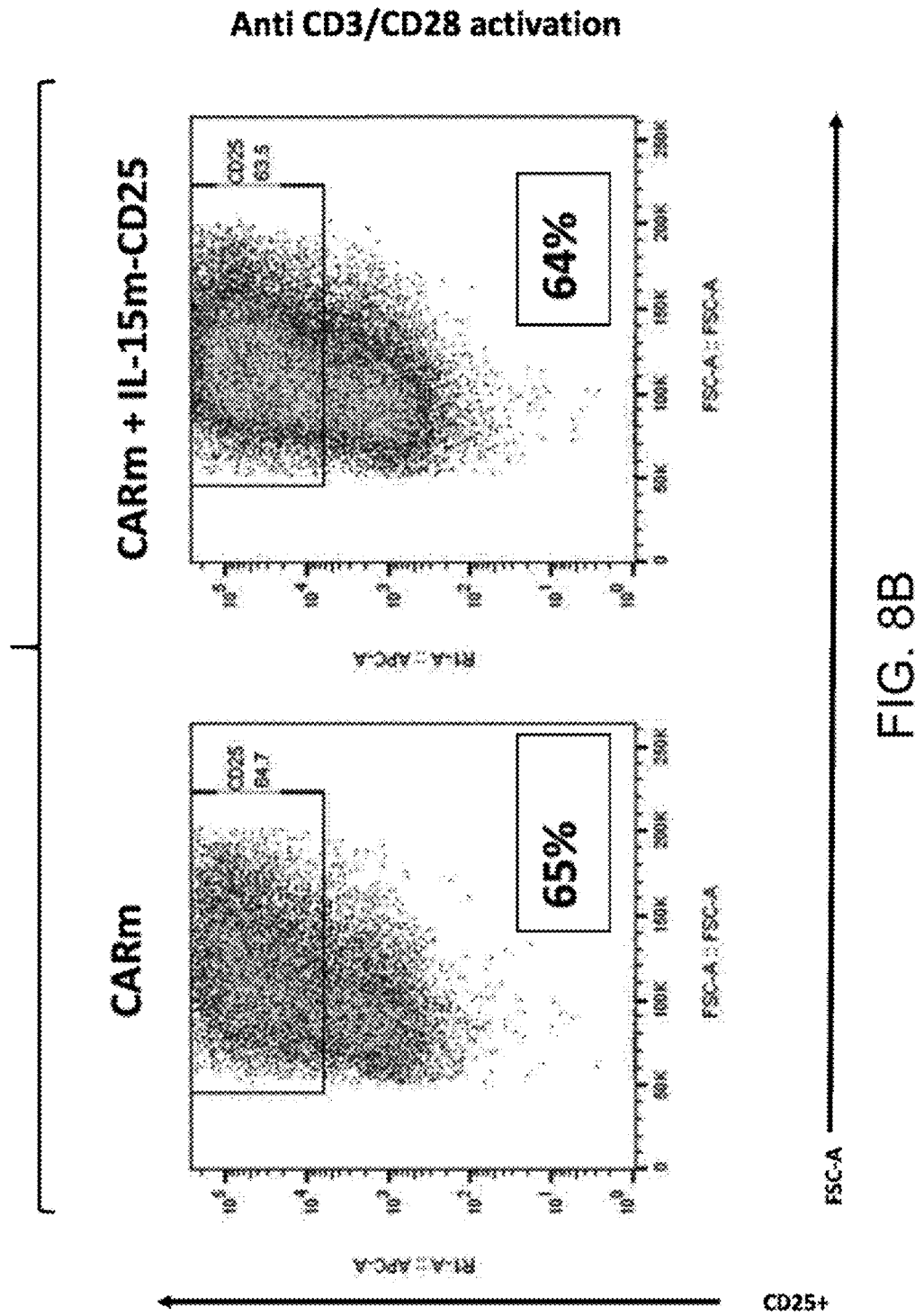
Figure 8C:
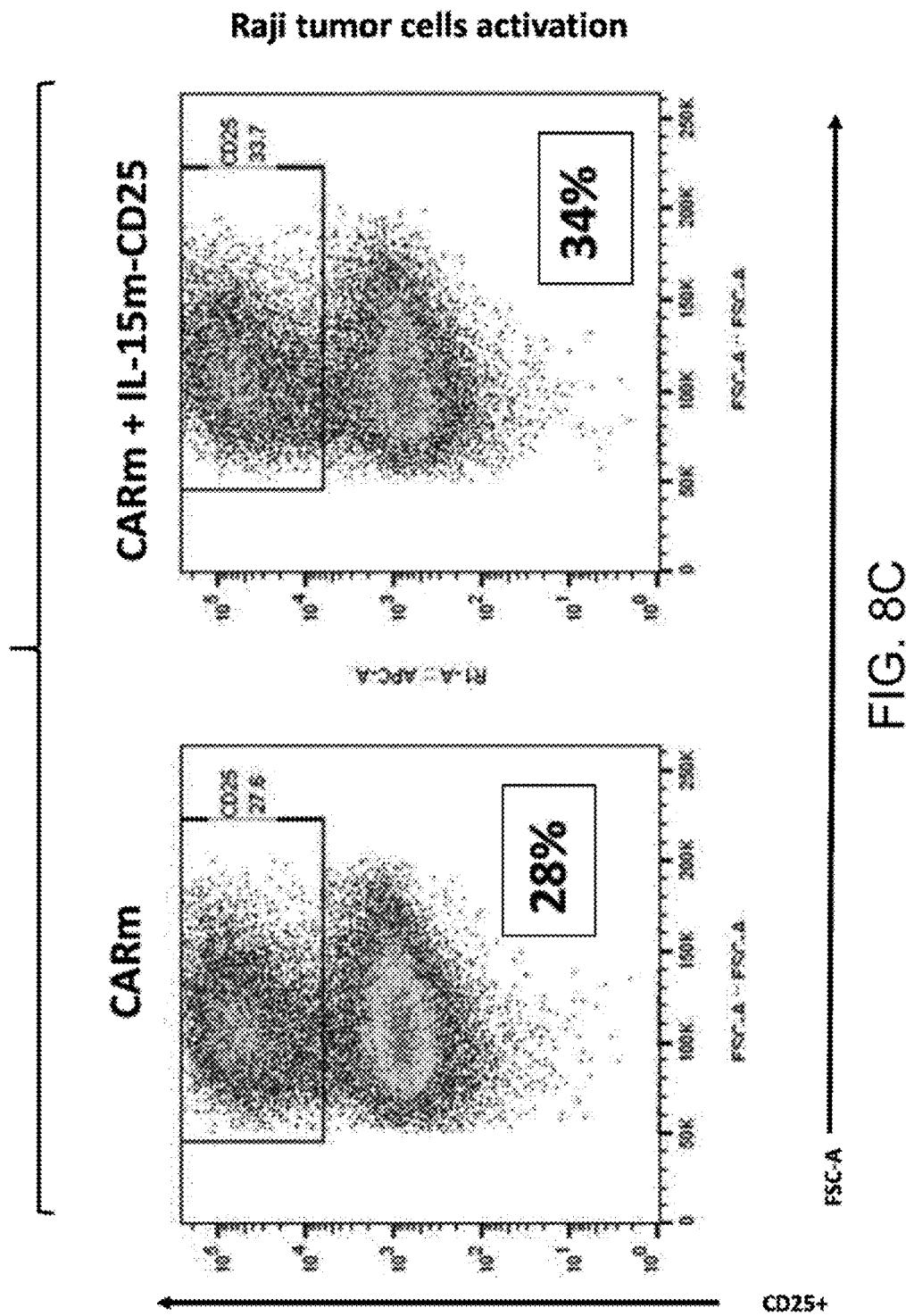

FIG. 4: Schematic representation of the exogenous sequences used in the experimental section to transfect the primary immune cells to obtain the results shown in FIGS. 5 and 6.

FIGS. 5A-C and 6A-C: Flow cytometry measures for LNGFR expression among viable T-cells transfected with donor templates of FIG. 4 and specific TALEN® (TCR and CD25), upon antiCD3/CD28 non-specific activation (Dynabeads®) and upon CAR dependent tumor cell activation (raji tumor cells). As shown in FIG. 6, LNGFR expression was specifically induced in [CAR anti-CD22]$^{positive}$ cells upon CAR/tumor engagement.

FIGS. 7A-C and 8A-C: Flow cytometry measures for CD25 expression among viable T-cells transfected with donor templates of FIG. 4 and specific TALEN® (TCR and CD25), upon antiCD3/CD28 non-specific activation (Dynabeads®) and Tumor cell activation (raji tumor cells). As shown in FIG. 8, CD25 expression was specifically induced in [CAR anti-CD22]$^{positive}$ cells upon CAR/tumor engagement.

Figure 9:
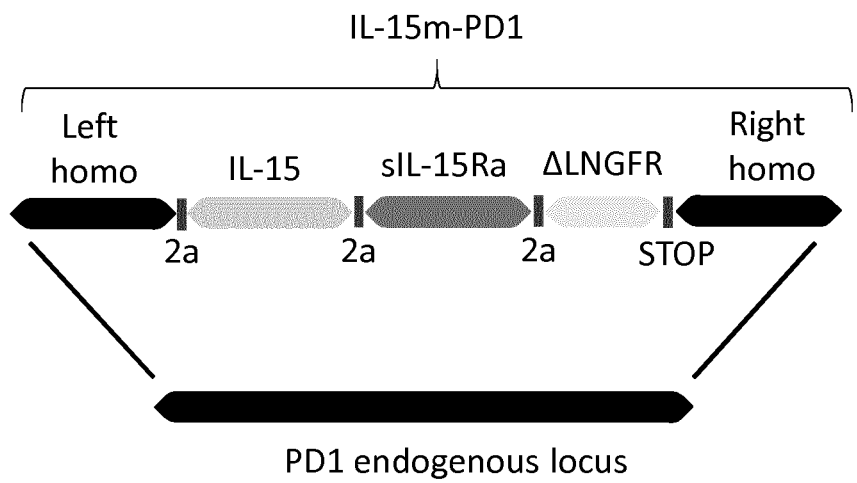
Figure 9:
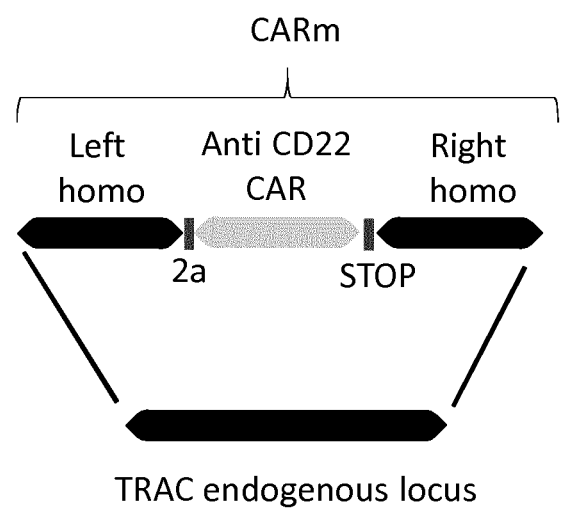
Figure 10A:
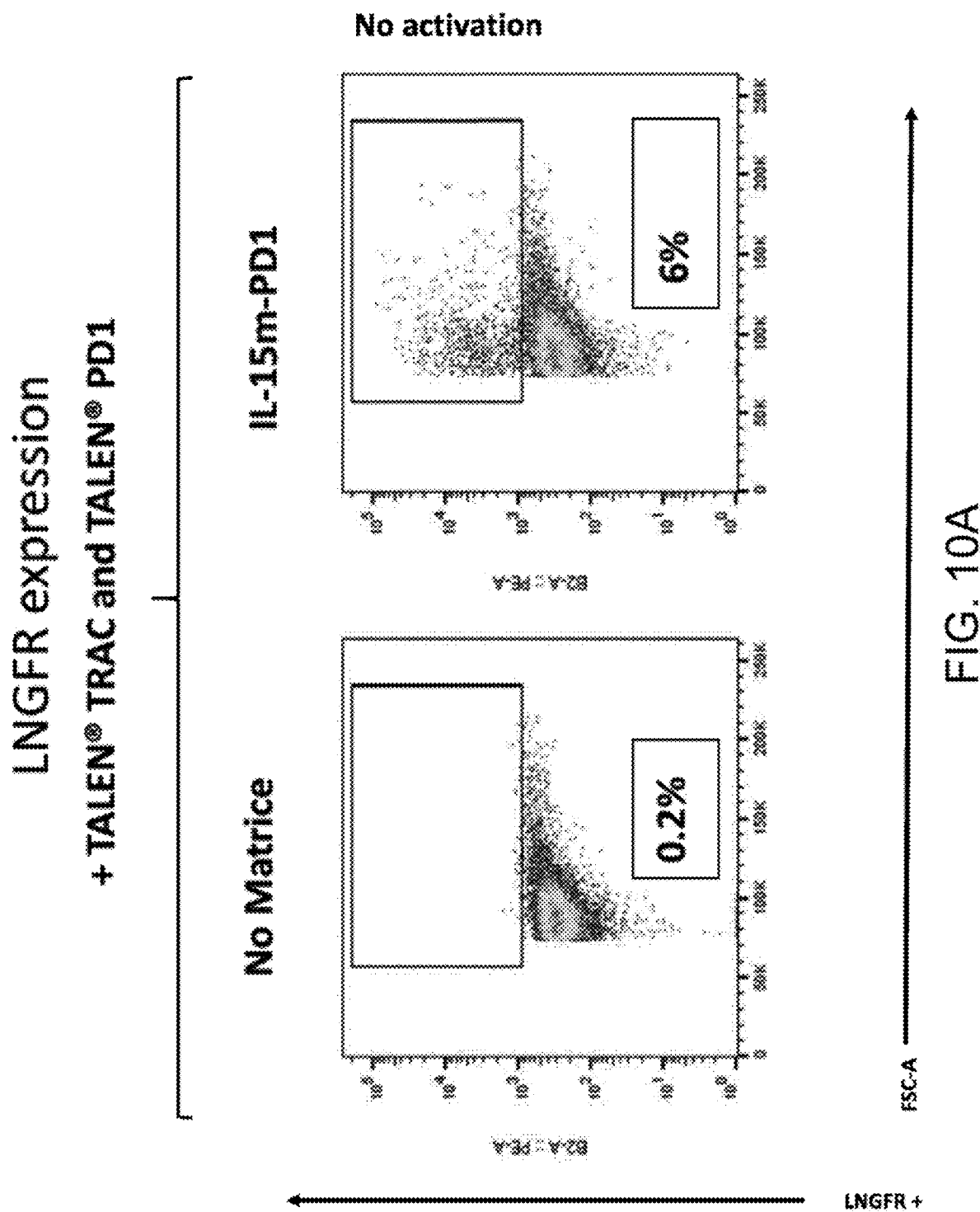
Figure 10B:
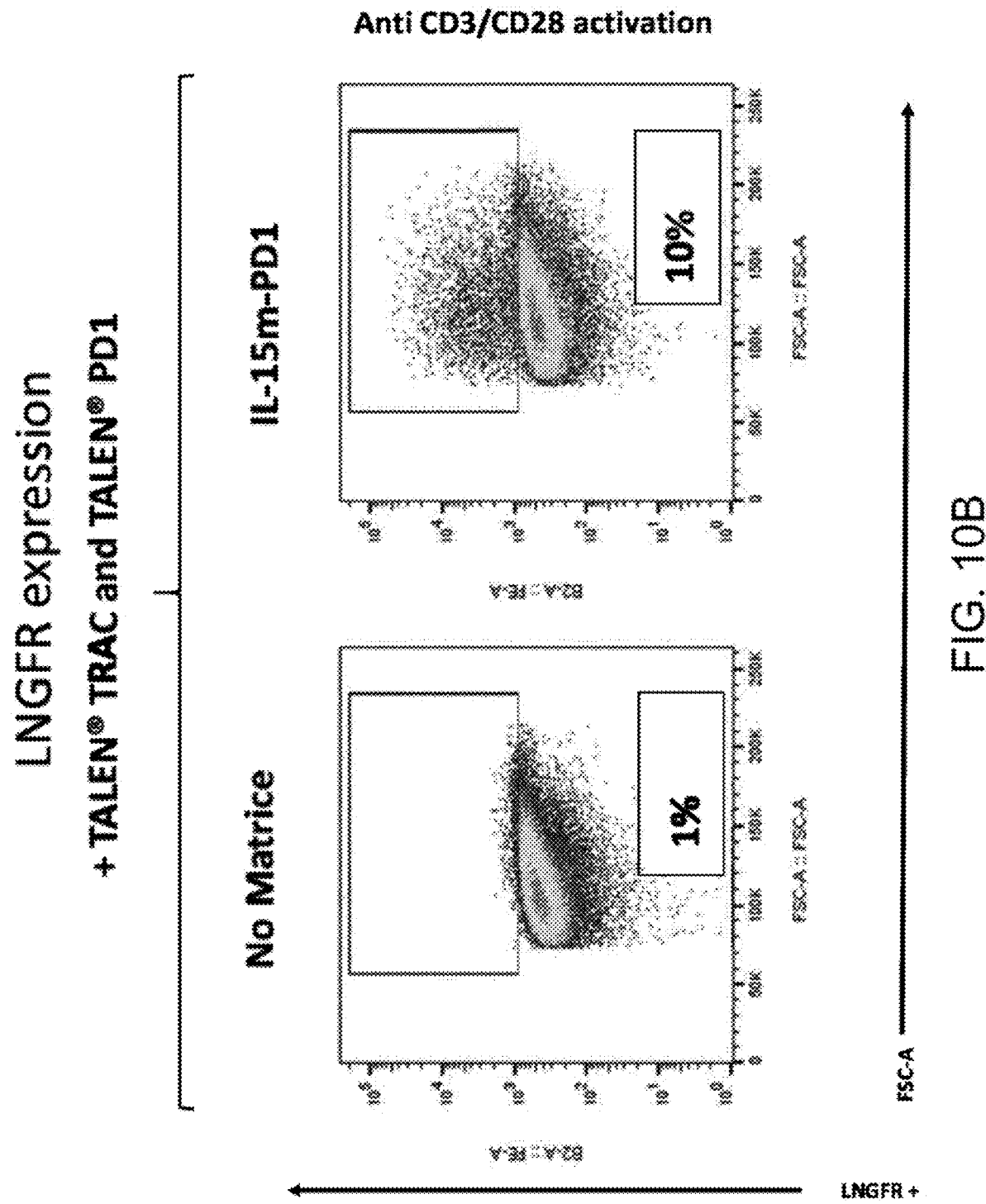
Figure 10C:
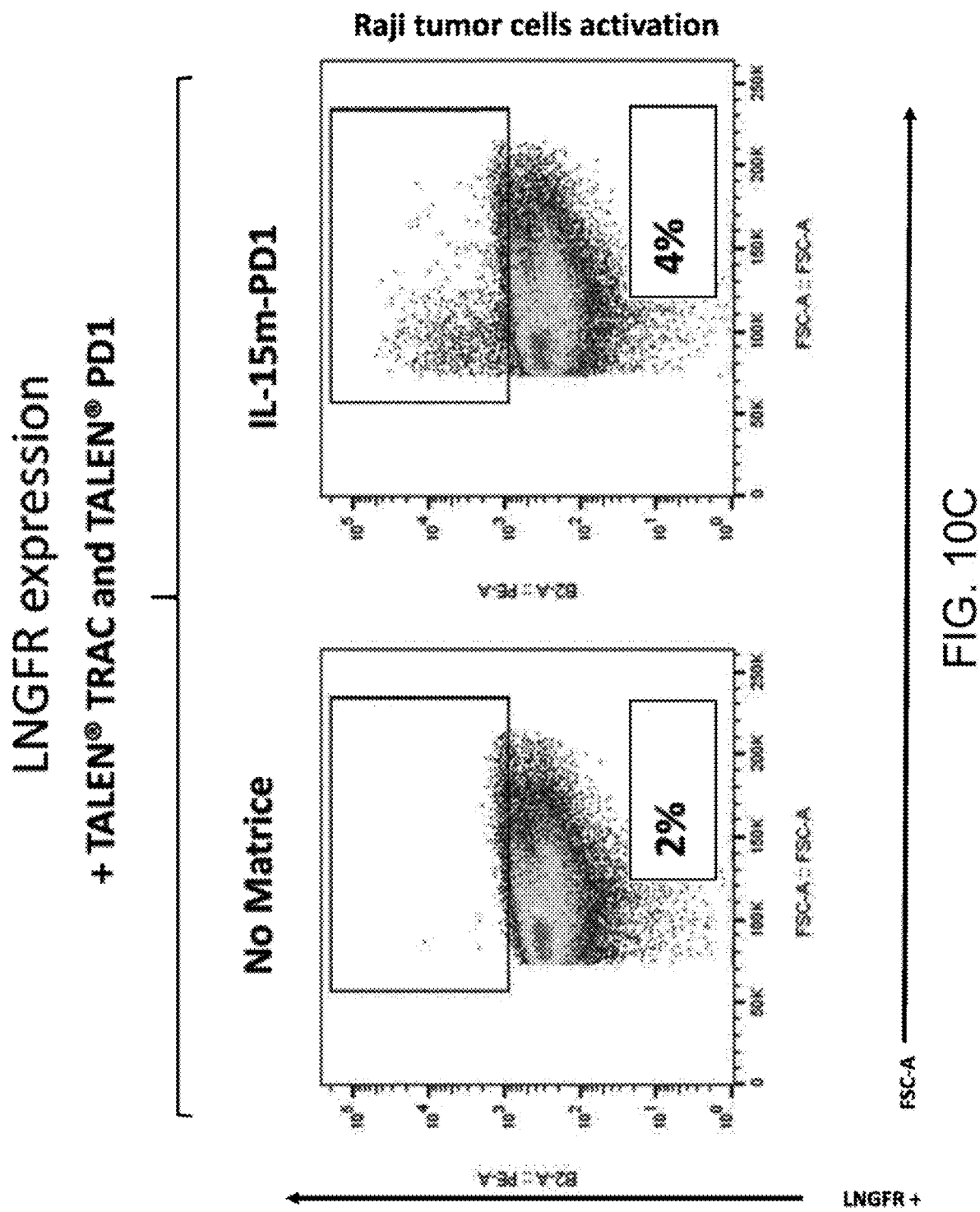
Figure 11A:
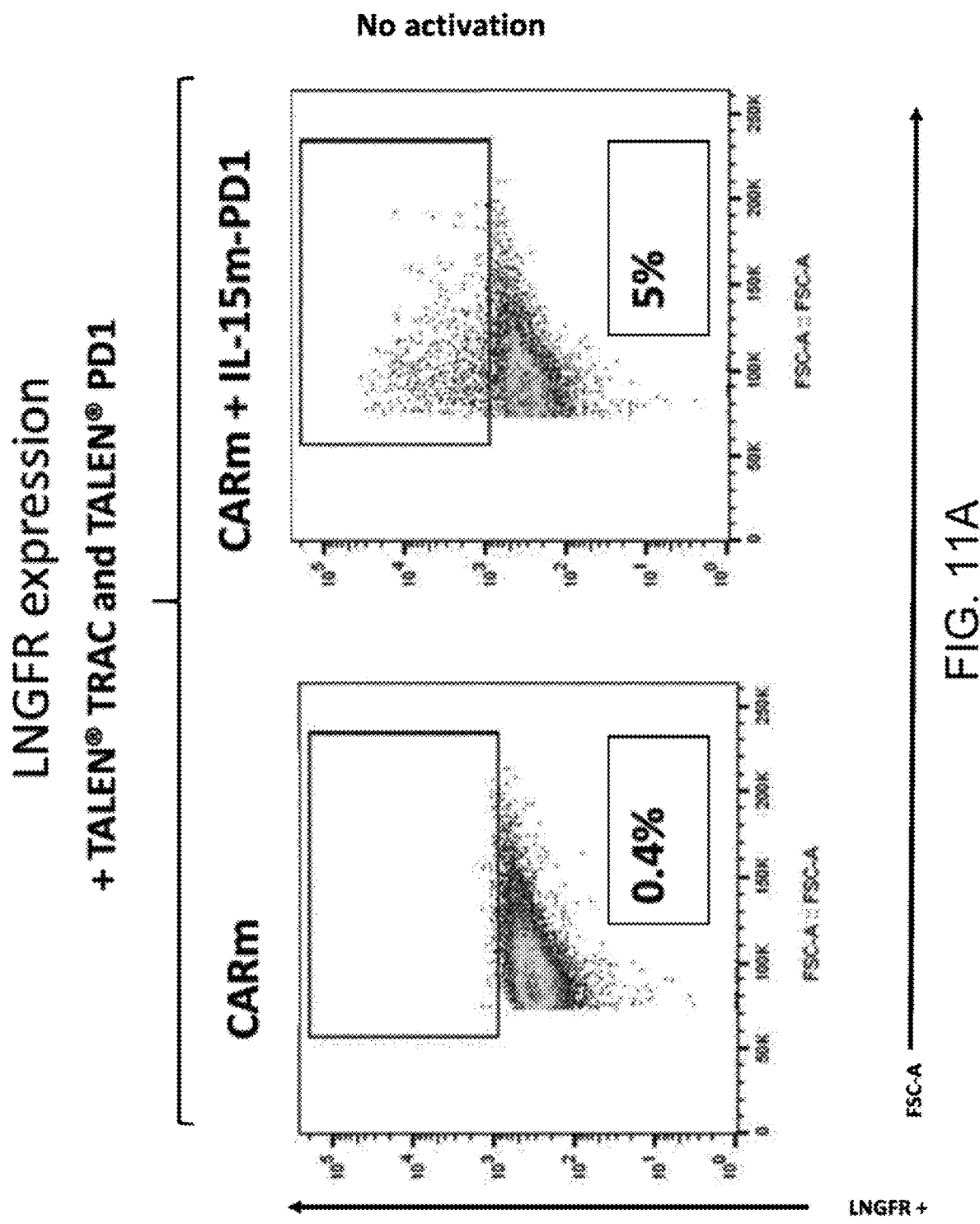
Figure 11B:
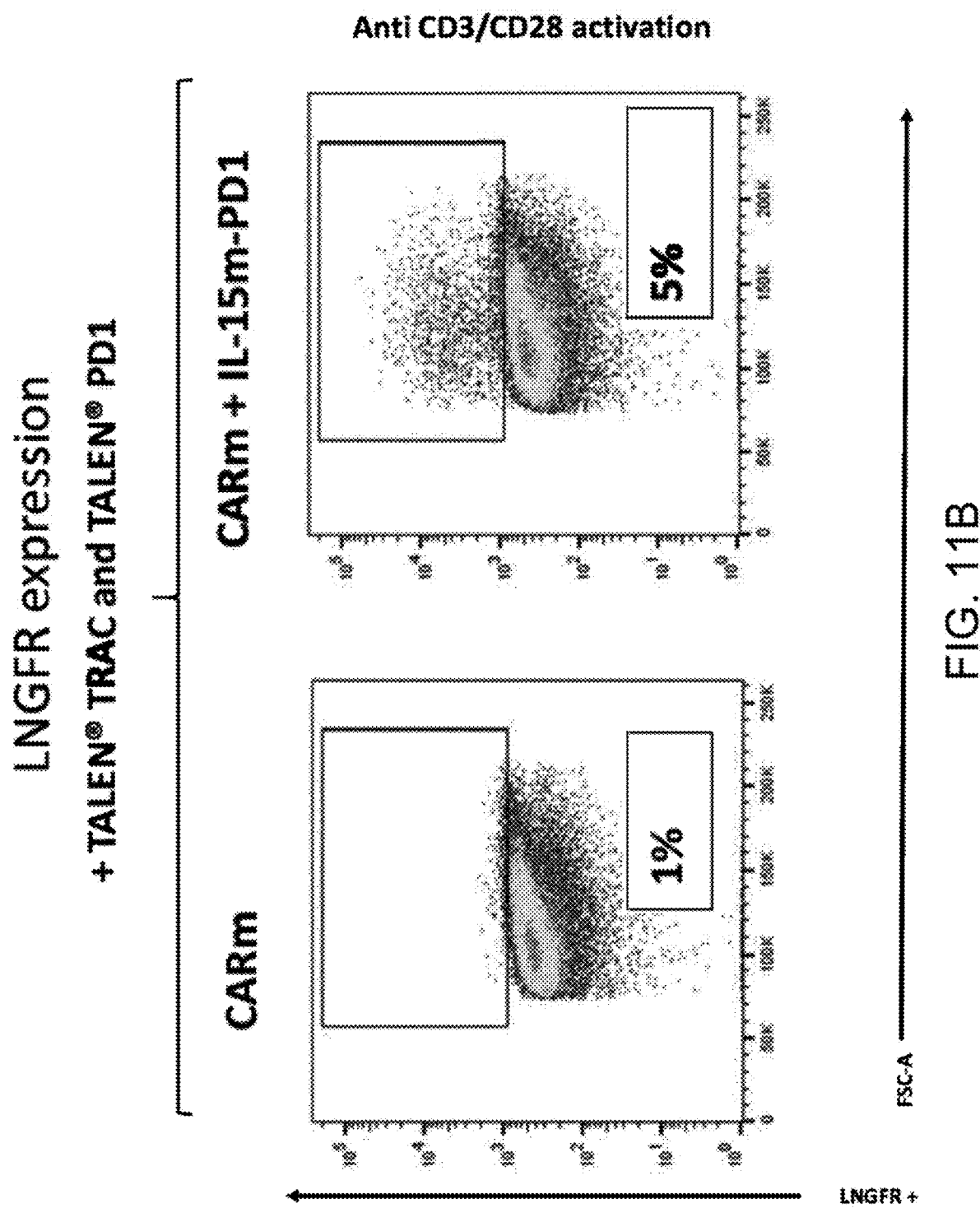
Figure 11C:
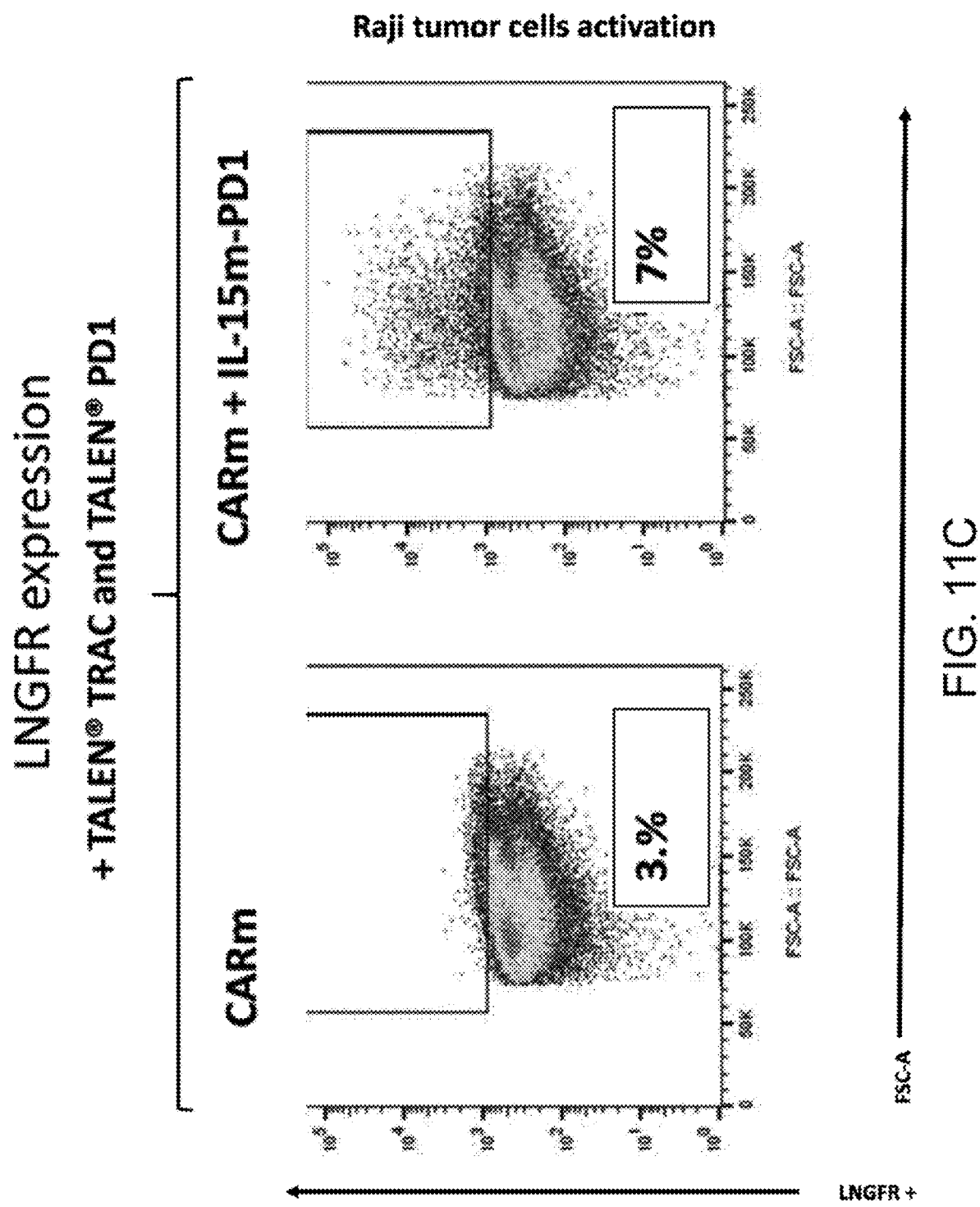

FIG. 9: Schematic representation of the exogenous sequences used in the experimental section to transfect the primary immune cells to obtain the results shown in FIGS. 11 and 12.

FIGS. 10A-C and 11A-C: Flow cytometry measures for LNGFR expression among viable T-cells transfected with donor templates of FIG. 9 and specific TALEN® (TCR and PD1) upon antiCD3/CD28 non-specific activation (Dynabeads®) and Tumor cell activation (raji tumor cells). As shown in FIG. 11, LNGFR expression was specifically induced in [CAR anti-CD22]$^{positive}$ cells upon CAR/tumor engagement.

Figure 12A:
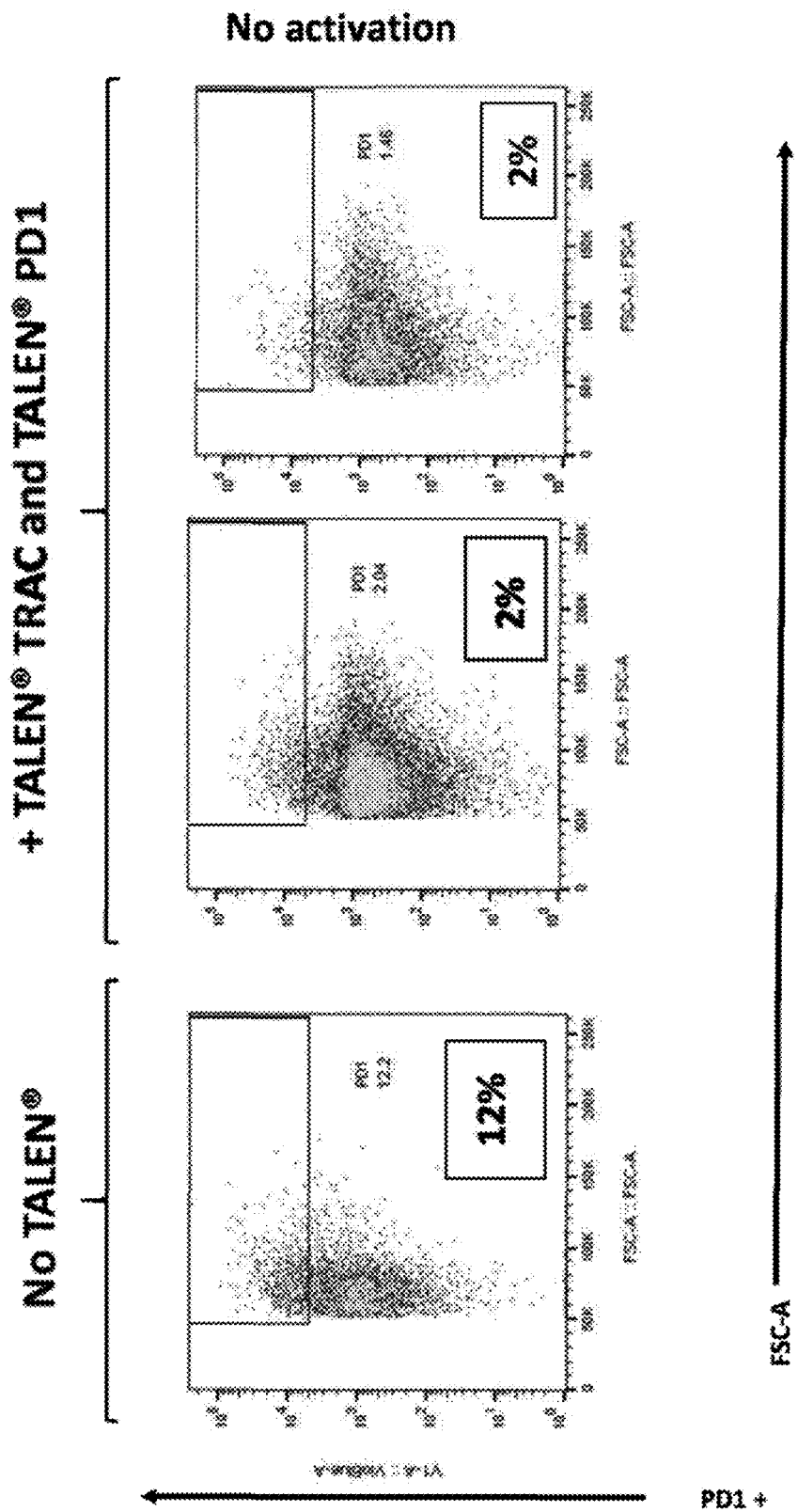
Figure 12B:
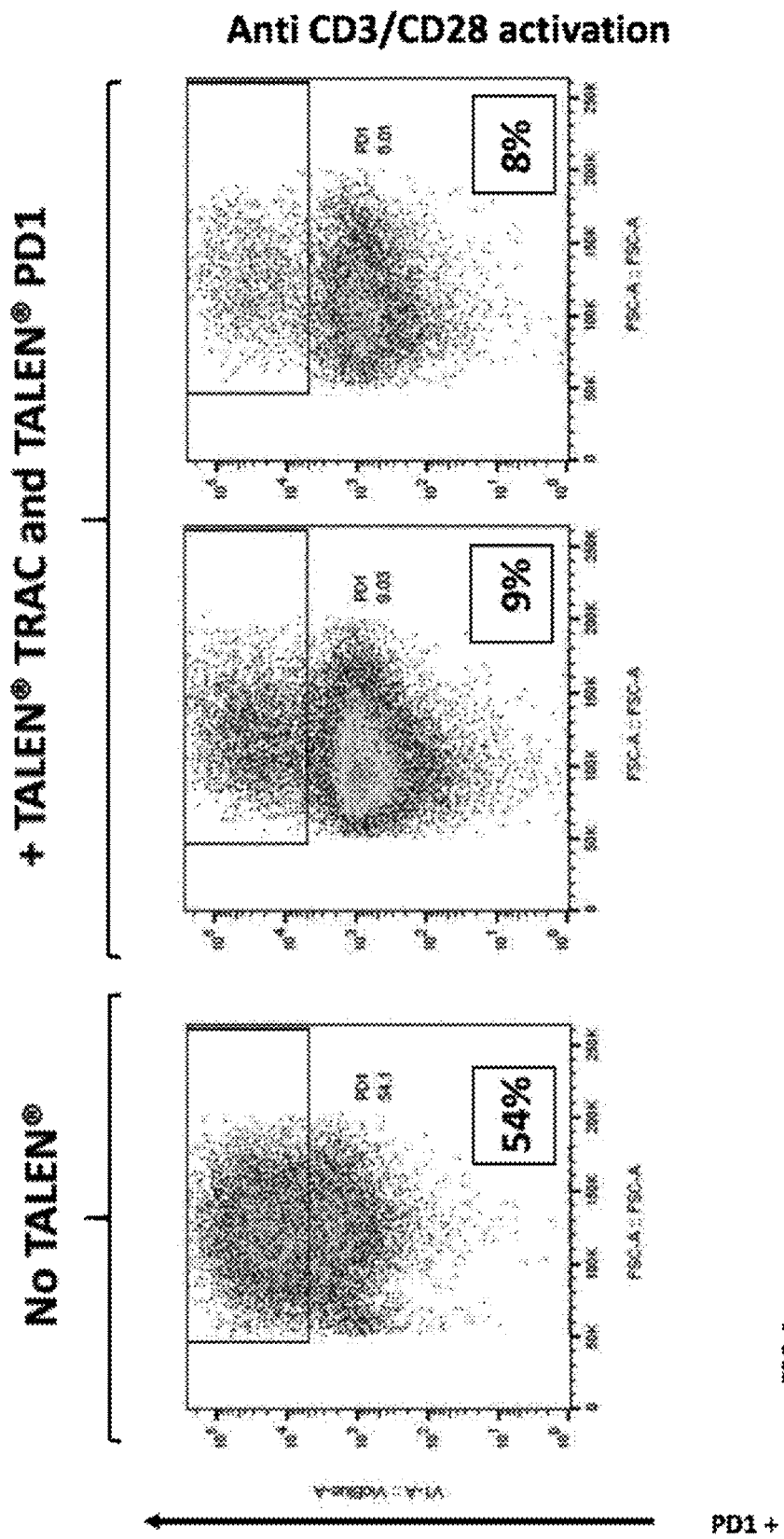
Figure 12C:
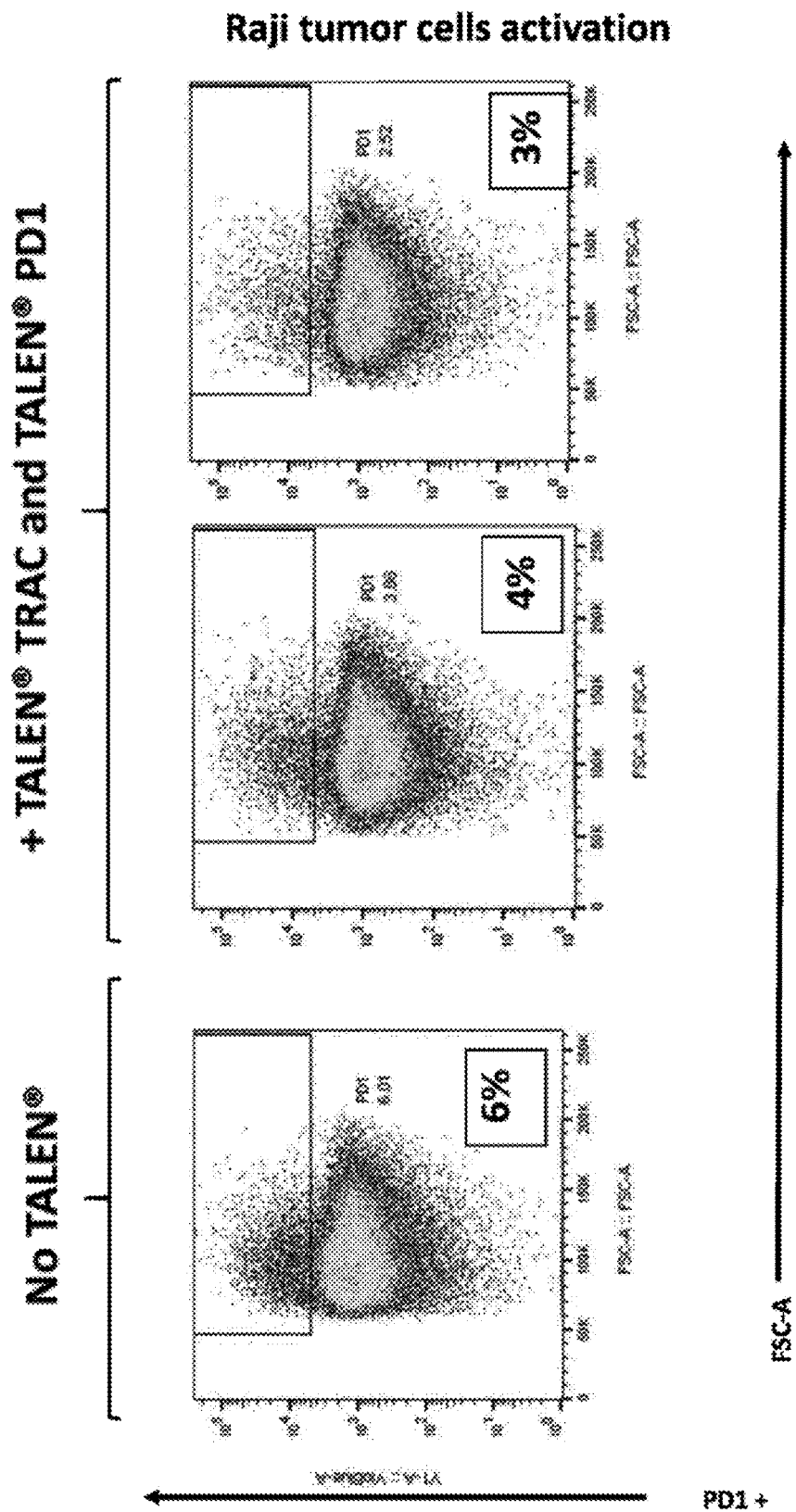

FIGS. 12A-C: Flow cytometry measures for endogenous PD1 expression among viable T-cells transfected with donor templates of FIG. 9 upon antiCD3/CD28 non-specific activation (Dynabeads®) and Tumor cell activation (raji tumor cells) with and without using TALEN® (TCR and PD1). PD1 was efficiently Knocked-out by TALEN treatment (8% remaining expression of PD1 out of 54%).

Figure 13:
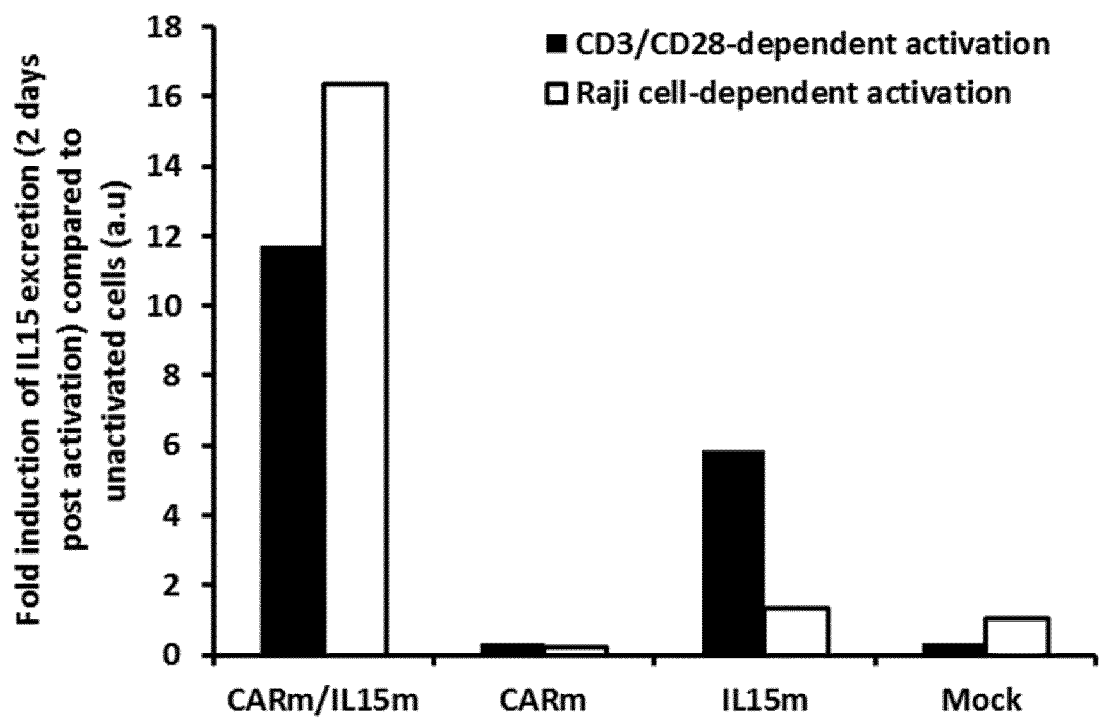

FIG. 13: Diagram showing IL-15 production in $[CAR]^{positive}$ (CARm) and $[CAR]^{negative}$ engineered immune cells according to the invention transfected with the donor template described in FIG. 2 (B) and TALEN® for insertion of IL-15 exogenous coding sequences into the PD1 locus. IL15, which transcription was under control of endogenous PD1 promoter, was efficiently induced upon antiCD3/CD28 non-specific activation (Dynabeads®) and Tumor cell activation (raji tumor cells) and secreted in the culture media.

Figure 14:
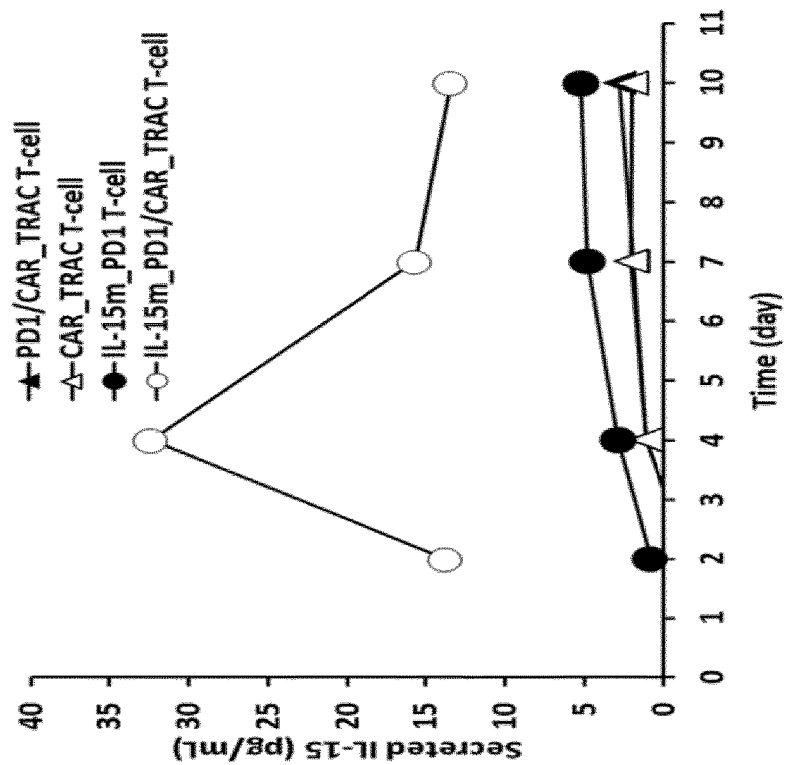
Figure 14:
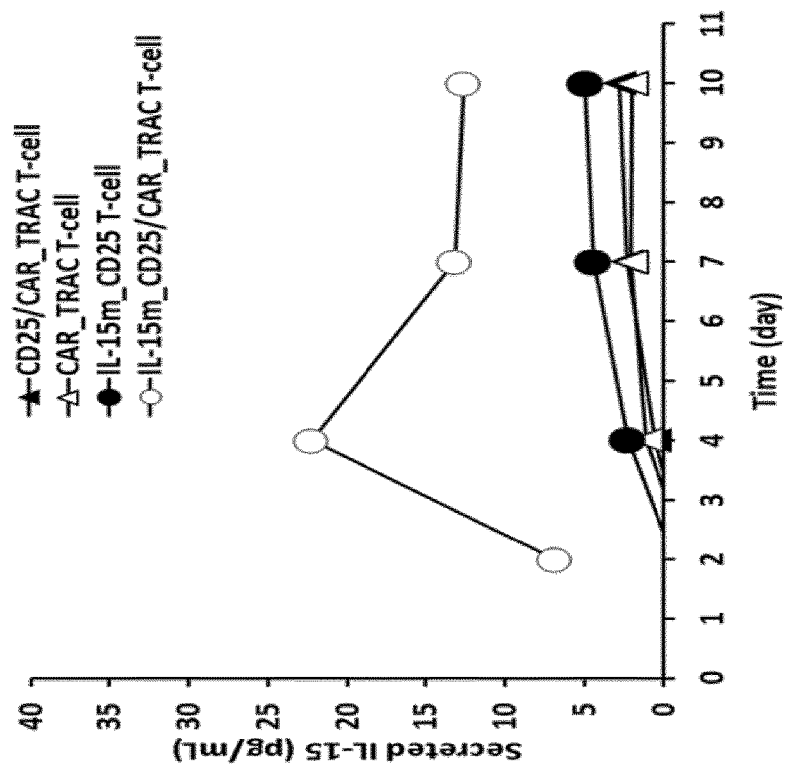

FIG. 14: Graph showing the amount of IL-15 secreted overtime (days) post activation by the immune cells engineered according to the invention. A: Cells engineered by integration of the IL-15 coding sequence at the CD25 locus using the DNA donor templates described in FIGS. 2A (IL-15m_CD25) and/or 2C (CARm). B: Cells engineered by integration of the IL-15 coding sequence at the PD1 locus using the DNA donor templates described in FIGS. 2B (IL-15m_PD1) and/or 2C (CARm). Integrations at both loci show similar IL-15 secretion profiles. Secretion of IL-15 is significant increased by tumor specific activation of CAR.

Figure 15:
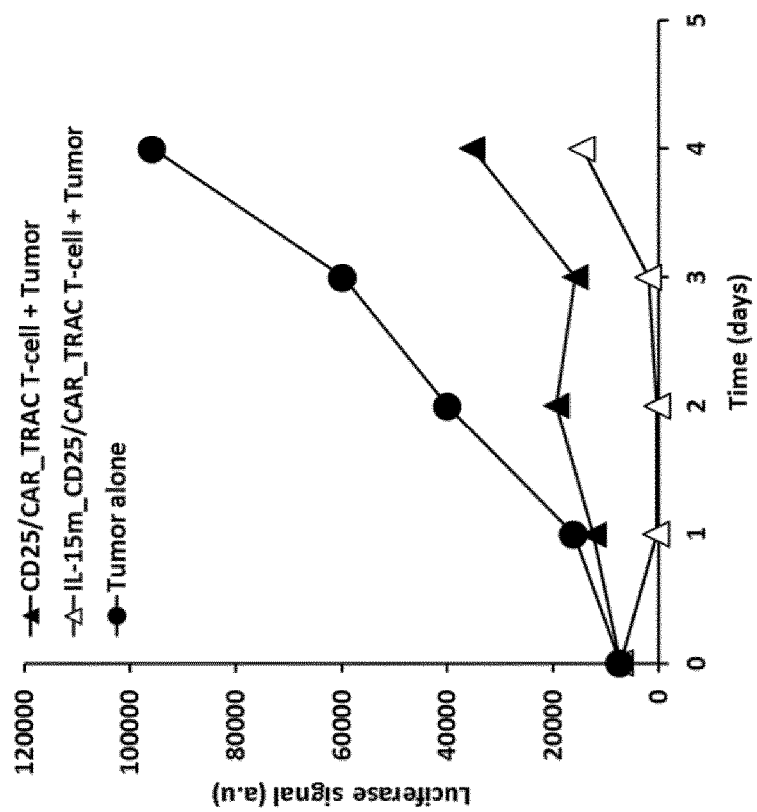
Figure 15:
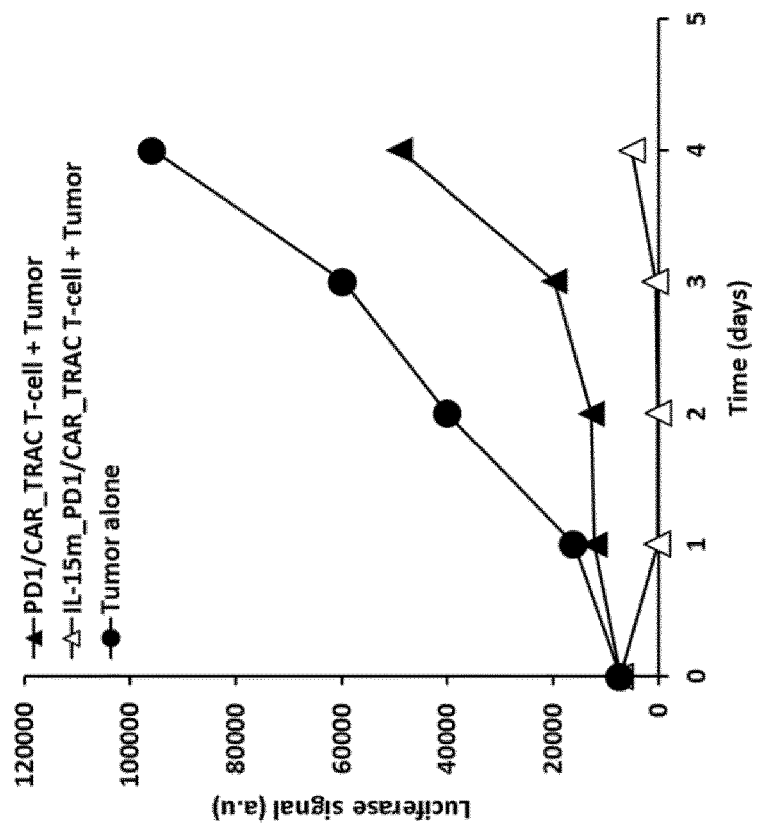

FIG. 15: Graph reporting number of Raji-Luc tumor cells expressing CD22 antigen (luciferase signal) over time in a survival assay (serial killing assay) as described in Example 2. The immune cells (PBMCs) have been engineered to integrate IL-15 coding sequences at the PD1 (A) or CD25 locus (B) and to express anti-CD22-CAR at the TCR locus (thereby disrupting TCR expression). In this assay, tumor cells are regularly added to the culture medium, while being partially or totally eliminated by the CAR positive cells. The re-expression of IL-15 at either PD1 or CD25 cells dramatically helps the elimination of the tumor cells by the CAR positive cells.

Figure 16:
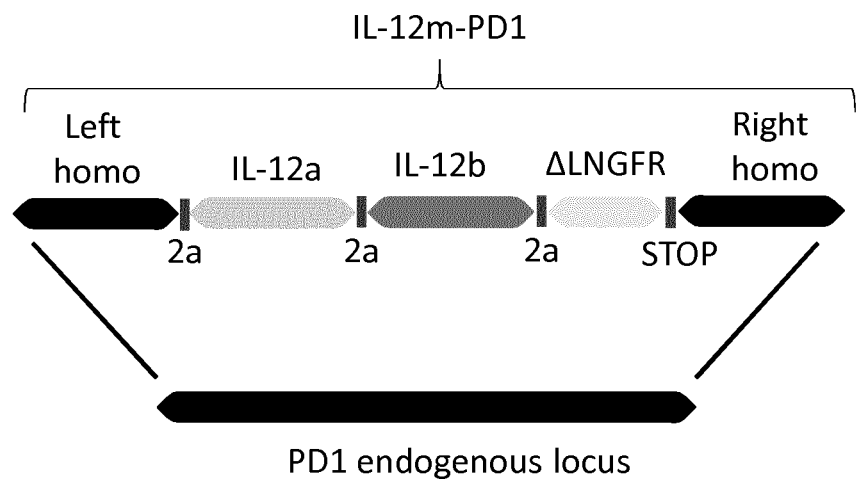
Figure 16:
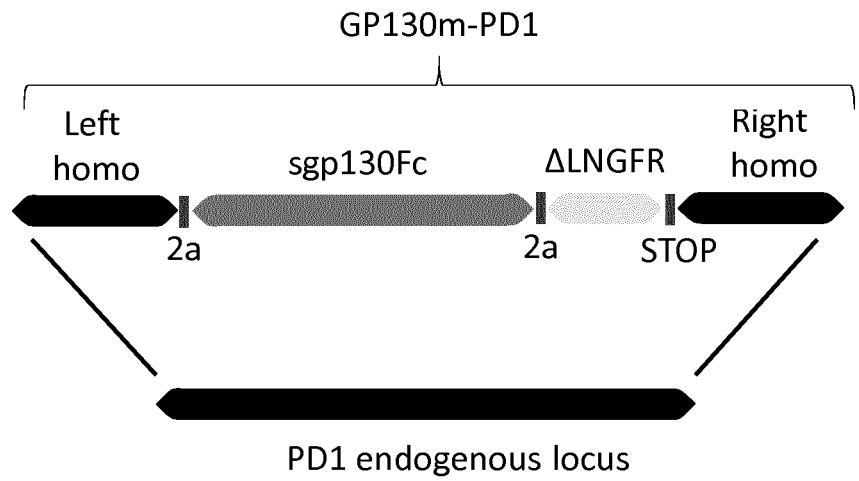

FIG. 16: Schematic representation of the donor sequences used in the experimental section to insert at the PD1 locus the exogenous sequences encoding IL-12 and gp130Fc. A: donor template (designated IL-12m-PD1) designed for site directed insertion of IL-12a and IL-12b coding sequences (SEQ ID NO:47 and 48) at the PD1 locus for obtaining co-transcription of IL-12a and IL-12b, while disrupting PD1 endogenous coding sequence. The right and left border sequences homologous to the PD1 locus sequences are at least 100 pb long, preferably at least 200 pb long, and more preferably at least 300 pb long and comprising SEQ ID NO:45 and 46. Sequences are detailed in Table 5. B: donor template (designated gp130Fcm-PD1) designed for site directed insertion of gp130Fc coding sequences (SEQ ID NO:51) for obtaining transcription at the PD1 locus under PD1 promoter, while disrupting PD1 endogenous coding sequence. The right and left border sequences homologous to the PD1 locus sequences are at least 100 pb long, preferably at least 200 pb long, and more preferably at least 300 pb long and comprising SEQ ID NO:45 and 46. Sequences are detailed in Table 5.

Figure 17:
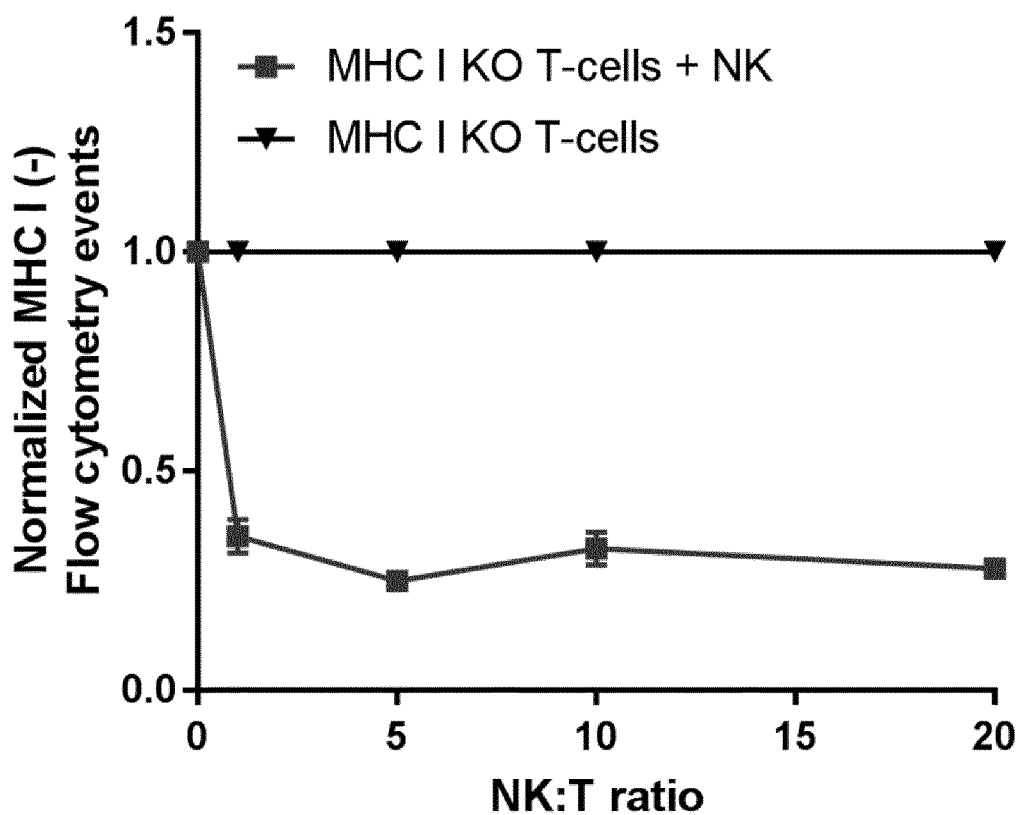

FIG. 17: MHC-I negative T cells can be targeted for NK cell attack. [β2m]$^{neg}$ T-cells were cultured in the presence or absence of CD2/NKp46 activated NK cells at the indicated E:T ratios. The data demonstrate greater than 50% depletion of MHC I negative T cells at all E:T ratios tested.

Figure 18:
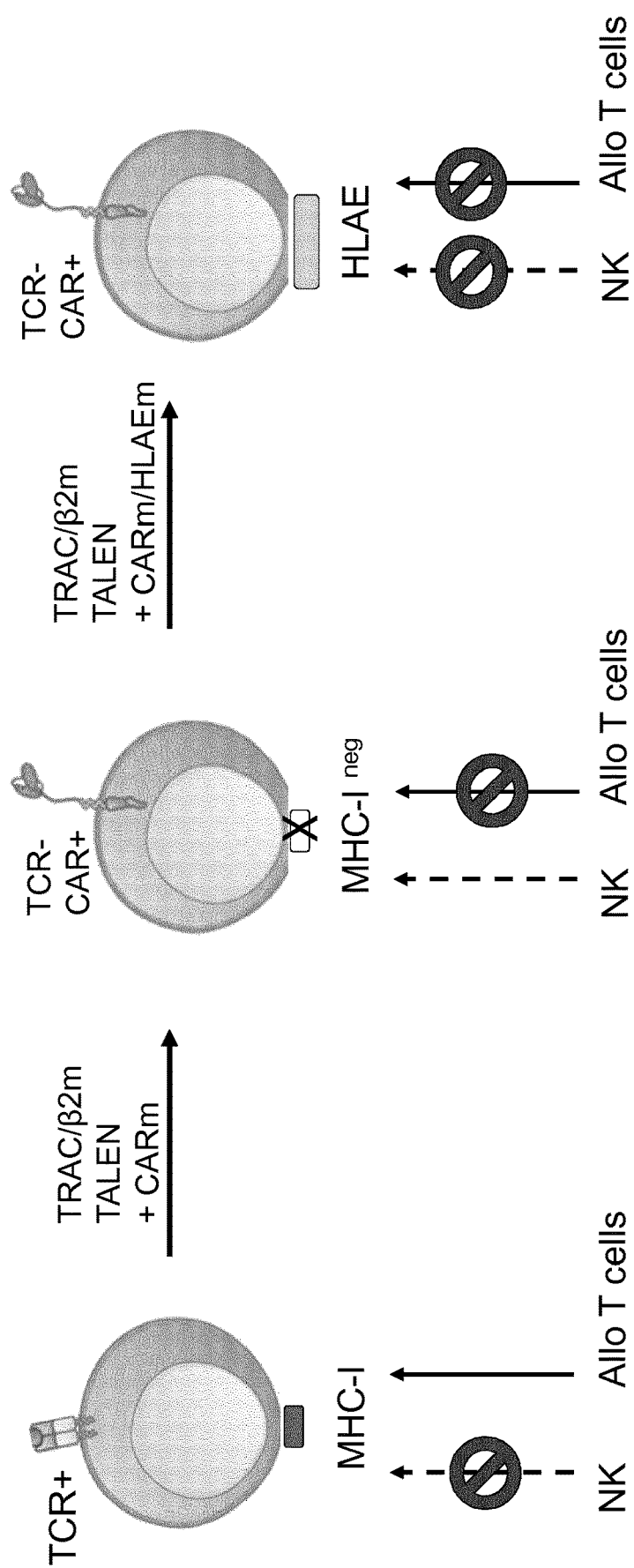

FIG. 18: Diagrams showing the strategy deployed as per the method of the present invention to obtain engineered CAR T cells products resistant to both NK and allogeneic T cell cytolytic activity.

Figure 19:
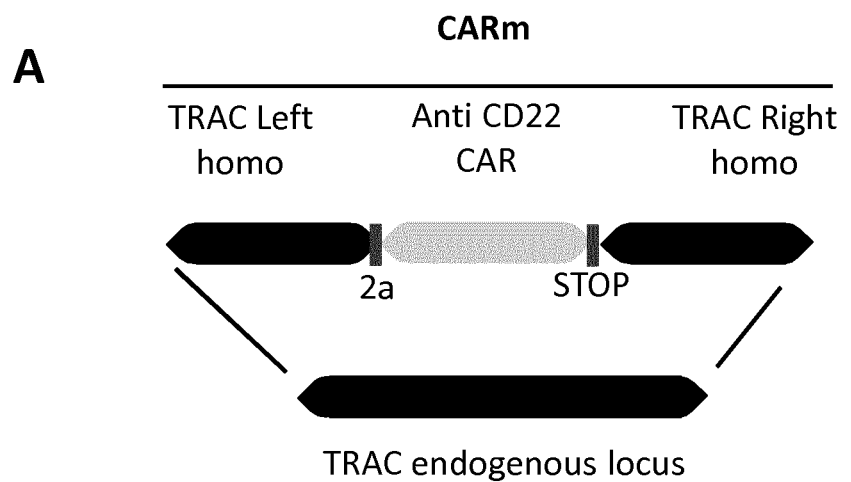
Figure 19:
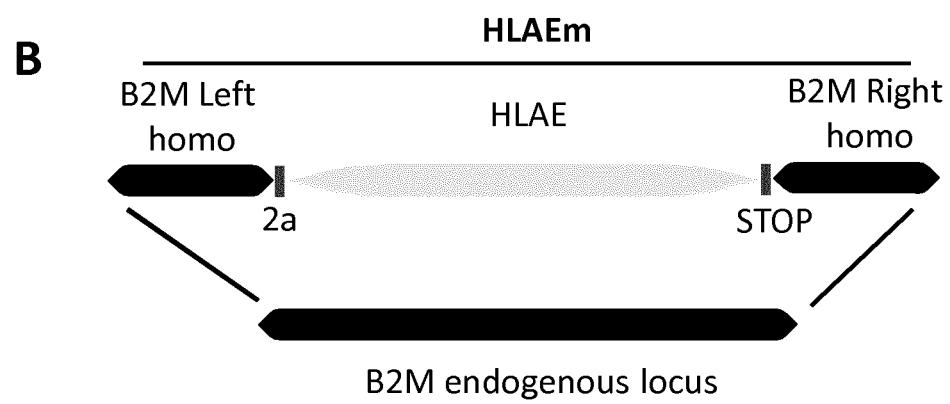

FIG. 19: Schematic of targeted integration constructs for double targeted integration of CAR and NK inhibitors at the TRAC and β2m loci respectively. (see example 3).

Figure 20:
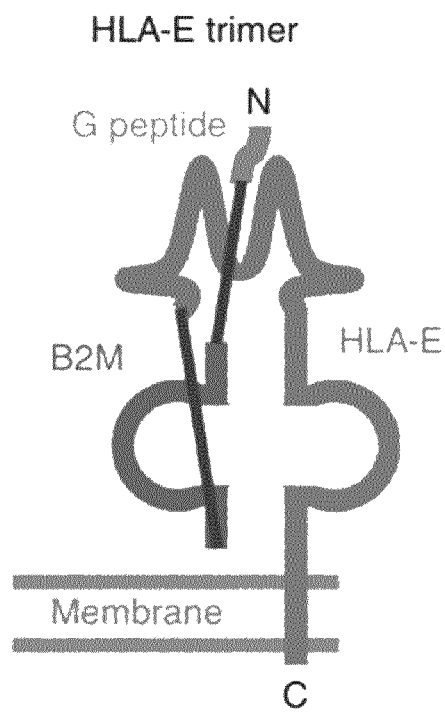

FIG. 20: General structure of HLA-E trimer that can be encoded by the exogenous sequence integrated at the β2m locus in the CAR positive T cells of the present invention.

Figure 21A:
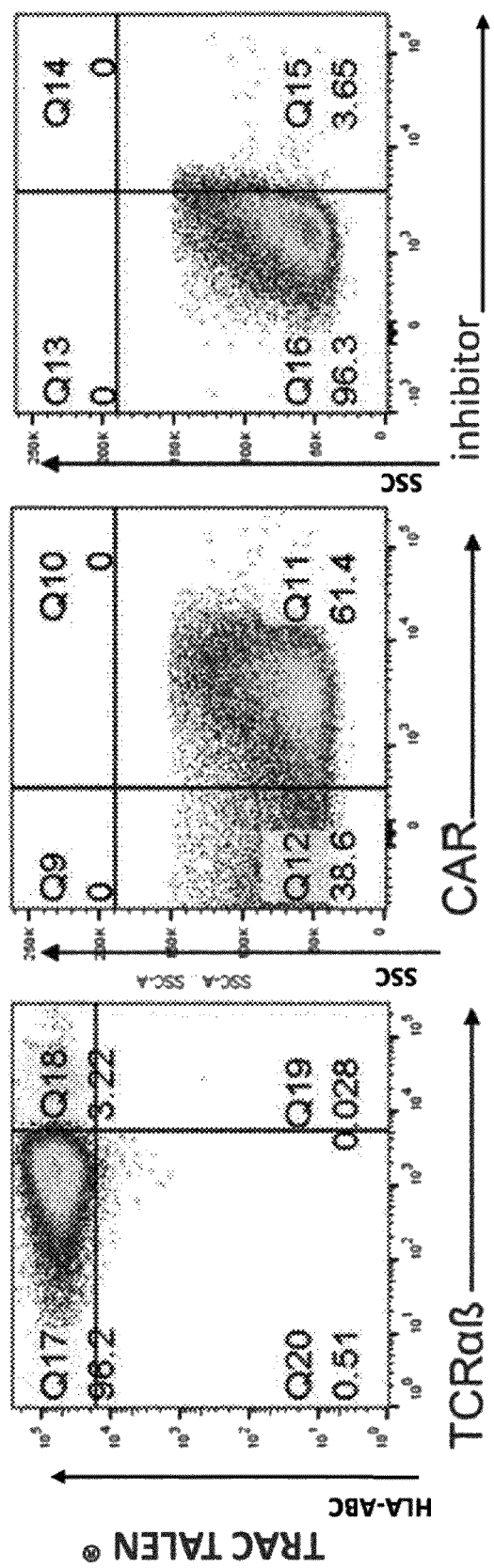
Figure 21B:
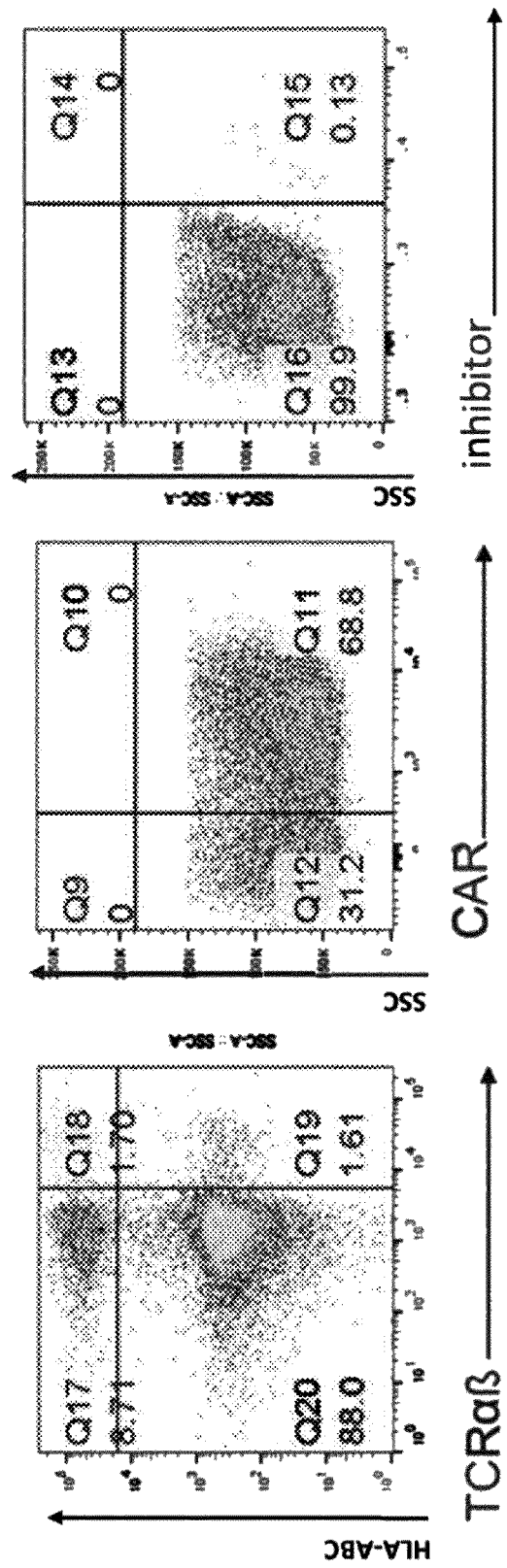
Figure 21C:
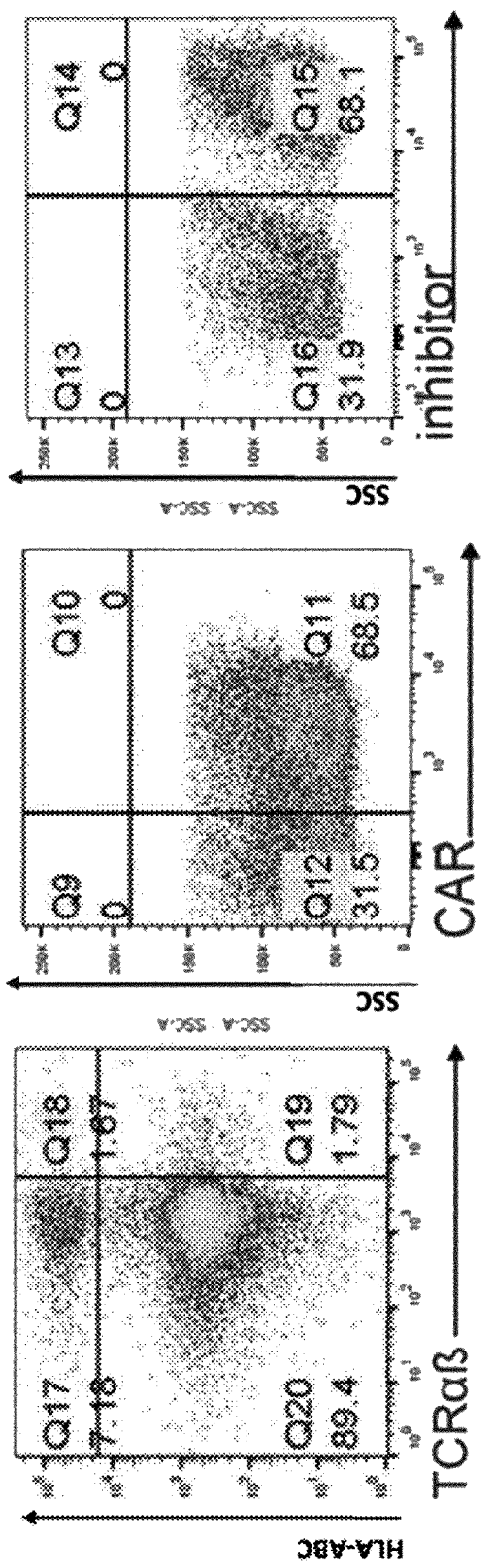

FIGS. 21A-C: Double targeted integration of CAR and NK inhibitor constructs in TRAC/B2M deficient T cells obtained as per the experiments presented in example 3. Flow cytometry analysis of engineered CAR T cells treated with TALENs and targeted integration constructions. NK inhibitor expression is documented within TRAC/B2M deficient CAR+ T cells.

Table 1: ISU domain variants from diverse viruses.

Table 2: Aminoacid sequences of FP polypeptide from natural and artificial origins.

Table 3: List of genes involved into immune cells inhibitory pathways, which can be advantageously modified or inactivated by inserting exogenous coding sequence according to the invention.

Table 4: sequences referred to in example 1.

Table 5: sequences referred to in example 2 and 3.

Table 6: List of human genes that are up-regulated upon T-cell activation (CAR activation sensitive promoters), in which gene targeted insertion is sought according to the present invention to improve immune cells therapeutic potential.

Table 7: Selection of genes that are steadily transcribed during immune cell activation (dependent or independent from T-cell activation).

Table 8: Selection of genes that are transiently upregulated upon T-cell activation.

Table 9: Selection of genes that are upregulated over more than 24 hours upon T-cell activation.

Table 10: Selection of genes that are down-regulated upon immune cell activation.

Table 11: Selection of genes that are silent upon T-cell activation (safe harbor gene targeted integration loci).

Table 12: List of gene loci upregulated in tumor exhausted infiltrating lymphocytes (compiled from multiple tumors) useful for gene integration of exogenous coding sequences as per the present invention.

Table 13: List of gene loci upregulated in hypoxic tumor conditions useful for gene integration of exogenous coding sequences as per the present invention.

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention is drawn to a general method of preparing primary immune cells for cell immunotherapy involving gene targeted integration of an exogenous coding sequence into the chromosomal DNA of said immune cells. According to some aspects, this integration is performed in such a way that said coding sequence is placed under the transcriptional control of at least one promoter endogenous to said cells, said endogenous promoter being preferably not a constitutive promoter, such as the one transcribing T-cell receptor alpha constant (TRAC—NCBI Gene ID #28755) A constitutive promoter as per the present invention is for instance a promoter that is active independently from CAR activation—ex: when T-cells are not yet activated.

Improving the Therapeutic Potential of Immune Cells by Gene Targeted Integration Gene editing techniques using polynucleotide sequence-specific reagents, such as rare-cutting endonucleases, have become the state of the art for the introduction of genetic modifications into primary cells. However, they have not been used so far in immune cells to introduce exogenous coding sequences under the transcriptional control of endogenous promoters.

The present invention aims to improve the therapeutic potential of immune cells through gene editing techniques, especially by gene targeted integration.

By "gene targeting integration" is meant any known site-specific methods allowing to insert, replace or correct a genomic sequence into a living cell. According to a preferred aspect of the present invention, said gene targeted integration involves homologous gene recombination at the locus of the targeted gene to result the insertion or replacement of at least one exogenous nucleotide, preferably a sequence of several nucleotides (i.e. polynucleotide), and more preferably a coding sequence.

By "sequence-specific reagent" is meant any active molecule that has the ability to specifically recognize a selected polynucleotide sequence at a genomic locus, preferably of at least 9 bp, more preferably of at least 10 bp and even more preferably of at least 12 pb in length, in view of modifying said genomic locus. According to a preferred aspect of the invention, said sequence-specific reagent is preferably a sequence-specific nuclease reagent.

By "immune cell" is meant a cell of hematopoietic origin functionally involved in the initiation and/or execution of innate and/or adaptative immune response, such as typically CD3 or CD4 positive cells. The immune cell according to the present invention can be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and from tumors, such as tumor infiltrating lymphocytes. In some embodiments, said immune cell can be derived from a healthy donor, from a patient diagnosed with cancer or from a patient diagnosed with an infection. In another embodiment, said cell is part of a mixed population of immune cells which present different phenotypic characteristics, such as comprising CD4, CD8 and CD56 positive cells.

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Primary cells are generally used in cell therapy as they are deemed more functional and less tumorigenic.

In general, primary immune cells are provided from donors or patients through a variety of methods known in the art, as for instance by leukapheresis techniques as reviewed by Schwartz J. et al. (Guidelines on the use of therapeutic apheresis in clinical practice-evidence-based approach from the Writing Committee of the American Society for Apheresis: the sixth special issue (2013) *J Clin Apher.* 28(3):145-284).

The primary immune cells according to the present invention can also be differentiated from stem cells, such as cord blood stem cells, progenitor cells, bone marrow stem cells, hematopoietic stem cells (HSC) and induced pluripotent stem cells (iPS).

By "nuclease reagent" is meant a nucleic acid molecule that contributes to an nuclease catalytic reaction in the target cell, preferably an endonuclease reaction, by itself or as a subunit of a complex such as a guide RNA/Cas9, preferably leading to the cleavage of a nucleic acid sequence target.

The nuclease reagents of the invention are generally "sequence-specific reagents", meaning that they can induce DNA cleavage in the cells at predetermined loci, referred to by extension as "targeted gene". The nucleic acid sequence which is recognized by the sequence specific reagents is referred to as "target sequence". Said target sequence is usually selected to be rare or unique in the cell's genome, and more extensively in the human genome, as can be determined using software and data available from human genome databases, such as http://www.ensembl.org/index.html.

"Rare-cutting endonucleases" are sequence-specific endonuclease reagents of choice, insofar as their recognition sequences generally range from 10 to 50 successive base pairs, preferably from 12 to 30 bp, and more preferably from 14 to 20 bp.

According to a preferred aspect of the invention, said endonuclease reagent is a nucleic acid encoding an "engineered" or "programmable" rare-cutting endonuclease, such as a homing endonuclease as described for instance by Arnould S., et al. (WO2004067736), a zing finger nuclease (ZFN) as described, for instance, by Urnov F., et al. (Highly efficient endogenous human gene correction using designed zinc-finger nucleases (2005) *Nature* 435:646-651), a TALE-Nuclease as described, for instance, by Mussolino et al. (A novel TALE nuclease scaffold enables high genome editing activity in combination with low toxicity (2011) *Nucl. Acids Res.* 39(21):9283-9293), or a MegaTAL nuclease as described, for instance by Boissel et al. (MegaTALs: a rare-cleaving nuclease architecture for therapeutic genome engineering (2013) Nucleic Acids Research 42 (4):2591-2601).

According to another embodiment, the endonuclease reagent is a RNA-guide to be used in conjunction with a RNA guided endonuclease, such as Cas9 or Cpf1, as per, inter alia, the teaching by Doudna, J., and Chapentier, E., (The new frontier of genome engineering with CRISPR-Cas9 (2014) *Science* 346 (6213):1077), which is incorporated herein by reference.

According to a preferred aspect of the invention, the endonuclease reagent is transiently expressed into the cells, meaning that said reagent is not supposed to integrate into the genome or persist over a long period of time, such as be the case of RNA, more particularly mRNA, proteins or complexes mixing proteins and nucleic acids (eg: Ribonucleoproteins).

In general, 80% the endonuclease reagent is degraded by 30 hours, preferably by 24, more preferably by 20 hours after transfection.

An endonuclease under mRNA form is preferably synthetized with a cap to enhance its stability according to techniques well known in the art, as described, for instance, by Kore A. L., et al. (Locked nucleic acid (LNA)-modified dinucleotide mRNA cap analogue: synthesis, enzymatic incorporation, and utilization (2009) *J Am Chem Soc.* 131 (18):6364-5).

In general, electroporation steps that are used to transfect immune cells are typically performed in closed chambers comprising parallel plate electrodes producing a pulse electric field between said parallel plate electrodes greater than 100 volts/cm and less than 5,000 volts/cm, substantially uniform throughout the treatment volume such as described in WO/2004/083379, which is incorporated by reference, especially from page 23, line 25 to page 29, line 11. One such electroporation chamber preferably has a geometric factor ($cm^{-1}$) defined by the quotient of the electrode gap squared (cm2) divided by the chamber volume ($cm^3$), wherein the geometric factor is less than or equal to 0.1 $cm^{-1}$, wherein the suspension of the cells and the sequence-specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

Due to their higher specificity, TALE-nuclease have proven to be particularly appropriate sequence specific nuclease reagents for therapeutic applications, especially under heterodimeric forms—i.e. working by pairs with a "right" monomer (also referred to as "5'" or "forward") and "left" monomer (also referred to as "3'" or "reverse") as reported for instance by Mussolino et al. (TALEN©facilitate targeted genome editing in human cells with high specificity and low cytotoxicity (2014) *Nucl. Acids Res.* 42(10): 6762-6773).

As previously stated, the sequence specific reagent is preferably under the form of nucleic acids, such as under DNA or RNA form encoding a rare cutting endonuclease a subunit thereof, but they can also be part of conjugates involving polynucleotide(s) and polypeptide(s) such as so-called "ribonucleoproteins". Such conjugates can be formed with reagents as Cas9 or Cpf1 (RNA-guided endonucleases) or Argonaute (DNA-guided endonucleases) as recently respectively described by Zetsche, B. et al. (Cpf1 Is a Single RNA-Guided Endonuclease of a Class 2 CRISPR-Cas System (2015) Cell 163(3): 759-771) and by Gao F. et al. (DNA-guided genome editing using the *Natronobacterium gregoryi* Argonaute (2016) *Nature Biotech*), which involve RNA or DNA guides that can be complexed with their respective nucleases.

"Exogenous sequence" refers to any nucleotide or nucleic acid sequence that was not initially present at the selected locus. This sequence may be homologous to, or a copy of, a genomic sequence, or be a foreign sequence introduced into the cell. By opposition "endogenous sequence" means a cell genomic sequence initially present at a locus. The exogenous sequence preferably codes for a polypeptide which expression confers a therapeutic advantage over sister cells that have not integrated this exogenous sequence at the locus. A endogenous sequence that is gene edited by the insertion of a nucleotide or polynucleotide as per the method of the present invention, in order to express a different polypeptide is broadly referred to as an exogenous coding sequence The method of the present invention can be associated with other methods involving physical of genetic transformations, such as a viral transduction or transfection using nanoparticles, and also may be combined with other gene inactivation and/or transgene insertions.

According to one aspect, the method according to the invention comprises the steps of:
providing a population of primary immune cells;
introducing into a proportion of said primary immune cells:
i) At least one nucleic acid comprising an exogenous nucleotide or polynucleotide sequence to be integrated at a selected endogenous locus to encode at least one molecule improving the therapeutic potential of said immune cells population;
ii) At least one sequence-specific reagent that specifically targets said selected endogenous locus,
wherein said exogenous nucleotide or polynucleotide sequence is inserted by targeted gene integration into said endogenous locus, so that said exogenous nucleotide or polynucleotide sequence forms an exogenous coding sequence under transcriptional control of an endogenous promoter present at said locus.

According to one aspect of the method, the sequence specific reagent is a nuclease and the targeted gene integration is operated by homologous recombination or NHEJ into said immune cells.

According to a further aspect of the invention, said endogenous promoter is selected to be active during immune cell activation and preferably up-regulated.

More specifically, the invention is drawn to a method for preparing engineered primary immune cells for cell immunotherapy, said method comprising:
providing a population of primary immune cells;
introducing into a proportion of said primary immune cells:
i) At least one exogenous nucleic acid comprising an exogenous coding sequence encoding at least one molecule improving the therapeutic potential of said immune cells population;
ii) At least one sequence-specific nuclease reagent that specifically targets a gene which is under control of an endogenous promoter active during immune cell activation;
wherein said coding sequence is introduced into the primary immune cells genome by targeted homologous recombination, so that said coding sequence is placed under the transcriptional control of at least one endogenous promoter of said gene.

By "improving therapeutic potential" is meant that the engineered immune cells gain at least one advantageous property for their use in cell therapy by comparison to their sister non-engineered immune cells. The therapeutic properties sought by the invention maybe any measurable one as referred to in the relevant scientific literature.

Improved therapeutic potential can be more particularly reflected by a resistance of the immune cells to a drug, an increase in their persistence in-vitro or in-vivo, or a safer/more convenient handling during manufacturing of therapeutic compositions and treatments.

In general said molecule improving the therapeutic potential is a polypeptide, but it can also be a nucleic acid able to direct or repress expression of other genes, such as interference RNAs or guide-RNAs. The polypeptides may act directly or indirectly, such as signal transducers or transcriptional regulators.

According to one embodiment of the present method, the exogenous sequence is introduced into the endogenous chromosomal DNA by targeted homologous recombination. Accordingly, the exogenous nucleic acid introduced into the immune cell comprises at least one coding sequence(s), along with sequences that can hybridize endogenous chromosomal sequences under physiological conditions. In general, such homologous sequences show at least 70%, preferably 80% and more preferably 90% sequence identity with the endogenous gene sequences located at the insertion locus. These homologous sequences may flank the coding sequence to improve the precision of recombination as already taught for instance in U.S. Pat. No. 6,528,313. Using available software and on-line genome databases, it is possible to design vectors that includes said coding sequence(s), in such a way that said sequence(s) is (are) introduced at a precise locus, under transcriptional control of at least one endogenous promoter, which is a promoter of an endogenous gene. The exogenous coding sequence(s) is (are) then preferably inserted "in frame" with said endogenous gene. The sequences resulting from the integration of the exogenous polynucleotide sequence(s) can encode many different types of proteins, including fusion proteins, tagged protein or mutated proteins. Fusion proteins allow adding new functional domains to the proteins expressed in the cell, such as a dimerization domain that can be used to switch-on or switch-off the activity of said protein, such as caspase-9 switch. Tagged proteins can be advantageous for the detection of the engineered immune cells and the follow-up of the patients treated with said cells. Introducing mutation into proteins can confer resistance to drugs or immune depletion agents as further described below.

Conferring Resistance to Drugs or Immune Depletion Agents

According to one aspect of the present method, the exogenous sequence that is integrated into the immune cells genomic locus encodes a molecule that confers resistance of said immune cells to a drug.

Examples of preferred exogenous sequences are variants of dihydrofolate reductase (DHFR) conferring resistance to folate analogs such as methotrexate, variants of inosine monophosphate dehydrogenase 2 (IMPDH2) conferring resistance to IMPDH inhibitors such as mycophenolic acid (MPA) or its prodrug mycophenolate mofetil (MMF), variants of calcineurin or methylguanine transferase (MGMT) conferring resistance to calcineurin inhibitor such as FK506 and/or CsA, variants of mTOR such as mTORmut conferring resistance to rapamycin) and variants of Lck, such as Lckmut conferring resistance to Imatinib and Gleevec.

The term "drug" is used herein as referring to a compound or a derivative thereof, preferably a standard chemotherapy agent that is generally used for interacting with a cancer cell, thereby reducing the proliferative or living status of the cell. Examples of chemotherapeutic agents include, but are not limited to, alkylating agents (e.g., cyclophosphamide, ifosamide), metabolic antagonists (e.g., purine nucleoside antimetabolite such as clofarabine, fludarabine or 2'-deoxyadenosine, methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

As used herein, an immune cell is made "resistant or tolerant" to a drug when said cell, or population of cells is modified so that it can proliferate, at least in-vitro, in a culture medium containing half maximal inhibitory concentration (IC50) of said drug (said IC50 being determined with respect to an unmodified cell(s) or population of cells).

In a particular embodiment, said drug resistance can be conferred to the immune cells by the expression of at least one "drug resistance coding sequence". Said drug resistance coding sequence refers to a nucleic acid sequence that confers "resistance" to an agent, such as one of the chemotherapeutic agents referred to above. A drug resistance coding sequence of the invention can encode resistance to anti-metabolite, methotrexate, vinblastine, cisplatin, alkylating agents, anthracyclines, cytotoxic antibiotics, anti-immunophilins, their analogs or derivatives, and the like (Takebe, N., S. C. Zhao, et al. (2001) "Generation of dual resistance to 4-hydroperoxycyclophosphamide and methotrexate by retroviral transfer of the human aldehyde dehydrogenase class 1 gene and a mutated dihydrofolate reductase gene". *Mol. Ther.* 3(1): 88-96), (Zielske, S. P., J. S. Reese, et al. (2003) "In vivo selection of MGMT(P140K) lentivirus-transduced human NOD/SCID repopulating cells without pretransplant irradiation conditioning." *J. Clin. Invest.* 112 (10): 1561-70) (Nivens, M. C., T. Felder, et al. (2004) "Engineered resistance to camptothecin and antifolates by retroviral coexpression of tyrosyl DNA phosphodiesterase-I and thymidylate synthase" Cancer Chemother Pharmacol 53(2): 107-15), (Bardenheuer, W., K. Lehmberg, et al. (2005). "Resistance to cytarabine and gemcitabine and in vitro selection of transduced cells after retroviral expression of cytidine deaminase in human hematopoietic progenitor cells". *Leukemia* 19(12): 2281-8), (Kushman, M. E., S. L. Kabler, et al. (2007) "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1" *Carcinogenesis* 28(1): 207-14).

The expression of such drug resistance exogenous sequences in the immune cells as per the present invention more particularly allows the use of said immune cells in cell therapy treatment schemes where cell therapy is combined with chemotherapy or into patients previously treated with these drugs.

Several drug resistance coding sequences have been identified that can potentially be used to confer drug resistance according to the invention. One example of drug resistance coding sequence can be for instance a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance coding sequence according to the present invention can be a nucleic acid sequence encoding a mutant form of human wild type DHFR (GenBank: AAH71996.1), which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer et al. (1990) "Dihydrofolate reductase as a therapeutic target" *Faseb J* 4(8): 2441-52; International application WO94/24277; and U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

Another example of drug resistance coding sequence can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (Genebank: NP_000875.2) leading to a significantly increased resistance to IMPDH inhibitor. Mutations in these variants are preferably at positions T333 and/or S351 (Yam, P., M. Jensen, et al. (2006) "Ex vivo selection and expansion of cells based on expression of a mutated inosine monophosphate dehydrogenase 2 after HIV vector transduction: effects on lymphocytes, monocytes, and CD34+ stem cells" *Mol. Ther.* 14(2): 236-44)(Jonnalagadda, M., et al. (2013) "Engineering human T cells for resistance to methotrexate and mycophenolate mofetil as an in vivo cell selection strategy." *PLoS One* 8(6): e65519).

Another drug resistance coding sequence is the mutant form of calcineurin. Calcineurin (PP2B—NCBI: ACX34092.1) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin et al. (2009) "Generation of EBV-specific cytotoxic T cells that are resistant to calcineurin inhibitors for the treatment of post-transplantation lymphoproliferative disease" Blood 114(23): 4792-803). In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue. In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagines at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence. Correspondence of amino acid positions described herein is frequently expressed in terms of the positions of the amino acids of the form of wild-type human calcineurin heterodimer b polypeptide (NCBI: ACX34095.1).

Another drug resistance coding sequence is 0(6)-methylguanine methyltransferase (MGMT—UniProtKB: P16455) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, R. et al. (1999) "Retroviral-mediated expression of the P140A, but not P140A/G156A, mutant form of 06-methylguanine DNA methyltransferase protects hematopoietic cells against 06-benzylguanine sensitization to chloroethylnitrosourea treatment" *J. Pharmacol. Exp. Ther.* 290(3): 1467-74). In a particular embodiment, AGT mutant form can comprise a mutated amino acid of the wild type AGT position P140. In a preferred embodiment, said proline at position 140 is replaced with a lysine residue.

Another drug resistance coding sequence can be multi-drug resistance protein (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (Genebank NP_000918).

Another drug resistance coding sequence can contribute to the production of cytotoxic antibiotics, such as those from ble or mcrA genes. Ectopic expression of ble gene or mcrA in an immune cell gives a selective advantage when exposed to the respective chemotherapeutic agents bleomycine and mitomycin C (Belcourt, M. F. (1999) "Mitomycin resistance in mammalian cells expressing the bacterial mitomycin C resistance protein MCRA". *PNAS.* 96(18):10489-94).

Another drug resistance coding sequence can come from genes encoded mutated version of drug targets, such as mutated variants of mTOR (mTOR mut) conferring resistance to rapamycin such as described by Lorenz M. C. et al. (1995) "TOR Mutations Confer Rapamycin Resistance by Preventing Interaction with FKBP12-Rapamycin" *The Journal of Biological Chemistry* 270, 27531-27537, or certain mutated variants of Lck (Lckmut) conferring resistance to Gleevec as described by Lee K. C. et al. (2010) "Lck is a key target of imatinib and dasatinib in T-cell activation", *Leukemia,* 24: 896-900.

As described above, the genetic modification step of the method can comprise a step of introduction into cells of an exogenous nucleic acid comprising at least a sequence encoding the drug resistance coding sequence and a portion of an endogenous gene such that homologous recombination occurs between the endogenous gene and the exogeneous nucleic acid. In a particular embodiment, said endogenous gene can be the wild type "drug resistance" gene, such that after homologous recombination, the wild type gene is replaced by the mutant form of the gene which confers resistance to the drug.

Enhancing Persistence of the Immune Cells In-Vivo

According to one aspect of the present method, the exogenous sequence that is integrated into the immune cells genomic locus encodes a molecule that enhances persistence of the immune cells, especially in-vivo persistence in a tumor environment.

By "enhancing persistence" is meant extending the survival of the immune cells in terms of life span, especially once the engineered immune cells are injected into the patient. For instance, persistence is enhanced, if the mean survival of the modified cells is significantly longer than that of non-modified cells, by at least 10%, preferably 20%, more preferably 30%, even more preferably 50%.

This especially relevant when the immune cells are allogeneic. This may be done by creating a local immune protection by introducing coding sequences that ectopically express and/or secrete immunosuppressive polypeptides at, or through, the cell membrane. A various panel of such polypeptides in particular antagonists of immune checkpoints, immunosuppressive peptides derived from viral envelope or NKG2D ligand can enhance persistence and/or an engraftment of allogeneic immune cells into patients.

According to one embodiment, the immunosuppressive polypeptide to be encoded by said exogenous coding sequence is a ligand of Cytotoxic T-Lymphocyte Antigen 4 (CTLA-4 also known as CD152, GenBank accession number AF414120.1). Said ligand polypeptide is preferably an anti-CTLA-4 immunoglobulin, such as CTLA-4a Ig and CTLA-4b Ig or a functional variant thereof.

According to one embodiment, the immunosuppressive polypeptide to be encoded by said exogenous coding sequence is an antagonist of PD1, such as PD-L1 (other names: CD274, Programmed cell death 1 ligand; ref. UniProt for the human polypeptide sequence Q9NZQ7), which encodes a type I transmembrane protein of 290 amino acids consisting of a Ig V-like domain, a Ig C-like domain, a hydrophobic transmembrane domain and a cytoplasmic tail of 30 amino acids. Such membrane-bound form of PD-L1 ligand is meant in the present invention under a native form (wild-type) or under a truncated form such as, for instance, by removing the intracellular domain, or with one or more mutation(s) (Wang S et al., 2003, *J Exp Med.* 2003; 197(9): 1083-1091). Of note, PD1 is not considered as being a membrane-bound form of PD-L1 ligand according to the present invention. According to another embodiment, said immunosuppressive polypeptide is under a secreted form. Such recombinant secreted PD-L1 (or soluble PD-L1) may be generated by fusing the extracellular domain of PD-L1 to the Fc portion of an immunoglobulin (Haile S T et al., 2014, *Cancer Immunol.* Res. 2(7): 610-615; Song M Y et al., 2015, Gut. 64(2):260-71). This recombinant PD-L1 can neutralize PD-1 and abrogate PD-1-mediated T-cell inhibition. PD-L1 ligand may be co-expressed with CTLA4 Ig for an even enhanced persistence of both.

According to another embodiment, the exogenous sequence encodes a polypeptide comprising a viral env immusuppressive domain (ISU), which is derived for instance from HIV-1, HIV-2, SIV, MoMuLV, HTLV-1, —II, MPMV, SRV-1, Syncitin 1 or 2, HERV-K or FELV.

The following Table 1 shows variants of ISU domain from diverse virus which can be expressed within the present invention.

TABLE 1

ISU domain variants from diverse viruses
ISU Amino acids sequences

| Amino acid positions | | | | | | | | | | | | | | Virus origin |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | Origin |
| L | Q | A | R | I/V | L | A | V | E | R | Y | L | K/R/Q | D | HIV-1 |
| L | Q | A | R | V | T | A | I | E | K | Y | L | K/A/Q | D/H | HIV-2 |
| L | Q | A | R | L | L | A | V | E | R | Y | L | K | D | SIV |
| L | Q | N | R | R | G | L | D | L | L | F | L | K | E | MoMuLV |
| A | Q | N | R | R | G | L | D | L | L | F | W | E | Q | HTLV-I, -II |
| L | Q | N | R | R | G | L | D | L | L | T | A | E | Q | MPMV, SRV-1 |
| L | Q | N | R | R | A | L | D | L | L | T | A | E | R | Syncitin 1 |
| L | Q | N | R | R | G | L | D | M | L | T | A | A | Q | Syncitin 2 |
| L | A | N | Q | I | N | D | L | R | Q | T | V | I | W | HERV-K |
| L | Q | N | R | R | G | L | D | I | L | F | L | Q | E | FELV |

According to another embodiment, the exogenous sequence encodes a FP polypeptide such as gp41. The following Table 2 represents several FP polypeptide from natural and artificial origins.

TABLE 2

Amino acid sequences of FP polypeptide from natural and artificial origins
FP Amino acids sequences

| Amino acid positions | | | | | | | | | |
|---|---|---|---|---|---|---|---|---|---|
| 1 | 2 | 3 | 4 | 5 | 6 | 7 | 8 | 9 | Origin |
| G | A | L | F | L | G | F | L | G | HIV-1 gp41 |
| A | G | F | G | L | L | L | G | F | Synthetic |
| A | G | L | F | L | G | F | L | G | Synthetic |

According to another embodiment, the exogenous sequence encodes a non-human MHC homolog, especially a viral MHC homolog, or a chimeric β2m polypeptide such as described by Margalit A. et al. (2003) "Chimeric β2 microglobulin/CD3ζ (polypeptides expressed in T cells convert MHC class I peptide ligands into T cell activation receptors: a potential tool for specific targeting of pathogenic CD8+ T cells" *Int. Immunol.* 15 (11): 1379-1387.

According to one embodiment, the exogenous sequence encodes NKG2D ligand. Some viruses such as cytomegaloviruses have acquired mechanisms to avoid NK cell mediate immune surveillance and interfere with the NKG2D pathway by secreting a protein able to bind NKG2D ligands and prevent their surface expression (Welte, S. A et al. (2003) "Selective intracellular retention of virally induced NKG2D ligands by the human cytomegalovirus UL16 glycoprotein". Eur. J. Immunol., 33, 194-203). In tumors cells, some mechanisms have evolved to evade NKG2D response by secreting NKG2D ligands such as ULBP2, MICB or MICA (Salih H R, Antropius H, Gieseke F, Lutz S Z, Kanz L, et al. (2003) Functional expression and release of ligands for the activating immunoreceptor NKG2D in leukemia. Blood 102: 1389-1396)

According to one embodiment, the exogenous sequence encodes a cytokine receptor, such as an IL-12 receptor. IL-12 is a well known activator of immune cells activation (Curtis J. H. (2008) "IL-12 Produced by Dendritic Cells Augments CD8+ T Cell Activation through the Production of the Chemokines CCL1 and CCL171". The Journal of Immunology. 181 (12): 8576-8584.

According to one embodiment the exogenous sequence encodes an antibody that is directed against inhibitory peptides or proteins. Said antibody is preferably be secreted under soluble form by the immune cells. Nanobodies from shark and camels are advantageous in this respect, as they are structured as single chain antibodies (Muyldermans S. (2013) "Nanobodies: Natural Single-Domain Antibodies" Annual Review of Biochemistry 82: 775-797). Same are also deemed more easily to fuse with secretion signal polypeptides and with soluble hydrophilic domains The different aspects developed above to enhance persistence of the cells are particularly preferred, when the exogenous coding sequence is introduced by disrupting an endogenous gene encoding β2m or another MHC component.

More specific embodiments concern the integration of NK cells inhibitors to enhance the persistence of the engineered T cells of the present invention, which are based on the methods detailed in this specification and more specifically illustrated in FIGS. 17 to 21 and Example 3.

In particular, the present invention further provides with methods for preparing engineered primary immune cells for cell immunotherapy, said method comprising:
  providing a population of cells comprising T-cells, preferably primary T-cells,
  introducing into a proportion of said T-cells:
  i) At least one nucleic acid comprising an exogenous polynucleotide sequence to be integrated at a selected endogenous locus to encode at least one NK cell inhibitor;
  ii) At least one sequence-specific reagent that specifically targets said selected endogenous locus,
wherein said exogenous polynucleotide sequence is inserted by targeted gene integration into said endogenous locus.

By NK cell inhibitor is meant a polypeptide which confers a protective effect to allogeneic T-cells against depletion by NK cells, in-vivo or in co-culture of immune cells. Such depletion, without NK cell inhibitor is observed for instance on the graph of FIG. 17.

Example of NK cell inhibitors are provided herein in example 3.

The exogenous polynucleotide sequence encoding the NK cell inhibitor, which preferably comprises one the sequences referred to in example 3, is preferably integrated under transcriptional control of an endogenous promoter present at said locus to obtain a more constant expression of said NK cell inhibitor.

According to a preferred aspect of the invention, said endogenous promoter is selected to be active during immune cell activation, such as the loci listed in Table 6, which are deemed actively transcribed during T-cell activation, at least deemed responsive to the activation of T-cells endowed with chimeric antigen receptor (CAR).

According to preferred embodiments, the exogenous sequence encoding the NK inhibitor is integrated at an endogenous locus, which is up-regulated over more than 24 hours upon T-cell activation such as one selected from Gzmb, Tbx21, Plek, Chek1, Slamf7, Zbtb32, Tigit, Lag3, Gzma, Wee1, IL12rb2, Eea1 and Dtl.

According to preferred embodiments, the exogenous sequence encoding the NK inhibitor is integrated at an endogenous locus, which is constitutively expressed, such as at the TCR locus.

According to the invention it can be advantageous to integrate the exogenous sequence encoding the NK inhibitor at a locus of insertion expressing a MHC I component, in particular at the β2m locus, which is also a locus constitutively transcribed.

According to the invention, it can be advantageous to inactivate the endogenous β2m endogenous coding sequence, while having the integrated exogenous sequence encoding the NK inhibitor being transcribed at this locus.

According to a preferred aspect of the invention, the engineered T-cells comprising said exogenous sequence encoding NK inhibitor are endowed with a chimeric antigen receptor (CAR) as described in different parts of the present specification. Said chimeric antigen receptor (CAR) can be advantageously integrated at the TCR locus, while the exogenous sequence encoding NK inhibitor is preferably integrated at the β2m locus, thereby preventing or reducing both TCR and/or β2m expression.

The sequence specific reagent used in this method is preferably a rare-cutting endonuclease as described before in the present specification or known by one skilled in the art. Targeted gene integration is generally operated by homologous recombination or NHEJ into said immune cells. Said specific endonuclease reagent is preferably selected from a RNA or DNA-guided endonuclease, such as Cas9 or Cpf1, a RNA or DNA guide, a TAL-endonuclease, a zing finger nuclease, a homing endonuclease or any combination thereof.

In one preferred embodiment of the present invention illustrated in example 3, TALE-nucleases have been optimized and successfully used to perform gene integration at the β2m locus by limiting off site cleavage in human T-cells. Better specificity and efficiency were unexpectedly obtained using TALE-nuclease heterodimers of polypeptide sequences SEQ ID NO. 80 and/or SEQ ID NO.81 or SEQ ID NO.82 and/or SEQ ID NO.83—right and left dimers respectively. The present patent application thus specifically pertains to the above polypeptide sequences encoding those specific β2m TALEN, alone or by pairs, or any endonuclease sequence involving TAL repeats comprising one of the following RVD sequences:
  HD-HD-NN-NG-NN-NN-HD-HD-NG-NG-NI-NN-HD-NG-NN
  HD-HD-NI-NN-NN-HD-HD-NI-NN-NI-NI-NI-NN-NI-NN
  NG-NI-NN-HD-NG-NN-NG-NN-HD-NG-HD-NN-HD-NN-HD
  NN-NN-NI-NG-NI-NN-HD-HD-NG-HD-HD-NI-NN-NN-HD
  as well as to any polynucleotides and vectors encoding these polypeptides.

Furthermore, it is an object of the present invention to carry out integration of an exogenous sequence into the genome of a T-cell by using an endonuclease that specifically recognizes or binds a β2m genomic sequence comprising one of the following target sequences SEQ ID NO.78 and SEQ ID NO.79.

It is also an object of the present invention to inactivate a β2m genomic sequence in a T-cell by using an endonuclease that specifically recognizes a sequence comprising the target sequences SEQ ID NO.78 and SEQ ID NO.79.

According to the present invention, said exogenous sequence encoding NK inhibitors preferably comprise sequences encoding non polymorphic class I molecules, such as HLA-G or HLA-E or at least fragment(s) comprising a heavy chain from these molecules.

According to a preferred aspect, said exogenous sequence, when integrated at β2m endogenous locus, results into the expression of a fusion of a HLA-E or HLA-G of fragment thereof with β2m fragments, which generally results into the expression of dimer or trimers of HLA-E or HLA-G, such as illustrated in FIG. 20 and exemplified in Example 3.

According to a preferred embodiment said exogenous sequence encodes a polypeptide displaying at least 80% amino acid sequence identity with one selected from SEQ ID NO.84 to 90.

Exogenous sequence encoding NK inhibitors can also comprise sequences encoding viral evasins of fragments comprising an epitope thereof, such as from UL16 (also called ULBP1—Uniprot ref.: #Q9BZM6) or UL18.

The integration of the exogenous sequence encoding NK inhibitor(s) into the T-cell genome, preferably operated at the β2m can be combined with the other exogenous sequence insertion described in the present specification in view of improving the potency and the suitability of the T-cells for adoptive cell immunotherapy.

Alternatively, the exogenous sequence encoding NK inhibitor(s) can be also advantageously integrated at loci encoding immune checkpoints, such as PD1 or CTLA4 (see complete list in the present specification), preferably with the effect of inactivating these genes.

Many examples of other successful loci are described elsewhere in the present application which could be appropriate to confer additional therapeutic advantage to the engineered T cells, such as for instance to confer resistance to drugs commonly used in cancer therapy, such as the DCK, HPRT or Glucocorticoids receptors (GR) loci.

As a result the present specification discloses engineered primary immune cells obtainable by the method described above.

Such immune cells can have the following features:
1) An engineered T-cell, which comprises an exogenous sequence encoding a NK inhibitor, which has been integrated under transcriptional control of an endogenous gene promoter.
2) An engineered T-cell according to any of item 1, wherein said endogenous gene promoter is selected at one locus listed in Table 6.
3) An engineered T-cell according to any one of items 1 or 2, wherein said exogenous sequence encoding a NK inhibitor has been integrated at a β2m locus.
4) An engineered T-cell according to any one of items 1 to 3, wherein said T-cell is endowed with a chimeric antigen receptor.
5) An engineered T-cell according to item 4, which has a genotype $[TCR]^{neg}[\beta 2m]^{neg}[CAR]^{pos}$
6) An engineered T-cell according to item 4 or 5, wherein the exogenous sequence(s) encoding said CAR has been integrated at a TCR locus.
7) An engineered T-cell according to any one of items 1 to 6, wherein said T-cell is a primary cell.
8) An engineered T-cell according to any one of items 1 to 7 for its use for the treatment of cancer or an infection.
9) A therapeutically effective population of immune cells, comprising at least 30%, preferably 50%, more preferably 80% of engineered T-cells according to any one of items 1 to 8.

Preferred engineered T-cells according to the present invention comprise a polynucleotide sequence, which shares at least 80%, more preferably 90%, even more preferably 95% identity with one of the polynucleotide sequences SEQ ID NO. 68, SEQ ID NO. 70, SEQ ID NO. 72, SEQ ID NO. 74 or SEQ ID NO. 76 (integration of trimer matrix at the β2m locus as disclosed in example 3).

Examples of preferred genotypes of the engineered T-cells of the present invention, in connection with the other gene editing steps disclosed in the present application, are as follows:

$[CAR]^{pos}[TCR]^{neg}[\beta 2m]^{neg}[PD1]^{neg}$
$[CAR]^{pos}[TCR]^{neg}[\beta 2m]^{neg}[DCK]^{neg}$
$[CAR]^{pos}[TCR]^{neg}[\beta 2m]^{neg}[CTLA4]^{neg}$ The present specification also provides with therapeutic compositions comprising the
engineered cells according to the present invention, in particular the following ones:
1) A therapeutically effective population of immune cells as per the present invention, wherein at least 30%, preferably 50%, more preferably 80% of cells originate from a donor, preferably one single donor.
2) A population of primary immune cells according to the above, wherein more than 50% of said immune cells are TCR negative T-cells.
3) A population of primary immune cells as described above, wherein more than 50% of said immune cells are CAR positive cells.
4) A pharmaceutical composition comprising an engineered immune cell population as described above.
5) A method for treating a patient in need thereof, wherein said method comprises:
preparing a population of engineered primary immune cells as previously described;
optionally, purifying or sorting said engineered primary immune cells;
activating said population of engineered primary immune cells upon or after infusion of said cells into said patient.
6) A method as described above, wherein said patient is treated for cancer.
7) A method as described above, wherein said patient is treated for an infection.

The invention further provides with a method for screening candidate NK inhibitors by integration of exogenous sequences into T-cells, such as summarized below:
1) A method for identifying an appropriate sequence encoding a NK inhibitor expressible in a T-cell, wherein said method comprises at least the steps of:
providing a T-cell in which both TCR and β2m expressions are repressed and/or inactivated;
integrating a candidate sequence coding a putative NK inhibitor at an endogenous locus under control of an endogenous promoter in said T-cell;

cultivating the resulting engineered T-cell in the presence of NK cells
2) A method for identifying an appropriate sequence encoding a NK inhibitor expressible in a T-cell, wherein said method comprises at least the steps of:
providing a T-cell in which TCR expression is repressed or inactivated;
Inactivating β2m expression in said T-cell by integrating a candidate sequence coding a putative NK inhibitor at the β2m locus, the expression of said putative NK inhibitor being placed under transcriptional control of a endogenous promoter of said β2m locus
cultivating the resulting engineered T-cell in the presence of NK cells
3) A method as described above, wherein said method further comprises the step of:
endowing said T-cell with a chimeric antigen receptor.
4) A method as described above, wherein said method further comprises the step of:
comparing the survival of said resulting engineered T-cell with same not expressing said candidate sequence.
Optionally, selecting the engineered cells that are more resistant to NK cells.

Enhancing the Therapeutic Activity of Immune Cells

According to one aspect of the present method, the exogenous sequence that is integrated into the immune cells genomic locus encodes a molecule that enhances the therapeutic activity of the immune cells.

By "enhancing the therapeutic activity" is meant that the immune cells, or population of cells, engineered according to the present invention, become more aggressive than non-engineered cells or population of cells with respect to a selected type of target cells. Said target cells generally belong to a defined type of cells, or population of cells, preferably characterized by common surface marker(s). In the present specification, "therapeutic potential" reflects the therapeutic activity, as measured through in-vitro experiments. In general sensitive cancer cell lines, such as Daudi cells, are used to assess whether the immune cells are more or less active towards said cells by performing cell lysis or growth reduction measurements. This can also be assessed by measuring levels of degranulation of immune cells or chemokines and cytokines production. Experiments can also be performed in mice with injection of tumor cells, and by monitoring the resulting tumor expansion. Enhancement of activity is deemed significant when the number of developing cells in these experiments is reduced by the immune cells by more than 10%, preferably more than 20%, more preferably more than 30%, even more preferably by more than 50%.

According to one aspect of the invention, said exogenous sequence encodes a chemokine or a cytokine, such as IL-12. It is particularly advantageous to express IL-12 as this cytokine is extensively referred to in the literature as promoting immune cell activation (Colombo M. P. et al. (2002) "Interleukin-12 in anti-tumor immunity and immunotherapy" *Cytokine Growth Factor Rev.* 13(2):155-68).

According to a preferred aspect of the invention the exogenous coding sequence encodes or promote secreted factors that act on other populations of immune cells, such as T-regulatory cells, to alleviate their inhibitory effect on said immune cells.

According to one aspect of the invention, said exogenous sequence encodes an inhibitor of regulatory T-cell activity is a polypeptide inhibitor of forkhead/winged helix transcription factor 3 (FoxP3), and more preferably is a cell-penetrating peptide inhibitor of FoxP3, such as that referred as β60 (Casares N. et al. (2010) "A peptide inhibitor of FoxP3 impairs regulatory T cell activity and improves vaccine efficacy in mice." *J Immunol* 185(9):5150-9).

By "inhibitor of regulatory T-cells activity" is meant a molecule or precursor of said molecule secreted by the T-cells and which allow T-cells to escape the down regulation activity exercised by the regulatory T-cells thereon. In general, such inhibitor of regulatory T-cell activity has the effect of reducing FoxP3 transcriptional activity in said cells.

According to one aspect of the invention, said exogenous sequence encodes a secreted inhibitor of Tumor Associated Macrophages (TAM), such as a CCR2/CCL2 neutralization agent. Tumor-associated macrophages (TAMs) are critical modulators of the tumor microenvironment. Clinicopathological studies have suggested that TAM accumulation in tumors correlates with a poor clinical outcome. Consistent with that evidence, experimental and animal studies have supported the notion that TAMs can provide a favorable microenvironment to promote tumor development and progression. (Theerawut C. et al. (2014) "Tumor-Associated Macrophages as Major Players in the Tumor Microenvironment" *Cancers* (Basel) 6(3): 1670-1690). Chemokine ligand 2 (CCL2), also called monocyte chemoattractant protein 1 (MCP1—NCBI NP_002973.1), is a small cytokine that belongs to the CC chemokine family, secreted by macrophages, that produces chemoattraction on monocytes, lymphocytes and basophils. CCR2 (C-C chemokine receptor type 2—NCBI NP_001116513.2), is the receptor of CCL2.

Enhancing Specificity and Safety of Immune Cells

Expressing chimeric antigen receptors (CAR) have become the state of the art to direct or improve the specificity of primary immune cells, such as T-Cells and NK-cells for treating tumors or infected cells. CARs expressed by these immune cells specifically target antigen markers at the surface of the pathological cells, which further help said immune cells to destroy these cells in-vivo (Sadelain M. et al. "The basic principles of chimeric antigen receptor design" (2013) *Cancer Discov.* 3(4):388-98). CARs are usually designed to comprise activation domains that stimulate immune cells in response to binding to a specific antigen (so-called positive CAR), but they may also comprise an inhibitory domain with the opposite effect (so-called negative CAR)(Fedorov, V. D. (2014) "Novel Approaches to Enhance the Specificity and Safety of Engineered T Cells" *Cancer Journal* 20 (2):160-165. Positive and negative CARs may be combined or co-expressed to finely tune the cells immune specificity depending of the various antigens present at the surface of the target cells.

The genetic sequences encoding CARs are generally introduced into the cells genome using retroviral vectors that have elevated transduction efficiency but integrate at random locations. Here, according to the present invention, components of chimeric antigen receptor (CAR) car be introduced at selected loci, more particularly under control of endogenous promoters by targeted gene recombination.

According to one aspect, while a positive CAR is introduced into the immune cell by a viral vector, a negative CAR can be introduced by targeted gene insertion and vice-versa, and be active preferably only during immune cells activation. Accordingly, the inhibitory (i.e. negative) CAR contributes to an improved specificity by preventing the immune cells to attack a given cell type that needs to be preserved. Still according to this aspect, said negative CAR can be an apoptosis CAR, meaning that said CAR comprise an apoptosis domain, such as FasL (CD95—NCBI:

NP_000034.1) or a functional variant thereof, that transduces a signal inducing cell death (Eberstadt M; et al. "NMR structure and mutagenesis of the FADD (Mort1) death-effector domain" (1998) Nature. 392 (6679): 941-5).

Accordingly, the exogenous coding sequence inserted according to the invention can encode a factor that has the capability to induce cell death, directly, in combination with, or by activating other compound(s).

As another way to enhance the safety of us of the primary immune cells, the exogenous coding sequence can encodes molecules that confer sensitivity of the immune cells to drugs or other exogenous substrates. Such molecules can be cytochrome(s), such as from the β450 family (Preissner S et al. (2010) "SuperCYP: a comprehensive database on Cytochrome β450 enzymes including a tool for analysis of CYP-drug interactions". *Nucleic Acids Res* 38 (Database issue): D237-43), such as CYP2D6-1 (NCBI—NP_000097.3), CYP2D6-2 (NCBI—NP_001020332.2), CYP2C9 ( ), CYP3A4 (NCBI—NP_000762.2), CYP2C19 (NCBI—NP_000760.1) or CYP1A2 (NCBI—NP_000752.2), conferring hypersensitivity of the immune cells to a drug, such as cyclophosphamide and/or isophosphamide.

According to a further aspect of the invention, an exogenous sequence is introduced into the engineered immune cells for its expression, especially in vivo, to reduce IL-6 or IL-8 trans signalling in view of controlling potential Cyokine Release Syndrome (CRS).

Such an exogenous sequence can encode for instance antibodies directed against IL-6 or IL-8 or against their receptors IL-6R or IL-8R [Shannon, L. et al. (2014) Managing Cytokine Release Syndrome Associated With Novel T Cell-Engaging Therapies. Cancer J. 20(2): 119-122].

More specifically, cytokine release syndrome (CRS) can be mitigated by interfering with the macrophage activated syndrome which is one component of CRS [Lee, D. W. et al. (2014) Current concepts in the diagnosis and management of cytokine release syndrome. *Blood.* 124:188-195]. To achieve this goal, the invention comprises integrating exogenous sequences encoding antagonists of the IL1 or IL18 activating pathways, such as IL1RA (Uniprot #β18510) or IL18BP (Uniprot #095998) or active fragments or variants thereof.

By "antagonists of the IL1 and IL18 activating pathway" is meant any polypeptide able to interfere with higher expression of IL1 or IL18. Accordingly, the present invention provides methods for generating therapeutic cells, wherein exogenous sequences encoding IL1RA or IL18BP are integrated at selected loci, especially PD1, CD25 or CD69, and more preferably in combination with the expression of a CAR, optionally integrated at the TCR and/or PD1 loci.

Preferred exogenous sequences encode antagonists or antibodies that have been approved by drug agencies, such as those marketed under the following names and references:

Anakinra (CAS registry no: 143090-92-0) (brand name Kineret) is a recombinant 10 version of the interleukin 1 receptor antagonist (IL1-RA). Anakinra is a variant form of IL1RA as it differs from native human IL-1Ra by the addition of a single methionine residue at its amino terminus. Anakinra blocks the biologic activity of naturally occurring IL-1 [Kalliolias, G D. et al. (2008) The future of the IL-1 receptor antagonist anakinra: from rheumatoid arthritis to adult-onset Still's disease and systemic-onset juvenile idiopathic arthritis. *Expert Opin Investig Drugs.* 17(3):349-59].

Rilonacept, (CAS registry no: 501081-76-1) also known as IL-1 Trap (marketed by Regeneron Pharmaceuticals under the brand name Arcalyst), is also an interleukin 1 inhibitor. It is a dimeric fusion protein consisting of the ligand-binding domains of the extracellular portions of the human interleukin-1 receptor component (IL-1R1) and IL-1 receptor accessory protein (IL-1RAcP) linked in-line to the fragment-crystallizable portion (Fc region) of human IgG1 that binds and neutralizes IL-1 [McDermott, M. F., (2009) Rilonacept in the treatment of chronic inflammatory disorders. *Drugs of Today.* 45(6):423-430].

Canakinumab (brand name Ilaris—CAS registry no: 914613-48-2) is a human monoclonal antibody targeted at interleukin-1 beta. It has no cross-reactivity with other members of the interleukin-1 family, including interleukin-1 alpha [Rondeau J. M. et al. (2015) The molecular mode of action and species specificity of canakinumab, a human monoclonal antibody neutralizing IL-1β. *MAbs.* 7(6):1151-60].

Tocilizumab (brand name Actemra—CAS registry no: 375823-41-9) is a humanized monoclonal antibody against the interleukin-6 receptor (IL-6R) [Venkiteshwaran, A. (2009) Tocilizumab. MAbs. 1(5): 432-438].

Siltuximab (brand name Sylvant—CAS registry no: 541502-14-1) is anti-IL-6 chimeric monoclonal antibody or cCLB8) is a chimeric (made from human and mouse proteins) monoclonal antibody that binds to interleukin-6 [Rhee, F. et al. (2010) Siltuximab, a Novel Anti-Interleukin-6 Monoclonal Antibody for Castleman's Disease. *Journal of Clinical Oncology* 28 (23):3701-3708].

According to a preferred aspect said exogenous sequence can encode soluble extracellular domain of GP130, such as one showing at least 80% identity with SEQ ID NO. 61

Such soluble extracellular domain of GP130 is described for instance by Rose-John S. [The Soluble Interleukine Receptor: Advanced Therapeutic Options in Inflammation (2017) *Clinical Pharmacology & Therapeutics,* 102(4):591-598] can be fused with fragments of immunoglobulins, such as sgp130Fc (SEQ ID NO.62). As stated before, said exogenous sequence can be stably integrated into the genome by site directed mutagenesis (i.e. using sequence specific nuclease reagents) and be placed under the transcriptional activity of an endogenous promoter at a locus which is active during immune cell activation, such as one listed in Tables 6, 8 or 9, and preferably up-regulated upon CAR activation or being CAR dependent.

According to a more preferred embodiment, the exogenous sequence is introduced into a CAR positive immune cell, such as one expressing an anti-CD22 CAR T-cell polynucleotide sequence such as SEQ ID NO:31. According to some more specific embodiments, said exogenous sequence coding for a polypeptide which can associate, and preferably interfere, with a cytokine receptor of the IL-6 receptor family, such as said soluble extracellular domain of GP130, is integrated at a PD1, CD25 or CD69 locus. As per the present invention, the endogenous sequence encoding PD1 locus is preferably disrupted by said exogenous sequence.

The invention thus provides with a method for treating or reducing CRS in cell immunotherapy, wherein cells or a therapeutic composition thereof are administered to patients, said cells being genetically modified to secrete polypeptide(s) comprising a soluble extracellular domain of GP130, sGP130Fc, an anti-IL-6 or anti-IL6R antibody, an anti-IL-8 or anti-IL8R antibody, or any fusion thereof.

Examples of preferred genotypes of the engineered immune cells are:

[CAR]$^{positive}$[GP130]$^{positive}$
[CAR]$^{positive}$[GP130]$^{positive}$[TCR]$^{negative}$
[CAR]$^{positive}$[TCR]$^{negative}$ [GP130]$^{positive}$ [PD1]$^{negative}$
[CAR]$^{positive}$[TCR]$^{negative}$ [GP130]$^{positive}$ [β2m]$^{negative}$
[CAR]$^{positive}$[GP130]$^{positive}$ [CD25]$^{negative}$
[CAR]$^{positive}$[TCR]$^{negative}$ [GP130]$^{positive}$ [CD25]$^{negative}$
[CAR]$^{positive}$[sGP130]$^{positive}$
[CAR]$^{positive}$[sGP130]$^{positive}$[TCR]$^{negative}$
[CAR]$^{positive}$[TCR]$^{negative}$ [sGP130]$^{positive}$ [PD1]$^{negative}$
[CAR]$^{positive}$[TCR]$^{negative}$ [sGP130]$^{positive}$ [β2m]$^{negative}$
[CAR]$^{positive}$[sGP130]$^{positive}$ [CD25]$^{negative}$
[CAR]$^{positive}$[TCR]$^{negative}$ [IL1 RA]$^{positive}$ [CD25]$^{negative}$
[CAR]$^{positive}$[L1 RA]$^{positive}$
[CAR]$^{positive}$ [IL1RA]$^{positive}$[TCR]$^{negative}$
[CAR]$^{positive}$[TCR]$^{negative}$ [IL1RA]$^{positive}$ [PD1]$^{negative}$
[CAR]$^{positive}$[TCR]$^{negative}$ [IL1 RA]$^{positive}$ [β2m]$^{negative}$
[CAR]$^{positive}$[L1 RA]$^{positive}$ [CD25]$^{negative}$
[CAR]$^{positive}$[TCR]$^{negative}$ [IL118BP]$^{positive}$ [CD25]$^{negative}$
[CAR]$^{positive}$[TCR]$^{negative}$ [IL18BP]$^{positive}$ [PD1]$^{negative}$
[CAR]$^{positive}$[TCR]$^{negative}$ [IL118BP]$^{positive}$ [β2m]$^{negative}$
[CAR]$^{positive}$[IL18BP]$^{positive}$ [CD25]$^{negative}$
[CAR]$^{positive}$[TCR]$^{negative}$ [IL118BP]$^{positive}$ [CD25]$^{negative}$ Improving the Efficiency of Gene Targeted Insertion in Primary Immune Cells Using AAV Vectors The present specification provides with donor templates and sequence specific reagents as illustrated in the figures that are useful to perform efficient insertion of a coding sequence in frame with endogenous promoters, in particular PD1 and CD25, as well as means and sequences for detecting proper insertion of said exogenous sequences at said loci.

The donor templates according to the present invention are generally polynucleotide sequences which can be included into a variety of vectors described in the art prompt to deliver the donor templates into the nucleus at the time the endonuclease reagents get active to obtain their site directed insertion into the genome generally by NHEJ or homologous recombination, Specifically, the present invention provides specific donor polynucleotides for expression of IL-15 (SEQ ID NO.59) at the PD1 locus comprising one or several of the following sequences:

Sequence encoding IL-15, such as one presenting identity with SEQ ID NO:50;
Upstream and downstream (also referred to left and right) sequences homologous to the PD1 locus, comprising preferably polynucleotide sequences SEQ ID NO:45 and SEQ ID NO:46;
optionally, a sequence encoding soluble form of an IL-15 receptor (sIL-15R), such as one presenting identity with SEQ ID NO:50
optionally, at least one -2A peptide cleavage site such as one of SEQ ID NO:53 (F2A), SEQ ID NO:54 (β2A) and/or SEQ ID NO:55 (T2A), Specifically, the present invention provides specific donor polynucleotides for expression of IL-12 (SEQ ID NO:58) at the PD1 locus comprising one or several of the following sequences:

Sequence encoding IL-12a, such as one presenting identity with SEQ ID NO:47;
Upstream and downstream (also referred to left and right) sequences homologous to the PD1 locus, comprising preferably polynucleotide sequences SEQ ID NO:45 and SEQ ID NO:46;
optionally, a sequence encoding IL-12b, such as one presenting identity with SEQ ID NO:48
optionally, at least one 2A peptide cleavage site such as one of SEQ ID NO:53 (F2A), SEQ ID NO:54 (β2A) and/or SEQ ID NO:55 (T2A), Specifically, the present invention provides specific donor polynucleotides for expression of soluble GP130 (comprising SEQ ID NO.61) at the PD1 locus comprising one or several of the following sequences:

Sequence encoding soluble GP130, preferably a soluble gp130 fused to a Fc, such as one presenting identity with SEQ ID NO:62;
Upstream and downstream (also referred to left and right) sequences homologous to the PD1 locus, comprising preferably polynucleotide sequences SEQ ID NO:45 and SEQ ID NO:46;
optionally, at least one 2A peptide cleavage site such as one of SEQ ID NO:53 (F2A), SEQ ID NO:54 (P2A) and/or SEQ ID NO:55 (T2A), Specifically, the present invention provides specific donor polynucleotides for expression of IL-15 (SEQ ID NO.59) at the CD25 locus comprising one or several of the following sequences:

Sequence encoding IL-15, such as one presenting identity with SEQ ID NO:50;
Upstream and downstream (also referred to left and right) sequences homologous to the CD25 locus, comprising preferably polynucleotide sequences SEQ ID NO:43 and SEQ ID NO:44;
optionally, a sequence encoding soluble form of an IL-15 receptor (sIL-15R), such as one presenting identity with SEQ ID NO:50
optionally, at least one 2A peptide cleavage site such as one of SEQ ID NO:53 (F2A), SEQ ID NO:54 (β2A) and/or SEQ ID NO:55 (T2A), Specifically, the present invention provides specific donor polynucleotides for expression of IL-12 (SEQ ID NO:58) at the CD25 locus comprising one or several of the following sequences:

Sequence encoding IL-12a, such as one presenting identity with SEQ ID NO:47;
Upstream and downstream (also referred to left and right) sequences homologous to the CD25 locus, comprising preferably polynucleotide sequences SEQ ID NO:43 and SEQ ID NO:44;
optionally, a sequence encoding IL-12b, such as one presenting identity with SEQ ID NO:48;
optionally, at least one 2A peptide cleavage site such as one of SEQ ID NO:53 (F2A), SEQ ID NO:54 (β2A) and/or SEQ ID NO:55 (T2A), Specifically, the present invention provides specific donor polynucleotides for expression of soluble GP130 (comprising SEQ ID NO.61) at the CD25 locus comprising one or several of the following sequences:

Sequence encoding soluble GP130, preferably a soluble gp130 fused to a Fc, such as one presenting identity with SEQ ID NO:62;
Upstream and downstream (also referred to left and right) sequences homologous to the CD25 locus, comprising preferably polynucleotide sequences SEQ ID NO:43 and SEQ ID NO:44;

optionally, at least one 2A peptide cleavage site such as one of SEQ ID NO:53 (F2A), SEQ ID NO:54 (β2A) and/or SEQ ID NO:55 (T2A), As illustrated in the examples herein, the inventors have significantly improved the rate of gene targeted insertion into human cells by using AAV vectors, especially vectors from the AAV6 family.

One broad aspect of the present invention is thus the transduction of AAV vectors in human primary immune cells, in conjunction with the expression of sequence specific endonuclease reagents, such as TALE endonucleases, more preferably introduced under mRNA form, to increase homologous recombination events in these cells.

According to one aspect of this invention, sequence specific endonuclease reagents can be introduced into the cells by transfection, more preferably by electroporation of mRNA encoding said sequence specific endonuclease reagents, such as TALE nucleases.

Still according to this broad aspect, the invention more particularly provides a method of insertion of an exogenous nucleic acid sequence into an endogenous polynucleotide sequence in a cell, comprising at least the steps of:
    transducing into said cell an AAV vector comprising said exogenous nucleic acid sequence and sequences homologous to the targeted endogenous DNA sequence, and
    Inducing the expression of a sequence specific endonuclease reagent to cleave said endogenous sequence at the locus of insertion.

The obtained insertion of the exogenous nucleic acid sequence may result into the introduction of genetic material, correction or replacement of the endogenous sequence, more preferably "in frame" with respect to the endogenous gene sequences at that locus.

According to another aspect of the invention, from $10^5$ to $10^7$ preferably from $10^6$ to $10^7$, more preferably about $5 \cdot 10^6$ viral genomes are transduced per cell.

According to another aspect of the invention, the cells can be treated with proteasome inhibitors, such as Bortezomib to further help homologous recombination.

As one object of the present invention, the AAV vector used in the method can comprise a promoterless exogenous coding sequence as any of those referred to in this specification in order to be placed under control of an endogenous promoter at one loci selected among those listed in the present specification.

As one object of the present invention, the AAV vector used in the method can comprise a 2A peptide cleavage site followed by the cDNA (minus the start codon) forming the exogenous coding sequence.

As one object of the present invention, said AAV vector comprises an exogenous sequence coding for a chimeric antigen receptor, especially an anti-CD19 CAR, an anti-CD22 CAR, an anti-CD123 CAR, an anti-CS1 CAR, an anti-CCL1 CAR, an anti-HSP70 CAR, an anti-GD3 CAR or an anti-ROR1 CAR.

The invention thus encompasses any AAV vectors designed to perform the method herein described, especially vectors comprising a sequence homologous to a locus of insertion located in any of the endogenous gene responsive to T-cell activation referred to in Table 4.

Many other vectors known in the art, such as plasmids, episomal vectors, linear DNA matrices, etc. can also be used following the teachings of the present invention.

As stated before, the DNA vector used according to the invention preferably comprises: (1) said exogenous nucleic acid comprising the exogenous coding sequence to be inserted by homologous recombination, and (2) a sequence encoding the sequence specific endonuclease reagent that promotes said insertion. According to a more preferred aspect, said exogenous nucleic acid under (1) does not comprise any promoter sequence, whereas the sequence under (2) has its own promoter. According to an even more preferred aspect, the nucleic acid under (1) comprises an Internal Ribosome Entry Site (IRES) or "self-cleaving" 2A peptides, such as T2A, β2A, E2A or F2A, so that the endogenous gene where the exogenous coding sequence is inserted becomes multi-cistronic. The IRES of 2A Peptide can precede or follow said exogenous coding sequence.

Preferred vectors of the present invention are vectors derived from AAV6, comprising donor polynucleotides as previously described herein or illustrated in the experimental section and figures. Examples of vectors according to the invention comprise or consist of polynucleotides having identity with sequences SEQ ID NO:37 (matrix for integration of sequence coding for IL-15 into the CD25 locus), SEQ ID NO:38 (matrix for integration of sequence coding for IL-15 into the PD1 locus), SEQ ID NO:39 (matrix for integration of sequence coding for IL-12 into the CD25 locus), SEQ ID NO:40 (matrix for integration of sequence coding for IL-12 into the PD1 locus), SEQ ID NO:69 (matrix for integration of HLAE VMAPRTLFL peptide (SEQ ID NO:97)), SEQ ID NO:71 (matrix for integration of HLAE VMAPRTLIL peptide (SEQ ID NO:91)), SEQ ID NO:73 (matrix for integration of UL18 actine peptide into the B2m locus, SEQ ID NO:75 (matrix for integration of UL18 HLACw peptide inserted at the B2m locus), and SEQ ID NO:77 (matrix for integration of UL18_βHLAG peptide into the β2m locus).

Gene Targeted Integration in Immune Cells Under Transcriptional Control of Endogenous Promoters The present invention, in one of its main aspects, is taking advantage of the endogenous transcriptional activity of the immune cells to express exogenous sequences that improve their therapeutic potential.

The invention provides with several embodiments based on the profile of transcriptional activity of the endogenous promoters and on a selection of promoter loci useful to carry out the invention. Preferred loci are those, which transcription activity is generally high upon immune cell activation, especially in response to CAR activation (CAR-sensitive promoters) when the cells are endowed with CARs.

Accordingly, the invention provides with a method for producing allogeneic therapeutic immune cells by expressing a first exogenous sequence encoding a CAR at the TCR locus, thereby disrupting TCR expression, and expressing a second exogenous coding sequence under transcriptional activity of an endogenous locus, preferably dependent from either:
    CD3/CD28 activation, such as dynabeads, which is useful for instance for promoting cells expansion;
    CAR activation, such as through the CD3zeta pathway, which is useful for instance to activate immune cells functions on-target;
    Transcriptional activity linked to the appearance of disease symptom or molecular marker, which is useful for instance for activating the cells in-situ in ill organs.
    Cell differentiation, which is useful for conferring therapeutic properties to cells at a given level of differentiation or to express protein into a particular lineage (see FIG. 1), for instance at the time hematopoietic cells gain their immune functions; or/and
    TME (Tumor microoenvironment), which is useful for redirect cells activity and their amplification to specific tumor conditions (hypoxia, low glucose . . . ), or for preventing exhaustion and/or sustaining activation;

CRS (cytokine release syndrome), which is useful to mitigate adverse events related to CAR T-cell activity The inventors have established a first list of endogenous genes (Table 6) which have been found to be particularly appropriate for applying the targeted gene recombination as per the present invention. To draw this list, they have come across several transcriptome murine databases, in particular that from the Immunological Genome Project Consortium referred to in Best J. A. et al. (2013) "Transcriptional insights into the CD8(+) T cell response to infection and memory T cell formation" *Nat. Immunol.* 14(4):404-12., which allows comparing transcription levels of various genes upon T-cell activation, in response to ovalbumin antigens. Also, because very few data is available with respect to human T-cell activation, they had to make some extrapolations and analysis from these data and compare with the human situation by studying available literature related to the human genes. The selected loci are particularly relevant for the insertion of sequences encoding CARs. Based on the first selection of Table 6, they made subsequent selections of genes based on their expected expression profiles (Tables 7 to 10).

On another hand, the inventors have identified a selection of transcriptional loci that are mostly inactive, which would be most appropriate to insert expression cassette(s) to express exogenous coding sequence under the transcriptional control of exogenous promoters. These loci are referred to as "safe harbor loci" as those being mostly transcriptionally inactive, especially during T-Cell activation. They are useful to integrate a coding sequence by reducing at the maximum the risk of interfering with genome expression of the immune cells.

Gene Targeted Insertion Under Control of Endogenous Promoters that are Steadily Active During Immune Cell Activation A selection of endogenous gene loci related to this embodiment is listed in Table 7. Accordingly the method of the present invention provides with the step of performing gene targeted insertion under control of an endogenous promoter that is constantly active during immune cell activation, preferably from of an endogenous gene selected from CD3G, Rn28s1, Rn18s, Rn7sk, Actg1, β2m, Rpl18a, Pabpc1, Gapdh, Rpl17, Rpl19, Rplp0, Cfl1 and Pfn1.

By "steadily active" means that the transcriptional activity observed for these promoters in the primary immune cell is not affected by a negative regulation upon the activation of the immune cell.

As reported elsewhere (Acuto, O. (2008) "Tailoring T-cell receptor signals by proximal negative feedback mechanisms". *Nature Reviews Immunology* 8:699-712), the promoters present at the TCR locus are subjected to different negative feedback mechanisms upon TCR engagement and thus may not be steadily active or up regulated during for the method of the present invention. The present invention has been designed to some extend to avoid using the TCR locus as a possible insertion site for exogenous coding sequences to be expressed during T-cell activation. Therefore, according to one aspect of the invention, the targeted insertion of the exogenous coding sequence is not performed at a TCRalpha or TCRbeta gene locus.

Examples of exogenous coding sequence that can be advantageously introduced at such loci under the control of steadily active endogenous promoters, are those encoding or positively regulating the production of a cytokine, a chemokine receptor, a molecule conferring resistance to a drug, a co-stimulation ligand, such as 4-1BRL and OX40L, or of a secreted antibody.

Gene Integration Under Endogenous Promoters that are Dependent from Immune Cell Activation or Dependent from CAR Activation As stated before, the method of the present invention provides with the step of performing gene targeted insertion under control of an endogenous promoter, which transcriptional activity is preferably up-regulated upon immune cell activation, either transiently or over more than 10 days.

By "immune cell activation" is meant production of an immune response as per the mechanisms generally described and commonly established in the literature for a given type of immune cells. With respect to T-cell, for instance, T-cell activation is generally characterized by one of the changes consisting of cell surface expression by production of a variety of proteins, including CD69, CD71 and CD25 (also a marker for Treg cells), and HLA-DR (a marker of human T cell activation), release of perforin, granzymes and granulysin (degranulation), or production of cytokine effectors IFN-γ, TNF and LT-alpha.

According to a preferred embodiment of the invention, the transcriptional activity of the endogenous gene is up-regulated in the immune cell, especially in response to an activation by a CAR. The CAR can be independently expressed in the immune cell. By "independently expressed" is meant that the CAR can be transcribed in the immune cell from an exogenous expression cassette introduced, for instance, using a retroviral vector, such as a lentiviral vector, or by transfecting capped messenger RNAs by electroporation encoding such CAR Many methods are known in the art to express a CAR into an immune cell as described for instance by (REF.)

Said endogenous gene whose transcriptional activity is up regulated are particularly appropriate for the integration of exogenous sequences to encode cytokine(s), such as IL-12 and IL-15, immunogenic peptide(s), or a secreted antibody, such as an anti-IDO1, anti-IL10, anti-PD1, anti-PDL1, anti-IL6 or anti-PGE2 antibody.

According to a preferred embodiment of the invention, the endogenous promoter is selected for its transcriptional activity being responsive to, and more preferably being dependent from CAR activation.

As shown herein, CD69, CD25 and PD1 are such loci, which are particularly appropriate for the insertion of expression of an exogenous coding sequences to be expressed when the immune cells get activated, especially into CAR positive immune cells.

The present invention thus combines any methods of expressing a CAR into an immune cell with the step of performing a site directed insertion of an exogenous coding sequence at a locus, the transcriptional activity of which is responsive to or dependent from the engagement of said CAR with a tumor antigen. Especially, the method comprises the step of introducing into a CAR positive or Recombinant TCR positive immune cell an exogenous sequence encoding IL-12 or IL-15 under transcriptional control of one promoter selected from PD1, CD25 and CD69 promoters.

In particular, CAR positive cells can obtained by following the steps of co-expressing into an immune cell, preferably a primary cell, and more preferably into a primary T-cell, at least one exogenous sequence encoding a CAR and another exogenous sequence placed under an endogenous promoter dependent, which transcriptional activity is dependent from said CAR, such a PD1, CD25 or CD71.

The expression "dependent from said CAR" means that the transcriptional activity of said endogenous promoter is necessary increased by more than 10%, preferably by more than 20%, more preferably by more than 50% and even more preferably more than 80%, as a result of the engagement of the CAR with its cognate antigen, in a situation where, in general, the antigens are exceeding the number of CARs present at the cell surface and the number of CARs expressed at the cell surface is more than 10 per cell, preferably more than 100, and more preferably more than 1000 molecules per cells.

The present invention thus teaches the expression of a CAR sequence, preferably inserted at the TCR locus and constitutively expressed, whereas another exogenous sequence integrated at another locus is co-expressed, in response to, or dependent from, the engagement of said CAR with its cognate antigen. Said another locus is for instance CD25, PD1 or CD71 or any loci being specifically transcribed upon CAR activation.

In other words, the invention provides the co-expression of a CAR and at least one exogenous coding sequence, the expression of said exogenous sequence being under control of an endogenous promoter the transcriptional activity of which is influenced by the CAR activity, this being done in view of obtaining engineered immune cells offering a better immune response.

As previously described, this can be performed by transfecting the cells with sequence-specific nuclease reagents targeting the coding regions of such loci being specifically CAR dependent, along with donor templates comprising sequences homologous to said genomic regions. The sequence specific nuclease reagents help the donor templates to be integrated by homologous recombination or NHEJ.

According to a preferred embodiment, the exogenous coding sequence is integrated in frame with the endogenous gene, so that the expression of said endogenous gene is preserved. This is the case for instance with respect to CD25 and CD69 in at least one example of the experimental section herein.

According to a preferred embodiment, the exogenous sequence disrupts the endogenous coding sequence of the gene to prevent its expression of one endogenous coding sequence, especially when this expression has a negative effect on the immune cell functions, as it the case for instance with PD1 in the experimental section herein.

According to an even more preferred embodiments, the exogenous coding sequence, which disrupts the endogenous gene sequence is placed in frame with the endogenous promoter, so that its expression is made dependent from the endogenous promoter as also shown in the experimental section.

The present invention is also drawn to the polynucleotide and polypeptide sequences encoding the different TAL-nucleases exemplified in the present patent application, especially those permitting the site directed insertion at the CD25 locus (SEQ ID NO:18 and 19), as well as their respective target and RVD sequences.

The present invention also encompasses kits for immune cells transfection comprising polynucleotides encoding the sequence-specific endonuclease reagents and the donor sequences designed to integrate the exogenous sequence at the locus targeted by said reagents. Examples of such kits are a kit comprising mRNA encoding rare-cutting endonuclease targeting PD1 locus (ex: PD1 TALEN®) and an AAV vector comprising an exogenous sequence encoding IL-12, a kit comprising mRNA encoding rare-cutting endonuclease targeting PD1 locus (ex: PD1 TALEN®) and an AAV vector comprising an exogenous sequence encoding IL-15, a kit comprising mRNA encoding rare-cutting endonuclease targeting CD25 locus (ex: CD25 TALEN®) and an AAV vector comprising an exogenous sequence encoding IL-12, a kit comprising mRNA encoding rare-cutting endonuclease targeting CD25 locus (ex: CD25 TALEN®) and an AAV vector comprising an exogenous sequence encoding IL-15, a kit comprising mRNA encoding rare-cutting endonuclease targeting PD1 locus (ex: PD1 TALEN®) and an AAV vector comprising an exogenous sequence encoding soluble gp130, a kit comprising mRNA encoding rare-cutting endonuclease targeting CD25 locus (ex: CD25 TALEN®) and an AAV vector comprising an exogenous sequence encoding soluble gp130, and any kits involving endonuclease reagents targeting a gene listed in table 6, and a donor matrix for introducing a coding sequence referred to in the present specification.

Further examples of such kits are a kit comprising mRNA encoding rare-cutting endonuclease targeting PD1 locus (ex: PD1 TALEN®) and an AAV vector comprising an exogenous sequence encoding IL-12, a kit comprising mRNA encoding rare-cutting endonuclease targeting PD1 locus (ex: PD1 TALEN®) and an AAV vector comprising an exogenous sequence encoding IL-15, a kit comprising mRNA encoding rare-cutting endonuclease targeting CD25 locus (ex: CD25 TALEN®) and an AAV vector comprising an exogenous sequence encoding IL-12, a kit comprising mRNA encoding rare-cutting endonuclease targeting CD25 locus (ex: CD25 TALEN®) and an AAV vector comprising an exogenous sequence encoding IL-15, a kit comprising mRNA encoding rare-cutting endonuclease targeting β2m locus (ex: β2m TALEN®) and an AAV vector comprising an exogenous sequence encoding NK inhibitor, such as comprising a heavy chain from HLA-E or HLA-G, a kit comprising mRNA encoding rare-cutting endonuclease targeting β2m locus (ex: β2m TALEN®) and an AAV vector comprising an exogenous sequence encoding soluble gp130, and any kits involving endonuclease reagents targeting a gene listed in table 6, and a donor matrix for introducing a coding sequence referred to in the present specification The present invention also provides kits for immune cells transfection comprising polynucleotides encoding sequence-specific endonuclease reagents and an exogenous polynucleotide sequence, preferably comprised into a AAV vector, said exogenous sequence comprising a sequence encoding antagonists of the IL1 and IL18 activating pathways, such as IL1 RA (Uniprot #P18510) or IL18BP (Uniprot #O95998) or active fragments or variants thereof.

According to one aspect of the invention, the endogenous gene is selected for a weak up-regulation. The exogenous coding sequence introduced into said endogenous gene whose transcriptional activity is weakly up regulated, can be advantageously a constituent of an inhibitory CAR, or of an apoptotic CAR, which expression level has generally to remain lower than that of a positive CAR. Such combination of CAR expression, for instance one transduced with a viral vector and the other introduced according to the invention, can greatly improve the specificity or safety of CAR immune cells Some endogenous promoters are transiently up-regulated, sometimes over less than 12 hours upon immune cell activation, such as those selected from the endogenous gene loci Spata6, Itga6, Rcbtb2, Cd1d1, St8sia4, Itgae and Fam214a (Table 8). Other endogenous promoters are up-regulated over less than 24 hours upon immune cell activation, such as those selected from the endogenous gene loci IL3, IL2, Ccl4, IL21, Gp49a, Nr4a3, Lilrb4, Cd200, Cdkn1a, Gzmc, Nr4a2, Cish, Ccr8, Lad1 and Crabp2 (Table 9) and others over more than 24 hours, more generally over more than 10 days, upon immune cell activation. Such as those selected from Gzmb, Tbx21, Plek, Chek1, Slamf7, Zbtb32, Tigit, Lag3, Gzma, Wee1, IL12rb2, Eea1 and Dtl (Table 9).

Alternatively, the inventors have found that endogenous gene under transcriptional control of promoters that are down-regulated upon immune cell activation, could also be of interest for the method according to the present invention. Indeed they have conceived that exogenous coding sequences encoding anti-apoptotic factors, such as of Bcl2 family, BclXL, NF-kB, Survivin, or anti-FAP (fibroblast activation protein), such as a constituent of a CAR anti-FAP, could be introduced at said loci. Said endogenous gene under transcriptional control of promoters that are down-regulated upon immune cell activation can be more particularly selected from Slc6a19, Cd55, Xkrx, Mturn, H2-Ob, Cnr2, Itgae, Raver2, Zbtb20, Arrb1, Abca1, Tet1, Sic16a5 and Ampd3 (Table 10)

Gene Integration Under Endogenous Promoters Activated Under Tumor Microenvironment (TME) Conditions One aspect of the present invention more particularly concerns methods to prevent immune cells exhaustion in tumor microenvironment (TME) conditions. Immune cells often get exhausted in response to nutrient depletion or molecular signals found in the microoenvironment of tumors, which helps tumor resistance. The method comprises the steps of engineering immune cells by integrating exogenous coding sequences under control of endogenous promoters which are up-regulated under arginine, cysteine, tryptophan and oxygen deprivation as well as extracellular acidosis (lactate build up).

Such exogenous sequences may encode chimeric antigen receptors, interleukins, or any polypeptide given elsewhere in this specification to bolster immune cells function or activation and/or confer a therapeutic advantage.

The inventors have listed a number of loci which have been found to be upregulated in a large number of exhausted tumor infiltrating lymphocytes (TIL), which are listed in tables 12 and 13. The invention provides with the step of integrating exogenous coding sequences at these preferred loci to prevent exhaustion of the immune cells, in particular T-cells, in tumor microoenvironment.

For instance, the exogenous sequences encoding a CAR can be placed under transcriptional control of the promoter of endogenous genes that are activated by the tumor microenvironment, such as HIF1a, transcription factor hypoxia-inducible factor, or the aryl hydrocarbon receptor (AhR), These gene are sensors respectively induced by hypoxia and xenobiotics in the close environment of tumors.

The present invention is thus useful to improve the therapeutic outcome of CAR T-cell therapies by integrating exogenous coding sequences, and more generally genetic attributes/circuits, under the control of endogenous T-cell promoters influenced by tumor microenvironment (TME).

Pursuant to the invention, upregulation of endogenous genes can be "hijacked" to re-express relevant exogenous coding sequences to improve the antitumor activity of CAR T-cells in certain tumor microenvironment.

Gene Targeted Insertion and Expression in Hematopoietic Stem Cells (HSCs)

One aspect of the present invention more particularly concerns the insertion of transgenes into hematopoietic stem cells (HSCs).

Hematopoietic stem cells (HSCs) are multipotent, self-renewing progenitor cells from which all differentiated blood cell types arise during the process of hematopoiesis. These cells include lymphocytes, granulocytes, and macrophages of the immune system as well as circulating erythrocytes and platelets. Classically, HSCs are thought to differentiate into two lineage-restricted, lymphoid and myelo-erythroid, oligopotent progenitor cells. The mechanisms controlling HSC self-renewal and differentiation are thought to be influenced by a diverse set of cytokines, chemokines, receptors, and intracellular signaling molecules. Differentiation of HSCs is regulated, in part, by growth factors and cytokines including colony-stimulating factors (CSFs) and interleukins (ILs) that activate intracellular signaling pathways. The factors depicted below are known to influence HSC multipotency, proliferation, and lineage commitment. HSCs and their differentiated progeny can be identified by the expression of specific cell surface lineage markers such as cluster of differentiation (CD) proteins and cytokine receptors into hematopoietic stem cells.

Gene therapy using HSCs has enormous potential to treat diseases of the hematopoietic system including immune diseases. In this approach, HSCs are collected from a patient, gene-modified ex-vivo using integrating retroviral vectors, and then infused into a patient. To date retroviral vectors have been the only effective gene delivery system for HSC gene therapy. Gene delivery to HSCs using integrating vectors thereby allowing for efficient delivery to HSC-derived mature hematopoietic cells. However, the gene-modified cells that are infused into a patient are a polyclonal population, where the different cells have vector proviruses integrated at different chromosomal locations, which can result into many adverse mutations, which may be amplified due to some proliferative/survival advantage of these mutations (Powers and Trobridge (2013) "Identification of Hematopoietic Stem Cell Engraftment Genes in Gene Therapy Studies" *J Stem Cell Res Ther* S3:004. doi:10.4172/2157-7633.S3-00).

HSCs are commonly harvested from the peripheral blood after mobilization (patients receive recombinant human granulocyte-colony stimulating factor (G-CSF)). The patient's peripheral blood is collected and enriched for HSCs using the CD34+ marker. HSCs are then cultured ex vivo and exposed to viral vectors. The ex vivo culture period varies from 1 to 4 days. Prior to the infusion of gene-modified HSCs, patients may be treated with chemotherapy agents or irradiation to help enhance the engraftment efficiency. Gene-modified HSCs are re-infused into the patient intravenously. The cells migrate into the bone marrow before finally residing in the sinusoids and perivascular tissue. Both homing and hematopoiesis are integral aspects of engraftment. Cells that have reached the stem cell niche through homing will begin producing mature myeloid and lymphoid cells from each blood lineage. Hematopoiesis continues through the action of long-term HSCs, which are capable of self-renewal for life-long generation of the patient's mature blood cells, in particular the production of common lymphoid progenitor cells, such as T cells and NK cells, which are key immune cells for eliminating infected and malignant cells.

The present invention provides with performing gene targeted insertion in HSCs to introduce exogenous coding sequences under the control of endogenous promoters, especially endogenous promoters of genes that are specifically activated into cells of a particular hematopoietic lineage or at particular differentiation stage, preferably at a late stage of differentiation. The HSCs can be transduced with a polynucleotide vector (donor template), such as an AAV vector, during an ex-vivo treatment as referred to in the previous paragraph, whereas a sequence specific nuclease reagent is expressed as to promote the insertion of the coding sequences at the selected locus. The resulting engineered HSCs can be then engrafted into a patient in need thereof for a long term in-vivo production of engineered immune cells that will comprise said exogenous coding sequences. Depending on the activity of the selected endogenous promoter, the coding sequences will be selectively expressed in certain lineages or in response to the local environment of the immune cells in-vivo, thereby providing adoptive immunotherapy.

According to one preferred aspect of the invention, the exogenous coding sequences are placed under the control of promoters of a gene, which transcriptional activity is specifically induced in common lymphoid progenitor cells, such as CD34, CD43, Flt-3/Flk-2, IL-7R alpha/CD127 and Neprilysin/CD10.

More preferably, the exogenous coding sequences are placed under the control of promoters of a gene, which transcriptional activity is specifically induced in NK cells, such as CD161, CD229/SLAMF3, CD96, DNAM-1/CD226, Fc gamma RII/CD32, Fc gamma RII/RIII (CD32/CD16), Fc gamma RIII (CD16), IL-2 R beta, Integrin alpha 2/CD49b, KIR/CD158, NCAM-1/CD56, NKG2A/CD159a, NKG2C/CD159c, NKG2D/CD314, NKp30/NCR3, NKp44/NCR2, NKp46/NCR1, NKp80/KLRF1, Siglec-7/CD328 and TIGIT, or induced in T-cells, such as CCR7, CD2, CD3, CD4, CD8, CD28, CD45, CD96, CD229/SLAMF3, DNAM-1/CD226, CD25/IL-2 R alpha, L-Selectin/CD62L and TIGIT.

The invention comprises as a preferred aspect the introduction of an exogenous sequence encoding a CAR, or a component thereof, into HSCs, preferably under the transcriptional control of a promoter of a gene that is not expressed in HSC, more preferably a gene that is only expressed in the hematopoietic cells produced by said HSC, and even more preferably of a gene that is only expressed in T-cells or NK cells.

Conditional CAR Expression in HSCs to Overpass the Thymus Barrier

A particular aspect of the present invention concerns the in-vivo production by the above engineered HSCs of hematopoietic immune cells, such as T-cells or NK-cells, expressing exogenous coding sequences, in particular a CAR or a component thereof.

One major bar of the production of hematopoietic CAR positive cells by engineered HSCs, for instance, is the rejection of the CAR positive cells by the immune system itself, especially by the thymus.

The blood-thymus barrier regulates exchange of substances between the circulatory system and thymus, providing a sequestered environment for immature T cells to develop. The barrier also prevents the immature T cells from contacting foreign antigens (since contact with antigens at this stage will cause the T cells to die by apoptosis).

One solution provided by the present invention is to place the sequences encoding the CAR components in the HSCs under the transcriptional control of promoters which are not significantly transcribed into the hematopoietic cells when they pass through the thymus barrier. One example of a gene that offers a conditional expression of the CAR into the hematopoietic cells with reduced or no significant transcriptional activity in the thymus is LCK (Uniprot: P06239).

According to a preferred aspect of the invention the exogenous sequence encoding a CAR, or a component thereof, is introduced into the HSC under the transcriptional control of a gene that is described as being specifically expressed in T-cells or NK cells, preferably in these types of cells only.

The invention thereby provides with a method of producing HSCs comprising an exogenous coding sequences to be expressed exclusively in selected hematopoietic lineage(s), said coding sequences encoding preferably at least one component of a CAR or of an antigen in order to stimulate the immune system.

More broadly, the invention provides with a method of engineering HSCs by gene targeted insertion of an exogenous coding sequences to be selectively expressed in the hematopoietic cells produced by said HSCs. As a preferred embodiment, said hematopoietic cells produced by said engineered HSCs express said exogenous coding sequences in response to selected environmental factors or in-vivo stimuli to improve their therapeutic potential.

Combining Targeted Sequence Insertion(s) in Immune Cells with the Inactivation of Endogenous Genomic Sequences One particular focus of the present invention is to perform gene inactivation in primary immune cells at a locus, by integrating exogenous coding sequence at said locus, the expression of which improves the therapeutic potential of said engineered cells. Examples of relevant exogenous coding sequences that can be inserted according to the invention have been presented above in connection with their positive effects on the therapeutic potential of the cells. Here below are presented the endogenous gene that are preferably targeted by gene targeted insertion and the advantages associated with their inactivation.

According to a preferred aspect of the invention, the insertion of the coding sequence has the effect of reducing or preventing the expression of genes involved into self and non-self recognition to reduce host versus graft disease (GVHD) reaction or immune rejection upon introduction of the allogeneic cells into a recipient patient. For instance, one of the sequence-specific reagents used in the method can reduce or prevent the expression of TCR in primary T-cells, such as the genes encoding TCR-alpha or TCR-beta.

As another preferred aspect, one gene editing step is to reduce or prevent the expression of the β2m protein and/or another protein involved in its regulation such as C2TA (Uniprot P33076) or in MHC recognition, such as HLA proteins. This permits the engineered immune cells to be less alloreactive when infused into patients.

By "allogeneic therapeutic use" is meant that the cells originate from a donor in view of being infused into patients having a different haplotype. Indeed, the present invention provides with an efficient method for obtaining primary cells, which can be gene edited in various gene loci involved into host-graft interaction and recognition.

Other loci may also be edited in view of improving the activity, the persistence of the therapeutic activity of the engineered primary cells as detailed here after:

Inactivation of Checkpoint Receptors and Immune Cells Inhibitory Pathways:

According to a preferred aspect of the invention, the inserted exogenous coding sequence has the effect of reducing or preventing the expression of a protein involved in immune cells inhibitory pathways, in particular those referred to in the literature as "immune checkpoint" (Pardoll, D. M. (2012) The blockade of immune checkpoints in cancer immunotherapy, *Nature Reviews Cancer,* 12:252-264). In the sense of the present invention, "immune cells inhibitory pathways" means any gene expression in immune cells that leads to a reduction of the cytotoxic activity of the lymphocytes towards malignant or infected cells. This can be for instance a gene involved into the expression of FOXP3, which is known to drive the activity of Tregs upon T cells (moderating T-cell activity).

"Immune checkpoints" are molecules in the immune system that either turn up a signal (co-stimulatory molecules) or turn down a signal of activation of an immune cell. As per the present invention, immune checkpoints more particularly designate surface proteins involved in the ligand-receptor interactions between T cells and antigen-presenting cells (APCs) that regulate the T cell response to antigen (which is mediated by peptide-major histocompatibility complex (MHC) molecule complexes that are recognized by the T cell receptor (TCR)). These interactions can occur at the initiation of T cell responses in lymph nodes (where the major APCs are dendritic cells) or in peripheral tissues or tumours (where effector responses are regulated). One important family of membrane-bound ligands that bind both co-stimulatory and inhibitory receptors is the B7 family. All of the B7 family members and their known ligands belong to the immunoglobulin superfamily. Many of the receptors for more recently identified B7 family members have not yet been identified. Tumour necrosis factor (TNF) family members that bind to cognate TNF receptor family molecules represent a second family of regulatory ligand-receptor pairs. These receptors predominantly deliver co-stimulatory signals when engaged by their cognate ligands. Another major category of signals that regulate the activation of T cells comes from soluble cytokines in the microenvironment. In other cases, activated T cells upregulate ligands, such as CD40L, that engage cognate receptors on APCs. A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD1, programmed cell death protein 1; PDL, PD1 ligand; TGFβ, transforming growth factor-β; TIM3, T cell membrane protein 3.

Examples of further endogenous genes, which expression could be reduced or suppressed to turn-up activation in the engineered immune cells according the present invention are listed in Table 3.

For instance, the inserted exogenous coding sequence(s) can have the effect of reducing or preventing the expression, by the engineered immune cell of at least one protein selected from PD1 (Uniprot Q15116), CTLA4 (Uniprot P16410), PPP2CA (Uniprot P67775), PPP2CB (Uniprot P62714), PTPN6 (Uniprot P29350), PTPN22 (Uniprot Q9Y2R2), LAG3 (Uniprot P18627), HAVCR2 (Uniprot Q8TDQ0), BTLA (Uniprot Q7Z6A9), CD160 (Uniprot 095971), TIGIT (Uniprot Q495A1), CD96 (Uniprot P40200), CRTAM (Uniprot 095727), LAIR1 (Uniprot Q6GTX8), SIGLEC7 (Uniprot Q9Y286), SIGLEC9 (Uniprot Q9Y336), CD244 (Uniprot Q9BZW8), TNFRSF10B (Uniprot 014763), TNFRSF10A (Uniprot 000220), CASP8 (Uniprot Q14790), CASP10 (Uniprot Q92851), CASP3 (Uniprot P42574), CASP6 (Uniprot P55212), CASP7 (Uniprot P55210), FADD (Uniprot Q13158), FAS (Uniprot P25445), TGFBRII (Uniprot P37173), TGFBRI (Uniprot Q15582), SMAD2 (Uniprot Q15796), SMAD3 (Uniprot P84022), SMAD4 (Uniprot Q13485), SMAD10 (Uniprot B7ZSB5), SKI (Uniprot P12755), SKIL (Uniprot P12757), TGIF1 (Uniprot Q15583), IL10RA (Uniprot Q13651), IL10RB (Uniprot Q08334), HMOX2 (Uniprot P30519), IL6R (Uniprot P08887), IL6ST (Uniprot P40189), EIF2AK4 (Uniprot Q9P2K8), CSK (Uniprot P41240), PAG1 (Uniprot Q9NWQ8), SIT1 (Uniprot Q9Y3P8), FOXP3 (Uniprot Q9BZS1), PRDM1 (Uniprot Q60636), BATF (Uniprot Q16520), GUCY1A2 (Uniprot P33402), GUCY1A3 (Uniprot Q02108), GUCY1B2 (Uniprot Q8BXH3) and GUCY1B3 (Uniprot Q02153). The gene editing introduced in the genes encoding the above proteins is preferably combined with an inactivation of TCR in CAR T cells.

Preference is given to inactivation of PD1 and/or CTLA4, in combination with the expression of non-endogenous immunosuppressive polypeptide, such as a PD-L1 ligand and/or CTLA-4 Ig (see also peptides of Table 1 and 2).

TABLE 3

List of genes involved into immune cells inhibitory pathways

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 BATF |
| Hypoxia mediated tolerance | iNOS induced guanylated cyclase | GUCY1A2, GUCY1A3, GUCY1B2, GUCY1B3 |

Inhibiting Suppressive Cytokines/Metabolites

According to another aspect of the invention, the inserted exogenous coding sequence has the effect of reducing or preventing the expression of genes encoding or positively regulating suppressive cytokines or metabolites or receptors thereof, in particular TGFbeta (Uniprot: P01137), TGFbR (Uniprot: P37173), IL10 (Uniprot: P22301), IL10R (Uniprot: Q13651 and/or Q08334), A2aR (Uniprot: P29274), GCN2 (Uniprot: P15442) and PRDM1 (Uniprot: 075626).

Preference is given to engineered immune cells in which a sequence encoding IL-2, IL-12 or IL-15 replaces the sequence of at least one of the above endogenous genes.

Inducing Resistance to Chemotherapy Drugs

According to another aspect of the present method, the inserted exogenous coding sequence has the effect of reducing or preventing the expression of a gene responsible for the sensitivity of the immune cells to compounds used in standard of care treatments for cancer or infection, such as drugs purine nucleotide analogs (PNA) or 6-Mercaptopurine (6MP) and 6 thio-guanine (6TG) commonly used in chemotherapy. Reducing or inactivating the genes involved into the mode of action of such compounds (referred to as "drug sensitizing genes") improves the resistance of the immune cells to same.

Examples of drug sensitizing gene are those encoding DCK (Uniprot P27707) with respect to the activity of PNA, such a clorofarabine et fludarabine, HPRT (Uniprot P00492) with respect to the activity of purine antimetabolites such as 6MP and 6TG, and GGH (Uniprot Q92820) with respect to the activity of antifolate drugs, in particular methotrexate.

This enables the cells to be used after or in combination with conventional anti-cancer chemotherapies.

Resistance to Immune-Suppressive Treatments

According to another aspect of the present invention, the inserted exogenous coding sequence has the effect of reducing or preventing the expression of receptors or proteins, which are drug targets, making said cells resistant to immune-depletion drug treatments. Such target can be glucocorticoids receptors or antigens, to make the engineered immune cells resistant to glucocorticoids or immune depletion treatments using antibodies such as Alemtuzumab, which is used to deplete CD52 positive immune cells in many cancer treatments.

Also the method of the invention can comprise gene targeted insertion in endogenous gene(s) encoding or regulating the expression of CD52 (Uniprot P31358) and/or GR (Glucocorticoids receptor also referred to as NR3C1—Uniprot P04150).

Improving CAR Positive Immune Cells Activity and Survival

According to another aspect of the present invention, the inserted exogenous coding sequence can have the effect of reducing or preventing the expression of a surface antigen, such as BCMA, CS1 and CD38, wherein such antigen is one targeted by a CAR expressed by said immune cells.

This embodiment can solve the problem of CAR targeting antigens that are present at the surface of infected or malignant cells, but also to some extent expressed by the immune cell itself.

According to a preferred embodiment the exogenous sequence encoding the CAR or one of its constituents is integrated into the gene encoding the antigen targeted by said CAR to avoid self-destruction of the immune cells.

Engineered Immune Cells and Populations of Immune Cells

The present invention is also drawn to the variety of engineered immune cells obtainable according to one of the method described previously under isolated form or as part of populations of cells.

According to a preferred aspect of the invention the engineered cells are primary immune cells, such as NK cells or T-cells, which are generally part of populations of cells that may involve different types of cells. In general, population deriving from patients or donors isolated by leukapheresis from PBMC (peripheral blood mononuclear cells).

According to a preferred aspect of the invention, more than 50% of the immune cells comprised in said population are TCR negative T-cells. According to a more preferred aspect of the invention, more than 50% of the immune cells comprised in said population are CAR positive T-cells.

The present invention encompasses immune cells comprising any combinations of the different exogenous coding sequences and gene inactivation, which have been respectively and independently described above. Among these combinations are particularly preferred those combining the expression of a CAR under the transcriptional control of an endogenous promoter that is steadily active during immune cell activation and preferably independently from said activation, and the expression of an exogenous sequence encoding a cytokine, such as IL-2, IL-12 or IL-15, under the transcriptional control of a promoter that is up-regulated during the immune cell activation.

Another preferred combination is the insertion of an exogenous sequence encoding a CAR or one of its constituents under the transcription control of the hypoxia-inducible factor 1 gene promoter (Uniprot: Q16665).

The invention is also drawn to a pharmaceutical composition comprising an engineered primary immune cell or immune cell population as previously described for the treatment of infection or cancer, and to a method for treating a patient in need thereof, wherein said method comprises:

preparing a population of engineered primary immune cells according to the method of the invention as previously described;

optionally, purifying or sorting said engineered primary immune cells;

activating said population of engineered primary immune cells upon or after infusion of said cells into said patient.

Activation and Expansion of T Cells

Whether prior to or after genetic modification, the immune cells according to the present invention can be activated or expanded, even if they can activate or proliferate independently of antigen binding mechanisms. T-cells, in particular, can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. T cells are generally expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1 L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Compositions and Applications

The method of the present invention described above allows producing engineered primary immune cells within a limited time frame of about 15 to 30 days, preferably between 15 and 20 days, and most preferably between 18 and 20 days so that they keep their full immune therapeutic potential, especially with respect to their cytotoxic activity.

These cells form a population of cells, which preferably originate from a single donor or patient. These populations of cells can be expanded under closed culture recipients to comply with highest manufacturing practices requirements and can be frozen prior to infusion into a patient, thereby providing "off the shelf" or "ready to use" therapeutic compositions.

As per the present invention, a significant number of cells originating from the same Leukapheresis can be obtained, which is critical to obtain sufficient doses for treating a patient. Although variations between populations of cells originating from various donors may be observed, the number of immune cells procured by a leukapheresis is generally about from $10^8$ to $10^{10}$ cells of PBMC. PBMC comprises several types of cells: granulocytes, monocytes and lymphocytes, among which from 30 to 60% of T-cells, which generally represents between $10^8$ to $10^9$ of primary T-cells from one donor. The method of the present invention generally ends up with a population of engineered cells that reaches generally more than about $10^8$ T-cells, more generally more than about $10^9$ T-cells, even more generally more than about $10^{10}$ T-cells, and usually more than $10^{11}$ T-cells.

The invention is thus more particularly drawn to a therapeutically effective population of primary immune cells, wherein at least 30%, preferably 50%, more preferably 80% of the cells in said population have been modified according to any one the methods described herein. Said therapeutically effective population of primary immune cells, as per the present invention, comprises immune cells that have integrated at least one exogenous genetic sequence under the transcriptional control of an endogenous promoter from at least one of the genes listed in Table 6.

Such compositions or populations of cells can therefore be used as medicaments; especially for treating cancer, particularly for the treatment of lymphoma, but also for solid tumors such as melanomas, neuroblastomas, gliomas or carcinomas such as lung, breast, colon, prostate or ovary tumors in a patient in need thereof.

The invention is more particularly drawn to populations of primary TCR negative T-cells originating from a single donor, wherein at least 20%, preferably 30%, more preferably 50% of the cells in said population have been modified using sequence-specific reagents in at least two, preferably three different loci.

In another aspect, the present invention relies on methods for treating patients in need thereof, said method comprising at least one of the following steps:

(a) Determining specific antigen markers present at the surface of patients tumors biopsies;
(b) providing a population of engineered primary immune cells engineered by one of the methods of the present invention previously described expressing a CAR directed against said specific antigen markers;
(c) Administrating said engineered population of engineered primary immune cells to said patient, Generally, said populations of cells mainly comprises CD4 and CD8 positive immune cells, such as T-cells, which can undergo robust in vivo T cell expansion and can persist for an extended amount of time in-vitro and in-vivo.

The treatments involving the engineered primary immune cells according to the present invention can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In another embodiment, said isolated cell according to the invention or cell line derived from said isolated cell can be used for the treatment of liquid tumors, and preferably of T-cell acute lymphoblastic leukemia.

Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The present invention thus can provide more than 10, generally more than 50, more generally more than 100 and usually more than 1000 doses comprising between $10^6$ to $10^8$ gene edited cells originating from a single donor's or patient's sampling.

The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycopliienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

When CARs are expressed in the immune cells or populations of immune cells according to the present invention, the preferred CARs are those targeting at least one antigen selected from CD22, CD38, CD123, CS1, HSP70, ROR1, GD3, and CLL1.

The engineered immune cells according to the present invention endowed with a CAR or a modified TCR targeting CD22 are preferably used for treating leukemia, such as acute lymphoblastic leukemia (ALL), those with a CAR or a modified TCR targeting CD38 are preferably used for treating leukemia such as T-cell acute lymphoblastic leukemia (T-ALL) or multiple myeloma (MM), those with a CAR or a modified TCR targeting CD123 are preferably used for treating leukemia, such as acute myeloid leukemia (AML), and blastic plasmacytoid dendritic cells neoplasm (BPDCN), those with a CAR or a modified TCR targeting CS1 are preferably used for treating multiple myeloma (MM).

The present invention also encompasses means for detecting the engineered cells of the present invention comprising the desired genetic insertions, especially by carrying out steps of using PCR methods for detecting insertions of exogenous coding sequences at the endogenous loci referred to in the present specification, especially at the PD1, CD25, CD69, TCR and β2m loci, by using probes or primers hybridizing any sequences represented by SEQ ID NO:36 to 40.

Immunological assays may also be performed for detecting the expression by the engineered cells of CARs, GP130, and to check absence or reduction of the expression of TCR, PD1, IL-6 or IL-8 in the cells where such genes have been knocked-out or their expression reduced.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 10 base pairs (bp) in length, more preferably of 14-55 bp. Rare-cutting endonucleases significantly increase homologous recombination by inducing DNA double-strand breaks (DSBs) at a defined locus thereby allowing gene repair or gene insertion therapies (Pingoud, A. and G. H. Silva (2007). Precision genome surgery. *Nat. Biotechnol.* 25(7): 743-4).

By "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

By "vector" is meant a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e. g. adeno-associated viruses (AAV), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

As used herein, the term "locus" is the specific physical location of a DNA sequence (e.g. of a gene) into a genome. The term "locus" can refer to the specific physical location of a rare-cutting endonuclease target sequence on a chromosome or on an infection agent's genome sequence. Such a locus can comprise a target sequence that is recognized and/or cleaved by a sequence-specific endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

EXAMPLES

Example 1: AAV Driven Homologous Recombination in Human Primary T-Cells at Various Loci Under Control of Endogenous Promoters with Knock-Out of the Endogenous Gene

INTRODUCTION

Sequence specific endonuclease reagents, such as TALEN® (Cellectis, 8 rue de la Croix Jarry, 75013 PARIS) enable the site-specific induction of double-stranded breaks (DSBs) in the genome at desired loci. Repair of DSBs by cellular enzymes occurs mainly through two pathways: non-homologous end joining (NHEJ) and homology directed repair (HDR). HDR uses a homologous piece of DNA (template DNA) to repair the DSB by recombination and can be used to introduce any genetic sequence comprised in the template DNA. As shown therein, said template DNA can be delivered by recombinant adeno-associated virus (rAAV) along with an engineered nuclease such as TALEN® to introduce a site-specific DSB.
Design of the Integration Matrices
1.1. Insertion of an Apoptosis CAR in an Upregulated Locus with Knock-Out of the Endogenous PD1 Gene Coding Sequence The location of the TALEN target site has been designed to be located in the targeted endogenous PDCD1 gene (Programmed cell death protein 1 referred to as PD1—Uniprot #Q15116). The sequence encompassing 1000 bp upstream and downstream the TALEN targets is given in SEQ ID NO.1 and SEQ ID NO.2. Target sequences of the TALEN (SEQ ID: SEQ ID NO.3 and NO.4) is given in SEQ ID NO.5. The integration matrix is designed to be composed of a sequence (300 bp) homologous to the endogenous gene upstream of the TALEN site (SEQ ID NO.1), followed by a 2A regulatory element (SEQ ID NO.6), followed by a sequence encoding an apoptosis inducing CAR without the start codon (SEQ ID NO.7), followed by a STOP codon (TAG), followed by a polyadenylation sequence (SEQ ID NO.8), followed by a sequence (1000 bp) homologous to the endogenous gene downstream of the TALEN site (SEQ ID NO.2)). The insertion matrix is subsequently cloned into a promoterless rAAV vector and used to produce AAV6.
1.2 Insertion of an Interleukin in an Upregulated Locus with Knock-Out of the Endogenous Gene The location of the TALEN target site is designed to be located in the targeted endogenous PDCD1 gene (Programmed cell death protein 1, PD1). The sequence encompassing 1000 bp upstream and downstream the TALEN targets is given in SEQ ID NO.1 and SEQ ID NO.2. Target sequences of the TALEN (SEQ ID: SEQ ID NO.3 and NO.4) is given in SEQ ID NO.5. The integration matrix is designed to be composed of a sequence (300 bp) homologous to the endogenous gene upstream of the TALEN site (SEQ ID NO.1), followed by a 2A regulatory element (SEQ ID NO.6), followed by a sequence encoding an engineered single-chained human IL-12 p35 (SEQ ID NO.9) and p40 (SEQ ID NO.10) subunit fusion protein, followed by a STOP codon (TAG), followed by a polyadenylation sequence (SEQ ID NO.8), followed by a sequence (1000 bp) homologous to the endogenous gene downstream of the TALEN site (SEQ ID NO.2). The insertion matrix is subsequently cloned into a promoterless rAAV vector and used to produce AAV6.
1.3 Insertion of an Apoptosis CAR in a Weakly Expressed Locus without Knocking Out the Endogenous Gene—N-Terminal Insertion The location of the TALEN target site is designed to be located as close as possible to the start codon of the targeted endogenous LCK gene (LCK, LCK proto-oncogene, Src family tyrosine kinase [*Homo sapiens* (human)]). The sequence encompassing 1000 bp upstream and downstream the start codon is given in SEQ ID NO.11 and NO.12. The integration matrix is designed to be composed of a sequence (1000 bp) homologous to the endogenous gene upstream of the start codon, followed by a sequence encoding an apoptosis inducing CAR containing a start codon (SEQ ID NO.13), followed by a 2A regulatory element (SEQ ID NO.8), followed by a sequence (1000 bp) homologous to the endogenous gene downstream of the start codon (SEQ ID NO.12). The insertion matrix is subsequently cloned into a promoterless rAAV vector and used to produce AAV6.
1.4 Insertion of an Apoptosis CAR in a Weakly Expressed Locus without Knocking Out the Endogenous Gene—C-Terminal Insertion The location of the TALEN target site is designed to be located as close as possible to the stop codon of the targeted endogenous LCK gene (LCK, LCK proto-oncogene, Src family tyrosine kinase [*Homo sapiens* (human)]). The sequence encompassing 1000 bp upstream and downstream the stop codon is given in SEQ ID NO.14 and NO.15. The integration matrix is designed to be composed of a sequence (1000 bp) homologous to the endogenous gene upstream of the stop codon, followed by a 2A regulatory element (SEQ ID NO.8), followed by a sequence encoding an apoptosis inducing CAR without the start codon (SEQ ID NO.7), followed by a STOP codon (TAG), followed by a sequence (1000 bp) homologous to the endogenous gene downstream of the stop codon (SEQ ID NO.15). The insertion matrix is subsequently cloned into a promoterless rAAV vector and used to produce AAV6.
Expression of the Sequence-Specific Nuclease Reagents in the Transduced Cells TALEN® mRNA is synthesized using the mMessage mMachine T7 Ultra kit (Thermo Fisher Scientific, Grand Island, NY) as each TALEN is cloned downstream of a T7 promoter, purified using RNeasy columns (Qiagen, Valencia, CA) and eluted in "cytoporation medium T" (Harvard Apparatus, Holliston, MA). Human T-cells are collected and activated from whole peripheral blood provided by ALLCELLS (Alameda, CA) in X-Vivo-15 medium (Lonza, Basel, Switzerland) supplemented with 20 ng/ml human IL-2 (Miltenyi Biotech, San Diego, CA), 5% human AB serum (Gemini Bio-Products, West San Francisco, CA) and Dynabeads Human T-activator CD3/CD28 at a 1:1 bead:cell ratio (Thermo Fisher Scientific, Grand Island, NY). Beads are removed after 3 days and $5\times10^6$ cells are electroporated with 10 μg mRNA of each of the two adequate TALEN® using Cytopulse (BTX Harvard Apparatus, Holliston, MA) by applying two 0.1 mS pulses at 3,000 V/cm followed by four 0.2 mS pulses at 325 V/cm in 0.4 cm gap cuvettes in a final volume of 200 μl of "cytoporation medium T" (BTX Harvard Apparatus, Holliston, Massachusetts). Cells are immediately diluted in X-Vivo-15 media with 20 ng/mL IL-2 and incubated at 37° C. with 5% $CO_2$. After two hours, cells are incubated with AAV6 particles at 3×10^5 viral genomes (vg) per cell (37° C., 16 hours). Cells are passaged and maintained in X-Vivo-15 medium supplemented with 5% human AB serum and 20 ng/mL IL-2 until examined by flow cytometry for expression of the respective inserted gene sequences.

TABLE 4

Sequences referred to in example 1

| Sequence name | Ref. sequences | Polynucleotide or polypeptide sequences |
|---|---|---|
| PD1 left homology | SEQ ID NO. 1 | CCAAGCCCTGACCCTGGCAGGCATATGTTTCAGGAGGTCCTTGTCTTGGG<br>AGCCCAGGGTCGGGGGCCCCGTGTCTGTCCACATCCGAGTCAATGGCCCA<br>TCTCGTCTCTGAAGCATCTTTGCTGTGAGCTCTAGTCCCCACTGTCTTGC<br>TGGAAAATGTGGAGGCCCCACTGCCCACTGCCCAGGGCAGCAATGCCCAT<br>ACCACGTGGTCCCAGCTCCGAGCTTGTCCTGAAAAGGGGGCAAAGACTGG<br>ACCCTGAGCCTGCCAAGGGGCCACACTCCTCCCAGGGCTGGGGTCTCCAT<br>GGGCAGCCCCCACCCACCCAGACCAGTTACACTCCCCTGTGCCAGAGCA<br>GTGCAGACAGGACCAGGCCAGGATGCCCAAGGGTCAGGGGCTGGGGATGG<br>GTAGCCCCCAAACAGCCCTTTCTGGGGGAACTGGCCTCAACGGGGAAGGG<br>GGTGAAGGCTCTTAGTAGGAAATCAGGGAGACCCAAGTCAGAGCCAGGTG<br>CTGTGCAGAAGCTGCAGCCTCACGTAGAAGGAAGAGGCTCTGCAGTGGAG<br>GCCAGTGCCCATCCCCGGGTGGCAGAGGCCCCAGCAGAGACTTCTCAATG<br>ACATTCCAGCTGGGGTGGCCCTTCCAGAGCCCTTGCTGCCCGAGGGATGT<br>GAGCAGGTGGCCGGGGAGGCTTTGTGGGGCCACCCAGCCCCTTCCTCACC<br>TCTCTCCATCTCTCAGACTCCCCAGACAGGCCCTGGAACCCCCCCACCTT<br>CTCCCCAGCCCTGCTCGTGGTGACCGAAGGGGACAACGCCACCTTCACCT<br>GCAGCTTCTCCAACACATCGGAGAGCTTCGTGCTAAACTGGTACCGCATG<br>AGCCCCAGCAACCAGACGGACAAGCTGGCCGCCTTCCCCGAGGACCGCAG<br>CCAGCCCGGCCAGGACTGCCGCTTCCGTGTCACACAACTGCCCAACGGGC<br>GTGACTTCCACATGAGCGTGGTCAGGGCCCGGCGCAATGACAGCGGCACC |
| PD1 right homology | SEQ ID NO. 2 | GCCTGCGGGCAGAGCTCAGGGTGACAGGTGCGGCCTCGGAGGCCCCGGGG<br>CAGGGGTGAGCTGAGCCGGTCCTGGGGTGGGTGTCCCCTCCTGCACAGGA<br>TCAGGAGCTCCAGGGTCGTAGGGCAGGGACCCCCCAGCTCCAGTCCAGGG<br>CTCTGTCCTGCACCTGGGGAATGGTGACCGGCATCTCTGTCCTCTAGCTC<br>TGGAAGCACCCCAGCCCCTCTAGTCTGCCCTCACCCCTGACCCTGACCCT<br>CCACCCTGACCCCGTCCTAACCCCTGACCTTTGTGCCCTTCCAGAGAGAA<br>GGGCAGAAGTGCCCACAGCCCACCCCAGCCCCTCACCCAGGCCAGCCGGC<br>CAGTTCCAAACCCTGGTGGTTGGTGTCGTGGGCGGCCTGCTGGGCAGCCT<br>GGTGCTGCTAGTCTGGGTCCTGGCCGTCATCTGCTCCCGGGCCGCACGAG<br>GTAACGTCATCCCAGCCCCTCGGCCTGCCCTGCCCTAACCCTGCTGGCGG<br>CCCTCACTCCCGCCTCCCCTTCCTCCACCCTTCCCTCACCCCACCCCACC<br>TCCCCCCATCTCCCCGCCAGGCTAAGTCCCTGATGAAGGCCCCTGGACTA<br>AGACCCCCCACCTAGGAGCACGGCTCAGGGTCGGCCTGGTGACCCCAAGT<br>GTGTTTCTCTGCAGGGACAATAGGAGCCAGGCGCACCGGCCAGCCCCTGG<br>TGAGTCTCACTCTTTTCCTGCATGATCCACTGTGCCTTCCTTCCTGGGTG<br>GGCAGAGGTGGAAGGACAGGCTGGGACCACACGGCCTGCAGGACTCACAT<br>TCTATTATAGCCAGGACCCCACCTCCCCAGCCCCAGGCAGCAACCTCAA<br>TCCCTAAAGCCATGATCTGGGGCCCCAGCCCACCTGCGGTCTCCGGGGGT<br>GCCCGGCCCATGTGTGTGCCTGCCTGCGGTCTCCAGGGGTGCCTGGCCCA<br>CGCGTGTGCCCGCCTGCGGTCTCTGGGGGTGCCCGGCCCACATATGTGCC |
| PD1_T3C-L2 | SEQ ID NO. 3 | ATGGGCGATCCTAAAAAGAAACGTAAGGTCATCGATATCGCCGATCTACG<br>CACGCTCGGCTACAGCCAGCAGCAACAGGAGAAGATCAAACCGAAGGTTC<br>GTTCGACAGTGGCGCAGCACCACGAGGCACTGGTCGGCCACGGGTTTACA<br>CACGCGCACATCGTTGCGTTAAGCCAACACCCGGCAGCGTTAGGGACCGT<br>CGCTGTCAAGTATCAGGACATGATCGCAGCGTTGCCAGAGGCGACACACG<br>AAGCGATCGTTGGCGTCGGCAAACAGTGGTCCGGCGCACGCGCTCTGGAG<br>GCCTTGCTCACGGTGGCGGGAGAGTTGAGAGGTCCACCGTTACAGTTGGA<br>CACAGGCCAACTTCTCAAGATTGCAAAACGTGGCGGCGTGACCGCAGTGG<br>AGGCAGTGCATGCATGCGCAATGCACTGACGGGTGCCCCGCTCAACTTG<br>ACCCCCGAGCAAGTGGTGGCTATCGCTTCCAAGCTGGGGGGAAAGCAGGC<br>CCTGGAGACCGTCCAGGCCCTTCTCCCAGTGCTTTGCCAGGCTCACGGAC<br>TGACCCCTGAACAGGTGGTGGCAATTGCCTCACACGACGGGGGCAAGCAG<br>GCACTGGAGACTGTCCAGCGGCTGCTGCCTGTCCTCTGCCAGGCCCACGG<br>ACTCACTCCTGAGCAGGTCGTGGCCATTGCCAGCCACGATGGGGGCAAAC<br>AGGCTCTGGAGACCGTGCAGCGCCTCCTCCCAGTGCTGTGCCAGGCTCAT<br>GGGCTGACCCCACAGCAGGTCGTCGCCATTGCCAGTAACGGCGGGGGGAA<br>GCAGGCCCTCGAAACAGTGCAGAGGCTGCTGCCCGTCTTGTGCCAAGCAC<br>ACGGCCTGACACCCGAGCAGGTGGTGGCCATCGCCTCTCATGACGGCGGC<br>AAGCAGGCCCTTGAGACAGTGCAGAGACTGTTGCCCGTGTTGTGTCAGGC<br>CCACGGGTTGACACCCCAGCAGGTGGTCGCCATCGCCAGCAATGGCGGGG<br>GAAAGCAGGCCCTTGAGACCGTGCAGCGGTTGCTTCAGTGTTGTGCCAG<br>GCACACGGACTGACCCCTCAACAGGTGGTCGCAATCGCCAGCTACAAGGG<br>CGGAAAGCAGGCTCTGGAGACAGTGCAGCGCCTCCTGCCCGTGCTGTGTC<br>AGGCTCACGGACTGACACCACAGCAGGTGGTCGCCATCGCCAGTAACGGG<br>GGCGGCAAGCAGGCTTTGGAGACCGTCCAGAGACTCCTCCCCGTCCTTTG<br>CCAGGCCCACGGGTTGACACCTCAGCAGGTCGTCGCCATTGCCTCCAACA<br>ACGGGGGCAAGCAGGCCCTCGAAACTGTGCAGAGGCTGCTGCCTGTGCTG<br>TGCCAGGCTCATGGGCTGACACCCCAGCAGGTGGTGGCCATTGCCTCTAA<br>CAACGGCGGCAAACAGGCACTGGAGACCGTGCAAAGGCTGCTGCCCGTCC<br>TCTGCCAAGCCCACGGGCTCACTCACAGCAGGTCGTGGCCATCGCCTCA<br>AACAATGGCGGGAAGCAGGCCCTGGAGACTGTGCAAAGGCTGCTCCCTGT<br>GCTCTGCCAGGCACACGGACTGACCCCTCAGCAGGTGGTGGCAATCGCTT<br>CCAACAACGGGGGAAAGCAGGCCCTCGAAACCGTGCAGCGCCTCCTCCCA |

TABLE 4-continued

Sequences referred to in example 1

| Sequence name | Ref. sequences | Polynucleotide or polypeptide sequences |
|---|---|---|
| | | GTGCTGTGCCAGGCACATGGCCTCACACCCGAGCAAGTGGTGGCTATCGC
CAGCCACGACGGAGGGAAGCAGGCTCTGGAGACCGTGCAGAGGCTGCTGC
CTGTCCTGTGCCAGGCCCACGGGCTTACTCCAGAGCAGGTCGTCGCCATC
GCCAGTCATGATGGGGGGAAGCAGGCCCTTGAGACAGTCCAGCGGCTGCT
GCCAGTCCTTTGCCAGGCTCACGGCTTGACTCCCGAGCAGGTCGTGGCCA
TTGCCCTCAAACATTGGGGGCAAACAGGCCCTGGAGACAGTGCAGGCCCTG
CTGCCCGTGTTGTGTCAGGCCCACGGCTTGACACCCCAGCAGGTGGTCGC
CATTGCCTCTAATGGCGGCGGGAGACCCGCCTTGGAGAGCATTGTTGCCC
AGTTATCTCGCCCTGATCCGGCGTTGGCCGCGTTGACCAACGACCACCTC
GTCGCCTTGGCCTGCCTCGGCGGGCGTCCTGCGCTGGATGCAGTGAAAAA
GGGGATTGGGGGATCCTATCAGCCGTTCCCAGCTGGTGAAGTCCGAGCTGG
AGGAGAAGAAATCCGAGTTGAGGCACAAGCTGAAGTACGTGCCCCACGAG
TACATCGAGCTGATCGAGATCGCCCGGAACAGCACCCAGGACCGTATCCT
GGAGATGAAGGTGATGGAGTTCTTCATGAAGGTGTACGGCTACAGGGGCA
AGCACCTGGGCGGCTCCAGGAAGCCCGACGGCGCCATCTACACCGTGGGC
TCCCCCATCGACTACGGCGTGATCGTGGACACCAAGGCCTACTCCGGCGG
CTACAACCTGCCCATCGGCCAGGCCGACGAAATGCAGAGGTACGTGGAGG
AGAACCAGACCAGGAACAAGCACATCAACCCCAACGAGTGGTGGAAGGTG
TACCCCTCCAGCGTGACCGAGTTCAAGTTCCTGTTCGTGTCCGGCCACTT
CAAGGGCAACTACAAGGCCCAGCTGACCAGGCTGAACCACATCACCAACT
GCAACGGCGCCGTGCTGTCCGTGGAGGAGCTCCTGATCGGCGGCGAGATG
ATCAAGGCCGGCACCCTGACCCTGGAGGAGGTGAGGAGGAAGTTCAACAA
CGGCGAGATCAACTTCGCGGCCGACTGATAA |
| PD1T3R | SEQ ID NO. 4 | ATGGGCGATCCTAAAAAGAAACGTAAGGTCATCGATATCGCCGATCTACG
CACGCTCGGCTACAGCCAGCAGCAACAGGAGAAGATCAAACCGAAGGTTC
GTTCGACAGTGGCGCAGCACCACGAGGCACTGGTCGGCCACGGGTTTACA
CACGCGCACATCGTTGCGTTAAGCCAACACCCGGCAGCGTTAGGGACCGT
CGCTGTCAAGTATCAGGACATGATCGCAGCGTTGCCAGAGGCGACACACG
AAGCGATCGTTGGCGTCGGCAAACAGTGGTCCGGCGCACGCGCTCTGGAG
GCCTTGCTCACGGTGGCGGGAGAGTTGAGAGGTCCACCGTTACAGTTGGA
CACAGGCCAACTTCTCAAGATTGCAAAACGTGGCGGCGTGACCGCAGTGG
AGGCAGTGCATGCATGGCGCAATGCACTGACGGGTGCCCCGCTCAACTTG
ACCCCCGAGCAAGTCGTCGCAATCGCCAGCCATGATGGAGGGAAGCAAGC
CCTCGAAACCGTGCAGCGGTTGCTTCCTGTGCTCTGCCAGGCCCACGGCC
TTACCCCTCAGCAGGTGGTGGCCATCGCAAGTAACGGAGGAGGAAAGCAA
GCCTTGGAGACAGTGCAGCGCCTGTTGCCCGTGCTGTGCCAGGCACACGG
CCTCACACCAGAGCAGGTCGTGGCCATTGCCTCCCATGACGGGGGGAAAC
AGGCTCTGGAGACCGTCCAGAGGCTGCTGCCCGTCCTCTGTCAAGCTCAC
GGCCTGACTCCCCAACAAGTGGTCGCCATCGCCTCTAATGGCGGCGGGAA
GCAGGCACTGGAAACAGTGCAGAGACTGCTCCCTGTGCTTTGCCAAGCTC
ATGGGTTGACCCCCAACAGGTCGTCGCTATTGCCTCAAACGGGGGGGGC
AAGCAGGCCCTTGAGACTGTGCAGAGGCTGTTGCCAGTGCTGTGTCAGGC
TCACGGGCTCACTCCACAACAGGTGGTCGCAATTGCCAGCAACGGCGGCG
GAAAGCAAGCTCTTGAAACCGTGCAACGCCTCCTGCCCGTGCTCTGTCAG
GCTCATGGCCTGACACCACAACAAGTCGTGGCCATCGCCAGTAATAATGG
CGGGAAACAGGCTCTTGAGACCGTCCAGAGGCTGCTCCCAGTGCTCTGCC
AGGCACACGGGCTGACCCCCGAGCAGGTGGTGGCTATCGCCAGCAATATT
GGGGGCAAGCAGGCCCTGGAAACAGTCCAGGCCCTGCTGCCAGTGCTTTG
CCAGGCTCACGGGCTCACTCCCCAGCAGGTCGTGGCAATCGCCTCCAACG
GCGGAGGGAAGCAGGCTCTGGAGACCGTGCAGAGACTGCTGCCCGTCTTG
TGCCAGGCCCACGGACTCACACCTGAACAGGTCGTCGCCATTGCCCTCTCA
CGATGGGGGCAAACAAGCCCTGGAGACAGTGCAGCGGCTGTTGCCCTGTGT
TGTGCCAAGCCCACGCGTTGACTCCTCAACAAGTGGTCGCCATCGCCTCA
AATGGCGGCGGAAAACAAGCTCTGGAGACAGTGCAGAGGTTGCTGCCCGT
CCTCTGCCAAGCCCACGGCCTGACTCCCCAACAGGTCGTCGCCATTGCCA
GCAACAACGGAGGAAAGCAGGCTCTCGAAACTGTGCAGCGGCTGCTTCCT
GTGCTGTGTCAGGCTCATGGGCTGACCCCCGAGCAAGTGGTGGCTATTGC
CTCTAATGGAGGCAAGCAAGCCCTTGAGACAGTCCAGAGGCTGTTGCCAG
TGCTGTGCCAGGCCCACGGGCTCACACCCCAGCAGGTGGTCGCCATCGCC
AGTAACAACGGGGGCAAACAGGCATTGGAAACCGTCCAGCGCCTGCTTCC
AGTGCTCTGCCAGGCACACGGACTGACACCCGAACAGGTGGTGGCCATTG
CATCCCATGATGGGGGCAAGCAGGCCCTGGAGACCGTGCAGAGACTCCTG
CCAGTGTTGTGCCAAGCTCACGGCCTCACCCCTCAGCAAGTCGTGGCCAT
CGCCTCAAACGGGGGGGGCCGGCCTGCACTGGAGAGCATTGTTGCCCAGT
TATCTCGCCCTGATCCGGCGTTGGCCGCGTTGACCAACGACCACCTCGTC
GCCTTGGCCTGCCTCGGCGGGCGTCCTGCGCTGGATGCAGTGAAAAAGGG
ATTGGGGGATCCTATCAGCCGTTCCCAGCTGGTGAAGTCCGAGCTGGAGG
AGAAGAAATCCGAGTTGAGGCACAAGCTGAAGTACGTGCCCCACGAGTAC
ATCGAGCTGATCGAGATCGCCCGGAACAGCACCCAGGACCGTATCCTGGA
GATGAAGGTGATGGAGTTCTTCATGAAGGTGTACGGCTACAGGGGCAAGC
ACCTGGGCGGCTCCAGGAAGCCCGACGGCGCCATCTACACCGTGGGCTCC
CCCATCGACTACGGCGTGATCGTGGACACCAAGGCCTACTCCGGCGGCTA
CAACCTGCCCATCGGCCAGGCCGACGAAATGCAGAGGTACGTGGAGGAGA
ACCAGACCAGGAACAAGCACATCAACCCCAACGAGTGGTGGAAGGTGTAC |

TABLE 4-continued

Sequences referred to in example 1

| Sequence name | Ref. sequences | Polynucleotide or polypeptide sequences |
|---|---|---|
| | | CCCTCCAGCGTGACCGAGTTCAAGTTCCTGTTCGTGTCCGGCCACTTCAA<br>GGGCAACTACAAGGCCCAGCTGACCAGGCTGAACCACATCACCAACTGCA<br>ACGGCGCCGTGCTGTCCGTGGAGGAGCTCCTGATCGGCGGCGAGATGATC<br>AAGGCCGGCACCCTGACCCTGGAGGAGGTGAGGGAGGAAGTTCAACAACGG<br>CGAGATCAACTTCGCGGCCGACTGATAA |
| PD1-T3 | SEQ ID NO. 5 | TACCTCTGTGGGGCCATCTCCCTGGCCCCCAAGGCGCAGATCAAAGAGA |
| 2A-element | SEQ ID NO. 6 | TCCGGTGAGGGCAGAGGAAGTCTTCTAACATGCGGTGACGTGGAGGAGAA<br>TCCGGGCCCC |
| apoptosis CAR (without start codon | SEQ ID NO. 7 | GCTTTGCCTGTCACTGCCTTGCTGCTTCCACTTGCTCTGTTGTTGCACGC<br>CGCAAGACCCGAGGTCAAGCTCCAGGAAAGCGGACCAGGGCTGGTGGCCC<br>CTAGTCAGTCATTGAGCGTCACTTGCACCGTCAGCGGCGTGTCTCTGCCC<br>GATTACGGCGTGAGCTGGATCAGACAGCCCCCAAGGAAGGGACTGGAGTG<br>GCTGGGCGTCATCTGGGGAGCGAGACTACCTACTACAACAGCGCCCTGA<br>AGAGCAGGCTGACCATCATTAAGGACAACTCCAAGTCCCAGGTCTTTCTG<br>AAAATGAACAGCCTGCAGACTGATGACACTGCCATCTACTACTGCGCCAA<br>GCATTACTACTACGGGGGCAGCTACGCTATGGACTACTGGGGGCAGGGGA<br>CCTCTGTCACAGTGTCAAGTGGCGGAGGAGGCAGTGGCGGAGGGGGAAGT<br>GGGGGCGGCGGCAGCGACATCCAGATGACCCAGACAACATCCAGCCTCTC<br>CGCCTCTCTGGGCGACAGAGTGACAATCAGCTGCGGGCAGTCAGGACA<br>TCAGCAAGTATCTCAATTGGTACCAGCAGAAACCAGACGGGACAGTGAAA<br>TTGCTGATCTACCACACATCCAGGCTGCACTCAGGAGTCCCCAGCAGGTT<br>TTCCGGCTCCGGCTCCGGGACAGATTACAGTCTGACCATTTCCAACCTGG<br>AGCAGGAGGATATTGCCACATACTTTTGCCAGCAAGGCAACACTCTGCCC<br>TATACCTTCGGCGGAGGCACAAAACTGGAGATTACTCGGTCGGATCCCGA<br>GCCCAAATCTCCTGACAAAACTCACACATGCCCACCGTGCCCAGCACCTC<br>CCGTGGCCGGCCCGTCAGTGTTCCTCTTCCCCCCAAAACCCAAGGACACC<br>CTCATGATCGCCCGGACCCCTGAGGTCACATGCGTGGTGGTGGACGTGAG<br>CCACGAGGACCCTGAGGTCAAGTTCAACTGGTACGTGGACGGCGTGGAGG<br>TGCATAATGCCAAGACAAAGCCGCGGGAGGAGCAGTACAACAGCACGTAC<br>CGTGTGGTCAGCGTCCTCACCGTCCTGCACCAGGACTGGCTGAATGGCAA<br>GGAGTACAAGTGCAAGGTGTCCAACAAAGCCCTCCCAGCCCCCATCGAGA<br>AAACCATCTCCAAAGCCAAAGGGCAGCCCCGAGAACCACAGGTGTACACC<br>CTGCCCCCATCCCGGGATGAGCTGACCAAGAACCAGGTCAGCCTGACCTG<br>CCTGGTCAAAGGCTTCTATCCCAGCGACATCGCCGTGGAGTGGGAGAGCA<br>ATGGGCAACCGGAGAACAACTACAAGACCACGCCTCCCGTGCTGGACTCC<br>GACGGCTCCTTCTTCCTCTACAGCAAGCTCACCGTGGACAAGAGCAGGTG<br>GCAGCAGGGGAACGTGTTCTCATGCTCCGTGATGCATGAGGCCCTGCACA<br>ATCACTATACCCAGAAATCTCTGAGTCTGAGCCCAGGCAAGAAGGATATT<br>TTGGGGTGGCTTTGCCTTCTTCTTTTGCCAATTCCACTAATTGTTTGGGT<br>GAAGAGAAAGGAAGTACAGAAAACATGCAGAAAGCACAGAAAGGAAAACC<br>AAGGTTCTCATGAATCTCCAACCTTAAATCCTGAAACAGTGGCAATAAAT<br>TTATCTGATGTTGACTTGAGTAAATATATCACCACTATTGCTGGAGTCAT<br>GACACTAAGTCAAGTTAAAGGCTTTGTTCGAAAGAATGGTGTCAATGAAG<br>CCAAAATAGATGAGATCAAGAATGACAATGTCCAAGACACAGCAGAACAG<br>AAAGTTCAACTGCTTCGTAATTGGCATCAACTTCATGGAAAGAAAGAAGC<br>GTATGACACATTGATTGCAGATCTCAAAAAAGCCAATCTTTGTACTCTTG<br>CAGAGAAAATTCAGACTATCATCCTCAAGGACATTACTAGTGACTCAGAA<br>AATTCAAACTTCAGAAATGAAATCCAGAGCTTGGTCGAA |
| BGH polyA | SEQ ID NO. 8 | TCTAGAGGGCCCGTTTAAACCCGCTGATCAGCCTCGACTGTGCCTTCTAG<br>TTGCCAGCCATCTGTTGTTTGCCCCTCCCCCGTGCCTTCCTTGACCCTGG<br>AAGGTGCCACTCCCACTGTCCTTTCCTAATAAAATGAGGAAATTGCATCG<br>CATTGTCTGAGTAGGTGTCATTCTATTCTGGGGGGTGGGGTGGGGCAGGA<br>CAGCAAGGGGGAGGATTGGGAAGACAATAGCAGGCATGCTGGGGATGCGG<br>TGGGCTCTATGACTAGTGGCGAATTC |
| Interleukin-12 subunit alpha | SEQ ID NO. 9 | MCPARSLLLVATLVLLDHLSLARNLPVATPDPGMFPCLHHSQNLLRAVSN<br>MLQKARQTLEFYPCTSEEIDHEDITKDKTSTVEACLPLELTKNESCLNSR<br>ETSFITNGSCLASRKTSFMMALCLSSIYEDLKMYQVEFKTMNAKLLMDPK<br>RQIFLDQNMLAVIDELMQALNFNSETVPQKSSLEEPDFYKTKIKLCILLH<br>AFRIRAVTIDRVMSYLNAS |
| Interleukin-12 subunit beta | SEQ ID NO. 10 | MCHQQLVISWFSLVFLASPLVAIWELKKDVYVVELDWYPDAPGEMVVLTC<br>DTPEEDGITWTLDQSSEVLGSGKTLTIQVKEFGDAGQYTCHKGGEVLSHS<br>LLLLHKKEDGIWSTDILKDQKEPKNKTFLRCEAKNYSGRFTCWWLTTIST<br>DLTFSVKSSRGSSDPQGVTCGAATLSAERVRGDNKEYEYSVECQEDSACP<br>AAEESLPIEVMVDAVHKLKYENYTSSFFIRDIIKPDPPKNLQLKPLKNSR<br>QVEVSWEYPDTWSTPHYFSLTFCVQVQGKSKREKKDRVFTDKTSATVIC<br>RKNASISVRAQDRYYSSSWSEWASVPCS |

TABLE 4-continued

Sequences referred to in example 1

| Sequence name | Ref. sequences | Polynucleotide or polypeptide sequences |
|---|---|---|
| Lck left homology | SEQ ID NO. 11 | GGGATAGGGGGTGCCTCTGTGTGTGTGTGAGAGTGTGTGTGTGTAGGG<br>TGTGTATATGTATAGGGTGTGTGTGAGTGTGTGTGTGAGAGAGTGTGT<br>GTGTGGCAGAATAGACTGCGGAGGTGGATTTCATCTTGATATGAAAGGTC<br>TGGAATGCATGGTACATTAAACTTTGAGGACAGCGCTTTCCAAGCACTCT<br>GAGGAGCAGCCCTAGAGAAGGAGGAGCTGCAGGGACTCCGGGGGCTTCAA<br>AGTGAGGGCCCCACTCTGCTTCAGGCAAAACAGGCACACATTTATCACTT<br>TATCTATGGAGTTCTGCTTGATTTCATCAGACAAAAAATTTCCACTGCTA<br>AAACAGGCAAATAAACAAAAAAAAAGTTATGGCCAACAGAGTCACTGGAG<br>GGTTTTCTGCTGGGGAGAAGCAAGCCCGTGTTTGAAGGAACCCTGTGAGA<br>TGACTGTGGGCTGTGTGAGGGGAACAGCGGGGGCTTGATGGTGGACTTCG<br>GGAGCAGAAGCCTCTTTCTCAGCCTCCTCAGCTAGACAGGGGAATTATAA<br>TAGGAGGTGTGGCGTGCACACCTCTCCAGTAGGGAGGGTCTGATAAGTC<br>AGGTCTCTCCCAGGCTTGGGAAAGTGTGTGTCATCTCTAGGAGGTGGTCC<br>TCCCAACACAGGGTACTGGCAGAGGGAGAGGGAGGGGGCAGAGGCAGGAA<br>GTGGGTAACTAGACTAACAAAGGTGCCTGTGGCGGTTTGCCCATCCCAGG<br>TGGGAGGGTGGGGCTAGGGCTCAGGGGCCGTGTGTGAATTTACTTGTAGC<br>CTGAGGGCTCAGAGGGAGCACCGGTTTGGAGCTGGGACCCCCTATTTTAG<br>CTTTTCTGTGGCTGGTGAATGGGGATCCCAGGATCTCACAATCTCAGGTA<br>CTTTTGGAACTTTCCAGGGCAAGGCCCCATTATATCTGATGTTGGGGGAG<br>CAGATCTTGGGGGAGCCCCTTCAGCCCCTCTTCCATTCCCTCAGGGACC |
| lck right homology | SEQ ID NO. 12 | GGCTGTGGCTGCAGCTCACACCCGGAAGATGACTGGATGGAAAACATCGA<br>TGTGTGTGAGAACTGCCATTATCCCATAGTCCCACTGGATGGCAAGGGCA<br>CGGTAAGAGGCGAGACAGGGGCCTTGGTGAGGGAGTTGGGTAGAGAATGC<br>AACCCAGGAGAAAGAAATGACCAGCACTACAGGCCCTTGAAAGAATAGAG<br>TGGCCCTCTCCCCTGAAATACAGAAAGGAAAAGAGGCCCAGAGAGGGGAA<br>GGGAATCTCCTAAGATCACACAGAAAGTAGTTGGTAAACTCAGGGATAAC<br>ATCTAACCAGGCTGGAGAGGCTGAGAGCAGAGCAGGGGGGAAGGGGGCCA<br>GGGTCTGACCCAATCTTCTGCTTTCTGACCCCACCCTCATCCCCCACTCC<br>ACAGCTGCTCATCCGAAATGGCTCTGAGGTGCGGGACCCACTGGTTACCT<br>ACGAAGGCTCCAATCCGCCGGCTTCCCCACTGCAAGGTGACCCCAGGCAG<br>CAGGGCCTGAAAGACAAGGCCTGCGGATCCCTGGCTGTTGGCTTCCACCT<br>CTCCCCCACCTACTTTCTCCCCGGTCTTGCCTTCCTTGTCCCCCACCCTG<br>TAACTCCAGGCTTCCTGCCGATCCCAGCTCGGTTCTCCCTGATGCCCCTT<br>GTCTTTACAGACAACCTGGTTATCGCTCTGCACAGCTATGAGCCCTCTCA<br>CGACGGAGATCTGGGCTTTGAGAAGGGGGAACAGCTCCGCATCCTGGAGC<br>AGTGAGTCCCTCTCCACCTTGCTCTGGCGGAGTCCGTGAGGGAGCGGCGA<br>TCTCCGCGACCCGCAGCCCTCCTGCGGCCCTTGACCAGCTCGGGGTGGCC<br>GCCCTTGGGACAAAATTCGAGGCTCAGTATTGCTGAGCCAGGGTTGGGGG<br>AGGCTGGCTTAAGGGGTGGAGGGGTCTTTGAGGGAGGGTCTCAGGTCGAC<br>GGCTGAGCGAGCCACACTGACCCACCTCCGTGGCGCAGGAGCGGCGAGTG |
| apoptosis CAR (with start codon) | SEQ ID NO. 13 | ATGGCTTTGCCTGTCACTGCCTTGCTGCTTCCACTTGCTCTGTTGTTGCA<br>CGCCGCAAGACCCGAGGTCAAGCTCCAGGAAAGCGGACCAGGGTCGGTGG<br>CCCCTAGTCAGTCATTGAGCGTCACTTGCACCGTCAGCGGCGTGTCTCTG<br>CCCGATTACGGCGTGAGCTGGATCAGACAGCCCCAAGGAAGGGACTGGA<br>GTGGCTGGGCGTCATCTGGGGAGCGAGACTACCTACTACAACAGCGCCC<br>TGAAGAGCAGGCTGACCATCATTAAGGACAACTCCAAGTCCCAGGTCTTT<br>CTGAAAATGAACAGCCTGCAGACTGATGACACTGCCATCTACTACTGCGC<br>CAAGCATTACTACTACGGGGGCAGCTACGCTATGGACTACTGGGGGCAGG<br>GGACCTCTGTCACAGTGTCAAGTGGCGGAGGAGGCAGTGGCGGAGGGGGA<br>AGTGGGGGCGGCGGCAGCGACATCCAGATGACCCAGACAACATCCAGCCT<br>CTCCGCCTCTCTGGGCGACAGAGTGACAATCAGCTGCCGGGCCAGTCAGG<br>ACATCAGCAAGTATCTCAATTGGTACCAGCAGAAACCAGACGGGACAGTG<br>AAATTGCTGATCTACCACACATCCAGGCTGCACTCAGGAGTCCCCAGCAG<br>GTTTTCCGGCTCCGGCTCCGGGACAGATTACAGTCTGACCATTTCCAACC<br>TGGAGCAGGAGGATATTGCCACATACTTTTGCCAGCAAGGCAACACTCTG<br>CCCTATACCTTCGGCGAGGCACAAAACTGGAGATTACTCGGTCGGATCC<br>CGAGCCCAAATCTCCTGACAAAACTCACACATGCCCACCGTGCCCAGCAC<br>CTCCCGTGGCCGGCCCGTCAGTGTTCCTCTTCCCCCCAAAACCCAAGGAC<br>ACCCTCATGATCGCCCGGACCCCTGAGGTCACATGCGTGGTGGTGGACGT<br>GAGCCACGAGGACCCTGAGGTCAAGTTCAACTGGTACGTGGACGGCGTGG<br>AGGTGCATAATGCCAAGACAAAGCCGCGGGAGGAGCAGTACAACAGCACG<br>TACCGTGTGGTCAGCGTCCTCACCGTCCTGCACCAGGACTGGCTGAATGG<br>CAAGGAGTACAAGTGCAAGGTGTCCAACAAAGCCCTCCCAGCCCCCATCG<br>AGAAAACCATCTCCAAAGCCAAAGGGCAGCCCCGAGAACCACAGGTGTAC<br>ACCCTGCCCCCATCCCGGGATGAGCTGACCAAGAACCAGGTCAGCCTGAC<br>CTGCCTGGTCAAAGGCTTCTATCCCAGCGACATCGCCGTGGAGTGGGAGA<br>GCAATGGGCAACCGGAGAACAACTACAAGACCACGCCTCCCGTGCTGGAC<br>TCCGACGGCTCCTTCTTCCTCTACAGCAAGCTCACCGTGGACAAGAGCAG<br>GTGGCAGCAGGGGAACGTGTTCTCATGCTCCGTGATGCATGAGGCCCTGC<br>ACAATCACTATACCCAGAAATCTCTGAGTCTGAGCCCAGGCAAGAAGGAT<br>ATTTTGGGGTGGCTTTGCCTTCTTCTTTTGCCAATTCCACTAATTGTTTG<br>GGTGAAGAGAAAGGAAGTACAGAAAACATGCAGAAAGCACAGAAAGGAAA |

TABLE 4-continued

Sequences referred to in example 1

| Sequence name | Ref. sequences | Polynucleotide or polypeptide sequences |
|---|---|---|
| | | ACCAAGGTTCTCATGAATCTCCAACCTTAAATCCTGAAACAGTGGCAATA<br>AATTTATCTGATGTTGACTTGAGTAAATATATCACCACTATTGCTGGAGT<br>CATGACACTAAGTCAAGTTAAAGGCTTTGTTCGAAAGAATGGTGTCAATG<br>AAGCCAAAATAGATGAGATCAAGAATGACAATGTCCAAGACACAGCAGAA<br>CAGAAAGTTCAACTGCTTCGTAATTGGCATCAACTTCATGGAAAGAAAGA<br>AGCGTATGACACATTGATTGCAGATCTCAAAAAAGCCAATCTTTGTACTC<br>TTGCAGAGAAAATTCAGACTATCATCCTCAAGGACATTACTAGTGACTCA<br>GAAAATTCAAACTTCAGAAATGAAATCCAGAGCTTGGTCGAA |
| Lck left homology | SEQ ID NO. 14 | CTCATAACAATTCTATGAGGTAGGAACAGTTATTTACTCTATTTTCCAAA<br>TAAGGAAACTGGGCTCGCCCAAGGTTCCACAACTAACATGTGTGTATTAT<br>TGAGCATTTAATTTACACCAGGGAAGCAGGTTGTGGTGGTGTGCACCTGT<br>TGTCCAGCTATTTAGGAGGCTGAGGTGAAAGGATCACTTGAACGGAGGAG<br>TTCAAATTTGCAATGTGCTATGATTGTGCCTGTGAACAGCTGCTGCACTC<br>CAGCCTGGGCAACATAGTGAGATCCCTTATCTAAAACATTTTTTTAAGT<br>AAATAATCAGGTGGGCACGGTGGCTCACGCCTGTAATCCAGCACTTTGGG<br>AGGCTGAGGCGGGCGGATCACCTGAGGTCAGGAGTTCAAGACCAGCCTGA<br>CCAACATGGAGAAACCCGTCTCTACTAAAAATACAAAATTAGCTTGGCGT<br>GGTGGTGCATGCCTGTAATCCCAGCTACTCGAGAAGCTGAGGCAGGAGAA<br>TTGTTTGAACCTGGGAGGTGGAGGTTGCGGTGAGCCGAGATCGCACCATT<br>GCACTCCAGCCTGGGCAACAAGAGTGAAATTGCATCTCAAAAAAAAAGAA<br>AAGGAAATAATCTATACCAGGCACTCCAAGTGGTGTGACTGATATTCAAC<br>AAGTACCTCTAGTGTGACCTTACCATTGATGAAGACCAAGATTCTTTTGG<br>ATTGGTGCTCACACTGTGCCAGTTAAATATTCCGAACATTACCCTTGCCT<br>GTGGGCTTCCAGTGCCTGACCTTGATGTCCTTTCACCCATCAACCCGTAG<br>GGATGACCAACCCGGAGGTGATTCAGAACCTGGAGCGAGGCTACCGCATG<br>GTGCGCCCTGACAACTGTCCAGAGGAGCTGTACCAACTCATGAGGCTGTG<br>CTGGAAGGAGCGCCCAGAGGACCGGCCCACCTTTGACTACCTGCGCAGTG<br>TGCTGGAGGACTTCTTCACGGCCACAGAGGGCCAGTACCAGCCTCAGCCT |
| Ick right homology | SEQ ID NO. 15 | GAGGCCTTGAGAGGCCCTGGGGTTCTCCCCCTTTCTCTCCAGCCTGACTT<br>GGGGAGATGGAGTTCTTGTGCCATAGTCACATGGCCTATGCACATATGGA<br>CTCTGCACATGAATCCCACCCACATGTGACACATATGCACCTTGTGTCTG<br>TACACGTGTCCTGTAGTTGCGTGGACTCTGCACATGTCTTGTACATGTGT<br>AGCCTGTGCATGTATGTCTTGGACACTGTACAAGGTACCCCTTTCTGGCT<br>CTCCCATTTCCTGAGACCACAGAGAGAGGGGAGAAGCCTGGGATTGACAG<br>AAGCTTCTGCCCACCTACTTTTCTTTCCTCAGATCATCCAGAAGTTCCTC<br>AAGGGCCAGGACTTTATCTAATACCTCTGTGTGCTCCTCCTTGGTGCCTG<br>GCCTGGCACACATCAGGAGTTCAATAAATGTCTGTTGATGACTGTTGTAC<br>ATCTCTTTGCTGTCCACTCTTTGTGGGTGGGCAGTGGGGGTTAAGAAAAT<br>GGTAATTAGGTCACCCTGAGTTGGGGTGAAAGATGGGATGAGTGGATGTC<br>TGGAGGCTCTGCAGACCCCTTCAAATGGGACAGTGCTCCTCACCCCTCCC<br>CAAAGGATTCAGGGTGACTCCTACCTGGAATCCCTTAGGGAATGGGTGCG<br>TCAAAGGACCTTCCTCCCCATTATAAAAGGGCAACAGCATTTTTTACTGA<br>TTCAAGGGCTATATTTGACCTCAGATTTTGTTTTTTTAAGGCTAGTCAAA<br>TGAAGCGGCGGGAATGGAGGAGGAACAAATAAATCTGTAACTATCCTCAG<br>ATTTTTTTTTTTTTTGAGACTGGGTCTCACTTTTTCATCCAGGCTGGAG<br>TGCAGTCGCATGATCACGGCTCACTGTAGCCTCAACCTCTCCAGCTCAAA<br>TGCTCCTCCTGTCTCAGCCTCCCGAGTACCTGGGACTACTTTCTTGAGGC<br>CAGGAATTCAAGAACAGAGTAAGATCCTGGTCTCCAAAAAAAGTTTTAAA |

Example 2: TALEN®-Mediated Double Targeted Integration of IL-15 and CAR Encoding Matrices in T-Cells Materials X-vivo-15 was obtained for Lonza (cat #BE04-418Q), IL-2 from Miltenyi Biotech (cat #130-097-748), human serum AB from Seralab (cat #GEM-100-318), human T activator CD3/CD28 from Life Technology (cat #11132D), QBEND10-APC from R&D Systems (cat #FAB7227A), vioblue-labeled anti-CD3, PE-labeled anti-LNGFR, APC-labeled anti-CD25 and PE-labeled anti-PD1 from Miltenyi (cat #130-094-363, 130-112-790, 130-109-021 and 130-104-892 respectively) 48 wells treated plates (CytoOne, cat #CC7682-7548), human IL-15 Quantikine ELISA kit from R&D systems (cat #S1500), ONE-Glo from Promega (cat #E6110). AAV6 batches containing the different matrices were obtained from Virovek, PBMC cells were obtained from AllCells, (cat #PB004F) and Raji-Luciferase cells were obtained after Firefly Luciferase-encoding lentiviral particles transduction of Raji cells from ATCC (cat #CCL-86).

Methods 2.1—Transfection-Transduction

The double targeted integration at TRAC and PD1 or CD25 loci were performed as follows. PBMC cells were first thawed, washed, resuspended and cultivated in X-vivo-15 complete media (X-vivo-15, 5% AB serum, 20 ng/mL IL-2). One day later, cells were activated by Dynabeads human T activator CD3/CD28 (25 uL of beads/$1E^6$ CD3 positive cells) and cultivated at a density of $1E^6$ cells/mL for 3 days in X-vivo complete media at 37° C. in the presence of 5% $CO_2$. Cells were then split in fresh complete media and transduced/transfected the next day according to the following procedure. On the day of transduction-transfection, cells were first de-beaded by magnetic separation (EasySep), washed twice in Cytoporation buffer T (BTX Harvard Apparatus, Holliston, Massachusetts) and resuspended at a final concentration of $28E^6$ cells/mL in the same solution. Cellular suspension was mixed with 5 µg mRNA encoding TRAC TALEN® arms (SEQ ID NO:16 and 17) in the presence or in the absence of 15 µg of mRNA encoding arms of either CD25 or PD1 TALEN® (SEQ ID NO:18 and 19 and SEQ ID NO:20 and 21 respectively) in a final volume of 200 µl. TALEN® is a standard format of TALE-nucleases resulting from a fusion of TALE with Fok-1 Transfection was performed using Pulse Agile technology, by applying two 0.1 mS pulses at 3,000 V/cm followed by four 0.2 mS pulses at 325 V/cm in 0.4 cm gap cuvettes and in a final volume of 200 µl of Cytoporation buffer T (BTX Harvard Apparatus, Holliston, Massachusetts). Electroporated cells were then immediately transferred to a 12-well plate containing 1 mL of prewarm X-vivo-15 serum-free media and incubated for 37° C. for 15 min. Cells were then concentrated to $8E^6$ cells/mL in 250 µL of the same media in the presence of AAV6 particles (MOI=$3E^6$ vg/cells) comprising the donor matrices in 48 wells regular treated plates. After 2 hours of culture at 30° C., 250 µL of Xvivo-15 media supplemented by 10% AB serum and 40 ng/ml IL-2 was added to the cell suspension and the mix was incubated 24 hours in the same culture conditions. One day later, cells were seeded at $1E^6$ cells/mL in complete X-vivo-15 media and cultivated at 37° C. in the presence of 5% $CO_2$.

2.2—Activation-Dependent Expression of ALNGFR and Secretion of IL15

Engineered T-cells were recovered from the transfection-transduction process described earlier and seeded at $1E^6$ cells/mL alone or in the presence of Raji cells (E:T=1:1) or Dynabeads (12.5 uL/$1E^6$ cells) in 100 µL final volume of complete X-vivo-15 media. Cells were cultivated for 48 hours before being recovered, labeled and analyzed by flow cytometry. Cells were labeled with two independent sets of antibodies. The first sets of antibodies, aiming at detecting the presence of ΔLNGFR, CAR and CD3 cells, consisted in QBEND10-APC (diluted 1/10), vioblue-labeled anti CD3 (diluted 1/25) and PE-labeled anti-ΔLNGFR (diluted 1/25). The second sets of antibodies, aiming at detecting expression of endogenous CD25 and PD1, consisted in APC-labeled anti-CD25 (diluted 1/25) and vioblue-labeled anti PD1 (diluted 1/25).

The same experimental set up was used to study IL-15 secretion in the media. Cells mixture were kept in co-culture for 2, 4, 7 and 10 days before collecting and analyzing supernatant using an IL-15 specific ELISA kit.

2.3—Serial Killing Assay

To assess the antitumor activity of engineered CAR T-cells, a serial killing assay was performed. The principle of this assay is to challenge CAR T-cell antitumor activity everyday by a daily addition of a constant amount of tumor cells. Tumor cell proliferation, control and relapse could be monitored via luminescence read out thanks to a Luciferase marker stably integrated in Tumor cell lines.

Typically, CAR T-cells are mixed to a suspension of $2.5 \times 10^5$ Raji-luc tumor cells at variable E:T ratio (E:T=5:1 or 1:1) in a total volume of 1 mL of Xvivo 5% AB, 20 ng/uL IL-2. The mixture is incubated 24 hours before determining the luminescence of 25 µL of cell suspension using ONE-Glo reagent. Cells mixture are then spun down, the old media is discarded and substituted with 1 mL of fresh complete X-vivo-15 media containing $2.5 \times 10^5$ Raji-Luc cells and the resulting cell mixture is incubated for 24 hours. This protocol is repeated 4 days.

Experiments and Results

This example describes methods to improve the therapeutic outcome of CAR T-cell therapies by integrating an IL-15/soluble IL-15 receptor alpha heterodimer (IL15/sIL15rα) expression cassette under the control of the endogenous T-cell promoters regulating PD1 and CD25 genes. Because both genes are known to be upregulated upon tumor engagement by CAR T-cells, they could be hijacked to re-express IL-IL15/sIL15rα only in vicinity of a tumor. This method aims to reduce the potential side effects of IL15/sIL15rα systemic secretion while maintaining its capacity to reduced activation induced T-cell death (AICD), promote T-cell survival, enhance T-cell antitumor activity and to reverse T-cell anergy.

The method developed to integrate IL15/sIL15rα at PD1 and CD25 loci consisted in generating a double-strand break at both loci using TALEN in the presence of a DNA repair matrix vectorized by AAV6. This matrix consists of two homology arms embedding IL15/sIL15rα coding regions separated by a 2A cis acting elements and regulatory elements (stop codon and polyA sequences). Depending on the locus targeted and its involvement in T-cell activity, the targeted endogenous gene could be inactivated or not via specific matrix design. When CD25 gene was considered as targeted locus, the insertion matrix was designed to knock-in (KI) IL15/sIL15rα without inactivating CD25 because the protein product of this gene is regarded as essential for T-cell function. By contrast, because PD1 is involved in T-cell inhibition/exhaustion of T-cells, the insertion matrix was designed to prevent its expression while enabling the expression and secretion of IL15/sIL15rα.

To illustrate this approach and demonstrate the feasibility of double targeted insertion in primary T-cells, three different matrices were designed (FIGS. 2A, 2B and 2C). The first one named CARm represented by SEQ ID NO:36 was designed to insert an anti-CD22 CAR cDNA at the TRAC locus in the presence of TRAC TALEN® (SEQ ID NO:16 and 17). The second one, IL-15_CD25m (SEQ ID NO:37) was designed to integrate IL15, sIL15rα and the surface marker named ΔLNGFR cDNAs separated by 2A cis-acting elements just before the stop codon of CD25 endogenous coding sequence using CD25 TALEN® (SEQ ID NO:18 and 19). The third one, IL-15_PD1m (SEQ ID NO:38), contained the same expression cassette and was designed to integrate in the middle of the PD1 open reading frame using PD1 TALEN® (SEQ ID NO:20 and 21). The three matrices contained an additional 2A cis-acting element located upstream expression cassettes to enable co-expression of IL15/sIL15rα and CAR with the endogenous gene targeted.

We first assessed the efficiency of double targeted insertion in T-cells by transducing them with one of the AAV6 encoding IL15/sIL15rα matrices (SEQ ID NO:41; pCLS30519) along with the one encoding the CAR and subsequently transfected the corresponding TALEN®. AAV6-assisted vectorization of matrices in the presence of mRNA encoding TRAC TALEN® (SEQ ID NO:22 and 23) and PD1 TALEN® (SEQ ID NO:24 and 25) or CD25 TALEN® (SEQ ID NO:26 and 27) enabled expression of the anti CD22 CAR in up to 46% of engineered T-cells (FIG. 3).

To determine the extent of IL15m integration at CD25 and PD1 locus, engineered T-cells were activated with either antiCD3/CD28 coated beads or with CD22 expressing Raji tumor cells. 2 days post activation, cells were recovered and analyzed by FACS using LNGFR expression as IL15/sIL15rα secretion surrogate (FIGS. 4 and 5). Our results showed that antiCD3/CD28 coated beads induced expression of ΔLNGFR by T-cells containing IL-15m_CD25 or IL-15m_PD1, independently of the presence of the anti CD22 CAR (FIG. 4A-B). Tumor cells however, only induced expression of ΔLNGFR by T-cell treated by both CARm and IL-15m. This indicated that expression of ΔLNGFR could be specifically induced through tumor cell engagement by the CAR (FIGS. 5 and 6).

As expected the endogenous CD25 gene was still expressed in activated treated T-cells (FIGS. 7 and 8) while PD1 expression was strongly impaired (FIG. 12).

To verify that expression of ΔLNGFR correlated with secretion of IL15 in the media, T-cells expressing the anti-CD22 CAR and ΔLNGFR were incubated in the presence of CD22 expressing Raji tumor cells (E:T ratio=1:1) for a total of 10 days. Supernatant were recovered at day 2, 4, 7 and 10 and the presence of IL15 was quantified by ELISA assay. Our results showed that IL15 was secreted in the media only by T-cells that were co-treated by both CARm and IL15m matrices along with their corresponding TALEN® (FIG. 13). T-cell treated with either one of these matrices were unable to secrete any significant level of IL15 with respect to resting T-cells. Interestingly, IL-15 secretion level was found transitory, with a maximum peak centered at day 4 (FIG. 14).

To assess whether the level of secreted IL-15 (SEQ ID NO:59) could impact CAR T-cell activity, CAR T-cell were co-cultured in the presence of tumor cells at E:T ratio of 5:1 for 4 days. Their antitumor activity was challenged everyday by pelleting and resuspended them in a culture media lacking IL-2 and containing fresh tumor cells. Antitumor activity of CAR T-cell was monitored everyday by measuring the luminescence of the remaining Raji tumor cells expressing luciferase. Our results showed that CAR T-cells co-expressing IL-15 had a higher antitumor activity than those lacking IL15 at all time points considered (FIG. 15).

Thus, together our results showed that we have developed a method allowing simultaneous targeted insertions of CAR and IL15 cDNA at TRAC and CD25 or PD1 loci. This double targeted insertion led to robust expression of an antiCD22 CAR and to the secretion of IL15 in the media. Levels of secreted IL15 were sufficient to enhance the activity of CAR T-cells.

TABLE 5

Sequences referred to in example 2 and 3.

| SEQ ID NO# | Sequence Name | Polypeptide sequence | RVD sequence |
|---|---|---|---|
| 16 | TALEN right TRAC | MGDPKKKRKVIDYPYDVPDYAIDIADLRTLGYSQQQQEKIKPKVRSTVAQHHE ALVGHGFTHAHIVALSQHPAALGTVAVKYQDMIAALPEATHEAIVGVGKQWSG ARALEALLTVAGELRGPPLQLDTGQLLKIAKRGGVTAVEAVHAWRNALTGAPL NLTPQQVVAIASNGGGKQALETVQRLLPVLCQAHGLTPQQVVAIASNNGGKQA LETVQRLLPVLCQAHGLTPQQVVAIASNGGGKQALETVQRLLPVLCQAHGLTP EQVVAIASHDGGKQALETVQRLLPVLCQAHGLTPEQVVAIASHDGGKQALETV QRLLPVLCQAHGLTPEQVVAIASHDGGKQALETVQRLLPVLCQAHGLTPEQVV AIASNIGGKQALETVQALLPVLCQAHGLTPQEVVAIASHDGGKQALETVQRLL PVLCQAHGLTPEQVVAIASNIGGKQALETVQALLPVLCQAHGLTPQQVVAIAS NNGGKQALETVQRLLPVLCQAHGLTPEQVVAIASNIGGKQALETVQALLPVLC QAHGLTPQQVVAIASNGGGKQALETVQRLLPVLCQAHGLTPEQVVAIASNIGG KQALETVQALLPVLCQAHGLTPQQVVAIASNGGGKQALETVQRLLPVLCQAHG LTPEQVVAIASHDGGKQALETVQRLLPVLCQAHGLTPQQVVAIASNGGGRPAL ESIVAQLSRPDPALAALTNDHLVALACLGGRPALDAVKKGLGDPISRSQLVKS ELEEKKSELRHKLKYVPHEYIELIEIARNSTQDRILEMKVMEFFMKVYGYRGK HLGGSRKPDGAIYTVGSPIDYGVIVDTKAYSGGYNLPIGQADEMQRYVEENQT RNKHINPNEWWKVYPSSVTEFKFLFVSGHFKGNYKAQLTRLNHITNCNGAVLS VEELLIGGEMIKAGTLTLEEVRRKFNNGEINFAAD | NG-NN-NG-HD-HD-HD-NI-HD-NI-NN-NI-NG-NI-NG-HD-NG# |
| 17 | TALEN Left TRAC | MGDPKKKRKVIDKETAAAKFERQHMDSIDIADLRTLGYSQQQQEKIKPKVRST VAQHHEALVGHGFTHAHIVALSQHPAALGTVAVKYQDMIAALPEATHEAIVGV GKQWSGARALEALLTVAGELRGPPLQLDTGQLLKIAKRGGVTAVEAVHAWRNA LTGAPLNLTPEQVVAIASHDGGKQALETVQRLLPVLCQAHGLTPQQVVAIASN GGGKQALETVQRLLPVLCQAHGLTPEQVVAIASHDGGKQALETVQRLLPVLCQ AHGLTPEQVVAIASNIGGKQALETVQALLPVLCQAHGLTPQQVVAIASNNGGK QALETVQRLLPVLCQAHGLTPEQVVAIASHDGGKQALETVQRLLPVLCQAHGL TPQQVVAIASNGGGKQALETVQRLLPVLCQAHGLTPQQVVAIASNNGGKQALE TVQRLLPVLCQAHGLTPQQVVAIASNNGGKQALETVQRLLPVLCQAHGLTPQQ VVAIASNGGGKQALETVQRLLPVLCQAHGLTPEQVVAIASNIGGKQALETVQA LLPVLCQAHGLTPEQVVAIASHDGGKQALETVQRLLPVLCQAHGLTPEQVVAI ASNIGGKQALETVQALLPVLCQAHGLTPEQVVAIASHDGGKWALETVQRLLPV LCQAHGLTPQQVVAIASNNGGKQALETVQRLLPVLCQAHGLTPQQVVAIASNG GGRPALESIVQALSRPDPALAALTNDHLVALACLGGRPALDAVKKGLGDPASR SQLVKSELEEKKSELRHKLKYVPHEYIELIEIARNSTQDRILEMKVMEFFMKV YGYRGKHLGGSRKPDGAIYTVGSPIDYGVIVDTKAYSGGYNLPIGQADEMQRY VEENQTRNKHINPNEWWKVYPSSVTEFKFLFVSGHFKGNYKAQLTRLNHITNC NGAVLSVEELLIGGEMIKAGTLTLEEVRRKFNNGEINFAAD | HD-NG-HD-NI-NN-HD-NG-NN-NN-NG-NI-HD-NN-NG-NI-HD-NN-NG# |
| 18 | TALEN right CD25 | MGDPKKKRKVIDYPYDVPDYAIDIADLRTLGYSQQQQEKIKPKVRSTVAQHHE ALVGHGFTHAHIVALSQHPAALGTVAVKYQDMIAALPEATHEAIVGVGKQWSG ARALEALLTVAGELRGPPLQLDTGQLLKIAKRGGVTAVEAVHAWRNALTGAPL NLTPQQVVAIASNNGGKQALETVQRLLPVLCQAHGLTPQQVVAIASNGGGKQA LETVQRLLPVLCQAHGLTPQQVVAIASNGGGKQALETVQRLLPVLCQAHGLTP EQVVAIASHDGGKQALETVQRLLPVLCQAHGLTPQQVVAIASNGGGKQALETV QRLLPVLCQAHGLTPQQVVAIASNGGGKQALETVQRLLPVLCQAHGLTPQQVV AIASNGGGKQALETVQRLLPVLCQAHGLTPQQVVAIASNGGGKQALETVQRLL PVLCQAHGLTPQQVVAIASNNGGKQALETVQRLLPVLCQAHGLTPQQVVAIAS NNGGKQALETVQRLLPVLCQAHGLTPQQVVAIASNGGGKQALETVQRLLPVLC QAHGLTPQQVVAIASNGGGKQALETVQRLLPVLCQAHGLTPQQVVAIASNGGG KQALETVQRLLPVLCQAHGLTPQQVVAIASNGGGKQALETVQRLLPVLCQAHG LTPEQVVAIASHDGGKQALETVQRLLPVLCQAHGLTPQQVVAIASNGGGRPAL | NN-NG-NG-HD-NG-NG-NG-NG-NN-NN-NG-NG-NN-NG-HD-NG# |

TABLE 5-continued

Sequences referred to in example 2 and 3.

| | | |
|---|---|---|
| | | ESIVAQLSRPDPSGSGSGGDPISRSQLVKSELEEKKSELRHKLKYVPHEYIEL<br>IEIARNSTQDRILEMKVMEFFMKVYGYRGKHLGGSRKPDGAIYTVGSPIDYGV<br>IVDTKAYSGGYNLPIGQADEMQRYVEENQTRNKHINPNEWWKVYPSSVTEFKF<br>FLFVSGHFGNYKAQLTRLNHITNCNGAVLSVEELLIGGEMIKAGTLTLEEVRR<br>KFNNGEINFAAD |
| 19 | TALEN left<br>CD25 | MGDPKKKRKVIDYPYDVPDYAIDIADLRTLGYSQQQQEKIKPKVRSTVAQHHE NI-HD-NI-NN-<br>ALVGHGFTHAHIVALSQHPAALGTVAVKYQDMIAALPEATHEAIVGVGKQWSG NN-NI-NN-NN-<br>ARALEALLTVAGELRGPPLQLDTGQLLKIAKRGGVTAVEAVHAWRNALTGAPL NI -NI-NN-NI-<br>NLTPEQVVAIASNIGGKQALETVQALLPVLCQAHGLTPEQVVAIASHDGGKQA NN-NG-NI-NG#<br>LETVQRLLPVLCQAHGLTPEQVVAIASNIGGKQALETVQALLPVLCQAHGLTP<br>QQVVAIASNNGGKQALETVQRLLPVLCQAHGLTPQQVVAIASNNGGKQALETV<br>QRLLPVLCQAHGLTPEQVVAIASNIGGKQALETVQALLPVLCQAHGLTPQQVV<br>AIASNNGGKQALETVQRLLPVLCQAHGLTPQQVVAIASNNGGKQALETVQRLL<br>PVLCQAHGLTPEQVVAIASNIGGKQALETVQALLPVLCQAHGLTPEQVVAIAS<br>NIGGKQALETVQALLPVLCQAHGLTPQQVVAIASNNGGKQALETVQRLLPVLC<br>QAHGLTPEQVVAIASNIGGKQALETVQALLPVLCQAHGLTPQQVVAIASNNGG<br>KQALETVQRLLPVLCQAHGLTPQQVVAIASNGGGKQALETVQRLLPVLCQAHG<br>LTPEQVVAIASNIGGKQALETVQALLPVLCQAHGLTPQQVVAIASNGGGRPAL<br>ESIVAQLSRPDPSGSGSGGDPISRSQLVKSELEEKKSELRHKLKYVPHEYIEL<br>IEIARNSTQDRILEMKVMEFFMKVYGYRGHKLGGSRKPDGAIYTVGSPIDYGV<br>IVDTKAYSGGYNKPIGQADEMQRYVEENQTRNKHINPNEWWKVYPSSVTEFKF<br>LFVSGHFKGNYKAQLTRLNHITNCNGAVLSVEELLIGGEMIKAGTLTLEEVRR<br>KFNNGIENFAAD |
| 20 | TALEN right<br>PD1 | MGDPKKKRKVIDYPYDVPDYAIDIADLRTLGYSQQQQEKIKPKVRSTVAQHHE KL-HD-HD-NG-<br>ALVGHGFTHAHIVALSQHPAALGTVAVKYQDMIAALPEATHEAIVGVGKQWSG HD-NG-YK-NG-<br>ARALEALLTVAGELRGPPLQLDTGQLLKIAKRGGVTAVEAVHAWRNALTGAPL NN-NN-NN-NN-<br>NLTPEQVVAIASKLGGKQALETVQALLPVLCQAHGLTPEQVVAIASHEGGKQA HD-HD-NI-NG#<br>LETVQRLLPVLCQAHGLTPEQVVAIASHDGGKQALETVQRLLPVLCQAHGLTP<br>QQVVAIASNGGGKQALETVQRLLPVLCQAHGLTPEQVVAIASHDGGKQALETV<br>QRLLPVLCQAHGLTPEQVVAIASNGGGKQALETVQRLLPVLCQAHGLTPQQVV<br>AIASYKGGKQALETVQRLLPVLCQAHGLTPQQVVAIASNGGGKQALETVQRLL<br>PVLCQAHGLTPQQVVAIASNNGGKQALETVQRLLPVLCQAHGLTPQQVVAIAS<br>NNGGKQALETVQRLLPVLCQAHGLTPQQVVAIASNNGGKQALETVQRLLPVLC<br>QAHGLTPEQVVAIASNNGGKQALETVQRLLPVLCQAHGLTPEQVVAIASHDGG<br>KQALETVQRLLPVLCQAHGLTPEQVVAIASHDGGKQALETVQRLLPVLCQAHG<br>LTPEQVVAIASNIGGKQALETVQALLPVLCQAHGLTPQQVVAIASNGGGRPAL<br>ESIVAQLSRPDPALAALTNDHLVALACLGGRPALDAVKKGLGDPISRSQLVKS<br>ELEEKKSELRHKLKYVPHEYIELIEIARNSTQDRILEMKVMEFFKKVYGYRGK<br>HLGGSRKPDGAIYTVGSPIDYGVIVDTKAYSGGYNLPIGQADEMQRYVEENQT<br>RNKHINPNEWWKVYPSSVTEFKFLFVSGHFKGNYKAQLTRLNHITNCNGAVLS<br>VEELLIGGEMIKAGTLTLEEVRRKFNNGEINFAAD |
| 21 | TALEN left<br>PD1 | MGDPKKKRKVIDKETAAAKFERQHMDSIDIADLRTLGYSQQQQEKIKPKVRST HD-NG-HD-NG-<br>VAQHHEALVGHGFTHAHIVALSQHPAALGTVAVKYQDMIAALPEATHEAIVGV NG-NG-NN-NI-<br>GKQWSGARALEALLTVAGELRGPPLQLDTGQLLKIAKRGGVTAVEAVHAWRNA NG-HD-NG-NN-<br>LTGAPLNLTPEQVVAIASHDGGKQALETVQRLLPVLCQAHGLTPQQVVAIASN N-NN-HD-NG#<br>GGGKQALETVQRLLPVLCQAHGLTPEQVVAIASHDGGKQALETVQRLLPVLCQ<br>AHGLTPQQVVAIASNGGGKQALETVQRLLPVLCQAHGLTPQQVVAIASNGGGK<br>QALETVQRLLPVLCQAHGLTPQQVVAIASNGGGKQALETVQRLLPVLCQAHGL<br>TPQQVVAIASNNGGKQALETVQRLLPVLCQAHGLTPEQVVAIASNIGGKQALE<br>TVQALLPVLCQAHGLTPQQVVAIASNGGGKQALETVQRLLPVLCQAHGLTPEQ<br>VVAIASHDGGKQALETVQRLLPVLCQAHGLTPQQVVAIASNGGGKQALETVQR<br>LLPVLCQAHGLTPQQVVAIASNNGGKQALETVQRLLPVLCQAHGLTPEQVVAI<br>ASNGGKQALETVQRLLPVLCQAHGLTPQQVVAIASNNGGKQALETVQRLLPVL<br>CQAHGLTPEQVVAIASHDGGKQALETVQRLLPVLCQAHGLTPQQVVAISNGG<br>GRPALESIVAQLSRPDPALAALTNDHLVALACLGGRPALDAVKKGLGDPISRS<br>QLVKSELEEKKSELRHKLKYVPHEYIELIEIARNSTQDRILEMKVMEFFMKVY<br>GYRGKHLGGSRKPDGAIYTVGSPIDYGVIVDTKAYSGGYNLPIGQADEMQRYV<br>EENQTRNKHINPNEWWKVYPSSVTEGKGLGVSGHFKGNYKAQLTRLNHITNCN<br>GAVLSVEELLIGGEMIKAGTLTLEEVRRKFNNGEINFAAD |

| SEQ<br>ID NO# | Sequence<br>Name | Polynucleotide sequence |
|---|---|---|
| 22 | TALEN TRAC<br>pCLS11370 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAACAGGAGAAGATCAAACCGAAGG<br>TTCGTTCGACAGTGGCGCAGCACCACGAGGCACTGGTCGGCCACGGGTTTACACACGCGCACATC<br>GTTGCGTTAAGCCAACACCCGGCAGCGTTAGGGACCGTCGCTGTCAAGTATCAGGACATGATCGC<br>AGCGTTGCCAGAGGCGACACACGAAGCGATCGTTGGCGTCGGCAAACAGTGGTCCGGCGCACGCG<br>CTCTGGAGGCCTTGCTCACGGTGGCGGGAGAGTTGAGAGGTCCACCGTTACAGTTGGACACAGGC<br>CAACTTCTCAAGATTGCAAAACGTGGCGGCGTGACCGCAGTGGAGGCAGTGCATGCATGGCGCAA<br>TGCACTGACGGGTGCCCCGCTCAACTTGACCCCCAGCAGGTGGTGGCCATCGCCAGCAATGGCG<br>GTGGCAAGCAGGCGCTGGAGACGGTCCAGCGGCTGTTGCCGGTGCTGTGCCAGGCCCACGGCTTG<br>ACCCCCAGCAGGTGGTGGCCATCGCCAGCAATAATGGTGGCAAGCAGGCGCTGGAGACGGTCCA<br>GCGGCTGTTGCCGGTGCTGTGCCAGGCCCACGGCTTGACCCCCAGCAGGTGGTGGCCATCGCCA<br>GCAATGGCGGTGGCAAGCAGGCGCTGGAGACGGTCCAGCGGCTGTTGCCGGTGCTGTGCCAGGCC<br>CACGGCTTGACCCCGGAGCAGGTGGTGGCCATCGCCAGCCACGATGGCGGCAAGCAGGCGCTGGA<br>GACGGTCCAGCGGCTGTTGCCGGTGCTGTGCCAGGCCCACGGCTTGACCCCGGAGCAGGTGGTGG<br>CCATCGCCAGCCACGATGGCGGCAAGCAGGCGCTGGAGACGGTCCAGCGGCTGTTGCCGGTGCTG |

TABLE 5-continued

Sequences referred to in example 2 and 3.

|  |  |  |
|---|---|---|
|  |  | TGCCAGGCCCACGGCTTGACCCCGGAGCAGGTGGTGGCCATCGCCAGCCACGATGGCGGCAAGCA GGCGCTGGAGACGGTCCAGCGGCTGTTTGCCGGTGCTGTGCCAGGCCCACGGCTTGACCCCGGAGC AGGTGGTGGCCATCGCCAGCAATATTGGTGGCAAGCAGGCGCTGGAGACGGTGCAGGCGCTGTTG CCGGTGCTGTGCCAGGCCCACGGCTTGACCCCGGAGCAGGTGGTGGCCATCGCCAGCCACGATGG CGGCAAGCAGGCGCTGGAGACGGTCCAGCGGCTGTTGCCGGTGCTGTGCCAGGCCCACGGCTTGA CCCCGGAGCAGGTGGTGGCCATCGCCAGCAATATTGGTGGCAAGCAGGCGCTGGAGACGGTGCAG GCGCTGTTGCCGGTGCTGTGCCAGGCCCACGGCTTGACCCCCAGCAGGTGGTGGCCATCGCCAG CAATAATGGTGGCAAGCAGGCGCTGGAGACGGTCCAGCGGCTGTTGCCGGTGCTGTGCCAGGCCC ACGGCTTGACCCCGGAGCAGGTGGTGGCCATCGCCAGCAATATTGGTGGCAAGCAGGCGCTGGAG ACGGTGCAGGCGCTGTTGCCGGTGCTGTGCCAGGCCCACGGCTTGACCCCCAGCAGGTGGTGGC CATCGCCAGCAATGGCGGTGGCAAGCAGGCGCTGGAGACGGTCCAGCGGCTGTTGCCGGTGCTGT GCCAGGCCCACGGCTTGACCCCGGAGCAGGTGGTGGCCATCGCCAGCAATATTGGTGGCAAGCAG GCGCTGGAGACGGTGCAGGCGCTGTTGCCGGTGCTGTGCCAGGCCCACGGCTTGACCCCCCAGCA GGTGGTGGCCATCGCCAGCAATGGCGGTGGCAAGCAGGCGCTGGAGACGGTCCAGCGGCTGTTGC CGGTGCTGTGCCAGGCCCACGGCTTGACCCCGGAGCAGGTGGTGGCCATCGCCAGCCACGATGGC GGCAAGCAGGCGCTGGAGACGGTCCAGCGGCTGTTGCCGGTGCTGTGCCAGGCCCACGGCTTGAC CCCTCAGCAGGTGGTGGCCATCGCCAGCAATGGCGGCGGCAGGCCGGCGCTGGAGAGCATTGTTG CCCAGTTATCTCGCCCTGATCCGGCGTTGGCCGCGTTGACCAACGACCACCTCGTCGCCTTGGCC TGCCTCGGCGGCGTCCTGCGCTGGATGCAGTGAAAAAGGGATTGGGGGATCCTATCAGCCGTTC CCAGCTGGTGAAGTCCGAGCTGGAGGAGAAGAAATCCGAGTTGAGGCACAAGCTGAAGTACGTGC CCCACGAGTACATCGAGCTGATCGAGATCGCCCGGAACAGCACCCAGGACCGTATCCTGGAGATG AAGGTGATGGAGTTCTTCATGAAGGTGTACGGCTACAGGGGCAAGCACCTGGGCGGCTCCAGGAA GCCCGACGGCGCCATCTACACCGTGGGCTCCCCCATCGACTACGGCGTGATCGTGGACACCAAGG CCTACTCCGGCGGCTACAACCTGCCCATCGGCCAGGCCGACGAAATGCAGAGGTACGTGGAGGAG AACCAGACCAGGAACAAGCACATCAACCCCAACGAGTGGTGGAAGGTGTACCCCTCCAGCGTGAC CGAGTTCAAGTTCCTGTTCGTGTCCGGCCACTTCAAGGGCAACTACAAGGCCCAGCTGACCAGGC TGAACCACATCACCAACTGCAACGGCGCCGTGCTGTCCGTGGAGGAGCTCCTGATCGGCGGCGAG ATGATCAAGGCCGGCACCCTGACCCTGGAGGAGGTGAGGAGGAAGTTCAACAACGGCGAGATCAA CTTCGCGGCCGACTGATAA |
| 23 | TALEN TRAC pCLS11369 | ATGGGCGATCCTAAAAAGAAACGTAAGGTCATCGATAAGGAGACCGCCGCTGCCAAGTTCGAGAG ACAGCACATGGACAGCATCGATATCGCCGATCTACGCACGCTCGGCTACAGCCAGCAGCAACAGG AGAAGATCAAACCGAAGGTTCGTTCGACAGTGGCGCAGCACCACGAGGCACTGGTCGGCCACGGG TTTACACACGCGCACATCGTTGCGTTAAGCCAACACCCGGCAGCGTTAGGGACCGTCGCTGTCAA GTATCAGGACATGATCGCAGCGTTGCCAGAGGCGACACACGAAGCGATCGTTGGCGTCGGCAAAC AGTGGTCCGGCGCACGCGCTCTGGAGGCCTTGCTCACGGTGGCGGGAGAGTTGAGAGGTCCACCG TTACAGTTGGACACAGGCCAACTTCTCAAGATTGCAAAACGTGGCGGCGTGACCGCAGTGGAGGC AGTCCATGCATGGCGCAATGCACTGACGGGTGCCCCGCTCAACTTGACCCCGGAGCAGGTGGTGG CCATCGCCAGCCACGATGGCGGCAAGCAGGCGCTGGAGACGGTCCAGCGGCTGTTGCCGGTGCTG TGCCAGGCCCACGGCTTGACCCCCAGCAGGTGGTGGCCATCGCCAGCAATGGCGGTGGCAAGCA GGCGCTGGAGACGGTCCAGCGGCTGTTGCCGGTGCTGTGCCAGGCCCACGGCTTGACCCCGGAGC AGGTGGTGGCCATCGCCAGCCACGATGGCGGCAAGCAGGCGCTGGAGACGGTCCAGCGGCTGTTG CCGGTGCTGTGCCAGGCCCACGGCTTGACCCCGGAGCAGGTGGTGGCCATCGCCAGCAATATTGG TGGCAAGCAGGCGCTGGAGACGGTGCAGGCGCTGTTGCCGGTGCTGTGCCAGGCCCACGGCTTGA CCCCCAGCAGGTGGTGGCCATCGCCAGCAATGGTGGCAAGCAGGCGCTGGAGACGGTGCAGCAG CGGCTGTTGCCGGTGCTGTGCCAGGCCCACGGCTTGACCCCGGAGCAGGTGGTGGCCATCGCCAG CCACGATGGCGGCAAGCAGGCGCTGGAGACGGTCCAGCGGCTGTTGCCGGTGCTGTGCCAGGCCC ACGGCTTGACCCCCAGCAGGTGGTGGCCATCGCCAGCAATGGCGGTGGCAAGCAGGCGCTGGAG ACGGTCCAGCGGCTGTTGCCGGTGCTGTGCCAGGCCCACGGCTTGACCCCCAGCAGGTGGTGGC CATCGCCAGCAATAATGGTGGCAAGCAGGCGCTGGAGACGGTCCAGCGGCTGTTGCCGGTGCTGT GCCAGGCCCACGGCTTGACCCCCAGCAGGTGGTGGCCATCGCCAGCAATAATGGTGGCAAGCAG GCGCTGGAGACGGTCCAGCGGCTGTTGCCGGTGCTGTGCCAGGCCCACGGCTTGACCCCCCAGCA GGTGGTGGCCATCGCCAGCAATGGCGGTGGCAAGCAGGCGCTGGAGACGGTCCAGCGGCTGTTGC CGGTGCTGTGCCAGGCCCACGGCTTGACCCCGGAGCAGGTGGTGGCCATCGCCAGCAATATTGGT GGCAAGCAGGCGCTGGAGACGGTGCAGGCGCTGTTGCCGGTGCTGTGCCAGGCCCACGGCTTGAC CCCGGAGCAGGTGGTGGCCATCGCCAGCCACGATGGCGGCAAGCAGGCGCTGGAGACGGTCCAGC GGCTGTTGCCGGTGCTGTGCCAGGCCCACGGCTTGACCCCGGAGCAGGTGGTGGCCATCGCCAGC AATATTGGTGGCAAGCAGGCGCTGGAGACGGTGCAGGCGCTGTTGCCGGTGCTGTGCCAGGCCCA CGGCTTGACCCCGGAGCAGGTGGTGGCCATCGCCAGCCACGATGGCGGCAAGCAGGCGCTGGAGA CGGTCCAGCGGCTGTTGCCGGTGCTGTGCCAGGCCCACGGCTTGACCCCCAGCAGGTGGTGGCC ATCGCCAGCAATAATGGTGGCAAGCAGGCGCTGGAGACGGTCCAGCGGCTGTTGCCGGTGCTGTG CCAGGCCCACGGCTTGACCCCTCAGCAGGTGGTGGCCATCGCCAGCAATGGCGGCGGCAGGCCGG CGCTGGAGAGCATTGTTGCCCAGTTATCTCGCCCTGATCCGGCGTTGGCCGCGTTGACCAACGAC CACCTCGTCGCCTTGGCCTGCCTCGGCGGCGTCCTGCGCTGGATGCAGTGAAAAAGGGATTGGG GGATCCTATCAGCCGTTCCCAGCTGGTGAAGTCCGAGCTGGAGGAGAAGAAATCCGAGTTGAGGC ACAAGCTGAAGTACGTGCCCCACGAGTACATCGAGCTGATCGAGATCGCCCGGAACAGCACCCAG GACCGTATCCTGGAGATGAAGGTGATGGAGTTCTTCATGAAGGTGTACGGCTACAGGGGCAAGCA CCTGGGCGGCTCCAGGAAGCCCGACGGCGCCATCTACACCGTGGGCTCCCCCATCGACTACGGCG TGATCGTGGACACCAAGGCCTACTCCGGCGGCTACAACCTGCCCATCGGCCAGGCCGACGAAATG CAGAGGTACGTGGAGGAGAACCAGACCAGGAACAAGCACATCAACCCCAACGAGTGGTGGAAGGT GTACCCCTCCAGCGTGACCGAGTTCAAGTTCCTGTTCGTGTCCGGCCACTTCAAGGGCAACTACA AGGCCCAGCTGACCAGGCTGAACCACATCACCAACTGCAACGGCGCCGTGCTGTCCGTGGAGGAG CTCCTGATCGGCGGCGAGATGATCAAGGCCGGCACCCTGACCCTGGAGGAGGTGAGGAGGAAGTT CAACAACGGCGAGATCAACTTCGCGGCCGACTGATAA |
| 24 | TALEN CD25 pCLS30480 | ATGGGCGATCCTAAAAAGAAACGTAAGGTCATCGATTACCCATACGATGTTCCAGATTACGCTAT CGATATCGCCGATCTACGCACGCTCGGCTACAGCCAGCAGCAACAGGAGAAGATCAAACCGAAGG TTCGTTCGACAGTGGCGCAGCACCACGAGGCACTGGTCGGCCACGGGTTTACACACGCGCACATC GTTGCGTTAAGCCAACACCCGGCAGCGTTAGGGACCGTCGCTGTCAAGTATCAGGACATGATCGC AGCGTTGCCAGAGGCGACACACGAAGCGATCGTTGGCGTCGGCAAACAGTGGTCCGGCGCACGCG |

TABLE 5-continued

Sequences referred to in example 2 and 3.

| | | |
|---|---|---|
| | | CTCTGGAGGCCTTGCTCACGGTGGCGGGAGAGTTGAGAGGTCCACCGTTACAGTTGGACACAGGC
CAACTTCTCAAGATTGCAAAACGTGGCGGCGTGACCGCAGTGGAGGCAGTGCATGCATGGCGCAA
TGCACTGACGGGTGCCCCGCTCAACTTGACCCCCCAGCAGGTGGTGGCCATCGCCAGCAATAATG
GTGGCAAGCAGGCGCTGGAGACGGTCCAGCGGCTGTTGCCGGTGCTGTGCCAGGCCCACGGCTTG
ACCCCCCAGCAGGTGGTGGCCATCGCCAGCAATGGCGGTGGCAAGCAGGCGCTGGAGACGGTCCA
GCGGCTGTTGCCGGTGCTGTGCCAGGCCCACGGCTTGACCCCCCAGCAGGTGGTGGCCATCGCCA
GCAATGGCGGTGGCAAGCAGGCGCTGGAGACGGTCCAGCGGCTGTTGCCGGTGCTGTGCCAGGCC
CACGGCTTGACCCCGGAGCAGGTGGTGGCCATCGCCAGCCACGATGGCGGCAAGCAGGCGCTGGA
GACGGTCCAGCGGCTGTTGCCGGTGCTGTGCCAGGCCCACGGCTTGACCCCCAGCAGGTGGTGG
CCATCGCCAGCAATGGCGGTGGCAAGCAGGCGCTGGAGACGGTCCAGCGGCTGTTGCCGGTGCTG
TGCCAGGCCCACGGCTTGACCCCCCAGCAGGTGGTGGCCATCGCCAGCAATGGCGGTGGCAAGCA
GGCGCTGGAGACGGTCCAGCGGCTGTTGCCGGTGCTGTGCCAGGCCCACGGCTTGACCCCCCAGC
AGGTGGTGGCCATCGCCAGCAATGGCGGTGGCAAGCAGGCGCTGGAGACGGTCCAGCGGCTGTTG
CCGGTGCTGTGCCAGGCCCACGGCTTGACCCCCCAGCAGGTGGTGGCCATCGCCAGCAATGGCGG
TGGCAAGCAGGCGCTGGAGACGGTCCAGCGGCTGTTGCCGGTGCTGTGCCAGGCCCACGGCTTGA
CCCCCCAGCAGGTGGTGGCCATCGCCAGCAATAATGGTGGCAAGCAGGCGCTGGAGACGGTCCAG
CGGCTGTTGCCGGTGCTGTGCCAGGCCCACGGCTTGACCCCCCAGCAGGTGGTGGCCATCGCCAG
CAATAATGGTGGCAAGCAGGCGCTGGAGACGGTCCAGCGGCTGTTGCCGGTGCTGTGCCAGGCCC
ACGGCTTGACCCCCCAGCAGGTGGTGGCCATCGCCAGCAATGGCGGTGGCAAGCAGGCGCTGGAG
ACGGTCCAGCGGCTGTTGCCGGTGCTGTGCCAGGCCCACGGCTTGACCCCCCAGCAGGTGGTGGC
CATCGCCAGCAATGGCGGTGGCAAGCAGGCGCTGGAGACGGTCCAGCGGCTGTTGCCGGTGCTGT
GCCAGGCCCACGGCTTGACCCCCCAGCAGGTGGTGGCCATCGCCAGCAATGGCGGTGGCAAGCAG
GCGCTGGAGACGGTCCAGCGGCTGTTGCCGGTGCTGTGCCAGGCCCACGGCTTGACCCCCCAGCA
GGTGGTGGCCATCGCCAGCAATGGCGGTGGCAAGCAGGCGCTGGAGACGGTCCAGCGGCTGTTGC
CGGTGCTGTGCCAGGCCCACGGCTTGACCCCGGAGCAGGTGGTGGCCATCGCCAGCCACGATGGC
GGCAAGCAGGCGCTGGAGACGGTCCAGCGGCTGTTGCCGGTGCTGTGCCAGGCCCACGGCTTGAC
CCCTCAGCAGGTGGTGGCCATCGCCAGCAATGGCGGCGGCAGGCCGGCGCTGGAGAGCATTGTTG
CCCAGTTATCTCGCCCTGATCCGAGTGGCAGCGGAAGTGGCGGGGATCCTATCAGCCGTTCCCAG
CTGGTGAAGTCCGAGCTGGAGGAGAAGAAATCCGAGTTGAGGCACAAGCTGAAGTACGTGCCCCA
CGAGTACATCGAGCTGATCGAGATCGCCCGGAACAGCACCCAGGACCGTATCCTGGAGATGAAGG
TGATGGAGTTCTTCATGAAGGTGTACGGCTACAGGGGCAAGCACCTGGGCGGCTCCAGGAAGCCC
GACGGCGCCATCTACACCGTGGGCTCCCCCATCGACTACGGCGTGATCGTGGACACCAAGGCCTA
CTCCGGCGGCTACAACCTGCCCATCGGCCAGGCCGACGAAATGCAGAGGTACGTGGAGGAGAACC
AGACCAGGAACAAGCACATCAACCCCAACGAGTGGTGGAAGGTGTACCCCTCCAGCGTGACCGAG
TTCAAGTTCCTGTTCGTGTCCGGCCACTTCAAGGGCAACTACAAGGCCCAGCTGACCAGGCTGAA
CCACATCACCAACTGCAACGGCGCCGTGCTGTCCGTGGAGGAGCTCCTGATCGGCGGCGAGATGA
TCAAGGCCGGCACCCTGACCCTGGAGGAGGTGAGGAGGAAGTTCAACAACGGCGAGATCAACTTC
GCGGCCGACTGATAA |
| 25 | TALEN CD25 pCLS30479 | ATGGGCGATCCTAAAAAGAAACGTAAGGTCATCGATTACCCATACGATGTTCCAGATTACGCTAT
CGATATCGCCGATCTACGCACGCTCGGCTACAGCCAGCAGCAACAGGAGAAGATCAAACCGAAGG
TTCGTTCGACAGTGGCGCAGCACCACGAGGCACTGGTCGGCCACGGGTTTACACACGCGCACATC
GTTGCGTTAAGCCAACACCCGGCAGCGTTAGGGACCGTCGCTGTCAAGTATCAGGACATGATCGC
AGCGTTGCCAGAGGCGACACACGAAGCGATCGTTGGCGTCGGCAAACAGTGGTCCGGCGCACGCG
CTCTGGAGGCCTTGCTCACGGTGGCGGGAGAGTTGAGAGGTCCACCGTTACAGTTGGACACAGGC
CAACTTCTCAAGATTGCAAAACGTGGCGGCGTGACCGCAGTGGAGGCAGTGCATGCATGGCGCAA
TGCACTGACGGGTGCCCCGCTCAACTTGACCCCGGAGCAGGTGGTGGCCATCGCCAGCAATATTG
GTGGCAAGCAGGCGCTGGAGACGGTGCAGGCGCTGTTGCCGGTGCTGTGCCAGGCCCACGGCTTG
ACCCCGGAGCAGGTGGTGGCCATCGCCAGCCACGATGGCGGCAAGCAGGCGCTGGAGACGGTCCA
GCGGCTGTTGCCGGTGCTGTGCCAGGCCCACGGCTTGACCCCGGAGCAGGTGGTGGCCATCGCCA
GCAATATTGGTGGCAAGCAGGCGCTGGAGACGGTGCAGGCGCTGTTGCCGGTGCTGTGCCAGGCC
CACGGCTTGACCCCCCAGCAGGTGGTGGCCATCGCCAGCAATAATGGTGGCAAGCAGGCGCTGGA
GACGGTCCAGCGGCTGTTGCCGGTGCTGTGCCAGGCCCACGGCTTGACCCCCAGCAGGTGGTGG
CCATCGCCAGCAATAATGGTGGCAAGCAGGCGCTGGAGACGGTCCAGCGGCTGTTGCCGGTGCTG
TGCCAGGCCCACGGCTTGACCCCGGAGCAGGTGGTGGCCATCGCCAGCAATATTGGTGGCAAGCA
GGCGCTGGAGACGGTGCAGGCGCTGTTGCCGGTGCTGTGCCAGGCCCACGGCTTGACCCCCCAGC
AGGTGGTGGCCATCGCCAGCAATAATGGTGGCAAGCAGGCGCTGGAGACGGTCCAGCGGCTGTTG
CCGGTGCTGTGCCAGGCCCACGGCTTGACCCCCCAGCAGGTGGTGGCCATCGCCAGCAATAATGG
TGGCAAGCAGGCGCTGGAGACGGTCCAGCGGCTGTTGCCGGTGCTGTGCCAGGCCCACGGCTTGA
CCCCGGAGCAGGTGGTGGCCATCGCCAGCAATATTGGTGGCAAGCAGGCGCTGGAGACGGTGCAG
GCGCTGTTGCCGGTGCTGTGCCAGGCCCACGGCTTGACCCCGGAGCAGGTGGTGGCCATCGCCAG
CAATATTGGTGGCAAGCAGGCGCTGGAGACGGTGCAGGCGCTGTTGCCGGTGCTGTGCCAGGCCC
ACGGCTTGACCCCCCAGCAGGTGGTGGCCATCGCCAGCAATAATGGTGGCAAGCAGGCGCTGGAG
ACGGTCCAGCGGCTGTTGCCGGTGCTGTGCCAGGCCCACGGCTTGACCCCGGAGCAGGTGGTGGC
CATCGCCAGCAATATTGGTGGCAAGCAGGCGCTGGAGACGGTGCAGGCGCTGTTGCCGGTGCTGT
GCCAGGCCCACGGCTTGACCCCCCAGCAGGTGGTGGCCATCGCCAGCAATAATGGTGGCAAGCAG
GCGCTGGAGACGGTCCAGCGGCTGTTGCCGGTGCTGTGCCAGGCCCACGGCTTGACCCCCCAGCA
GGTGGTGGCCATCGCCAGCAATGGCGGTGGCAAGCAGGCGCTGGAGACGGTCCAGCGGCTGTTGC
CGGTGCTGTGCCAGGCCCACGGCTTGACCCCGGAGCAGGTGGTGGCCATCGCCAGCAATATTGGT
GGCAAGCAGGCGCTGGAGACGGTGCAGGCGCTGTTGCCGGTGCTGTGCCAGGCCCACGGCTTGAC
CCCTCAGCAGGTGGTGGCCATCGCCAGCAATGGCGGCGGCAGGCCGGCGCTGGAGAGCATTGTTG
CCCAGTTATCTCGCCCTGATCCGAGTGGCAGCGGAAGTGGCGGGGATCCTATCAGCCGTTCCCAG
CTGGTGAAGTCCGAGCTGGAGGAGAAGAAATCCGAGTTGAGGCACAAGCTGAAGTACGTGCCCCA
CGAGTACATCGAGCTGATCGAGATCGCCCGGAACAGCACCCAGGACCGTATCCTGGAGATGAAGG
TGATGGAGTTCTTCATGAAGGTGTACGGCTACAGGGGCAAGCACCTGGGCGGCTCCAGGAAGCCC
GACGGCGCCATCTACACCGTGGGCTCCCCCATCGACTACGGCGTGATCGTGGACACCAAGGCCTA
CTCCGGCGGCTACAACCTGCCCATCGGCCAGGCCGACGAAATGCAGAGGTACGTGGAGGAGAACC
AGACCAGGAACAAGCACATCAACCCCAACGAGTGGTGGAAGGTGTACCCCTCCAGCGTGACCGAG
TTCAAGTTCCTGTTCGTGTCCGGCCACTTCAAGGGCAACTACAAGGCCCAGCTGACCAGGCTGAA |

TABLE 5-continued

Sequences referred to in example 2 and 3.

| | | |
|---|---|---|
| | | CCACATCACCAACTGCAACGGCGCCGTGCTGTCCGTGGAGGAGCTCCTGATCGGCGGCGAGATGA<br>TCAAGGCCGGCACCCTGACCCTGGAGGAGGTGAGGAGGAAGTTCAACAACGGCGAGATCAACTTC<br>GCGGCCGACTGATAA |
| 26 | TALEN PD1<br>pCLS28959 | ATGGGCGATCCTAAAAAGAAACGTAAGGTCATCGATTACCCATACGATGTTCCAGATTACGCTAT<br>CGATATCGCCGATCTACGCACGCTCGGCTACAGCCAGCAGCAACAGGAGAAGATCAAACCGAAGG<br>TTCGTTCGACAGTGGCGCAGCACCACGAGGCACTGGTCGGCCACGGGTTTACACACGCGCACATC<br>GTTGCGTTAAGCCAACACCCGGCAGCGTTAGGGACCGTCGCTGTCAAGTATCAGGACATGATCGC<br>AGCGTTGCCAGAGGCGACACACGAAGCGATCGTTGGCGTCGGCAAACAGTGGTCCGGCGCACGCG<br>CTCTGGAGGCCTTGCTCACGGTGGCGGGAGAGTTGAGAGGTCCACCGTTACAGTTGGACACAGGC<br>CAACTTCTCAAGATTGCAAAACGTGGCGGCGTGACCGCAGTGGAGGCAGTGCATGCATGGCGCAA<br>TGCACTGACGGGTGCCCCGCTCAACTTGACCCCCGAGCAAGTGGTGGCTATCGCTTCCAAGCTGG<br>GGGGAAAGCAGGCCCTGGAGACCGTCCAGGCCCTTCTCCCAGTGCTTTGCCAGGCTCACGGACTG<br>ACCCCTGAACAGGTGGTGGCAATTGCCTCACACGACGGGGGCAAGCAGGCACTGGAGACTGTCCA<br>GCGGCTGCTGCCTGTCCTCTGCCAGGCCCACGGACTCACTCCTGAGCAGGTCGTGGCCATTGCCA<br>GCCACGATGGGGGCAAACAGGCTCTGGAGACCGTGCAGCGCCTCCTCCCAGTGCTGTGCCAGGCT<br>CATGGGCTGACCCCACAGCAGGTCGTCGCCATTGCCAGTAACGGCGGGGGGAAGCAGGCCCTCGA<br>AACAGTGCAGAGGCTGCTGCCCGTCTTGTGCCAAGCACACGGCCTGACACCCGAGCAGGTGGTGG<br>CCATCGCCTCTCATGACGGCGGCAAGCAGGCCCTTGAGACAGTGCAGAGACTGTTGCCCGTGTTG<br>TGTCAGGCCCACGGGTTGACACCCCAGCAGGTGGTCGCCATCGCCAGCAATGGCGGGGGAAAGCA<br>GGCCCTTGAGACCGTGCAGCGGTTGCTTCCAGTGTTGTGCCAGGCACACGGACTGACCCCTCAAC<br>AGGTGGTCGCAATCGCCAGCTACAAGGGCGGAAAGCAGGCTCTGGAGACAGTGCAGCGCCTCCTG<br>CCCGTGCTGTGTCAGGCTCACGGACTGACACCACAGCAGGTGGTCGCCATCGCCAGTAACGGGGG<br>CGGCAAGCAGGCTTTGGAGACCGTCCAGAGACTCCTCCCCGTCCTTTGCCAGGCCCACGGGTTGA<br>CACCTCAGCAGGTCGTCGCCATTGCCTCCAACAACGGGGGCAAGCAGGCCCTCGAAACTGTGCAG<br>AGGCTGCTGCCTGTGCTGTGCCAGGCTCATGGGCTGACACCCCAGCAGGTGGTGGCCATTGCCTC<br>TAACAACGGCGGCAAACAGGCACTGGAGACCGTGCAAAGGCTGCTGCCCGTCCTCTGCCAAGCCC<br>ACGGGCTCACTCCACAGCAGGTCGTGGCCATCGCCTCAAACAATGGCGGGAAGCAGGCCCTGGAG<br>ACTGTGCAAAGGCTGCTCCCTGTGCTCTGCCAGGCACACGGACTGACCCCTCAGCAGGTGGTGGC<br>AATCGCTTCCAACAACGGGGGAAAGCAGGCCCTGAAACCGTGCAGCGCCTCCTCCCAGTGCTGTG<br>CCAGGCACATGGCCTCACACCCGAGCAAGTGGTGGCTATCGCCAGCCACGACGGAGGGAAGCAG<br>GCTCTGGAGACCGTGCAGAGGCTGCTGCCTGTCCTGTGCCAGGCCCACGGGCTTACTCCAGAGCA<br>GGTCGTCGCCATCGCCAGTCATGATGGGGGGAAGCAGGCCCTTGAGACAGTCCAGCGGCTGCTGC<br>CAGTCCTTTGCCAGGCTCACGGCTTGACTCCCGAGCAGGTCGTGGCCATTGCCTCAAACATTGGG<br>GGCAAACAGGCCCTGGAGACAGTGCAGGCCCTGCTGCCCGTGTTGTGTCAGGCCCACGGCTTGAC<br>ACCCCAGCAGGTGGTCGCCATTGCCTCTAATGGCGGCGGGAGACCCGCCTTGGAGAGCATTGTTG<br>CCCAGTTATCTCGCCCTGATCCGGCGTTGGCCGCGTTGACCAACGACCACCTCGTCGCCTTGGCC<br>TGCCTCGGCGGGCGTCCTGCGCTGGATGCAGTGAAAAAGGGGATTGGGGGATCCTATCAGCCGTTC<br>CCAGCTGGTGAAGTCCGAGCTGGAGGAGAAGAAATCCGAGTTGAGGCACAAGCTGAAGTACGTGC<br>CCCACGAGTACATCGAGCTGATCGAGATCGCCCGGAACAGCACCCAGGACCGTATCCTGGAGATG<br>AAGGTGATGGAGTTCTTCATGAAGGTGTACGGCTACAGGGGCAAGCACCTGGGCGGCTCCAGGAA<br>GCCCGACGGCGCCATCTACACCGTGGGCTCCCCCATCGACTACGGCGTGATCGTGGACACCAAGG<br>CCTACTCCGGCGGCTACAACCTGCCCATCGGCCAGGCCGACGAAATGCAGAGGTACGTGGAGGAG<br>AACCAGACCAGGAACAAGCACATCAACCCCAACGAGTGGTGGAAGGTGTACCCCTCCAGCGTGAC<br>CGAGTTCAAGTTCCTGTTCGTGTCCGGCCACTTCAAGGGCAACTACAAGGCCCAGCTGACCAGGC<br>TGAACCACATCACCAACTGCAACGGCGCCGTGCTGTCCGTGGAGGAGCTCCTGATCGGCGGCGAG<br>ATGATCAAGGCCGGCACCCTGACCCTGGAGGAGGTGAGGAGGAAGTTCAACAACGGCGAGATCAA<br>CTTCGCGGCCGACTGATAA |
| 27 | TALEN PD1<br>pCLS18792 | ATGGGCGATCCTAAAAAGAAACGTAAGGTCATCGATAAGGAGACCGCCGCTGCCAAGTTCGAGAG<br>ACAGCACATGGACAGCATCGATATCGCCGATCTACGCACGCTCGGCTACAGCCAGCAGCAACAGG<br>AGAAGATCAAACCGAAGGTTCGTTCGACAGTGGCGCAGCACCACGAGGCACTGGTCGGCCACGGG<br>TTTACACACGCGCACATCGTTGCGTTAAGCCAACACCCGGCAGCGTTAGGGACCGTCGCTGTCAA<br>GTATCAGGACATGATCGCAGCGTTGCCAGAGGCGACACACGAAGCGATCGTTGGCGTCGGCAAAC<br>AGTGGTCCGGCGCACGCGCTCTGGAGGCCTTGCTCACGGTGGCGGGAGAGTTGAGAGGTCCACCG<br>TTACAGTTGGACACAGGCCAACTTCTCAAGATTGCAAACGTGGCGGCGTGACCGCAGTGGAGGC<br>AGTGCATGCATGGCGCAATGCACTGACGGGTGCCCCGCTCAACTTGACCCCCGAGCAAGTCGTCG<br>CAATCGCCAGCCATGATGGAGGGAAGCAAGCCTCGAAACCGTGCAGCGGTTGCTTCCTGTGCTC<br>TGCCAGGCCCACGGCCTTACCCCTCAGCAGGTGGTGGCCATCGCAAGTAACGGAGGAGGAAAGCA<br>AGCCTTGGAGACAGTGCAGCGCCTGTTGCCCGTGCTGTGCCAGGCACACGGCCTCACACCAGAGC<br>AGGTCGTGGCCATTGCCTCCCATGACGGGGGAAACAGGCTCTGGAGACCGTCCAGAGGCTGCTG<br>CCCGTCCTCTGTCAAGCTCACGGCCTGACTCCCCAACAAGTGGTCGCCATCGCCTCTAATGGCGG<br>CGGGAAGCAGGCACTGGAAACAGTGCAGAGACTGCTCCCTGTGCTTTGCCAAGCTCATGGGTTGA<br>CCCCCCAACAGGTCGTCGCTATTGCCTCAAACGGGGGGCAAGCAGGCCCTTGAGACTGTGCAG<br>AGGCTGTTGCCAGTGCTGTGTCAGGCTCACGGGCTCACTCCACAACAGGTGGTCGCAATTGCCAG<br>CAACGGCGGCGAAAGCAAGCTCTTGAAACCGTGCAACGCCTCCTGCCCGTGCTCTGTCAGGCTC<br>ATGGCCTGACACCACAACAAGTCGTGGCCATCGCCAGTAATAATGGCGGGAAACAGGCTCTTGAG<br>ACCGTCCAGAGGCTGCTCCCAGTGCTCTGCCAGGCACACGGGCTGACCCCCGAGCAGGTGGTGGC<br>TATCGCCAGCAATATTGGGGGCAAGCAGGCCCTGGAAACAGTCCAGGCCCTGCTGCCAGTGCTTT<br>GCCAGGCTCACGGGCTCACTCCCCAGCAGGTCGTGGCAATCGCCTCCAACGGCGGAGGGAAGCAG<br>GCTCTGGAGACCGTGCAGAGACTGCTGCCCGTCTTGTGCCAGGCCCACGGACTCACACCTGAACA<br>GGTCGTCGCCATTGCCTCTCACGATGGGGCAAACAAGCCCGGAGACAGTGCAGCGGCTGTTGC<br>CTGTGTTGTGCCAAGCCCACGGCTTGACTCCTCAACAAGTGGTCGCCATCGCCTCAAATGGCGGC<br>GGAAAACAAGCTCTGGAGACAGTGCAGAGGTTGCTGCCCGTCCTCTGCCAAGCCCACGGCCTGAC<br>TCCCCAACAGGTCGTCGCCATTGCCAGCAACAACGGAGGAAAGCAGGCTCTCGAAACTGTGCAGG<br>GGCTGCTTCCTGTGCTGTGTCAGGCTCATGGGCTGACCCCCGAGCAAGTGGTGGCTATTGCCTCT<br>AATGGAGGCAAGCAAGCCCTTGAGACAGTCCAGAGGCTGTTGCCAGTGCTGTGCCAGGCCCACGG<br>GCTCACACCCCAGCAGGTGGTCGCCATCGCCAGTAACAACGGGGGCAAACAGGCATTGGAAACCG<br>TCCAGCGCCTGCTTCCAGTGCTCTGCCAGGCACACGGACTGACACCCGAACAGGTGGTGGCCATT<br>GCATCCCATGATGGGGGCAAGCAGGCCCTGGAGACCGTGCAGAGACTCCTGCCAGTGTTGTGCCA |

TABLE 5-continued

Sequences referred to in example 2 and 3.

| | | |
|---|---|---|
| | | AGCTCACGGCCTCACCCCTCAGCAAGTCGTGGCCATCGCCTCAAACGGGGGGGCCGGCCTGCAC
TGGAGAGCATTGTTGCCCAGTTATCTCGCCCTGATCCGGCGTTGGCCGCGTTGACCAACGACCAC
CTCGTCGCCTTGGCCTGCCTCGGCGGGCGTCCTGCGCTGGATGCAGTGAAAAAGGGATTGGGGGA
TCCTATCAGCCGTTCCCAGCTGGTGAAGTCCGAGCTGGAGGAGAAGAAATCCGAGTTGAGGCACA
AGCTGAAGTACGTGCCCCACGAGTACATCGAGCTGATCGAGATCGCCCGGAACAGCACCCAGGAC
CGTATCCTGGAGATGAAGGTGATGGAGTTCTTCATGAAGGTGTACGGCTACAGGGGCAAGCACCT
GGGCGGCTCCAGGAAGCCCGACGGCGCCATCTACACCGTGGGCTCCCCCATCGACTACGGCGTGA
TCGTGGACACCAAGGCCTACTCCGGCGGCTACAACCTGCCCATCGGCCAGGCCGACGAAATGCAG
AGGTACGTGGAGGAGAACCAGACCAGGAACAAGCACATCAACCCCAACGAGTGGTGGAAGGTGTA
CCCCTCCAGCGTGACCGAGTTCAAGTTCCTGTTCGTGTCCGGCCACTTCAAGGGCAACTACAAGG
CCCAGCTGACCAGGCTGAACCACATCACCAACTGCAACGGCGCCGTGCTGTCCGTGGAGGAGCTC
CTGATCGGCGGCGAGATGATCAAGGCCGGCACCCTGACCCTGGAGGAGGTGAGGAGGAAGTTCAA
CAACGGCGAGATCAACTTCGCGGCCGACTGATAA |
| 28 | TALEN target TRAC | TTGTCCCACAGATATCCAGAACCCTGACCCTGCCGTGTACCAGCTGAGA |
| 29 | TALEN target CD25 | TACAGGAGGAAGAGTAGAAGAACAATCTAGAAAACCAAAAGAACA |
| 30 | TALEN target PD1 | TACCTCTGTGGGGCCATCTCCCTGGCCCCCAAGGCGCAGATCAAAGAGA |
| 31 | Matrice TRAC locus_CubiCA R CD22 pCLS30056 | TTGCTGGGCCTTTTTCCCATGCCTGCCTTTACTCTGCCAGAGTTATATTGCTGGGGTTTTGAAGA
AGATCCTATTAAATAAAAGAATAAGCAGTATTATTAAGTAGCCCTGCATTTCAGGTTTCCTTGAG
TGGCAGGCCAGGCCTGGCCGTGAACGTTCACTGAAATCATGGCCTCTTGGCCAAGATTGATAGCT
TGTGCCTGTCCCTGAGTCCCAGTCCATCACGAGCAGCTGGTTTCTAAGATGCTATTTCCCGTATA
AAGCATGAGACCGTGACTTGCCAGCCCCACAGAGCCCCGCCCTTGTCCATCACTGGCATCTGGAC
TCCAGCCTGGGTTGGGGCAAAGAGGGAAATGAGATCATGTCCTAACCCTGATCCTCTTGTCCCAC
AGATATCCAGTACCCCTACGACGTGCCCGACTACGCCTCCGGTGAGGGCAGAGGAAGTCTTCTAA
CATGCGGTGACGTGGAGGAGAATCCGGGCCCCGGATCCGCTCTGCCCGTCACCGCTCTGCTGCTG
CCACTGGCACTGCTGCTGCACGCTGCTAGGCCCGGAGGGGGAGGCAGCTGCCCCTACAGCAACCC
CAGCCTGTGCAGCGGAGGCGGCGGCAGCGGCGGAGGGGGTAGCCAGGTGCAGCTGCAGCAGAGCG
GCCCTGGCCTGGTGAAGCCAAGCCAGACACTGTCCCTGACCTGCGCCATCAGCGGCGATTCCGTG
AGCTCCAACTCCGCCGCCTGGAATTGGATCAGGCAGTCCCCTTCTCGGGGCCTGGAGTGGCTGGG
AAGGACATACTATCGGTCTAAGTGGTACAACGATTATGCCGTGTCTGTGAAGAGCAGAATCACAA
TCAACCCTGACACCTCCAAGAATCAGTTCTCTCTGCAGCTGAATAGCGTGACACCAGAGGACACC
GCCGTGTACTATTGCGCCAGGGAGGTGACCGGCGACCTGGAGGATGCCTTTGACATCTGGGGCCA
GGGCACAATGGTGACCGTGAGCTCCGGAGGCGGCGGATCTGGCGGAGGAGGAAGTGGGGGCGGCG
GGAGTGATATCCAGATGACACAGTCCCCATCCTCTCTGAGCGCCTCCGTGGGCGACAGAGTGACA
ATCACCTGTAGGGCCTCCCAGACCATCTGGTCTTACCTGAACTGGTATCAGCAGAGGCCCGGCAA
GGCCCCTAATCTGCTGATCTACGCAGCAAGCTCCCTGCAGAGCGGAGTGCCATCCAGATTCTCTG
GCAGGGGCTCCGGCACAGACTTCACCCTGACCATCTCTAGCCTGCAGGCCGAGGACTTCGCCACC
TACTATTGCCAGCAGTCTTATAGCATCCCCCAGACATTTGGCCAGGGCACCAAGCTGGAGATCAA
GTCGGATCCCGGAAGCGGAGGGGGAGGCAGCTGCCCCTACAGCAACCCCAGCCTGTGCAGCGGAG
GCGGCGGCAGCGAGCTGCCCACCCAGGGCACCTTCTCCAACGTGTCCACCAACGTGAGCCCAGCC
AAGCCCACCACCACCGCCGTGCCTTATTCCAATCCTTCCCTGTGTGCTCCCACCACAACCCCCGC
TCCAAGGCCCCCTACCCCCGCACCAACTATTGCCTCCCAGCCACTCTCACTGCGGCCTGAGGCCT
GTCGGCCCGCTGCTGGAGGCGCAGTGCATACAAGGGGCCTCGATTTCGCCTGCGATATTTACATC
TGGGCACCCCTCGCCGGCACCTGCGGGGTGCTTCTCCTCTCCTGGTGATTACCCTGTATTGCAG
ACGGGGCCGGAAGAAGCTCCTCTACATTTTTAAGCAGCCTTTCATGCGGCCAGTGCAGACAACCC
AAGAGGAGGATGGGTGTTCCTGCAGATTCCTGAGGAAGAGGAAGGCGGGTGCGAGCTGAGAGTG
AAGTTCTCCAGGAGCGCAGATGCCCCCGCCTATCAACAGGGCCAGAACCAGCTCTACAACGAGCT
TAACCTCGGGAGGCGCGAAGAATACGACGTGTTGGATAAGAGAAGGGGGCGGGACCCCGAGATGG
GAGGAAAGCCCCGGAGGAAGAACCCTCAGGAGGGCCTGTACAACGAGCTGCAGAAGGATAAGATG
GCCGAGGCCTACTCAGAGATCGGGATGAAGGGGGAGCGGCGCCGCGGGAAGGGGCACGATGGGCT
CTACCAGGGGCTGAGCACAGCCACAAAGGACACATACGACGCCTTGCACATGCAGGCCCTTCCAC
CCCGGGAATAGTCTAGAGGGCCCGTTTAAACCCGCTGATCAGCCTCGACTGTGCCTTCTAGTTGC
CAGCCATCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGGGG
GTGGGGTGGGGCAGGACAGCAAGGGGGAGGATTGGGAAGACAATAGCAGGCATGCTGGGGATGCG
GTGGGCTCTATGACTAGTGGCGAATTCCCGTGTACCAGCTGAGAGACTCTAAATCCAGTGACAAG
TCTGTCTGCCTATTCACCGATTTTGATTCTCAAACAAATGTGTCACAAAGTAAGGATTCTGATGT
GTATATCACAGACAAAACTGTGCTAGACATGAGGTCTATGGACTTCAAGAGCAACAGTGCTGTGG
CCTGGAGCAACAAATCTGACTTTGCATGTGCAAACGCCTTCAACAACAGCATTATTCCAGAAGAC
ACCTTCTTCCCCAGCCCAGGTAAGGGCAGCTTTGGTGCCTTCGCAGGCTGTTTCCTTGCTTCAGG
AATGGCCAGGTTCTGCCCAGAGCTCTGGTCAATGATGTCTAAAACTCCTCTGATTGGTGGTCTCG
GCCTTATCCATTGCCACCAAAACCCTCTTTTTACTAA |
| 32 | Matrice CD25 locus_IL15_ 2A_sIL15Ra pCLS30519 | GTTTATTATTCCTGTTCCACAGCTATTGTTCCATATAAAAACTTAGGCCAGGCACAGTGGCTC
ACACCTGTAATCCCAGCACTTTGGAAGGCCGAGGCAGGCAGATCACAAGGTCAGGAGTTCGAGAC
CAGCCTGGCCAACATAGCAAAACCCCATCTCTACTAAAAATACAAAAATTAGCCAGGCATGGTGG
CGTGTGCACTGGTTTAGAGTGAGGACCACATTTTTTGGTGCCGTGTTACACATATGACCGTGAC
TTTGTTACACCACTACAGGAGGAAGAGTAGAAGAACAATCGGTTCTGGCGTGAAACAGACTTTGA
ATTTTGACCTTCTCAAGTTGGCGGGAGACGTGGAGTCCAACCCAGGGCCCGGTACCGGGTCCGCC
ACCATGGACTGGACCTGGATTCTGTTCCTCGTGGCTGCTGCTACAAGAGTGCACAGCGGCATTCA
TGTCTTCATTTTGGGCTGTTTCAGTGCAGGGCTTCCTAAAACAGAAGCCAACTGGGTGAATGTAA
TAAGTGATTTGAAAAAAATTGAAGATCTTATTCAATCTATGCATATTGATGCTACTTTATATACG
GAAAGTGATGTTCACCCCAGTTGCAAAGTAACAGCAATGAAGTGCTTTCTCTTGGAGTTACAAGT
TATTTCACTTGAGTCCGGAGATGCAAGTATTCATGATACAGTAGAAAATCTGATCATCCTAGCAA
ACAACAGTTTGTCTTCTAATGGGAATGTAACAGAATCTGGATGCAAAGAATGTGAGGAACTGGAG
GAAAAAAATATTAAAGAATTTTTGCAGAGTTTTGTACATATTGTCCAAATGTTCATCAACACTTC
TGGAAGCGGAGCTACTAACTTCAGCCTGCTGAAGCAGGCTGGAGACGTGGAGGAGAACCCTGGAC |

TABLE 5-continued

Sequences referred to in example 2 and 3.

| | | |
|---|---|---|
| | | CTGGGACCGGCTCTGCAACCATGGATTGGACGTGGATCCTGTTTCTCGTGGCAGCTGCCACAAGA<br>GTTCACAGTATCACGTGCCCTCCCCCCATGTCCGTGGAACACGCAGACATCTGGGTCAAGAGCTA<br>CAGCTTGTACTCCAGGGAGCGGTACATTTGTAACTCTGGTTTCAAGCGTAAAGCCGGCACGTCCA<br>GCCTGACGGAGTGCGTGTTGAACAAGGCCACGAATGTCGCCCACTGGACAACCCCCAGTCTCAAA<br>TGCATTAGAGACCCTGCCCTGGTTCACCAAAGGCCAGCGCCACCCTCCACAGTAACGACGGCAGG<br>GGTGACCCCACAGCCAGAGAGCCTCTCCCCTTCTGGAAAAGAGCCCGCAGCTTCATCTCCCAGCT<br>CAAACAACACAGCGGCCACAACAGCAGCTATTGTCCCGGGCTCCCAGCTGATGCCTTCAAAATCA<br>CCTTCCACAGGAACCACAGAGATAAGCAGTCATGAGTCCTCCCACGGCACCCCCTCTCAGACAAC<br>AGCCAAGAACTGGGAACTCACAGCATCCGCCTCCCACCAGCCGCCAGGTGTGTATCCACAGGGCC<br>ACAGCGACACCACTGAGGGCAGAGGCAGCCTGCTGACCTGCGGCGACGTCGAGGAGAACCCCGGG<br>CCCATGGGGGCAGGTGCCACCGGCCGCGCCATGGACGGGCCGCGCCTGCTGTTGCTGCTTCT<br>GGGGGTGTCCCTTGGAGGTGCCAAGGAGGCATGCCCCACAGGCCTGTACACACACAGCGGTGAGT<br>GCTGCAAAGCCTGCAACCTGGGCGAGGGTGTGGCCCAGCCTTGTGGAGCCAACCAGACCGTGTGT<br>GAGCCCTGCCTGGACAGCGTGACGTTCTCCGACGTGGTGAGCGCGACCGAGCCGTGCAAGCCGTG<br>CACCGAGTGCGTGGGGCTCCAGAGCATGTCGGCGCCGTGCGTGGAGGCCGATGACGCCGTGTGCC<br>GCTGCGCCTACGGCTACTACCAGGATGAGACGACTGGGCGCTGCGAGGCGTGCCGCGTGTGCGAG<br>GCGGGCTCGGGCCTCGTGTTCTCCTGCCAGGACAAGCAGAACACCGTGTGCGAGGAGTGCCCCGA<br>CGGCACGTATTCCGACGAGGCCAACCACGTGGACCCGTGCCTGCCCTGCACCGTGTGCGAGGACA<br>CCGAGCGCCAGCTCCGCGAGTGCACACGCTGGGCCGACGCCGAGTGCGAGGAGATCCCTGGCCGT<br>TGGATTACACGGTCCACACCCCCAGAGGGCTCGGACAGCACAGCCCCCAGCACCCAGGAGCCTGA<br>GGCACCTCCAGAACAAGACCTCATAGCCAGCACGGTGGCAGGTGTGGTGACCACAGTGATGGGCA<br>GCTCCCAGCCCGTGGTGACCCGAGGCACCACCGACAACCTCATCCCTGTCTATTGCTCCATCCTG<br>GCTGCTGTGGTTGTGGGTCTTGTGGCCTACATAGCCTTCAAGAGGTGAAAAACCAAAAGAACAAG<br>AATTTCTTGGTAAGAAGCCGGGAACAGACAACAGAAGTCATGAAGCCCAAGTGAAATCAAAGGTG<br>CTAAATGGTCGCCCAGGAGACATCCGTTGTGCTTGCCTGCGTTTTGGAAGCTCTGAAGTCACATC<br>ACAGGACACGGGGCAGTGGCAACCTTGTCTCTATGCAGCTCAGTCCCATCAGAGAGCGAGCGCT<br>ACCCACTTCTAAATAGCAATTTCGCCGTTGAAGAGGAAGGGCAAAACCACTAGAACTCTCCATCT<br>TATTTTCATGTATATGTGTTCAT |
| 33 | Matrice PD1<br>locus_IL15_<br>2A_sIL15Ra<br>pCLS30513 | GACTCCCCAGACAGGCCCTGGAACCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTACC<br>GCATGAGCCCCAGCAACCAGACGGACAAGCTGGCCGCCTTCCCCGAGGACCGCAGCCAGCCCGGC<br>CAGGACTGCCGCTTCCGTGTCACACAACTGCCCAACGGGCGTGACTTCCACATGAGCGTGGTCAG<br>GGCCCGGCGCAATGACAGCGGCACCTACCTCTGTGGGGCCGGTTCTGGCGTGAAACAGACTTTGA<br>ATTTTGACCTTCTCAAGTTGGCGGGAGACGTGGAGTCCAACCCAGGGCCCGGTACCGGGTCCGCC<br>ACCATGGACTGGACCTGGATTCTGTTCCTCGTGGCTGCTGCTACAAGAGTGCACAGCGGCATTCA<br>TGTCTTCATTTTGGGCTGTTTCAGTGCAGGGCTTCCTAAAACAGAAGCCAACTGGGTGAATGTAA<br>TAAGTGATTTGAAAAAAATTGAAGATCTTATTCAATCTATGCATATTGATGCTACTTTATATACG<br>GAAAGTGATGTTCACCCCAGTTGCAAAGTAACAGCAATGAAGTGCTTTCTCTTGGAGTTACAAGT<br>TATTTCACTTGAGTCCGGAGATGCAAGTATTCATGATACAGTAGAAAATCTGATCATCCTAGCAA<br>ACAACAGTTTGTCTTCTAATGGGAATGTAACAGAATCTGGATGCAAAGAATGTGAGGAACTGGAG<br>GAAAAAAATATTAAAGAATTTTTTGCAGAGTTTTGTACATATTGTCCAAATGTTCATCAACACTTC<br>TGGAAGCGGAGCTACTAACTTCAGCCTGCTGAAGCAGGCTGGAGACGTGGAGGAGAACCCTGGAC<br>CTGGGACCGGCTCTGCAACCATGGATTGGACGTGGATCCTGTTTCTCGTGGCAGCTGCCACAAGA<br>GTTCACAGTATCACGTGCCCTCCCCCCATGTCCGTGGAACACGCAGACATCTGGGTCAAGAGCTA<br>CAGCTTGTACTCCAGGGAGCGGTACATTTGTAACTCTGGTTTCAAGCGTAAAGCCGGCACGTCCA<br>GCCTGACGGAGTGCGTGTTGAACAAGGCCACGAATGTCGCCCACTGGACAACCCCCAGTCTCAAA<br>TGCATTAGAGACCCTGCCCTGGTTCACCAAAGGCCAGCGCCACCCTCCACAGTAACGACGGCAGG<br>GGTGACCCCACAGCCAGAGAGCCTCTCCCCTTCTGGAAAAGAGCCCGCAGCTTCATCTCCCAGCT<br>CAAACAACACAGCGGCCACAACAGCAGCTATTGTCCCGGGCTCCCAGCTGATGCCTTCAAAATCA<br>CCTTCCACAGGAACCACAGAGATAAGCAGTCATGAGTCCTCCCACGGCACCCCCTCTCAGACAAC<br>AGCCAAGAACTGGGAACTCACAGCATCCGCCTCCCACCAGCCGCCAGGTGTGTATCCACAGGGCC<br>ACAGCGACACCACTGAGGGCAGAGGCAGCCTGCTGACCTGCGGCGACGTCGAGGAGAACCCCGGG<br>CCCATGGGGGCAGGTGCCACCGGCCGCGCCATGGACGGGCCGCGCCTGCTGCTGTTGCTGCTTCT<br>GGGGGTGTCCCTTGGAGGTGCCAAGGAGGCATGCCCCACAGGCCTGTACACACACAGCGGTGAGT<br>GCTGCAAAGCCTGCAACCTGGGCGAGGGTGTGGCCCAGCCTTGTGGAGCCAACCAGACCGTGTGT<br>GAGCCCTGCCTGGACAGCGTGACGTTCTCCGACGTGGTGAGCGCGACCGAGCCGTGCAAGCCGTG<br>CACCGAGTGCGTGGGGCTCCAGAGCATGTCGGCGCCGTGCGTGGAGGCCGATGACGCCGTGTGCC<br>GCTGCGCCTACGGCTACTACCAGGATGAGACGACTGGGCGCTGCGAGGCGTGCCGCGTGTGCGAG<br>GCGGGCTCGGGCCTCGTGTTCTCCTGCCAGGACAAGCAGAACACCGTGTGCGAGGAGTGCCCCGA<br>CGGCACGTATTCCGACGAGGCCAACCACGTGGACCCGTGCCTGCCCTGCACCGTGTGCGAGGACA<br>CCGAGCGCCAGCTCCGCGAGTGCACACGCTGGGCCGACGCCGAGTGCGAGGAGATCCCTGGCCGT<br>TGGATTACACGGTCCACACCCCCAGAGGGCTCGGACAGCACAGCCCCCAGCACCCAGGAGCCTGA<br>GGCACCTCCAGAACAAGACCTCATAGCCAGCACGGTGGCAGGTGTGGTGACCACAGTGATGGGCA<br>GCTCCCAGCCCGTGGTGACCCGAGGCACCACCGACAACCTCATCCCTGTCTATTGCTCCATCCTG<br>GCTGCTGTGGTTGTGGGTCTTGTGGCCTACATAGCCTTCAAGAGGTGATCTAGAGGGCCCGTTTA<br>AACCCGCTGATCAGCCTCGACTGTGCCTTCTAGTTGCCAGCCATCTGTTGTTTGCCCCTCCCCCG<br>TGCCTTCCTTGACCCTGGAAGGTGCCACTCCCACTGTCCTTTCCTAATAAAATGAGGAAATTGCA<br>TCGCATTGTCTGAGTAGGTGTCATTCTATTCTGGGGGGTGGGTGGGGCAGGACAGCAAGGGGGA<br>GGATTGGGAAGACAATAGCAGGCATGCTGGGGATGCGGTGGGCTCTATGACTAGTGGCGAATTCG<br>GCGCAGATCAAAGAGAGCCTGCGGGCAGAGCTCAGGGTGACAGGTGCGGCCTCGGAGGCCCCGGG<br>GCAGGGGTGAGCTGAGCCGTCCTGGGGTGGGTGTCCCTCCTGCACAGGATCAGGAGCTCCAGG<br>GTCGTAGGGCAGGGACCCCCAGCTCCAGTCCAGGGCTCTGTCCTGCACCTGGGGAATGGTGACC<br>GGCATCTCTGTCCTCTAGCTCTGGAAGCACCCCAGCCCTCTAGTCTGCCCTCACCCCTGACCCT<br>GACCCTCCACCCTGACCCCGTCCTAACCCCTGACCTTTG |
| 34 | Matrice CD25<br>locus_IL12a_<br>2A_IL12b<br>pCLS30520 | GTTTATTATTCCTGTTCCACAGCTATTGTCTGCCATATAAAACTTAGGCCAGGCACAGTGGCTC<br>ACACCTGTAATCCCAGCACTTTGGAAGGCCGAGGCAGGCAGATCACAAGGTCAGGAGTTCGAGAC<br>CAGCCTGGCCAACATAGCAAAACCCCATCTCTACTAAAAATACAAAAATTAGCCAGGCATGGTGG<br>CGTGTGCACTGGTTTAGAGTGAGGACCACATTTTTTGGTGCCGTGTTACACATATGACCGTGAC |

TABLE 5-continued

Sequences referred to in example 2 and 3.

| | | |
|---|---|---|
| | | TTTGTTACACCACTACAGGAGGAAGAGTAGAAGAACAATCGGTTCTGGCGTGAAACAGACTTTGA<br>ATTTTGACCTTCTCAAGTTGGCGGGAGACGTGGAGTCCAACCCAGGGCCCATGTGGCCCCCTGGG<br>TCAGCCTCCCAGCCACCGCCCTCACCTGCCGCGGCCACAGGTCTGCATCCAGCGGCTCGCCCTGT<br>GTCCCTGCAGTGCCGGCTCAGCATGTGTCCAGCGCGCAGCCTCCTCCTTGTGGCTACCCTGGTCC<br>TCCTGGACCACCTCAGTTTGGCCAGAAACCTCCCCGTGGCCACTCCAGACCCAGGAATGTTCCCA<br>TGCCTTCACCACTCCCAAAACCTGCTGAGGGCCGTCAGCAACATGCTCCAGAAGGCCAGACAAAC<br>TCTAGAATTTTACCCTTGCACTTCTGAAGAGATTGATCATGAAGATATCACAAAAGATAAAACCA<br>GCACAGTGGAGGCCTGTTTACCATTGGAATTAACCAAGAATGAGAGTTGCCTAAATTCCAGAGAG<br>ACCTCTTTCATAACTAATGGGAGTTGCCTGGCCTCCAGAAAGACCTCTTTTATGATGGCCCTGTG<br>CCTTAGTAGTATTTATGAAGACTTGAAGATGTACCAGGTGGAGTTCAAGACCATGAATGCAAAGC<br>TTCTGATGGATCCTAAGAGGCAGATCTTTCTAGATCAAAACATGCTGGCAGTTATTGATGAGCTG<br>ATGCAGGCCCTGAATTTCAACAGTGAGACTGTGCCACAAAAATCCTCCCTTGAAGAACCGGATTT<br>TTATAAAACTAAAATCAAGCTCTGCATACTTCTTCATGCTTTCAGAATTCGGGCAGTGACTATTG<br>ATAGAGTGATGAGCTATCTGAATGCTTCCGGAAGCGGAGCTACTAACTTCAGCCTGCTGAAGCAG<br>GCTGGAGACGTGGAGGAGAACCCTGGACCTATGTGTCACCAGCAGTTGGTCATCTCTTGGTTTTC<br>CCTGGTTTTTCTGGCATCTCCCCTCGTGGCCATATGGGAACTGAAGAAAGATGTTTATGTCGTAG<br>AATTGGATTGGTATCCGGATGCCCCTGGAGAAATGGTGGTCCTCACCTGTGACACCCCTGAAGAA<br>GATGGTATCACCTGGACCTTGGACCAGAGCAGTGAGGTCTTAGGCTCTGGCAAAACCCTGACCAT<br>CCAAGTCAAAGAGTTTGGAGATGCTGGCCAGTACACCTGTCACAAAGGAGGCGAGGTTCTAAGCC<br>ATTCGCTCCTGCTGCTTCACAAAAAGGAAGATGGAATTTGGTCCACTGATATTTTAAAGGACCAG<br>AAAGAACCCAAAAATAAGACCTTTCTAAGATGCGAGGCCAAGAATTATTCTGGACGTTTCACCTG<br>CTGGTGGCTGACGACAATCAGTACTGATTTGACATTCAGTGTCAAAAGCAGCAGAGGCTCTTCTG<br>ACCCCCAAGGGGTGACGTGCGGAGCTGCTACACTCTCTGCAGAGAGAGTCAGAGGGGACAACAAG<br>GAGTATGAGTACTCAGTGGAGTGCCAGGAGGACAGTGCCTGCCCAGCTGCTGAGGAGAGTCTGCC<br>CATTGAGGTCATGGTGGATGCCGTTCACAAGCTCAAGTATGAAAACTACACCAGCAGCTTCTTCA<br>TCAGGGACATCATCAAACCTGACCCACCCAAGAACTTGCAGCTGAAGCCATTAAAGAATTCTCGG<br>CAGGTGGAGGTCAGCTGGGAGTACCCTGACACCTGGAGTACTCCACATTCCTACTTCTCCCTGAC<br>ATTCTGCGTTCAGGTCCAGGGCAAGAGCAAGAGAGAAAAGAAAGATAGAGTCTTCACGGACAAGA<br>CCTCAGCCACGGTCATCTGCCGCAAAAATGCCAGCATTAGCGTGCGGGCCCAGGACCGCTACTAT<br>AGCTCATCTTGGAGCGAATGGGCATCTGTGCCCTGCAGTGAGGGCAGAGGCAGCCTGCTGACCTG<br>CGGCGACGTCGAGGAGAACCCCGGGCCCATGGGGGCAGGTGCCACCGGCCGCGCCATGGACGGGC<br>CGCGCCTGCTGCTGTTGCTGCTTCTGGGGGTGTCCCTTGGAGGTGCCAAGGAGGCATGCCCCACA<br>GGCCTGTACACACACAGCGGTGAGTGCTGCAAAGCCTGCAACCTGGGCGAGGGTGTGGCCCAGCC<br>TTGTGGAGCCAACCAGACCGTGTGTGAGCCCTGCCTGGACAGCGTGACGTTCTCCGACGTGGTGA<br>GCGCGACCGAGCCGTGCAAGCCGTGCACCGAGTGCGTGGGGCTCCAGAGCATGTCGGCGCCGTGC<br>GTGGAGGCCGATGACGCCGTGTGCCGCTGCGCCTACGGCTACTACCAGGATGAGACGACTGGGCG<br>CTGCGAGGCGTGCCGCGTGTGCGAGGCGGGCTCGGGCCTCGTGTTCTCCTGCCAGGACAAGCAGA<br>ACACCGTGTGCGAGGAGTGCCCCGACGGCACGTATTCCGACGAGGCCAACCACGTGGACCCGTGC<br>CTGCCCTGCACCGTGTGCGAGGACACCGAGCGCCAGCTCCGCGAGTGCACACGCTGGGCCGACGC<br>CGAGTGCGAGGAGATCCCTGGCCGTTGGATTACACGGTCCACACCCCCAGAGGGCTCGGACAGCA<br>CAGCCCCCAGCACCCAGGAGCCTGAGGCACCTCCAGAACAAGACCTCATAGCCAGCACGGTGGCA<br>GGTGTGGTGACCACAGTGATGGGCAGCTCCCAGCCCGTGGTGACCCGAGGCACCACCGACAACCT<br>CATCCCTGTCTATTGCTCCATCCTGGCTGCTGTGGTTGTGGGTCTTGTGGCCTACATAGCCTTCA<br>AGAGGTGAAAAACCAAAAGAACAAGAATTTCTTGGTAAGAAGCCGGGAACAGACAACAGAAGTCA<br>TGAAGCCCAAGTGAAATCAAAGGTGCTAAATGGTCGCCCAGGAGACATCCGTTGTGCTTGCCTGC<br>GTTTTTGGAAGCTCTGAAGTCACATCACAGGACACGGGGCAGTGGCAACCTTGTCTCTATGCCAGC<br>TCAGTCCCATCAGAGAGCGAGCGCTACCCACTTCTAAATAGCAATTTCGCCGTTGAAGAGGAAGG<br>GCAAAACCACTAGAACTCTCCATCTTATTTTCATGTATATGTGTTCAT |
| 35 | Matrice PD1<br>locus_IL12a_<br>2A_IL12b<br>pCSL30511 | GACTCCCCAGACAGGCCCTGGAACCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTACC<br>GCATGAGCCCCAGCAACCAGACGGACAAGCTGGCCGCCTTCCCGGAGGACCGCAGCCAGCCCGGC<br>CAGGACTGCCGCTTCCGTGTCACACAACTGCCCAACGGGCGTGACTTCCACATGAGCGTGGTCAG<br>GGCCCGGCGCAATGACAGCGGCACCTACCTCTGTGGGGCCGGTTCTGGCGTGAAACAGACTTTGA<br>ATTTTGACCTTCTCAAGTTGGCGGGAGACGTGGAGTCCAACCCAGGGCCCATGTGGCCCCCTGGG<br>TCAGCCTCCCAGCCACCGCCCTCACCTGCCGCGGCCACAGGTCTGCATCCAGCGGCTCGCCCTGT<br>GTCCCTGCAGTGCCGGCTCAGCATGTGTCCAGCGCGCAGCCTCCTCCTTGTGGCTACCCTGGTCC<br>TCCTGGACCACCTCAGTTTGGCCAGAAACCTCCCCGTGGCCACTCCAGACCCAGGAATGTTCCCA<br>TGCCTTCACCACTCCCAAAACCTGCTGAGGGCCGTCAGCAACATGCTCCAGAAGGCCAGACAAAC<br>TCTAGAATTTTACCCTTGCACTTCTGAAGAGATTGATCATGAAGATATCACAAAAGATAAAACCA<br>GCACAGTGGAGGCCTGTTTACCATTGGAATTAACCAAGAATGAGAGTTGCCTAAATTCCAGAGAG<br>ACCTCTTTCATAACTAATGGGAGTTGCCTGGCCTCCAGAAAGACCTCTTTTATGATGGCCCTGTG<br>CCTTAGTAGTATTTATGAAGACTTGAAGATGTACCAGGTGGAGTTCAAGACCATGAATGCAAAGC<br>TTCTGATGGATCCTAAGAGGCAGATCTTTCTAGATCAAAACATGCTGGCAGTTATTGATGAGCTG<br>ATGCAGGCCCTGAATTTCAACAGTGAGACTGTGCCACAAAAATCCTCCCTTGAAGAACCGGATTT<br>TTATAAAACTAAAATCAAGCTCTGCATACTTCTTCATGCTTTCAGAATTCGGGCAGTGACTATTG<br>ATAGAGTGATGAGCTATCTGAATGCTTCCGGAAGCGGAGCTACTAACTTCAGCCTGCTGAAGCAG<br>GCTGGAGACGTGGAGGAGAACCCTGGACCTATGTGTCACCAGCAGTTGGTCATCTCTTGGTTTTC<br>CCTGGTTTTTCTGGCATCTCCCCTCGTGGCCATATGGGAACTGAAGAAAGATGTTTATGTCGTAG<br>AATTGGATTGGTATCCGGATGCCCCTGGAGAAATGGTGGTCCTCACCTGTGACACCCCTGAAGAA<br>GATGGTATCACCTGGACCTTGGACCAGAGCAGTGAGGTCTTAGGCTCTGGCAAAACCCTGACCAT<br>CCAAGTCAAAGAGTTTGGAGATGCTGGCCAGTACACCTGTCACAAAGGAGGCGAGGTTCTAAGCC<br>ATTCGCTCCTGCTGCTTCACAAAAAGGAAGATGGAATTTGGTCCACTGATATTTTAAAGGACCAG<br>AAAGAACCCAAAAATAAGACCTTTCTAAGATGCGAGGCCAAGAATTATTCTGGACGTTTCACCTG<br>CTGGTGGCTGACGACAATCAGTACTGATTTGACATTCAGTGTCAAAAGCAGCAGAGGCTCTTCTG<br>ACCCCCAAGGGGTGACGTGCGGAGCTGCTACACTCTCTGCAGAGAGAGTCAGAGGGGACAACAAG<br>GAGTATGAGTACTCAGTGGAGTGCCAGGAGGACAGTGCCTGCCCAGCTGCTGAGGAGAGTCTGCC<br>CATTGAGGTCATGGTGGATGCCGTTCACAAGCTCAAGTATGAAAACTACACCAGCAGCTTCTTCA<br>TCAGGGACATCATCAAACCTGACCCACCCAAGAACTTGCAGCTGAAGCCATTAAAGAATTCTCGG |

TABLE 5-continued

Sequences referred to in example 2 and 3.

| | | |
|---|---|---|
| | | CAGGTGGAGGTCAGCTGGGAGTACCCTGACACCTGGAGTACTCCACATTCCTACTTCTCCCTGAC<br>ATTCTGCGTTCAGGTCCAGGGCAAGAGCAAGAGAGAAAAGAAAGATAGAGTCTTCACGGACAAGA<br>CCTCAGCCACGGTCATCTGCCGCAAAAATGCCAGCATTAGCGTGCGGGCCCAGGACCGCTACTAT<br>AGCTCATCTTGGAGCGAATGGGCATCTGTGCCCTGCAGTGAGGGCAGAGGCAGCCTGCTGACCTG<br>CGGCGACGTCGAGGAGAACCCCGGGCCCATGGGGGCAGGTGCCACCGGCCGCGCCATGGACGGGC<br>CGCGCCTGCTGCTGTTGCTGCTTCTGGGGGTGTCCCTTGGAGGTGCCAAGGAGGCATGCCCCACA<br>GGCCTGTACACACACAGCGGTGAGTGCTGCAAAGCCTGCAACCTGGGCGAGGGTGTGGCCCAGCC<br>TTGTGGAGCCAACCAGACCGTGTGTGAGCCCTGCCTGGACAGCGTGACGTTCTCCGACGTGGTGA<br>GCGCGACCGAGCCGTGCAAGCCGTGCACCGAGTGCGTGGGGCTCCAGAGCATGTCGGCGCCGTGC<br>GTGGAGGCCGATGACGCCGTGTGCCGCTGCGCCTACGGCTACTACCAGGATGAGACGACTGGGCG<br>CTGCGAGGCGTGCCGCGTGTGCGAGGCGGGCTCGGGCCTCGTGTTCTCCTGCCAGGACAAGCAGA<br>ACACCGTGTGCGAGGAGTGCCCCGACGGCACGTATTCCGACGAGGCCAACCACGTGGACCCGTGC<br>CTGCCCTGCACCGTGTGCGAGGACACCGAGCGCAGCTCCGCGAGTGCACACGCTGGGCCGACGC<br>CGAGTGCGAGGAGATCCCTGGCCGTTGGATTACACGGTCCACACCCCCAGAGGGCTCGGACAGCA<br>CAGCCCCCAGCACCCAGGAGCCTGAGGCACCTCCAGAACAAGACCTCATAGCCAGCACGGTGGCA<br>GGTGTGGTGACCACAGTGATGGGCAGCTCCCAGCCCGTGGTGACCCGAGGCACCACCGACAACCT<br>CATCCCTGTCTATTGCTCCATCCTGGCTGCTGTGGTTGTGGGTCTTGTGGCCTACATAGCCTTCA<br>AGAGGTGATCTAGAGGGCCCGTTTAAACCCGCTGATCAGCCTCGACTGTGCCTTCTAGTTGCCAG<br>CCATCTGTTGTTTGCCCCTCCCCCGTGCCTTCCTTGACCCTGGAAGGTGCCACTCCCACTGTCCT<br>TTCCTAATAAAATGAGGAAATTGCATCGCATTGTCTGAGTAGGTGTCATTCTATTCTGGGGGGTG<br>GGGTGGGGCAGGACAGCAAGGGGGAGGATTGGGAAGACAATAGCAGGCATGCTGGGGATGCGGTG<br>GGCTCTATGACTAGTGGCGAATTCGGCGCAGATCAAAGAGAGCCTGCGGGCAGAGCTCAGGGTGA<br>CAGGTGCGGCCTCGGAGGCCCCGGGGCAGGGGTGAGCTGAGCCGGTCCTGGGGTGGGTGTCCCCT<br>CCTGCACAGGATCAGGAGCTCCAGGGTCGTAGGGCAGGGACCCCCCAGCTCCAGTCCAGGGGTCT<br>GTCCTGCACCTGGGGAATGGTGACCGGCATCTCTGTCCTCTAGCTCTGGAAGCACCCCAGCCCCT<br>CTAGTCTGCCCTCACCCCTGACCCTGACCCTCCACCCTGACCCCGTCCTAACCCCTGACCTTTG |
| 36 | Inserted<br>matrice TRAC<br>locus_CubiCA<br>R CD22 (60<br>nucleotides<br>upstream and<br>downstream) | ATGAGATCATGTCCTAACCCTGATCCTCTTGTCCCACAGATATCCAGAACCCTGACCCTGTTGCT<br>GGGCCTTTTTCCCATGCCTGCCTTTACTCTGCCAGAGTTATATTGCTGGGGTTTTGAAGAAGATC<br>CTATTAAATAAAAGAATAAGCAGTATTATTAAGTAGCCCTGCATTTCAGGTTTCCTTGAGTGGCA<br>GGCCAGGCCTGGCCGTGAACGTTCACTGAAATCATGGCCTCTTGGCCAAGATTGATAGCTTGTGC<br>CTGTCCCTGAGTCCCAGTCCATCACGAGCAGCTGGTTTCTAAGATGCTATTTCCCGTATAAAGCA<br>TGAGACCGTGACTTGCCAGCCCCACAGAGCCCCGCCCTTGTCCATCACTGGCATCTGGACTCCAG<br>CCTGGGTTGGGGCAAAGAGGGAAATGAGATCATGTCCTAACCCTGATCCTCTTGTCCCACAGATA<br>TCCAGTACCCCTACGACGTGCCCGACTACGCCTCCGGTGAGGGCAGAGGAAGTCTTCTAACATGC<br>GGTGACGTGGAGGAGAATCCGGGCCCCGGATCCGCTCTGCCCGTCACCGCTCTGCTGCTGCCACT<br>GGCACTGCTGCTGCACGCTGCTAGGCCCGGAGGGGGAGGCAGCTGCCCCTACAGCAACCCCAGCC<br>TGTGCAGCGGAGGCGGCGGCAGCGGCGGAGGGGGTAGCCAGGTGCAGCTGCAGCAGAGCGGCCCT<br>GGCCTGGTGAAGCCAAGCCAGACACTGTCCCTGACCTGCGCCATCAGCGGCGATTCCGTGAGCTC<br>CAACTCCGCCGCCTGGAATTGGATCAGGCAGTCCCCTTCTCGGGGCCTGGAGTGGCTGGGAAGGA<br>CATACTATCGGTCTAAGTGGTACAACGATTATGCCGTGTCTGTGAAGAGCAGAATCAATCAAC<br>CCTGACACCTCCAAGAATCAGTTCTCTCTGCAGCTGAATAGCGTGACACCAGAGGACACCGCCGT<br>GTACTATTGCGCCAGGGAGGTGACCGGCGACCTGGAGGATGCCTTTGACATCTGGGGCCAGGGCA<br>CAATGGTGACCGTGAGCTCCGGAGGCGGCGGATCTGGCGGAGGAGGAAGTGGGGGCGGCGGGAGT<br>GATATCCAGATGACACAGTCCCCATCCTCTCTGAGCGCCTCCGTGGGCGACAGAGTGACAATCAC<br>CTGTAGGGCCTCCCAGACCATCTGGTCTTACCTGAACTGGTATCAGCAGAGGCCCGGCAAGGCCC<br>CTAATCTGCTGATCTACGCAGCAAGCTCCCTGCAGAGCGGAGTGCCATCCAGATTCTCTGGCAGG<br>GGCTCCGGCACAGACTTCACCCTGACCATCTCTAGCCTGCAGGCCGAGGACTTCGCCACCTACTA<br>TTGCCAGCAGTCTTATAGCATCCCCCAGACATTTGGCCAGGGCACCAAGCTGGAGATCAAGTCGG<br>ATCCCGGAAGCGGAGGGGGAGGCAGCTGCCCCTACAGCAACCCCAGCCTGTGCAGCGGAGGCGGC<br>GGCAGCGAGCTGCCCACCCAGGGCACCTTCTCCAACGTGTCCACCAACGTGAGCCCAGCCAAGCC<br>CACCACCACCGCCTGTCCTTATTCCAATCCTTCCCTGTGTGCTCCACCACAACCCCCGCTCCAA<br>GGCCCCCTACCCCCGCACCAACTATTGCCTCCCAGCCACTCTCACTGCGGCCTGAGGCCTGTCGG<br>CCCGCTGCTGGAGGCGCAGTGCATACAAGGGGCCTCGATTTCGCCTGCGATATTTACATCTGGGC<br>ACCCCTCGCCGGCACCTGCGGGGTGCTTCTCCTCTCCCTGGTGATTACCCTGTATTGCAGACGGG<br>GCCGGAAGAAGCTCCTCTACATTTTTAAGCAGCCTTTCATGCGGCCAGTGCAGACAACCCAAGAG<br>GAGGATGGGTGTTCCTGCAGATTCCCTGAGGAAGAGGAAGGCGGGTGCGAGCTGAGAGTGAAGTT<br>CTCCAGGAGCGCAGATGCCCCCGCCTATCAACAGGGCCAGAACCAGCTCTACAACGAGCTTAACC<br>TCGGGAGGCGCGAAGAATACGACGTGTTGGATAAGAGAAGGGGGCGGGACCCCGAGATGGGAGGA<br>AAGCCCCGGAGGAAGAACCCTCAGGAGGGCCTGTACAACGAGCTGCAGAAGGATAAGATGGCCGA<br>GGCCTACTCAGAGATCGGGATGAAGGGGGAGCGGCGCCGCGGGAAGGGGCACGATGGGCTCTACC<br>AGGGGCTGAGCACAGCCACAAAGGACACATACGACGCCTTGCACATGCAGGCCTTCCACCCCGG<br>GAATAGTCTAGAGGGCCCGTTTAAACCCGCTGATCAGCCTCGACTGTGCCTTCTAGTTGCCAGCC<br>ATCTGTTGTTTGCCCCTCCCCCGTGCCTTCCTTGACCCTGGAAGGTGCCACTCCCACTGTCCTTT<br>CCTAATAAAATGAGGAAATTGCATCGCATTGTCTGAGTAGGTGTCATTCTATTCTGGGGGGTGGG<br>GTGGGGCAGGACAGCAAGGGGGAGGATTGGGAAGACAATAGCAGGCATGCTGGGGATGCGGTGGG<br>CTCTATGACTAGTGGCGAATTCCCGTGTACCAGCTGAGAGACTCTAAATCCAGTGACAAGTCTGT<br>CTGCCTATTCACCGATTTTGATTCTCAAACAAATGTGTCACAAAGTAAGGATTCTGATGTGTATA<br>TCACAGACAAAACTGTGCTAGACATGAGGTCTATGGACTTCAAGAGCAACAGTGCTGTGGCCTGG<br>AGCAACAAATCTGACTTTGCATGTGCAAACGCCTTCAACAACAGCATTATTCCAGAAGACACCTT<br>CTTCCCCAGCCCAGGTAAGGGCAGCTTTGGTGCCTTCGCAGGCTGTTTCCTTGCTTCAGGAATGG<br>CCAGGTTCTGCCCAGAGCTCTGGTCAATGATGTCTAAAACTCCTCTGATTGGTGGTCTCGGCCTT<br>ATCCATTGCCACCAAAACCCTCTTTTTACTAAGAAACAGTGAGCCTTGTTCTGGCAGTCCAGAGA<br>ATGACACGGGAAAAAAGCAGATGAAGA |
| 37 | Inserted<br>matrice CD25<br>locus_IL15_<br>2A_sIL15Ra (60<br>nucleotides | AGTGCTGGCTAGAAACCAAGTGCTTTACTGCATGCACATCATTTAGCACAGTTAGTTGCTGTTTA<br>TTATTCCTGTTCCACAGCTATTGTCTGCCATATAAAAACTTAGGCCAGGCACAGTGGCTCACACC<br>TGTAATCCCAGCACTTTGGAAGGCCGAGGCAGGCAGATCACAAGGTCAGGAGTTCGAGACCAGCC<br>TGGCCAACATAGCAAAACCCCATCTCTACTAAAAATACAAAAATTAGCCAGGCATGGTGGCGTGT<br>GCACTGGTTTAGAGTGAGGACCACATTTTTTGGTGCCGTGTTACACATATGACCGTGACTTTGT |

TABLE 5-continued

Sequences referred to in example 2 and 3.

|  |  |  |
|---|---|---|
| | upstream and downstream) | TACACCACTACAGGAGGAAGAGTAGAAGAACAATCGGTTCTGGCGTGAAACAGACTTTGAATTTT<br>GACCTTCTCAAGTTGGCGGGAGACGTGGAGTCCAACCCAGGGCCCGGTACCGGGTCCGCCACCAT<br>GGACTGGACCTGGATTCTGTTCCTCGTGGCTGCTGCTACAAGAGTGCACAGCGGCATTCATGTCT<br>TCATTTTGGGCTGTTTCAGTGCAGGGCTTCCTAAAACAGAAGCCAACTGGGTGAATGTAATAAGT<br>GATTTGAAAAAAATTGAAGATCTTATTCAATCTATGCATATTGATGCTACTTTATATACGGAAAG<br>TGATGTTCACCCCAGTTGCAAAGTAACAGCAATGAAGTGCTTTCTCTTGGAGTTACAAGTTATTT<br>CACTTGAGTCCGGAGATGCAAGTATTCATGATACAGTAGAAAATCTGATCATCCTAGCAAACAAC<br>AGTTTGTCTTCTAATGGGAATGTAACAGAATCTGGATGCAAAGAATGTGAGGAACTGGAGGAAAA<br>AAATATTAAAGAATTTTTGCAGAGTTTTGTACATATTGTCCAAATGTTCATCAACACTTCTGGAA<br>GCGGAGCTACTAACTTCAGCCTGCTGAAGCAGGCTGGAGACGTGGAGGAGAACCCTGGACCTGGG<br>ACCGGCTCTGCAACCATGGATTGGACGTGGATCCTGTTTCTCGTGGCAGCTGCCACAAGAGTTCA<br>CAGTATCACGTGCCCTCCCCCCATGTCCGTGGAACACGCAGACATCTGGGTCAAGAGCTACAGCT<br>TGTACTCCAGGGAGCGGTACATTTGTAACTCTGGTTTCAAGCGTAAAGCCGGCACGTCCAGCCTG<br>ACGGAGTGCGTGTTGAACAAGGCCACGAATGTCGCCCACTGGACAACCCCCAGTCTCAAATGCAT<br>TAGAGACCCTGCCCTGGTTCACCAAAGGCCAGCGCCACCCTCCACAGTAACGACGGCAGGGGTGA<br>CCCCACAGCCAGAGAGCCTCTCCCCTTCTGGAAAAGAGCCCGCAGCTTCATCTCCCAGCTCAAAC<br>AACACAGCGGCCACAACAGCAGCTATTGTCCCGGGCTCCCAGCTGATGCCTTCAAAATCACCTTC<br>CACAGGAACCACAGAGATAAGCAGTCATGAGTCCTCCCACGGCACCCCCTCTCAGACAACAGCCA<br>AGAACTGGGAACTCACAGCATCCGCCTCCCACCAGCCGCCAGGTGTGTATCCACAGGGCCACAGC<br>GACACCACTGAGGGCAGAGGCAGCCTGCTGACCTGCGGCGACGTCGAGGAGAACCCCGGGCCCAT<br>GGGGGCAGGTGCCACCGGCCGCGCCATGGACGGGCCGCGCCTGCTGCTGTTGCTGCTTCTGGGGG<br>TGTCCCTTGGAGGTGCCAAGGAGGCATGCCCCACAGGCCTGTACACACACAGCGGTGAGTGCTGC<br>AAAGCCTGCAACCTGGGCGAGGGTGTGGCCCAGCCTTGTGAGCCAACCAGACCGTGTGTGAGCC<br>CTGCCTGGACAGCGTGACGTTCTCCGACGTGGTGAGCGCGACCGAGCCGTGCAAGCCGTGCACCG<br>AGTGCGTGGGGCTCCAGAGCATGTCGGCGCCGTGCGTGGAGGCCGATGACGCCGTGTGCCGCTGC<br>GCCTACGGCTACTACCAGGATGAGACGACTGGGCGCTGCGAGGCGTGCCGCGTGTGCGAGGCGGG<br>CTCGGGCCTCGTGTTCTCCTGCCAGGACAAGCAGAACACCGTGTGCGAGGAGTGCCCCGACGGCA<br>CGTATTCCGACGAGGCCAACCACGTGGACCCGTGCCTGCCCTGCACCGTGTGCGAGGACACCGAG<br>CGCCAGCTCCGCGAGTGCACACGCTGGGCCGACGCGAGTGCGAGGAGATCCCTGGCCGTTGGAT<br>TACACGGTCCACACCCCCAGAGGGCTCGGACAGCACAGCCCCAGCACCCAGGAGCCTGAGGCAC<br>CTCCAGAACAAGACCTCATAGCCAGCACGGTGGCAGGTGTGGTGACCACAGTGATGGGCAGCTCC<br>CAGCCCGTGGTGACCCGAGGCACCACCGACAACCTCATCCCTGTCTATTGCTCCATCCTGGCTGC<br>TGTGGTTGTGGGTCTTGTGGCCTACATAGCCTTCAAGAGGTGAAAAACCAAAAGAACAAGAATTT<br>CTTGGTAAGAAGCCGGGAACAGACAACAGAAGTCATGAAGCCCAAGTGAAATCAAAGGTGCTAAA<br>TGGTCGCCCAGGAGACATCCGTTGTGCTTGCCTGCGTTTTGGAAGCTCTGAAGTCACATCACAGG<br>ACACGGGGCAGTGGCAACCTTGTCTCTATGCCAGCTCAGTCCCATCAGAGAGCGAGCGCTACCCA<br>CTTCTAAATAGCAATTTCGCCGTTGAAGAGGAAGGGCAAAACCACTAGAACTCTCCATCTTATTT<br>TCATGTATATGTGTTCATTAAAGCATGAATGGTATGGAACTCTCTCCACCCTATATGTAGTATAA<br>AGAAAAGTAGGTT |
| 38 | Inserted matrix CD25 locus_IL12a_2A_IL12b (60 nucleotides upstream and downstream) | GGTGGCCGGGAGGCTTTGTGGGGCCACCCAGCCCCTTCCTCACCTCTCTCCATCTCTCAGACTC<br>CCCAGACAGGCCCTGGAACCCCCCACCTTCTCCCCAGCCCTGCTCGTGGTGACCGAAGGGGACA<br>ACGCCACCTTCACCTGCAGCTTCTCCAACACATCGGAGAGCTTCGTGCTAAACTGGTACCGCATG<br>AGCCCCAGCAACCAGACGGACAAGCTGGCCGCCTTCCCCGAGGACCGCAGCCAGCCCGGCCAGGA<br>CTGCCGCTTCCGTGTCACACAACTGCCCACCGGCGATGACTTCCACATGAGCGTGGTCAGGGCCC<br>GGCGCAATGACAGCGGCACCTACCTCTGTGGGCCGGTTCTGGCGTGAAACAGACTTTGAATTTT<br>GACCTTCTCAAGTTGGCGGGAGACGTGGAGTCCAACCCAGGGCCCGGTACCGGGTCCGCCACCAT<br>GGACTGGACCTGGATTCTGTTCCTCGTGGCTGCTGCTACAAGAGTGCACAGCGGCATTCATGTCT<br>TCATTTTGGGCTGTTTCAGTGCAGGGCTTCCTAAAACAGAAGCCAACTGGGTGAATGTAATAAGT<br>GATTTGAAAAAAATTGAAGATCTTATTCAATCTATGCATATTGATGCTACTTTATATACGGAAAG<br>TGATGTTCACCCCAGTTGCAAAGTAACAGCAATGAAGTGCTTTCTCTTGGAGTTACAAGTTATTT<br>CACTTGAGTCCGGAGATGCAAGTATTCATGATACAGTAGAAAATCTGATCATCCTAGCAAACAAC<br>AGTTTGTCTTCTAATGGGAATGTAACAGAATCTGGATGCAAAGAATGTGAGGAACTGGAGGAAAA<br>AAATATTAAAGAATTTTTGCAGAGTTTTGTACATATTGTCCAAATGTTCATCAACACTTCTGGAA<br>GCGGAGCTACTAACTTCAGCCTGCTGAAGCAGGCTGGAGACGTGGAGGAGAACCCTGGACCTGGG<br>ACCGGCTCTGCAACCATGGATTGGACGTGGATCCTGTTTCTCGTGGCAGCTGCCACAAGAGTTCA<br>CAGTATCACGTGCCCTCCCCCCATGTCCGTGGAACACGCAGACATCTGGGTCAAGAGCTACAGCT<br>TGTACTCCAGGGAGCGGTACATTTGTAACTCTGGTTTCAAGCGTAAAGCCGGCACGTCCAGCCTG<br>ACGGAGTGCGTGTTGAACAAGGCCACGAATGTCGCCCACTGGACAACCCCCAGTCTCAAATGCAT<br>TAGAGACCCTGCCCTGGTTCACCAAAGGCCAGCGCCACCCTCCACAGTAACGACGGCAGGGGTGA<br>CCCCACAGCCAGAGAGCCTCTCCCCTTCTGGAAAAGAGCCCGCAGCTTCATCTCCCAGCTCAAAC<br>AACACAGCGGCCACAACAGCAGCTATTGTCCCGGGCTCCCAGCTGATGCCTTCAAAATCACCTTC<br>CACAGGAACCACAGAGATAAGCAGTCATGAGTCCTCCCACGGCACCCCCTCTCAGACAACAGCCA<br>AGAACTGGGAACTCACAGCATCCGCCTCCCACCAGCCGCCAGGTGTGTATCCACAGGGCCACAGC<br>GACACCACTGAGGGCAGAGGCAGCCTGCTGACCTGCGGCGACGTCGAGGAGAACCCCGGGCCCAT<br>GGGGGCAGGTGCCACCGGCCGCGCCATGGACGGGCCGCGCCTGCTGCTGTTGCTGCTTCTGGGGG<br>TGTCCCTTGGAGGTGCCAAGGAGGCATGCCCCACAGGCCTGTACACACACAGCGGTGAGTGCTGC<br>AAAGCCTGCAACCTGGGCGAGGGTGTGGCCCAGCCTTGTGAGCCAACCAGACCGTGTGTGAGCC<br>CTGCCTGGACAGCGTGACGTTCTCCGACGTGGTGAGCGCGACCGAGCCGTGCAAGCCGTGCACCG<br>AGTGCGTGGGGCTCCAGAGCATGTCGGCGCCGTGCGTGGAGGCCGATGACGCCGTGTGCCGCTGC<br>GCCTACGGCTACTACCAGGATGAGACGACTGGGCGCTGCGAGGCGTGCCGCGTGTGCGAGGCGGG<br>CTCGGGCCTCGTGTTCTCCTGCCAGGACAAGCAGAACACCGTGTGCGAGGAGTGCCCCGACGGCA<br>CGTATTCCGACGAGGCCAACCACGTGGACCCGTGCCTGCCCTGCACCGTGTGCGAGGACACCGAG<br>CGCCAGCTCCGCGAGTGCACACGCTGGGCCGACGCGAGTGCGAGGAGATCCCTGGCCGTTGGAT<br>TACACGGTCCACACCCCCAGAGGGCTCGGACAGCACAGCCCCAGCACCCAGGAGCCTGAGGCAC<br>CTCCAGAACAAGACCTCATAGCCAGCACGGTGGCAGGTGTGGTGACCACAGTGATGGGCAGCTCC<br>CAGCCCGTGGTGACCCGAGGCACCACCGACAACCTCATCCCTGTCTATTGCTCCATCCTGGCTGC<br>TGTGGTTGTGGGTCTTGTGGCCTACATAGCCTTCAAGAGGTGATCTAGAGGGCCCGTTTAAACCC<br>GCTGATCAGCCTCGACTGTGCCTTCTAGTTGCCAGCCATCTGTTGTTTGCCCCTCCCCCGTGCCT |

TABLE 5-continued

Sequences referred to in example 2 and 3.

| | | |
|---|---|---|
| | | TCCTTGACCCTGGAAGGTGCCACTCCCACTGTCCTTTCCTAATAAAATGAGGAAATTGCATCGCA<br>TTGTCTGAGTAGGTGTCATTCTATTCTGGGGGGTGGGGTGGGGCAGGACAGCAAGGGGGAGGATT<br>GGGAAGACAATAGCAGGCATGCTGGGGATGCGGTGGGCTCTATGACTAGTGGCGAATTCGGCGCA<br>GATCAAAGAGAGCCTGCGGGCAGAGCTCAGGGTGACAGGTGCGGCCTCGGAGGCCCCGGGGCAGG<br>GGTGAGCTGAGCCGGTCCTGGGGTGGGTGTCCCCTCCTGCACAGGATCAGGAGCTCCAGGGTCGT<br>AGGGCAGGGACCCCCCAGCTCCAGTCCAGGGCTCTGTCCTGCACCTGGGGAATGGTGACCGGCAT<br>CTCTGTCCTCTAGCTCTGGAAGCACCCCAGCCCCTCTAGTCTGCCCTCCACCCCTGACCCTGACC<br>TCCACCCTGACCCCGTCCTAACCCCTGACCTTTGTGCCCTTCCAGAGAGAAGGGCAGAAGTGCCC<br>ACAGCCCACCCCAGCCCCTCACCCAGGCC |
| 39 | Inserted<br>matrice CD25<br>locus_IL12a_<br>2A_IL12b (60<br>nucleotides<br>upstream and<br>downstream) | AGTGCTGGCTAGAAACCAAGTGCTTTACTGCATGCACATCATTTAGCACAGTTAGTTGCTGTTTA<br>TTATTCCTGTTCCACAGCTATTGTCTGCCATATAAAAACTTAGGCCAGGCACAGTGGCTCACACC<br>TGTAATCCCAGCACTTTGGAAGGCCGAGGCAGGCAGATCACAAGGTCAGGAGTTCGAGACCAGCC<br>TGGCCAACATAGCAAAACCCCATCTCTACTAAAAATACAAAAATTAGCCAGGCATGGTGGCGTGT<br>GCACTGGTTTAGAGTGAGGACCACATTTTTTTGGTGCCGTGTTACACATATGACCGTGACTTTGT<br>TACACCACTACAGGAGGAAGAGTAGAAGACAATCGGTTCTGGCGTGAAACAGACTTTGAATTTT<br>GACCTTCTCAAGTTGGCGGGAGACGTGGAGTCCAACCCAGGGCCCATGTGGCCCCTGGGTCAGC<br>CTCCCAGCCACCGCCCTCACCTGCCGCGGCCACAGGTCTGCATCCAGCGGCTCGCCCTGTGTCCC<br>TGCAGTGCCGGCTCAGCATGTGTCCAGCGCGCAGCCTCCTCCTTGTGGCTACCCTGGTCCTCCTG<br>GACCACCTCAGTTTGGCCAGAAACCTCCCCGTGGCCACTCCAGACCCAGGAATGTTCCCATGCCT<br>TCACCACTCCCAAAACCTGCTGAGGGCCGTCAGCAACATGCTCCAGAAGGCCAGACAAACTCTAG<br>AATTTTACCCTTGCACTTCTGAAGAGATTGATCATGAAGATATCACAAAAGATAAAACCAGCACA<br>GTGGAGGCCTGTTTACCATTGGAATTAACCAAGAATGAGAGTTGCCTAAATTCCAGAGAGACCTC<br>TTTCATAACTAATGGGAGTTGCCTGGCCTCCAGAAAGACCTCTTTTATGATGGCCCTGTGCCTTA<br>GTAGTATTTATGAAGACTTGAAGATGTACCAGGTGGAGTTCAAGACCATGAATGCAAAGCTTCTG<br>ATGGATCCTAAGAGGCAGATCTTTCTAGATCAAAACATGCTGGCAGTTATTGATGAGCTGATGCA<br>GGCCCTGAATTTCAACAGTGAGACTGTGCCACAAAAATCCTCCCTTGAAGAACCGGATTTTTATA<br>AACTAAAATCAAGCTCTGCATACTTCTTCATGCTTTTCAGAATTCGGGCAGTGACTATTGATAGA<br>GTGATGAGCTATCTGAATGCTTCCGGAAGCGGAGCTACTAACTTCAGCCTGCTGAAGCAGGCTGG<br>AGACGTGGAGGAGAACCCTGGACCTATGTGTCACCAGCAGTTGGTCATCTCTTGGTTTTCCCTGG<br>TTTTTCTGGCATCTCCCCTCGTGGCCATATGGGAACTGAAGAAAGATGTTTATGTCGTAGAATTG<br>GATTGGTATCCGGATGCCCCTGGAGAAATGGTGGTCCTCACCTGTGACACCCCTGAAGAAGATGG<br>TATCACCTGGACCTTGGACCAGAGCAGTGAGGTCTTAGGCTCTGGCAAAACCCTGACCATCCAAG<br>TCAAAGAGTTTGGAGATGCTGGCCAGTACACCTGTCACAAAGGAGGCGAGGTTCTAAGCCATTCG<br>CTCCTGCTGCTTCACAAAAAGGAAGATGGAATTTGGTCCACTGATATTTTAAAGGACCAGAAAGA<br>ACCCAAAAATAAGACCTTTCTAAGATGCGAGGCCAAGAATTATTCTGGACGTTTCACCTGCTGGT<br>GGCTGACGACAATCAGTACTGATTTGACATTCAGTGTCAAAAGCAGCAGAGGCTCTTCTGACCCC<br>CAAGGGGTGACGTGCGGAGCTGCTACACTCTCTGCAGAGAGAGTCAGAGGGGACAACAAGGAGTA<br>TGAGTACTCAGTGGAGTGCCAGGAGGACAGTGCCTGCCCAGCTGCTGAGGAGAGTCTGCCCATTG<br>AGGTCATGGTGGATGCCGTTCACAAGCTCAAGTATGAAAACTACACCAGCAGCTTCTTCATCAGG<br>GACATCATCAAACCTGACCCACCCAAGAATTGCAGCTGAAGCCATTAAAGAATTCTCGGCAGGT<br>GGAGGTCAGCTGGGAGTACCCTGACACCTGGAGTACTCCACATTCCTACTTCTCCCTGACATTCT<br>GCGTTCAGGTCCAGGGCAAGAGCAAGAGAGAAAAGAAAGATAGAGTCTTCACGGACAAGACCTCA<br>GCCACGGTCATCTGCCGCAAAAATGCCAGCATTAGCGTGCGGGCCCAGGACCGCTACTATAGCTC<br>ATCTTGGAGCGAATGGGCATCTGTGCCCTGCAGTGAGGGCAGAGGCAGCCTGCTGACCTGCGGCG<br>ACGTCGAGGAGAACCCCGGGCCCATGGGGGCAGGTGCCACCGGCCGCGCCATGGACGGGCCGCGC<br>CTGCTGCTGTTGCTGCTTCTGGGGGTGTCCCTTGGAGGTGCCAAGGAGGCATGCCCCACAGGCCT<br>GTACACACACAGCGGTGAGTGCTGCAAAGCCTGCAACCTGGGCGAGGGTGTGGCCCAGCCTTGTG<br>GAGCCAACCAGACCGTGTGTGAGCCCTGCCTGGACAGCGTGACGTTCTCCGACGTGGTGAGCGCG<br>ACCGAGCCGTGCAAGCCGTGCACCGAGTGCGTGGGGCTCCAGAGCATGTCGGCGCCGTGCGTGGA<br>GGCCGATGACGCCGTGTGCCGCTGCGCCTACGGCTACTACCAGGATGAGACGACTGGGCGCTGCG<br>AGGCGTGCCGCGTGTGCGAGGCGGGCTCGGGCCTCGTGTTCTCCTGCCAGGACAAGCAGAACACC<br>GTGTGCGAGGAGTGCCCCGACGGCACGTATTCCGACGAGGCCAACCACGTGGACCCGTGCCTGCC<br>CTGCACCGTGTGCGAGGACACCGAGCGCCAGCTCCGCGAGTGCACACGCTGGGCCGACGCCGAGT<br>GCGAGGAGATCCCTGGCCGTTGGATTACACGGTCCACACCCCCAGAGGGCTCGGACAGCACAGCC<br>CCCAGCACCCAGGAGCCTGAGGCACCTCCAGAACAAGACCTCATAGCCAGCACGGTGGCAGGTGT<br>GGTGACCACAGTGATGGGCAGCTCCCAGCCCGTGGTGACCCGAGGCACCACCGACAACCTCATCC<br>CTGTCTATTGCTCCATCCTGGCTGCTGTGGTTGTGGGTCTTGTGGCCTACATAGCCTTCAAGAGG<br>TGAAAAACCAAAAGAACAAGAATTCTTGGTAAGAAGCCGGGAACAGACAACAGAAGTCATGAAG<br>CCCAAGTGAAATCAAAGGTGCTAAATGGTCGCCCAGGAGACATCCGTTGTGCTTGCCTGCGTTTT<br>GGAAGCTCTGAAGTCACATCACAGGACACGGGCAGTGGCAACCTTGTCTCTATGCCAGCTCAGT<br>CCCATCAGAGAGCGAGCGCTACCCACTTCTAAATAGCAATTTCGCCGTTGAAGAGGAAGGGCAAA<br>ACCACTAGAACTCTCCATCTTATTTTCATGTATATGTGTTCATGAATGGTATGGAACTCTCTCCA<br>CCCTATATGTAGTATAAAGAAAAGTAGGTT |
| 40 | Inserted<br>matrice PD1<br>locus_IL12a_<br>2A_IL12b (60<br>nucleotides<br>upstream and<br>downstream | GGTGGCCGGGGAGGCTTTGTGGGGCCACCCAGCCCCTTCCTCACCTCTCTCCATCTCTCAGACTC<br>CCAGACAGGCCCTGGAACCCCCCCACCTTCTCCCCAGCCCTGCTCGTGGTGACCGAGGGGACA<br>ACGCCACCTTCACCTGCAGCTTCTCCAACACATCGGAGAGCTTCGTGCTAAACTGGTACCGCATG<br>AGCCCCAGCAACCAGACGGACAAGCTGGCCGCCTTCCCCGAGGACCGCAGCCAGCCCGGCCAGGA<br>CTGCCGCTTCCGTGTCACACAACTGCCCAACGGGCGTGACTTCCACATGAGCGTGGTCAGGGCCC<br>GGCGCAATGACAGCGGCACCTACCTCTGTGGGGCCGGTTCTGGCGTGAAACAGACTTTGAATTTT<br>GACCTTCTCAAGTTGGCGGGAGACGTGGAGTCCAACCCAGGGCCCATGTGGCCCCTGGGTCAGC<br>CTCCCAGCCACCGCCCTCACCTGCCGCGGCCACAGGTCTGCATCCAGCGGCTCGCCCTGTGTCCC<br>TGCAGTGCCGGCTCAGCATGTGTCCAGCGCGCAGCCTCCTCCTTGTGGCTACCCTGGTCCTCCTG<br>GACCACCTCAGTTTGGCCAGAAACCTCCCCGTGGCCACTCCAGACCCAGGAATGTTCCCATGCCT<br>TCACCACTCCCAAAACCTGCTGAGGGCCGTCAGCAACATGCTCCAGAAGGCCAGACAAACTCTAG<br>AATTTTACCCTTGCACTTCTGAAGAGATTGATCATGAAGATATCACAAAAGATAAAACCAGCACA<br>GTGGAGGCCTGTTTACCATTGGAATTAACCAAGAATGAGAGTTGCCTAAATTCCAGAGAGACCTC<br>TTTCATAACTAATGGGAGTTGCCTGGCCTCCAGAAAGACCTCTTTTATGATGGCCCTGTGCCTTA<br>GTAGTATTTATGAAGACTTGAAGATGTACCAGGTGGAGTTCAAGACCATGAATGCAAAGCTTCTG |

TABLE 5-continued

Sequences referred to in example 2 and 3.

|  |  |  |
|---|---|---|
|  |  | ATGGATCCTAAGAGGCAGATCTTTCTAGATCAAAACATGCTGGCAGTTATTGATGAGCTGATGCA<br>GGCCCTGAATTTCAACAGTGAGACTGTGCCACACAAAATCCTCCCTTGAAGAACCGGATTTTTATA<br>AAACTAAAATCAAGCTCTGCATACTTCTTCATGCTTTCAGAATTCGGGCAGTGACTATTGATAGA<br>GTGATGAGCTATCTGAATGCTTCCGGAAGCGGAGCTACTAACTTCAGCCTGCTGAAGCAGGCTGG<br>AGACGTGGAGGAGAACCCTGGACCTATGTGTCACCAGCAGTTGGTCATCTCTTGGTTTTCCCTGG<br>TTTTTCTGGCATCTCCCCTCGTGGCCATATGGGAACTGAAGAAAGATGTTTATGTCGTAGAATTG<br>GATTGGTATCCGGATGCCCCTGGAGAAATGGTGGTCCTCACCTGTGACACCCCTGAAGAAGATGG<br>TATCACCTGGACCTTGGACCAGAGCAGTGAGGTCTTAGGCTCTGGCAAAACCCTGACCATCCAAG<br>TCAAAGAGTTTGGAGATGCTGGCCAGTACACCTGTCACAAAGGAGGCGAGGTTCTAAGCCATTCG<br>CTCCTGCTGCTTCACAAAAAGGAAGATGGAATTTGGTCCACTGATATTTTAAAGGACCAGAAAGA<br>ACCCAAAAATAAGACCTTTCTAAGATGCGAGGCCAAGAATTATTCTGGACGTTTCACCTGCTGGT<br>GGCTGACGACAATCAGTACTGATTTGACATTCAGTGTCAAAAGCAGCAGAGGCTCTTCTGACCCC<br>CAAGGGGTGACGTGCGGAGCTGCTACACTCTCTGCAGAGAGTCAGAGGGGACAACAAGGAGTA<br>TGAGTACTCAGTGGAGTGCCAGGAGGACAGTGCCTGCCCAGCTGCTGAGGAGAGTCTGCCCATTG<br>AGGTCATGGTGGATGCCGTTCACAAGCTCAAGTATGAAAACTACACCAGCAGCTTCTTCATCAGG<br>GACATCATCAAACCTGACCCACCCAAGAACTTGCAGCTGAAGCCATTAAAGAATTCTCGGCAGGT<br>GGAGGTCAGCTGGGAGTACCCTGACACCTGGAGTACTCCACATTCCTACTTCTCCCTGACATTCT<br>GCGTTCAGGTCCAGGGCAAGAGCAAGAGAGAAAAGAAAGATAGAGTCTTCACGGACAAGACCTCA<br>GCCACGGTCATCTGCCGCAAAAATGCCAGCATTAGCGTGCGGGCCCAGGACCGCTACTATAGCTC<br>ATCTTGGAGCGAATGGGCATCTGTGCCCTGCAGTGAGGGCAGAGGCAGCCTGCTGACCTGCGGCG<br>ACGTCGAGGAGAACCCCGGGCCCATGGGGGCAGGTGCCACCGGCCGCGCCATGGACGGGCCGCGC<br>CTGCTGCTGTTGCTGCTTCTGGGGGTGTCCCTTGGAGGTGCCAAGGAGGCATGCCCCACAGGCCT<br>GTACACACAGCGGTGAGTGCTGCAAAGCCTGCAACCTGGGCGAGGGTGTGGCCCAGCCTTGTG<br>GAGCCAACCAGACCGTGTGTGAGCCCTGCCTGGACAGCGTGACGTTCTCCGACGTGGTGAGCGCG<br>ACCGAGCCGTGCAAGCCGTGCACCGAGTGCGTGGGGCTCCAGAGCATGTCGGCGCCGTGCGTGGA<br>GGCCGATGACGCCGTGTGCCGCTGCGCCTACGGCTACTACCAGGATGAGACGACTGGGCGCTGCG<br>AGGCGTGCCGCGTGTGCGAGGCGGGCTCGGGCCTCGTGTTCTCCTGCCAGGACAAGCAGAACACC<br>GTGTGCGAGGAGTGCCCCGACGGCACGTATTCCGACGAGGCCAACCACGTGGACCCGTGCCTGCC<br>CTGCACCGTGTGCGAGGACACCGAGCGCCAGCTCCGCGAGTGCACACGCTGGGCCGACGCCGAGT<br>GCGAGGAGATCCCTGGCCGTTGGATTACACGGTCCACACCCCCAGAGGGCTCGGACAGCACAGCC<br>CCCAGCCACCCAGGAGCCTGAGGCACCTCCAGAACAAGACCTCATAGCCAGCACGGTGGCAGGTGT<br>GGTGACCACAGTGATGGGCAGCTCCCAGCCCGTGGTGACCCGAGGCACCACCGACAACCTCATCC<br>CTGTCTATTGCTCCATCCTGGCTGCTGTGGTTGTGGGTCTTGTGGCCTACATAGCCTTCAAGAGG<br>TGATCTAGAGGGCCCGTTTAAACCCGCTGATCAGCCTCGACTGTGCCTTCTAGTTGCCAGCCATC<br>TGTTGTTTGCCCCTCCCCCGTGCCTTCCTTGACCCTGGAAGGTGCCACTCCCACTGTCCTTTCCT<br>AATAAAATGAGGAAATTGCATCGCATTGTCTGAGTAGGTGTCATTCTATTCTGGGGGGTGGGGTG<br>GGGCAGGACAGCAAGGGGGAGGATTGGGAAGACAATAGCAGGCATGCTGGGGATGCGGTGGGCTC<br>TATGACTAGTGGCGAATTCGGCGCAGATCAAAGAGAGCCTGCGGGCAGAGCTCAGGGTGACAGGT<br>GCGGCCTCGGAGGCCCGGGGCAGGGGTGAGCTGAGCCGGTCCTGGGGTGGGTGTCCCCTCCTGC<br>ACAGGATCAGGAGCTCCAGGGTCGTAGGGCAGGGACCCCCCAGCTCCAGTCCAGGGCTCTGTCCT<br>GCACCTGGGGAATGGTGACCGGCATCTCTGTCCTCTAGCTCTGGAAGCACCCCAGCCCCTCTAGT<br>CTGCCCTCACCCCTGACCCTGACCCTCCACCCTGACCCCGTCCTAACCCCTGACCTTTGTGCCCT<br>TCCAGAGAGAAGGGCAGAAGTGCCCACAGCCCACCCCAGCCCCTCACCCAGGCC |
| 41 | upstream<br>TRAC locus<br>polynucleotide<br>sequence | ATGAGATCATGTCCTAACCCTGATCCTCTTGTCCCACAGATATCCAGAACCCTGACCCTG |
| 42 | downstream<br>TRAC locus<br>polynucleotide<br>sequence | GAAACAGTGAGCCTTGTTCTGGCAGTCCAGAGAATGACACGGGAAAAAAGCAGATGAAGA |
| 43 | upstream<br>CD25 locus<br>polynucleotide<br>sequence | AGTGCTGGCTAGAAACCAAGTGCTTTACTGCATGCACATCATTTAGCACAGTTAGTTGCT |
| 44 | downstream<br>CD25 locus<br>polynucleotide<br>sequence | GAATGGTATGGAACTCTCTCCACCCTATATGTAGTATAAAGAAAAGTAGGTT |
| 45 | upstream<br>PD1 locus<br>polynucleotide<br>sequence | GGTGGCCGGGGAGGCTTTGTGGGGCCACCCAGCCCCTTCCTCACCTCTCTCCATCTCTCA |
| 46 | downstream<br>PD1 locus<br>polynucleotide<br>sequence | TGCCCTTCCAGAGAGAAGGGCAGAAGTGCCCACAGCCCACCCCAGCCCCTCACCCAGGCC |
| 47 | IL-12a<br>polynucleotide | ATGTGGCCCCCTGGGTCAGCCTCCCAGCCACCGCCCTCACCTGCCGCGGCCACAGGTCTGCATCC<br>AGCGGCTCGCCCTGTGTCCCTGCAGTGCCGGCTCAGCATGTGTCCAGCGCGCAGCCTCCTCCTTG<br>TGGCTACCCTGGTCCTCCTGGACCACCTCAGTTTGGCCAGAAACCTCCCCGTGGCCACTCCAGAC<br>CCAGGAATGTTCCCATGCCTTCACCACTCCCAAAACCTGCTGAGGGCCGTCAGCAACATGCTCCA<br>GAAGGCCAGACAAACTCTAGAATTTTACCCTTGCACTTCTGAAGAGATTGATCATGAAGATATCA<br>CAAAAGATAAAACCAGCACAGTGGAGGCCTGTTTACCATTGGAATTAACCAAGAATGAGAGTTGC<br>CTAAATTCCAGAGAGACCTCTTTCATAACTAATGGGAGTTGCCTGGCCTCCAGAAAGACCTCTTT<br>TATGATGGCCCTGTGCCTTAGTAGTATTTATGAAGACTTGAAGATGTACCAGGTGGAGTTCAAGA<br>CCATGAATGCAAAGCTTCTGATGGATCCTAAGAGGCAGATCTTTCTAGATCAAAACATGCTGGCA |

TABLE 5-continued

Sequences referred to in example 2 and 3.

| | | |
|---|---|---|
| 48 | IL12b polynucleotide | GTTATTGATGAGCTGATGCAGGCCCTGAATTTCAACAGTGAGACTGTGCCACAAAAATCCTCCCT<br>TGAAGAACCGGATTTTTATAAAACTAAAATCAAGCTCTGCATACTTCTTCATGCTTTCAGAATTC<br>GGGCAGTGACTATTGATAGAGTGATGAGCTATCTGAATGCTTCC<br>ATGTGTCACCAGCAGTTGGTCATCTCTTGGTTTTCCCTGGTTTTTCTGGCATCTCCCCTCGTGGC<br>CATATGGGAACTGAAGAAAGATGTTTATGTCGTAGAATTGGATTGGTATCCGGATGCCCCTGGAG<br>AAATGGTGGTCCTCACCTGTGACACCCCTGAAGAAGATGGTATCACCTGGACCTTGGACCAGAGC<br>AGTGAGGTCTTAGGCTCTGGCAAAACCCTGACCATCCAAGTCAAAGAGTTTGGAGATGCTGGCCA<br>GTACACCTGTCACAAAGGAGGCGAGGTTCTAAGCCATTCGCTCCTGCTGCTTCACAAAAAGGAAG<br>ATGGAATTTGGTCCACTGATATTTTAAAGGACCAGAAAGAACCCAAAAATAAGACCTTTCTAAGA<br>TGCGAGGCCAAGAATTATTCTGGACGTTTCACCTGCTGGTGGCTGACGACAATCAGTACTGATTT<br>GACATTCAGTGTCAAAAGCAGCAGAGGCTCTTCTGACCCCCAAGGGGTGACGTGCGGAGCTGCTA<br>CACTCTCTGCAGAGAGTCAGAGGGGACAACAAGGAGTATGAGTACTCAGTGGAGTGCCAGGAG<br>GACAGTGCCTGCCCAGCTGCTGAGGAGAGTCTGCCCATTGAGGTCATGGTGGATGCCGTTCACAA<br>GCTCAAGTATGAAAACTACACCAGCAGCTTCTTCATCAGGGACATCATCAAACCTGACCCACCCA<br>AGAACTTGCAGCTGAAGCCATTAAAGAATTCTCGGCAGGTGGAGGTCAGCTGGGAGTACCCTGAC<br>ACCTGGAGTACTCCACATTCCTACTTCTCCCTGACATTCTGCGTTCAGGTCCAGGGCAAGAGCAA<br>GAGAGAAAAGAAAGATAGAGTCTTCACGGACAAGACCTCAGCCACGGTCATCTGCCGCAAAAATG<br>CCAGCATTAGCGTGCGGGCCCAGGACCGCTACTATAGCTCATCTTGGAGCGAATGGGCATCTGTG<br>CCCTGCAGT |
| 49 | IL15 polynucleotide | GGCATTCATGTCTTCATTTTGGGCTGTTTCAGTGCAGGGCTTCCTAAAACAGAAGCCAACTGGGT<br>GAATGTAATAAGTGATTTGAAAAAAATTGAAGATCTTATTCAATCTATGCATATTGATGCTACTT<br>TATATACGGAAAGTGATGTTCACCCCAGTTGCAAAGTAACAGCAATGAAGTGCTTTCTCTTGGAG<br>TTACAAGTTATTTCACTTGAGTCCGGAGATGCAAGTATTCATGATACAGTAGAAAATCTGATCAT<br>CCTAGCAAACAACAGTTTGTCTTCTAATGGGAATGTAACAGAATCTGGATGCAAAGAATGTGAGG<br>AACTGGAGGAAAAAAATATTAAAGAATTTTTGCAGAGTTTTGTACATATTGTCCAAATGTTCATC<br>AACACTTCT |
| 50 | sIL15ra polynucleotide | ATCACGTGCCCTCCCCCCATGTCCGTGGAACACGCAGACATCTGGGTCAAGAGCTACAGCTTGTA<br>CTCCAGGGAGCGGTACATTTGTAACTCTGGTTTCAAGCGTAAAGCCGGCACGTCCAGCCTGACGG<br>AGTGCGTGTTGAACAAGGCCACGAATGTCGCCCACTGGACAACCCCAGTCTCAAATGCATTAGA<br>GACCCTGCCCTGGTTCACCAAAGGCCAGCGCCACCCTCCACAGTAACGACGGCAGGGGTGACCCC<br>ACAGCCAGAGAGCCTCTCCCCTTCTGGAAAAGAGCCCGCAGCTTCATCTCCCAGCTCAAACAACA<br>CAGCGGCCACAACAGCAGCTATTGTCCCGGGCTCCCAGCTGATGCCTTCAAAATCACCTTCCACA<br>GGAACCACAGAGATAAGCAGTCATGAGTCCTCCCACGGCACCCCCTCTCAGACAACAGCCAAGAA<br>CTGGGAACTCACAGCATCCGCCTCCCACCAGCCGCCAGGTGTGTATCCACAGGGCCACAGCGACA<br>CCACT |
| 51 | soluble GP130 polynucleotide | ATGCTGACACTGCAGACTTGGCTGGTGCAGGCACTGTTTATTTTTCTGACTACTGAATCAACTGG<br>CGAACTGCTGGACCCTTGTGGCTACATCAGCCCTGAGTCCCCAGTGGTGCAGCTGCACAGCAACT<br>TCACCGCCGTGTGCGTGCTGAAGGAGAAGTGTATGGACTACTTTCACGTGAACGCCAATTATATC<br>GTGTGGAAAACCAACCACTTCACAATCCCCAAGGAGCAGTACACCATCATCAATAGGACAGCCAG<br>CTCCGTGACCTTTACAGACATCGCCTCCCTGAACATCCAGCTGACCTGCAATATCCTGACATTCG<br>GCCAGCTGGAGCAGAACGTGTATGGCATCACCATCATCTCTGGCCTGCCCCCTGAGAAGCCTAAG<br>AACCTGAGCTGCATCGTGAATGAGGGCAAGAAGATGCGGTGTGAGTGGGACGGCGGCAGAGAGAC<br>ACACCTGGAGACAAACTTCACCCTGAAGTCCGAGTGGGCCACACACAAGTTTGCCGACTGCAAGG<br>CCAAGCGCGATACCCCAACATCCTGTACCGTGGATTACTCTACAGTGTATTTTGTGAACATCGAA<br>GTGTGGGTGGAGGCCGAGAATGCCCTGGGCAAGGTGACCTCCGACCACATCAACTTCGATCCCGT<br>GTACAAGGTGAAGCCTAACCCACCCCACAATCTGAGCGTGATCAATTCCGAGGAGCTGTCTAGCA<br>TCCTGAAGCTGACCTGGACAAACCCATCTATCAAGAGCGTGATCATCCTGAAGTACAATATCCAG<br>TATCGGACCAAGGACGCCTCCACATGGAGCCAGATCCCTCCAGAGGGATACCGCCAGCACAAGATC<br>CTCTTTCACCGTGCAGGACCTGAAGCCCTTCACAGAGTACGTGTTTCGGATCAGATGTATGAAGG<br>AGGACGGCAAGGGCTACTGGAGCGATTGGTCCGAGGAGGCCAGCGGCATCACCTATGAGGACAGG<br>CCTTCTAAGGCCCCCAGCTTCTGGTACAAGATCGATCCATCCCACACCCAGGGCTATCGCACAGT<br>GCAGCTGGTGTGGAAAACCCTGCCCCCTTTCGAGGCCAACGGCAAGATCCTGGACTACGAGGTGA<br>CCCTGACACGGTGGAAGTCCACCTGCAGAACTATACCGTGAATGCCACCAAGCTGACAGTGAAC<br>CTGACAAATGATCGGTACCTGGCCACCCTGACAGTGAGAAACCTGGTGGGCAAGTCTGACGCCGC<br>CGTGCTGACCATCCCTGCCTGCGATTTCCAGGCCACACACCCAGTGATGGACCTGAAGGCCTTTC<br>CCAAGGATAATATGCTGTGGGTGGAGTGGACCACACCTAGAGAGTCCGTGAAGAAGTACATCCTG<br>GAGTGGTGCGTGCTGTCTGACAAGGCCCCATGTATCACCGACTGGCAGCAGGAGGATGGCACCGT<br>GCACAGGACATATCTGCGCGGCAACCTGGCCGAGTCTAAGTGTTACCTGATCACCGTGACACCCG<br>TGTATGCAGACGGACCAGGCTCTCCTGAGAGCATCAAGGCCTACCTGAAGCAGGCACCACCAAGC<br>AAGGGACCAACCGTGCGGACAAAGAAGGTCGGCAAGAATGAGGCCGTGCTGGAGTGGGACCAGCT<br>GCCTGTGGATGTGCAGAACGGCTTCATCAGGAATTACACCATCTTTTATCGCACAATCATCGGCA<br>ACGAGACAGCCGTGAATGTGGACAGCTCCCACACCGAGTATACACTGTCTAGCCTGACCTCCGAT<br>ACACTGTACATGGTGAGGATGGCCGCCTATACAGACGAGGGCGGCAAGGATGGCCCCGAGTTT |
| 52 | IgE signal sequence | GGTACCGGGTCCGCCACCATGGACTGGACCTGGATTCTGTTCCTCGTGGCTGCTGCTACAAGAGT<br>GCACAGC |
| 53 | F2A | GGTTCTGGCGTGAAACAGACTTTGAATTTTGACCTTCTCAAGTTGGCGGGAGACGTGGAGTCCAA<br>CCCAGGGCCC |
| 54 | P2A | GGAAGCGGAGCTACTAACTTCAGCCTGCTGAAGCAGGCTGGAGACGTGGAGGAGAACCCTGGACC<br>T |
| 55 | T2A | GAGGGCAGAGGCAGCCTGCTGACCTGCGGCGACGTCGAGGAGAACCCCGGGCCC |
| 56 | LNGFR | ATGGGGGCAGGTGCCACCGGCCGCGCCATGGACGGGCCGCGCCTGCTGCTGTTGCTGCTTCTGGG<br>GGTGTCCCTTGGAGGTGCCAAGGAGGCATGCCCCACAGGCCTGTACACACACAGCGGTGAGTGCT<br>GCAAAGCCTGCAACCTGGGCGAGGGTGTGGCCCAGCCTTGTGGAGCCAACCAGACCGTGTGTGAG<br>CCCTGCCTGGACAGCGTGACGTTCTCCGACGTGGTGAGCGCGACCGAGCCGTGCAAGCCGTGCAC<br>CGAGTGCGTGGGGCTCCAGAGCATGTCGGCGCCGTGCGTGGAGGCCGATGACGCCGTGTGCCGCT<br>GCGCCTACGGCTACTACCAGGATGAGACGACTGGGCGCTGCGAGGCGTGCCGCGTGTGCGAGGCG<br>GCTCGGGCCTCGTGTTCTCCTGCCAGGACAAGCAGAACACCGTGTGCGAGGAGTGCCCCGACGG<br>CACGTATTCCGACGAGGCCAACCACGTGGACCCCGTGCCTGCCCTGCACCGTGTGCGAGGACACCG TABLE 5-continued Sequences referred to in example 2 and 3.

```
AGCGCCAGCTCCGCGAGTGCACACGCTGGGCCGACGCCGAGTGCGAGGAGATCCCTGGCCGTTGG
ATTACACGGTCCACACCCCCAGAGGGCTCGGACAGCACAGCCCCCAGCACCCAGGAGCCTGAGGC
ACCTCCAGAACAAGACCTCATAGCCAGCACGGTGGCAGGTGTGGTGACCACAGTGATGGGCAGCT
CCCAGCCCGTGGTGACCCGAGGCACCACCGACAACCTCATCCCTGTCTATTGCTCCATCCTGGCT
GCTGTGGTTGTGGGTCTTGTGGCCTACATAGCCTTCAAGAGGTGA
```

| SEQ ID NO# | Sequence Name | Polypeptide sequence |
|---|---|---|
| 57 | IL-12a polypeptide | MWPPGSASQPPPSPAAATGLHPAARPVSLQCRLSMCPARSLLLVATLVLLDHLSLARNLPVATPD PGMFPCLHHSQNLLRAVSNMLQKARQTLEFYPCTSEEIDHEDITKDKTSTVEACLPLELTKNESC LNSRETSFITNGSCLASRKTSFMMALCLSSIYEDLKMYQVEFKTMNAKLLMDPKRQIFLDQNMLA VIDELMQALNFNSETVPQKSSLEEPDFYKTKIKLCILLHAFRIRAVTIDRVMSYLNAS |
| 58 | IL12b polypeptide | MCHQQLVISWFSLVFLASPLVAIWELKKDVYWELDWYPDAPGEMWLTCDTPEEDGITWTLDQSSE VLGSGKTLTIQVKEFGDAGQYTCHKGGEVLSHSLLLLHKKEDGIWSTDILKDQKEPKNKTFLRCE AKNYSGRFTCWWLTTISTDLTFSVKSSRGSSDPQGVTCGAATLSAERVRGDNKEYEYSVECQEDS ACPAAEESLPIEVMVDAVHKLKYENYTSSFFIRDIIKPDPPKNLQLKPLKNSRQVEVSWEYPDTW STPHSYFSLTFCVQVQGKSKREKKDRVFTDKTSATVICRKNASISVRAQDRYYSSSWSEWASVPC S |
| 59 | IL15 polypeptide | GIHVFILGCFSAGLPKTEANWVNVISDLKKIEDLIQSMHIDATLYTESDVHPSCKVTAMKCFLLE LQVISLESGDASIHDTVENLIILANNSLSSNGNVTESGCKECEELEEKNIKEFLQSFVHIVQMFI NTS |
| 60 | sIL15ra polypeptide | ITCPPPMSVEHADIWVKSYSLYSRERYICNSGFKRKAGTSSLTECVLNKATNVAHWTTPSLKCIR DPALVHQRPAPPSTVTTAGVTPQPESLSPSGKEPAASSPSSNNTAATTAAIVPGSQLMPSKSPST GTTEISSHESSHGTPSQTTAKNWELTASASHQPPGVYPQGHSDTT |
| 61 | soluble gp130 | MLTLQTWLVQALFIFLTTESTGELLDPCGYISPESPWQLHSNFTAVCVLKEKCMDYFHVNANYIV WKTNHFTIPKEQYTIINRTASSVTFTDIASLNIQLTCNILTFGQLEQNVYGITIISGLPPEKPKN LSCIVNEGKKMRCEWDGGRETHLETNFTLKSEWATHKFADCKAKRDTPTSCTVDYSTVYFVNIEV WVEAENALGKVTSDHINFDPVYKVKPNPPHNLSVINSEELSSILKLTWTNPSIKSVIILKYNIQY RTKDASTWSQIPPEDTASTRSSFTVQDLKPFTEYVFRIRCMKEDGKGYWSDWSEEASGITYEDRP SKAPSFWYKIDPSHTQGYRTVQLVWKTLPPFEANGKILDYEVTLTRWKSHLQNYTVNATKLTVNL TNDRYLATLTVRNLVGKSDAAVLTIPACDFQATHPVMDLKAFPKDNMLWVEWTTPRESVKKYILE WCVLSDKAPCITDWQQEDGTVHRTYLRGNLAESKCYLITVTPVYADGPGSPESIKAYLKQAPPSK GPTVRTKKVGKNEAVLEWDQLPVDVQNGFIRNYTIFYRTIIGNETAVNVDSSHTEYTLSSLTSDT LYMVRMAAYTDEGGKDGPEF |
| 62 | soluble gp130 fused to a Fc | MLTLQTWLVQALFIFLTTESTGELLDPCGYISPESPWQLHSNFTAVCVLKEKCMDYFHVNANYIV WKTNHFTIPKEQYTIINRTASSVTFTDIASLNIQLTCNILTFGQLEQNVYGITIISGLPPEKPKN LSCIVNEGKKMRCEWDGGRETHLETNFTLKSEWATHKFADCKAKRDTPTSCTVDYSTVYFVNIEV WVEAENALGKVTSDHINFDPVYKVKPNPPHNLSVINSEELSSILKLTWTNPSIKSVIILKYNIQY RTKDASTWSQIPPEDTASTRSSFTVQDLKPFTEYVFRIRCMKEDGKGYWSDWSEEASGITYEDRP SKAPSFWYKIDPSHTQGYRTVQLVWKTLPPFEANGKILDYEVTLTRWKSHLQNYTVNATKLTVNL TNDRYLATLTVRNLVGKSDAAVLTIPACDFQATHPVMDLKAFPKDNMLWVEWTTPRESVKKYILE WCVLSDKAPCITDWQQEDGTVHRTYLRGNLAESKCYLITVTPVYADGPGSPESIKAYLKQAPPSK GPTVRTKKVGKNEAVLEWDQLPVDVQNGFIRNYTIFYRTIIGNETAVNVDSSHTEYTLSSLTSDT LYMVRMAAYTDEGGKDGPEFRSCDKTHTCPPCPAPEAEGGPSVFLFPPKPKDTLMISRTPEVTCW VDVSHEDPEVKFNWYVDGVEVHNAKTKPREEQYNSTYRWSVLTVLHQDWLNGKEYKCKVSNKALP APIEKTISKAKGQPREPQVYTLPPSREEMTKNQVSLTCLVKGFYPSDIAVEWESNGQPENNYKTT PPVLDSDGSFFLYSKLTVDKSRWQQGNVFSCSVMHEALHNHYTQKSLSLSPGK |
| 63 | Matrice TRAC locus_CubiCA R CD22 pCLS30056 full sequence | GTGGCACTTTTCGGGGAAATGTGCGCGGAACCCCTATTTGTTTATTTTTCTAAATACATTCAAAT ATGTATCCGCTCATGAGACAATAACCCTGATAAATGCTTCAATAATATTGAAAAAGGAAGAGTAT GAGTATTCAACATTTCCGTGTCGCCCTTATTCCCTTTTTTGCGGCATTTTGCCTTCCTGTTTTTG CTCACCCAGAAACGCTGGTGAAAGTAAAAGATGCTGAAGATCAGTTGGGTGCACGAGTGGGTTAC ATCGAACTGGATCTCAACAGCGGTAAGATCCTTGAGAGTTTTCGCCCCGAAGAACGTTTTCCAAT GATGAGCACTTTTAAAGTTCTGCTATGTGGCGCGGTATTATCCCGTATTGACGCCGGGCAAGAGC AACTCGGTCGCCGCATACACTATTCTCAGAATGACTTGGTTGAGTACTCACCAGTCACAGAAAAG CATCTTACGGATGGCATGACAGTAAGAGAATTATGCAGTGCTGCCATAACCATGAGTGATAACAC TGCGGCCAACTTACTTCTGACAACGATCGGAGGACCGAAGGAGCTAACCGCTTTTTTGCACAACA TGGGGGATCATGTAACTCGCCTTGATCGTTGGGAACCGGAGCTGAATGAAGCCATACCAAACGAC GAGCGTGACACCACGATGCCTGTAGCAATGGCAACAACGTTGCGCAAACTATTAACTGGCGAACT ACTTACTCTAGCTTCCCGGCAACAATTAATAGACTGGATGGAGGCGGATAAAGTTGCAGGACCAC TTCTGCGCTCGGCCCTTCCGGCTGGCTGGTTTATTGCTGATAAATCTGGAGCCGGTGAGCGTGGT TCTCGCGGTATCATTGCAGCACTGGGGCCAGATGGTAAGCCCTCCCGTATCGTAGTTATCTACAC GACGGGGAGTCAGGCAACTATGGATGAACGAAATAGACAGATCGCTGAGATAGGTGCCTCACTGA TTAAGCATTGGTAACTGTCAGACCAAGTTTACTCATATATACTTTAGATTGATTTAAAACTTCAT TTTTAATTTAAAAGGATCTAGGTGAAGATCCTTTTTGATAATCTCATGACCAAAATCCCTTAACG TGAGTTTTCGTTCCACTGAGCGTCAGACCCCGTAGAAAAGATCAAAGGATCTTCTTGAGATCCTT TTTTTCTGCGCGTAATCTGCTGCTTGCAAACAAAAAAACCACCGCTACCAGCGGTGGTTTGTTTG CCGGATCAAGAGCTACCAACTCTTTTTCCGAAGGTAACTGGCTTCAGCAGAGCGCAGATACCAAA TACTGTTCTTCTAGTGTAGCCGTAGTTAGGCCACCACTTCAAGAACTCTGTAGCACCGCCTACAT ACCTCGCTCTGCTAATCCTGTTACCAGTGGCTGCTGCCAGTGGCGATAAGTCGTGTCTTACCGGG TTGGACTCAAGACGATAGTTACCGGATAAGGCGCAGCGGTCGGGCTGAACGGGGGGTTCGTGCAC ACAGCCCAGCTTGGAGCGAACGACCTACACCGAACTGAGATACCTACAGCGTGAGCTATGAGAAA GCGCCACGCTTCCCGAAGGGAGAAAGGCGGACAGGTATCCGGTAAGCGGCAGGGTCGGAACAGGA GAGCGCACGAGGGAGCTTCCAGGGGGAAACGCCTGGTATCTTTATAGTCCTGTCGGGTTTCGCCA CCTCTGACTTGAGCGTCGATTTTTGTGATGCTCGTCAGGGGGGCGGAGCCTATGGAAAAACGCCA GCAACGCGGCCTTTTTACGGTTCCTGGCCTTTTGCTGGCCTTTTGCTCACATGGTCTTTCCTGCG TTATCCCCTGATTCTGTGGATAACCGTATTACCGCCTTTGAGTGAGCTGATACCGCTCGCCGCAG CCGAACGACCGAGCGCAGCGAGTCAGTGAGCGAGGAAGCGGAGAGCGCCCAATACGCAAACCGCC |

TABLE 5-continued

Sequences referred to in example 2 and 3.

TCTCCCCGCGCGTTGGCCGATTCATTAATGCAGCTGGCACGACAGGTTTCCCGACTGGAAAGCGG
GCAGTGAGCGCAACGCAATTAATGTGAGTTAGCTCACTCATTAGGCACCCCAGGCTTTACACTTT
ATGCTTCCGGCTCGTATGTTGTGTGGAATTGTGAGCGGATAACAATTTCACACAGGAAACAGCTA
TGACCATGATTACGCCAAGCGCGTCAATTAACCCTCACTAAAGGGAACAAAAGCTGTTAATTAAT
TGCTGGGCCTTTTTCCCATGCCTGCCTTTACTCTGCCAGAGTTATATTGCTGGGGTTTTGAAGAA
GATCCTATTAAATAAAAGAATAAGCAGTATTATTAAGTAGCCCTGCATTTCAGGTTTCCTTGAGT
GGCAGGCCAGGCCTGGCCGTGAACGTTCACTGAAATCATGGCCTCTTGGCCAAGATTGATAGCTT
GTGCCTGTCCCTGAGTCCCAGTCCATCACGAGCAGCTGGTTTCTAAGATGCTATTTCCCGTATAA
AGCATGAGACCGTGACTTGCCAGCCCCACAGAGCCCGCCCTTGTCCATCACTGGCATCTGGACT
CCAGCCTGGGTTGGGGCAAAGAGGGAAATGAGATCATGTCCTAACCCTGATCCTCTTGTCCCACA
GATATCCAGTACCCCTACGACGTGCCCGACTACGCCTCCGGTGAGGGCAGAGGAAGTCTTCTAAC
ATGCGGTGACGTGGAGGAGAATCCGGGCCCCGGATCCGCTCTGCCCGTCACCGCTCTGCTGCTGC
CACTGGCACTGCTGCTGCACGCTGCTAGGCCCGGAGGGGGAGGCAGCTGCCCCTACAGCAACCCC
AGCCTGTGCAGCGGAGGCGGCGGCAGCGGCGGAGGGGGTAGCCAGGTGCAGCTGCAGCAGAGCGG
CCCTGGCCTGGTGAAGCCAAGCCAGACACTGTCCCTGACCTGCGCCATCAGCGGCGATTCCGTGA
GCTCCAACTCCGCCGCCTGGAATTGGATCAGGCAGTCCCCTTCTCGGGGCCTGGAGTGGCTGGGA
AGGACATACTATCGGTCTAAGTGGTACAACGATTATGCCGTGTCTGTGAAGAGCAGAATCACAAT
CAACCCTGACACCTCCAAGAATCAGTTCTCTCTGCAGCTGAATAGCGTGACACCAGAGGACACCG
CCGTGTACTATTGCGCCAGGGAGGTGACCGGCGACCTGGAGGATGCCTTTGACATCTGGGGCCAG
GGCACAATGGTGACCGTGAGCTCCGAGGCGGCGGATCTGGCGGAGGAGGAAGTGGGGGCGGCGG
GAGTGATATCCAGATGACACAGTCCCCATCCTCTCTGAGCGCCTCCGTGGGCGACAGAGTGACAA
TCACCTGTAGGGCCTCCCAGACCATCTGGTCTTACCTGAACTGGTATCAGCAGAGGCCCGGCAAG
GCCCCTAATCTGCTGATCTACGCAGCAAGCTCCCTGCAGAGCGGAGTGCCATCCAGATTCTCTGG
CAGGGGCTCCGGCACAGACTTCACCCTGACCATCTCTAGCCTGCAGGCCGAGGACTTCGCCACCT
ACTATTGCCAGCAGTCTTATAGCATCCCCAGACATTTGGCCAGGGCACCAAGCTGGAGATCAAG
TCGGATCCCGGAAGCGGAGGGGGAGGCAGCTGCCCCTACAGCAACCCCAGCCTGTGCAGCGGAGG
CGGCGGCAGCGAGCTGCCCACCCAGGGCACCTTCTCCAACGTGTCCACCAACGTGAGCCCAGCCA
AGCCCACCACCACCGCCTGTCCTTATTCCAATCCTTCCCTGTGTGCTCCCACCACAACCCCCGCT
CCAAGGCCCCCTACCCCCGCACCAACTATTGCCTCCCAGCCACTCTCACTGCGGCCTGAGGCCTG
TCGGCCCGCTGCTGGAGGCGCAGTGCATACAAGGGGCCTCGATTTCGCCTGCGATATTTACATCT
GGGCACCCCTCGCCGGCACCTGCGGGGTGCTTCTCCTCTCCCTGGTGATTACCCTGTATTGCAGA
CGGGGCCGGAAGAAGCTCCTCTACATTTTTAAGCAGCCTTTCATGCGGCCAGTGCAGACAACCCA
AGAGGAGGATGGGTGTTCCTGCAGATTCCCTGAGGAAGAGGAAGGCGGGTGCGAGCTGAGAGTGA
AGTTCTCCAGGAGCGCAGATGCCCCCGCCTATCAACAGGGCCAGAACCAGCTCTACAACGAGCTT
AACCTCGGGAGGCGCGAAGAATACGACGTGTTGGATAAGAGAAGGGGGCGGGACCCCGAGATGGG
AGGAAAGCCCCGGAGGAAGAACCCTCAGGAGGGCCTGTACAACGAGCTGCAGAAGGATAAGATGG
CCGAGGCCTACTCAGAGATCGGGATGAAGGGGGAGCGGCGCCGCGGGAAGGGGCACGATGGGCTC
TACCAGGGGCTGAGCACAGCCACAAAGGACACATACGACGCCTTGCACATGCAGGCCCTTCCACC
CCGGGAATAGTCTAGAGGGCCCGTTTAAACCCGCTGATCAGCCTCGACTGTGCCTTCTAGTTGCC
AGCCATCTGTTGTTTGCCCCTCCCCCGTGCCTTCCTTGACCCTGGAAGGTGCCACTCCCACTGTC
CTTTCCTAATAAAATGAGGAAATTGCATCGCATTGTCTGAGTAGGTGTCATTCTATTCTGGGGGG
TGGGGTGGGGCAGGACAGCAAGGGGGAGGATTGGGAAGACAATAGCAGGCATGCTGGGGATGCGG
TGGGCTCTATGACTAGTGGCGAATTCCCGTGTACCAGCTGAGAGACTCTAAATCCAGTGACAAGT
CTGTCTGCCTATTCACCGATTTTGATTCTCAAACAAATGTGTCACAAAGTAAGGATTCTGATGTG
TATATCACAGACAAAACTGTGCTAGACATGAGGTCTATGGACTTCAAGAGCAACAGTGCTGTGGC
CTGGAGCAACAAATCTGACTTTGCATGTGCAAACGCCTTCAACAACAGCATTATTCCAGAAGACA
CCTTCTTCCCCAGCCCAGGTAAGGGCAGCTTTGGTGCCTTCGCAGGCTGTTTCCTTGCTTCAGGA
ATGGCCAGGTTCTGCCCAGAGCTCTGGTCAATGATGTCTAAAACTCCTCTGATTGGTGGTCTCGG
CCTTATCCATTGCCACCAAAACCCTCTTTTTACTAAGCGATCGCTCCGGTGCCCGTCAGTGGGCA
GAGCGCACATCGCCCACAGTCCCCGAGAAGTTGGGGGGAGGGGTCGGCAATTGAACGGGTGCCTA
GAGAAGGTGGCGCGGGGTAAACTGGGAAAGTGATGTCGTGTACTGGCTCCGCCTTTTTCCCGAGG
GTGGGGGAGAACCGTATATAAGTGCAGTAGTCGCCGTGAACGTTCTTTTTCGCAACGGGTTTGCC
GCCAGAACACAGCTGAAGCTTCGAGGGGCTCGCATCTCTCCTTCACGCGCCCGCCGCCCTACCTG
AGGCCGCCATCCACGCCGGTTGAGTCGCGTTCTGCCGCCTCCCGCCTGTGGTGCCTCCTGAACTG
CGTCCGCCGTCTAGGTAAGTTTAAAGCTCAGGTCGAGACCGGGCCTTTGTCCGGCGCTCCCTTGG
AGCCTACCTAGACTCAGCCGGCTCTCCACGCTTTGCCTGACCCTGCTTGCTCAACTCTACGTCTT
TGTTTCGTTTTCTGTTCTGCGCCGTTACAGATCCAAGCTGTGACCGGCGCCTACCTGAGATCACC
GGCGCCACCATGGCTTCTTACCCTGGACACCAGCATGCTTCTGCCTTTGACCAGGCTGCCAGATC
CAGGGGCCACTCCAACAGGAGAACTGCCCTAAGACCCAGAAGACAGCAGGAAGCCACTGAGGTGA
GGCCTGAGCAGAAGATGCCAACCCTGCTGAGGGTGTACATTGATGGACCTCATGGCATGGGCAAG
ACCACCACCACTCAACTGCTGGTGGCACTGGGCTCCAGGGATGACATTGTGTATGTGCCTGAGCC
AATGACCTACTGGAGAGTGCTAGGAGCCTCTGAGACCATTGCCAACATCTACACCACCCAGCACA
GGCTGGACCAGGGAGAAATCTCTGCTGGAGATGCTGCTGTGGTGATGACCTCTGCCCAGATCACA
ATGGGAATGCCCTATGCTGTGACTGATGCTGTTCTGGCTCCTCACATTGGAGGAGAGGCTGGCTC
TTCTCATGCCCTTCCACCTGCCCTGACCCTGATCTTTGACAGACACCCCATTGCAGCCCTGCTGT
GCTACCCAGCAGCAAGGTACCTCATGGGCTCCATGACCCCACAGGCTGTGCTGGCTTTTGTGGCC
CTGATCCCTCCAACCCTCCCTGGCACCAACATTGTTCTGGGAGCACTGCCTGAAGACAGACACAT
TGACAGGCTGGCAAAGAGGCAGAGACCTGGAGAGAGACTGGACCTGGCCATGCTGGCTGCAATCA
GAAGGGTGTATGACTGCTGGCAAACACTGTGAGATACCTCCAGTGTGGAGGCTCTTGGAGAGAG
GACTGGGACAGCTCTCTGGAACAGCAGTGCCCCCTCAAGGAGCTGAGCCCCAGTCCAATGCTGG
TCCAAGACCCCACATTGGGGACACCCTGTTCACCCTGTTCAGAGCCCCTGAGCTGCTGGCTCCCA
ATGGAGACCTGTACAATGTGTTTGCCTGGGCTCTGGATGTTCTAGCCAAGAGGCTGAGGTCCATG
CATGTGTTCATCCTGGACTATGACCAGTCCCCTGCTGGATGCTGAGGATGCTCTGCTGCAACTAAC
CTCTGGCATGGTGCAGACCCATGTGACCACCCCTGGCAGCATCCCCACCATCTGTGACCTAGCCA
GAACCTTTGCCAGGGAGATGGGAGAGGCCAACTAAGGCGCGCCACTCGAGCGCTAGCTGGCCAGA
CATGATAAGATACATTGATGAGTTTGGACAAACCACAACTAGAATGCAGTGAAAAAAATGCTTTA
TTTGTGAAATTTGTGATGCTATTGCTTTATTTGTAACCATTATAAGCTGCAATAAACAAGTTAAC
AACAACAATTGCATTCATTTTATGTTTCAGGTTCAGGGGGAGGTGTGGGAGGTTTTTTAAAGCAA

TABLE 5-continued

Sequences referred to in example 2 and 3.

| | | |
|---|---|---|
| | | GTAAAACCTCTACAAATGTGGTATGGAAGGCGCGCCCAATTCGCCCTATAGTGAGTCGTATTACG<br>TCGCGCTCACTGGCCGTCGTTTTACAACGTCGTGACTGGGAAAACCCTGGCGTTACCCAACTTAA<br>TCGCCTTGCAGCACATCCCCCTTTCGCCAGCTGGCGTAATAGCGAAGAGGCCCGCACCGAAACGC<br>CCTTCCCAACAGTTGCGCAGCCTGAATGGCGAATGGGAGCGCCCTGTAGCGGCGCATTAAGCGCG<br>GCGGGTGTGGTGGTTACGCGCAGCGTGACCGCTACACTTGCCAGCGCCCTAGCGCCCGCTCCTTT<br>CGCTTTCTTCCCTTCCTTTCTCGCCACGTTCGCCGGCTTTCCCCGTCAAGCTCTAAATCGGGGGC<br>TCCCTTTAGGGTTCCGATTTAGTGCTTTACGGCACCTCGACCCCAAAAAACTTGATTAGGGTGAT<br>GGTTGGCCTGTAGTGGGCCATAGCCCTGATAGACGGTTTTTCGCCCTTTGACGTTGGAGTCCACG<br>TTCTTTAATAGTGGACTCTTGTTCCAAACTGGAACAACACTCAACCCTATCTCGGTCTATTCTTT<br>TGATTTATAAGGGATTTTGCCGATTTCGGCCTATTGGTTAAAAAATGAGCTGATTTAACAAAAAT<br>TTAACGCGAATTTTAACAAAATATTAACGCTTACAATTTAG |
| 64 | Matrice CD25<br>locus_IL15_<br>2A_sIL15Ra<br>pCSL30519<br>full sequence | GTTTATTATTCCTGTTCCACAGCTATTGTCTGCCATATAAAAACTTAGGCCAGGCACAGTGGCTC<br>ACACCTGTAATCCCAGCACTTTGGAAGGCCGAGGCAGGCAGATCACAAGGTCAGGAGTTCGAGAC<br>CAGCCTGGCCAACATAGCAAAACCCCATCTCTACTAAAAATACAAAAATTAGCCAGGCATGGTGG<br>CGTGTGCACTGGTTTAGAGTGAGGACCACATTTTTTTGGTGCCGTGTTACACATATGACCGTGAC<br>TTTGTTACACCACTACAGGAGGAAGAGTAGAAGAACAATCGGTTCTGGCGTGAAACAGACTTTGA<br>ATTTTGACCTTCTCAAGTTGGCGGGAGACGTGGAGTCCAACCCAGGGCCCGGTACCGGGTCCGCC<br>ACCATGGACTGGACCTGGATTCTGTTCCTCGTGGCTGCTGCTACAAGAGTGCACAGCGGCATTCA<br>TGTCTTCATTTTGGGCTGTTTCAGTGCAGGGCTTCCTAAAACAGAAGCCAACTGGGTGAATGTAA<br>TAAGTGATTTGAAAAAAATTGAAGATCTTATTCAATCTATGCATATTGATGCTACTTTATATACG<br>GAAAGTGATGTTCACCCCAGTTGCAAAGTAACAGCAATGAAGTGCTTTCTCTTGGAGTTACAAGT<br>TATTTCACTTGAGTCCGGAGATGCAAGTATTCATGATACAGTAGAAAATCTGATCATCCTAGCAA<br>ACAACAGTTTGTCTTCTAATGGGAATGTAACAGAATCTGGATGCAAAGAATGTGAGGAACTGGAG<br>GAAAAAAATATTAAAGAATTTTTGCAGAGTTTTGTACATATTGTCCAAATGTTCATCAACACTTC<br>TGGAAGCGGAGCTACTAACTTCAGCCTGCTGAAGCAGGCTGGAGACGTGGAGGAGAACCCTGGAC<br>CTGGGACCGGCTCTGCAACCATGGATTGGACGTGGATCCTGTTTCTCGTGGCAGCTGCCACAAGA<br>GTTCACAGTATCACGTGCCCTCCCCCCATGTCCGTGGAACACGCAGACATCTGGGTCAAGAGCTA<br>CAGCTTGTACTCCAGGGAGCGGTACATTTGTAACTCTGGTTTCAAGCGTAAAGCCGGCACGTCCA<br>GCCTGACGGAGTGCGTGTTGAACAAGGCCACGAATGTCGCCCACTGGACAACCCCCAGTCTCAAA<br>TGCATTAGAGACCCTGCCCTGGTTCACCAAAGGCCAGCGCCACCCTCCACAGTAACGACGGCAGG<br>GGTGACCCCACAGCCAGAGACCCTCTCCCCTTCTGGAAAAGAGCCCGCAGCTTCATCTCCCAGCT<br>CAAACAACACAGCGGCCACAACAGCAGCTATTGTCCCGGGCTCCCAGCTGATGCCTTCAAAATCA<br>CCTTCCACAGGAACCACAGAGATAAGCAGTCATGAGTCCTCCCACGGCACCCCCTCTCAGACAAC<br>AGCCAAGAACTGGGAACTCACAGCATCCGCCTCCCACCAGCCGCCAGGTGTGTATCCACAGGGCC<br>ACAGCGACACCACTGAGGGCAGAGGCAGCCTGCTGACCTGCGGCGACGTCGAGGAGAACCCCGGG<br>CCCATGGGGGCAGGTGCCACCGGCCGCGCCATGGACGGGCCGCGCCTGCTGCTGTTGCTGCTTCT<br>GGGGGTGTCCCTTGGAGGTGCCAAGGAGGCATGCCCCACAGGCCTGTACACACACAGCGGTGAGT<br>GCTGCAAAGCCTGCAACCTGGGCGAGGGTGTGGCCCAGCCTTGTGGAGCCAACCAGACCGTGTGT<br>GAGCCCTGCCTGGACAGCGTGACGTTCTCCGACGTGGTGAGCGCGACCGAGCCGTGCAAGCCGTG<br>CACCGAGTGCGTGGGGCTCCAGAGCATGTCGGCGCCGTGCGTGGAGGCCGATGACGCCGTGTGCC<br>GCTGCGCCTACGGCTACTACCAGGATGAGACGACTGGGCGCTGCGAGGCGTGCCGCGTGTGCGAG<br>GCGGGCTCGGGCCTCGTGTTCTCCTGCCAGGACAAGCAGAACACCGTGTGCGAGGAGTGCCCCGA<br>CGGCACGTATTCCGACGAGGCCAACCACGTGGACCCGTGCCTGCCCTGCACCGTGTGCGAGGACA<br>CCGAGCGCCAGCTCCGCGAGTGCACACGCTGGGCCGACGCCGAGTGCGAGGAGATCCCTGGCCGT<br>TGGATTACACGGTCCACACCCCCAGAGGGCTCGGACAGCACAGCCCCCAGCACCCAGGAGCCTGA<br>GGCACCTCCAGAACAAGACCTCATAGCCAGCACGGTGGCAGGTGTGGTGACCACAGTGATGGGCA<br>GCTCCCAGCCCGTGGTGACCCGAGGCACCACCGACAACCTCATCCCTGTCTATTGCTCCATCCTG<br>GCTGCTGTGGTTGTGGGTCTTGTGGCCTACATAGCCTTCAAGAGGTGAAAAACCAAAAGAACAAG<br>AATTTCTTGGTAAGAAGCCGGGAACAGACAACAGAAGTCATGAAGCCCAAGTGAAATCAAAGGTG<br>CTAAATGGTCGCCCAGGAGACATCCGTTGTGCTTGCCTGCGTTTTGGAAGCTCTGAAGTCACATC<br>ACAGGACACGGGCAGTGGCAACCTTGTCTCTATGCCAGCTCAGTCCCATCAGAGAGCGAGCGCT<br>ACCCACTTCTAAATAGCAATTTCGCCGTTGAAGAGGAAGGGCAAAACCACTAGAACTCTCCATCT<br>TATTTTCATGTATATGTGTTCATGCGATCGCTCCGGTGCCCGTCAGTGGGCAGAGCGCACATCGC<br>CCACAGTCCCCGAGAAGTTGGGGGGAGGGGTCGGCAATTGAACGGGTGCCTAGAGAAGGTGGCGC<br>GGGGTAAACTGGGAAAGTGATGTCGTGTACTGGCTCCGCCTTTTCCCGAGGGTGGGGGAGAACC<br>GTATATAAGTGCAGTAGTCGCCGTGAACGTTCTTTTTCGCAACGGGTTTGCCGCCAGAACACAGC<br>TGAAGCTTCGAGGGGCTCGCATCTCTCCTTCACGCGCCCGCCGCCCTACCTGAGGCCGCCATCCA<br>CGCCGGTTGAGTCGCGTTCTGCCGCCTCCCGCCTGTGGCCTCCTGAACTGCGTCCGCCGTCTA<br>GGTAAGTTTAAAGCTCAGGTCGAGACCGGGCCTTTGTCCGGCGCTCCCTTGGAGCCTACCTAGAC<br>TCAGCCGGCTCTCCACGCTTTGCCTGACCCTGCTTGCTCAACTCTACGTCTTTGTTTCGTTTTCT<br>GTTCTGCGCCGTTACAGATCCAAGCTGTGACCGGCGCCTACCTGAGATCACCGGCGCCACCATGG<br>CTTCTTACCCTGGACACCAGCATGCTTCTGCCTTTGACCAGGCTGCCAGATCCAGGGGCCACTCC<br>AACAGGAGAACTGCCCTAAGACCCAGAAGACAGCAGGAAGCCACTGAGGTGAGGCCTGAGCAGAA<br>GATGCCAACCCTGCTGAGGGTGTACATTGATGGACCTCATGGCATGGGCAAGACCACCACCACTC<br>AACTGCTGGTGGCACTGGGCTCCAGGGATGACATTGTGTATGTGCCTGAGCCAATGACCTACTGG<br>AGAGTGCTAGGAGCCTCTGAGACCATTGCCAACATCTACACCACCCAGCACAGGCTGGACCAGGG<br>AGAAATCTGCTGGAGATGCTGCTGTGGTGATGACCTCTGCCCAGATCACAATGGGAATGCCCT<br>ATGCTGTGACTGATGCTGTTCGGCTCCTCACATTGGAGGAGAGGCTGGCTCTTCTCATGCCCCT<br>CCACCTGCCCTGACCCTGATCTTTGACAGACACCCCATTGCAGCCCTGCTGTGCTACCCAGCAG<br>AAGGTACCTCATGGGCTCCATGACCCCACAGGCTGTGCTGGCTTTTGTGGCCCTGATCCCTCCAA<br>CCCTCCCTGGCACCAACATTGTTCTGGGAGCACTGCCTGAAGACAGACACATTGACAGGCTGGCA<br>AAGAGGCAGAGACCTGGAGAGAGACTGGACCTGGCCATGCTGGCTGCAATCAGAAGGGTGTATGG<br>ACTGCTGGCAAACACTGTGAGATACCTCCAGTGTGGAGGCTCTTGGAGAGGAGACTGGGGACAGG<br>TCTCTGGAACAGCAGTGCCCCCTCAAGGAGCTGAGCCCCAGTCCAATGCTGGTCCAAGACCCCAC<br>ATTGGGGACACCCTGTTCACCCTGTTCAGAGCCCCTGAGCTGCTGCTCCAATGGAGACCCTGTA<br>CAATGTGTTTGCCTGGGCTCTGGATGTTCTAGCCAAGAGGCTGAGGTCCATGCATGTGTTCATCC<br>TGGACTATGACCAGTCCCCTGCTGGATGCAGAGATGCTCTGCTGCAACTAACCTCTGGCATGGTG<br>CAGACCCATGTGACCACCCCTGGCAGCATCCCCACCATCTGTGACCTAGCCAGAACCTTTGCCAG |

| | | |
|---|---|---|
| | | TABLE 5-continued |
| | | Sequences referred to in example 2 and 3. |
| | | GGAGATGGGAGAGGCCAACTAAGGCGCGCCACTCGAGCGCTAGCTGGCCAGACATGATAAGATAC<br>ATTGATGAGTTTGGACAAACCACAACTAGAATGCAGTGAAAAAAATGCTTTATTTGTGAAATTTG<br>TGATGCTATTGCTTTATTTGTAACCATTATAAGCTGCAATAAACAAGTTAACAACAACAATTGCA<br>TTCATTTTATGTTTCAGGTTCAGGGGGAGGTGTGGGAGGTTTTTTAAAGCAAGTAAAACCTCTAC<br>AAATGTGGTATGGAAGGCGCGCCCAATTCGCCCTATAGTGAGTCGTATTACGTCGCGCTCACTGG<br>CCGTCGTTTTACAACGTCGTGACTGGGAAAACCCTGGCGTTACCCAACTTAATCGCCTTGCAGCA<br>CATCCCCCTTTCGCCAGCTGGCGTAATAGCGAAGAGGCCCGCACCGAAACGCCCTTCCCAACAGT<br>TGCGCAGCCTGAATGGCGAATGGGAGCGCCCTGTAGCGGCGCATTAAGCGCGGCGGGTGTGGTGG<br>TTACGCGCAGCGTGACCGCTACACTTGCCAGCGCCCTAGCGCCCGCTCCTTTCGCTTTCTTCCCT<br>TCCTTTCTCGCCACGTTCGCCGGCTTTCCCCGTCAAGCTCTAAATCGGGGGCTCCCTTTAGGGTT<br>CCGATTTAGTGCTTTACGGCACCTCGACCCCAAAAAACTTGATTAGGGTGATGGTTGGCCTGTAG<br>TGGGCCATAGCCCTGATAGACGGTTTTTCGCCCTTTGACGTTGGAGTCCACGTTCTTTAATAGTG<br>GACTCTTGTTCCAAACTGGAACAACACTCAACCCTATCTCGGTCTATTCTTTTGATTTATAAGGG<br>ATTTTGCCGATTTCGGCCTATTGGTTAAAAAATGAGCTGATTTAACAAAAATTTAACGCGAATTT<br>TAACAAAATATTAACGCTTACAATTTAGGTGGCACTTTTCGGGGAAATGTGCGCGGAACCCCTAT<br>TTGTTTATTTTTCTAAATACATTCAAATATGTATCCGCTCATGAGACAATAACCCTGATAAATGC<br>TTCAATAATATTGAAAAAGGAAGAGTATGAGTATTCAACATTTCCGTGTCGCCCTTATTCCCTTT<br>TTTGCGGCATTTTGCCTTCCTGTTTTTGCTCACCCAGAAACGCTGGTGAAAGTAAAAGATGCTGA<br>AGATCAGTTGGGTGCACGAGTGGGTTACATCGAACTGGATCTCAACAGCGGTAAGATCCTTGAGA<br>GTTTTCGCCCCGAAGAACGTTTTCCAATGATGAGCACTTTTAAAGTTCTGCTATGTGGCGCGGTA<br>TTATCCCGTATTGACGCCGGGCAAGAGCAACTCGGTCGCCGCATACACTATTCTCAGAATGACTT<br>GGTTGAGTACTCACCAGTCACAGAAAAGCATCTTACGGATGGCATGACAGTAAGAGAATTATGCA<br>GTGCTGCCATAACCATGAGTGATAACACTGCGGCCAACTTACTTCTGACAACGATCGGAGGACCG<br>AAGGAGCTAACCGCTTTTTTGCACAACATGGGGGATCATGTAACTCGCCTTGATCGTTGGGAACC<br>GGAGCTGAATGAAGCCATACCAAACGACGAGCGTGACACCACGATGCCTGTAGCAATGGCAACAA<br>CGTTGCGCAAACTATTAACTGGCGAACTACTTACTCTAGCTTCCCGGCAACAATTAATAGACTGG<br>ATGGAGGCGGATAAAGTTGCAGGACCACTTCTGCGCTCGGCCCTTCCGGCTGGCTGGTTTATTGC<br>TGATAAATCTGGAGCCGGTGAGCGTGGTTCTCGCGGTATCATTGCAGCACTGGGGCCAGATGGTA<br>AGCCCTCCCGTATCGTAGTTATCTACACGACGGGGAGTCAGGCAACTATGGATGAACGAAATAGA<br>CAGATCGCTGAGATAGGTGCCTCACTGATTAAGCATTGGTAACTGTCAGACCAAGTTTACTCATA<br>TATACTTTAGATTGATTTAAAACTTCATTTTTAATTTAAAAGGATCTAGGTGAAGATCCTTTTTG<br>ATAATCTCATGACCAAAATCCCTTAACGTGAGTTTTCGTTCCACTGAGCGTCAGACCCCGTAGAA<br>AAGATCAAAGGATCTTCTTGAGATCCTTTTTTTCTGCGCGTAATCTGCTGCTTGCAAACAAAAAA<br>ACCACCGCTACCAGCGGTGGTTTGTTTGCCGGATCAAGAGCTACCAACTCTTTTTCCGAAGGTAA<br>CTGGCTTCAGCAGAGCGCAGATACCAAATACTGTTCTTCTAGTGTAGCCGTAGTTAGGCCACCAC<br>TTCAAGAACTCTGTAGCACCGCCTACATACCTCGCTCTGCTAATCCTGTTACCAGTGGCTGCTGC<br>CAGTGGCGATAAGTCGTGTCTTACCGGGTTGGACTCAAGACGATAGTTACCGGATAAGGCGCAGC<br>GGTCGGGCTGAACGGGGGGTTCGTGCACACAGCCCAGCTTGGAGCGAACGACCTACACCGAACTG<br>AGATACCTACAGCGTGAGCTATGAGAAAGCGCCACGCTTCCCGAAGGGAGAAAGGCGGACAGGTA<br>TCCGGTAAGCGGCAGGGTCGGAACAGGAGAGCGCACGAGGGAGCTTCCAGGGGGAAACGCCTGGT<br>ATCTTTATAGTCCTGTCGGGTTTCGCCACCTCTGACTTGAGCGTCGATTTTTGTGATGCTCGTCA<br>GGGGGGCGGAGCCTATGGAAAAACGCCAGCAACGCGGCCTTTTTACGGTTCCTGGCCTTTTGCTG<br>GCCTTTTGCTCACATGGTCTTTCCTGCGTTATCCCCTGATTCTGTGGATAACCGTATTACCGCCT<br>TTGAGTGAGCTGATACCGCTCGCCGCAGCCGAACGACCGAGCGCAGCGAGTCAGTGAGCGAGGAA<br>GCGGAGAGCGCCCAATACGCAAACCGCCTCTCCCCGCGCGTTGGCCGATTCATTAATGCAGCTGG<br>CACGACAGGTTTCCCGACTGGAAAGCGGGCAGTGAGCGCAACGCAATTAATGTGAGTTAGCTCAC<br>TCATTAGGCACCCCAGGCTTTACACTTTATGCTTCCGGCTCGTATGTTGTGTGGAATTGTGAGCG<br>GATAACAATTTCACACAGGAAACAGCTATGACCATGATTACGCCAAGCGCGTCAATTAACCCTCA<br>CTAAAGGGAACAAAAGCTGTTAATTAA |
| 65 | Matrice PD1<br>locus_IL15_<br>2A_sIL15Ra<br>pCLS30513<br>full sequence | GACTCCCCAGACAGGCCCTGGAACCCCCCCACCTTCTCCCCAGCCCTGCTCGTGGTGACCGAAGG<br>GGACAACGCCACCTTCACCTGCAGCTTCTCCAACACATCGGAGAGCTTCGTGCTAAACTGGTACC<br>GCATGAGCCCCAGCAACCAGACGGACAAGCTGGCCGCCTTCCCCGAGGACCGCAGCCAGCCCGGC<br>CAGGACTGCCGCTTCCGTGTCACACAACTGCCCAACGGGCGTGACTTCCACATGAGCGTGGTCAG<br>GGCCCGGCGCAATGACAGCGGCACCTACCTCTGTGGGGCCGGTTCTGGCGTGAAACAGACTTTGA<br>ATTTTGACCTTCTCAAGTTGGCGGGAGACGTGGAGTCCAACCCAGGGCCCGGTACCGGGTCCGCC<br>ACCATGGACTGGACCTGGATTCTGTTCCTCGTGGCTGCTGCTACAAGAGTGCACAGCGGCATTCA<br>TGTCTTCATTTTGGGCTGTTTCAGTGCAGGGCTTCCTAAAACAGAAGCCAACTGGGTGAATGTAA<br>TAAGTGATTTGAAAAAAATTGAAGATCTTATTCAATCTATGCATATTGATGCTACTTTATATACG<br>GAAAGTGATGTTCACCCCAGTTGCAAAGTAACAGCAATGAAGTGCTTTCTCTTGGAGTTACAAGT<br>TATTTCACTTGAGTCCGGAGATGCAAGTATTCATGATACAGTAGAAAATCTGATCATCCTAGCAA<br>ACAACAGTTTGTCTTCTAATGGGAATGTAACAGAATCTGGATGCAAAGAATGTGAGGAACTGGAG<br>GAAAAAATATTAAAGAATTTTTGCAGAGTTTTGTACATATTGTCCAAATGTTCATCAACACTTC<br>TGGAAGCGGAGCTACTAACTTCAGCCTGCTGAAGCAGGCTGGAGACGTGGAGGAGAACCCTGGAC<br>CTGGGACCGGCTCTGCAACCATGGATTGGACGTGGATCCTGTTTCTCGTGGCAGCTGCCACAAGA<br>GTTCACAGTATCACGTGCCCTCCCCCATGTCCGTGGAACACGCAGACATCTGGGTCAAGAGCTA<br>CAGCTTGTACTCCAGGGAGCGGTACATTTGTAACTCTGGTTTCAAGCGTAAAGCCGGCACGTCCA<br>GCCTGACGGAGTGCGTGTTGAACAAGGCCACGAATGTGCCCCACTGGCAACCCCCAGTCTCAAA<br>TGCATTAGAGACCCTGCCCTGGTTCACCAAAGGCCAGCGCCACCCTCCACAGTAACGACGGCAGG<br>GGTGACCCCACAGCCAGAGCCTCTCCCCTTCTGGAAAAGAGCCCGCAGCTTCATCTCCCAGCT<br>CAAACAACACAGCGGCCACAACAGCAGCTATTGTCCCGGGCTCCCAGCTGATGCCTTCAAAATCA<br>CCTTCCACAGGAACCACAGAGATAAGCAGTCATGAGTCCTCCCACGGCACCCCCTCTCAGACAAC<br>AGCCAAGAACTGGGAACTCACAGCATCCGCCTCCCACCAGCCGCCAGGTGTGTATCCACAGGGCC<br>ACAGCGACACCACTGAGGGCAGAGGCAGCCTGCTGACCTGCGGCGACGTCGAGGAGAACCCCGGG<br>CCCATGGGGGCAGGTGCCACCGGCCGCGCCATGGACGGGCCGCGCCTGCTGCTGTTGCTGCTTCT<br>GGGGGTGTCCCTTGGAGGTGCCAAGGAGGCATGCCCCACAGGCCTGTACACACACAGCGGTGAGT<br>GCTGCAAAGCCTGCAACCTGGGCGAGGGTGTGGCCCAGCCTTGTGGAGCCAACCAGACCGTGTGT<br>GAGCCCTGCCTGGACAGCGTGACGTTCTCCGACGTGGTGAGCGCGACCGAGCCGTGCAAGCCGTG<br>CACCGAGTGCGTGGGGCTCCAGAGCATGTCGGCGCCGTGCGTGGAGGCCGATGACGCCGTGTGCC |

TABLE 5-continued

Sequences referred to in example 2 and 3.

```
GCTGCGCCTACGGCTACTACCAGGATGAGACGACTGGGCGCTGCGAGGCGTGCCGCGTGTGCGAG
GCGGGCTCGGGCCTCGTGTTCTCCTGCCAGGACAAGCAGAACACCGTGTGCGAGGAGTGCCCCGA
CGGCACGTATTCCGACGAGGCCAACCACGTGGACCCGTGCCTGCCCTGCACCGTGTGCGAGGACA
CCGAGCGCCAGCTCCGCGAGTGCACACGCTGGGCCGACGCCGAGTGCGAGGAGATCCCTGGCCGT
TGGATTACACGGTCCACACCCCCAGAGGGCTCGGACAGCACAGCCCCCAGCACCCAGGAGCCTGA
GGCACCTCCAGAACAAGACCTCATAGCCAGCACGGTGGCAGGTGTGGTGACCACAGTGATGGGCA
GCTCCCAGCCCGTGGTGACCCGAGGCACCACCGACAACCTCATCCCTGTCTATTGCTCCATCCTG
GCTGCTGTGGTTGTGGGTCTTGTGGCCTACATAGCCTTCAAGAGGTGATCTAGAGGGCCCGTTTA
AACCCGCTGATCAGCCTCGACTGTGCCTTCTAGTTGCCAGCCATCTGTTGTTTGCCCCTCCCCCG
TGCCTTCCTTGACCCTGGAAGGTGCCACTCCCACTGTCCTTTCCTAATAAAATGAGGAAATTGCA
TCGCATTGTCTGAGTAGGTGTCATTCTATTCTGGGGGGTGGGGTGGGGCAGGACAGCAAGGGGGA
GGATTGGGAAGACAATAGCAGGCATGCTGGGGATGCGGTGGGCTCTATGACTAGTGGCGAATTCG
GCGCAGATCAAAGAGAGCCTGCGGGCAGAGCTCAGGGTGACAGGTGCGGCCTCGGAGGCCCCGGG
GCAGGGGTGAGCTGAGCCGGTCCTGGGGTGGGTGTCCCCTCCTGCACAGGATCAGGAGCTCCAGG
GTCGTAGGGCAGGGACCCCCCAGCTCCAGTCCAGGGCTCTGTCCTGCACCTGGGGAATGGTGACC
GGCATCTCTGTCCTCTAGCTCTGGAAGCACCCCAGCCCCTCTAGTCTGCCCTCACCCCTGACCCT
GACCCTCCACCCTGACCCCGTCCTAACCCCTGACCTTTGGCGATCGCTCCGGTGCCCGTCAGTGG
GCAGAGCGCACATCGCCCACAGTCCCCGAGAAGTTGGGGGGAGGGGTCGGCAATTGAACGGGTGC
CTAGAGAAGGTGGCGCGGGGTAAACTGGGAAAGTGATGTCGTGTACTGGCTCCGCCTTTTTCCCG
AGGGTGGGGGAGAACCGTATATAAGTGCAGTAGTCGCCGTGAACGTTCTTTTTCGCAACGGGTTT
GCCGCCAGAACACAGCTGAAGCTTCGAGGGGCTCGCATCTCTCCTTCACGCGCCCGCCGCCCTAC
CTGAGGCCGCCATCCACGCCGGTTGAGTCGCGTTCTGCCGCCTCCCGCCTGTGGTGCCTCCTGAA
CTGCGTCCGCCGTCTAGGTAAGTTTAAAGCTCAGGTCGAGACCGGGCCTTTGTCCGGCGCTCCCT
TGGAGCCTACCTAGACTCAGCCGGCTCTCCACGCTTTGCCTGACCCTGCTTGCTCAACTCTACGT
CTTTGTTTCGTTTTCTGTTCTGCGCCGTTACAGATCCAAGCTGTGACCGGCGCCTACCTGAGATC
ACCGGCGCCACCATGGCTTCTTACCCTGGACACCAGCATGCTTCTGCCTTTGACCAGGCTGCCAG
ATCCAGGGGCCACTCCAACAGGAGAACTGCCCTAAGACCCAGAAGACAGCAGGAAGCCACTGAGG
TGAGGCCTGAGCAGAAGATGCCAACCCTGCTGAGGGTGTACATTGATGGACCTCATGGCATGGGC
AAGACCACCACCACTCAACTGCTGGTGGCACTGGGCTCCAGGGATGACATTGTGTATGTGCCTGA
GCCAATGACCTACTGGAGAGTGCTAGGAGCCTCTGAGACCATTGCCAACATCTACACCACCCAGC
ACAGGCTGGACCAGGGAGAAATCTCTGCTGGAGATGCTGCTGTGGTGATGACCTCTGCCCAGATC
ACAATGGGAATGCCCTATGCTGTGACTGATGCTGTTCTGGCTCCTCACATTGGAGGAGAGGCTGG
CTCTTCTCATGCCCCTCCACCTGCCCTGACCCTGATCTTTGACAGACACCCCATTGCAGCCCTGC
TGTGCTACCCAGCAGCAAGGTACCTCATGGGCTCCATGACCCCACAGGCTGTGCTGGCTTTTGTG
GCCCTGATCCCTCCAACCCTCCCTGGCACCAACATTGTTCTGGGAGCACTGCCTGAAGACAGACA
CATTGACAGGCTGGCAAAGAGGCAGAGACCTGGAGAGAGACTGGACCTGGCCATGCTGGCTGCAA
TCAGAAGGGTGTATGGACTGCTGGCAAACACTGTGAGATACCTCCAGTGTGGAGGCTCTTGGAGA
GAGGACTGGGACAGCTCTCTGGAACAGCAGTGCCCCTCAAGGAGCTGAGCCCCAGTCCAATGC
TGGTCCAAGACCCCACATTGGGGACACCCTGTTCACCCTGTTCAGAGCCCTGAGCTGCTGGCTC
CCAATGGAGACCTGTACAATGTGTTTGCCTGGGCTCTGGATGTTCTAGCCAAGAGGCTGAGGTCC
ATGCATGTGTTCATCCTGGACTATGACCAGTCCCCTGCTGGATGCAGAGATGCTCTGCTGCAACT
AACCTCTGGCATGGTGCAGACCCATGTGACCACCCCTGGCAGCATCCCCACCATCTGTGACCTAG
CCAGAACCTTTGCCAGGGAGATGGGAGAGGCCAACTAAGGCGCGCCACTCGAGCGCTAGCTGGCC
AGACATGATAAGATACATTGATGAGTTTGGACAAACCACAACTAGAATGCAGTGAAAAAAATGCT
TTATTTGTGAAATTTGTGATGCTATTGCTTTATTTGTAACCATTATAAGCTGCAATAAACAAGTT
AACAACAACAATTGCATTCATTTTATGTTTCAGGTTCAGGGGGAGGTGTGGGAGGTTTTTTAAAG
CAAGTAAAACCTCTACAAATGTGGTATGGAAGGCGCGCCCAATTCGCCCTATAGTGAGTCGTATT
ACGTCGCGCTCACTGGCCGTCGTTTTACAACGTCGTGACTGGGAAAACCCTGGCGTTACCCAACT
TAATCGCCTTGCAGCACATCCCCCTTTCGCCAGCTGGCGTAATAGCGAAGAGGCCCGCACCGAAA
CGCCCTTCCCAACAGTTGCGCAGCCTGAATGGCGAATGGGAGCGCCCTGTAGCGGCGCATTAAGC
GCGGCGGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGGG
GGCTCCCTTTAGGGTTCCGATTTAGTGCTTTACGGCACCTCGACCCCAAAAAACTTGATTAGGGT
GATGGTTGGCCTGTAGTGGGCCATAGCCCTGATAGACGGTTTTTCGCCCTTTGACGTTGGAGTCC
ACGTTCTTTAATAGTGGACTCTTGTTCCAAACTGGAACAACACTCAACCCTATCTCGGTCTATTC
TTTTGATTTATAAGGGATTTTGCCGATTTCGGCCTATTGGTTAAAAAATGAGCTGATTTAACAAA
AATTTAACGCGAATTTTAACAAAATATTAACGCTTACAATTTAGGTGGCACTTTTCGGGGAAATG
TGCGCGGAACCCCTATTTGTTTATTTTTCTAAATACATTCAAATATGTATCCGCTCATGAGACAA
TAACCCTGATAAATGCTTCAATAATATTGAAAAAGGAAGAGTATGAGTATTCAACATTTCCGTGT
CGCCCTTATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCAACAGC
GGTAAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCATACACT
ATTCTCAGAATGACTTGGTTGAGTACTCACCAGTCACAGAAAAGCATCTTACGGATGGCATGACA
GTAAGAGAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGATGCCT
GTAGCAATGGCAACAACGTTGCGCAAACTATTAACTGGCGAACTACTTACTCTAGCTTCCCGGCA
ACAATTAATAGACTGGATGGAGGCGGATAAAGTTGCAGGACCACTTCTGCGCTCGGCCCTTCCGG
CTGGCTGGTTTATTGCTGATAAATCTGGAGCCGGTGAGCGTGGTTCTCGCGGTATCATTGCAGCA
CTGGGGCCAGATGGTAAGCCCTCCCGTATCGTAGTTATCTACACGACGGGGAGTCAGGCAACTAT
GGATGAACGAAATAGACAGATCGCTGAGATAGGTGCCTCACTGATTAAGCATTGGTAACTGTCAG
ACCAAGTTTACTCATATATACTTTAGATTGATTTAAAACTTCATTTTTAATTTAAAAGGATCTAG
GTGAAGATCCTTTTTGATAATCTCATGACCAAAATCCCTTAACGTGAGTTTTCGTTCCACTGAGC
GTCAGACCCCGTAGAAAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGATCAAGAGCTACCAACT
CTTTTTCCGAAGGTAACTGGCTTCAGCAGAGCGCAGATACCAAATACTGTTCTTCTAGTGTAGCC
GTAGTTAGGCCACCACTTCAAGAACTCTGTAGCACCGCCTACATACCTCGCTCTGCTAATCCTGT
```

TABLE 5-continued

Sequences referred to in example 2 and 3.

| | | |
|---|---|---|
| | | TACCAGTGGCTGCTGCCAGTGGCGATAAGTCGTGTCTTACCGGGTTGGACTCAAGACGATAGTTA<br>CCGGATAAGGCGCAGCGGTCGGGCTGAACGGGGGGTTCGTGCACACAGCCCAGCTTGGAGCGAAC<br>GACCTACACCGAACTGAGATACCTACAGCGTGAGCTATGAGAAAGCGCCACGCTTCCCGAAGGGA<br>GAAAGGCGGACAGGTATCCGGTAAGCGGCAGGGTCGGAACAGGAGAGCGCACGAGGGAGCTTCCA<br>GGGGGAAACGCCTGGTATCTTTATAGTCCTGTCGGGTTTCGCCACCTCTGACTTGAGCGTCGATT<br>TTTGTGATGCTCGTCAGGGGGCGGAGCCTATGGAAAAACGCCAGCAACGCGGCCTTTTTACGGT<br>TCCTGGCCTTTTGCTGGCCTTTTGCTCACATGGTCTTTCCTGCGTTATCCCCTGATTCTGTGGAT<br>AACCGTATTACCGCCTTTGAGTGAGCTGATACCGCTCGCCGCAGCCGAACGACCGAGCGCAGCGA<br>GTCAGTGAGCGAGGAAGCGGAGAGCGCCCAATACGCAAACCGCCTCTCCCCGCGCGTTGGCCGAT<br>TCATTAATGCAGCTGGCACGACAGGTTTCCCGACTGGAAAGCGGGCAGTGAGCGCAACGCAATTA<br>ATGTGAGTTAGCTCACTCATTAGGCACCCCAGGCTTTACACTTTATGCTTCCGGCTCGTATGTTG<br>TGTGGAATTGTGAGCGGATAACAATTTCACACAGGAAACAGCTATGACCATGATTACGCCAAGCG<br>CGTCAATTAACCCTCACTAAAGGGAACAAAAGCTGTTAATTAA |
| 66 | Matrice CD25<br>locus_IL12a_<br>2A_IL12b_<br>pCLS30520<br>full sequence | GTTTATTATTCCTGTTCCACAGCTATTGTCTGCCATATAAAAACTTAGGCCAGGCACAGTGGCTC<br>ACACCTGTAATCCCAGCACTTTGGAAGGCCGAGGCAGGCAGATCACAAGGTCAGGAGTTCGAGAC<br>CAGCCTGGCCAACATAGCAAAACCCCATCTCTACTAAAAATACAAAAATTAGCCAGGCATGGTGG<br>CGTGTGCACTGGTTTAGAGTGAGGACCACATTTTTTGGTGCCGTGTTACACATATGACCGTGAC<br>TTTGTTACACCACTACAGGAGGAAGAGTAGAAGAACAATCGGTTCTGGCGTGAAACAGACTTTGA<br>ATTTTGACCTTCTCAAGTTGGCGGGAGACGTGGAGTCCAACCCAGGGCCCATGTGGCCCCCTGGG<br>TCAGCCTCCCAGCCACCGCCCTCACCTGCCGCGGCCACAGGTCTGCATCCAGCGGCTCGCCCTGT<br>GTCCCTGCAGTGCCGGCTCAGCATGTGTCCAGCGCGCAGCCTCCTCCTTGTGGCTACCCTGGTCC<br>TCCTGGACCACCTCAGTTTGGCCAGAAACCTCCCCGTGGCCACTCCAGACCCAGGAATGTTCCCA<br>TGCCTTCACCACTCCCAAAACCTGCTGAGGGCCGTCAGCAACATGCTCCAGAAGGCCAGACAAAC<br>TCTAGAATTTTACCCTTGCACTTCTGAAGAGATTGATCATGAAGATATCACAAAAGATAAAACCA<br>GCACAGTGGAGGCCTGTTTACCATTGGAATTAACCAAGAATGAGAGTTGCCTAAATTCAGAGAG<br>ACCTCTTTCATAACTAATGGGAGTTGCCTGGCCTCCAGAAAGACCTCTTTTATGATGGCCCTGTG<br>CCTTAGTAGTATTTATGAAGACTTGAAGATGTACCAGGTGGAGTTCAAGACCATGAATGCAAAGC<br>TTCTGATGGATCCTAAGAGGCAGATCTTTCTAGATCAAAACATGCTGGCAGTTATTGATGAGCTG<br>ATGCAGGCCCTGAATTTCAACAGTGAGACTGTGCCACAAAAATCCTCCCTTGAAGAACCGGATTT<br>TTATAAAACTAAAATCAAGCTCTGCATACTTCTTCATGCTTTCAGAATTCGGGCAGTGACTATTG<br>ATAGAGTGATGAGCTATCTGAATGCTTCCGGAAGCGGAGCTACTAACTTCAGCCTGCTGAAGCAG<br>GCTGGAGACGTGGAGGAGAACCCTGACCTATGTGTCACCAGCAGTTGGTCATCTCTTGGTTTTC<br>CCTGGTTTTTCTGGCATCTCCCCTCGTGGCCATATGGGAACTGAAGAAAGATGTTTATGTCGTAG<br>AATTGGATTGGTATCCGGATGCCCTGGAGAAATGGTGGTCCTCACCTGTGACACCCCTGAAGAA<br>GATGGTATCCACCTGGACCTTGGACCAGAGCAGTGAGGTCTTAGGCTCTGGCAAAACCCTGACCAT<br>CCAAGTCAAAGAGTTTGGAGATGCTGGCCAGTACACCTGTCACAAAGGAGGCGAGGTTCTAAGCC<br>ATTCGCTCCTGCTGCTTCACAAAAAGGAAGATGGAATTTGGTCCACTGATATTTTAAAGGACCAG<br>AAAGAACCCAAAAATAAGACCTTTCTAAGATGCGAGGCAAGAATTATTCTGGACGTTTCACCTG<br>CTGGTGGCTGACGACAATCAGTACTGATTTGACATTCAGTGTCAAAAGCAGCAGAGGCTCTTCTG<br>ACCCCCAAGGGGTGACGTGCGGAGCTGCTACACTCTCTGCAGAGAGAGTCAGAGGGGACAACAAG<br>GAGTATGAGTACTCAGTGGAGTGCCAGGAGGACAGTGCCTGCCCAGCTGCTGAGGAGAGTCTGCC<br>CATTGAGGTCATGGTGGATGCCGTTCACAAGCTCAAGTATGAAAACTACACCAGCAGCTTCTTCA<br>TCAGGGACATCATCAAACCTGACCCACCCAAGAACTTGCAGCTGAAGCCATTAAAGAATTCTCGG<br>CAGGTGGAGGTCAGCTGGGAGTACCCTGACACCTGGAGTACTCCACATTCCTACTTCTCCCTGAC<br>ATTCTGCGTTCAGGTCCAGGGCAAGAGCAAGAGAGAAAAGAAAGATAGAGTCTTCACGGACAAGA<br>CCTCAGCCACGGTCATCTGCCGCAAAAATGCCAGCATTAGCGTGCGGGCCCAGGACCGCTACTAT<br>AGCTCATCTTGGAGCGAATGGGCATCTGTGCCCTGCAGTGAGGGCAGAGGCAGCCTGCTGACCTG<br>CGGCGACGTCGAGGAGAACCCCGGGCCCATGGGGGCAGGTGCCACCGGCCGCGCCATGGACGGGC<br>CGCGCCTGCTGCTGTTGCTGCTTCTGGGGGTGTCCCTTGGAGGTGCCAAGGAGGCATGCCCCACA<br>GGCCTGTACACACACAGCGGTGAGTGCTGCAAAGCCTGCAACCTGGGCGAGGGTGTGGCCCAGCC<br>TTGTGGAGCCAACCAGACCGTGTGTGAGCCCTGCCTGGACAGCGTGACGTTCTCCGACGTGGTGA<br>GCGCGACCGAGCCGTGCAAGCCGTGCACCGAGTGCGTGGGGCTCCAGAGCATGTCGCGCGTGC<br>GTGGAGGCCGATGACGCCGTGTGCCGCTGCGCCTACGGCTACTACCAGGATGAGACGACTGGGCG<br>CTGCGAGGCGTGCCGCGTGTGCGAGGCGGGCTCGGGCCTCGTGTTCTCCTGCCAGGACAAGCAGA<br>ACACCGTGTGCGAGGAGTGCCCCGACGGCACGTATTCCGACGAGGCCAACCACGTGGACCCGTGC<br>CTGCCCTGCACCGTGTGCGAGGACACCGAGCGCCAGCTCCGCGAGTGCACACGCTGGGCCGACGC<br>CGAGTGCGAGGAGATCCCTGGCCGTTGGATTACACGGTCCACACCCCCAGAGGGCTCGGACAGCA<br>CAGCCCCCAGCACCCAGGAGCCTGAGGCACCTCCAGAACAAGACCTCATAGCCAGCACGGTGGCA<br>GGTGTGGTGACCACAGTGATGGGCAGCTCCCAGCCCGTGGTGACCCGAGGCACCACCGACAACCT<br>CATCCCTGTCTATTGCTCCATCCTGGCTGCTGTGGTTGTGGGTCTTGTGGCCTACATAGCCTTCA<br>AGAGGTGAAAAACCAAAAGAACAAGAATTTCTTGGTAAGAAGCCGGGAACAGACAACAGAAGTCA<br>TGAAGCCCAAGTGAAATCAAAGGTGCTAAATGGTCGCCCAGGAGACATCCGTTGTGCTTGCCTGC<br>GTTTTGGAAGCTCTGAAGTCACATCACAGGACACGGGGCAGTGGCAACCTTGTCTCTATGCCAGC<br>TCAGTCCCATCAGAGAGCGAGCGCTACCCACTTCTAAATAGCAATTTCGCCGTTGAAGAGGAAGG<br>GCAAAACCACTAGAACTCTCCATCTTATTTTCATGTATATGTGTTCATGCGATCGCTCCGGTGCC<br>CGTCAGTGGGCAGAGCGCACATCGCCCACAGTCCCCGAGAAGTTGGGGGGAGGGGTCGGCAATTG<br>AACGGGTGCCTAGAGAAGGTGGCGCGGGGTAAACTGGGAAAGTGATGTCGTGTACTGGCTCCGCC<br>TTTTTCCCGAGGGTGGGGGAGAACCGTATATAAGTGCAGTAGTCGCCGTGAACGTTCTTTTTCGC<br>AACGGGTTTGCCGCCAGAACACAGCTGAAGCTTCGAGGGGCTCGCATCTCTCCTTCACGCGCCCG<br>CCGCCCTACCTGAGGCCGCCATCCACGCCGGTTGAGTCGCGTTCTGCCGCCTCCCGCCTGTGGTG<br>CCTCCTGAACTGCGTCCGCCGTCTAGGTAAGTTTAAAGCTCAGGTCGAGACCGGGCCTTTGTCCG<br>GCGCTCCCTTGGAGCCTACCTAGACTCAGCCGGCTCTCCACGCTTTGCCTGACCCTGCTTGCTCA<br>ACTCTACGTCTTTGTTTCGTTTTCTGTTCTGCGCCGTTACAGATCCAAGCTGTGACCGGCGCCTA<br>CCTGAGATCACCGGCGCCACCATGGCTTCTTACCCTGGACACCAGCATGCTTCTGCCTTTGACCA<br>GGCTGCCAGATCCAGGGGCCACTCCAACAGGAGAACTGCCCTAAGACCCAGAAGACAGCAGGAAG<br>CCACTGAGGTGAGGCCTGAGCAGAAGATGCCAACCCTGCTGAGGGTGTACATTGATGGACCTCAT<br>GGCATGGGCAAGACCACCACCACTCAACTGCTGGTGGCACTGGGCTCCAGGGATGACATTGTGTA<br>TGTGCCTGAGCCAATGACCTACTGGAGAGTGCTAGGAGCCTCTGAGACCATTGCCAACATCTACA |

TABLE 5-continued

Sequences referred to in example 2 and 3.

| | | |
|---|---|---|
| | | CCACCCAGCACAGGCTGGACCAGGGAGAAATCTCTGCTGGAGATGCTGCTGTGGTGATGACCTCT<br>GCCCAGATCACAATGGGAATGCCCTATGCTGTGACTGATGCTGTTCTGGCTCCTCACATTGGAGG<br>AGAGGCTGGCTCTTCTCATGCCCCTCCACCTGCCCTGACCCTGATCTTTGACAGACACCCCATTG<br>CAGCCCTGCTGTGCTACCCAGCAGCAAGGTACCTCATGGGCTCCATGACCCCACAGGCTGTGCTG<br>GCTTTTGTGGCCCTGATCCCTCCAACCCTCCCTGGCACCAACATTGTTCTGGGAGCACTGCCTGA<br>AGACAGACACATTGACAGGCTGGCAAAGAGGCAGAGACCTGGAGAGAGACTGGACCTGGCCATGC<br>TGGCTGCAATCAGAAGGGTGTATGGACTGCTGGCAAACACTGTGAGATACCTCCAGTGTGGAGGC<br>TCTTGGAGAGAGGACTGGGGACAGCTCTCTGGAACAGCAGTGCCCCCTCAAGGAGCTGAGCCCCA<br>GTCCAATGCTGGTCCAAGACCCCACATTGGGACACCCTGTTCACCCTGTTCAGAGCCCCTGAGC<br>TGCTGGCTCCCAATGGAGACCTGTACAATGTGTTTGCCTGGGCTCTGGATGTTCTAGCCAAGAGG<br>CTGAGGTCCATGCATGTGTTCATCCTGGACTATGACCAGTCCCCTGCTGGATGCAGAGATGCTCT<br>GCTGCAACTAACCTCTGGCATGGTGCAGACCCATGTGACCACCCCTGGCAGCATCCCCACCATCT<br>GTGACCTAGCCAGAACCTTTGCCAGGGAGATGGGAGAGGCCAACTAAGGCGCGCCACTCGAGCGC<br>TAGCTGGCCAGACATGATAAGATACATTGATGAGTTTGGACAAACCACAACTAGAATGCAGTGAA<br>AAAAATGCTTTATTTGTGAAATTTGTGATGCTATTGCTTTATTTGTAACCATTATAAGCTGCAAT<br>AAACAAGTTAACAACAACAATTGCATTCATTTTATGTTTCAGGTTCAGGGGGAGGTGTGGGAGGT<br>TTTTTAAAGCAAGTAAAACCTCTACAAATGTGGTATGGAAGGCGCGCCCAATTCGCCCTATAGTG<br>AGTCGTATTACGTCGCGCTCACTGGCCGTCGTTTTACAACGTCGTGACTGGGAAAACCCTGGCGT<br>TACCCAACTTAATCGCCTTGCAGCACATCCCCCTTTCGCCAGCTGGCGTAATAGCGAAGAGGCCC<br>GCACCGAAACGCCCTTCCCAACAGTTGCGCAGCCTGAATGGCGAATGGGAGCGCCCTGTAGCGGC<br>GCATTAAGCGCGGCGGGTGTGGTGGTTACGCGCAGCGTGACCGCTACACTTGCCAGCGCCCTAGC<br>GCCCGCTCCTTTCGCTTTCTTCCCTTCCTTTCTCGCCACGTTCGCCGGCTTTCCCCGTCAAGCTC<br>TAAATCGGGGGCTCCCTTTAGGGTTCCGATTTAGTGCTTTACGGCACCTCGACCCCAAAAAACTT<br>GATTAGGGTGATGGTTGGCCTGTAGTGGGCCATAGCCCTGATAGACGGTTTTTCGCCCTTTGACG<br>TTGGAGTCCACGTTCTTTAATAGTGGACTCTTGTTCCAAACTGGAACAACACTCAACCCTATCTC<br>GGTCTATTCTTTTGATTTATAAGGGATTTTGCCGATTTCGGCCTATTGGTTAAAAAATGAGCTGA<br>TTTAACAAAAATTTAACGCGAATTTTAACAAAATATTAACGCTTACAATTTAGGTGGCACTTTTC<br>GGGGAAATGTGCGCGGAACCCCTATTTGTTTATTTTTCTAAATACATTCAAATATGTATCCGCTC<br>ATGAGACAATAACCCTGATAAATGCTTCAATAATATTGAAAAAGGAAGAGTATGAGTATTCAACA<br>TTTCCGTGTCGCCCTTATTCCCTTTTTTGCGGCATTTTGCCTTCCTGTTTTTGCTCACCCAGAAA<br>CGCTGGTGAAAGTAAAAGATGCTGAAGATCAGTTGGGTGCACGAGTGGGTTACATCGAACTGGAT<br>CTCAACAGCGGTAAGATCCTTGAGAGTTTTCGCCCCGAAGAACGTTTTCCAATGATGAGCACTTT<br>TAAAGTTCTGCTATGTGGCGCGGTATTATCCCGTATTGACGCCGGGCAAGAGCAACTCGGTCGCC<br>GCATACACTATTCTCAGAATGACTTGGTTGAGTACTCACCAGTCACAGAAAAGCATCTTACGGAT<br>GGCATGACAGTAAGAGAATTATGCAGTGCTGCCATAACCATGAGTGATAACACTGCGGCCAACTT<br>ACTTCTGACAACGATCGGAGGACCGAAGGAGCTAACCGCTTTTTTGCACAACATGGGGGATCATG<br>TAACTCGCCTTGATCGTTGGGAACCGGAGCTGAATGAAGCCATACCAAACGACGAGCGTGACACC<br>ACGATGCCTGTAGCAATGGCAACAACGTTGCGCAAACTATTAACTGGCGAACTACTTACTCTAGC<br>TTCCCGGCAACAATTAATAGACTGGATGGAGGCGGATAAAGTTGCAGGACCACTTCTGCGCTCGG<br>CCCTTCCGGCTGGCTGGTTTATTGCTGATAAATCTGGAGCCGGTGAGCGTGGTTCTCGCGGTATC<br>ATTGCAGCACTGGGGCCAGATGGTAAGCCCTCCCGTATCGTAGTTATCTACACGACGGGGAGTCA<br>GGCAACTATGGATGAACGAAATAGACAGATCGCTGAGATAGGTGCCTCACTGATTAAGCATTGGT<br>AACTGTCAGACCAAGTTTACTCATATATACTTTAGATTGATTTAAAACTTCATTTTTAATTTAAA<br>AGGATCTAGGTGAAGATCCTTTTTGATAATCTCATGACCAAAATCCCTTAACGTGAGTTTTCGTT<br>CCACTGAGCGTCAGACCCCGTAGAAAAGATCAAAGGATCTTCTTGAGATCCTTTTTTTCTGCGCG<br>TAATCTGCTGCTTGCAAACAAAAAAACCACCGCTACCAGCGGTGGTTTGTTTGCCGGATCAAGAG<br>CTACCAACTCTTTTTCCGAAGGTAACTGGCTTCAGCAGAGCGCAGATACCAAATACTGTTCTTCT<br>AGTGTAGCCGTAGTTAGGCCACCACTTCAAGAACTCTGTAGCACCGCCTACATACCTCGCTCTGC<br>TAATCCTGTTACCAGTGGCTGCTGCCAGTGGCGATAAGTCGTGTCTTACCGGGTTGGACTCAAGA<br>CGATAGTTACCGGATAAGGCGCAGCGGTCGGGCTGAACGGGGGGTTCGTGCACACAGCCCAGCTT<br>GGAGCGAACGACCTACACCGAACTGAGATACCTACAGCGTGAGCTATGAGAAAGCGCCACGCTTC<br>CCGAAGGGAGAAAGGCGGACAGGTATCCGGTAAGCGGCAGGGTCGGAACAGGAGAGCGCACGAGG<br>GAGCTTCCAGGGGGAAACGCCTGGTATCTTTATAGTCCTGTCGGGTTTCGCCACCTCTGACTTGA<br>GCGTCGATTTTTGTGATGCTCGTCAGGGGGGCGGAGCCTATGGAAAAACGCCAGCAACGCGGCCT<br>TTTTACGGTTCCTGGCCTTTTGCTGGCCTTTTGCTCACATGGTCTTTCCTGCGTTATCCCCTGAT<br>TCTGTGGATAACCGTATTACCGCCTTTGAGTGAGCTGATACCGCTCGCCGCAGCCGAACGACCGA<br>GCGCAGCGAGTCAGTGAGCGAGGAAGCGGAAGAGCGCCCAATACGCAAACCGCCTCTCCCCGCGCG<br>TTGGCCGATTCATTAATGCAGCTGGCACGACAGGTTTCCCGACTGGAAAGCGGGCAGTGAGCGCA<br>ACGCAATTAATGTGAGTTAGCTCACTCATTAGGCACCCCAGGCTTTACACTTTATGCTTCCGGCT<br>CGTATGTTGTGTGGAATTGTGAGCGGATAACAATTTCACACAGGAAACAGCTATGACCATGATTA<br>CGCCAAGCGCGTCAATTAACCTCACTAAAGGGAACAAAAGCTGTTAATTAA |
| 67 | Matrice PD1<br>locus_IL12a_<br>2A_IL12b<br>pCLS30511<br>full sequence | CGCGCGTTTCGGTGATGACGGTGAAAACCTCTGACACATGCAGCTCCCGGAGACGGTCACAGCT<br>TGTCTGTAAGCGGATGCCGGGAGCAGACAAGCCCGTCAGGGCGCGTCAGCGGGTGTTGGCGGGTG<br>TCGGGGCTGGCTTAACTATGCGGCATCAGAGCAGATTGTACTGAGAGTGCACCATATGCGGTGTG<br>AAATACCGCACAGATGCGTAAGGAGAAAATACCGCATCAGGCGCCATTCGCCATTCAGGCTGCGC<br>AACTGTTGGGAAGGGCGATCGGTGCGGGCCTCTTCGCTATTACGCCAGCTGGCGAAAGGGGGATG<br>TGCTGCAAGGCGATTAAGTTGGGTAACGCCAGGGTTTTCCCAGTCACGACGTTGTAAAACGACGG<br>CCAGTGAATTCGAGCTCGGTACCTCGCGAATGCATCTAGATGACTCCCCAGACAGGCCCTGGAAC<br>CCCCCACCTTCTCCCAGCCCTGCTCGTGGTGACCGAAGGGGACAACGCCACCTTCACCTGCAG<br>CTTCTCCAACACATCGGAGAGCTTCGTGCTAAACTGGTACCGCATGAGCCCCAGCAACCAGACGG<br>ACAAGCTGGCCGCTTCCCCGAGGACCGCAGCCAGCCCGGCCAGGACTGCCGCTTCCGTGTCACA<br>CAACTGCCCAACGGGCGTGACTTCCACATGAGCGTGGTCAGGGCCCGGCGCAATGACAGCGGCAC<br>CTACCTCTGTGGGGCCATCTCTGGCGTGAAACAGACTTTGAATTTTGACCTTCTCAAGTTGGCGG<br>GAGACGTGGAGTTCAACCCAGGGCCCATGTGGCCCCCTGGGTCAGCTCCCAGCCACCGCCCTCA<br>CCTGCCGCGGCCACAGGTCTGCATCCAGCGGCTCGCCCTGTGTCCCTGCAGTGCCGGCTCAGCAT<br>GTGTCCAGCGCGCAGCCTCCTCCTTGTGGCTACCCTGGTCCTCCTGGACCACCTCAGTTTGGCCA<br>GAAACCTCCCCGTGGCCACTCCAGACCCAGGAATGTTCCCATGCCTTCACCACTCCCAAAACCTG<br>CTGAGGGCCGTCAGCAACATGCTCCAGAAGGCCAGACAAACTCTAGAATTTTACCCTTGCACTTC |

TABLE 5-continued

Sequences referred to in example 2 and 3.

```
TGAAGAGATTGATCATGAAGATATCACAAAAGATAAAACCAGCACAGTGGAGGCCTGTTTACCAT
TGGAATTAACCAAGAATGAGAGTTGCCTAAATTCCAGAGAGACCTCTTTCATAACTAATGGGAGT
TGCCTGGCCTCCAGAAAGACCTCTTTTATGATGGCCCTGTGCCTTAGTAGTATTTATGAAGACTT
GAAGATGTACCAGGTGGAGTTCAAGACCATGAATGCAAAGCTTCTGATGGATCCTAAGAGGCAGA
TCTTTCTAGATCAAAACATGCTGGCAGTTATTGATGAGCTGATGCAGGCCCTGAATTTCAACAGT
GAGACTGTGCCACAAAAATCCTCCCTTGAAGAACCGGATTTTTATAAAACTAAAATCAAGCTCTG
CATACTTCTTCATGCTTTCAGAATTCGGGCAGTGACTATTGATAGAGTGATGAGCTATCTGAATG
CTTCCGGAAGCGGAGCTACTAACTTCAGCCTGCTGAAGCAGGCTGGAGACGTGGAGGAGAACCCT
GGACCTATGTGTCACCAGCAGTTGGTCATCTCTTGGTTTTCCCTGGTTTTTCTGGCATCTCCCCT
CGTGGCCATATGGGAACTGAAGAAAGATGTTTATGTCGTAGAATTGGATTGGTATCCGGATGCCC
CTGGAGAAATGGTGGTCCTCACCTGTGACACCCCTGAAGAAGATGGTATCACCTGGACCTTGGAC
CAGAGCAGTGAGGTCTTAGGCTCTGGCAAAACCCTGACCATCCAAGTCAAAGAGTTTGGAGATGC
TGGCCAGTACACCTGTCACAAAGGAGGCGAGGTTCTAAGCCATTCGCTCCTGCTGCTTCACAAAA
AGGAAGATGGAATTTGGTCCACTGATATTTTAAAGGACCAGAAAGAACCCAAAAATAAGACCTTT
CTAAGATGCGAGGCCAAGAATTATTCTGGACGTTTCACCTGCTGGTGGCTGACGACAATCAGTAC
TGATTTGACATTCAGTGTCAAAAGCAGCAGAGGCTCTTCTGACCCCCAAGGGGTGACGTGCGGAG
CTGCTACACTCTCTGCAGAGAGAGTCAGAGGGGACAACAAGGAGTATGAGTACTCAGTGGAGTGC
CAGGAGGACAGTGCCTGCCCAGCTGCTGAGGAGAGTCTGCCCATTGAGGTCATGGTGGATGCCGT
TCACAAGCTCAAGTATGAAAACTACACCAGCAGCTTCTTCATCAGGGACATCATCAAACCTGACC
CACCCAAGAACTTGCAGCTGAAGCCATTAAAGAATTCTCGGCAGGTGGAGGTCAGCTGGGAGTAC
CCTGACACCTGGAGTACTCCACATTCCTACTTCTCCCTGACATTCTGCGTTCAGGTCCAGGGCAA
GAGCAAGAGAGAAAGAAAGATAGAGTCTTCACGGACAAGACCTCAGCCACGGTCATCTGCCGCA
AAAATGCCAGCATTAGCGTGCGGGCCCAGGACCGCTACTATAGCTCATCTTGGAGCGAATGGGCA
TCTGTGCCCTGCAGTGAGGGCAGAGGCAGCCTGCTGACCTGCGGCGACGTCGAGGAGAACCCCGG
GCCCATGGGGGCAGGTGCCACCGGCCGCGCCATGGACGGGCCGCGCCTGCTGCTGTTGCTGCTTC
TGGGGGTGTCCCTTGGAGGTGCCAAGGAGGCATGCCCCACAGGCCTGTACACACACAGCGGTGAG
TGCTGCAAAGCCTGCAACCTGGGCGAGGGTGTGGCCCAGCCTTGTGGAGCCAACCAGACCGTGTG
TGAGCCCTGCCTGGACAGCGTGACGTTCTCCGACGTGGTGAGCGCGACCGAGCCGTGCAAGCCGT
GCACCGAGTGCGTGGGGCTCCAGAGCATGTCGGCGCCTGCGTGGAGGCCGATGACGCCGTGTGC
CGCTGCGCCTACGGCTACTACCAGGATGAGACGACTGGGCGCTGCGAGGCGTGCCGCGTGTGCGA
GGCGGGCTCGGGCCTCGTGTTCTCCTGCCAGGACAAGCAGAACACCGTGTGCGAGGAGTGCCCCG
ACGGCACGTATTCCGACGAGGCCAACCACGTGGACCCGTGCCTGCCCTGCACCGTGTGCGAGGAC
ACCGAGCGCCAGCTCCGCGAGTGCACACGCTGGGCCGACGCCGAGTGCGAGGAGATCCCTGGCCG
TTGGATTACACGGTCCACACCCCCAGAGGGCTCGGACAGCACAGCCCCAGCACCCAGGAGCCTG
AGGCACCTCCAGAACAAGACCTCATAGCCAGCACGGTGGCAGGTGTGGTGACCACAGTGATGGGC
AGCTCCCAGCCCGTGGTGACCCGAGGCACCACCGACAACCTCATCCCTGTCTATTGCTCCATCCT
GGCTGCTGTGGTTGTGGGTCTTGTGGCCTACATAGCCTTCAAGAGGTGATCTAGAGGGCCCGTTT
AAACCCGCTGATCAGCCTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAAGGGGG
AGGATTGGGAAGACAATAGCAGGCATGCTGGGGATGCGGTGGGCTCTATGACTAGTGGCGAATTC
GGCGCAGATCAAAGAGAGCCTGCGGGCAGAGCTCAGGGTGACAGGTGCGGCCTCGGAGGCCCCGG
GGCAGGGGTGAGCTGAGCCGGTCCTGGGGTGGGTGTCCCCTCCTGCACAGGATCAGGAGCTCCAG
GGTCGTAGGGCAGGGACCCCCCAGCTCCAGTCCAGGGCTCTGTCCTGCACCTGGGGAATGGTGAC
CGGCATCTCTGTCCTCTAGCTCTGGAAGCACCCCAGCCCCTCTAGTCTGCCCTCACCCCTGACCC
TGACCCTCCACCCTGACCCCGTCCTAACCCTGACCTTTGATCGGATCCCGGGCCCGTCGACTGC
AGAGGCCTGCATGCAAGCTTGGCGTAATCATGGTCATAGCTGTTTCCTGTGTGAAATTGTTATCC
GCTCACAATTCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACCTGTCGTGC
CAGCTGCATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTCACTCAA
AGGCGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAA
GTGGTGGCCTAACTACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTAT
CAAAAAGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATTTATCA
GCAATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCAC
TGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAATACGGGATAA
TACCGCGCCACATAGCAGAACTTTAAAAGTGCTCATCATTGGAAAACGTTCTTCGGGGCGAAAAC
TCTCAAGGATCTTACCGCTGTTGAGATCCAGTTCGATGTAACCCACTCGTGCACCCAACTGATCT
TCAGCATCTTTTACTTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTTCAATATTATTGAA
```

TABLE 5-continued

Sequences referred to in example 2 and 3.

| | | |
|---|---|---|
| | | GCATTTATCAGGGTTATTGTCTCATGAGCGGATACATATTTGAATGTATTTAGAAAAATAAACAA ATAGGGGTTCCGCGCACATTTCCCCGAAAAGTGCCACCTGACGTCTAAGAAACCATTATTATCAT GACATTAACCTATAAAAATAGGCGTATCACGAGGCCCTTTCGTC |
| 68 | HLAE trimer matrix (VMAPRTLFL peptide) inserted at the B2m locus | cacttagcatctctggggccagtctgcaaagcgaggggggcagccttaatgtgcctccagcctgaa gtcctagaatgagcgcccggtgtcccaagctggggCGCGCACCCCAGATCGGAGGGCGCCGATGT ACAGACAGCAAACTCACCCAGTCTAGTGCATGCCTTCTTAAACATCACGAGACTCTAAGAAAAGG AAACTGAAAACGGGAAAGTCCCTCTCTCTAACCTGGCACTGCGTCGCTGGCTTGGAGACAGGTGA CGGTCCCTGCGGGCCTTGTCCTGATTGGCTGGGCACGCGTTTAATATAAGTGGAGGCGTCGCGCT GGCGGGCATTCCTGAAGCTGACAGCATTCGGGCCGAGATGTCTCGCTCCGTGGCCTTAGCTGTGC TCGCGCTACTCTCTCTTAGCGGCCTCGAAGCTGTTATGGCTCCGCGGACTTTATTCTTAGGTGGT GGCGGATCCGGTGGTGGCGGTTCTGGTGGTGGCGGCTCCATCCAGCGTACGCCCAAAATTCAAGT CTACAGCCGACATCCTGCAGAGAACGGCAAATCTAATTTCCTGAACTGCTATGTATCAGGCTTTC ACCCTAGCGATATAGAAGTGGACCTGCTGAAAAACGGAGAGAGGATAGAAAAGGTCGAACACAGC GACCTCTCCTTTTCCAAGGACTGGAGCTTTTATCTTCTGTATTATACTGAATTTACACCCACGGA AAAAGATGAGTATGCGTGCCGAGTAAACCACGTCACGCTGTCACAGCCCAAAATAGTAAAATGGG ATCGCGACATGGGTGGTGGCGGTTCTGGTGGTGGCGGTAGTGGCGGCGGAGGAAGCGGTGGTGGC GGTTCCGGATCTCACTCCTTGAAGTATTTCCACACTTCCGTGTCCCGGCCCGGCCGCGGGGAGCC CCGCTTCATCTCTGTGGGCTACGTGGACGACACCCAGTTCGTGCGCTTCGACAACGACGCCGCGA GTCCGAGGATGGTGCCGCGGGCGCCGTGGATGGAGCAGGAGGGGTCAGAGTATTGGGACCGGGAG ACACGGAGCGCCAGGGACACCGCACAGATTTTCCGAGTGAACCTGCGGACGCTGCGCGGCTACTA CAATCAGAGCGAGGCCGGGTCTCACACCCTGCAGTGGATGCATGGCTGCGAGCTGGGGCCCGACA GGCGCTTCCTCCGCGGGTATGAACAGTTCGCCTACGACGGCAAGGATTATCTCACCCTGAATGAG GACCTGCGCTCCTGGACCGCGGTGGACACGGCGGCTCAGATCTCCGAGCAAAAGTCAAATGATGC CTCTGAGGCGGAGCACCAGAGAGCCTACCTGGAAGACACATGCGTGGAGTGGCTCCACAAATACC TGGAGAAGGGGAAGGAGACGCTGCTTCACCTGGAGCCCCCAAAGACACACGTGACTCACCACCCC ATCTCTGACCATGAGGCCACCCTGAGGTGCTGGGCTCTGGGCTTCTACCCTGCGGAGATCACACT GACCTGGCAGCAGGATGGGGAGGGCCATACCCAGGACACGGAGCTCGTGGAGACCAGGCCTGCAG GGGATGGAACCTTCCAGAAGTGGGCAGCTGTGGTGGTGCCTTCTGGAGAGGAGCAGAGATACACG TGCCATGTGCAGCATGAGGGGCTACCCGAGCCCGTCACCCTGAGATGGAAGCCGGCTTCCCAGCC CACCATCCCCATCGTGGGCATCATTGCTGGCCTGGTTCTCCTTGGATCTGTGGTCrCTGGAGCTG TGGTTGCTGCTGTGATATGGAGGAAGAAGAGCTCAGGTGGAAAAGGAGGGAGCTACTATAAGGCT GAGTGGAGCGACAGTGCCCAGGGGTCTGAGTCTCACAGCTTGTAACTGTGCCTTCTAGTTGCCAG CCATCTGTTGTTTGCCCCTCCCCCGTGCCTTCCTTGACCCTGGAAGGTGCCACTCCCACTGTCCT TTCCTAATAAAATGAGGAAATTGCATCGCATTGTCTGAGTAGGTGTCATTCTATTCTGGGGGGTG GGGTGGGGCAGGACAGCAAGGGGGAGGATTGGGAAGACAATAGCAGGCATGCTGGGGATGCGGTG GGCTCTATGTCTCTTTCTGGCCTGGAGGCTATCCAGCGTGAGTCTCTCCTACCCTCCCGCTCTGG TCCTTCCTCTCCCGCTCTGCACCCTCTGTGGCCCTCGCTGTGCTCTCTCGCTCCGTGACTTCCCT TCTCCAAGTTCTCCTTGGTGGCCCGCCGTGGGGCTAGTCCAGGGCTGGATCTCGGGGAAGCGGCG GGGTGGCCTGGGAGTGGGGAAGGGGGTGCGCACCCGGGACGCGCGCTACTTGCCCCTTTCGGCGG GGAGCAGGGGAGACCTTTGGCCTACGGCGACGGGAGGGGGCACAAAGtttagggcgtcgataa gcgtcagagcgccgaggttgggggagggtttctcttccgctctttcgcggggcctctggctcccc cagcgcagctggagtgggg |
| 69 | HLAE trimer matrix (VMAPRTLFL peptide) | CGCGCACCCCAGATCGGAGGGCGCCGATGTACAGACAGCAAACTCACCCAGTCTAGTGCATGCCT TCTTAAACATCACGAGACTCTAAGAAAAGGAAACTGAAAACGGGAAAGTCCCTCTCTCTAACCTG GCACTGCGTCGCTGGCTTGGAGACAGGTGACGGTCCCTGCGGGCCTTGTCCTGATTGGCTGGGCA CGCGTTTAATATAAGTGGAGGCGTCGCGCTGGCGGGCATTCCTGAAGCTGACAGCATTCGGGCCG AGATGTCTCGCTCCGTGGCCTTAGCTGTGCTCGCGCTACTCTCTCTTAGCGGCCTCGAAGCTGTT ATGGCTCCGCGGACTTTATTCTTAGGTGGTGGCGGATCCGGTGGTGGCGGTTCTGGTGGTGGCGG CTCCATCCAGCGTACGCCCAAAATTCAAGTCTACAGCCGACATCCTGCAGAGAACGGCAAATCTA ATTTCCTGAACTGCTATGTATCAGGCTTTCACCCTAGCGATATAGAAGTGGACCTGCTGAAAAAC GGAGAGAGGATAGAAAAGGTCGAACACAGCGACCTCTCCTTTTCCAAGGACTGGAGCTTTTATCT TCTGTATTATACTGAATTTACACCCACGGAAAAAGATGAGTATGCGTGCCGAGTAAACCACGTCA CGCTGTCACAGCCCAAAATAGTAAAATGGGATCGCGACATGGGTGGTGGCGGTTCTGGTGGTGGC GGTAGTGGCGGCGGAGGAAGCGGTGGTGGCGGTTCCGGATCTCACTCCTTGAAGTATTTCCACAC TTCCGTGTCCCGGCCCGGCCGCGGGGAGCCCCGCTTCATCTCTGTGGGCTACGTGGACGACACCC AGTTCGTGCGCTTCGACAACGACGCCGCGAGTCCGAGGATGGTGCCGCGGGCGCCGTGGATGGAG CAGGAGGGGTCAGAGTATTGGGACCGGGAGACACGGAGCGCCAGGGACACCGCACAGATTTTCCG AGTGAACCTGCGGACGCTGCGCGGCTACTACAATCAGAGCGAGGCCGGGTCTCACACCCTGCAGT GGATGCATGGCTGCGAGCTGGGGCCCGACAGGCGCTTCCTCCGCGGGTATGAACAGTTCGCCTAC GACGGCAAGGATTATCTCACCCTGAATGAGGACCTGCGCTCCTGGACCGCGGTGGACACGGCGGC TCAGATCTCCGAGCAAAAGTCAAATGATGCCTCTGAGGCGGAGCACCAGAGAGCCTACCTGGAAG ACACATGCGTGGAGTGGCTCCACAAATACCTGGAGAAGGGGAAGGAGACGCTGCTTCACCTGGAG CCCCCAAAGACACACGTGACTCACCACCCCATCTCTGACCATGAGGCCACCCTGAGGTGCTGGGC TCTGGGCTTCTACCCTGCGGAGATCACACTGACCTGGCAGCAGGATGGGGAGGGCCATACCCAGG ACACGGAGCTCGTGGAGACCAGGCCTGCAGGGGATGGAACCTTCCAGAAGTGGGCAGCTGTGGTG GTGCCTTCTGGAGAGGAGCAGAGATACACGTGCCATGTGCAGCATGAGGGGCTACCCGAGCCCGT CACCCTGAGATGGAAGCCGGCTTCCCAGCCCACCATCCCCATCGTGGGCATCATTGCTGGCCTGG TTCTCCTTGGATCTGTGGTCTCTGGAGCTGTGGTTGCTGCTGTGATATGGAGGAAGAAGAGCTCA GGTGGAAAAGGAGGGAGCTACTATAAGGCTGAGTGGAGCGACAGTGCCCAGGGGTCTGAGTCTCA CAGCTTGTAACTGTGCCTTCTAGTTGCCAGCCATCTGTTGTTTGCCCCTCCCCCGTGCCTTCCTT GACCCTGGAAGGTGCCACTCCCACTGTCCTTTCCTAATAAAATGAGGAAATTGCATCGCATTGTC TGAGTAGGTGTCATTCTATTCTGGGGGGTGGGGTGGGCAGGACAGCAAGGGGGAGGATTGGGAA GACAATAGCAGGCATGCTGGGGATGCGGTGGGCTCTATGTCTCTTTCTGGCCTGGAGGCTATCCA GCGTGAGTCTCTCCTACCCTCCCGCTCTGGTCCTTCCTCTCCCGCTCTGCACCCTCTGTGGCCCT CGCTGTGCTCTCTCGCTCCGTGACTTCCCTTCTCCAAGTTCTCCTTGGTGGCCCGCCGTGGGGCT AGTCCAGGGCTGGATCTCGGGGAAGCGGCGGGGTGGCCTGGGAGTGGGGAAGGGGGTGCGCACCC GGGACGCGCGCTACTTGCCCCTTTCGGCGGGGAGCAGGGGAGACCTTTGGCCTACGGCGACGGGA GGGTCGGGACAAAG |

TABLE 5-continued

Sequences referred to in example 2 and 3.

| 70 | HLAE trimer matrix (VMAPRTLIL peptide) inserted at the B2m locus | cacttagcatctctggggccagtctgcaaagcgaggggggcagccttaatgtgcctccagcctgaa
gtcctagaatgagcgcccggtgtcccaagctggggCGCGCACCCCAGATCGGAGGGCGCCGATGT
ACAGACAGCAAACTCACCCAGTCTAGTGCATGCCTTCTTAAACATCACGAGACTCTAAGAAAAGG
AAACTGAAAACGGGAAAGTCCCTCTCTCTAACCTGGCACTGCGTCGCTGGCTTGGAGACAGGTGA
CGGTCCCTGCGGGCCTTGTCCTGATTGGCTGGGCACGCGTTTAATATAAGTGGAGGCGTCGCGCT
GGCGGGCATTCCTGAAGCTGACAGCATTCGGGCCGAGATGTCTCGCTCCGTGGCCTTAGCTGTGC
TCGCGCTACTCTCTCTTAGCGGCCTCGAAGCTGTTATGGCTCCGCGGACTTTAATTTTAGGTGGT
GGCGGATCCGGTGGTGGCGGTTCTGGTGGTGGCGGCTCCATCCAGCGTACGCCCAAAATTCAAGT
CTACAGCCGACATCCTGCAGAGAACGGCAAATCTAATTTCCTGAACTGCTATGTATCAGGCTTTC
ACCCTAGCGATATAGAAGTGGACCTGCTGAAAAACGGAGAGAGGATAGAAAAGGTCGAACACAGC
GACCTCTCCTTTTCCAAGGACTGGAGCTTTTATCTTCTGTATTATACTGAATTTACACCCACGGA
AAAAGATGAGTATGCGTGCCGAGTAAACCACGTCACGCTGTCACAGCCCAAAATAGTAAAATGGG
ATCGCGACATGGGTGGTGGCGGTTCTGGTGGTGGCGGTAGTGGCGGCGGAGGAAGCGGTGGTGGC
GGTTCCGGATCTCACTCCTTGAAGTATTTCCACACTTCCGTGTCCCGGCCCGGCCGCGGGGAGCC
CCGCTTCATCTCTGTGGGCTACGTGGACGACACCCAGTTCGTGCGCTTCGACAACGACGCCGCGA
GTCCGAGGATGGTGCCGCGGGCGCCGTGGATGGAGCAGGAGGGGTCAGAGTATTGGGACCGGGAG
ACACGGAGCGCCAGGGACACCGCACAGATTTTCCGAGTGAACCTGCGGACGCTGCGCGGCTACTA
CAATCAGAGCGAGGCCGGGTCTCACACCCTGCAGTGGATGCATGGCTGCGAGCTGGGGCCCGACA
GGCGCTTCCTCCGCGGGTATGAACAGTTCGCCTACGACGGCAAGGATTATCTCACCCTGAATGAG
GACCTGCGCTCCTGGACCGCGGTGGACACGGCGGCTCAGATCTCCGAGCAAAAGTCAAATGATGC
CTCTGAGGCGGAGCACCAGAGAGCCTACTGGAAGACACATGCGTGGAGTGGCTCCACAAATACC
TGGAGAAGGGGAAGGAGACGCTGCTTCACCTGGAGCCCCCAAAGACACACGTGACTCACCACCCC
ATCTCTGACCATGAGGCCACCCTGAGGTGCTGGGCTCTGGGCTTCTACCCTGCGGAGATCACACT
GACCTGGCAGCAGGATGGGGAGGGCCATACCCAGGACACGGAGCTCGTGGAGACCAGGCCTGCAG
GGGATGGAACCTTCCAGAAGTGGGCAGCTGTGGTGGTGCCTTCTGGAGAGGAGCAGAGATACACG
TGCCATGTGCAGCATGAGGGGCTACCCGAGCCCGTCACCCTGAGATGGAAGCCGGCTTCCCAGCC
CACCATCCCCATCGTGGGCATCATTGCTGGCCTGGTTCTCCTTGGATCTGTGGTCTCTGGAGCTG
TGGTTGCTGCTGTGATATGGAGGAAGAAGAGCTCAGGTGGAAAAGGAGGGAGCTACTATAAGGCT
GAGTGGAGCGACAGTGCCCAGGGGTCTGAGTCTCACAGCTTGTAACTGTGCCTTCTAGTTGCCAG
CCATCTGTTGTTTGCCCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGCTGGGGATGCGGTG
GGCTCTATGTCTCTTTCTGGCCTGGAGGCTATCCAGCGTGAGTCTCTCCTACCCTCCCGCTCTGG
TCCTTCCTCTCCCGCTCTGCACCCTCTGTGGCCCTCGCTGTGCTCTCTCGCTCCGTGACTTCCCT
TCTCCAAGTTCTCCTTGGTGGCCCGCCGTGGGGCTAGTCCAGGGCTGGATCTCGGGGAAGCGGCG
GGGTGGCCTGGGAGTGGGGAAGGGGGTGCGCACCCGGGACGCGCGCTACTTGCCCCCTTTCGGCGG
GGAGCAGGGGAGACCTTTGGCCTACGGCGACGGGAGGGTCGGGACAAAGtttagggcgtcgataa
gcgtcagagcgccgaggttgggggagggtttctcttccgctctttcgcggggcctctggctcccc
cagcgcagctggagtgggg |
| 71 | HLAE trimer matrix (VMAPTRLIL peptide) | CGCGCACCCCAGATCGGAGGGCGCCGATGTACAGACAGCAAACTCACCCAGTCTAGTGCATGCCT
TCTTAAACATCACGAGACTCTAAGAAAAGGAAACTGAAAACGGGAAAGTCCCTCTCTCTAACCTG
GCACTGCGTCGCTGGCTTGGAGACAGGTGACGGTCCCTGCGGGCCTTGTCCTGATTGGCTGGGCA
CGCGTTTAATATAAGTGGAGGCGTCGCGCTGGCGGGCATTCCTGAAGCTGACAGCATTCGGGCCG
AGATGTCTCGCTCCGTGGCCTTAGCTGTGCTCGCGCTACTCTCTCTTAGCGGCCTCGAAGCTGTT
ATGGCTCCGCGGACTTTAATTTTAGGTGGTGGCGGATCCGGTGGTGGCGGTTCTGGTGGTGGCGG
CTCCATCCAGCGTACGCCCAAAATTCAAGTCTACAGCCGACATCCTGCAGAGAACGGCAAATCTA
ATTTCCTGAACTGCTATGTATCAGGCTTTCACCCTAGCGATATAGAAGTGGACCTGCTGAAAAAC
GGAGAGAGGATAGAAAAGGTCGAACACAGCGACCTCTCCTTTTCCAAGGACrGAGCTTTTTATCT
TCTGTATTATACTGAATTTACACCCACGGAAAAAGATGAGTATGCGTGCCGAGTAAACCACGTCA
CGCTGTCACAGCCCAAAATAGTAAAATGGGATCGCGACATGGGTGGTGGCGGTTCTGGTGGTGGC
GGTAGTGGCGGCGGAGGAAGCGGTGGTGGCGGTTCCGGATCTCACTCCTTGAAGTATTTCCACAC
TTCCGTGTCCCGGCCCGGCCGCGGGGAGCCCCGCTTCATCTCTGTGGGCTACGTGGACGACACCC
AGTTCGTGCGCTTCGACAACGACGCCGCGAGTCCGAGGATGGTGCCGCGGGCGCCGTGGATGGAG
CAGGAGGGGTCAGAGTATTGGGACCGGGAGACACGGAGCGCCAGGGACACCGCACAGATTTTCCG
AGTGAACCTGCGGACGCTGCGCGGCTACTACAATCAGAGCGAGGCCGGGTCTCACACCCTGCAGT
GGATGCATGGCTGCGAGCTGGGGCCCGACAGGCGCTTCCTCCGCGGGTATGAACAGTTCGCCTAC
GACGGCAAGGATTATCTCACCCTGAATGAGGACCTGCGCTCCTGGACCGCGGTGGACACGGCGGC
TCAGATCTCCGAGCAAAAGTCAAATGATGCCTCTGAGGCGGAGCACCAGAGAGCCTACTGGAAG
ACACATGCGTGGAGTGGCTCCACAAATACCTGGAGAAGGGGAAGGAGACGCTGCTTCACCTGGAG
CCCCCAAAGACACACGTGACTCACCACCCCATCTCTGACCATGAGGCCACCCTGAGGTGCTGGGC
TCTGGGCTTCTACCCTGCGGAGATCACACTGACCTGGCAGCAGGATGGGGAGGGCCATACCCAGG
ACACGGAGCTCGTGGAGACCAGGCCTGCAGGGGATGGAACCTTCCAGAAGTGGGCAGCTGTGGTG
GTGCCTTCTGGAGAGGAGCAGAGATACACGTGCCATGTGCAGCATGAGGGGCTACCCGAGCCCGT
CACCCTGAGATGGAAGCCGGCTTCCCAGCCCACCATCCCCATCGTGGGCATCATTGCTGGCCTGG
TTCTCCTTGGATCTGTGGTCTCTGGAGCTGTGGTTGCTGCTGTGATATGGAGGAAGAAGAGCTCA
GGTGGAAAAGGAGGGAGCTACTATAAGGCTGAGTGGAGCGACAGTGCCCAGGGGTCTGAGTCTCA
CAGCTTGTAACTGTGCCTTCTAGTTGCCAGCCATCTGTTGTTTGCCCCTCCCCGTGCCTTCCTT
GACCCTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGATTGGGAA
GACAATAGCAGGCATGCTGGGGATGCGGTGGGCTCTATGTCTCTTTCTGGCCTGGAGGCTATCCA
GCGTGAGTCTCTCCTACCCTCCCGCTCTGGTCCTTCCTCTCCCGCTCTGCACCCTCTGTGGCCCT
CGCTGTGCTCTCTCGCTCCGTGACTTCCCTTCTCCAAGTTCTCCTTGGTGGCCCGCCGTGGGGCT
AGTCCAGGGCTGGATCTCGGGGAAGCGGCGGGGTGGCCTGGGAGTGGGGAAGGGGGTGCGCACCC
GGGACGCGCGCTACTTGCCCCCTTTCGGCGGGAGCAGGGGAGACCTTTGGCCTACGGCGACGGGA
GGGTCGGGACAAAG |
| 72 | UL18Trimer matrix_Actine peptide | cacttagcatctctggggccagtctgcaaagcgaggggggcagccttaatgtgcctccagcctgaa
gtcctagaatgagcgcccggtgtcccaagctggggCGCGCACCCCAGATCGGAGGGCGCCGATGT
ACAGACAGCAAACTCACCCAGTCTAGTGCATGCCTTCTTAAACATCACGAGACTCTAAGAAAAGG |

TABLE 5-continued

Sequences referred to in example 2 and 3.

| | | |
|---|---|---|
| | inserted at the B2m locus | AAACTGAAAACGGGAAAGTCCCTCTCTCTAACCTGGCACTGCGTCGCTGGCTTGGAGACAGGTGA<br>CGGTCCCTGCGGGCCTTGTCCTGATTGGCTGGGCACGCGTTTAATATAAGTGGAGGCGTCGCGCT<br>GGCGGGCATTCCTGAAGCTGACAGCATTCGGGCCGAGATGTCTCGCTCCGTGGCCTTAGCTGTGC<br>TCGCGCTACTCTCTCTTAGCGGCCTCGAAGCTGCCCTGCCCCACGCCATTTTGCGGCTCGGTGGT<br>GGCGGATCCGGTGGTGGCGGTTCTGGTGGTGGCGGCTCCATCCAGCGTACGCCCAAAATTCAAGT<br>CTACAGCCGACATCCTGCAGAGAACGGCAAATCTAATTTCCTGAACTGCTATGTATCAGGCTTTC<br>ACCCTAGCGATATAGAAGTGGACCTGCTGAAAAACGGAGAGAGGATAGAAAAGGTCGAACACAGC<br>GACCTCTCCTTTTCCAAGGACTGGAGCTTTTATCTTCTGTATTATACTGAATTTACACCCACGGA<br>AAAAGATGAGTATGCGTGCCGAGTAAACCACGTCACGCTGTCACAGCCCAAAATAGTAAAATGGG<br>ATCGCGACATGGGTGGTGGCGGTTCTGGTGGTGGCGGTAGTGGCGGCGGAGGAAGCGGTGGTGGC<br>GGTTCCGGATCTATGCACGTGCTGAGATACGGATATACCGGCATCTTCGACGATACATCCCATAT<br>GACTCTGACCGTGGTCGGGATTTTTGACGGACAGCACTTCTTTACATACCATGTGAACAGCTCCG<br>ATAAGGCTTCTAGTCGAGCAAATGGCACCATCTCATGGATGGCAACGTGAGCGCAGCCTACCCC<br>ACATATCTGGACGGAGAACGCGCTAAAGGCGATCTGATCTTCAATCAGACCGAGCAGAACCTGCT<br>GGAGCTGGAAATTGCTCTGGGGTACAGGTCTCAGAGTGTCCTGACATGGACTCACGAATGTAATA<br>CCACAGAGAACGGGAGCTTCGTGGCAGGATATGAGGGCTTTGGGTGGGACGGAGAAACACTGATG<br>GAGCTGAAGGATAATCTGACTCTGTGGACCGGCCCTAACTACGAAATCAGCTGGCTGAAGCAGAA<br>CAAGACTTACATCGACGGAAAGATCAAAAACATCAGCGAGGGCGATACTACCATCCAGCGCAATT<br>ACCTGAAGGGCAACTGCACCCAGTGGAGCGTGATCTACTCTGGGTTCCAGACACCTGTCACTCAC<br>CCAGTGGTCAAAGGGGGAGTGCGAAACCAGAATGACAACCGGGCCGAGGCCTTCTGTACATCCTA<br>CGGCTTCTTTCCCGGGGAGATCAATATTACTTTTATCCATTACGGCAACAAGGCCCCCGACGATT<br>CTGAGCCTCAGTGCAATCCCCTGCTGCCTACCTTCGATGGCACATTTCACCAGGGGTGCTACGTC<br>GCTATCTTCTGCAATCAGAACTATACTTGCCGGGTGACCCATGGGAACTGGACTGTGGAAATCCC<br>AATTTCAGTCACCAGCCCCGACGATTCAAGCTCCGGAGAGGTGCCAGATCACCCCACCGCAAATA<br>AGAGATACAACACCATGACAATCTCTAGTGTGCTGCTGGCCCTGCTGCTGTGCGCACTGCTGTTC<br>GCTTTTCTGCATTACTTCACAACTCTGAAGCAGTATCTGCGGAACCTGGCATTTGCCTGGCGGTA<br>CAGAAAAGTGAGATCAAGCTGACTGTGCCTTCTAGTTGCCAGCCATCTGTTGTTTGCCCCTCCCC<br>CGTGCCTTCCTTGACCCTGGAAGGTGCCACTCCCACTGTCCTTTCCTAATAAAATGAGGAAATTG<br>CATCGCATTGTCTGAGTAGGTGTCATTCTATTCTGGGGGGTGGGTGGGGCAGGACAGCAAGGGG<br>GAGGATTGGGAAGACAATAGCAGGCATGCTGGGGATGCGGTGGGCTCTATGTCTCTTTCTGGCCT<br>GGAGGCTATCCAGCGTGAGTCTCTCCTACCCTCCCGCTCTGGTCCTTCCTCTCCCGCTCTGCACC<br>CTCTGTGGCCCTCGCTGTGCTCTCTCGCTCCGTGACTTCCCTTCTCCAAGTTCTCCTTGGTGGCC<br>CGCCGTGGGGCTAGTCCAGGGCTGGATCTCGGGGAAGCGGCGGGGTGGCCTGGGAGTGGGGAAGG<br>GGGTGCGCACCCGGGACGCGCGCTACTTGCCCCTTTCGGCGGGGAGCAGGGGAGACCTTTGGCCT<br>ACGGCGACGGGAGGGTCGGGACAAAGtttagggcgtcgataagcgtcagagcgccgaggttgggg<br>gagggtttctcttccgctctttcgcggggcctctggctccccccagcgcagctggagtgggg |
| 73 | UL18Trimer matrix_Actine peptide | CGCGCACCCCAGATCGGAGGGCGCCGATGTACAGACAGCAAACTCACCCAGTCTAGTGCATGCCT<br>TCTTAAACATCACGAGACTCTAAGAAAAGGAAACTGAAAACGGGAAAGTCCCTCTCTCTAACCTG<br>GCACTGCGTCGCTGGCTTGGAGACAGGTGACGGTCCCTGCGGGCCTTGTCCTGATTGGCTGGGCA<br>CGCGTTTAATATAAGTGGAGGCGTCGCGCTGGCGGGCATTCCTGAAGCTGACAGCATTCGGGCCG<br>AGATGTCTCGCTCCGTGGCCTTAGCTGTGCTCGCGCTACTCTCTCTTAGCGGCCTCGAAGCTGCC<br>CTGCCCCACGCCATTTTGCGGCTCGGTGGTGGCGGATCCGGTGGTGGCGGTTCTGGTGGTGGCGG<br>CTCCATCCAGCGTACGCCCAAAATTCAAGTCTACAGCCGACATCCTGCAGAGAACGGCAAATCTA<br>ATTTCCTGAACTGCTATGTATCAGGCTTTCACCCTAGCGATATAGAAGTGGACCTGCTGAAAAAC<br>GGAGAGAGGATAGAAAAGGTCGAACACAGCGACCTCTCCTTTTCCAAGGACTGGAGCTTTTATCT<br>TCTGTATTATACTGAATTTACACCCACGGAAAAAGATGAGTATGCGTGCCGAGTAAACCACGTCA<br>CGCTGTCACAGCCCAAAATAGTAAAATGGGATCGCGACATGGGTGGTGGCGGTTCTGGTGGTGGC<br>GGTAGTGGCGGCGGAGGAAGCGGTGGTGGCGGTTCCGGATCTATGCACGTGCTGAGATACGGATA<br>TACCGGCATCTTCGACGATACATCCCATATGACTCTGACCGTGGTCGGGATTTTTGACGGACAGC<br>ACTTCTTTACATACCATGTGAACAGCTCCGATAAGGCTTCTAGTCGAGCAAATGGCACCATCTCA<br>TGGATGGCAACGTGAGCGCAGCCTACCCCACATATCTGGACGGAGAACGCGCTAAAGGCGATCT<br>GATCTTCAATCAGACCGAGCAGAACCTGCTGGAGCTGGAAATTGCTCTGGGGTACAGGTCTCAGA<br>GTGTCCTGACATGGACTCACGAATGTAATACCACAGAGAACGGGAGCTTCGTGGCAGGATATGAG<br>GGCTTTGGGTGGGACGGAGAAACACTGATGGAGCTGAAGGATAATCTGACTCrGTGGACCGGCCC<br>TAACTACGAAATCAGCTGGCTGAAGCAGAACAAGACTTACATCGACGGAAAGATCAAAAACATCA<br>GCGAGGGCGATACTACCATCCAGCGCAATTACCTGAAGGGCAACTGCACCCAGTGGAGCGTGATC<br>TACTCTGGGTTCCAGACACCTGTCACTCACCCAGTGGTCAAAGGGGGAGTGCGAAACCAGAATGA<br>CAACCGGGCCGAGGCCTTCTGTACATCCTACGGCTTCTTTCCCGGGGAGATCAATATTACTTTTA<br>TCCATTACGGCAACAAGGCCCCCGACGATTCTGAGCCTCAGTGCAATCCCCTGCTGCCTACCTTC<br>GATGGCACATTTCACCAGGGGTGCTACGTCGCTATCTTCTGCAATCAGAACTATACTTGCCGGGT<br>GACCCATGGGAACTGGACTGTGGAAATCCCAATTTCAGTCACCAGCCCCGACGATTCAAGCTCCG<br>GAGAGGTGCCAGATCACCCCACCGCAAATAAGAGATACAACACCATGACAATCTCTAGTGTGCTG<br>CTGGCCCTGCTGCTGTGCGCACTGCTGTTCGCTTTTCTGCATTACTTCACAACTCTGAAGCAGTA<br>TCTGCGGAACCTGGCATTTGCCTGGCGGTACAGAAAAGTGAGATCAAGCTGACTGTGCCTTCTAG<br>TTGCCAGCCATCTGTTGTTTGCCCCTCCCCCGTGCCTTCCTTGACCCTGGAAGGTGCCACTCCCA<br>CTGTCCTTTCCTAATAAAATGAGGAAATTGCATCGCATTGTCTGAGTAGGTGTCATTCTATTCTG<br>GGGGGTGGGTGGGCAGGACAGCAAGGGGGAGGATTGGGAAGACAATAGCAGGCATGCTGGGGA<br>TGCGGTGGGCTCTATGTCTCTTTCTGGCCTGGAGGCTATCCAGCGTGAGTCTCTCCTACCCTCCC<br>GCTCTGGTCCTTCCTCTCCCGCTCTGCACCCTCTGTGGCCCTCGCTGTGCTCTCTCGCTCCGTGA<br>CTTCCCTTCTCCAAGTTCTCCTTGGTGGCCCGCCGTGGGGCTAGTCCAGGGCTGGATCTCGGGGA<br>AGCGGCGGGTGGCCTGGGAGTGGGGAAGGGGGTGCGCACCCGGGACGCGCGCTACTTGCCCCTT<br>TCGGCGGGGAGCAGGGGAGACCTTTGGCCTACGGCGACGGGAGGGTCGGGACAAAG |
| 74 | UL18Trimer matrix_HLACw peptide inserted at the B2m locus | cacttagcatctctggggccagtctgcaaagcgaggggcagccttaatgtgcctccagcctgaa<br>gtcctagaatgagcgcccggtgtcccaagctggggCGCGCACCCCAGATCGGAGGGCGCCGATGT<br>ACAGACAGCAAACTCACCCAGTCTAGTGCATGCCTTCTTAAACATCACGAGACTCTAAGAAAAGG<br>AAACTGAAAACGGGAAAGTCCCTCTCTCTAACCTGGCACTGCGTCGCTGGCTTGGAGACAGGTGA<br>CGGTCCCTGCGGGCCTTGTCCTGATTGGCTGGGCACGCGTTTAATATAAGTGGAGGCGTCGCGCT<br>GGCGGGCATTCCTGAAGCTGACAGCATTCGGGCCGAGATGTCTCGCTCCGTGGCCTTAGCTGTGC |

TABLE 5-continued

Sequences referred to in example 2 and 3.

| | | |
|---|---|---|
| | | TCGCGCTACTCTCTCTTAGCGGCCTCGAAGCTGTTATGGCTCCGCGGACTTTAATTTTAGGTGGT<br>GGCGGATCCGGTGGTGGCGGTTCTGGTGGTGGCGGCTCCATCCAGCGTACGCCCAAAATTCAAGT<br>CTACAGCCGACATCCTGCAGAGAACGGCAAATCTAATTTCCTGAACTGCTATGTATCAGGCTTTC<br>ACCCTAGCGATATAGAAGTGGACCTGCTGAAAAACGGAGAGAGGATAGAAAAGGTCGAACACAGC<br>GACCTCTCCTTTTCCAAGGACTGGAGCTTTTATCTTCTGTATTATACTGAATTTACACCCACGGA<br>AAAAGATGAGTATGCGTGCCGAGTAAACCACGTCACGCTGTCACAGCCCAAAATAGTAAAATGGG<br>ATCGCGACATGGGTGGTGGCGGTTCTGGTGGTGGCGGTAGTGGCGGCGGAGGAAGCGGTGGTGGC<br>GGTTCCGGATCTATGCACGTGCTGAGATACGGATATACCGGCATCTTCGACGATACATCCCATAT<br>GACTCTGACCGTGGTCGGGATTTTTGACGGACAGCACTTCTTTACATACCATGTGAACAGCTCCG<br>ATAAGGCTTCTAGTCGAGCAAATGGCACCATCTCATGGATGGCCAACGTGAGCGCAGCCTACCCC<br>ACATATCTGGACGGAGAACGCGCTAAAGGCGATCTGATCTTCAATCAGACCGAGCAGAACCTGCT<br>GGAGCTGGAAATTGCTCTGGGGTACAGGTCTCAGAGTGTCCTGACATGGACTCACGAATGTAATA<br>CCACAGAGAACGGGAGCTTCGTGGCAGGATATGAGGGCTTTGGGTGGGACGGAGAAACACrGATG<br>GAGCTGAAGGATAATCTGACTCTGTGGACCGGCCCTAACTACGAAATCAGCTGGCTGAAGCAGAA<br>CAAGACTTACATCGACGGAAAGATCAAAAACATCAGCGAGGGCGATACTACCATCCAGCGCAATT<br>ACCTGAAGGGCAACTGCACCCAGTGGAGCGTGATCTACTCTGGGTTCCAGACACCTGTCACTCAC<br>CCAGTGGTCAAAGGGGAGTGCGAAACCAGAATGACAACCGGGCCGAGGCCTTCTGTACATCCTA<br>CGGCTTCTTTCCCGGGGAGATCAATATTACTTTTATCCATTACGGCAACAAGGCCCCCGACGATT<br>CTGAGCCTCAGTGCAATCCCCTGCTGCCTACCTTCTGATGGCACATTTCACCAGGGGTGCTACGTC<br>GCTATCTTCTGCAATCAGAACTATACTTGCCGGGTGACCCATGGGAACTGGACTGTGGAAATCCC<br>AATTTCAGTCACCAGCCCCGACGATTCAAGCTCCGGAGAGGTGCCAGATCACCCCACCGCAAATA<br>AGAGATACAACACCATGACAATCTCTAGTGTGCTGCTGGCCCTGCTGCTGTGCGCACTGCTGTTC<br>GCTTTTCTGCATTACTTCACAACTCTGAAGCAGTATCTGCGGAACCTGGCATTTGCCTGGCGGTA<br>CAGAAAAGTGAGATCAAGCTGACTGTGCCTTCTAGTTGCCAGCCATCTGTTGTTTGCCCCTCCCC<br>CGTGCCTTCCTTGACCCTGGAAGGTGCCACTCCCACTGTCCTTTCCTAATAAAATGAGGAAATTG<br>CATCGCATTGTCTGAGTAGGTGTCATTCTATTCTGGGGGGTGGGGTGGGGCAGGACAGCAAGGGG<br>GAGGATTGGGAAGACAATAGCAGGCATGCTGGGGATGCGGTGGGCTCTATGTCTCTTTCTGGCCT<br>GGAGGCTATCCAGCGTGAGTCTCTCCTACCCTCCCGCTCTGGTCCTTCCTCTCCCGCTCTGCACC<br>CTCTGTGGCCCTCGCTGTGCTCTCGCTCCGTGACTTCCCTTCTCCAAGTTCTCCTTGGTGGCC<br>CGCCGTGGGCTAGTCCAGGGCTGGATCTCGGGGAAGCGGCGGGGTGGCCTGGGAGTGGGGAAGG<br>GGGTGCGCACCCGGGACGCGCGCTACTTGCCCCTTTCGGCGGGGAGCAGGGGAGACCTTTGGCCT<br>ACGGCGACGGGAGGGTCGGGACAAAGtttaggggcgtcgataagcgtcagagcgccgaggttgggg<br>gagggtttctcttccgctctttcgcggggcctctggctccccagcgcagctggagtgggg |
| 75 | UL18Trimer<br>matrix_HLACw<br>peptide | CGCGCACCCCAGATCGGAGGGCGCCGATGTACAGACAGCAAACTCACCCAGTCTAGTGCATGCCT<br>TCTTAAACATCACGAGACTCTAAGAAAAGGAAACTGAAAACGGGAAAGTCCCTCTCTCTAACCTG<br>GCACTGCGTCGCTGGCTTGGAGACAGGTGACGGTCCCTGCGGGCCTTGTCCTGATTGGCTGGGCA<br>CGCGTTTAATATAAGTGGAGGCGTCGCGCTGGCGGGCATTCCTGAAGCTGACAGCATTCGGGCCG<br>AGATGTCTCGCTCCGTGGCCTTAGCTGTGCTCGCGCTACTCTCTTAGCGGCCTCGAAGCTGTT<br>ATGGCTCCGCGGACTTTAATTTTAGGTGGTGGCGGATCCGGTGGTGGCGGTTCTGGTGGTGGCGG<br>CTCCATCCAGCGTACGCCCAAAATTCAAGTCTACAGCCGACATCCTGCAGAGAACGGCAAATCTA<br>ATTTCCTGAACTGCTATGTATCAGGCTTTCACCCTAGCGATATAGAAGTGGACCTGCTGAAAAAC<br>GGAGAGAGGATAGAAAAGGTCGAACACAGCGACCTCTCCTTTTCCAAGGACTGGAGCTTTTATCT<br>TCTGTATTATACTGAATTTACACCCACGGAAAAAGATGAGTATGCGTGCCGAGTAAACCACGTCA<br>CGCTGTCACAGCCCAAAATAGTAAAATGGGATCGCGACATGGGTGGTGGCGGTTCTGGTGGTGGC<br>GGTAGTGGCGGCGGAGGAAGCGGTGGTGGCGGTTCCGGATCTATGCACGTGCTGAGATACGGATA<br>TACCGGCATCTTCGACGATACATCCCATATGACTCTGACCGTGGTCGGGATTTTTGACGGACAGC<br>ACTTCTTTACATACCATGTGAACAGCTCCGATAAGGCTTCTAGTCGAGCAAATGGCACCATCTCA<br>TGGATGGCCAACGTGAGCGCAGCCTACCCCACATATCTGGACGGAGAACGCGCTAAAGGCGATCT<br>GATCTTCAATCAGACCGAGCAGAACCTGCTGGAGCTGGAAATTGCTCTGGGGTACAGGTCTCAGA<br>GTGTCCTGACATGGACTCACGAATGTAATACCACAGAGAACGGGAGCTTCGTGGCAGGATATGAG<br>GGCTTTGGGTGGGACGGAGAAACACTGATGGAGCTGAAGGATAATCTGACTCTGTGGACCGGCCC<br>TAACTACGAAATCAGCTGGCTGAAGCAGAACAAGACTTACATCGACGGAAAGATCAAAAACATCA<br>GCGAGGGCGATACTACCATCCAGCGCAATTACCTGAAGGGCAACTGCACCCAGTGGAGCGTGATC<br>TACTCTGGGTTCCAGACACCTGTCACTCACCCAGTGGTCAAAGGGGAGTGCGAAACCAGAATGA<br>CAACCGGGCCGAGGCCTTCTGTACATCCTACGGCTTCTTTCCCGGGGAGATCAATATTACTTTTA<br>TCCATTACGGCAACAAGGCCCCCGACGATTCTGAGCCTCAGTGCAATCCCCTGCTGCCTACCTTC<br>GATGGCACATTTCACCAGGGGTGCTACGTCGCTATCTTCTGCAATCAGAACTATACTTGCCGGGT<br>GACCCATGGGAACTGGACTGTGGAAATCCCAATTTCAGTCACCAGCCCCGACGATTCAAGCTCCG<br>GAGAGGTGCCAGATCACCCCACCGCAAATAAGAGATACAACACCATGACAATCTCTAGTGTGCTG<br>CTGGCCCTGCTGCTGTGCGCACTGCTGTTCGCTTTTCTGCATTACTTCACAACTCTGAAGCAGTA<br>TCTGCGGAACCTGGCATTTGCCTGGCGGTACAGAAAAGTGAGATCAAGCTGACTGTGCCTTCTAG<br>TTGCCAGCCATCTGTTGTTTGCCCCTCCCCCGTGCCTTCCTTGACCCTGGAAGGTGCCACTCCCA<br>CTGTCCTTTCCTAATAAAATGAGGAAATTGCATCGCATTGTCTGAGTAGGTGTCATTCTATTCTG<br>GGGGGTGGGGTGGGGCAGGACAGCAAGGGGGAGGATTGGGAAGACAATAGCAGGCATGCTGGGGA<br>TGCGGTGGGCTCTATGTCTCTTTCTGGCCTGGAGGCTATCCAGCGTGAGTCTCTCCTACCCTCCC<br>GCTCTGGTCCTTCCTCTCCCGCTCTGCACCCTCTGTGGCCCTCGCTGTGCTCTCGCTCCGTGA<br>CTTCCCTTCTCCAAGTTCTCCTTGGTGGCCCGCCGTGGGCTAGTCCAGGGCTGGATCTCGGGGA<br>AGCGGCGGGGTGGCCTGGGAGTGGGGAAGGGGGTGCGCACCCGGGACGCGCGCTACTTGCCCCTT<br>TCGGCGGGGAGCAGGGGAGACCTTTGGCCTACGGCGACGGGAGGGTCGGGACAAAG |
| 76 | UL18Trimer<br>matrix_HLAG<br>peptide<br>inserted at<br>the B2m locus | cacttagcatctctggggccagtctgcaaagcgaggggcagccttaatgtgcctccagcctgaa<br>gtcctagaatgagcgcccggtgtcccaagctggggCGCGCACCCCAGATCGGAGGGCGCCGATGT<br>ACAGACAGCAAACTCACCCAGTCTAGTGCATGCCTTCTTAAACATCACGAGACTCTAAGAAAAGG<br>AAACTGAAAACGGGAAAGTCCCTCTCTCTAACCTGGCACTGCGTCGCTGGCTTGGAGACAGGTGA<br>CGGTCCCTGCGGGCCTTGTCCTGATTGGCTGGGCACGCGTTTAATATAAGTGGAGGCGTCGCGCT<br>GGCGGGCATTCCTGAAGCTGACAGCATTCGGGCCGAGATGTCTCGCTCCGTGGCCTTAGCTGTGC<br>TCGCGCTACTCTCTCTTAGCGGCCTCGAAGCTGTTATGGCTCCGCGGACTTTATTCTTAGGTGGT<br>GGCGGATCCGGTGGTGGCGGTTCTGGTGGTGGCGGCTCCATCCAGCGTACGCCCAAAATTCAAGT<br>CTACAGCCGACATCCTGCAGAGAACGGCAAATCTAATTTCCTGAACTGCTATGTATCAGGCTTTC |

TABLE 5-continued

Sequences referred to in example 2 and 3.

| | | |
|---|---|---|
| | | ACCCTAGCGATATAGAAGTGGACCTGCTGAAAAACGGAGAGAGGATAGAAAAGGTCGAACACAGC<br>GACCTCTCCTTTTCCAAGGACTGGAGCTTTTATCTTCTGTATTATACTGAATTTACACCCACGGA<br>AAAAGATGAGTATGCGTGCCGAGTAAACCACGTCACGCTGTCACAGCCCAAAATAGTAAAATGGG<br>ATCGCGACATGGGTGGTGGCGGTTCTGGTGGTGGCGGTAGTGGCGGCGGAGGAAGCGGTGGTGGC<br>GGTTCCGGATCTATGCACGTGCTGAGATACGGATATACCGGCATCTTCGACGATACATCCCATAT<br>GACTCTGACCGTGGTCGGGATTTTTGACGGAACAGCACTTCTTTACATACCATGTGAACAGCTCCG<br>ATAAGGCTTCTAGTCGAGCAAATGGCACCATCTCATGGATGGCCAACGTGAGCGCAGCCTACCCC<br>ACATATCTGGACGGAGAACGCGCTAAAGGCGATCTGATCTTCAATCAGACCGAGCAGAACCTGCT<br>GGAGCTGGAAATTGCTCTGGGGTACAGGTCTCAGAGTGTCCTGACATGGACTCACGAATGTAATA<br>CCACAGAGAACGGGAGCTTCGTGGCAGGATATGAGGGCTTTGGGTGGGACGGAGAAACACTGATG<br>GAGCTGAAGGATAATCTGACTCTGTGGACCGGCCCTAACTACGAAATCAGCTGGCTGAAGCAGAA<br>CAAGACTTACATCGACGGAAAGATCAAAAACATCAGCGAGGGCGATACTACCATCCAGCGCAATT<br>ACCTGAAGGGCAACTGCACCCAGTGGAGCGTGATCTACTCTGGGTTCCAGACACCTGTCACTCAC<br>CCAGTGGTCAAAGGGGGAGTGCGAAACCAGAATGACAACCGGGCCGAGGCCTTCTGTACATCCTA<br>CGGCTTCTTTCCCGGGGAGATCAATATTACTTTTATCCATTACGGCAACAAGGCCCCCGACGATT<br>CTGAGCCTCAGTGCAATCCCCTGCTGCCTACCTTCGATGGCACATTTCACCAGGGGTGCTACGTC<br>GCTATCTTCTGCAATCAGAACTATACTTGCCGGGTGACCCATGGGAACTGGACTGTGGAAATCCC<br>AATTTCAGTCACCAGCCCCGACGATTCAAGCTCCGGAGAGGTGCCAGATCACCCCACCGCAAATA<br>AGAGATACAACACCATGACAATCTCTAGTGTGCTGCTGGCCCTGCTGCTGTGCGCACTGCTGTTC<br>GCTTTTCTGCATTACTTCACAACTCTGAAGCAGTATCTGCGGAACCTGGCATTTGCCTGGCGGTA<br>CAGAAAAGTGAGATCAAGCTGACTGTGCCTTCTAGTTGCCAGCCATCTGTTGTTTGCCCCTCCCC<br>CGTGCCTTCCTTGACCCTGGAAGGTGCCACTCCCACTGTCCTTTCCTAATAAMTGAGGAAATTGC<br>ATCGCATTGTCTGAGTAGGTGTCATTCTATTCTGGGGGGTGGGGTGGGGCAGGACAGCAAGGGGG<br>AGGATTGGGAAGACAATAGCAGGCATGCTGGGGATGCGGTGGGCTCTATGTCTCTTTCTGGCCTG<br>GAGGCTATCCAGCGTGAGTCTCTCCTACCCTCCCGCTCTGGTCCTTCCTCTCCCGCTCTGCACCC<br>TCTGTGGCCCTCGCTGTGCTCTCTCGCTCCGTGACTTCCCTTCTCCAAGTTCTCCTTGGTGGCCC<br>GCCGTGGGGCTAGTCCAGGGCTGGATCTCGGGGAAGCGGCGGGGTGGCCTGGGAGTGGGGAAGGG<br>GGTGCGCACCCGGGACGCGCGCTACTTGCCCCTTTCGGCGGGGAGCAGGGGAGACCTTTGGCCTA<br>CGGCGACGGGAGGGTCGGGACAAAGtttagggcgtcgataagcgtcagagcgccgaggttgggg<br>agggtttctcttccgctctttcgcggggcctctggctccccagcgcagctggagtgggg |
| 77 | UL18Trimer matrix_HLAG peptide | CGCGCACCCCAGATCGGAGGGCGCCGATGTACAGACAGCAAACTCACCCAGTCTAGTGCATGCCT<br>TCTTAAACATCACGAGACTCTAAGAAAAGGAAACTGAAAACGGGAAAGTCCCTCTCTCTAACCTG<br>GCACTGCGTCGCTGGCTTGGAGACAGGTGACGGTCCCTGCGGGCCTTGTCCTGATTGGCTGGGCA<br>CGCGTTTAATATAAGTGGAGGCGTCGCGCTGGCGGGCATTCCTGAAGCTGACAGCATTCGGGCCG<br>AGATGCTCGCTCCGTGGCCTTGAGCTGTGCTCGCGCTACTCTCTTAGCGGCCTCGAAGCTGTT<br>ATGGCTCCGCGGACTTTATTCTTAGGTGGTGGCGGATCCGGTGGTGGCGGTTCTGGTGGTGGCGG<br>CTCCATCCAGCGTACGCCCAAAATTCAAGTCTACAGCCGACATCCTGCAGAGAACGGCAAATCTA<br>ATTTCCTGAACTGCTATGTATCAGGCTTTCACCCTAGCGATATAGAAGTGGACCTGCTGAAAAAC<br>GGAGAGAGGATAGAAAAGGTCGAACACAGCGACCTCTCCTTTTCCAAGGACTGGAGCTTTTATCT<br>TCTGTATTATACTGAATTTACACCCACGGAAAAAGATGAGTATGCGTGCCGAGTAAACCACGTCA<br>CGCTGTCACAGCCCAAAATAGTAAAATGGGATCGCGACATGGGTGGTGGCGGTTCTGGTGGTGGC<br>GGTAGTGGCGGCGGAGGAAGCGGTGGTGGCGGTTCCGGATCTATGCACGTGCTGAGATACGGATA<br>TACCGGCATCTTCGACGATACATCCCATATGACTCTGACCGTGGTCGGGATTTTTGACGGACAGC<br>ACTTCTTTACATACCATGTGAACAGCTCCGATAAGGCTTCTAGTCGAGCAAATGGCACCATCTCA<br>TGGATGGCCAACGTGAGCGCAGCCTACCCCACATATCTGGACGGAGAACGCGCTAAAGGCGATCT<br>GATCTTCAATCAGACCGAGCAGAACCTGCTGGAGCTGGAAATTGCTCTGGGGTACAGGTCTCAGA<br>GTGTCCTGACATGGACTCACGAATGTAATACCACAGAGAACGGGAGCTTCGTGGCAGGATATGAG<br>GGCTTTGGGTGGGACGGAGAAACACTGATGGAGCTGAAGGATAATCTGACTCTGTGGACCGGCCC<br>TAACTACGAAATCAGCTGGCTGAAGCAGAACAAGACTTACATCGACGGAAAGATCAAAAACATCA<br>GCGAGGGCGATACTACCATCCAGCGCAATTACCTGAAGGGCAACTGCACCCAGTGGAGCGTGATC<br>TACTCTGGGTTCCAGACACCTGTCACTCACCCAGTGGTCAAAGGGGGAGTGCGAAACCAGAATGA<br>CAACCGGGCCGAGGCCTTCTGTACATCCTACGGCTTCTTTCCCGGGGAGATCAATATTACTTTTA<br>TCCATTACGGCAACAAGGCCCCCGACGATTCTGAGCCTCAGTGCAATCCCCTGCTGCCTACCTTC<br>GATGGCACATTTCACCAGGGGTGCTACGTCGCTATCTTCTGCAATCAGAACTATACTTGCCGGGT<br>GACCCATGGGAACTGGACTGTGGAAATCCCAATTTCAGTCACCAGCCCCGACGATTCAAGCTCCG<br>GAGAGGTGCCAGATCACCCCACCGCAAATAAGAGATACAACACCATGACAATCTCTAGTGTGCTG<br>CTGGCCCTGCTGCTGTGCGCACTGCTGTTCGCTTTTCTGCATTACTTCACAACTCTGAAGCAGTA<br>TCTGCGGAACCTGGCATTTGCCTGGCGGTACAGAAAAGTGAGATCAAGCTGACTGTGCCTTCTAG<br>TTGCCAGCCATCTGTTGTTTGCCCCTCCCCGTGCCTTCCTTGACCCTGGAAGGTGCCACTCCCA<br>CTGTCCTTTCCTAATAAAATGAGGAAATTGCATCGCATTGTCTGAGTAGGTGTCATTCTATTCTG<br>GGGGGTGGGGTGGGGCAGGACAGCAAGGGGGAGGATTGGGAAGACAATAGCAGGCATGCTGGGGA<br>TGCGGTGGGCTCTATGTCTCTTTCTGGCCTGGAGGCTATCCAGCGTGAGTCTCTCCTACCCTCCC<br>GCTCTGGTCCTTCCTCTCCCGCTCTGCACCCTCTGTGGCCCTCGCTGTGCTCTCTCGCTCCGTGA<br>CTTCCCTTCTCCAAGTTCTCCTTGGTGGCCCGCCGTGGGGCTAGTCCAGGGCTGGATCTCGGGGA<br>AGCGGCGGGGTGGCCTGGGAGTGGGGAAGGGGGTGCGCACCCGGGACGCGCGCTACTTGCCCCTT<br>TCGGCGGGGAGCAGGGGAGACCTTTGGCCTACGGCGACGGGAGGGTCGGGACAAAG |
| 78 | TALEN target B2m1 | TCCGTGGCCTTAGCTGTGCTCGCGCTACTCTCTCTTTCTGGCCTGGA |
| 79 | TALEN target B2m2 | TTAGCTGTGCTCGCGCTACTCTCTCTTTCTGGCCTGGAGGCTATCCA |
| 80 | pCSL31134 right TALEN B2m1 RVD sequence: HD-HD-NN-NG-NN-NN-HD-HD-NG-NG-NI-NN-HD-NG-NN-NG# | MGDPKKKRKVIDYPYDVPDYAIDIADLRTLGYSQQQQEKIKPKVRSTVAQHHEALVGHGFTHAHI<br>VALSQHPAALGTVAVKYQDMIAALPEATHEAIVGVGKQWSGARALEALLTVAGELRGPPLQLDTG<br>QLLKIAKRGGVTAVEAVHAWRNALTGAPLNLTPEQVVAIASHDGGKQALETVQRLLPVLCQAHGL<br>TPEQVVAIASHDGGKQALETVQRLLPVLCQAHGLTPQQVVAIASNNGGKQALETVQRLLPVLCQA<br>HGLTPQQVVAIASNNGGKQALETVQRLLPVLCQAHGLTPQQVVAIASNNGGKQALETVQRLLPVL<br>CQAHGLTPQQVVAIASNNGGKQALETVQRLLPVLCQAHGLTPEQVVAIASHDGGKQALETVQRLL<br>PVLCQAHGLTPEQVVAIASHDGGKQALETVQRLLPVLCQAHGLTPQQVVAISSNGGGKQALETVQ<br>RLLPVLCQAHGLTPQQVVAIASNGGGKQAALETVQRLLPVLCQAHGLTPEQVVAIASNIGGKQAL |

TABLE 5-continued

Sequences referred to in example 2 and 3.

| | | |
|---|---|---|
| | | ETVQALLPVLCQAHGLTPQQVVAIASNNGGKQALETVQRLLPVLCQAHGLTPEQVVAIASHDGGK<br>QALETVQRLLPVLCQAHGLTPQQVVAIASNGGGKQALETVQRLLPVLCQAHGLTPQQVVAIASNN<br>GGKQALETVQRLLPVLCQAHGLTPQQVVAIASNGGGRPALESIVAQLSRPDPALAALTNDHLVAL<br>ACLGGRPALDAVKKGLGDPISRSQLVKSELEEKKSELRHKLKYVPHEYIELIEIARNSTQDRILE<br>MKVMEFFMKVYGYRGKHLGGSRKPDGAIYTVGSPIDYGVIVDTKAYSGGYNLPIGQADEMQRYVE<br>ENQTRNKHINPNEWWKVYPSSVTEFKFLFVSGHFKGNYKAQLTRLNHITNCNGAVLSVEELLIGG<br>EMIKAGTLTEEVRRKFNNGEINFAAD |
| 81 | pCSL31135<br>left TALEN<br>B2m1<br>RVD sequence:<br>HD-HD-NI-NN-<br>NN-HD-HD-NI-<br>NN-NI-NI-NI-<br>NN-NI-NN-NG# | MGDPKKKRKVIDYPYDVPDYAIDIADLRTLGYSQQQQEKIKPKVRSTVAQHHEALVGHGFTHAHI<br>VALSQHPAALGTVAVKYQDMIAAKPEATHEAIVGVGKQWSGARALEALLTVAGELRGPPLQLDTG<br>QLLKIAKRGGVTAVEAVHAWRNALTGAPLNLTPEQVVAIASHDGGKQALETQRLLPVLCQAHGLT<br>PEQVVAIASHDGGKQALETVQRLLPVLCQAHGLTPQQVVAIASNGGGKQALETVQRLLPVLCQAH<br>GLTPQQVVAIASNNGGKQALETVQRLLPVLCAQHGLTPQQVVAIASNNGGKQALETVQRLLPVLC<br>QAHGLTPEQVVAIASHDGGKQALETVQRLLPVLCQAHGLTPEQVVAIASHDGGKQALETVQRLLP<br>VLCQAHGLTPEQVVAIASNIGGKQALETVQALLPVLCQAHGLTPQQVVAIASNNGGKQALETVQR<br>LLPVLCQAHGLTPEQVVAIASNIGGKQALETVQALLPVLCQAHGLTPEQVVAIASNIGGKQALET<br>VQALLPVLCQAHGLTPEQVVAIASNIGGKQALETVQALLPVLCQAHGLTPQQVVAIASNNGGKQA<br>LETVQRLLPVLCQAHGLTPQQVVAIASNGGGRPALESIVAQLSRPDPALAATNDHLVALACL<br>GGRPALDAVKKGLGDPISRSQLVKSELEEKKSELRHKLKYVPHEYIELIEIARNSTQDRILEMKV<br>MEFFMKVYGYRGKHLGGSRKPDGAIYTVGSPIDYGVIVDTKAYSGGYNLPIGQADEMQRYVEENQ<br>TRNKHINPNEWWKVYPSSVTEFKFLFVSGHFKGNYKAQLTRLNHITNCNGAVLSVEELLIGGEMI<br>KAGTLTEEVRRKFNNGEINFAAD |
| 82 | pCLS31136<br>right TALEN<br>B2m2<br>RVD sequence:<br>NG-NI-NN-HD-<br>NG-NN-NG-NN-<br>HD-NG-ND-NN-<br>ND-NN-HD-NG# | MGDPKKKRKVIDYPYDVPDYAIDIADLRTLGYSQQQQEKIKPKVRSTVAQHHEALVGHGFTHAHI<br>VALSQHPAALGTVAVKYQDMIAAKPEATHEAIVGVGKQWSGARALEALLTVAGELRGPPLQLDTG<br>QLLKIAKRGGVTAVEAVHAWRNALTGAPLNLTPQQVVAIASNGGGKQALETVQRLLPVLCQAHGL<br>TPEQVVAIASNIGGKQALETVQALLPVLCQAHGLTPQQVVAIASNNGGKQALETVQRLLPVLCQA<br>HGLTPEQVVAIASHDGGKQALETVQRLLPVLCQAHGLTPQQVVAIASNGGGKQALETVQRLLPVL<br>CQAHGLTPQQVVAIASNNGGKQALETVQRLLPVLCQAHGLTPQQVVAIASNGGGKQALETVQRLL<br>PVLCQAHGLTPQQVVAIASNNGGKQALETVQRLLPVLCQAHGLTPEQVVAIASHDGGKQALETVQ<br>QLLPVLCQAHGLTPQQVVAIASNGGGKQALETVQRLLPVLCQAHGLTPEQVVAIASHDGGKQALE<br>TVQRLLPVLCQAHGLTPQQVVAIASNNGGKQALETVQRLLPVLCQAHGLTPEQVVAIASHDGGKQA<br>LETVQRLLPVLCQAHGLTPQQVVAIASNNGGKQALETVQRLLPVLCQAHGLTPEQVVAIASHDGG<br>KQALETVQRLLPVLCQAHGLTPQQVVAIASNGGGRPALESIVAQLSRPDPALAALTNDHLVALAC<br>LGGRPALDAVKKGLGDPISRSQLVKSELEEKKSELRHKLKYVPHEYIELIEIARNSTQDRILEMK<br>VMEFFMKVYGYRGKHLGGSRKPDGAIYTVGSPIDYGVIVDTKAYSGGYNKPIGQADEMQRYVEEN<br>QTRNKHINPNEWWKVYPSSVTEFKFLFVSHGKFNYKAQLTRLNHITNCNGAVLSVEELLIGGEMI<br>KAGTLTEEVRRKFNNGEINFAAD |
| 83 | pCLS31137<br>left TALEN<br>B2m2<br>RVD sequence:<br>NN-NN-NI-NG-<br>NI-NN-HD-HD-<br>NG-HD-ND-NI-<br>NN-NN-HD-NG# | MGDPKKKRKVIDYPYDVPDYAIDIADLRTLGYSQQQQEKIKPKVRSTVAQHHEALVGHGFTHAHI<br>VALSQHPAALGTVAVKYQDMIAAKPEATHEAIVGVGKQWSGARALEALLTVAGELRGPPLQLDTG<br>QLLKIAKRGGVTAVEAVHAWRNALTGAPLNLTPEQVVAIASNNGGKQALETVQRLLPVLCQAHGL<br>TPQQVVAIASNNGGKQALETVQRLLPVLCQAHGLTPEQVVAIASNIGGKQALETVQALLPVLCQA<br>HGLTPQQVVAIASNGGGKQALETVQRLLPVLCQAHGLTPEQVVAIASNIGGKQALETVQALLPVL<br>CQAHGLTPQQVVAIASNGGGKQALETVQRLLPVLCQAHGLTPEQVVAIASHDGGKQALETVQRLL<br>PVLCQAHGLTPEQVVAIASHDGGKQALETVQRLLPVLCQAHGLTPQQVVAIASNGGGKQALETVQ<br>RLLPVLCQAHGLTPEQVVAIASHDGGKQALETVQRLLPVLCQAHGLTPEQVVAIASHDGGKQALE<br>TVQRLLPVLCQAHGLTPEQVVAIASNIGGKQALETVQALLPVLCQAHGLTPQQVVAIASNNGGKQ<br>ALETVQRLLPVLCQAHGLTPQQVVAIASNNGGKQALETVQRRLLPVLCQAHGLTPEQVVAIASHDG<br>GKQALETVQRLLPVLCQAHGLTPQQVVAIASNGGGRPALESIVAQLSRPDPALAALTNDHLVALA<br>CLGGRPALDAVKKGLGDPISRSQLVKSELEEKKSELRHKLKYVPHEYIELIEIARNSTQDRILEM<br>KVMEFFMKVYGYRGKHLGGSRKPDGAIYTVGSPIDYGVIVDTKAYSGGYNLPIGQADEMQRYVEE<br>NQTRNKHINPNEWWKVYPSSVTEFKFLFVSGHFKGNYKAQLTRLNHITNCNGAVLSVEELLIGGE<br>MIKAGTLTEEVRRKFNNGEINFAAD |
| 84 | HLAG1 | MVVMAPRTLFLLLSGALTLTETWAGSHSMRYFSAAVSRPGRGEPRFIAMGYVDDTQFVRFDSDSA<br>CPRMEPRAPWVEQEGPEYWEEETRNTKAHAQTDRMNLQTLRGYYNQSEASSHTLQWMIGCDLGSD<br>GRLLRGYEQYAYDGKDYLALNEDLRSWTAADTAAQISKRKCEAANVAEQRRAYLEGTCVEWLHRY<br>LENGKEMLQRADPPKTHVTHHPVFDYEATLRCWALGFYPAEIILTWQRDGEDQTQDVELVETRPA<br>GDGTFQKWAAVVVPSGEEQRYTCHVQHEGLPEPLMLRWKQSSLPTIPIMGIVAGLVVLAAVVTGA<br>AVAAVLWRKKSSD |
| 85 | HLAG2 | MVVMAPRTLFLLLSGALTLTETWAGSHSMRYFSAAVSRPGRGEPRFIAMGYVDDTQFVRFDSDSA<br>CPRMEPRAPWVEQEGPEYWEEETRNTKAHAQTDRMNLQTLRGYYNQSEAKPPKTHVTHHPVFDYE<br>ATLRCWALGFYPAEIILTWQRDGEDQTQDVELVETRPAGDGTFQKWAAVVVPSGEEQRYTCHVQH<br>EGLPEPLMLRWKQSSLPTIPIMGIVAGLVVLAAVVTGAAVAAVLWRKKSSD |
| 86 | HLAG3 | MVVMAPRTLFLLLSGALTLTETWAGSHSMRYFSAAVSRPGRGEPRFIAMGYVDDTQFVRFDSDSA<br>CPRMEPRAPWVEQEGPEYWEEETRNTKAHAQTDRMNLQTLRGYYNQSEAKQSSLPTIPIMGIVAG<br>LVVLAAVVTGAAVAAVLWRKKSSD |
| 87 | HLAG4 | MVVMAPRTLFLLLSGALTLTETWAGSHSMRYFSAAVSRPGRGEPRFIAMGYVDDTQFVRFDSDSA<br>CPRMEPRAPWVEQEGPEYWEEETRNTKAHAQTDRMNLQTLRGYYNQSEASSHTLQWMIGCDLGSD<br>GRLLRGYEQYAYDGKDYLALNEDLRSWTAADTAAQISKRKCEAANVAEQRRAYLEGTCVEWLHRY<br>LENGKEMLQRAKQSSLPTIPIMGIVAGLVVLAAVVTGAAVAAVLWRKKSSD |
| 88 | HLAG5 | MVVMAPRTLFLLLSGALTLTETWAGSHSMRYFSAAVSRPGRGEPRFIAMGYVDDTQFVRFDSDSA<br>CPRMEPRAPWVEQEGPEYWEEETRNTKAHAQTDRMNLQTLRGYYNQSEASSHTLQWMIGCDLGSD<br>GRLLRGYEQYAYDGKDYLALNEDLRSWTAADTAAQISKRKCEAANVAEQRRAYLEGTCVEWLHRY<br>LENGKEMLQRADPPKTHVTHHPVFDYEATLRCWALGFYPAEIILTWQRDGEDQTQDVELVETRPA<br>GDGTFQKWAAVVVPSGEEQRYTCHVQHEGLPEPLMLRWSKEGDGGIMSVRESRSLSEDL |

TABLE 5-continued

Sequences referred to in example 2 and 3.

| 89 | HLAG6 | MVVMAPRTLFLLLSGALTLTETWAGSHSMRYFSAAVSRPGRGEPRFIAMGYVDDTQFVRFDSDSA CPRMEPRAPWVEQEGPEYWEEETRNTKAHAQTDRMNLQTLRGYYNQSEAKPPKTHVTHHPVFDYE ATLRCWALGFYPAEIILTWQRDGEDQTQDVELVETRPAGDGTFQKWAAVVVPSGEEQRYTCHVQH EGLPEPLMLRWSKEGDGGIMSVRESRSLSEDL |
| 90 | HLAG7 | MVVMAPRTLFLLLSGALTLTETWASSHSMRYFSAAVSRPGRGEPRFIAMGYVDDTQFVRFDSDSA CPRMEPRPAPWVEQEGPEYWEEETRNTKAHAQTDRMNLQTLRGYYNQSEASE |

Example 3: TALEN®-Mediated Double Targeted Integration of NK Inhibitor and CAR Encoding Matrices at the B2M and TRAC Loci in Primary T-Cells This example describes methods to improve the therapeutic outcome of CAR T-cell therapies by extending their persistence in vivo. It consists in a simultaneous TALEN® mediated knock-out of B2M and TCR in the presence of AAV6 repair vectors delivering the CAR at the TRAC locus and an NK inhibitor at the B2M locus. This method prevents CAR T-cell to attack host tissues in a non-specific and TCR-mediated manner (graft versus host attack) and to divert host T- and NK-cells-mediated depletion of CAR T-cells.

The method developed to integrate a NK inhibitor at the B2m locus consisted in generating a double-strand break in one of the first B2M exons using TALEN® in the presence of a DNA repair matrix vectorized by AAV6. This matrix consists of two B2M homology arms embedding the NK inhibitor coding sequence separated by a 2A cis acting elements and regulatory elements (stop codon and polyA sequences). Because expression of B2M at the surface of CAR T-cells is likely to promote their depletion when transfer in an allogeneic setting, insertion of the repair matrix was designed to inactivate B2M and promote expression of the NK inhibitor.

To illustrate this approach and demonstrate the feasibility of double targeted insertion in primary T-cells, two different matrices were designed (FIG. 19). The first one named CARm (SEQ ID NO 31) was designed to insert an anti-CD22 CAR cDNA at the TRAC locus in the presence of TRAC TALEN® (SEQ ID NO 16 and 17). The second one, HLAEm, under two variants (SEQ ID NO 69 and 71) was designed to integrate a single chain protein consisting of a fusion of B2M, HLAE and HLAG peptide moieties in the middle of the B2M open reading frame using B2M TALEN@(SEQ ID NO 80 and 81 or 82 and 83—right and left dimers respectively). The two matrices contained an additional 2A cis-acting element located upstream expression cassettes to enable co-expression of the single chain B2M-HLAE-HLAG peptide and CAR with the endogenous gene targeted. Polynucleotide and polypeptides sequences are listed in Table 5.

We assessed the efficiency of double targeted insertion in T-cells by transfecting them with the TRAC and B2M TALEN® and subsequently transducing them with the AAV6 repair matrices encoding the anti-CD22 CAR and the single chain B2M-HLAE-HLAG peptide. Such treatment led to more than 88% of TCR and HLA-ABC double knockout, to the expression of about 68% of anti-CD22 CAR among the double knockout population and to about 68% of HLAE expression among the double knockout CAR expressing T-cells. Overall, this method enabled to generate about 40% of TCR/HLA-ABC negative, CAR/HLAE positive T-cells (FIG. 21).

These engineered cells can be assayed for their resistance to NK and alloresponsive T-cells attack. The same engineering approach can be used to generate TCR/HLA-ABC negative, CAR positive T-cell bearing NK cells inhibitors other than HLAE and assess their ability to resist to NK cells attack. Such assessment can be performed on a collection of TCR/HLA-ABC negative, CAR positive T-cell bearing different NK cells inhibitors as illustrated in FIG. 18. This approach can consist in transfecting T-cells, for instance, with TRAC and B2M TALEN® and subsequently transducing them with the AAV6 repair matrix encoding a CAR, such as anti-CD22 CAR and a library (or collection) of repair matrices encoding different NK inhibitors:

HLAE trimer matrix comprising VMAPRTLFL (SEQ ID NO:97) peptide (SEQ ID NO.68), which can be inserted at the B2m locus (SEQ ID NO.69), HLAE trimer matrix comprising VMAPRTLIL (SEQ ID NO:91) peptide (SEQ ID NO.70), which can be inserted at the B2m locus (SEQ ID NO.71), UL18Trimer matrix_Actine peptide (SEQ ID NO.72), which can be inserted at the B2m locus (SEQ ID NO.73), UL18Trimer matrix_HLACw peptide (SEQ ID NO.74), which can be inserted at the B2m locus (SEQ ID NO.75), UL18Trimer matrix_HLAG (SEQ ID NO.76), which can be inserted at the B2m locus (SEQ ID NO.77), Trimers can also comprises HLAG peptides can be used to form these trimers, such as one selected from the following ones:

HLAG1 (SEQ ID NO.84)
HLAG2 (SEQ ID NO.85)
HLAG3 (SEQ ID NO.86)
HLAG4 (SEQ ID NO.87)
HLAG5 (SEQ ID NO.88)
HLAG6 (SEQ ID NO.89)
HLAG7 (SEQ ID NO.90)

HLAE or HLAG trimers can also comprise G peptides (as shown in FIG. 20) selected from the following ones (non limiting examples):

Peptide 1 VMAPRTLIL (SEQ ID NO:91)
Peptide 2 VMAPRTLLL (SEQ ID NO:92)
Peptide 3 VMAPRTLVL (SEQ ID NO:93)
Peptide 4 AMAPRTLIL (SEQ ID NO:94)
Peptide 5 VMAPRSLIL (SEQ ID NO:95)
Peptide 6 VMAPRSLLL (SEQ ID NO:96)
Peptide 7 VMAPRTLFL (SEQ ID NO:97)
Peptide 8 VMAPRILIL (SEQ ID NO:98)
Peptide 9 YLLPRRGPRL (SEQ ID NO:99)
peptide 10 ALPHAILRL (SEQ ID NO:100)

The resulting library of TCR negative CAR and NK inhibitor positive T-cells would be cultivated in the presence of NK cells and the remaining viable cells could be recovered and analyzed by high throughput DNA sequence to identify the NK inhibitor (s) responsible for resistance to NK cell attack.

TABLE 6

Preferred human endogenous gene loci responsive to T-cell activation

| symbol | description | inductionRatio12hr | T.8Nve.Sp.OT1 | T.8Eff.Sp.OT1.12hr.LisOva | T.8Eff.Sp.OT1.48hr.LisOva | T.8Eff.Sp.OT1.d6.LisOva |
|---|---|---|---|---|---|---|
| Il3 | interleukin 21 | 16.4 | 12.8 | 208.9 | 18.4 | 13.6 |
| Il2 | interleukin 3 | 97.0 | 16.0 | 1554.4 | 17.7 | 18.1 |
| Ccl4 | isopentenyl-diphosphate delta isomerase 2 | 2.1 | 16.8 | 35.6 | 17.6 | 19.7 |
| Il21 | granzyme C | 9.2 | 17.4 | 160.5 | 20.4 | 24.9 |
| Gp49a | chemokine (C-C motif) receptor 8 | 5.9 | 18.5 | 108.4 | 31.5 | 20.9 |
| Cxcl10 | interleukin 2 | 58.4 | 21.1 | 1229.6 | 32.7 | 17.9 |
| Nr4a3 | interleukin 1 receptor, type I | 2.6 | 21.2 | 54.6 | 35.5 | 21.7 |
| Lilrb4 | tumor necrosis factor (ligand) superfamily, member 4 | 4.1 | 21.8 | 88.8 | 29.3 | 20.0 |
| Cd200 | neuronal calcium sensor 1 | 4.5 | 24.1 | 109.6 | 46.3 | 23.2 |
| Cdkn1a | CDK5 and Abl enzyme substrate 1 | 3.1 | 26.2 | 80.9 | 49.1 | 32.8 |
| Gzmc | transmembrane and tetratricopeptide repeat containing 2 | 2.0 | 26.8 | 53.9 | 26.2 | 29.4 |
| Nr4a2 | LON peptidase N-terminal domain and ring finger 1 | 3.2 | 28.4 | 90.4 | 50.4 | 28.3 |
| Cish | glycoprotein 49 A | 15.0 | 31.6 | 472.4 | 30.6 | 212.5 |
| Nr4a1 | polo-like kinase 2 | 3.6 | 31.7 | 114.3 | 39.0 | 32.5 |
| Tnf | lipase, endothelial | 2.1 | 32.4 | 66.7 | 35.9 | 33.3 |
| Ccr8 | cyclin-dependent kinase inhibitor 1A (P21) | 9.7 | 34.6 | 335.4 | 54.4 | 71.0 |
| Lad1 | grainyhead-like 1 (*Drosophila*) | 2.1 | 35.1 | 73.4 | 52.0 | 44.1 |
| Slamf1 | cellular retinoic acid binding protein II | 5.3 | 35.4 | 187.2 | 43.3 | 36.3 |
| Crabp2 | adenylate kinase 4 | 2.2 | 35.9 | 80.4 | 58.5 | 39.8 |
| Furin | microtubule-associated protein 1B | 2.1 | 36.2 | 77.7 | 36.4 | 38.4 |
| Gadd45g | acyl-CoA synthetase long-chain family member 6 | 2.0 | 37.2 | 76.0 | 45.2 | 41.3 |
| Bcl2l1 | zinc finger E-box binding homeobox 2 | 2.1 | 38.6 | 80.7 | 44.9 | 455.4 |
| Ncs1 | CD200 antigen | 9.8 | 41.2 | 404.3 | 70.4 | 36.8 |
| Ciart | carboxypeptidase D | 3.1 | 41.6 | 127.7 | 71.4 | 71.6 |
| Ahr | thioredoxin reductase 3 | 3.6 | 43.4 | 157.8 | 61.7 | 28.8 |
| Spry1 | myosin IE | 2.3 | 43.6 | 100.2 | 61.3 | 77.0 |
| Tnfsf4 | RNA binding protein with multiple splicing 2 | 2.1 | 43.6 | 91.5 | 49.8 | 36.5 |
| Myo10 | mitogen-activated protein kinase kinase 3, opposite strand | 2.9 | 44.8 | 127.9 | 66.4 | 43.1 |
| Dusp5 | PERP, TP53 apoptosis effector | 2.8 | 44.9 | 127.2 | 78.4 | 72.4 |
| Myc | myosin X | 4.1 | 45.5 | 184.9 | 81.6 | 57.5 |
| Psrc1 | immediate early response 3 | 2.7 | 45.6 | 121.6 | 63.9 | 66.2 |
| St6galnac4 | folliculin interacting protein 2 | 2.6 | 47.5 | 124.2 | 87.4 | 96.6 |
| Nfkbid | leukocyte immunoglobulin-like receptor, subfamily B, member 4 | 9.9 | 48.9 | 483.3 | 64.5 | 179.1 |
| Bst2 | circadian associated repressor of transcription | 4.5 | 50.6 | 225.5 | 100.3 | 33.8 |
| Txnrd3 | RAR-related orphan receptor gamma | 2.1 | 51.7 | 106.7 | 47.5 | 52.8 |
| Plk2 | proline/serine-rich coiled-coil 1 | 3.9 | 52.9 | 205.9 | 92.3 | 79.6 |
| Gfi1 | cysteine rich protein 2 | 2.4 | 54.2 | 127.7 | 90.3 | 182.9 |
| Pim1 | cAMP responsive element modulator | 2.0 | 55.7 | 112.6 | 54.4 | 57.3 |
| Pvt1 | chemokine (C-C motif) ligand 4 | 20.2 | 55.8 | 1125.8 | 103.1 | 89.0 |
| Nfkbib | nuclear receptor subfamily 4, group A, member 2 | 7.8 | 58.5 | 457.6 | 78.7 | 72.0 |
| Gnl2 | transglutaminase 2, C polypeptide | 2.3 | 58.7 | 132.1 | 69.8 | 64.7 |
| Cd69 | synapse defective 1, Rho GTPase, homolog 2 (*C. elegans*) | 2.1 | 62.5 | 132.7 | 111.3 | 31.0 |
| Dgat2 | sprouty homolog 1 (*Drosophila*) | 4.2 | 63.8 | 268.5 | 76.8 | 61.4 |
| Atf3 | activating transcription factor 3 | 3.2 | 65.8 | 210.3 | 88.3 | 75.8 |
| Tnfrsf21 | pogo transposable element with KRAB domain | 2.9 | 68.6 | 196.9 | 91.1 | 293.2 |
| Lonrf1 | tumor necrosis factor receptor superfamily, member 21 | 3.2 | 70.6 | 224.5 | 126.5 | 72.9 |
| Cables1 | cytokine inducible SH2-containing protein | 7.5 | 74.3 | 558.7 | 82.5 | 133.9 |
| Cpd | lymphotoxin A | 2.6 | 74.6 | 197.2 | 93.4 | 58.6 |
| Qtrtd1 | FBJ osteosarcoma oncogene | 3.0 | 74.9 | 224.1 | 89.0 | 61.1 |
| Polr3d | signaling lymphocytic activation molecule family member 1 | 5.4 | 75.6 | 412.0 | 108.4 | 190.4 |
| Kcnq5 | syndecan 3 | 2.4 | 76.0 | 180.0 | 77.2 | 85.3 |
| Fos | mitochondrial ribosomal protein L47 | 2.1 | 77.2 | 161.7 | 152.0 | 72.3 |
| Slc19a2 | ladinin | 5.5 | 77.3 | 423.2 | 152.5 | 70.4 |
| Hif1a | E2F transcription factor 5 | 2.5 | 77.7 | 198.0 | 92.0 | 65.2 |
| Il15ra | ISG15 ubiquitin-like modifier | 2.8 | 77.9 | 221.0 | 88.9 | 45.1 |
| Nfkb1 | aryl-hydrocarbon receptor | 4.2 | 78.7 | 333.2 | 145.7 | 91.4 |
| Phlda3 | diacylglycerol O-acyltransferase 2 | 3.2 | 81.0 | 259.2 | 150.0 | 84.4 |
| Mtrr | FBJ osteosarcoma oncogene B | 2.0 | 81.3 | 163.7 | 139.3 | 98.5 |
| Pogk | pleckstrin homology-like domain, family A, member 3 | 2.9 | 84.8 | 244.5 | 126.9 | 83.8 |

TABLE 6-continued

Preferred human endogenous gene loci responsive to T-cell activation

| symbol | description | inductionRatio12hr | T.8Nve.Sp.OT1 | T.8Eff.Sp.OT1.12hr.LisOva | T.8Eff.Sp.OT1.48hr.LisOva | T.8Eff.Sp.OT1.d6.LisOva |
|---|---|---|---|---|---|---|
| Map2k3os | potassium voltage-gated channel, subfamily Q, member 5 | 3.0 | 86.3 | 261.0 | 118.1 | 63.4 |
| Egr2 | tumor necrosis factor receptor superfamily, member 10b | 2.5 | 88.6 | 219.0 | 106.1 | 51.0 |
| Isg15 | Mir17 host gene 1 (non-protein coding) | 2.1 | 90.4 | 190.1 | 120.0 | 51.2 |
| Perp | glucose-fructose oxidoreductase domain containing 1 | 2.2 | 92.9 | 208.5 | 168.7 | 237.4 |
| Ipo4 | plexin A1 | 2.1 | 94.8 | 200.7 | 118.0 | 90.3 |
| Mphosph10 | heat shock factor 2 | 2.4 | 96.8 | 233.2 | 191.0 | 104.8 |
| Plk3 | carbohydrate sulfotransferase 11 | 2.4 | 96.8 | 235.1 | 180.8 | 385.7 |
| Ifitm3 | growth arrest and DNA-damage-inducible 45 gamma | 4.8 | 104.6 | 504.8 | 109.3 | 95.0 |
| Polr1b | solute carrier family 5 (sodium-dependent vitamin transporter), member 6 | 2.1 | 107.0 | 227.3 | 192.8 | 75.8 |
| Usp18 | interferon induced transmembrane protein 3 | 2.8 | 109.2 | 302.6 | 43.9 | 106.4 |
| Top1mt | DENN/MADD domain containing 5A | 2.6 | 109.5 | 279.9 | 102.0 | 517.4 |
| Dkc1 | plasminogen activator, urokinase receptor | 2.1 | 112.4 | 234.8 | 55.7 | 57.3 |
| Polr1c | solute carrier family 19 (thiamine transporter), member 2 | 3.0 | 115.4 | 343.1 | 221.7 | 138.4 |
| Cdk6 | ubiquitin domain containing 2 | 2.2 | 117.4 | 255.7 | 198.9 | 122.2 |
| Ier3 | nuclear receptor subfamily 4, group A, member 3 | 11.8 | 118.0 | 1394.1 | 114.2 | 69.6 |
| Lta | zinc finger protein 52 | 2.5 | 118.8 | 295.6 | 160.9 | 167.4 |
| Ptprs | SH3 domain containing ring finger 1 | 2.4 | 119.3 | 280.9 | 116.5 | 156.5 |
| Fnip2 | dihydrouridine synthase 2 | 2.1 | 122.7 | 260.3 | 237.7 | 202.8 |
| Asna1 | cyclin-dependent kinase 5, regulatory subunit 1 (p35) | 2.1 | 122.7 | 259.3 | 168.4 | 124.0 |
| Mybbp1a | processing of precursor 7, ribonuclease P family, (S. cerevisiae) | 2.1 | 125.9 | 264.9 | 235.7 | 150.6 |
| Il1r1 | growth factor independent 1 | 3.5 | 126.8 | 437.7 | 212.0 | 156.6 |
| Dennd5a | interleukin 15 receptor, alpha chain | 2.9 | 130.9 | 380.1 | 144.3 | 167.8 |
| E2f5 | BCL2-like 1 | 4.7 | 133.7 | 627.4 | 257.4 | 231.2 |
| Rcl1 | protein tyrosine phosphatase, receptor type, S | 2.6 | 136.6 | 358.8 | 157.5 | 125.0 |
| Fosl2 | plasmacytoma variant translocation 1 | 3.4 | 136.7 | 465.5 | 179.8 | 140.7 |
| Atad3a | fos-like antigen 2 | 2.5 | 137.0 | 347.5 | 107.2 | 177.8 |
| Bax | BCL2-associated X protein | 2.5 | 138.0 | 347.3 | 260.1 | 150.2 |
| Phf6 | solute carrier family 4, sodium bicarbonate cotransporter, member 7 | 2.3 | 140.3 | 328.2 | 258.7 | 397.5 |
| Zfp52 | tumor necrosis factor receptor superfamily, member 4 | 2.2 | 141.7 | 311.1 | 161.7 | 111.6 |
| Crtam | chemokine (C—X—C motif) ligand 10 | 12.7 | 141.7 | 1798.3 | 242.1 | 59.4 |
| Nop14 | polo-like kinase 3 | 2.8 | 144.8 | 406.3 | 200.1 | 119.9 |
| Rel | CD3E antigen, epsilon polypeptide associated protein | 2.2 | 158.7 | 350.2 | 260.9 | 111.4 |
| Gramd1b | tumor necrosis factor (ligand) superfamily, member 11 | 2.1 | 162.4 | 342.1 | 242.1 | 169.7 |
| Ifi27l2a | polymerase (RNA) III (DNA directed) polypeptide D | 3.0 | 166.3 | 503.7 | 296.1 | 121.6 |
| Tnfrsf10b | early growth response 2 | 2.8 | 173.5 | 494.0 | 136.3 | 68.2 |
| Rpl7l1 | DnaJ (Hsp40) homolog, subfamily C, member 2 | 2.1 | 173.6 | 369.4 | 346.2 | 254.3 |
| Eif1a | DNA topoisomerase 1, mitochondrial | 2.7 | 182.2 | 498.2 | 338.6 | 114.4 |
| Nfkb2 | tripartite motif-containing 30D | 2.3 | 182.6 | 423.4 | 65.8 | 90.6 |
| Heatr1 | DnaJ (Hsp40) homolog, subfamily C, member 21 | 2.0 | 190.1 | 389.4 | 285.5 | 228.2 |
| Utp20 | SAM domain, SH3 domain and nuclear localization signals, 1 | 2.2 | 191.5 | 422.1 | 222.8 | 304.1 |
| Chst11 | solute carrier family 5 (inositol transporters), member 3 | 2.1 | 191.6 | 400.2 | 210.0 | 123.4 |
| Ddx21 | mitochondrial ribosomal protein L15 | 2.1 | 191.6 | 396.3 | 329.8 | 137.7 |
| Hsf2 | dual specificity phosphatase 5 | 4.0 | 203.6 | 818.1 | 307.5 | 560.7 |
| Bccip | apoptosis enhancing nuclease | 2.3 | 211.1 | 478.5 | 288.2 | 137.9 |
| Tagap | ets variant 6 | 2.3 | 218.3 | 508.1 | 220.5 | 297.3 |
| Sdc3 | DIM1 dimethyladenosine transferase 1-like (S. cerevisiae) | 2.2 | 218.4 | 486.0 | 356.0 | 129.7 |
| Sytl3 | 2'-5' oligoadenylate synthetase-like 1 | 2.1 | 229.0 | 473.3 | 130.7 | 124.3 |
| Gtpbp4 | UTP18, small subunit (SSU) processome component, homolog (yeast) | 2.1 | 232.0 | 494.3 | 384.9 | 189.5 |
| Crip2 | BRCA2 and CDKN1A interacting protein | 2.4 | 234.6 | 563.3 | 437.5 | 269.8 |
| Sh3rf1 | synaptotagmin-like 3 | 2.4 | 242.4 | 572.9 | 316.7 | 700.7 |
| Nsfl1c | 5-methyltetrahydrofolate-homocysteine methyltransferase reductase | 2.9 | 245.7 | 706.5 | 334.6 | 150.6 |

TABLE 6-continued

Preferred human endogenous gene loci responsive to T-cell activation

| symbol | description | inductionRatio12hr | T.8Nve.Sp.OT1 | T.8Eff.Sp.OT1.12hr.LisOva | T.8Eff.Sp.OT1.48hr.LisOva | T.8Eff.Sp.OT1.d6.LisOva |
|---|---|---|---|---|---|---|
| Gtf2f1 | URB2 ribosome biogenesis 2 homolog (*S, cerevisiae*) | 2.0 | 245.7 | 500.2 | 489.8 | 184.6 |
| Slc4a7 | ubiquitin-conjugating enzyme E2C binding protein | 2.1 | 251.2 | 530.5 | 288.2 | 85.2 |
| Etv6 | lysine (K)-specific demethylase 2B | 2.2 | 251.8 | 547.1 | 332.7 | 262.1 |
| Trim30d | queuine tRNA-ribosyltransferase domain containing 1 | 3.0 | 260.3 | 788.7 | 358.0 | 75.5 |
| Ddx27 | ubiquitin specific peptidase 31 | 2.0 | 265.2 | 533.2 | 277.1 | 176.2 |
| Pwp2 | eukaryotic translation initiation factor 2-alpha kinase 2 | 2.0 | 267.7 | 540.5 | 260.8 | 244.8 |
| Chchd2 | ATPase family, AAA domaincontaining 3A | 2.5 | 268.8 | 679.7 | 523.1 | 147.1 |
| Myo1e | adhesion molecule, interacts with CXADR antigen 1 | 2.3 | 269.5 | 610.9 | 272.9 | 182.8 |
| Eif5b | SUMO/sentrin specific peptidase 3 | 2.0 | 272.5 | 548.7 | 544.5 | 298.4 |
| Stat5a | ESF1, nucleolar pre-rRNA processing protein, homolog (*S, cerevisiae*) | 2.2 | 276.3 | 610.4 | 482.2 | 266.5 |
| Cops6 | deoxynucleotidyltransferase, terminal, interacting protein 2 | 2.1 | 282.9 | 600.4 | 359.9 | 326.1 |
| D19Bwg1357e | TGFB-induced factor homeobox 1 | 2.1 | 300.5 | 618.9 | 217.5 | 210.6 |
| Aatf | eukaryotic translation initiation factor 1A | 2.5 | 300.8 | 738.7 | 597.7 | 262.8 |
| Aen | interferon-stimulated protein | 2.1 | 305.7 | 651.2 | 144.3 | 138.4 |
| Amica1 | pleiomorphic adenoma gene-like 2 | 2.1 | 311.5 | 651.9 | 376.2 | 405.9 |
| Wdr43 | PWP2 periodic tryptophan protein homolog (yeast) | 2.3 | 321.8 | 743.3 | 586.5 | 189.3 |
| Cct4 | furin (paired basic amino acid cleaving enzyme) | 5.2 | 329.7 | 1728.3 | 271.7 | 421.5 |
| Nifk | tumor necrosis factor | 6.6 | 330.7 | 2188.4 | 489.9 | 213.3 |
| Tgm2 | apoptosis antagonizing transcription factor | 2.3 | 331.4 | 754.8 | 523.1 | 221.5 |
| Ero1l | interferon, alpha-inducible protein 27 like 2A | 2.5 | 334.0 | 828.1 | 296.0 | 221.4 |
| Gfod1 | ST6 (alpha-N-acetyl-neuraminyl-2,3-beta-galactosyl-1,3)-N-acetylgalactosaminide alpha-2,6-sialyltransferase 4 | 3.9 | 338.4 | 1311.3 | 636.0 | 298.2 |
| Ak4 | methyltransferase like 1 | 2.2 | 339.4 | 744.7 | 662.8 | 94.5 |
| Sdad1 | notchless homolog 1 (*Drosophila*) | 2.0 | 339.4 | 690.3 | 610.3 | 158.1 |
| Dimt1 | mitochondrial ribosomal protein L3 | 2.1 | 340.0 | 725.5 | 651.4 | 359.8 |
| Esf1 | UBX domain protein 2A | 2.1 | 343.8 | 732.9 | 532.1 | 428.5 |
| Cd3eap | guanine nucleotide binding protein-like 2 (nucleolar) | 3.2 | 347.6 | 1124.7 | 647.4 | 227.5 |
| Samsn1 | programmed cell death 11 | 2.0 | 353.9 | 711.8 | 435.9 | 287.4 |
| Tnfrsf4 | cyclin-dependent kinase 8 | 2.0 | 364.0 | 731.1 | 702.5 | 346.2 |
| Mettl1 | eukaryotic translation initiation factor 5B | 2.3 | 365.1 | 838.2 | 544.5 | 355.5 |
| Cd274 | RNA terminal phosphate cyclase-like 1 | 2.5 | 373.3 | 948.8 | 746.4 | 155.8 |
| Ubtd2 | NSFL1 (p97) cofactor (p47) | 2.3 | 374.1 | 876.1 | 725.9 | 369.7 |
| Icos | nuclear factor of kappa light polypeptide gene enhancer in B cells inhibitor, delta | 3.9 | 378.5 | 1465.1 | 389.9 | 224.0 |
| Kdm2b | M-phase phosphoprotein 10 (U3 small nucleolar ribonucleoprotein) | 2.8 | 379.8 | 1069.3 | 738.4 | 290.8 |
| Larp4 | GRAM domain containing 1B | 2.5 | 382.7 | 949.6 | 363.4 | 659.2 |
| Eif3d | ERO1-like (*S, cerevisiae*) | 2.2 | 387.7 | 872.3 | 773.0 | 520.9 |
| Tnfaip3 | nuclear receptor subfamily 4, group A, member 1 | 6.8 | 387.8 | 2639.0 | 343.7 | 220.7 |
| Map1b | surfeit gene 2 | 2.1 | 399.8 | 852.2 | 696.3 | 204.0 |
| Cdv3 | N(alpha)-acetyltransferase 25, NatB auxiliary subunit | 2.1 | 405.7 | 847.3 | 669.5 | 194.1 |
| Plac8 | yrdC domain containing (*E, coli*) | 2.0 | 406.7 | 830.8 | 635.3 | 267.0 |
| Mrpl3 | La ribonucleoprotein domain family, member 4 | 2.2 | 408.8 | 887.9 | 586.6 | 358.3 |
| Surf2 | SDA1 domain containing 1 | 2.2 | 419.8 | 939.9 | 631.4 | 284.7 |
| Ubxn2a | importin 4 | 2.8 | 420.3 | 1183.6 | 777.8 | 173.5 |
| Utp18 | inducible T cell co-stimulator | 2.2 | 423.9 | 920.9 | 818.8 | 796.9 |
| Isg20 | solute carrier family 7 (cationic amino acid transporter, y+ system), member 1 | 2.1 | 439.4 | 934.4 | 842.6 | 344.6 |
| Dnajc2 | arsA arsenite transporter, ATP-binding, homolog 1 (bacterial) | 2.6 | 446.6 | 1165.0 | 717.9 | 963.9 |
| Jak2 | polymerase (RNA) I polypeptide C | 2.7 | 447.8 | 1208.4 | 854.0 | 295.9 |
| Slc7a1 | spermatogenesis associated 5 | 2.0 | 450.8 | 920.2 | 516.0 | 361.6 |
| Syde2 | ubiquitin specific peptidase 18 | 2.7 | 451.8 | 1240.5 | 296.0 | 250.7 |
| Slc5a6 | placenta-specific 8 | 2.1 | 452.4 | 967.3 | 888.6 | 590.8 |
| Dnttip2 | general transcription factor IIF, polypeptide 1 | 2.3 | 454.8 | 1063.9 | 890.0 | 680.8 |
| Idi2 | nuclear factor of kappa light polypeptide gene enhancer in B cells inhibitor, beta | 3.4 | 456.4 | 1535.5 | 679.1 | 502.7 |
| Dus2 | PHD finger protein 6 | 2.5 | 462.0 | 1159.5 | 775.8 | 510.4 |
| Pitrm1 | RRN3 RNA polymerase I transcription factor homolog (yeast) | 2.1 | 462.2 | 948.4 | 913.2 | 388.9 |

TABLE 6-continued

Preferred human endogenous gene loci responsive to T-cell activation

| symbol | description | inductionRatio12hr | T.8Nve.Sp.OT1 | T.8Eff.Sp.OT1.12hr.LisOva | T.8Eff.Sp.OT1.48hr.LisOva | T.8Eff.Sp.OT1.d6.LisOva |
|---|---|---|---|---|---|---|
| Plxna1 | cytotoxic and regulatory T cell molecule | 2.5 | 473.7 | 1177.8 | 586.8 | 431.8 |
| Cdk5r1 | COP9 (constitutive photomorphogenic) homolog, subunit 6 (Arabidopsis thaliana) | 2.3 | 483.6 | 1101.9 | 947.8 | 560.3 |
| Ube2cbp | asparagine-linked glycosylation 3 (alpha-1,3-mannosyltransferase) | 2.1 | 485.9 | 1006.3 | 758.7 | 339.4 |
| Tnfsf11 | tryptophanyl-tRNA synthetase | 2.0 | 486.1 | 987.1 | 897.1 | 504.7 |
| Pop7 | hypoxia up-regulated 1 | 2.0 | 494.3 | 996.6 | 802.4 | 690.3 |
| Psme3 | family with sequence similarity 60, member A | 2.0 | 500.8 | 1002.1 | 834.7 | 417.6 |
| Mir17hg | bone marrow stromal cell antigen 2 | 3.8 | 502.5 | 1922.9 | 925.5 | 246.0 |
| Tsr1 | nuclear factor of kappa light polypeptide gene enhancer in B cells 2, p49/p100 | 2.4 | 503.2 | 1231.8 | 494.0 | 341.8 |
| Rbpms2 | UTP20, small subunit (SSU) processome component, homolog (yeast) | 2.4 | 510.5 | 1240.2 | 696.4 | 245.8 |
| Mrpl47 | CD274 antigen | 2.2 | 516.6 | 1128.7 | 246.9 | 220.2 |
| Rab8b | proviral integration site 1 | 3.4 | 518.4 | 1766.4 | 676.9 | 970.0 |
| Plagl2 | signal transducer and activator of transcription 5A | 2.3 | 530.0 | 1210.4 | 496.6 | 507.8 |
| Grhl1 | CD69 antigen | 3.2 | 535.7 | 1725.8 | 289.5 | 153.9 |
| Zeb2 | pitrilysin metallepetidase 1 | 2.1 | 544.9 | 1153.8 | 968.4 | 349.3 |
| sept-02 | cyclin-dependent kinase 6 | 2.7 | 550.3 | 1476.5 | 1064.0 | 642.1 |
| Slc5a3 | DEAD (Asp-Glu-Ala-Asp) box polypeptide 27 | 2.3 | 556.2 | 1286.9 | 987.2 | 480.4 |
| Naa25 | polymerase (RNA) I polypeptide B | 2.8 | 556.2 | 1536.0 | 1070.4 | 201.3 |
| Plaur | tumor necrosis factor, alpha-induced protein 3 | 2.2 | 560.6 | 1212.2 | 255.5 | 446.0 |
| Metap1 | nodal modulator 1 | 2.1 | 563.0 | 1161.0 | 988.9 | 439.8 |
| Alg3 | NOP14 nucleolar protein | 2.5 | 570.9 | 1418.9 | 925.3 | 398.0 |
| Mrpl15 | ribosomal protein L7-like 1 | 2.5 | 586.7 | 1448.7 | 1030.2 | 687.2 |
| Oasl1 | methionyl aminopeptidase 1 | 2.1 | 597.5 | 1244.1 | 1139.3 | 433.4 |
| Rorc | hypoxia inducible factor 1, alpha subunit | 3.0 | 624.2 | 1854.6 | 809.4 | 838.4 |
| Nomo1 | Janus kinase 2 | 2.1 | 624.5 | 1328.7 | 390.6 | 917.8 |
| Tgif1 | nuclear factor of kappa light polypeptide gene enhancer in B cells 1, p105 | 2.9 | 661.5 | 1913.3 | 713.9 | 720.5 |
| Lipg | reticuloendotheliosis oncogene | 2.5 | 678.9 | 1686.4 | 409.8 | 580.5 |
| Rrn3 | septin 2 | 2.1 | 687.3 | 1436.0 | 1354.1 | 1181.3 |
| Dnajc21 | nucleolar protein interacting with the FHA domain of MKI67 | 2.3 | 733.4 | 1658.2 | 1280.0 | 407.2 |
| Yrdc | elongation factor Tu GTP binding domain containing 2 | 2.0 | 739.3 | 1483.5 | 1439.0 | 904.3 |
| Acsl6 | myelocytomatosis oncogene | 4.0 | 761.0 | 3022.8 | 1064.0 | 211.5 |
| Spata5 | dyskeratosis congenita 1, dyskerin | 2.7 | 778.2 | 2112.0 | 1549.5 | 484.2 |
| Urb2 | carnitine deficiency-associated gene expressed in ventricle 3 | 2.1 | 801.6 | 1718.2 | 1274.7 | 1010.3 |
| Nle1 | GTP binding protein 4 | 2.4 | 824.2 | 1942.6 | 1578.7 | 567.3 |
| Wars | HEAT repeat containing 1 | 2.4 | 830.3 | 2020.6 | 1235.5 | 495.4 |
| Crem | proteaseome (prosome, macropain) activator subunit 3 (PA28 gamma, Ki) | 2.1 | 838.4 | 1763.5 | 1471.1 | 936.1 |
| Larp1 | La ribonucleoprotein domain family, member 1 | 2.0 | 861.7 | 1742.1 | 1250.9 | 854.3 |
| Eif2ak2 | DNA segment, Chr 19, Brigham & Women's Genetics 1357 expressed | 2.3 | 868.6 | 1978.4 | 1218.0 | 653.4 |
| Hyou1 | eukaryotic translation initiation factor 3, subunit D | 2.2 | 909.1 | 1971.6 | 1641.9 | 920.6 |
| Senp3 | TSR1 20S rRNA accumulation | 2.1 | 913.9 | 1915.9 | 1474.6 | 477.2 |
| Tmtc2 | MYB binding protein (P160) 1a | 2.6 | 1140.0 | 2962.9 | 2200.7 | 459.8 |
| Fosb | T cell activation Rho GTPase activating protein | 2.4 | 1176.7 | 2794.4 | 489.3 | 704.2 |
| Pdcd11 | RAB8B, member RAS oncogene family | 2.1 | 1189.5 | 2492.2 | 1671.3 | 2512.5 |
| Usp31 | DEAD (Asp-Glu-Ala-Asp) box polypeptide 21 | 2.4 | 1210.2 | 2928.0 | 2221.1 | 1098.2 |
| Cdk8 | chaperonin containing Tcp1, subunit 4 (delta) | 2.3 | 1321.4 | 2989.7 | 2462.5 | 1294.8 |
| Eftud2 | coiled-coil-helix-coiled-coil-helix domain containing 2 | 2.3 | 1374.2 | 3171.2 | 2636.9 | 1008.9 |
| Fam60a | WD repeat domain 43 | 2.3 | 1727.6 | 3912.6 | 2927.5 | 1014.9 |

TABLE 7

Selection of preferred endogenous genes that are constantly active during immune cell activation (dependent or independent from T-cell activation).

| Symbol | Gene description |
| --- | --- |
| CD3G | CD3 gamma |
| Rn28s1 | 28S ribosomal RNA |
| Rn18s | 18S ribosomal RNA |
| Rn7sk | RNA, 7SK, nuclear |
| Actg1 | actin, gamma, cytoplasmic 1 |
| B2m | beta-2 microglobulin |
| Rpl18a | ribosomal protein L18A |
| Pabpc1 | poly(A) binding protein, cytoplasmic 1 |
| Gapdh | glyceraldehyde-3-phosphate dehydrogenase |
| Rpl19 | ribosomal protein L19 |
| Rpl17 | ribosomal protein L17 |
| Rplp0 | ribosomal protein, large, P0 |
| Cfl1 | cofilin 1, non-muscle |
| Pfn1 | profilin 1 |

TABLE 8

Selection of genes that are transiently upregulated upon T-cell activation.

| Symbol | Gene description |
| --- | --- |
| Il3 | interleukin 3 |
| Il2 | interleukin 2 |
| Ccl4 | chemokine (C-C motif) ligand 4 |
| Il21 | interleukin 21 |
| Gp49a | glycoprotein 49 A |
| Nr4a3 | nuclear receptor subfamily 4, group A, member 3 |
| Lilrb4 | leukocyte immunoglobulin-like receptor, subfamily B, member 4 |
| Cd200 | CD200 antigen |
| Cdkn1a | cyclin-dependent kinase inhibitor 1A (P21) |
| Gzmc | granzyme C |
| Nr4a2 | nuclear receptor subfamily 4, group A, member 2 |
| Cish | cytokine inducible SH2-containing protein |
| Ccr8 | chemokine (C-C motif) receptor 8 |
| Lad1 | ladinin |
| Crabp2 | cellular retinoic acid binding protein II |

TABLE 9

Selection of genes that are upregulated over more than 24 hours upon T-cell activation.

| Symbol | Description |
| --- | --- |
| Gzmb | granzyme B |
| Tbx21 | T-box 21 |
| Pdcd1 | programmed cell death 1 |
| Plek | pleckstrin |
| Chek1 | checkpoint kinase 1 |
| Slamf7 | SLAM family member 7 |
| Zbtb32 | zinc finger and BTB domain containing 32 |
| Tigit | T cell immunoreceptor with Ig and ITIM domains |
| Lag3 | lymphocyte-activation gene 3 |
| Gzma | granzyme A |
| Wee1 | WEE 1 homolog 1 (*S. pombe*) |
| Il12rb2 | interleukin 12 receptor, beta 2 |
| Ccr5 | chemokine (C-C motif) receptor 5 |
| Eea1 | early endosome antigen 1 |
| Dtl | denticleless homolog (*Drosophila*) |

TABLE 10

Selection of genes that are down-regulated upon immune cell activation.

| Symbol | Gene description |
| --- | --- |
| Spata6 | spermatogenesis associated 6 |
| Itga6 | integrin alpha 6 |
| Rcbtb2 | regulator of chromosome condensation (RCC1) and BTB (POZ) domain containing protein 2 |
| Cd1d1 | CD1d1 antigen |
| St8sia4 | ST8 alpha-N-acetyl-neuraminide alpha-2,8-sialyltransferase 4 |
| Itgae | integrin alpha E, epithelial-associated |
| Fam214a | family with sequence similarity 214, member A |
| Slc6a19 | solute carrier family 6 (neurotransmitter transporter), member 19 |
| Cd55 | CD55 antigen |
| Xkrx | X Kell blood group precursor related X linked |
| Mturn | maturin, neural progenitor differentiation regulator homolog (*Xenopus*) |
| H2-Ob | histocompatibility 2, O region beta locus |
| Cnr2 | cannabinoid receptor 2 (macrophage) |
| Itgae | integrin alpha E, epithelial-associated |
| Raver2 | ribonucleoprotein, PTB-binding 2 |
| Zbtb20 | zinc finger and BTB domain containing 20 |
| Arrb1 | arrestin, beta 1 |
| Abca1 | ATP-binding cassette, sub-family A (ABC1), member 1 |
| Tet1 | tet methylcytosine dioxygenase 1 |
| Slc16a5 | solute carrier family 16 (monocarboxylic acid transporters), member 5 |
| Trav14-1 | T cell receptor alpha variable 14-1 |
| Ampd3 | adenosine monophosphate deaminase 3 |

TABLE 11

Selection of human genes that are silent upon T-cell activation (safe harbor gene targeted integration loci).

| Symbol | Gene description |
| --- | --- |
| Zfp640 | zinc finger protein 640 |
| LOC100038422 | uncharacterized LOC100038422 |
| Zfp600 | zinc finger protein 600 |
| Serpinb3a | serine (or cysteine) peptidase inhibitor, clade B (ovalbumin), member 3A |
| Tas2r106 | taste receptor, type 2, member 106 |
| Magea3 | melanoma antigen, family A, 3 |
| Omt2a | oocyte maturation, alpha |
| Cpxcr1 | CPX chromosome region, candidate 1 |
| Hsf3 | heat shock transcription factor 3 |
| Pbsn | Probasin |
| Sbp | spermine binding protein |
| Wfdc6b | WAP four-disulfide core domain 6B |
| Meiob | meiosis specific with OB domains |
| Dnm3os | dynamin 3, opposite strand |
| Skint11 | selection and upkeep of intraepithelial T cells 11 |

TABLE 12

List of gene loci upregulated in tumor exhausted infiltrating lymphocytes (compiled from multiple tumors) useful for gene integration of exogenous coding sequences as per the present invention

| Gene names | Uniprot ID (human) |
| --- | --- |
| CXCL13 | O43927 |
| TNFRSF1B | P20333 |
| RGS2 | P41220 |
| TIGIT | Q495A1 |
| CD27 | P26842 |
| TNFRSF9 | Q12933 |
| SLA | Q13239 |
| INPP5F | Q01968 |
| XCL2 | Q9UBD3 |

TABLE 12-continued

List of gene loci upregulated in tumor exhausted infiltrating lymphocytes (compiled from multiple tumors) useful for gene integration of exogenous coding sequences as per the present invention

| Gene names | Uniprot ID (human) |
|---|---|
| HLA-DMA | P28067 |
| FAM3C | Q92520 |
| WARS | P23381 |
| EIF3L | Q9Y262 |
| KCNK5 | O95279 |
| TMBIM6 | P55061 |
| CD200 | P41217 |
| C3H7A | O60880 |
| SH2D1A | O60880 |
| ATP1B3 | P54709 |
| THADA | Q6YHU6 |
| PARK7 | Q99497 |
| EGR2 | P11161 |
| FDFT1 | P37268 |
| CRTAM | O95727 |
| IFI16 | Q16666 |

TABLE 13

List of gene loci upregulated in hypoxic tumor conditions useful for gene integration of exogenous coding sequences as per the present invention

| Gene names | Strategy | |
|---|---|---|
| CTLA-4 | KO/KI | Target shown to be upregulated in T-cells upon hypoxia exposure and T cell exhaustion |
| LAG-3 (CD223) | KO/KI | |
| PD1 | KO/KI | |
| 4-1BB (CD137) | KI | |
| GITR | KI | |
| OX40 | KI | |
| IL10 | KO/KI | |
| ABCB1 | KI | HIF target |
| ABCG2 | KI | |
| ADM | KI | |
| ADRA1B | KI | |
| AK3 | KI | |
| ALDOA | KI | |
| BHLHB2 | KI | |
| BHLHB3 | KI | |
| BNIP3 | KI | |
| BNIP3L | KI | |
| CA9 | KI | |
| CCNG2 | KI | |
| CD99 | KI | |
| CDKN1A | KI | |
| CITED2 | KI | |
| COL5A1 | KI | |
| CP | KI | |
| CTGF | KI | |
| CTSD | KI | |
| CXCL12 | KI | |
| CXCR4 | KI | |
| CYP2S1 | KI | |
| DDIT4 | KI | |
| DEC1 | KI | |
| EDN1 | KI | |
| EGLN1 | KI | |
| EGLN3 | KI | |
| ENG | KI | |
| ENO1 | KI | |
| EPO | KI | |
| ETS1 | KI | |
| FECH | KI | |
| FN1 | KI | |
| FURIN | KI | |
| GAPDH | KI | |
| GPI | KI | |
| GPX3 | KI | |
| HK1 | KI | |
| HK2 | KI | |

TABLE 13-continued

List of gene loci upregulated in hypoxic tumor conditions useful for gene integration of exogenous coding sequences as per the present invention

| Gene names | Strategy |
|---|---|
| HMOX1 | KI |
| HSP90B1 | KI |
| ID2 | KI |
| IGF2 | KI |
| IGFBP1 | KI |
| IGFBP2 | KI |
| IGFBP3 | KI |
| ITGB2 | KI |
| KRT14 | KI |
| KRT18 | KI |
| KRT19 | KI |
| LDHA | KI |
| LEP | KI |
| LOX | KI |
| LRP1 | KI |
| MCL1 | KI |
| MET | KI |
| MMP14 | KI |
| MMP2 | KI |
| MXI1 | KI |
| NOS2A | KI |
| NOS3 | KI |
| NPM1 | KI |
| NR4A1 | KI |
| NT5E | KI |
| PDGFA | KI |
| PDK1 | KI |
| PFKFB3 | KI |
| PFKL | KI |
| PGK1 | KI |
| PH-4 | KI |
| PKM2 | KI |
| PLAUR | KI |
| PMAIP1 | KI |
| PPP5C | KI |
| PROK1 | KI |
| SERPINE1 | KI |
| SLC2A1 | KI |
| TERT | KI |
| TF | KI |
| TFF3 | KI |
| TFRC | KI |
| TGFA | KI |
| TGFB3 | KI |
| TGM2 | KI |
| TPI1 | KI |
| VEGFA | KI |
| VIM | KI |
| TMEM45A | KI |
| AKAP12 | KI |
| SEC24A | KI |
| ANKRD37 | KI |
| RSBN1 | KI |
| GOPC | KI |
| SAMD12 | KI |
| CRKL | KI |
| EDEM3 | KI |
| TRIM9 | KI |
| GOSR2 | KI |
| MIF | KI |
| ASPH | KI |
| WDR33 | KI |
| DHX40 | KI |
| KLF10 | KI |
| R3HDM1 | KI |
| RARA | KI |
| LOC162073 | KI |
| PGRMC2 | KI |
| ZWILCH | KI |
| TPCN1 | KI |
| WSB1 | KI |
| SPAG4 | KI |
| GYS1 | KI |
| RRP9 | KI |

TABLE 13-continued

List of gene loci upregulated in hypoxic tumor conditions
useful for gene integration of exogenous coding
sequences as per the present invention

| Gene names | Strategy |
|---|---|
| SLC25A28 | KI |
| NTRK2 | KI |
| NARF | KI |
| ASCC1 | KI |
| UFM1 | KI |
| TXNIP | KI |
| MGAT2 | KI |
| VDAC1 | KI |
| SEC61G | KI |
| SRP19 | KI |
| JMJD2C | KI |
| SNRPD1 | KI |
| RASSF4 | KI |

The invention claimed is:

1. A method for preparing at least $10^6$ engineered primary T cells for cell immunotherapy, said method comprising:
   providing a population of cells comprising primary T cells;
   introducing into a proportion of said primary T-cells:
   at least one nucleic acid comprising an exogenous polynucleotide sequence encoding an HLA-E heavy chain to be integrated at an endogenous β2m locus, wherein said exogenous polynucleotide sequence encoding HLA-E heavy chain comprises SEQ ID NO:68 or SEQ ID NO:70; and
   at least one sequence-specific reagent that specifically targets said endogenous β2m locus,
   wherein said exogenous polynucleotide sequence encoding an HLA-E heavy chain is inserted by targeted gene integration into said endogenous β2m locus to generate at least $10^6$ engineered primary T cells with the exogenous polynucleotide sequence encoding an HLA-E heavy chain inserted into said endogenous β2m locus.

2. The method of claim 1, wherein said targeted gene integration is by homologous recombination or NHEJ into said primary T cells.

3. The method of claim 1, wherein said exogenous polynucleotide sequence encoding an HLA-E heavy chain is integrated under transcriptional control of an endogenous β2m promoter present at said locus.

4. The method of claim 1, wherein said insertion of said exogenous polynucleotide sequence encoding an HLA-E heavy chain inactivates β2m expression at said endogenous locus.

5. The method according to claim 1, wherein said exogenous polynucleotide sequence encoding HLA-E heavy chain comprises SEQ ID NO:68.

6. The method according to claim 1, wherein said exogenous polynucleotide sequence encoding HLA-E heavy chain comprises SEQ ID NO:70.

7. The method according to claim 1, wherein said exogenous polynucleotide sequence encoding an HLA-E heavy chain, when integrated at β2m endogenous locus, results in the expression of a fusion of the HLA-E heavy chain with β2m fragments.

8. The method according to claim 7, wherein said fusion of the HLA-E heavy chain with β2m fragments results in the expression of dimer or trimers of HLA-E heavy chain.

9. The method according to claim 1, wherein said sequence specific reagent is a specific rare-cutting endonuclease.

10. The method according to claim 9, wherein said specific rare-cutting endonuclease is selected from an RNA or DNA-guided endonuclease, Cas9 or Cpf1, a TAL-endonuclease, a zinc finger nuclease, a homing endonuclease or any combination thereof.

11. The method according to claim 10, wherein said specific rare-cutting endonuclease is an RNA guided endonuclease.

12. The method according to claim 10, wherein said specific rare-cutting endonuclease is Cas9.

13. The method according to claim 10, wherein said specific rare-cutting endonuclease is Cpf1.

14. The method according to claim 10, wherein said specific rare-cutting endonuclease is a TAL-endonuclease.

15. The method according to claim 10, wherein said specific rare-cutting endonuclease is a zinc finger nuclease.

16. The method according to claim 10, wherein said specific rare-cutting endonuclease is a homing endonuclease.

17. The method according to claim 1, wherein said engineered primary T-cells are further endowed with chimeric antigen receptor (CAR).

18. The method according to claim 17, wherein said chimeric antigen receptor (CAR) is encoded by a second exogenous sequence that is integrated at a TCR locus.

19. The method according to claim 18, wherein said second exogenous sequence prevents the expression of the endogenous TCR sequences.

20. A population of at least $10^6$ engineered primary T cells prepared by the method of claim 1.

* * * * *

SEQUENCE LISTING

<160> NUMBER OF SEQ ID NOS: 100

<210> SEQ ID NO 1
<211> LENGTH: 1000
<212> TYPE: DNA
<213> ORGANISM: artificial sequence
<220> FEATURE:
<223> OTHER INFORMATION: PD1 left homology

<400> SEQUENCE: 1

```
ccaagccctg accctggcag gcatatgttt caggaggtcc ttgtcttggg agcccagggt      60 cggggggcccc gtgtctgtcc acatccgagt caatggccca tctcgtctct gaagcatctt     120
tgctgtgagc tctagtcccc actgtcttgc tggaaaatgt ggaggcccca ctgcccactg     180
cccagggcag caatgcccat accacgtggt cccagctccg agcttgtcct gaaaaggggg     240
caaagactgg accctgagcc tgccaagggg ccacactcct cccagggctg gggtctccat     300
gggcagcccc ccacccaccc agaccagtta cactcccctg tgccagagca gtgcagacag     360
gaccaggcca ggatgcccaa gggtcagggg ctggggatgg gtagccccca aacagccctt     420 tctggggaa ctggcctcaa cggggaaggg ggtgaaggct cttagtagga aatcagggag      480
acccaagtca gagccaggtg ctgtgcagaa gctgcagcct cacgtagaag gaagaggctc     540
tgcagtggag gccagtgccc atccccgggt ggcagaggcc ccagcagaga cttctcaatg     600
acattccagc tggggtggcc cttccagagc ccttgctgcc cgagggatgt gagcaggtgg     660
ccggggaggc tttgtggggc cacccagccc cttcctcacc tctctccatc tctcagactc     720
cccagacagg ccctggaacc cccccacctt ctccccagcc ctgctcgtgg tgaccgaagg     780
ggacaacgcc accttcacct gcagcttctc caacacatcg gagagcttcg tgctaaactg     840
gtaccgcatg agcccagca accagacgga caagctggcc gccttccccg aggaccgcag     900
ccagcccggc caggactgcc gcttccgtgt cacacaactg cccaacgggc gtgacttcca     960
catgagcgtg gtcagggccc ggcgcaatga cagcggcacc                         1000
```

<210> SEQ ID NO 2
<211> LENGTH: 1000
<212> TYPE: DNA
<213> ORGANISM: artificial sequence
<220> FEATURE:
<223> OTHER INFORMATION: PD1 right homology

<400> SEQUENCE: 2

```
gcctgcgggc agagctcagg gtgacaggtg cggcctcgga ggccccgggg caggggtgag      60
ctgagccggt cctggggtgg gtgtcccctc ctgcacagga tcaggagctc cagggtcgta     120
gggcagggac cccccagctc cagtccaggg ctctgtcctg cacctgggga atggtgaccg     180
```

```
gcatctctgt cctctagctc tggaagcacc ccagccctc tagtctgccc tcacccctga    240
ccctgaccct ccaccctgac cccgtcctaa ccctgacct ttgtgccctt ccagagagaa    300
gggcagaagt gcccacagcc caccccagcc cctcacccag gccagccggc cagttccaaa    360
ccctggtggt tggtgtcgtg gcggcctgc tgggcagcct ggtgctgcta gtctgggtcc    420
tggccgtcat ctgctcccgg gccgcacgag gtaacgtcat cccagcccct cggcctgccc    480
tgccctaacc ctgctggcgg ccctcactcc cgcctcccct tcctcaccc ttccctcacc    540 ccaccccacc tcccccatc tccccgccag gctaagtccc tgatgaaggc ccctggacta    600
agacccccca cctaggagca cggctcaggg tcggcctggt gacccaagt gtgtttctct    660 gcagggacaa taggagccag gcgcaccggc cagcccctgg tgagtctcac tcttttcctg    720
catgatccac tgtgccttcc ttcctgggtg ggcagaggtg gaaggacagg ctgggaccac    780
acggcctgca ggactcacat tctattatag ccaggacccc acctccccag cccccaggca    840
gcaacctcaa tccctaaagc catgatctgg ggccccagcc cacctgcggt ctccgggggt    900
gcccggccca tgtgtgtgcc tgcctgcggt ctccaggggt gcctggccca cgcgtgtgcc    960
cgcctgcggt ctctgggggt gcccggccca catatgtgcc                         1000

<210> SEQ ID NO 3
<211> LENGTH: 2781
<212> TYPE: DNA
<213> ORGANISM: artificial sequence
<220> FEATURE:
<223> OTHER INFORMATION: PD1_T3C-L2

<400> SEQUENCE: 3
atgggcgatc ctaaaaagaa acgtaaggtc atcgatatcg ccgatctacg cacgctcggc     60
tacagccagc agcaacagga gaagatcaaa ccgaaggttc gttcgacagt ggcgcagcac    120
cacgaggcac tggtcggcca cgggtttaca cacgcgcaca tcgttgcgtt aagccaacac    180
ccggcagcgt tagggaccgt cgctgtcaag tatcaggaca tgatcgcagc gttgccagag    240
gcgacacacg aagcgatcgt tggcgtcggc aaacagtggt ccggcgcacg cgctctggag    300
gccttgctca cggtggcggg agagttgaga ggtccaccgt tacagttgga cacaggccaa    360
cttctcaaga ttgcaaaacg tggcggcgtg accgcagtgg aggcagtgca tgcatggcgc    420
aatgcactga cgggtgcccc gctcaacttg accccgagc aagtggtggc tatcgcttcc    480
aagctggggg gaaagcaggc cctggagacc gtccaggccc ttctcccagt gctttgccag    540
gctcacggac tgaccctga acaggtggtg gcaattgcct cacacgacgg gggcaagcag    600
gcactggaga ctgtccagcg gctgctgcct gtcctctgcc aggcccacgg actcactcct    660
gagcaggtcg tggccattgc cagccacgat gggggcaaac aggctctgga ccgtgcag    720 cgcctcctcc cagtgctgtg ccaggctcat gggctgaccc cacagcaggt cgtcgccatt    780
gccagtaacg gcgggggggaa gcaggccctc gaaacagtgc agaggctgct gccgtcttg    840 tgccaagcac acggcctgac acccgagcag gtggtggcca tcgcctctca tgacggcggc    900
aagcaggccc ttgagacagt gcagagactg ttgcccgtgt tgtgtcaggc cacggggttg    960 acccccagc aggtggtcgc catcgccagc aatggcgggg gaaagcaggc ccttgagacc   1020
gtgcagcggt tgcttccagt gttgtgccag gcacacggac tgaccctca acaggtggtc   1080 gcaatcgcca gctacaaggg cggaaagcag gctctggaga cagtgcagcg cctcctgccc   1140
gtgctgtgtc aggctcacgg actgacacca cagcaggtgg tcgccatcgc cagtaacggg   1200
```

-continued

| | |
|---|---|
| ggcggcaagc aggctttgga gaccgtccag agactcctcc ccgtcctttg ccaggcccac | 1260 |
| gggttgacac ctcagcaggt cgtcgccatt gcctccaaca acgggggcaa gcaggccctc | 1320 |
| gaaactgtgc agaggctgct gcctgtgctg tgccaggctc atgggctgac accccagcag | 1380 |
| gtggtggcca ttgcctctaa caacggcggc aaacaggcac tggagaccgt gcaaaggctg | 1440 |
| ctgcccgtcc tctgccaagc ccacgggctc actccacagc aggtcgtggc catcgcctca | 1500 |
| aacaatggcg ggaagcaggc cctggagact gtgcaaaggc tgctccctgt gctctgccag | 1560 |
| gcacacggac tgacccctca gcaggtggtg gcaatcgctt ccaacaacgg ggaaagcag | 1620 |
| gccctcgaaa ccgtgcagcg cctcctccca gtgctgtgcc aggcacatgg cctcacaccc | 1680 |
| gagcaagtgg tggctatcgc cagccacgac ggagggaagc aggctctgga gaccgtgcag | 1740 |
| aggctgctgc ctgtcctgtg ccaggcccac gggcttactc cagagcaggt cgtcgccatc | 1800 |
| gccagtcatg atggggggaa gcaggccctt gagacagtcc agcggctgct gccagtcctt | 1860 |
| tgccaggctc acggcttgac tcccgagcag gtcgtggcca ttgcctcaaa cattggggc | 1920 |
| aaacaggccc tggagacagt gcaggccctg ctgcccgtgt tgtgtcaggc ccacggcttg | 1980 |
| acacccagc aggtggtcgc cattgcctct aatggcggcg ggagaccgc cttggagagc | 2040 |
| attgttgccc agtatctcg ccctgatccg gcgttggccg cgttgaccaa cgaccacctc | 2100 |
| gtcgccttgg cctgcctcgg cgggcgtcct gcgctggatg cagtgaaaaa gggattgggg | 2160 |
| gatcctatca gccgttccca gctggtgaag tccgagctgg aggagaagaa atccgagttg | 2220 |
| aggcacaagc tgaagtacgt gccccacgag tacatcgagc tgatcgagat cgcccggaac | 2280 |
| agcacccagg accgtatcct ggagatgaag gtgatggagt tcttcatgaa ggtgtacggc | 2340 |
| tacaggggca agcacctggg cggctccagg aagcccgacg cgccatcta caccgtgggc | 2400 |
| tcccccatcg actacggcgt gatcgtggac accaaggcct actccggcgg ctacaacctg | 2460 |
| cccatcggcc aggccgacga aatgcagagg tacgtggagg agaaccagac caggaacaag | 2520 |
| cacatcaacc ccaacgagtg gtggaaggtg taccctcca gcgtgaccga gttcaagttc | 2580 |
| ctgttcgtgt ccggccactt caagggcaac tacaaggccc agctgaccag gctgaaccac | 2640 |
| atcaccaact gcaacggcgc cgtgctgtcc gtggaggagc tcctgatcgg cggcgagatg | 2700 |
| atcaaggccg gcaccctgac cctggaggag gtgaggagga agttcaacaa cggcgagatc | 2760 |
| aacttcgcgg ccgactgata a | 2781 |

<210> SEQ ID NO 4
<211> LENGTH: 2778
<212> TYPE: DNA
<213> ORGANISM: artificial sequence
<220> FEATURE:
<223> OTHER INFORMATION: PD1T3R

<400> SEQUENCE: 4

| | |
|---|---|
| atgggcgatc ctaaaaagaa acgtaaggtc atcgatatcg ccgatctacg cacgctcggc | 60 |
| tacagccagc agcaacagga gaagatcaaa ccgaaggttc gttcgacagt ggcgcagcac | 120 |
| cacgaggcac tggtcggcca cgggtttaca cacgcgcaca tcgttgcgtt aagccaacac | 180 |
| ccggcagcgt tagggaccgt cgctgtcaag tatcaggaca tgatcgcagc gttgccagag | 240 |
| gcgacacacg aagcgatcgt tggcgtcggc aaacagtggt ccggcgcacg cgctctggag | 300 |
| gccttgctca cggtggcggg agagttgaga ggtccaccgt tacagttgga cacaggccaa | 360 |
| cttctcaaga ttgcaaaacg tggcggcgtg accgcagtgg aggcagtgca tgcatggcgc | 420 |
| aatgcactga cgggtgcccc gctcaacttg accccgagc aagtcgtcgc aatcgccagc | 480 |

```
catgatggag ggaagcaagc cctcgaaacc gtgcagcggt tgcttcctgt gctctgccag      540
gcccacggcc ttaccgctca gcaggtggtg gccatcgcaa gtaacggagg aggaaagcaa      600
gccttggaga cagtgcagcg cctgttgccc gtgctgtgcc aggcacacgg cctcacacca      660
gagcaggtcg tggccattgc ctcccatgac ggggggaaac aggctctgga gaccgtccag      720
aggctgctgc ccgtcctctg tcaagctcac ggcctgactc cccaacaagt ggtcgccatc      780
gcctctaatg gcggcgggaa gcaggcactg gaaacagtgc agagactgct ccctgtgctt      840
tgccaagctc atgggttgac ccccaacag tcgtcgcta ttgcctcaaa cggggggggc        900
aagcaggccc ttgagactgt gcagaggctg ttgccagtgc tgtgtcaggc tcacgggctc      960
actccacaac aggtggtcgc aattgccagc aacggcggcg gaaagcaagc tcttgaaacc     1020
gtgcaacgcc tcctgcccgt gctctgtcag gctcatggcc tgacaccaca acaagtcgtg     1080
gccatcgcca gtaataatgg cgggaaacag gctcttgaga ccgtcagag gctgctccca      1140 gtgctctgcc aggcacacgg gctgaccccc gagcaggtgg tggctatcgc cagcaatatt     1200
gggggcaagc aggccctgga aacagtccag gccctgctgc cagtgctttg ccaggctcac     1260
gggctcactc cccagcaggt cgtggcaatc gcctccaacg gcggagggaa gcaggctctg     1320
gagaccgtgc agagactgct gcccgtcttg tgccaggccc acggactcac acctgaacag     1380
gtcgtcgcca ttgcctctca cgatggggc aaacaagccc tggagacagt gcagcggctg     1440
ttgcctgtgt tgtgccaagc ccacggcttg actcctcaac aagtggtcgc catcgcctca     1500
aatggcggcg gaaaacaagc tctggagaca gtgcagaggt tgctgcccgt cctctgccaa     1560
gcccacggcc tgactcccca caggtcgtc gccattgcca gcaacaacgg aggaaagcag      1620
gctctcgaaa ctgtgcagcg gctgcttcct gtgctgtgtc aggctcatgg gctgaccccc     1680
gagcaagtgg tggctattgc ctctaatgga ggcaagcaag cccttgagac agtccagagg     1740
ctgttgccag tgctgtgcca ggcccacggg ctcacacccc agcaggtggt cgccatcgcc     1800
agtaacaacg ggggcaaaca ggcattggaa accgtccagc gcctgcttcc agtgctctgc     1860
caggcacacg gactgacacc cgaacaggtg gtggccattg catcccatga tgggggcaag     1920
caggccctgg agaccgtgca gagactcctg ccagtgttgt gccaagctca cggcctcacc     1980
cctcagcaag tcgtggccat cgcctcaaac gggggggggcc ggcctgcact ggagagcatt    2040 gttgccagt tatctcgccc tgatccggcg ttggccgcgt tgaccaacga ccacctcgtc      2100
gccttggcct gcctcggcgg gcgtcctgcg ctggatgcag tgaaaaaggg attgggggat     2160
cctatcagcc gttcccagct ggtgaagtcc gagctggagg agaagaaatc cgagttgagg     2220
cacaagctga agtacgtgcc ccacgagtac atcgagctga tcgagatcgc ccggaacagc     2280
acccaggacc gtatcctgga gatgaaggtg atggagttct tcatgaaggt gtacggctac     2340
aggggcaagc acctgggcgg ctccaggaag cccgacggcg ccatctacac cgtgggctcc     2400
cccatcgact acggcgtgat cgtggacacc aaggcctact ccggcggcta caacctgccc     2460
atcggccagg ccgacgaaat gcagaggtac gtggaggaga accagaccag gaacaagcac     2520
atcaaccgca cgagtggtg gaaggtgtac ccctccagcg tgaccgagtt caagttcctg      2580
ttcgtgtccg gccacttcaa gggcaactac aaggcccagc tgaccaggct gaaccacatc     2640
accaactgca acggcgccgt gctgtccgtg gaggagctcc tgatcggcgg cgagatgatc     2700
aaggccggca cctgaccct ggaggaggtg aggaggaagt tcaacaacgg cgagatcaac      2760
ttcgcggccg actgataa                                                   2778
```

<210> SEQ ID NO 5
<211> LENGTH: 49
<212> TYPE: DNA
<213> ORGANISM: artificial sequence
<220> FEATURE:
<223> OTHER INFORMATION: PD1-T3

<400> SEQUENCE: 5

```
tacctctgtg gggccatctc cctggccccc aaggcgcaga tcaaagaga         49
```

<210> SEQ ID NO 6
<211> LENGTH: 60
<212> TYPE: DNA
<213> ORGANISM: artificial sequence
<220> FEATURE:
<223> OTHER INFORMATION: 2A-element

<400> SEQUENCE: 6

```
tccggtgagg gcagaggaag tcttctaaca tgcggtgacg tggaggagaa tccgggcccc         60
```

<210> SEQ ID NO 7
<211> LENGTH: 1989
<212> TYPE: DNA
<213> ORGANISM: artificial sequence
<220> FEATURE:
<223> OTHER INFORMATION: apoptosis CAR

<400> SEQUENCE: 7

```
gctttgcctg tcactgcctt gctgcttcca cttgctctgt tgttgcacgc cgcaagaccc         60
gaggtcaagc tccaggaaag cggaccaggg ctggtggccc tagtcagtc attgagcgtc        120 acttgcaccg tcagcggcgt gtctctgccc gattacggcg tgagctggat cagacagccc        180
ccaaggaagg gactggagtg gctgggcgtc atctggggga gcgagactac ctactacaac        240
agcgccctga gagcaggct gaccatcatt aaggacaact ccaagtccca ggtctttctg        300
aaaatgaaca gcctgcagac tgatgacact gccatctact actgcgccaa gcattactac        360
tacgggggca gctacgctat ggactactgg gggcagggga cctctgtcac agtgtcaagt        420
ggcggaggag gcagtggcgg aggggggaagt ggggcggcg gcagcgacat ccagatgacc        480
cagacaacat ccagcctctc cgcctctctg ggcgacagag tgacaatcag ctgccgggcc        540
agtcaggaca tcagcaagta tctcaattgg taccagcaga accgacgg gacagtgaaa        600 ttgctgatct accacacatc caggctgcac tcaggagtcc ccagcaggtt ttccggctcc        660
ggctccggga cagattacag tctgaccatt tccaacctgg agcaggagga tattgccaca        720
tacttttgcc agcaaggcaa cactctgccc tataccttcg gcggaggcac aaaactggag        780
attactcggt cggatcccga gcccaaatct cctgacaaaa ctcacacatg cccaccgtgc        840
ccagcacctc ccgtggccgg cccgtcagtg ttcctcttcc ccccaaaacc caaggacacc        900
ctcatgatcg cccggacccc tgaggtcaca tgcgtggtgg tggacgtgag ccacgaggac        960
cctgaggtca agttcaactg gtacgtggac ggcgtggagg tgcataatgc caagacaaag       1020
ccgcgggagg agcagtacaa cagcacgtac cgtgtggtca gcgtcctcac cgtcctgcac       1080
caggactggc tgaatggcaa ggagtacaag tgcaaggtgt ccaacaaagc cctcccagcc       1140
cccatcgaga aaaccatctc caaagccaaa gggcagcccc gagaaccaca ggtgtacacc       1200
ctgcccccat cccgggatga gctgaccaag aaccaggtca gcctgacctg cctggtcaaa       1260
ggcttctatc ccagcgacat cgccgtggag tgggagagca atgggcaacc ggagaacaac       1320
tacaagacca cgcctcccgt gctggactcc gacggctcct tcttcctcta cagcaagctc       1380
```

```
accgtggaca agagcaggtg gcagcagggg aacgtgttct catgctccgt gatgcatgag    1440
gccctgcaca atcactatac ccagaaatct ctgagtctga gcccaggcaa gaaggatatt    1500
ttggggtggc tttgccttct tcttttgcca attccactaa ttgtttgggt gaagagaaag    1560
gaagtacaga aaacatgcag aaagcacaga aaggaaaacc aaggttctca tgaatctcca    1620
accttaaatc ctgaaacagt ggcaataaat ttatctgatg ttgacttgag taaatatatc    1680
accactattg ctggagtcat gacactaagt caagttaaag ctttgttcg aaagaatggt     1740 gtcaatgaag ccaaaataga tgagatcaag aatgacaatg tccaagacac agcagaacag    1800
aaagttcaac tgcttcgtaa ttggcatcaa cttcatggaa agaagaagc gtatgacaca     1860 ttgattgcag atctcaaaaa agccaatctt tgtactcttg cagagaaaat tcagactatc    1920
atcctcaagg acattactag tgactcagaa aattcaaact tcagaaatga aatccagagc    1980
ttggtcgaa                                                            1989

<210> SEQ ID NO 8
<211> LENGTH: 276
<212> TYPE: DNA
<213> ORGANISM: artificial sequence
<220> FEATURE:
<223> OTHER INFORMATION: BGH polyA

<400> SEQUENCE: 8
tctagagggc ccgtttaaac ccgctgatca gcctcgactg tgccttctag ttgccagcca      60
tctgttgttt gcccctcccc cgtgccttcc ttgaccctgg aaggtgccac tcccactgtc     120
ctttcctaat aaaatgagga aattgcatcg cattgtctga gtaggtgtca ttctattctg     180 ggggggtgggg tggggcagga cagcaagggg gaggattggg aagacaatag caggcatgct   240
ggggatgcgg tgggctctat gactagtggc gaattc                              276

<210> SEQ ID NO 9
<211> LENGTH: 1000
<212> TYPE: DNA
<213> ORGANISM: artificial sequence
<220> FEATURE:
<223> OTHER INFORMATION: Lck left homology

<400> SEQUENCE: 9 gggataggg gtgcctctgt gtgtgtgtgt gagagtgtgt gtgtgtaggg tgtgtatatg       60
tatagggtgt gtgtgagtgt gtgtgtgtga gagagtgtgt gtgtggcaga atagactgcg    120
gaggtggatt tcatcttgat atgaaaggtc tggaatgcat ggtacattaa actttgagga    180
cagcgctttc caagcactct gaggagcagc cctagagaag gaggagctgc agggactccg    240 gggcttcaa agtgagggcc ccactctgct tcaggcaaaa caggcacaca tttatcactt     300
tatctatgga gttctgcttg atttcatcag acaaaaaatt tccactgcta aaacaggcaa    360
ataaacaaaa aaaagttat ggccaacaga gtcactggag ggttttctgc tggggagaag     420
caagcccgtg tttgaaggaa ccctgtgaga tgactgtggg ctgtgtgagg ggaacagcgg    480
gggcttgatg gtggacttcg ggagcagaag cctctttctc agcctcctca gctagacagg    540
ggaattataa taggaggtgt ggcgtgcaca cctctccagt aggggagggt ctgataagtc    600
aggtctctcc caggcttggg aaagtgtgtg tcatctctag gaggtggtcc tcccaacaca    660
gggtactggc agagggagag ggaggggggca gaggcaggaa gtgggtaact agactaacaa   720
aggtgcctgt ggcggtttgc ccatcccagg tgggagggtg gggctagggc tcaggggccg    780
```

-continued

```
tgtgtgaatt tacttgtagc ctgagggctc agagggagca ccggtttgga gctgggaccc      840
cctattttag cttttctgtg gctggtgaat ggggatccca ggatctcaca atctcaggta      900
cttttggaac tttccagggc aaggccccat tatatctgat gttggggag cagatcttgg        960 gggagcccct tcagccccct cttccattcc ctcagggacc                             1000
```

```
<210> SEQ ID NO 10
<211> LENGTH: 219
<212> TYPE: PRT
<213> ORGANISM: artificial sequence
<220> FEATURE:
<223> OTHER INFORMATION: Interleukin-12 subunit alpha

<400> SEQUENCE: 10
```

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

```
<210> SEQ ID NO 11
<211> LENGTH: 328
<212> TYPE: PRT
<213> ORGANISM: artificial sequence
<220> FEATURE:
<223> OTHER INFORMATION: Interleukin-12 subunit beta

<400> SEQUENCE: 11
```

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

```
Thr Cys Asp Thr Pro Glu Glu Asp Gly Ile Thr Trp Thr Leu Asp Gln
 50                  55                  60
Ser Ser Glu Val Leu Gly Ser Gly Lys Thr Leu Thr Ile Gln Val Lys
 65                  70                  75                  80
Glu Phe Gly Asp Ala Gly Gln Tyr Thr Cys His Lys Gly Gly Glu Val
                 85                  90                  95
Leu Ser His Ser Leu Leu Leu His Lys Lys Glu Asp Gly Ile Trp
                100                 105                 110
Ser Thr Asp Ile Leu Lys Asp Gln Lys Glu Pro Lys Asn Lys Thr Phe
                115                 120                 125
Leu Arg Cys Glu Ala Lys Asn Tyr Ser Gly Arg Phe Thr Cys Trp Trp
130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Asn Lys Glu Tyr Glu Tyr Ser Val Glu
                180                 185                 190
Cys Gln Glu Asp Ser Ala Cys Pro Ala Ala Glu Glu Ser Leu Pro Ile
            195                 200                 205
Glu Val Met Val Asp Ala Val His Lys Leu Lys Tyr Glu Asn Tyr Thr
210                 215                 220
Ser Ser Phe Phe Ile Arg Asp Ile Ile Lys Pro Asp Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
                260                 265                 270
Phe Cys Val Gln Val Gln Gly Lys Ser Lys Arg Glu Lys Lys Asp Arg
            275                 280                 285
Val Phe Thr Asp Lys Thr Ser Ala Thr Val Ile Cys Arg Lys Asn Ala
            290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser
                325
```

<210> SEQ ID NO 12
<211> LENGTH: 1000
<212> TYPE: DNA
<213> ORGANISM: artificial sequence
<220> FEATURE:
<223> OTHER INFORMATION: lck right homology

<400> SEQUENCE: 12

```
ggctgtggct gcagctcaca cccggaagat gactggatgg aaaacatcga tgtgtgtgag      60
aactgccatt atcccatagt cccactggat ggcaagggca cggtaagagg cgagacaggg     120
gccttggtga gggagttggg tagagaatgc aacccaggag aaagaaatga ccagcactac     180
aggcccttga agaatagag tggccctctc ccctgaaata cagaaggaa aagaggccca      240
gagaggggaa gggaatctcc taagatcaca cagaaagtag ttggtaaact cagggataac     300
atctaaccag gctggagagg ctgagagcag agcaggggg aagggggcca gggtctgacc      360
caatcttctg ctttctgacc ccaccctcat ccccactcc acagctgctc atccgaaatg      420
gctctgaggt gcgggaccca ctggttacct acgaaggctc caatccgccg gcttccccac     480
```

```
tgcaaggtga ccccaggcag cagggcctga agacaaggc ctgcggatcc ctggctgttg      540
gcttccacct ctcccccacc tactttctcc ccggtcttgc cttccttgtc ccccaccctg      600
taactccagg cttcctgccg atcccagctc ggttctccct gatgccctt gtctttacag       660 acaacctggt tatcgctctg cacagctatg agccctctca cgacgagat ctgggctttg       720 agaaggggga acagctccgc atcctggagc agtgagtccc tctccacctt gctctggcgg      780
agtccgtgag ggagcggcga tctccgcgac ccgcagccct cctgcggccc ttgaccagct      840
cggggtggcc gcccttggga caaaattcga ggctcagtat tgctgagcca gggttggggg      900
aggctggctt aagggtgga gggtctttg agggagggtc tcaggtcgac ggctgagcga        960
gccacactga cccacctccg tggcgcagga gcggcgagtg                            1000
```

<210> SEQ ID NO 13
<211> LENGTH: 1992
<212> TYPE: DNA
<213> ORGANISM: artificial sequence
<220> FEATURE:
<223> OTHER INFORMATION: apoptosis CAR

<400> SEQUENCE: 13

```
atggctttgc ctgtcactgc cttgctgctt ccacttgctc tgttgttgca cgccgcaaga      60
cccgaggtca agctccagga aagcggacca gggctggtgg cccctagtca gtcattgagc      120
gtcacttgca ccgtcagcgg cgtgtctctg cccgattacg gcgtgagctg gatcagacag      180
cccccaagga agggactgga gtggctgggc gtcatctggg ggagcgagac tacctactac      240
aacagcgccc tgaagagcag gctgaccatc attaaggaca actccaagtc ccaggtcttt      300
ctgaaaatga acagcctgca gactgatgac actgccatct actactgcgc caagcattac      360
tactacgggg gcagctacgc tatggactac tggggggcagg ggacctctgt cacagtgtca      420
agtggcggag gaggcagtgg cggaggggga agtgggggcg gcggcagcga catccagatg      480
acccagacaa catccagcct ctccgcctct ctgggcgaca gagtgacaat cagctgccgg      540
gccagtcagg acatcagcaa gtatctcaat tggtaccagc agaaaccaga cgggacagtg      600
aaattgctga tctaccacac atccaggctg cactcaggag tccccagcag gttttccggc      660
tccggctccg ggacagatta cagtctgacc atttccaacc tggagcagga ggatattgcc      720
acatactttt gccagcaagg caacactctg ccctatacct cggcggagg cacaaaactg      780 gagattactc ggtcggatcc cgagcccaaa tctcctgaca aaactcacac atgcccaccg      840
tgcccagcac ctcccgtggc cggccgtca gtgttcctct ccccccaaa acccaaggac        900 accctcatga tcgcccggac ccctgaggtc acatgcgtgg tggtggacgt gagccacgag      960
gaccctgagg tcaagttcaa ctggtacgtg gacggcgtgg aggtgcataa tgccaagaca      1020
aagccgcggg aggagcagta caacagcacg taccgtgtgg tcagcgtcct caccgtcctg      1080
caccaggact ggctgaatgg caaggagtac aagtgcaagg tgtccaacaa agccctccca      1140
gcccccatcg agaaaaccat ctccaaagcc aaagggcagc ccgagaaacc acaggtgtac      1200
accctgcccc catcccggga tgagctgacc aagaaccagg tcagcctgac ctgcctggtc      1260
aaaggcttct atcccagcga catcgccgtg gagtgggaga gcaatgggca accggagaac      1320
aactacaaga ccacgcctcc cgtgctggac tccgacggct ccttcttcct ctacagcaag      1380
ctcaccgtgg acaagagcag gtggcagcag gggaacgtgt tctcatgctc cgtgatgcat      1440
gaggccctgc acaatcacta tacccagaaa tctctgagtc tgagcccagg caagaaggat      1500
```

```
attttggggt ggctttgcct tcttcttttg ccaattccac taattgtttg ggtgaagaga    1560
aaggaagtac agaaaacatg cagaaagcac agaaaggaaa accaaggttc tcatgaatct    1620
ccaaccttaa atcctgaaac agtggcaata aatttatctg atgttgactt gagtaaatat    1680
atcaccacta ttgctggagt catgacacta agtcaagtta aaggctttgt tcgaaagaat    1740
ggtgtcaatg aagccaaaat agatgagatc aagaatgaca atgtccaaga cacagcagaa    1800
cagaaagttc aactgcttcg taattggcat caacttcatg gaagaaaga agcgtatgac     1860 acattgattg cagatctcaa aaagccaat ctttgtactc ttgcagagaa aattcagact     1920
atcatcctca aggacattac tagtgactca gaaaattcaa acttcagaaa tgaaatccag    1980
agcttggtcg aa                                                         1992

<210> SEQ ID NO 14
<211> LENGTH: 1000
<212> TYPE: DNA
<213> ORGANISM: artificial sequence
<220> FEATURE:
<223> OTHER INFORMATION: Lck left homology

<400> SEQUENCE: 14
ctcataacaa ttctatgagg taggaacagt tatttactct attttccaaa taaggaaact     60
gggctcgccc aaggttccac aactaacatg tgtgtattat tgagcattta atttacacca   120
gggaagcagg ttgtggtggt gtgcacctgt tgtccagcta tttaggaggc tgaggtgaaa   180
ggatcacttg aacggaggag ttcaaatttg caatgtgcta tgattgtgcc tgtgaacagc   240
tgctgcactc cagcctgggc aacatagtga gatcccttat ctaaaacatt ttttttaagt   300
aaataatcag gtgggcacgg tggctcacgc ctgtaatcca gcactttggg aggctgaggc   360
gggcggatca cctgaggtca ggagttcaag accagcctga ccaacatgga gaaaccgtc    420 tctactaaaa atacaaaatt agcttggcgt ggtggtgcat gcctgtaatc ccagctactc   480
gagaagctga ggcaggagaa ttgtttgaac ctggggaggtg gaggttgcgg tgagccgaga   540
tcgcaccatt gcactccagc ctgggcaaca agagtgaaat tgcatctcaa aaaaaagaa    600 aaggaaataa tctataccag gcactccaag tggtgtgact gatattcaac aagtacctct   660
agtgtgacct taccattgat gaagaccaag attcttttgg attggtgctc acactgtgcc   720
agttaaatat tccgaacatt accccttgcct gtgggcttcc agtgcctgac cttgatgtcc   780
tttcacccat caacccgtag ggatgaccaa cccggaggtg attcagaacc tggagcgagg   840
ctaccgcatg gtgcgccctg acaactgtcc agaggagctg taccaactca tgaggctgtg   900
ctggaaggag cgcccagagg accggcccac ctttgactac ctgcgcagtg tgctggagga   960
cttcttcacg gccacagagg gccagtacca gcctcagcct                        1000

<210> SEQ ID NO 15
<211> LENGTH: 1000
<212> TYPE: DNA
<213> ORGANISM: artificial sequence
<220> FEATURE:
<223> OTHER INFORMATION: lck right homology

<400> SEQUENCE: 15
gaggccttga gaggccctgg ggttctcccc ctttctctcc agcctgactt ggggagatgg     60
agttcttgtg ccatagtcac atggcctatg cacatatgga ctctgcacat gaatcccacc   120
cacatgtgac acatatgcac cttgtgtctg tacgcgtgtc ctgtagttgc gtggactctg   180
cacatgtctt gtacatgtgt agcctgtgca tgtatgtctt ggacactgta caaggtaccc   240
```

```
ctttctggct ctcccatttc ctgagaccac agagagaggg gagaagcctg ggattgacag    300
aagcttctgc ccacctactt ttctttcctc agatcatcca gaagttcctc aagggccagg    360
actttatcta atacctctgt gtgctcctcc ttggtgcctg gcctggcaca catcaggagt    420
tcaataaatg tctgttgatg actgttgtac atctctttgc tgtccactct ttgtgggtgg    480
gcagtggggg ttaagaaaat ggtaattagg tcaccctgag ttggggtgaa agatgggatg    540
agtggatgtc tggaggctct gcagacccct tcaaatggga cagtgctcct cacccctccc    600
caaaggattc agggtgactc ctacctggaa tcccttaggg aatgggtgcg tcaaaggacc    660
ttcctcccca ttataaaagg gcaacagcat tttttactga ttcaagggct atatttgacc    720
tcagattttg ttttttttaag gctagtcaaa tgaagcggcg ggaatggagg aggaacaaat    780
aaatctgtaa ctatcctcag attttttttt tttttttgaga ctgggtctca cttttcatc    840 caggctggag tgcagtcgca tgatcacggc tcactgtagc ctcaacctct ccagctcaaa    900
tgctcctcct gtctcagcct cccgagtacc tgggactact ttcttgaggc caggaattca    960
agaacagagt aagatcctgg tctccaaaaa aagttttaaa                         1000
```

<210> SEQ ID NO 16  
<211> LENGTH: 936  
<212> TYPE: PRT  
<213> ORGANISM: artificial sequence  
<220> FEATURE:  
<223> OTHER INFORMATION: TALEN TRAC

<400> SEQUENCE: 16

```
Met Gly Asp Pro Lys Lys Lys Arg Lys Val Ile Asp Tyr Pro Tyr Asp
 1               5                  10                  15

Val Pro Asp Tyr Ala Ile Asp Ile Ala Asp Leu Arg Thr Leu Gly Tyr
             20                  25                  30

Ser Gln Gln Gln Glu Lys Ile Lys Pro Lys Val Arg Ser Thr Val
         35                  40                  45

Ala Gln His His Glu Ala Leu Val Gly His Gly Phe Thr His Ala His
     50                  55                  60

Ile Val Ala Leu Ser Gln His Pro Ala Ala Leu Gly Thr Val Ala Val
 65                  70                  75                  80

Lys Tyr Gln Asp Met Ile Ala Ala Leu Pro Glu Ala Thr His Glu Ala
                 85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Ala Ile Ala Ser Asn Gly Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
    210                 215                 220
```

-continued

```
Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
            245                 250                 255

Leu Cys Gln Ala His Gly Leu Thr Pro Glu Gln Val Val Ala Ile Ala
        260                 265                 270

Ser His Asp Gly Gly Lys Gln Ala Leu Glu Thr Val Gln Arg Leu Leu
    275                 280                 285

Pro Val Leu Cys Gln Ala His Gly Leu Thr Pro Glu Gln Val Val Ala
290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser Asn Ile Gly Gly Lys Gln Ala Leu Glu
    370                 375                 380

Thr Val Gln Ala Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Glu Gln Val Val Ala Ile Ala Ser Asn Ile Gly Gly Lys
        435                 440                 445

Gln Ala Leu Glu Thr Val Gln Ala Leu Leu Pro Val Leu Cys Gln Ala
    450                 455                 460

His Gly Leu Thr Pro Gln Gln Val Val Ala Ile Ala Ser Asn Asn Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser Asn
            500                 505                 510

Ile Gly Gly Lys Gln Ala Leu Glu Thr Val Gln Ala Leu Leu Pro Val
        515                 520                 525

Leu Cys Gln Ala His Gly Leu Thr Pro Gln Gln Val Val Ala Ile Ala
    530                 535                 540

Ser Asn Gly Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser Asn Ile Gly Gly Lys Gln Ala Leu Glu Thr Val Gln Ala
            580                 585                 590

Leu Leu Pro Val Leu Cys Gln Ala His Gly Leu Thr Pro Gln Gln Val
        595                 600                 605

Val Ala Ile Ala Ser Asn Gly Gly Gly Lys Gln Ala Leu Glu Thr Val
    610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
```

```
                        645                 650                 655
Thr Val Gln Arg Leu Leu Pro Val Leu Cys Gln Ala His Gly Leu Thr
                660                 665                 670
Pro Gln Gln Val Val Ala Ile Ala Ser Asn Gly Gly Arg Pro Ala
            675                 680                 685
Leu Glu Ser Ile Val Ala Gln Leu Ser Arg Pro Asp Pro Ala Leu Ala
        690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
                740                 745                 750
His Lys Leu Lys Tyr Val Pro His Glu Tyr Ile Glu Leu Ile Glu Ile
            755                 760                 765
Ala Arg Asn Ser Thr Gln Asp Arg Ile Leu Glu Met Lys Val Met Glu
        770                 775                 780
Phe Phe Met Lys Val Tyr Gly Tyr Arg Gly Lys His Leu Gly Gly Ser
785                 790                 795                 800
Arg Lys Pro Asp Gly Ala Ile Tyr Thr Val Gly Ser Pro Ile Asp Tyr
                805                 810                 815
Gly Val Ile Val Asp Thr Lys Ala Tyr Ser Gly Gly Tyr Asn Leu Pro
            820                 825                 830
Ile Gly Gln Ala Asp Glu Met Gln Arg Tyr Val Glu Glu Asn Gln Thr
        835                 840                 845
Arg Asn Lys His Ile Asn Pro Asn Glu Trp Trp Lys Val Tyr Pro Ser
    850                 855                 860
Ser Val Thr Glu Phe Lys Phe Leu Phe Val Ser Gly His Phe Lys Gly
865                 870                 875                 880
Asn Tyr Lys Ala Gln Leu Thr Arg Leu Asn His Ile Thr Asn Cys Asn
                885                 890                 895
Gly Ala Val Leu Ser Val Glu Glu Leu Leu Ile Gly Gly Glu Met Ile
            900                 905                 910
Lys Ala Gly Thr Leu Thr Leu Glu Glu Val Arg Arg Lys Phe Asn Asn
        915                 920                 925
Gly Glu Ile Asn Phe Ala Ala Asp
    930                 935
```

<210> SEQ ID NO 17
<211> LENGTH: 942
<212> TYPE: PRT
<213> ORGANISM: artificial sequence
<220> FEATURE:
<223> OTHER INFORMATION: TALEN TRAC

<400> SEQUENCE: 17

```
Met Gly Asp Pro Lys Lys Lys Arg Lys Val Ile Asp Lys Glu Thr Ala
1               5                   10                  15
Ala Ala Lys Phe Glu Arg Gln His Met Asp Ser Ile Asp Ile Ala Asp
                20                  25                  30
Leu Arg Thr Leu Gly Tyr Ser Gln Gln Gln Gln Glu Lys Ile Lys Pro
            35                  40                  45
Lys Val Arg Ser Thr Val Ala Gln His His Glu Ala Leu Val Gly His
        50                  55                  60
Gly Phe Thr His Ala His Ile Val Ala Leu Ser Gln His Pro Ala Ala
```

-continued

```
                65                  70                  75                  80
Leu Gly Thr Val Ala Val Lys Tyr Gln Asp Met Ile Ala Ala Leu Pro
                    85                  90                  95

Glu Ala Thr His Glu Ala Ile Val Gly Val Gly Lys Gln Trp Ser Gly
                100                 105                 110

Ala Arg Ala Leu Glu Ala Leu Leu Thr Val Ala Gly Glu Leu Arg Gly
                115                 120                 125

Pro Pro Leu Gln Leu Asp Thr Gly Gln Leu Leu Lys Ile Ala Lys Arg
                130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Glu Gln Val Val Ala Ile Ala
                165                 170                 175

Ser His Asp Gly Gly Lys Gln Ala Leu Glu Thr Val Gln Arg Leu Leu
                180                 185                 190

Pro Val Leu Cys Gln Ala His Gly Leu Thr Pro Gln Gln Val Val Ala
                195                 200                 205

Ile Ala Ser Asn Gly Gly Lys Gln Ala Leu Glu Thr Val Gln Arg
                210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Glu
                260                 265                 270

Gln Val Val Ala Ile Ala Ser Asn Ile Gly Gly Lys Gln Ala Leu Glu
                275                 280                 285

Thr Val Gln Ala Leu Leu Pro Val Leu Cys Gln Ala His Gly Leu Thr
                290                 295                 300

Pro Gln Gln Val Val Ala Ile Ala Ser Asn Asn Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Glu Gln Val Val Ala Ile Ala Ser His Asp Gly Gly Lys
                340                 345                 350

Gln Ala Leu Glu Thr Val Gln Arg Leu Leu Pro Val Leu Cys Gln Ala
                355                 360                 365

His Gly Leu Thr Pro Gln Gln Val Val Ala Ile Ala Ser Asn Gly Gly
                370                 375                 380

Gly Lys Gln Ala Leu Glu Thr Val Gln Arg Leu Leu Pro Val Leu Cys
385                 390                 395                 400

Gln Ala His Gly Leu Thr Pro Gln Gln Val Val Ala Ile Ala Ser Asn
                405                 410                 415

Asn Gly Gly Lys Gln Ala Leu Glu Thr Val Gln Arg Leu Leu Pro Val
                420                 425                 430

Leu Cys Gln Ala His Gly Leu Thr Pro Gln Gln Val Val Ala Ile Ala
                435                 440                 445

Ser Asn Asn Gly Gly Lys Gln Ala Leu Glu Thr Val Gln Arg Leu Leu
                450                 455                 460

Pro Val Leu Cys Gln Ala His Gly Leu Thr Pro Gln Gln Val Val Ala
465                 470                 475                 480

Ile Ala Ser Asn Gly Gly Gly Lys Gln Ala Leu Glu Thr Val Gln Arg
                485                 490                 495
```

```
Leu Leu Pro Val Leu Cys Gln Ala His Gly Leu Thr Pro Glu Gln Val
            500                 505                 510

Val Ala Ile Ala Ser Asn Ile Gly Gly Lys Gln Ala Leu Glu Thr Val
            515                 520                 525

Gln Ala Leu Leu Pro Val Leu Cys Gln Ala His Gly Leu Thr Pro Glu
            530                 535                 540

Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Glu Gln Val Val Ala Ile Ala Ser Asn Ile Gly Gly Lys Gln Ala
                    580                 585                 590

Leu Glu Thr Val Gln Ala Leu Leu Pro Val Leu Cys Gln Ala His Gly
                595                 600                 605

Leu Thr Pro Glu Gln Val Val Ala Ile Ala Ser His Asp Gly Gly Lys
            610                 615                 620

Gln Ala Leu Glu Thr Val Gln Arg Leu Leu Pro Val Leu Cys Gln Ala
625                 630                 635                 640

His Gly Leu Thr Pro Gln Gln Val Val Ala Ile Ala Ser Asn Asn Gly
                645                 650                 655

Gly Lys Gln Ala Leu Glu Thr Val Gln Arg Leu Leu Pro Val Leu Cys
                660                 665                 670

Gln Ala His Gly Leu Thr Pro Gln Gln Val Val Ala Ile Ala Ser Asn
            675                 680                 685

Gly Gly Gly Arg Pro Ala Leu Glu Ser Ile Val Ala Gln Leu Ser Arg
            690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
                725                 730                 735

Gly Asp Pro Ile Ser Arg Ser Gln Leu Val Lys Ser Glu Leu Glu Glu
                740                 745                 750

Lys Lys Ser Glu Leu Arg His Lys Leu Lys Tyr Val Pro His Glu Tyr
            755                 760                 765

Ile Glu Leu Ile Glu Ile Ala Arg Asn Ser Thr Gln Asp Arg Ile Leu
            770                 775                 780

Glu Met Lys Val Met Glu Phe Phe Met Lys Val Tyr Gly Tyr Arg Gly
785                 790                 795                 800

Lys His Leu Gly Gly Ser Arg Lys Pro Asp Gly Ala Ile Tyr Thr Val
                805                 810                 815

Gly Ser Pro Ile Asp Tyr Gly Val Ile Val Asp Thr Lys Ala Tyr Ser
                820                 825                 830

Gly Gly Tyr Asn Leu Pro Ile Gly Gln Ala Asp Glu Met Gln Arg Tyr
            835                 840                 845

Val Glu Glu Asn Gln Thr Arg Asn Lys His Ile Asn Pro Asn Glu Trp
850                 855                 860

Trp Lys Val Tyr Pro Ser Ser Val Thr Glu Phe Lys Phe Leu Phe Val
865                 870                 875                 880

Ser Gly His Phe Lys Gly Asn Tyr Lys Ala Gln Leu Thr Arg Leu Asn
                885                 890                 895

His Ile Thr Asn Cys Asn Gly Ala Val Leu Ser Val Glu Glu Leu Leu
            900                 905                 910
```

Ile Gly Gly Glu Met Ile Lys Ala Gly Thr Leu Thr Leu Glu Glu Val
915                 920                 925

Arg Arg Lys Phe Asn Asn Gly Glu Ile Asn Phe Ala Ala Asp
930                 935                 940

<210> SEQ ID NO 18
<211> LENGTH: 913
<212> TYPE: PRT
<213> ORGANISM: artificial sequence
<220> FEATURE:
<223> OTHER INFORMATION: TALEN CD25

<400> SEQUENCE: 18

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Gly Gly
        195                 200                 205

Gly Lys Gln Ala Leu Glu Thr Val Gln Arg Leu Leu Pro Val Leu Cys
210                 215                 220

Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
290                 295                 300

Ile Ala Ser Asn Gly Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

-continued

```
Val Ala Ile Ala Ser Asn Gly Gly Lys Gln Ala Leu Glu Thr Val
                340                 345                 350

Gln Arg Leu Leu Pro Val Leu Cys Gln Ala His Gly Leu Thr Pro Gln
    355                 360                 365

Gln Val Val Ala Ile Ala Ser Asn Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Gln Gln Val Val Ala Ile Ala Ser Asn Gly Gly Lys Gln Ala
                405                 410                 415

Leu Glu Thr Val Gln Arg Leu Leu Pro Val Leu Cys Gln Ala His Gly
                420                 425                 430

Leu Thr Pro Gln Gln Val Val Ala Ile Ala Ser Asn Asn Gly Gly Lys
                435                 440                 445

Gln Ala Leu Glu Thr Val Gln Arg Leu Leu Pro Val Leu Cys Gln Ala
    450                 455                 460

His Gly Leu Thr Pro Gln Gln Val Val Ala Ile Ala Ser Asn Asn Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Gln Gln Val Val Ala Ile Ala Ser Asn
                500                 505                 510

Gly Gly Gly Lys Gln Ala Leu Glu Thr Val Gln Arg Leu Leu Pro Val
                515                 520                 525

Leu Cys Gln Ala His Gly Leu Thr Pro Gln Gln Val Val Ala Ile Ala
530                 535                 540

Ser Asn Gly Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Gly Gly Gly Lys Gln Ala Leu Glu Thr Val Gln Arg
                580                 585                 590

Leu Leu Pro Val Leu Cys Gln Ala His Gly Leu Thr Pro Gln Gln Val
                595                 600                 605

Val Ala Ile Ala Ser Asn Gly Gly Gly Lys Gln Ala Leu Glu Thr Val
                610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
                645                 650                 655

Thr Val Gln Arg Leu Leu Pro Val Leu Cys Gln Ala His Gly Leu Thr
                660                 665                 670

Pro Gln Gln Val Val Ala Ile Ala Ser Asn Gly Gly Gly Arg Pro Ala
                675                 680                 685

Leu Glu Ser Ile Val Ala Gln Leu Ser Arg Pro Asp Pro Ser Gly Ser
                690                 695                 700

Gly Ser Gly Gly Asp Pro Ile Ser Arg Ser Gln Leu Val Lys Ser Glu
705                 710                 715                 720

Leu Glu Glu Lys Lys Ser Glu Leu Arg His Lys Leu Lys Tyr Val Pro
                725                 730                 735

His Glu Tyr Ile Glu Leu Ile Glu Ile Ala Arg Asn Ser Thr Gln Asp
                740                 745                 750

Arg Ile Leu Glu Met Lys Val Met Glu Phe Phe Met Lys Val Tyr Gly
```

-continued

```
                755                 760                 765
Tyr Arg Gly Lys His Leu Gly Gly Ser Arg Lys Pro Asp Gly Ala Ile
            770                 775                 780

Tyr Thr Val Gly Ser Pro Ile Asp Tyr Gly Val Ile Val Asp Thr Lys
785                 790                 795                 800

Ala Tyr Ser Gly Gly Tyr Asn Leu Pro Ile Gly Gln Ala Asp Glu Met
                805                 810                 815

Gln Arg Tyr Val Glu Glu Asn Gln Thr Arg Asn Lys His Ile Asn Pro
            820                 825                 830

Asn Glu Trp Trp Lys Val Tyr Pro Ser Ser Val Thr Glu Phe Lys Phe
                835                 840                 845

Leu Phe Val Ser Gly His Phe Lys Gly Asn Tyr Lys Ala Gln Leu Thr
            850                 855                 860

Arg Leu Asn His Ile Thr Asn Cys Asn Gly Ala Val Leu Ser Val Glu
865                 870                 875                 880

Glu Leu Leu Ile Gly Gly Glu Met Ile Lys Ala Gly Thr Leu Thr Leu
                885                 890                 895

Glu Glu Val Arg Arg Lys Phe Asn Asn Gly Glu Ile Asn Phe Ala Ala
            900                 905                 910

Asp

<210> SEQ ID NO 19
<211> LENGTH: 913
<212> TYPE: PRT
<213> ORGANISM: artificial sequence
<220> FEATURE:
<223> OTHER INFORMATION: TALEN CD25

<400> SEQUENCE: 19

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser Asn Ile Gly Gly Lys
                165                 170                 175

Gln Ala Leu Glu Thr Val Gln Ala Leu Leu Pro Val Leu Cys Gln Ala
            180                 185                 190

His Gly Leu Thr Pro Glu Gln Val Val Ala Ile Ala Ser His Asp Gly
        195                 200                 205
```

```
Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser Asn
225                 230                 235                 240

Ile Gly Gly Lys Gln Ala Leu Glu Thr Val Gln Ala Leu Leu Pro Val
                245                 250                 255

Leu Cys Gln Ala His Gly Leu Thr Pro Gln Gln Val Val Ala Ile Ala
        260                 265                 270

Ser Asn Asn Gly Gly Lys Gln Ala Leu Glu Thr Val Gln Arg Leu Leu
    275                 280                 285

Pro Val Leu Cys Gln Ala His Gly Leu Thr Pro Gln Gln Val Val Ala
290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser Asn Ile Gly Gly Lys Gln Ala Leu Glu Thr Val
        340                 345                 350

Gln Ala Leu Leu Pro Val Leu Cys Gln Ala His Gly Leu Thr Pro Gln
    355                 360                 365

Gln Val Val Ala Ile Ala Ser Asn Asn Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Gln Gln Val Val Ala Ile Ala Ser Asn Asn Gly Gly Lys Gln Ala
                405                 410                 415

Leu Glu Thr Val Gln Arg Leu Leu Pro Val Leu Cys Gln Ala His Gly
        420                 425                 430

Leu Thr Pro Glu Gln Val Val Ala Ile Ala Ser Asn Ile Gly Gly Lys
    435                 440                 445

Gln Ala Leu Glu Thr Val Gln Ala Leu Leu Pro Val Leu Cys Gln Ala
450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
                485                 490                 495

Gln Ala His Gly Leu Thr Pro Gln Gln Val Val Ala Ile Ala Ser Asn
        500                 505                 510

Asn Gly Gly Lys Gln Ala Leu Glu Thr Val Gln Arg Leu Leu Pro Val
    515                 520                 525

Leu Cys Gln Ala His Gly Leu Thr Pro Glu Gln Val Val Ala Ile Ala
530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
        580                 585                 590

Leu Leu Pro Val Leu Cys Gln Ala His Gly Leu Thr Pro Gln Gln Val
    595                 600                 605

Val Ala Ile Ala Ser Asn Gly Gly Gly Lys Gln Ala Leu Glu Thr Val
610                 615                 620
```

```
Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
            645                 650                 655

Thr Val Gln Ala Leu Leu Pro Val Leu Cys Gln Ala His Gly Leu Thr
        660                 665                 670

Pro Gln Gln Val Val Ala Ile Ala Ser Asn Gly Gly Arg Pro Ala
    675                 680                 685

Leu Glu Ser Ile Val Ala Gln Leu Ser Arg Pro Asp Pro Ser Gly Ser
690                 695                 700

Gly Ser Gly Gly Asp Pro Ile Ser Arg Ser Gln Leu Val Lys Ser Glu
705                 710                 715                 720

Leu Glu Glu Lys Lys Ser Glu Leu Arg His Lys Leu Lys Tyr Val Pro
                725                 730                 735

His Glu Tyr Ile Glu Leu Ile Glu Ile Ala Arg Asn Ser Thr Gln Asp
                740                 745                 750

Arg Ile Leu Glu Met Lys Val Met Glu Phe Phe Met Lys Val Tyr Gly
        755                 760                 765

Tyr Arg Gly Lys His Leu Gly Gly Ser Arg Lys Pro Asp Gly Ala Ile
770                 775                 780

Tyr Thr Val Gly Ser Pro Ile Asp Tyr Gly Val Ile Val Asp Thr Lys
785                 790                 795                 800

Ala Tyr Ser Gly Gly Tyr Asn Leu Pro Ile Gly Gln Ala Asp Glu Met
                805                 810                 815

Gln Arg Tyr Val Glu Glu Asn Gln Thr Arg Asn Lys His Ile Asn Pro
            820                 825                 830

Asn Glu Trp Trp Lys Val Tyr Pro Ser Ser Val Thr Glu Phe Lys Phe
        835                 840                 845

Leu Phe Val Ser Gly His Phe Lys Gly Asn Tyr Lys Ala Gln Leu Thr
850                 855                 860

Arg Leu Asn His Ile Thr Asn Cys Asn Gly Ala Val Leu Ser Val Glu
865                 870                 875                 880

Glu Leu Leu Ile Gly Gly Glu Met Ile Lys Ala Gly Thr Leu Thr Leu
                885                 890                 895

Glu Glu Val Arg Arg Lys Phe Asn Asn Gly Glu Ile Asn Phe Ala Ala
            900                 905                 910

Asp

<210> SEQ ID NO 20
<211> LENGTH: 936
<212> TYPE: PRT
<213> ORGANISM: artificial sequence
<220> FEATURE:
<223> OTHER INFORMATION: TALEN PD1

<400> SEQUENCE: 20

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
```

```
                65                  70                  75                  80
Lys Tyr Gln Asp Met Ile Ala Ala Leu Pro Glu Ala Thr His Glu Ala
                    85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
                115                 120                 125

Thr Gly Gln Leu Leu Lys Ile Ala Lys Arg Gly Gly Val Thr Ala Val
            130                 135                 140

Glu Ala Val His Ala Trp Arg Asn Ala Leu Thr Gly Ala Pro Leu Asn
145                 150                 155                 160

Leu Thr Pro Glu Gln Val Ala Ile Ala Ser Lys Leu Gly Gly Lys
                165                 170                 175

Gln Ala Leu Glu Thr Val Gln Ala Leu Leu Pro Val Leu Cys Gln Ala
                180                 185                 190

His Gly Leu Thr Pro Glu Gln Val Val Ala Ile Ala Ser His Asp Gly
                195                 200                 205

Gly Lys Gln Ala Leu Glu Thr Val Gln Arg Leu Leu Pro Val Leu Cys
            210                 215                 220

Gln Ala His Gly Leu Thr Pro Glu Gln Val Val Ala Ile Ala Ser His
225                 230                 235                 240

Asp Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
                260                 265                 270

Ser Asn Gly Gly Gly Lys Gln Ala Leu Glu Thr Val Gln Arg Leu Leu
            275                 280                 285

Pro Val Leu Cys Gln Ala His Gly Leu Thr Pro Glu Gln Val Val Ala
290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Gly Gly Gly Lys Gln Ala Leu Glu Thr Val
                340                 345                 350

Gln Arg Leu Leu Pro Val Leu Cys Gln Ala His Gly Leu Thr Pro Gln
            355                 360                 365

Gln Val Val Ala Ile Ala Ser Tyr Lys Gly Gly Lys Gln Ala Leu Glu
370                 375                 380

Thr Val Gln Arg Leu Leu Pro Val Leu Cys Gln Ala His Gly Leu Thr
385                 390                 395                 400

Pro Gln Gln Val Val Ala Ile Ala Ser Asn Gly Gly Lys Gln Ala
                405                 410                 415

Leu Glu Thr Val Gln Arg Leu Leu Pro Val Leu Cys Gln Ala His Gly
                420                 425                 430

Leu Thr Pro Gln Gln Val Val Ala Ile Ala Ser Asn Gly Gly Lys
            435                 440                 445

Gln Ala Leu Glu Thr Val Gln Arg Leu Leu Pro Val Leu Cys Gln Ala
            450                 455                 460

His Gly Leu Thr Pro Gln Gln Val Val Ala Ile Ala Ser Asn Asn Gly
465                 470                 475                 480

Gly Lys Gln Ala Leu Glu Thr Val Gln Arg Leu Leu Pro Val Leu Cys
            485                 490                 495
```

```
Gln Ala His Gly Leu Thr Pro Gln Gln Val Ala Ile Ala Ser Asn
            500                 505                 510

Asn Gly Gly Lys Gln Ala Leu Glu Thr Val Gln Arg Leu Leu Pro Val
        515                 520                 525

Leu Cys Gln Ala His Gly Leu Thr Pro Gln Gln Val Ala Ile Ala
    530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
            565                 570                 575

Ile Ala Ser His Asp Gly Gly Lys Gln Ala Leu Glu Thr Val Gln Arg
            580                 585                 590

Leu Leu Pro Val Leu Cys Gln Ala His Gly Leu Thr Pro Glu Gln Val
                595                 600                 605

Val Ala Ile Ala Ser His Asp Gly Gly Lys Gln Ala Leu Glu Thr Val
            610                 615                 620

Gln Arg Leu Leu Pro Val Leu Cys Gln Ala His Gly Leu Thr Pro Glu
625                 630                 635                 640

Gln Val Val Ala Ile Ala Ser Asn Ile Gly Gly Lys Gln Ala Leu Glu
                645                 650                 655

Thr Val Gln Ala Leu Leu Pro Val Leu Cys Gln Ala His Gly Leu Thr
            660                 665                 670

Pro Gln Gln Val Val Ala Ile Ala Ser Asn Gly Gly Gly Arg Pro Ala
            675                 680                 685

Leu Glu Ser Ile Val Ala Gln Leu Ser Arg Pro Asp Pro Ala Leu Ala
            690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
            850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910
```

```
Lys Ala Gly Thr Leu Thr Leu Glu Glu Val Arg Arg Lys Phe Asn Asn
            915                 920                 925

Gly Glu Ile Asn Phe Ala Ala Asp
        930                 935

<210> SEQ ID NO 21
<211> LENGTH: 941
<212> TYPE: PRT
<213> ORGANISM: artificial sequence
<220> FEATURE:
<223> OTHER INFORMATION: TALEN PD1

<400> SEQUENCE: 21

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125

Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Glu Gln Val Val Ala Ile Ala
                165                 170                 175

Ser His Asp Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
        195                 200                 205

Ile Ala Ser Asn Gly Gly Gly Lys Gln Ala Leu Glu Thr Val Gln Arg
    210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Gln
            260                 265                 270

Gln Val Val Ala Ile Ala Ser Asn Gly Gly Gly Lys Gln Ala Leu Glu
        275                 280                 285

Thr Val Gln Arg Leu Leu Pro Val Leu Cys Gln Ala His Gly Leu Thr
    290                 295                 300

Pro Gln Gln Val Val Ala Ile Ala Ser Asn Gly Gly Gly Lys Gln Ala
305                 310                 315                 320

Leu Glu Thr Val Gln Arg Leu Leu Pro Val Leu Cys Gln Ala His Gly
                325                 330                 335
```

```
Leu Thr Pro Gln Gln Val Val Ala Ile Ala Ser Asn Gly Gly Lys
            340                 345                 350

Gln Ala Leu Glu Thr Val Gln Arg Leu Leu Pro Val Leu Cys Gln Ala
        355                 360                 365

His Gly Leu Thr Pro Gln Gln Val Val Ala Ile Ala Ser Asn Asn Gly
    370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
            405                 410                 415

Ile Gly Gly Lys Gln Ala Leu Glu Thr Val Gln Ala Leu Leu Pro Val
        420                 425                 430

Leu Cys Gln Ala His Gly Leu Thr Pro Gln Gln Val Val Ala Ile Ala
        435                 440                 445

Ser Asn Gly Gly Gly Lys Gln Ala Leu Glu Thr Val Gln Arg Leu Leu
    450                 455                 460

Pro Val Leu Cys Gln Ala His Gly Leu Thr Pro Glu Gln Val Val Ala
465                 470                 475                 480

Ile Ala Ser His Asp Gly Gly Lys Gln Ala Leu Glu Thr Val Gln Arg
            485                 490                 495

Leu Leu Pro Val Leu Cys Gln Ala His Gly Leu Thr Pro Gln Gln Val
                500                 505                 510

Val Ala Ile Ala Ser Asn Gly Gly Gly Lys Gln Ala Leu Glu Thr Val
        515                 520                 525

Gln Arg Leu Leu Pro Val Leu Cys Gln Ala His Gly Leu Thr Pro Gln
530                 535                 540

Gln Val Val Ala Ile Ala Ser Asn Asn Gly Gly Lys Gln Ala Leu Glu
545                 550                 555                 560

Thr Val Gln Arg Leu Leu Pro Val Leu Cys Gln Ala His Gly Leu Thr
            565                 570                 575

Pro Glu Gln Val Val Ala Ile Ala Ser Asn Gly Gly Lys Gln Ala Leu
        580                 585                 590

Glu Thr Val Gln Arg Leu Leu Pro Val Leu Cys Gln Ala His Gly Leu
        595                 600                 605

Thr Pro Gln Gln Val Val Ala Ile Ala Ser Asn Asn Gly Gly Lys Gln
    610                 615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser His Asp Gly Gly
            645                 650                 655

Lys Gln Ala Leu Glu Thr Val Gln Arg Leu Leu Pro Val Leu Cys Gln
                660                 665                 670

Ala His Gly Leu Thr Pro Gln Gln Val Val Ala Ile Ala Ser Asn Gly
        675                 680                 685

Gly Gly Arg Pro Ala Leu Glu Ser Ile Val Ala Gln Leu Ser Arg Pro
    690                 695                 700

Asp Pro Ala Leu Ala Ala Leu Thr Asn Asp His Leu Val Ala Leu Ala
705                 710                 715                 720

Cys Leu Gly Gly Arg Pro Ala Leu Asp Ala Val Lys Lys Gly Leu Gly
            725                 730                 735

Asp Pro Ile Ser Arg Ser Gln Leu Val Lys Ser Glu Leu Glu Glu Lys
                740                 745                 750

Lys Ser Glu Leu Arg His Lys Leu Lys Tyr Val Pro His Glu Tyr Ile
```

|   |   |   |   |   |   |   |   |   |   |   |   |
|---|---|---|---|---|---|---|---|---|---|---|---|
|   |   | 755 |   |   |   | 760 |   |   |   | 765 |   |

Glu Leu Ile Glu Ile Ala Arg Asn Ser Thr Gln Asp Arg Ile Leu Glu
 770             775                 780

Met Lys Val Met Glu Phe Phe Met Lys Val Tyr Gly Tyr Arg Gly Lys
785             790              795                 800

His Leu Gly Gly Ser Arg Lys Pro Asp Gly Ala Ile Tyr Thr Val Gly
             805                 810                 815

Ser Pro Ile Asp Tyr Gly Val Ile Val Asp Thr Lys Ala Tyr Ser Gly
         820                 825                 830

Gly Tyr Asn Leu Pro Ile Gly Gln Ala Asp Glu Met Gln Arg Tyr Val
     835                 840                 845

Glu Glu Asn Gln Thr Arg Asn Lys His Ile Asn Pro Asn Glu Trp Trp
 850             855                 860

Lys Val Tyr Pro Ser Ser Val Thr Glu Phe Lys Phe Leu Phe Val Ser
865             870              875                 880

Gly His Phe Lys Gly Asn Tyr Lys Ala Gln Leu Thr Arg Leu Asn His
             885                 890                 895

Ile Thr Asn Cys Asn Gly Ala Val Leu Ser Val Glu Glu Leu Leu Ile
         900                 905                 910

Gly Gly Glu Met Ile Lys Ala Gly Thr Leu Thr Leu Glu Glu Val Arg
     915                 920                 925

Arg Lys Phe Asn Asn Gly Glu Ile Asn Phe Ala Ala Asp
 930             935                 940

<210> SEQ ID NO 22
<211> LENGTH: 2814
<212> TYPE: DNA
<213> ORGANISM: artificial sequence
<220> FEATURE:
<223> OTHER INFORMATION: TALEN TRAC pCLS11370

<400> SEQUENCE: 22

| atgggcgatc | ctaaaaagaa | acgtaaggtc | atcgattacc | catacgatgt | tccagattac |   60 |
| gctatcgata | tcgccgatct | acgcacgctc | ggctacagcc | agcagcaaca | ggagaagatc |  120 |
| aaaccgaagg | ttcgttcgac | agtggcgcag | caccacgagg | cactggtcgg | ccacgggttt |  180 |
| acacacgcgc | acatcgttgc | gttaagccaa | caccggcag | cgttagggac | cgtcgctgtc |  240 |
| aagtatcagg | acatgatcgc | agcgttgcca | gaggcgacac | acgaagcgat | cgttggcgtc |  300 |
| ggcaaacagt | ggtccggcgc | acgcgctctg | gaggccttgc | tcacggtggc | gggagagttg |  360 |
| agaggtccac | cgttacagtt | ggacacaggc | caacttctca | agattgcaaa | acgtggcggc |  420 |
| gtgaccgcag | tggaggcagt | gcatgcatgg | cgcaatgcac | tgacgggtgc | cccgctcaac |  480 |
| ttgacccccc | agcaggtggt | ggccatcgcc | agcaatggcg | gtggcaagca | ggcgctggag |  540 |
| acggtccagc | ggctgttgcc | ggtgctgtgc | caggcccacg | gcttgacccc | ccagcaggtg |  600 |
| gtggccatcg | ccagcaataa | tggtggcaag | caggcgctgg | agacggtcca | gcggctgttg |  660 |
| ccggtgctgt | gccaggccca | cggcttgacc | ccccagcagg | tggtggccat | cgccagcaat |  720 |
| ggcggtggca | agcaggcgct | ggagacggtc | agcggctgt | tgccggtgct | gtgccaggcc |  780 |
| cacggcttga | ccccggagca | ggtggtggcc | atcgccagcc | acgatggcgg | caagcaggcg |  840 |
| ctggagacgg | tccagcggct | gttgccggtg | ctgtgccagg | cccacggctt | gaccccggag |  900 |
| caggtggtgg | ccatcgccag | ccacgatggc | ggcaagcagg | cgctggagac | ggtccagcgg |  960 |
| ctgttgccgg | tgctgtgcca | ggcccacggc | ttgaccccgg | agcaggtggt | ggccatcgcc | 1020 |

```
agccacgatg gcggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccggagcagg tggtggccat cgccagccac gatggcggca agcaggcgct ggagacggtc    1260
cagcggctgt tgccggtgct gtgccaggcc cacggcttga ccccggagca ggtggtggcc    1320
atcgccagca atattggtgg caagcaggcg ctggagacgg tgcaggcgct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt tgccggtgct gtgccaggcc    1800
cacggcttga ccccccagca ggtggtggcc atcgccagca atggcggtgg caagcaggcg    1860
ctggagacgt ccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatga gttcttcat gaaggtgtac ggctacaggg gcaagcacct gggcggctcc    2400
aggaagcccg acggcgccat ctacaccgtg gcctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca cccccaacga gtggtggaag    2580
gtgtaccccc tccagcgtga ccgagttcaag ttcctgttcg tgtccggcca cttcaagggc    2640
aactacaagg cccagctgac caggctgaac cacatcacca ctgcaacgg cgccgtgctg    2700 tccgtggagc tctcctgat cggcggcgag atgatcaagg ccggcaccct gacccctggag    2760 gaggtgagga ggaagttcaa caacggcgag atcaacttcg cggccgactg ataa          2814
```

<210> SEQ ID NO 23
<211> LENGTH: 2832
<212> TYPE: DNA
<213> ORGANISM: artificial sequence
<220> FEATURE:
<223> OTHER INFORMATION: TALEN TRAC pCLS11369

<400> SEQUENCE: 23

```
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
```

```
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccggag caggtggtgg ccatcgccag ccacgatggc     540
ggcaagcagg cgctggagac ggtccagcgg ctgttgccgg tgctgtgcca ggcccacggc     600
ttgacccccc agcaggtggt ggccatcgcc agcaatggcg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagcaat     840
attggtggca agcaggcgct ggagacggtg caggcgctgt gccggtgct gtgccaggcc      900 cacggcttga ccccccagca ggtggtggcc atcgccagca ataatggtgg caagcaggcg     960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgaccccc agcaggtggt ggccatcgcc     1140
agcaatggcg gtggcaagca ggcgctggag acggtccagc ggctgttgcc ggtgctgtgc    1200
caggcccacg gcttgacccc cagcaggtg gtggccatcg ccagcaataa tggtggcaag     1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccggagcagg tggtggccat cgccagccac    1860 gatgcggca agcaggcgct ggagacggtc agcggctgt tgccggtgct gtgccaggcc      1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttgcc gcgttgacca acgaccacct cgtcgccttg      2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag      2280 ctgaagtacg tgcccacga gtacatcgag ctgatcgaga tcgcccggaa cagcacccag     2340
gaccgtatcc tggagatgaa ggtgatggag ttcttcatga aggtgtacgg ctacagggc      2400 aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgaca aaatgcagag gtacgtggag gagaaccaga ccaggaacaa gcacatcaac    2580
cccaacgagt ggtggaaggt gtacccctcc agcgtgaccg agttcaagtt cctgttcgtg    2640
```

```
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760
ggcaccctga ccctggagga ggtgaggagg aagttcaaca acggcgagat caacttcgcg    2820
gccgactgat aa                                                        2832

<210> SEQ ID NO 24
<211> LENGTH: 2745
<212> TYPE: DNA
<213> ORGANISM: artificial sequence
<220> FEATURE:
<223> OTHER INFORMATION: TALEN CD25 pCLS30480

<400> SEQUENCE: 24
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa cgtggcggc     420 gtgaccgcag tggaggcagt gcatgcatgg cgcaatgcac tgacgggtgc cccgctcaac     480
ttgacccccc agcaggtggt ggccatcgcc agcaataatg gtggcaagca ggcgctggag     540
acggtccagc ggctgttgcc ggtgctgtgc caggcccacg gcttgacccc ccagcaggtg     600
gtggccatcg ccagcaatgg cggtggcaag caggcgctgg agacggtcca gcggctgttg     660
ccggtgctgt gccaggccca cggcttgacc cccagcagg tggtggccat cgccagcaat     720
ggcggtggca agcaggcgct ggagacggtc cagcggctgt tgccggtgct gtgccaggcc     780
cacggcttga cccccagca ggtggtggcc atcgccagcc acgatggcgg caagcaggcg     840
ctggagacgg tccagcggct gttgccggtg ctgtgccagg cccacggctt gaccccccag     900
caggtggtgg ccatcgccag caatggcggt ggcaagcagg cgctggagac ggtccagcgg     960
ctgttgccgg tgctgtgcca ggcccacggc ttgacccccc agcaggtggt ggccatcgcc    1020
agcaatggcg gtggcaagca ggcgctggag acggtccagc ggctgttgcc ggtgctgtgc    1080
caggcccacg gcttgacccc ccagcaggtg gtggccatcg ccagcaatgg cggtggcaag    1140
caggcgctgg agacggtcca gcggctgttg ccggtgctgt gccaggccca cggcttgacc    1200
ccccagcagg tggtggccat cgccagcaat ggcggtggca agcaggcgct ggagacggtc    1260
cagcggctgt tgccggtgct gtgccaggcc cacggcttga cccccagca ggtggtggcc    1320 atcgccagca ataatggtgg caagcaggcg ctggagacgg tccagcggct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgacccccc agcaggtggt ggccatcgcc agcaatggcg gtggcaagca ggcgctggag    1560
acggtccagc ggctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc cccagcagg tggtggccat cgccagcaat    1740
ggcggtggca agcaggcgct ggagacggtc cagcggctgt tgccggtgct gtgccaggcc    1800
cacggcttga cccccagca ggtggtggcc atcgccagca atggcggtgg caagcaggcg    1860
```

```
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccgagtggca gcggaagtgg cggggatcct atcagccgtt cccagctggt gaagtccgag    2160
ctggaggaga agaaatccga gttgaggcac aagctgaagt acgtgcccca cgagtacatc    2220
gagctgatcg agatcgcccg gaacagcacc caggaccgta tcctggagat gaaggtgatg    2280
gagttcttca tgaaggtgta cggctacagg ggcaagcacc tgggcggctc caggaagccc    2340
gacggcgcca tctacaccgt gggctccccc atcgactacg gcgtgatcgt ggacaccaag    2400
gcctactccg gcggctacaa cctgcccatc ggccaggccg acgaaatgca gaggtacgtg    2460
gaggagaacc agaccaggaa caagcacatc aaccccaacg agtggtggaa ggtgtacccc    2520
tccagcgtga ccgagttcaa gttcctgttc gtgtccggcc acttcaaggg caactacaag    2580
gcccagctga ccaggctgaa ccacatcacc aactgcaacg gcgccgtgct gtccgtggag    2640
gagctcctga tcggcggcga gatgatcaag gccggcaccc tgaccctgga ggaggtgagg    2700
aggaagttca acaacggcga gatcaacttc gcggccgact gataa                    2745
```

<210> SEQ ID NO 25
<211> LENGTH: 2745
<212> TYPE: DNA
<213> ORGANISM: artificial sequence
<220> FEATURE:
<223> OTHER INFORMATION: TALEN CD25 pCLS30479

<400> SEQUENCE: 25

```
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgacccccg agcaggtggt ggccatcgcc agcaatattg tggcaagca ggcgctggag    540 acggtgcagg cgctgttgcc ggtgctgtgc caggcccacg gcttgacccc ggagcaggtg    600
gtggccatcg ccagccacga tgcggcaag caggcgctgg agacggtcca gcggctgttg    660
ccggtgctgt gccaggccca cggcttgacc ccggagcagg tggtggccat cgccagcaat    720
attggtggca gcaggcgct ggagacggtg caggcgctgt gccggtgct gtgccaggcc    780 cacggcttga ccccccagca ggtggtggcc atcgccagca ataatggtgg caagcaggcg    840
ctggagacgg tccagcggct gttgccggtg ctgtgccagg cccacggctt gaccccccag    900
caggtggtgg ccatcgccag caataatggt ggcaagcagg cgctggagac ggtccagcgg    960
ctgttgccgg tgctgtgcca ggcccacggc ttgaccccgg agcaggtggt ggccatcgcc   1020
agcaatattg tggcaagca ggcgctggag acggtgcagg cgctgttgcc ggtgctgtgc   1080
caggcccacg gcttgacccc ccagcaggtg gtggccatcg ccagcaataa tggtggcaag   1140
```

-continued

```
caggcgctgg agacggtcca gcggctgttg ccggtgctgt gccaggccca cggcttgacc    1200
ccccagcagg tggtggccat cgccagcaat aatggtggca agcaggcgct ggagacggtc    1260
cagcggctgt tgccggtgct gtgccaggcc cacggcttga ccccggagca ggtggtggcc    1320
atcgccagca atattggtgg caagcaggcg ctggagacgg tgcaggcgct gttgccggtg    1380
ctgtgccagg cccacggctt gacccggag caggtggtgg ccatcgccag caatattggt    1440
ggcaagcagg cgctggagac ggtgcaggcg ctgttgccgg tgctgtgcca ggcccacggc    1500 ttgaccccc agcaggtggt ggccatcgcc agcaataatg gtggcaagca ggcgctggag    1560
acggtccagc ggctgttgcc ggtgctgtgc caggcccacg gcttgacccc ggagcaggtg    1620
gtggccatcg ccagcaatat tggtggcaag caggcgctgg agacggtgca ggcgctgttg    1680
ccggtgctgt gccaggccca cggcttgacc ccccagcagg tggtggccat cgccagcaat    1740
aatggtggca agcaggcgct ggagacggtc cagcggctgt tgccggtgct gtgccaggcc    1800
cacggcttga ccccccagca ggtggtggcc atcgccagca atggcggtgg caagcaggcg    1860
ctggagacgg tccagcggct gttgccgtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgaccctc agcaggtggt ggccatcgcc    2040
agcaatggcg gcggcaggcc ggcgctggag agcattgttg cccagttatc tcgccctgat    2100
ccgagtggca gcggaagtgg cggggatcct atcagccgtt cccagctggt gaagtccgag    2160
ctggaggaga agaaatccga gttgaggcac aagctgaagt acgtgcccca cgagtacatc    2220
gagctgatcg agatcgcccg gaacagcacc caggaccgta tcctggagat gaaggtgatg    2280
gagttcttca tgaaggtgta cggctacagg ggcaagcacc tgggcggctc caggaagccc    2340
gacggcgcca tctacaccgt gggctccccc atcgactacg gcgtgatcgt ggacaccaag    2400
gcctactccg gcggctacaa cctgcccatc ggccaggccg acgaaatgca gaggtacgtg    2460
gaggagaacc agaccaggaa caagcacatc aaccccaacg agtggtggaa ggtgtacccc    2520
tccagcgtga ccgagttcaa gttcctgttc gtgtccggcc acttcaaggg caactacaag    2580
gcccagctga ccaggctgaa ccacatcacc aactgcaacg gcgccgtgct gtccgtggag    2640
gagctcctga tcggcggcga gatgatcaag gccggcaccc tgaccctgga ggaggtgagg    2700
aggaagttca acaacggcga gatcaacttc gcggccgact ataa                    2745
```

<210> SEQ ID NO 26
<211> LENGTH: 2814
<212> TYPE: DNA
<213> ORGANISM: artificial sequence
<220> FEATURE:
<223> OTHER INFORMATION: TALEN PD1 pCLS28959

<400> SEQUENCE: 26

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa caccccgcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac    480
```

```
ttgaccccg   agcaagtggt  ggctatcgct  tccaagctgg  ggggaaagca  ggccctggag    540
accgtccagg  cccttctccc  agtgctttgc  caggctcacg  gactgacccc  tgaacaggtg    600
gtggcaattg  cctcacacga  cgggggcaag  caggcactgg  agactgtcca  gcggctgctg    660
cctgtcctct  gccaggccca  cggactcact  cctgagcagg  tcgtggccat  tgccagccac    720 gatggggca   aacaggctct  ggagaccgtg  cagcgcctcc  tcccagtgct  gtgccaggct    780
catgggctga  ccccacagca  ggtcgtcgcc  attgccagta  acggcggggg  gaagcaggcc    840
ctcgaaacag  tgcagaggct  gctgcccgtc  ttgtgccaag  cacacggcct  gacacccgag    900 caggtggtg   ccatcgcctc  tcatgacggc  ggcaagcagg  cccttgagac  agtgcagaga    960
ctgttgcccg  tgttgtgtca  ggcccacggg  ttgacacccc  agcaggtggt  cgccatcgcc   1020
agcaatggcg  ggggaaagca  ggcccttgag  accgtgcagc  ggttgcttcc  agtgttgtgc   1080
caggcacacg  gactgacccc  tcaacaggtg  gtcgcaatcg  ccagctacaa  gggcggaaag   1140
caggctctgg  agacagtgca  gcgcctcctg  cccgtgctgt  gtcaggctca  cggactgaca   1200
ccacagcagg  tggtcgccat  cgccagtaac  gggggcggca  gcaggctttt  ggagaccgtc   1260
cagagactcc  tccccgtcct  ttgccaggcc  cacgggttga  cacctcagca  ggtcgtcgcc   1320
attgcctcca  acaacggggg  caagcaggcc  ctcgaaactg  tgcagaggct  gctgcctgtg   1380
ctgtgccagg  ctcatgggct  gacaccccag  caggtggtgg  ccattgcctc  taacaacggc   1440
ggcaaacagg  cactggagac  cgtgcaaagg  ctgctgcccg  tcctctgcca  agcccacggg   1500
ctcactccac  agcaggtcgt  ggccatcgcc  tcaaacaatg  gcgggaagca  ggccctggag   1560
actgtgcaaa  ggctgctccc  tgtgctctgc  caggcacacg  gactgacccc  tcagcaggtg   1620
gtggcaatcg  cttccaacaa  cgggggaaag  caggccctcg  aaaccgtgca  gcgcctcctc   1680
ccagtgctgt  gccaggcaca  tggcctcaca  cccgagcaag  tggtggctat  cgccagccac   1740 gacgaggga   agcaggctct  ggagaccgtg  cagaggctgc  tgcctgtcct  gtgccaggcc   1800
cacgggctta  ctccagagca  ggtcgtcgcc  atcgccagtc  atgatggggg  gaagcaggcc   1860
cttgagacag  tccagcggct  gctgccagtc  ctttgccagg  ctcacggctt  gactcccgag   1920
caggtcgtgg  ccattgcctc  aaacattggg  ggcaaacagg  ccctggagac  agtgcaggcc   1980
ctgctgcccg  tgttgtgtca  ggcccacggc  ttgacacccc  agcaggtggt  cgccattgcc   2040
tctaatggcg  gcgggagacc  cgccttggag  agcattgttg  cccagttatc  tcgccctgat   2100
ccggcgttgg  ccgcgttgac  caacgaccac  ctcgtcgcct  tggcctgcct  cggcgggcgt   2160
cctgcgctgg  atgcagtgaa  aaagggattg  ggggatccta  tcagccgttc  ccagctggtg   2220
aagtccgagc  tggaggagaa  gaaatccgag  ttgaggcaca  agctgaagta  cgtgcccac    2280 gagtacatcg  agctgatcga  gatcgcccgg  aacagcaccc  aggaccgtat  cctggagatg   2340
aaggtgatgg  agttcttcat  gaaggtgtac  ggctacaggg  gcaagcacct  gggcggctcc   2400
aggaagcccg  acgcgccat   ctacaccgtg  ggctcccca   tcgactacgg  cgtgatcgtg   2460
gacaccaagg  cctactccgg  cggctacaac  ctgcccatcg  ccaggccga   cgaaatgcag   2520 aggtacgtgg  aggagaacca  gaccaggaac  aagcacatca  ccccaacga   gtggtggaag   2580 gtgtacccct  ccagcgtgac  cgagttcaag  ttcctgttcg  tgtccggcca  cttcaagggc   2640
aactacaagg  cccagctgac  caggctgaac  cacatcacca  actgcaacgg  cgccgtgctg   2700
tccgtggagg  agctcctgat  cggcggcgag  atgatcaagg  ccggcacct   gaccctggag   2760 gaggtgagga  ggaagttcaa  caacggcgag  atcaacttcg  cggccgactg  ataa         2814
```

<210> SEQ ID NO 27
<211> LENGTH: 2829
<212> TYPE: DNA
<213> ORGANISM: artificial sequence
<220> FEATURE:
<223> OTHER INFORMATION: TALEN PD1 pCLS18792

<400> SEQUENCE: 27

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccgag caagtcgtcg caatcgccag ccatgatgga     540
gggaagcaag ccctcgaaac cgtgcagcgg ttgcttcctg tgctctgcca ggcccacggc     600
cttacccctc agcaggtggt ggccatcgca gtaacggag gaggaaagca agccttggag     660
acagtgcagc gcctgttgcc cgtgctgtgc caggcacacg gcctcacacc agagcaggtc     720
gtggccattg cctcccatga cgggggaaa caggctctgg agaccgtcca gaggctgctg     780
cccgtcctct gtcaagctca cggcctgact ccccaacaag tggtcgccat cgcctctaat     840
ggcggcggga agcaggcact ggaaacagtg cagagactgc tccctgtgct ttgccaagct     900
catgggttga cccccaaca ggtcgtcgct attgcctcaa cggggggg caagcaggcc     960
cttgagactg tgcagaggct gttgccagtg ctgtgtcagg ctcacgggct cactccacaa    1020
caggtggtcg caattgccag caacggcggc ggaaagcaag ctcttgaaac cgtgcaacgc    1080
ctcctgcccg tgctctgtca ggctcatggc ctgacaccac aacaagtcgt ggccatcgcc    1140
agtaataatg gcgggaaaca ggctcttgag accgtccaga ggctgctccc agtgctctgc    1200
caggcacacg gctgaccccc cgagcaggtg gtggctatcg ccagcaatat tgggggcaag    1260
caggccctgg aaacagtcca ggccctgctg ccagtgcttt gccaggctca cgggctcact    1320
ccccagcagg tcgtggcaat cgcctccaac ggcggaggga agcaggctct ggagaccgtg    1380
cagagactgc tgcccgtctt gtgccaggcc acggactca cacctgaaca ggtcgtcgcc    1440
attgcctctc acgatggggg caaacaagcc ctggagacag tgcagcggct gttgcctgtg    1500
ttgtgccaag cccacggctt gactcctcaa caagtggtcg ccatcgcctc aaatggcggc    1560
ggaaaacaag ctctggagac agtgcagagg ttgctgcccg tcctctgcca agcccacggc    1620
ctgactcccc aacaggtcgt cgccattgcc agcaacaacg gaggaaagca ggctctcgaa    1680
actgtgcagc ggctgcttcc tgtgctgtgt caggctcatg gctgaccc cgagcaagtg    1740
gtggctattg cctctaatgg aggcaagcaa gcccttgaga cagtccagag gctgttgcca    1800
gtgctgtgcc aggcccacgg gctcacaccc agcaggtgg tcgccatcgc cagtaacaac    1860
gggggcaaac aggcattgga aaccgtccag cgcctgcttc agtgctctg ccaggcacac    1920
ggactgacac ccgaacaggt ggtggccatt gcatcccatg atgggggcaa gcaggccctg    1980
gagaccgtgc agagactcct gccagtgttg tgccaagctc acggcctcac ccctcagcaa    2040
gtcgtggcca tcgcctcaaa cgggggggc cggcctgcac tggagagcat tgttgcccag    2100
```

-continued

```
ttatctcgcc ctgatccggc gttggccgcg ttgaccaacg accacctcgt cgccttggcc    2160
tgcctcggcg ggcgtcctgc gctggatgca gtgaaaaagg gattggggga tcctatcagc    2220
cgttcccagc tggtgaagtc cgagctggag gagaagaaat ccgagttgag gcacaagctg    2280
aagtacgtgc cccacgagta catcgagctg atcgagatcg cccggaacag cacccaggac    2340
cgtatcctgg agatgaaggt gatggagttc ttcatgaagg tgtacggcta caggggcaag    2400
cacctgggcg gctccaggaa gcccgacggc gccatctaca ccgtgggctc ccccatcgac    2460
tacggcgtga tcgtggacac caaggcctac tccggcggct acaacctgcc catcggccag    2520
gccgacgaaa tgcagaggta cgtggaggag aaccagacca ggaacaagca catcaacccc    2580
aacgagtggt ggaaggtgta ccctccagc gtgaccgagt tcaagttcct gttcgtgtcc    2640
ggccacttca agggcaacta caaggcccag ctgaccaggc tgaaccacat caccaactgc    2700
aacggcgccg tgctgtccgt ggaggagctc ctgatcggcg gcgagatgat caaggccggc    2760
accctgaccc tggaggaggt gaggaggaag ttcaacaacg gcgagatcaa cttcgcggcc    2820
gactgataa                                                            2829
```

<210> SEQ ID NO 28
<211> LENGTH: 49
<212> TYPE: DNA
<213> ORGANISM: artificial sequence
<220> FEATURE:
<223> OTHER INFORMATION: TALEN target TRAC

<400> SEQUENCE: 28

```
ttgtcccaca gatatccaga accctgaccc tgccgtgtac cagctgaga                  49
```

<210> SEQ ID NO 29
<211> LENGTH: 45
<212> TYPE: DNA
<213> ORGANISM: artificial sequence
<220> FEATURE:
<223> OTHER INFORMATION: TALEN target CD25

<400> SEQUENCE: 29

```
tacaggagga agagtagaag aacaatctag aaaaccaaaa gaaca                      45
```

<210> SEQ ID NO 30
<211> LENGTH: 49
<212> TYPE: DNA
<213> ORGANISM: artificial sequence
<220> FEATURE:
<223> OTHER INFORMATION: TALEN target PD1

<400> SEQUENCE: 30

```
tacctctgtg gggccatctc cctggccccc aaggcgcaga tcaaagaga                  49
```

<210> SEQ ID NO 31
<211> LENGTH: 2897
<212> TYPE: DNA
<213> ORGANISM: artificial sequence
<220> FEATURE:
<223> OTHER INFORMATION: Matrice TRAC locus_CubiCAR CD22 pCLS30056

<400> SEQUENCE: 31

```
ttgctgggcc ttttccat gcctgccttt actctgccag agttatattg ctggggtttt       60
gaagaagatc ctattaaata aaagaataag cagtattatt aagtagccct gcatttcagg     120
tttccttgag tggcaggcca ggcctggccg tgaacgttca ctgaaatcat ggcctcttgg     180
```

```
ccaagattga tagcttgtgc ctgtccctga gtcccagtcc atcacgagca gctggtttct    240
aagatgctat ttcccgtata aagcatgaga ccgtgacttg ccagccccac agagccccgc    300
ccttgtccat cactggcatc tggactccag cctgggttgg ggcaaagagg gaaatgagat    360
catgtcctaa ccctgatcct cttgtcccac agatatccag taccoctacg acgtgcccga    420
ctacgcctcc ggtgagggca gaggaagtct tctaacatgc ggtgacgtgg aggagaatcc    480
gggcccccgga tccgctctgc ccgtcaccgc tctgctgctg ccactggcac tgctgctgca    540
cgctgctagg cccggagggg gaggcagctg ccctacagc aaccccagcc tgtgcagcgg    600
aggcggcggc agcggcggag ggggtagcca ggtgcagctg cagcagagcg gcctggcct    660
ggtgaagcca agccagacac tgtccctgac ctgcgccatc agcggcgatt ccgtgagctc    720
caactccgcc gcctggaatt ggatcaggca gtccccttct cggggcctgg agtggctggg    780
aaggacatac tatcggtcta agtggtacaa cgattatgcc gtgtctgtga agagcagaat    840
cacaatcaac cctgacacct ccaagaatca gttctctctg cagctgaata gcgtgacacc    900
agaggacacc gccgtgtact attgcgccag ggaggtgacc ggcgacctgg aggatgcctt    960
tgacatctgg ggccagggca caatggtgac cgtgagctcc ggaggcggcg gatctggcgg    1020
aggaggaagt gggggcggcg ggagtgatat ccagatgaca cagtccccat cctctctgag    1080
cgcctccgtg ggcgacagag tgacaatcac ctgtagggcc tcccagacca tctggtctta    1140
cctgaactgg tatcagcaga ggcccggcaa ggccctaat ctgctgatct acgcagcaag    1200
ctccctgcag agcggagtgc catccagatt ctctggcagg ggctccggca cagacttcac    1260
cctgaccatc tctagcctgc aggccgagga cttcgccacc tactattgcc agcagtctta    1320
tagcatcccc cagacatttg gccagggcac caagctggag atcaagtcgg atcccggaag    1380
cggagggggga ggcagctgcc cctacagcaa ccccagcctg tgcagcggag gcggcggcag    1440
cgagctgccc acccagggca cctcctccaa cgtgtccacc aacgtgagcc cagccaagcc    1500
caccaccacc gcctgtcctt attccaatcc ttccctgtgt gctcccacca caacccccgc    1560
tccaaggccc cctaccccog caccaactat tgcctcccag ccactctcac tgcggcctga    1620
ggcctgtcgg cccgctgctg gaggcgcagt gcatacaagg ggcctcgatt tcgcctgcga    1680
tatttacatc tgggcacccc tcgccggcac ctgcggggtg cttctcctct ccctggtgat    1740
taccctgtat tgcagacggg gccggaagaa gctcctctac attttaagc agcctttcat    1800
gcggccagtg cagacaaccc aagaggagga tgggtgttcc tgcagattcc ctgaggaaga    1860
ggaaggcggg tgcgagctga gagtgaagtt ctccaggagc gcagatgccc ccgcctatca    1920
acagggccag aaccagctct acaacgagct taacctcggg aggcgcgaag aatacgacgt    1980
gttggataag agaagggggc gggaccccga gatgggagga aagccccgga ggaagaaccc    2040
tcaggagggc ctgtacaacg agctgcagaa ggataagatg gccgaggcct actcagagat    2100
cgggatgaag gggagcggc gccgcggaa ggggcacgat gggctctacc aggggctgag    2160
cacagccaca aaggacacat acgacgcctt gcacatgcag gcccttccac cccgggaata    2220
gtctagaggg cccgtttaaa cccgctgatc agcctcgact gtgccttcta gttgccagcc    2280
atctgttgtt tgcccctccc ccgtgccttc cttgaccctg gaaggtgcca ctcccactgt    2340
cctttcctaa taaaatgagg aaattgcatc gcattgtctg agtaggtgtc attctattct    2400
ggggggtggg gtggggcagg acagcaaggg ggaggattgg gaagacaata gcaggcatgc    2460
tggggatgcg gtgggctcta tgactagtgg cgaattcccg tgtaccagct gagagactct    2520
aaatccagtg acaagtctgt ctgcctattc accgattttg attctcaaac aaatgtgtca    2580
```

-continued

```
caaagtaagg attctgatgt gtatatcaca gacaaaactg tgctagacat gaggtctatg    2640
gacttcaaga gcaacagtgc tgtggcctgg agcaacaaat ctgactttgc atgtgcaaac    2700
gccttcaaca acagcattat tccagaagac accttcttcc ccagcccagg taagggcagc    2760
tttggtgcct tcgcaggctg tttccttgct tcaggaatgg ccaggttctg cccagagctc    2820
tggtcaatga tgtctaaaac tcctctgatt ggtggtctcg gccttatcca ttgccaccaa    2880
aaccctcttt ttactaa                                                   2897
```

<210> SEQ ID NO 32
<211> LENGTH: 2688
<212> TYPE: DNA
<213> ORGANISM: artificial sequence
<220> FEATURE:
<223> OTHER INFORMATION: Matrice CD25 locus_IL15_2A_sIL15Ra pCLS30519

<400> SEQUENCE: 32

```
gtttattatt cctgttccac agctattgtc tgccatataa aaacttaggc caggcacagt      60
ggctcacacc tgtaatccca gcactttgga aggccgaggc aggcagatca caaggtcagg     120
agttcgagac cagcctggcc aacatagcaa accccatctc tactaaaaaa tacaaaaatt     180
agccaggcat ggtggcgtgt gcactggttt agagtgagga ccacattttt ttggtgccgt     240
gttacacata tgaccgtgac tttgttacac cactacagga ggaagagtag aagaacaatc     300
ggttctggcg tgaaacagac tttgaatttt gaccttctca agttggcggg agacgtggag     360
tccaacccag ggcccggtac cgggtccgcc accatggact ggacctggat tctgttcctc     420
gtggctgctg ctacaagagt gcacagcggc attcatgtct cattttgggg ctgtttcagt     480
gcagggcttc ctaaaacaga agccaactgg gtgaatgtaa taagtgattt gaaaaaaatt     540
gaagatctta ttcaatctat gcatattgat gctactttat atacggaaag tgatgttcac     600
cccagttgca aagtaacagc aatgaagtgc tttctcttgg agttacaagt tatttcactt     660
gagtccggag atgcaagtat tcatgataca gtagaaaatc tgatcatcct agcaaacaac     720
agtttgtctt ctaatgggaa tgtaacagaa tctggatgca aagaatgtga ggaactggag     780
gaaaaaaata ttaagaatt tttgcagagt tttgtacata ttgtccaaat gttcatcaac     840
acttctggaa gcggagctac taacttcagc ctgctgaagc aggctggaga cgtggaggag     900
aaccctggac ctgggaccgg ctctgcaacc atggattgga gtggatcct gtttctcgtg     960 gcagctgcca aagagttca gtatcacgt gccctccccc ccatgtccgt ggaacacgca    1020
gacatctggg tcaagagcta cagcttgtac tccaggagc ggtacatttg taactctggt    1080
ttcaagcgta agccggcac gtccagcctg acggagtgcg tgttgaacaa ggccacgaat    1140
gtcgcccact ggacaacccc cagtctcaaa tgcattagag accctgccct ggttcaccaa    1200
aggccagcgc cacccttcca gtaacgacg gcaggggtga ccccacagcc agagagcctc    1260
tccccttctg gaaaagagcc cgcagcttca tctcccagct caaacaacac agcggccaca    1320
acagcagcta ttgtccccggg ctcccagctg atgccttcaa aatcaccttc cacaggaacc    1380
acagagataa gcagtcatga gtcctcccac ggcacccccct tcagacaac agccaagaac    1440 tgggaactca cagcatccgc ctcccaccag ccgccaggtg tgtatccaca gggccacagc    1500
gacaccactg agggcagagg cagcctgctg acctgcggcg acgtcgagga aaccccgggg    1560
cccatggggg caggtgccac cggccgcgcc atggacgggc gcgcctgct gctgttgctg    1620 cttctggggg tgtcccttgg aggtgccaag gaggcatgcc cacaggcct gtacacacac    1680
```

```
agcggtgagt gctgcaaagc ctgcaacctg ggcgagggtg tggcccagcc ttgtggagcc    1740
aaccagaccg tgtgtgagcc ctgcctggac agcgtgacgt tctccgacgt ggtgagcgcg    1800
accgagccgt gcaagccgtg caccgagtgc gtggggctcc agagcatgtc ggcgccgtgc    1860
gtggaggccg atgacgccgt gtgccgctgc gcctacggct actaccagga tgagacgact    1920
gggcgctgcg aggcgtgccg cgtgtgcgag gcgggctcgg gcctcgtgtt ctcctgccag    1980
gacaagcaga acaccgtgtg cgaggagtgc cccgacggca cgtattccga cgaggccaac    2040
cacgtggacc cgtgcctgcc ctgcaccgtg tgcgaggaca ccgagcgcca gctccgcgag    2100
tgcacacgct gggccgacgc cgagtgcgag gagatccctg gccgttggat tacacggtcc    2160
acacccccag agggctcgga cagcacagcc cccagcaccc aggagcctga ggcacctcca    2220
gaacaagacc tcatagccag cacggtggca ggtgtggtga ccacagtgat gggcagctcc    2280
cagcccgtgg tgacccgagg caccaccgac aacctcatcc ctgtctattg ctccatcctg    2340
gctgctgtgg ttgtgggtct tgtgccctac atagccttca gaggtgaaa aaccaaaaga    2400 acaagaattt cttggtaaga agccgggaac agacaacaga agtcatgaag cccaagtgaa    2460
atcaaaggtg ctaaatggtc gcccaggaga catccgttgt gcttgcctgc gttttggaag    2520
ctctgaagtc acatcacagg acacggggca gtggcaacct tgtctctatg ccagctcagt    2580
cccatcagag agcgagcgct acccacttct aaatagcaat ttcgccgttg aagaggaagg    2640
gcaaaaccac tagaactctc catcttattt tcatgtatat gtgttcat              2688
```

<210> SEQ ID NO 33
<211> LENGTH: 2964
<212> TYPE: DNA
<213> ORGANISM: artificial sequence
<220> FEATURE:
<223> OTHER INFORMATION: Matrice PD1 locus_IL15_2A_sIL15Ra pCLS30513

<400> SEQUENCE: 33

```
gactccccag acaggccctg gaaccccccc accttctccc cagccctgct cgtggtgacc      60
gaaggggaca acgccacctt cacctgcagc ttctccaaca catcggagag cttcgtgcta     120
aactggtacc gcatgagccc cagcaaccag acggacaagc tggccgcctt ccccgaggac     180
cgcagccagc ccggccagga ctgccgcttc cgtgtcacac aactgcccaa cgggcgtgac     240
ttccacatga gcgtggtcag ggccggcgc aatgacagcg gcacctacct ctgtggggcc     300
ggttctggcg tgaaacagac tttgaatttt gaccttctca gttggcggg agacgtggag     360 tccaacccag ggcccggtac cgggtccgcc accatggact ggacctggat tctgttcctc     420
gtggctgctg ctacaagagt gcacagcggc attcatgtct tcattttggg ctgtttcagt     480
gcagggcttc ctaaaacaga agccaactgg gtgaatgtaa taagtgattt gaaaaaaatt     540
gaagatctta ttcaatctat gcatattgat gctactttat atacggaaag tgatgttcac     600
cccagttgca aagtaacagc aatgaagtgc tttctcttgg agttacaagt tatttcactt     660
gagtccggag atgcaagtat tcatgataca gtagaaaatc tgatcatcct agcaaacaac     720
agtttgtctt ctaatgggaa tgtaacagaa tctggatgca agaatgtga ggaactggag     780 gaaaaaaata ttaagaattt tttgcagagt tttgtacata ttgtccaaat gttcatcaac     840
acttctggaa gcggagctac taacttcagc ctgctgaagc aggctggaga cgtggaggag     900
aaccctggac ctgggaccgg ctctgcaacc atggattgga cgtggatcct gtttctcgtg     960
gcagctgcca caagagttca gtatcacgt gccctcccc ccatgccgt ggaacacgca    1020 gacatctggg tcaagagcta cagcttgtac tccagggagc ggtacatttg taactctggt    1080
```

```
ttcaagcgta aagccggcac gtccagcctg acggagtgcg tgttgaacaa ggccacgaat    1140
gtcgcccact ggacaacccc cagtctcaaa tgcattagag accctgccct ggttcaccaa    1200
aggccagcgc caccctccac agtaacgacg gcaggggtga ccccacagcc agagagcctc    1260
tccccttctg gaaaagagcc cgcagcttca tctcccagct caaacaacac agcggccaca    1320
acagcagcta ttgtcccggg ctcccagctg atgccttcaa aatcaccttc cacaggaacc    1380
acagagataa gcagtcatga gtcctcccac ggcaccccct ctcagacaac agccaagaac    1440
tgggaactca cagcatccgc ctcccaccag ccgccaggtg tgtatccaca gggccacagc    1500
gacaccactg agggcagagg cagcctgcta acctgcggcg acgtcgagga gaaccccggg    1560
cccatggggg caggtgccac cggccgcgcc atggacgggc gcgcctgct gctgttgctg     1620
cttctggggg tgtcccttgg aggtgccaag gaggcatgcc ccacaggcct gtacacacac    1680
agcggtgagt gctgcaaagc ctgcaacctg ggcgagggtg tggcccagcc ttgtggagcc    1740
aaccagaccg tgtgtgagcc ctgcctggac agcgtgacgt tctccgacgt ggtgagcgcg    1800
accgagccgt gcaagccgtg caccgagtgc gtggggctcc agagcatgtc ggcgccgtgc    1860
gtggaggcca tgacgccgt gtgccgctgc gcctacggct actaccagga tgagacgact    1920
gggcgctgcg aggcgtgccg cgtgtgcgag gcgggctcgg gcctcgtgtt ctcctgccag    1980
gacaagcaga acaccgtgtg cgaggagtgc cccgacggca cgtattccga cgaggccaac    2040
cacgtggacc cgtgcctgcc ctgcaccgtg tgcgaggaca ccgagcgcca gctccgcgag    2100
tgcacacgct gggccgacgc cgagtgcgag gagatccctg gccgttggat tacacggtcc    2160
acaccccag agggctcgga cagcacagcc cccagcaccc aggagcctga ggcacctcca    2220
gaacaagacc tcatagccag cacggtggca ggtgtggtga ccacagtgat gggcagctcc    2280
cagcccgtgg tgacccgagg caccaccgac aacctcatcc ctgtctattg ctccatcctg    2340
gctgctgtgg ttgtgggtct tgtggcctac atagccttca agaggtgatc tagagggccc    2400
gtttaaaccc gctgatcagc ctcgactgtg ccttctagtt gccagccatc tgttgtttgc    2460
ccctcccccg tgccttcctt gaccctggaa ggtgccactc ccactgtcct ttcctaataa    2520
aatgaggaaa ttgcatcgca ttgtctgagt aggtgtcatt ctattctggg gggtggggtg    2580
gggcaggaca gcaaggggga ggattgggaa gacaatagca ggcatgctgg ggatgcggtg    2640
ggctctatga ctagtggcga attcggcgca gatcaaagag agcctgcggg cagagctcag    2700
ggtgacaggt gcggcctcgg aggccccggg gcaggggtga gctgagccgg tcctggggtg    2760
ggtgtcccct cctgcacagg atcaggagct ccagggtcgt agggcaggga ccccccagct    2820
ccagtccagg gctctgtcct gcacctgggg aatggtgacc ggcatctctg tcctctagct    2880
ctggaagcac cccagcccct ctagtctgcc ctcacccctg accctgaccc tccaccctga    2940
ccccgtccta accctgacc tttg                                            2964

<210> SEQ ID NO 34
<211> LENGTH: 3363
<212> TYPE: DNA
<213> ORGANISM: artificial sequence
<220> FEATURE:
<223> OTHER INFORMATION: Matrice CD25 locus_IL12a_2A_IL12b pCLS30520

<400> SEQUENCE: 34
gtttattatt cctgttccac agctattgtc tgccatataa aaacttaggc caggcacagt      60
ggctcacacc tgtaatccca gcactttgga aggccgaggc aggcagatca caaggtcagg     120
```

```
agttcgagac cagcctggcc aacatagcaa aaccccatct ctactaaaaa tacaaaaatt    180
agccaggcat ggtggcgtgt gcactggttt agagtgagga ccacattttt ttggtgccgt    240
gttacacata tgaccgtgac tttgttacac cactacagga ggaagagtag aagaacaatc    300
ggttctggcg tgaaacagac tttgaatttt gaccttctca agttggcggg agacgtggag    360
tccaacccag ggcccatgtg gccccctggg tcagcctccc agccaccgcc ctcacctgcc    420
gcggccacag tctgcatcc agcggctcgc cctgtgtccc tgcagtgccg gctcagcatg    480
tgtccagcgc gcagcctcct ccttgtggct accctggtcc tcctggacca cctcagtttg    540
gccagaaacc tccccgtggc cactccagac ccaggaatgt tcccatgcct tcaccactcc    600
caaaacctgc tgagggccgt cagcaacatg ctccagaagg ccagacaaac tctagaattt    660 taccccttgca cttctgaaga gattgatcat gaagatatca caaaagataa aaccagcaca    720
gtggaggcct gtttaccatt ggaattaacc aagaatgaga gttgcctaaa ttccagagag    780
acctctttca taactaatgg gagttgcctg gcctccagaa agacctcttt tatgatggcc    840
ctgtgcctta gtagtattta tgaagacttg aagatgtacc aggtggagtt caagaccatg    900
aatgcaaagc ttctgatgga tcctaagagg cagatctttc tagatcaaaa catgctggca    960
gttattgatg agctgatgca ggccctgaat ttcaacagtg agactgtgcc acaaaaatcc   1020
tcccttgaag aaccggattt ttataaaact aaaatcaagc tctgcatact tcttcatgct   1080
ttcagaattc gggcagtgac tattgataga gtgatgagct atctgaatgc ttccggaagc   1140
ggagctacta acttcagcct gctgaagcag gctggagacg tggaggagaa ccctggacct   1200
atgtgtcacc agcagttggt catctcttgg ttttccctgg tttttctggc atctcccctc   1260
gtggccatat gggaactgaa gaaagatgtt tatgtcgtag aattggattg gtatccggat   1320
gcccctggag aaatggtggt cctcacctgt gacacccctg aagaagatgg tatcacctgg   1380
accttggacc agagcagtga ggtcttaggc tctggcaaaa ccctgaccat ccaagtcaaa   1440
gagtttggag atgctggcca gtacacctgt cacaaaggag cgaggttct aagccattcg    1500 ctcctgctgc ttcacaaaaa ggaagatgga atttggtcca ctgatatttt aaaggaccag   1560
aaagaaccca aaaataagac cttttctaaga tgcgaggcca agaattattc tggacgtttc   1620
acctgctggt ggctgacgac aatcagtact gatttgacat tcagtgtcaa aagcagcaga   1680
ggctcttctg acccccaagg ggtgacgtgc ggagctgcta cactctctgc agagagagtc   1740
agaggggaca acaaggagta tgagtactca gtggagtgcc aggaggacag tgcctgccca   1800
gctgctgagg agagtctgcc cattgaggtc atggtggatg ccgttcacaa gctcaagtat   1860
gaaaactaca ccagcagctt cttcatcagg gacatcatca aacctgaccc acccaagaac   1920
ttgcagctga gccattaaa gaattctcgg caggtggagg tcagctggga gtaccctgac   1980
acctggagta ctccacattc ctacttctcc ctgacattct gcgttcaggt ccagggcaag   2040
agcaagagag aaaagaaaga tagagtcttc acgacaagaa cctcagccac ggtcatctgc   2100
cgcaaaaatg ccagcattag cgtgcgggcc caggaccgct actatagctc atcttggagc   2160
gaatgggcat ctgtgccctg cagtgagggc agaggcagcc tgctgacctg cggcgacgtc   2220
gaggagaacc ccgggcccat gggggcaggt gccaccggcc gcgccatgga cgggccgcgc   2280
ctgctgctgt tgctgcttct gggggtgtcc cttggaggtg ccaaggaggc atgccccaca   2340
ggcctgtaca cacacagcgg tgagtgctgc aaagcctgca acctgggcga gggtgtggcc   2400
cagccttgtg gagccaacca gaccgtgtgt gagccctgcc tggacagcgt gacgttctcc   2460
gacgtggtga gcgcgaccga gccgtgcaag ccgtgcaccg agtgcgtggg gctccagagc   2520
```

```
atgtcggcgc cgtgcgtgga ggccgatgac gccgtgtgcc gctgcgccta cggctactac    2580
caggatgaga cgactgggcg ctgcgaggcg tgccgcgtgt gcgaggcggg ctcgggcctc    2640
gtgttctcct gccaggacaa gcagaacacc gtgtgcgagg agtgccccga cggcacgtat    2700
tccgacgagg ccaaccacgt ggacccgtgc ctgccctgca ccgtgtgcga ggacaccgag    2760
cgccagctcc gcgagtgcac acgctgggcc gacgccgagt gcgaggagat ccctggccgt    2820
tggattacac ggtccacacc cccagagggc tcggacagca cagcccccag cacccaggag    2880
cctgaggcac ctccagaaca agacctcata gccagcacgg tggcaggtgt ggtgaccaca    2940
gtgatgggca gctcccagcc cgtggtgacc cgaggcacca ccgacaacct catccctgtc    3000
tattgctcca tcctggctgc tgtggttgtg ggtcttgtgg cctacatagc cttcaagagg    3060
tgaaaaacca aaagaacaag aatttcttgg taagaagccg ggaacagaca acagaagtca    3120
tgaagcccaa gtgaaatcaa aggtgctaaa tggtcgccca ggagacatcc gttgtgcttg    3180
cctgcgtttt ggaagctctg aagtcacatc acaggacacg gggcagtggc aaccttgtct    3240
ctatgccagc tcagtcccat cagagagcga gcgctaccca cttctaaata gcaatttcgc    3300
cgttgaagag gaagggcaaa accactagaa ctctccatct tattttcatg tatatgtgtt    3360
cat                                                                  3363

<210> SEQ ID NO 35
<211> LENGTH: 3639
<212> TYPE: DNA
<213> ORGANISM: artificial sequence
<220> FEATURE:
<223> OTHER INFORMATION: Matrice PD1 locus_IL12a_2A_IL12b pCLS30511

<400> SEQUENCE: 35
gactccccag acaggccctg gaaccccccc accttctccc cagccctgct cgtggtgacc      60 gaagggggaca cgccacctt cacctgcagc ttctccaaca catcggagag cttcgtgcta     120
aactggtacc gcatgagccc cagcaaccag acggacaagc tggccgcctt ccccgaggac     180
cgcagccagc ccggccagga ctgccgcttc cgtgtcacac aactgcccaa cgggcgtgac     240
ttccacatga gcgtggtcag ggcccggcgc aatgacagcg gcacctacct ctgtggggcc     300
ggttctggcg tgaaacagac tttgaatttt gaccttctca agttggcggg agacgtggag     360
tccaacccag ggcccatgtg gccccctggg tcagcctccc agccaccgcc ctcacctgcc     420
gcggccacag gtctgcatcc agcggctcgc cctgtgtccc tgcagtgccg gctcagcatg     480
tgtccagcgc gcagcctcct ccttgtggct accctggtcc tcctggacca cctcagtttg     540
gccagaaacc tccccgtggc cactccagac ccaggaatgt tcccatgcct tcaccactcc     600
caaaacctgc tgagggccgt cagcaacatg ctccagaagg ccagacaaac tctagaattt     660
tacccttgca cttctgaaga gattgatcat gaagatatca caaaagataa aaccagcaca     720
gtggaggcct gtttaccatt ggaattaacc aagaatgaga gttgcctaaa ttccagagag     780
acctctttca taactaatgg gagttgcctg gcctccagaa agacctcttt tatgatggcc     840
ctgtgcctta gtagtattta tgaagacttg aagatgtacc aggtggagtt caagaccatg     900
aatgcaaagc ttctgatgga tcctaagagg cagatctttc tagatcaaaa catgctggca     960
gttattgatg agctgatgca ggccctgaat ttcaacagtg agactgtgcc acaaaaatcc    1020
tcccttgaag aaccggattt ttataaaact aaaatcaagc tctgcatact tcttcatgct    1080
ttcagaattc gggcagtgac tattgataga gtgatgagct atctgaatgc ttccggaagc    1140
```

```
ggagctacta acttcagcct gctgaagcag gctggagacg tggaggagaa ccctggacct      1200
atgtgtcacc agcagttggt catctcttgg tttttccctgg tttttctggc atctcccctc     1260
gtggccatat gggaactgaa gaaagatgtt tatgtcgtag aattggattg gtatccggat      1320
gcccctggag aaatggtggt cctcacctgt gacacccctg aagaagatgg tatcacctgg      1380
accttggacc agagcagtga ggtcttaggc tctggcaaaa ccctgaccat ccaagtcaaa      1440
gagtttggag atgctggcca gtacacctgt cacaaaggag cgaggttct aagccattcg       1500 ctcctgctgc ttcacaaaaa ggaagatgga atttggtcca ctgatatttt aaaggaccag     1560
aaagaaccca aaataagac ctttctaaga tgcgaggcca agaattattc tggacgtttc       1620
acctgctggt ggctgacgac aatcagtact gatttgacat tcagtgtcaa aagcagcaga    1680
ggctcttctg accccaagg ggtgacgtgc ggagctgcta cactctctgc agagagagtc      1740 agagggaca acaaggagta tgagtactca gtggagtgcc aggaggacag tgcctgccca      1800
gctgctgagg agagtctgcc cattgaggtc atggtggatg ccgttcacaa gctcaagtat     1860
gaaaactaca ccagcagctt cttcatcagg gacatcatca aacctgaccc acccaagaac     1920
ttgcagctga agccattaaa gaattctcgg caggtggagg tcagctggga gtaccctgac     1980
acctggagta ctccacattc ctacttctcc ctgacattct gcgttcaggt ccagggcaag    2040
agcaagagag aaaagaaaga tagagtcttc acggacaaga cctcagccac ggtcatctgc    2100
cgcaaaaatg ccagcattag cgtgcgggcc caggaccgct actatagctc atcttggagc    2160
gaatgggcat ctgtgccctg cagtgagggc agaggcagcc tgctgacctg cggcgacgtc    2220
gaggagaacc ccgggcccat gggggcaggt gccaccggcc gcgccatgga cgggccgcgc    2280
ctgctgctgt tgctgcttct ggggggtgtcc cttggaggtg ccaaggaggc atgccccaca   2340
ggcctgtaca cacacagcgg tgagtgctgc aaagcctgca acctgggcga gggtgtggcc    2400
cagccttgtg gagccaacca gaccgtgtgt gagccctgcc tggacagcgt gacgttctcc    2460
gacgtggtga gcgcgaccga gccgtgcaag ccgtgcaccg agtgcgtggg gctccagagc    2520
atgtcggcgc cgtgcgtgga ggccgatgac gccgtgtgcc gctgcgccta cggctactac    2580
caggatgaga cgactgggcg ctgcgaggcg tgccgcgtgt gcgaggcggg ctcgggcctc    2640
gtgttctcct gccaggacaa gcagaacacc gtgtgcgagg agtgccccga cggcacgtat    2700
tccgacgagg ccaaccacgt ggacccgtgc ctgccctgca ccgtgtgcga ggacaccgag    2760
cgccagctcc gcgagtgcac acgctgggcc gacgccgagt gcgaggagat ccctggccgt    2820
tggattacac ggtccacacc cccagagggc tcggacagca cagccccag cacccaggag     2880 cctgaggcac ctccagaaca agacctcata gccagcacgg tggcaggtgt ggtgaccaca    2940
gtgatgggca gctcccagcc cgtggtgacc cgaggcacca ccgacaacct catccctgtc    3000
tattgctcca tcctggctgc tgtggttgtg ggtcttgtgg cctacatagc cttcaagagg    3060
tgatctagag ggcccgttta aacccgctga tcagcctcga ctgtgccttc tagttgccag    3120
ccatctgttg tttgccccte ccccgtgcct tccttgaccc tggaaggtgc cactcccact    3180
gtcctttcct aataaaatga ggaaattgca tcgcattgtc tgagtaggtg tcattctatt    3240
ctggggggtg ggtggggca ggacagcaag ggggaggatt gggaagacaa tagcaggcat    3300
gctggggatg cggtgggctc tatgactagt ggcgaattcg gcgcagatca aagagagcct    3360
gcgggcagag ctcagggtga caggtgcggc ctcggaggcc ccgggcagg ggtgagctga     3420 gccggtcctg gggtgggtgt ccctcctgc acaggatcag gagctccagg gtcgtagggc    3480
agggaccccc cagctccagt ccagggctct gtcctgcacc tggggaatgg tgaccggcat   3540
```

-continued

```
ctctgtcctc tagctctgga agcacccag ccctctagt ctgccctcac ccctgaccct    3600
gaccctccac cctgaccccg tcctaacccc tgacctttg                         3639
```

<210> SEQ ID NO 36
<211> LENGTH: 3017
<212> TYPE: DNA
<213> ORGANISM: artificial sequence
<220> FEATURE:
<223> OTHER INFORMATION: Inserted matrice TRAC locus_CubiCAR CD22 (60
      nucleotides upstream and downstream)

<400> SEQUENCE: 36

```
atgagatcat gtcctaaccc tgatcctctt gtcccacaga tatccagaac cctgaccctg      60
ttgctgggcc ttttcccat gcctgccttt actctgccag agttatattg ctggggtttt      120
gaagaagatc ctattaaata aaagaataag cagtattatt aagtagccct gcatttcagg     180
tttccttgag tggcaggcca ggcctggccg tgaacgttca ctgaaatcat ggcctcttgg     240
ccaagattga tagcttgtgc ctgtccctga gtcccagtcc atcacgagca gctggtttct     300
aagatgctat ttcccgtata aagcatgaga ccgtgacttg ccagcccac agagccccgc     360 ccttgtccat cactggcatc tggactccag cctgggttgg ggcaaagagg gaaatgagat    420
catgtcctaa ccctgatcct cttgtcccac agatatccag taccctacg acgtgcccga    480 ctacgcctcc ggtgagggca gaggaagtct tctaacatgc ggtgacgtgg aggagaatcc    540
gggccccgga tccgctctgc ccgtcaccgc tctgctgctg ccactggcac tgctgctgca    600
cgctgctagg cccggagggg gaggcagctg cccctacagc aacccccagcc tgtgcagcgg    660 aggcggcggc agcggcggag ggggtagcca ggtgcagctg cagcagagcg gccctggcct    720
ggtgaagcca agccagacac tgtccctgac ctgcgccatc agcggcgatt ccgtgagctc    780
caactccgcc gctggaatt ggatcaggca gtccccttct cggggcctgg agtggctggg    840
aaggacatac tatcggtcta agtggtacaa cgattatgcc gtgtctgtga agagcagaat    900
cacaatcaac cctgacacct ccaagaatca gttctctctg cagctgaata gcgtgacacc    960
agaggacacc gccgtgtact attgcgccag ggaggtgacc ggcgacctgg aggatgcctt   1020
tgacatctgg ggccagggca atggtgac cgtgagctcc ggaggcggcg gatctggcgg    1080
aggaggaagt gggggcggcg ggagtgatat ccagatgaca cagtccccat cctctctgag    1140
cgcctccgtg ggcgacagag tgacaatcac ctgtagggcc tcccagacca tctggtctta   1200
cctgaactgg tatcagcaga ggccccggcaa ggccccctaat ctgctgatct acgcagcaag    1260
ctccctgcag agcggagtgc catccagatt tctctggcagg ggctccggca cagacttcac   1320
cctgaccatc tctagcctgc aggccgagga cttcgccacc tactattgcc agcagtctta   1380
tagcatcccc cagacatttg gccagggcac caagctggag atcaagtcgg atcccggaag   1440
cggaggggga ggcagctgcc cctacagcaa ccccagcctg tgcagcggag cggcggcag    1500 cgagctgccc acccagggca ccttctccaa cgtgtccacc aacgtgagcc cagccaagcc   1560
caccaccacc gcctgtcctt attccaatcc ttccctgtgt gctcccacca aaccccgc    1620 tccaaggccc cctaccccg caccaactat gctctcccag ccactctcac tgcggcctga   1680
ggcctgtcgg cccgctgctg gaggcgcagt gcatacaagg ggcctcgatt tcgcctgcga   1740
tatttacatc tgggcacccc tcgcggcac ctgcggggtg cttctcctct ccctggtgat   1800 tacctgtat gcagacgggg ccggaagaa gctcctctac atttttaagc agccttcat   1860 gcggccagtg cagacaaccc aagaggaga tgggtgttcc tgcagattcc ctgaggaaga   1920
```

```
ggaaggcggg tgcgagctga gagtgaagtt ctccaggagc gcagatgccc ccgcctatca    1980
acagggccag aaccagctct acaacgagct taacctcggg aggcgcgaag aatacgacgt    2040
gttggataag agaaggggc gggaccccga gatgggagga agccccgga ggaagaaccc     2100 tcaggagggc ctgtacaacg agctgcagaa ggataagatg gccgaggcct actcagagat    2160
cgggatgaag ggggagcggc gccgcgggaa ggggcacgat gggctctacc aggggctgag    2220
cacagccaca aaggacacat acgacgcctt gcacatgcag gcccttccac ccgggaata    2280 gtctagaggg cccgtttaaa cccgctgatc agcctcgact gtgccttcta gttgccagcc    2340
atctgttgtt tgcccctccc ccgtgccttc cttgaccctg gaaggtgcca ctcccactgt    2400
cctttcctaa taaatgagg aaattgcatc gcattgtctg agtaggtgtc attctattct     2460 gggggtggg gtggggcagg acagcaaggg ggaggattgg gaagacaata gcaggcatgc     2520
tggggatgcg gtgggctcta tgactagtgg cgaattcccg tgtaccagct gagagactct    2580
aaatccagtg acaagtctgt ctgcctattc accgattttg attctcaaac aaatgtgtca    2640
caaagtaagg attctgatgt gtatatcaca gacaaaactg tgctagacat gaggtctatg    2700
gacttcaaga gcaacagtgc tgtggcctgg agcaacaaat ctgactttgc atgtgcaaac    2760
gccttcaaca acagcattat tccagaagac accttcttcc ccagcccagg taagggcagc    2820
tttggtgcct tcgcaggctg tttccttgct tcaggaatgg ccaggttctg cccagagctc    2880
tggtcaatga tgtctaaaac tcctctgatt ggtggtctcg gccttatcca ttgccaccaa    2940
aaccctcttt ttactaagaa acagtgagcc ttgttctggc agtccagaga atgacacggg    3000
aaaaaagcag atgaaga                                                   3017

<210> SEQ ID NO 37
<211> LENGTH: 2808
<212> TYPE: DNA
<213> ORGANISM: artificial sequence
<220> FEATURE:
<223> OTHER INFORMATION: Inserted matrice CD25 locus_IL15_2A_sIL15Ra (60
      nucleotides upstream and downstream)

<400> SEQUENCE: 37
agtgctggct agaaaccaag tgctttactg catgcacatc atttagcaca gttagttgct      60
gtttattatt cctgttccac agctattgtc tgccatataa aaacttaggc caggcacagt     120
ggctcacacc tgtaatccca gcactttgga aggccgaggc aggcagatca aaggtcagg      180 agttcgagac cagcctggcc aacatagcaa aaccccatct ctactaaaaa tacaaaaatt     240
agccaggcat ggtggcgtgt gcactggttt agagtgagga ccacattttt ttggtgccgt     300
gttacacata tgaccgtgac tttgttacac cactacagga ggaagagtag aagaacaatc     360
ggttctggcg tgaaacagac tttgaatttt gaccttctca agttggcggg agacgtggag     420
tccaacccag ggcccggtac cgggtccgcc accatggact ggacctggat tctgttcctc     480
gtggctgctg ctacaagagt gcacagcggc attcatgtct catttttggg ctgtttcagt    540
gcagggcttc ctaaaacaga agccaactgg gtgaatgtaa taagtgattt gaaaaaaatt    600
gaagatctta ttcaatctat gcatattgat gctactttat atacggaaag tgatgttcac    660
cccagttgca aagtaacagc aatgaagtgc tttctcttgg agttacaagt tatttcactt    720
gagtccggag atgcaagtat tcatgataca gtagaaaatc tgatcatcct agcaaacaac    780
agtttgtctt ctaatgggaa tgtaacagaa tctggatgca aagaatgtga ggaactggag    840
gaaaaaaata ttaaagaatt tttgcagagt tttgtacata ttgtccaaat gttcatcaac    900
```

```
acttctggaa gcggagctac taacttcagc ctgctgaagc aggctggaga cgtggaggag    960
aaccctggac ctgggaccgg ctctgcaacc atgattgga cgtggatcct gtttctcgtg   1020
gcagctgcca caagagttca cagtatcacg tgccctcccc ccatgtccgt ggaacacgca   1080
gacatctggg tcaagagcta cagcttgtac tccaggagc ggtacatttg taactctggt    1140
ttcaagcgta aagccggcac gtccagcctg acggagtgcg tgttgaacaa ggccacgaat   1200
gtcgcccact ggacaacccc cagtctcaaa tgcattagag accctgccct ggttcaccaa   1260
aggccagcgc caccctccac agtaacgacg cagggtgta ccccacagcc agagagcctc    1320
tccccttctg gaaagagcc cgcagcttca tctcccagct caaacaacac agcggccaca    1380
acagcagcta ttgtcccggg ctcccagctg atgccttcaa aatcaccttc cacaggaacc   1440
acagagataa gcagtcatga gtcctcccac ggcacccct ctcagacaac agccaagaac    1500
tgggaactca cagcatccgc ctcccaccag ccgccaggtg tgtatccaca gggccacagc   1560
gacaccactg agggcagagg cagcctgctg acctgcggcg acgtcgagga aaccccggg    1620 cccatggggg caggtgccac cggccgcgcc atggacgggc cgcgcctgct gctgttgctg   1680
cttctggggg tgtcccttgg aggtgccaag gaggcatgcc ccacaggcct gtacacacac   1740
agcggtgagt gctgcaaagc ctgcaacctg ggcgagggtg tggcccagcc ttgtggagcc   1800
aaccagaccg tgtgtgagcc ctgcctggac agcgtgacgt tctccgacgt ggtgagcgcg   1860
accgagccgt gcaagccgtg caccgagtgc gtggggctcc agagcatgtc ggcgccgtgc   1920
gtggaggccg atgacgccgt gtgccgctgc gcctacggct actaccagga tgagacgact   1980
gggcgctgcg aggcgtgccg cgtgtgcgag gcgggctcgg gcctcgtgtt ctcctgccag   2040
gacaagcaga acaccgtgtg cgaggagtgc cccgacggca cgtattccga cgaggccaac   2100
cacgtggacc cgtgcctgcc ctgcaccgtg tgcgaggaca ccgagcgcca gctccgcgag   2160
tgcacacgct gggccgacgc cgagtgcgag gagatccctg gccgttggat tacacggtcc   2220
acacccccag agggctcgga cagcacagcc cccagcaccc aggagcctga ggcacctcca   2280
gaacaagacc tcatagccag cacggtggca ggtgtggtga ccacagtgat gggcagctcc   2340
cagcccgtgg tgacccgagg caccaccgac aacctcatcc ctgtctattg ctccatcctg   2400
gctgctgtgg ttgtgggtct tgtggcctac atagccttca agaggtgaaa aaccaaaaga   2460
acaagaattt cttggtaaga agccgggaac agacaacaga agtcatgaag cccaagtgaa   2520
atcaaaggtg ctaaatggtc gcccaggaga catccgttgt gcttgcctgc gttttggaag   2580
ctctgaagtc acatcacagg acacggggca gtggcaacct tgtctctatg ccagctcagt   2640
cccatcagag agcgagcgct acccacttct aaatagcaat ttcgccgttg aagaggaagg   2700
gcaaaaccac tagaactctc catcttattt tcatgtatat gtgttcatta aagcatgaat   2760
ggtatggaac tctctccacc ctatatgtag tataaagaaa agtaggtt              2808
```

<210> SEQ ID NO 38
<211> LENGTH: 3084
<212> TYPE: DNA
<213> ORGANISM: artificial sequence
<220> FEATURE:
<223> OTHER INFORMATION: Inserted matrice PD1 locus_IL15_2A_sIL15Ra (60
      nucleotides upstream and downstream)

<400> SEQUENCE: 38

```
ggtggccggg gaggctttgt ggggccaccc agcccttcc tcacctctct ccatctctca      60
gactccccag acaggccctg gaacccccc accttctccc cagccctgct cgtggtgacc     120
```

```
gaaggggaca acgccacctt cacctgcagc ttctccaaca catcggagag cttcgtgcta    180
aactggtacc gcatgagccc cagcaaccag acggacaagc tggccgcctt ccccgaggac    240
cgcagccagc ccggccagga ctgccgcttc cgtgtcacac aactgcccaa cgggcgtgac    300
ttccacatga gcgtggtcag ggcccggcgc aatgacagcg gcacctacct ctgtggggcc    360
ggttctggcg tgaaacagac tttgaatttt gaccttctca agttggcggg agacgtggag    420
tccaacccag ggcccggtac cgggtccgcc accatggact ggacctggat tctgttcctc    480
gtggctgctg ctacaagagt gcacagcggc attcatgtct tcattttggg ctgtttcagt    540
gcagggcttc ctaaaacaga agccaactgg gtgaatgtaa taagtgattt gaaaaaaatt    600
gaagatctta ttcaatctat gcatattgat gctactttat atacggaaag tgatgttcac    660
cccagttgca aagtaacagc aatgaagtgc tttctcttgg agttacaagt tatttcactt    720
gagtccggag atgcaagtat tcatgataca gtagaaaatc tgatcatcct agcaaacaac    780
agtttgtctt ctaatgggaa tgtaacagaa tctggatgca agaatgtga ggaactggag     840 gaaaaaata ttaagaatt tttgcagagt tttgtacata ttgtccaaat gttcatcaac       900
acttctggaa gcggagctac taacttcagc ctgctgaagc aggctggaga cgtggaggag    960
aaccctggac ctgggaccgg ctctgcaacc atggattgga cgtggatcct gtttctcgtg    1020
gcagctgcca aagagttca cagtatcacg tgccctcccc ccatgtccgt ggaacacgca    1080
gacatctggg tcaagagcta cagcttgtac tccagggagc ggtacatttg taactctggt    1140
ttcaagcgta aagccggcac gtccagcctg acggagtgcg tgttgaacaa ggccacgaat    1200
gtcgcccact ggacaacccc cagtctcaaa tgcattagag accctgccct ggttcaccaa    1260
aggccagcgc caccctccac agtaacgacg gcaggggtga ccccacagcc agagagcctc    1320
tccccttctg gaaaagagcc cgcagcttca tctcccagct caaacaacac agcggccaca    1380
acagcagcta ttgtcccggg ctcccagctg atgccttcaa aatcaccttc cacaggaacc    1440
acagagataa gcagtcatga gtcctcccac ggcacccct ctcagacaac agccaagaac     1500
tgggaactca cagcatccgc ctcccaccag ccgccaggtg tgtatccaca gggcacagc    1560 gacaccactg agggcagagg cagcctgctg acctgcggcg acgtcgagga gaaccccggg    1620
cccatggggg caggtccac cggccgcgcc atggacgggc cgcgcctgct gctgttgctg    1680
cttctggggg tgtcccttgg aggtgccaag gaggcatgcc ccacaggcct gtacacacac    1740
agcggtgagt gctgcaaagc ctgcaacctg ggcgagggtg tggcccagcc ttgtggagcc    1800
aaccagaccg tgtgtgagcc ctgcctggac agcgtgacgt tctccgacgt ggtgagcgcg    1860
accgagccgt gcaagccgtg caccgagtgc gtggggctcc agagcatgtc ggcgccgtgc    1920
gtggaggcca tgacgccgt gtgccgctgc gcctacggct actaccagga tgagacgact    1980
gggcgctgcg aggcgtgccg cgtgtgcgag gcgggctcgg gcctcgtgtt ctcctgccag    2040
gacaagcaga acaccgtgtg cgaggagtgc cccgacggca cgtattccga cgaggccaac    2100
cacgtggacc cgtgcctgcc ctgcaccgtg tgcgaggaca ccgagcgcca gctccgcgag    2160
tgcacacgct gggccgacgc cgagtgcgag gagatccctg gccgttggat tacacggtcc    2220 acaccccag agggctcgga cagcacagcc cccagcaccc aggagcctga ggcacctcca    2280
gaacaagacc tcatagccag cacggtggca ggtgtggtga ccacagtgat gggcagctcc    2340
cagcccgtgg tgacccgagg caccaccgac aacctcatcc ctgtctattg ctccatcctg    2400
gctgctgtgg ttgtgggtct tgtggcctac atagccttca agaggtgatc tagagggccc    2460
```

-continued

```
gtttaaaccc gctgatcagc ctcgactgtg ccttctagtt gccagccatc tgttgtttgc     2520
ccctcccccg tgccttcctt gaccctggaa ggtgccactc ccactgtcct ttcctaataa     2580
aatgaggaaa ttgcatcgca ttgtctgagt aggtgtcatt ctattctggg gggtggggtg     2640
gggcaggaca gcaagggga ggattgggaa gacaatagca ggcatgctgg ggatgcggtg      2700
ggctctatga ctagtggcga attcggcgca gatcaaagag agcctgcggg cagagctcag     2760
ggtgacaggt gcggcctcgg aggccccggg gcaggggtga gctgagccgg tcctggggtg     2820 ggtgtccct cctgcacagg atcaggagct ccagggtcgt agggcaggga cccccagct       2880 ccagtccagg gctctgtcct gcacctgggg aatggtgacc ggcatctctg tcctctagct    2940
ctggaagcac cccagcccct ctagtctgcc ctcacccctg accctgaccc tccaccctga    3000
ccccgtccta accctgacc tttgtgccct tccagagaga agggcagaag tgcccacagc     3060
ccaccccagc ccctcacccca ggcc                                           3084
```

<210> SEQ ID NO 39
<211> LENGTH: 3475
<212> TYPE: DNA
<213> ORGANISM: artificial sequence
<220> FEATURE:
<223> OTHER INFORMATION: Inserted matrice  CD25 locus_IL12a_2A_IL12b (60 nucleotides upstream and downstream)

<400> SEQUENCE: 39

```
agtgctggct agaaaccaag tgctttactg catgcacatc atttagcaca gttagttgct     60
gtttattatt cctgttccac agctattgtc tgccatataa aaactaggc caggcacagt     120 ggctcacacc tgtaatccca gcactttgga aggccgaggc aggcagatca caaggtcagg    180
agttcgagac cagcctggcc aacatagcaa aaccccatct ctactaaaaa tacaaaaatt    240
agccaggcat ggtggcgtgt gcactggttt agagtgagga ccacattttt ttggtgccgt    300
gttacacata tgaccgtgac tttgttacac cactacagga ggaagagtag aagaacaatc    360
ggttctggcg tgaaacagac tttgaatttt gaccttctca agttggcggg agacgtggag    420
tccaacccag ggcccatgtg gccccctggg tcagcctccc agccaccgcc ctcacctgcc    480
gcggccacag gtctgcatcc agcggctcgc cctgtgtccc tgcagtgccg gctcagcatg    540
tgtccagcgc gcagcctcct ccttgtggct accctggtcc tcctggacca cctcagtttg    600
gccagaaacc tccccgtggc cactccagac ccaggaatgt tcccatgcct tcaccactcc    660
caaaacctgc tgagggccgt cagcaacatg ctccagaagg ccagacaaac tctagaattt    720
tacccttgca cttctgaaga gattgatcat gaagatatca caaagataa aaccagcaca    780 gtggaggcct gtttaccatt ggaattaacc aagaatgaga gttgcctaaa ttccagagag    840
acctctttca taactaatgg gagttgcctg gcctccagaa agacctcttt tatgatggcc    900
ctgtgcctta gtagtattta tgaagacttg aagatgtacc aggtggagtt caagaccatg    960
aatgcaaagc ttctgatgga tcctaagagg cagatctttc tagatcaaaa catgctggca    1020
gttattgatg agctgatgca ggccctgaat ttcaacagtg agactgtgcc acaaaaatcc    1080
tcccttgaag aaccggattt ttataaaact aaaatcaagc tctgcatact tcttcatgct    1140
ttcagaattc gggcagtgac tattgataga gtgatgagct atctgaatgc ttccggaagc    1200
ggagctacta acttcagcct gctgaagcag gctggagacg tggaggagaa ccctggacct    1260
atgtgtcacc agcagttggt catctcttgg tttttccctgg ttttttctggc atctccctc    1320 gtggccatat gggaactgaa gaaagatgtt tatgtcgtag aattggattg gtatccggat    1380
```

```
gccccctggag aaatggtggt cctcacctgt gacacccctg aagaagatgg tatcacctgg    1440
accttggacc agagcagtga ggtcttaggc tctggcaaaa ccctgaccat ccaagtcaaa    1500
gagtttggag atgctggcca gtacacctgt cacaaaggag gcgaggttct aagccattcg    1560
ctcctgctgc ttcacaaaaa ggaagatgga atttggtcca ctgatatttt aaaggaccag    1620
aaagaaccca aaataagac ctttctaaga tgcgaggcca agaattattc tggacgtttc    1680
acctgctggt ggctgacgac aatcagtact gatttgacat tcagtgtcaa agcagcaga    1740 ggctcttctg accccaagg ggtgacgtgc ggagctgcta cactctctgc agagagagtc    1800
agaggggaca caaggagta tgagtactca gtggagtgcc aggaggacag tgcctgccca    1860
gctgctgagg agagtctgcc cattgaggtc atggtggatg ccgttcacaa gctcaagtat    1920
gaaaactaca ccagcagctt cttcatcagg gacatcatca aacctgaccc acccaagaac    1980
ttgcagctga agccattaaa gaattctcgg caggtggagg tcagctggga gtaccctgac    2040
acctggagta ctccacattc ctacttctcc ctgacattct gcgttcaggt ccagggcaag    2100
agcaagagag aaaagaaaga tagagtcttc acggacaaga cctcagccac ggtcatctgc    2160
cgcaaaaatg ccagcattag cgtgcgggcc caggaccgct actatagctc atcttggagc    2220
gaatgggcat ctgtgccctg cagtgagggc agaggcagcc tgctgacctg cggcgacgtc    2280
gaggagaacc ccgggcccat gggggcaggt gccaccggcc gcgccatgga cgggccgcgc    2340
ctgctgctgt tgctgcttct gggggtgtcc cttggaggtg ccaaggaggc atgccccaca    2400
ggcctgtaca cacacagcgg tgagtgctgc aaagcctgca acctgggcga gggtgtggcc    2460
cagccttgtg gagccaacca gaccgtgtgt gagccctgcc tggacagcgt gacgttctcc    2520
gacgtggtga gcgcgaccga gccgtgcaag ccgtgcaccg agtgcgtggg gctccagagc    2580
atgtcggcgc cgtgcgtgga ggccgatgac gccgtgtgcc gctgcgccta cggctactac    2640
caggatgaga cgactgggcg ctgcgaggcg tgccgcgtgt gcgaggcggg ctcgggcctc    2700
gtgttctcct gccaggacaa gcagaacacc gtgtgcgagg agtgccccga cggcacgtat    2760
tccgacgagg ccaaccacgt ggacccgtgc ctgccctgca cgtgtgcga ggacaccgag    2820 cgccagctcc gcgagtgcac acgctgggcc gacgccgagt gcgaggagat ccctggccgt    2880
tggattacac ggtccacacc cccagagggc tcggacagca cagcccccag cacccaggag    2940
cctgaggcac ctcagaaca agacctcata gccagcacgg tggcaggtgt ggtgaccaca    3000
gtgatgggca gctcccagcc cgtggtgacc cgaggcacca ccgacaacct catccctgtc    3060
tattgctcca tcctggctgc tgtggttgtg ggtcttgtgg cctacatagc cttcaagagg    3120
tgaaaaacca aagaacaag aatttcttgg taagaagccg ggaacagaca acagaagtca    3180
tgaagcccaa gtgaaatcaa aggtgctaaa tggtcgccca ggagacatcc gttgtgcttg    3240
cctgcgtttt ggaagctctg aagtcacatc acaggacacg gggcagtggc aaccttgtct    3300
ctatgccagc tcagtcccat cagagagcga gcgctaccca cttctaaata gcaatttcgc    3360
cgttgaagag gaagggcaaa accactagaa ctctccatct tattttcatg tatatgtgtt    3420
catgaatggt atggaactct ctccacccta tatgtagtat aaagaaaagt aggtt         3475
```

<210> SEQ ID NO 40
<211> LENGTH: 3759
<212> TYPE: DNA
<213> ORGANISM: artificial sequence
<220> FEATURE:
<223> OTHER INFORMATION: Inserted matrice PD1 locus_IL12a_2A_IL12b (60 nucleotides upstream and downstream)

<400> SEQUENCE: 40

```
ggtggccggg gaggctttgt ggggccaccc agcccttcc tcacctctct ccatctctca        60
gactccccag acaggccctg gaaccccccc accttctccc cagccctgct cgtggtgacc      120
gaagggaca  acgccacctt cacctgcagc ttctccaaca catcggagag cttcgtgcta      180
aactggtacc gcatgagccc cagcaaccag acggacaagc tggccgcctt ccccgaggac      240
cgcagccagc ccggccagga ctgccgcttc cgtgtcacac aactgcccaa cgggcgtgac      300
ttccacatga gcgtggtcag ggcccggcgc aatgacagcg gcacctacct ctgtggggcc      360
ggttctggcg tgaaacagac tttgaatttt gaccttctca agttggcggg agacgtggag      420
tccaacccag ggcccatgtg ccccctggg  tcagcctccc agccaccgcc ctcacctgcc      480
gcggccacag gtctgcatcc agcggctcgc cctgtgtccc tgcagtgccg gctcagcatg      540
tgtccagcgc gcagcctcct ccttgtggct accctggtcc tcctggacca cctcagtttg      600
gccagaaacc tccccgtggc cactccagac ccaggaatgt tcccatgcct tcaccactcc      660
caaaacctgc tgagggccgt cagcaacatg ctccagaagg ccagacaaac tctagaattt      720
taccccttgca cttctgaaga gattgatcat gaagatatca caaagataa  aaccagcaca     780
gtggaggcct gtttaccatt ggaattaacc aagaatgaga gttgcctaaa ttccagagag      840
acctctttca taactaatgg gagttgcctg gcctccagaa agacctcttt tatgatggcc      900
ctgtgccttta gtagtattta tgaagacttg aagatgtacc aggtggagtt caagaccatg      960
aatgcaaagc ttctgatgga tcctaagagg cagatctttc tagatcaaaa catgctggca     1020
gttattgatg agctgatgca ggccctgaat ttcaacagtg agactgtgcc acaaaaatcc     1080
tcccttgaag aaccggattt ttataaaact aaaatcaagc tctgcatact tcttcatgct     1140
ttcagaattc gggcagtgac tattgataga gtgatgagct atctgaatgc ttccggaagc     1200
ggagctacta acttcagcct gctgaagcag gctggagacg tggaggagaa ccctggacct     1260
atgtgtcacc agcagttggt catctcttgg tttttccctgg tttttctggc atctccccctc   1320
gtggccatat gggaactgaa gaaagatgtt tatgtcgtag aattggattg gtatccggat     1380
gcccctggag aaatggtggt cctcacctgt gacacccctg aagaagatgg tatcacctgg     1440
accttggacc agagcagtga ggtcttaggc tctggcaaaa ccctgaccat ccaagtcaaa     1500
gagtttggag atgctggcca gtacacctgt cacaaaggag cgaggttct  aagccattcg     1560
ctcctgctgc ttcacaaaaa ggaagatgga atttggtcca ctgatatttt aaaggaccag     1620
aaagaaccca aaaataagac ctttctaaga tgcgaggcca agaattattc tggacgtttc     1680
acctgctggt ggctgacgac aatcagtact gatttgacat tcagtgtcaa aagcagcaga     1740
ggctcttctg accccaagg  ggtgacgtgc ggagctgcta cactctctgc agagagagtc     1800
agaggggaca acaaggagta tgagtactca gtggagtgcc aggaggacag tgcctgccca     1860
gctgctgagg agagtctgcc cattgaggtc atggtggatg ccgttcacaa gctcaagtat     1920
gaaaactaca ccagcagctt cttcatcagg gacatcatca accctgaccc acccaagaac     1980
ttgcagctga agccattaaa gaattctcgg caggtggagg tcagctggga gtaccctgac     2040
acctggagta ctccacattc ctacttctcc ctgacattct gcgttcaggt ccagggcaag     2100
agcaagagag aaaagaaaga tagagtcttc acggacaaga cctcagccac ggtcatctgc     2160
cgcaaaaatg ccagcattag cgtgcgggcc caggaccgct actatagctc atcttggagc     2220
gaatgggcat ctgtgccctg cagtgagggc agaggcagcc tgctgacctg cggcgacgtc     2280
gaggagaacc ccgggcccat ggggcaggt  gccaccggcc gcgccatgga cgggccgcgc     2340
```

```
ctgctgctgt tgctgcttct gggggtgtcc cttggaggtg ccaaggaggc atgcccaca    2400 ggcctgtaca cacacagcgg tgagtgctgc aaagcctgca acctgggcga gggtgtggcc    2460
cagccttgtg gagccaacca gaccgtgtgt gagccctgcc tggacagcgt gacgttctcc    2520
gacgtggtga gcgcgaccga gccgtgcaag ccgtgcaccg agtgcgtggg gctccagagc    2580
atgtcggcgc cgtgcgtgga ggccgatgac gccgtgtgcc gctgcgccta cggctactac    2640
caggatgaga cgactgggcg ctgcgaggcg tgccgcgtgt gcgaggcggg ctcgggcctc    2700
gtgttctcct gccaggacaa gcagaacacc gtgtgcgagg agtgccccga cggcacgtat    2760
tccgacgagg ccaaccacgt ggacccgtgc ctgccctgca ccgtgtgcga ggacaccgag    2820
cgccagctcc gcgagtgcac acgctgggcc gacgccgagt gcgaggagat ccctggccgt    2880
tggattacac ggtccacacc cccagagggc tcggacagca cagcccccag cacccaggag    2940
cctgaggcac ctccagaaca agacctcata gccagcacgg tggcaggtgt ggtgaccaca    3000
gtgatgggca gctcccagcc cgtggtgacc cgaggcacca ccgacaacct catccctgtc    3060
tattgctcca tcctggctgc tgtggttgtg ggtcttgtgg cctacatagc cttcaagagg    3120
tgatctagag ggcccgttta aacccgctga tcagcctcga ctgtgccttc tagttgccag    3180
ccatctgttg tttgccccte cccgtgcct tccttgaccc tggaaggtgc cactcccact    3240
gtcctttcct aataaaatga ggaaattgca tcgcattgtc tgagtaggtg tcattctatt    3300 ctgggggtg gggtggggca ggacagcaag ggggaggatt gggaagacaa tagcaggcat    3360 gctgggatg cggtgggctc tatgactagt ggcgaattcg gcgcagatca aagagagcct    3420
gcgggcagag ctcagggtga caggtgcggc ctcggaggcc ccggggcagg ggtgagctga    3480
gccggtcctg gggtgggtgt cccctcctgc acaggatcag gagctccagg gtcgtagggc    3540
agggaccccc cagctccagt ccagggctct gtcctgcacc tggggaatgg tgaccggcat    3600
ctctgtcctc tagctctgga agcaccccag cccctctagt ctgccctcac ccctgaccct    3660
gaccctccac cctgaccccg tcctaacccc tgaccttgt gcccttccag agagaagggc    3720
agaagtgccc acagcccacc ccagcccctc acccaggcc                          3759
```

<210> SEQ ID NO 41
<211> LENGTH: 60
<212> TYPE: DNA
<213> ORGANISM: artificial sequence
<220> FEATURE:
<223> OTHER INFORMATION: upstream TRAC locus polynucleotide sequence

<400> SEQUENCE: 41
atgagatcat gtcctaaccc tgatcctctt gtcccacaga tatccagaac cctgaccctg    60

<210> SEQ ID NO 42
<211> LENGTH: 60
<212> TYPE: DNA
<213> ORGANISM: artificial sequence
<220> FEATURE:
<223> OTHER INFORMATION: downstream TRAC locus polynucleotide sequence

<400> SEQUENCE: 42
gaaacagtga gccttgttct ggcagtccag agaatgacac gggaaaaaag cagatgaaga    60

<210> SEQ ID NO 43
<211> LENGTH: 60
<212> TYPE: DNA
<213> ORGANISM: artificial sequence
<220> FEATURE:

<223> OTHER INFORMATION: upstream CD25 locus polynucleotide sequence

<400> SEQUENCE: 43
agtgctggct agaaaccaag tgctttactg catgcacatc atttagcaca gttagttgct    60

<210> SEQ ID NO 44
<211> LENGTH: 52
<212> TYPE: DNA
<213> ORGANISM: artificial sequence
<220> FEATURE:
<223> OTHER INFORMATION: downstream CD25 locus polynucleotide sequence

<400> SEQUENCE: 44
gaatggtatg gaactctctc caccctatat gtagtataaa gaaaagtagg tt            52

<210> SEQ ID NO 45
<211> LENGTH: 60
<212> TYPE: DNA
<213> ORGANISM: artificial sequence
<220> FEATURE:
<223> OTHER INFORMATION: upstream PD1 locus polynucleotide sequence

<400> SEQUENCE: 45
ggtggccggg gaggctttgt ggggccaccc agcccttcc tcacctctct ccatctctca    60

<210> SEQ ID NO 46
<211> LENGTH: 60
<212> TYPE: DNA
<213> ORGANISM: artificial sequence
<220> FEATURE:
<223> OTHER INFORMATION: downstream PD1 locus polynucleotide sequence

<400> SEQUENCE: 46
tgcccttcca gagagaaggg cagaagtgcc cacagcccac cccagcccct cacccaggcc    60

<210> SEQ ID NO 47
<211> LENGTH: 759
<212> TYPE: DNA
<213> ORGANISM: artificial sequence
<220> FEATURE:
<223> OTHER INFORMATION: IL-12a polynucleotide

<400> SEQUENCE: 47
atgtggcccc ctgggtcagc ctcccagcca ccgccctcac ctgccgcggc cacaggtctg    60
catccagcgg ctcgccctgt gtccctgcag tgccggctca gcatgtgtcc agcgcgcagc   120
ctcctccttg tggctaccct ggtcctcctg gaccacctca gtttggccag aaacctcccc   180
gtggccactc cagacccagg aatgttccca tgccttcacc actcccaaaa cctgctgagg   240
gccgtcagca acatgctcca gaaggccaga caaactctag aattttaccc ttgcacttct   300
gaagagattg atcatgaaga tatcacaaaa gataaaacca gcacagtgga ggcctgttta   360
ccattggaat taaccaagaa tgagagttgc ctaaattcca gagagacctc tttcataact   420
aatgggagtt gcctggcctc cagaaagacc tcttttatga tggccctgtg ccttagtagt   480
atttatgaag acttgaagat gtaccaggtg gagttcaaga ccatgaatgc aaagcttctg   540
atggatccta gaggcagat cttttctagat caaaacatgc tggcagttat tgatgagctg   600
atgcaggccc tgaatttcaa cagtgagact gtgccacaaa atcctccct tgaagaaccg   660 gattttttata aaactaaaat caagctctgc atacttcttc atgctttcag aattcgggca   720
gtgactattg atagagtgat gagctatctg aatgcttcc                         759

<210> SEQ ID NO 48
<211> LENGTH: 984
<212> TYPE: DNA
<213> ORGANISM: artificial sequence
<220> FEATURE:
<223> OTHER INFORMATION: IL12b polynucleotide

<400> SEQUENCE: 48

```
atgtgtcacc agcagttggt catctcttgg ttttccctgg ttttctggc atctcccctc      60
gtggccatat gggaactgaa gaaagatgtt tatgtcgtag aattggattg gtatccggat    120
gcccctggag aaatggtggt cctcacctgt gacacccctg aagaagatgg tatcacctgg    180
accttggacc agagcagtga ggtcttaggc tctggcaaaa ccctgaccat ccaagtcaaa    240
gagtttggag atgctggcca gtacacctgt cacaaaggag gcgaggttct aagccattcg    300
ctcctgctgc ttcacaaaaa ggaagatgga atttggtcca ctgatatttt aaaggaccag    360
aaagaaccca aaataagac ctttctaaga tgcgaggcca agaattattc tggacgtttc    420
acctgctggt ggctgacgac aatcagtact gatttgacat tcagtgtcaa aagcagcaga    480
ggctcttctg acccccaagg ggtgacgtgc ggagctgcta cactctctgc agagagagtc    540
agagggaca caaggagta tgagtactca gtggagtgcc aggaggacag tgcctgccca    600
gctgctgagg agagtctgcc cattgaggtc atggtggatg ccgttcacaa gctcaagtat    660
gaaaactaca ccagcagctt cttcatcagg gacatcatca acctgacccc acccaagaac    720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagt                                           984
```

<210> SEQ ID NO 49
<211> LENGTH: 399
<212> TYPE: DNA
<213> ORGANISM: artificial sequence
<220> FEATURE:
<223> OTHER INFORMATION: IL15 polynucleotide

<400> SEQUENCE: 49

```
ggcattcatg tcttcatttt gggctgtttc agtgcagggc ttcctaaaac agaagccaac     60
tgggtgaatg taataagtga tttgaaaaaa attgaagatc ttattcaatc tatgcatatt    120
gatgctactt tatatacgga aagtgatgtt caccccagtt gcaaagtaac agcaatgaag    180
tgctttctct tggagttaca agttatttca cttgagtccg agatgcaag tattcatgat    240
acagtagaaa atctgatcat cctagcaaac aacagtttgt cttctaatgg gaatgtaaca    300
gaatctggat gcaaagaatg tgaggaactg gaggaaaaaa atattaaaga atttttgcag    360
agttttgtac atattgtcca aatgttcatc aacacttct                           399
```

<210> SEQ ID NO 50
<211> LENGTH: 525
<212> TYPE: DNA
<213> ORGANISM: artificial sequence
<220> FEATURE:
<223> OTHER INFORMATION: sIL15ra polynucleotide

<400> SEQUENCE: 50

```
atcacgtgcc ctccccccat gtccgtggaa cacgcagaca tctgggtcaa gagctacagc     60
```

```
ttgtactcca gggagcggta catttgtaac tctggtttca agcgtaaagc cggcacgtcc    120
agcctgacgg agtgcgtgtt gaacaaggcc acgaatgtcg cccactggac aacccccagt    180
ctcaaatgca ttagagaccc tgccctggtt caccaaaggc cagcgccacc ctccacagta    240
acgacggcag gggtgacccc acagccagag agcctctccc cttctggaaa agagcccgca    300
gcttcatctc ccagctcaaa caacacagcg ccacaacag cagctattgt cccgggctcc     360
cagctgatgc cttcaaaatc accttccaca ggaaccacag agataagcag tcatgagtcc    420
tcccacggca cccctctca gacaacagcc aagaactggg aactcacagc atccgcctcc     480
caccagccgc caggtgtgta tccacagggc acagcgaca ccact                    525
```

<210> SEQ ID NO 51
<211> LENGTH: 1818
<212> TYPE: DNA
<213> ORGANISM: artificial sequence
<220> FEATURE:
<223> OTHER INFORMATION: soluble GP130 polynucleotide

<400> SEQUENCE: 51

```
atgctgacac tgcagacttg gctggtgcag gcactgttta tttttctgac tactgaatca    60
actggcgaac tgctggaccc ttgtggctac atcagccctg agtccccagt ggtgcagctg   120
cacagcaact tcaccgccgt gtgcgtgctg aaggagaagt gtatggacta ctttcacgtg   180
aacgccaatt atatcgtgtg aaaaccaac cacttcacaa tccccaagga gcagtacacc    240
atcatcaata ggacagccag ctccgtgacc tttacagaca tcgcctccct gaacatccag   300
ctgacctgca atatcctgac attcggccag ctggagcaga acgtgtatgg catcaccatc    360
atctctggcc tgcccctga aagcctaag aacctgagct gcatcgtgaa tgagggcaag     420
aagatgcggt gtgagtggga cggcggcaga gagacacacc tggagacaaa cttcacccctg   480 aagtccgagt gggccacaca caagtttgcc gactgcaagg ccaagcgcga tacccccaaca   540 tcctgtaccg tggattactc tacagtgtat tttgtgaaca tcgaagtgtg ggtggaggcc    600
gagaatgccc tgggcaaggt gacctccgac cacatcaact tcgatcccgt gtacaaggtg    660
aagcctaacc cacccacaa tctgagcgtg atcaattccg aggagctgtc tagcatcctg    720
aagctgacct ggacaaaccc atctatcaag agcgtgatca tcctgaagta caatatccag    780
tatcggacca aggacgcctc cacatggagc cagatccctc cagaggatac cgccagcaca    840
agatcctctt tcaccgtgca ggacctgaag cccttcacag agtacgtgtt tcggatcaga    900
tgtatgaagg aggacggcaa gggctactgg agcgattggt ccgaggaggc cagcggcatc    960
acctatgagg acaggccttc taaggccccc agcttctggt acaagatcga tccatcccac   1020
acccagggct atcgcacagt gcagctggtg tggaaaaccc tgcccccttt cgaggccaac   1080
ggcaagatcc tggactacga ggtgaccctg acacggtgga agtcccacct gcagaactat   1140
accgtgaatg ccaccaagct gacagtgaac ctgacaaaatg atcggtacct ggccaccctg   1200
acagtgagaa acctggtggg caagtctgac gccgccgtgc tgaccatccc tgcctgcgat   1260
ttccaggcca cacccagt gatggacctg aaggcctttc caaggataa tatgctgtgg   1320 gtggagtgga ccacacctag agagtccgtg aagaagtaca tcctggagtg gtgcgtgctg   1380
tctgacaagg ccccatgtat caccgactgg cagcaggagg atggcaccgt gcacaggaca   1440
tatctgcgcg gcaacctggc cgagtctaag tgttacctga tcaccgtgac acccgtgtat   1500
gcagacggac caggctctcc tgagagcatc aaggcctacc tgaagcaggc caccaccaagc   1560 aagggaccaa ccgtgcggac aaagaaggtc ggcaagaatg aggccgtgct ggagtgggac   1620
```

```
cagctgcctg tggatgtgca gaacggcttc atcaggaatt acaccatctt ttatcgcaca    1680
atcatcggca acgagacagc cgtgaatgtg acagctccc acaccgagta tacactgtct    1740
agcctgacct ccgatacact gtacatggtg aggatggccg cctatacaga cgagggcggc    1800
aaggatggcc ccgagttt                                                  1818

<210> SEQ ID NO 52
<211> LENGTH: 72
<212> TYPE: DNA
<213> ORGANISM: artificial sequence
<220> FEATURE:
<223> OTHER INFORMATION: IgE signal sequence

<400> SEQUENCE: 52
ggtaccgggt ccgccaccat ggactggacc tggattctgt tcctcgtggc tgctgctaca    60
agagtgcaca gc                                                        72

<210> SEQ ID NO 53
<211> LENGTH: 75
<212> TYPE: DNA
<213> ORGANISM: artificial sequence
<220> FEATURE:
<223> OTHER INFORMATION: F2A

<400> SEQUENCE: 53
ggttctggcg tgaaacagac tttgaatttt gaccttctca agttggcggg agacgtggag    60
tccaacccag ggccc                                                     75

<210> SEQ ID NO 54
<211> LENGTH: 66
<212> TYPE: DNA
<213> ORGANISM: artificial sequence
<220> FEATURE:
<223> OTHER INFORMATION: P2A

<400> SEQUENCE: 54
ggaagcggag ctactaactt cagcctgctg aagcaggctg agacgtgga ggagaaccct    60 ggacct                                                               66

<210> SEQ ID NO 55
<211> LENGTH: 54
<212> TYPE: DNA
<213> ORGANISM: artificial sequence
<220> FEATURE:
<223> OTHER INFORMATION: T2A

<400> SEQUENCE: 55
gagggcagag gcagcctgct gacctgcggc gacgtcgagg agaacccgg gccc           54

<210> SEQ ID NO 56
<211> LENGTH: 825
<212> TYPE: DNA
<213> ORGANISM: artificial sequence
<220> FEATURE:
<223> OTHER INFORMATION: LNGFR

<400> SEQUENCE: 56
atgggggcag gtgccaccgg ccgcgccatg gacgggccgc gcctgctgct gttgctgctt    60 ctggggtgt cccttggagg tgccaaggag gcatgcccca caggcctgta cacacacagc   120
ggtgagtgct gcaaagcctg caactctggc gagggtgtgg cccagccttg tggagccaac   180
```

-continued

```
cagaccgtgt gtgagccctg cctggacagc gtgacgttct ccgacgtggt gagcgcgacc    240
gagccgtgca agccgtgcac cgagtgcgtg gggctccaga gcatgtcggc gccgtgcgtg    300
gaggccgatg acgccgtgtg ccgctgcgcc tacggctact accaggatga gacgactggg    360
cgctgcgagg cgtgccgcgt gtgcgaggcg ggctcgggcc tcgtgttctc ctgccaggac    420
aagcagaaca ccgtgtgcga ggagtgcccc gacggcacgt attccgacga ggccaaccac    480
gtggacccgt gcctgccctg caccgtgtgc gaggacaccg agcgccagct ccgcgagtgc    540
acacgctggg ccgacgccga gtgcgaggag atccctggcc gttggattac acggtccaca    600
cccccagagg gctcggacag cacagccccc agcacccagg agcctgaggc acctccagaa    660
caagacctca tagccagcac ggtggcaggt gtggtgacca cagtgatggg cagctcccag    720
cccgtggtga cccgaggcac caccgacaac ctcatccctg tctattgctc catcctggct    780
gctgtggttg tgggtcttgt ggcctacata gccttcaaga ggtga                    825
```

<210> SEQ ID NO 57
<211> LENGTH: 253
<212> TYPE: PRT
<213> ORGANISM: artificial sequence
<220> FEATURE:
<223> OTHER INFORMATION: IL-12a polypeptide

<400> SEQUENCE: 57

```
Met Trp Pro Pro Gly Ser Ala Ser Gln Pro Pro Ser Pro Ala Ala
1               5                   10                  15

Ala Thr Gly Leu His Pro Ala Arg Pro Val Ser Leu Gln Cys Arg
            20                  25                  30

Leu Ser Met Cys Pro Ala Arg Ser Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Arg
65                  70                  75                  80

Ala Val Ser Asn Met Leu Gln Lys Ala Arg Gln Thr Leu Glu Phe Tyr
            85                  90                  95

Pro Cys Thr Ser Glu Glu Ile Asp His Glu Asp Ile Thr Lys Asp Lys
        100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

-continued

```
<210> SEQ ID NO 58
<211> LENGTH: 328
<212> TYPE: PRT
<213> ORGANISM: artificial sequence
<220> FEATURE:
<223> OTHER INFORMATION: IL12b polypeptide

<400> SEQUENCE: 58

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 59
<211> LENGTH: 133
<212> TYPE: PRT
<213> ORGANISM: artificial sequence
```

<220> FEATURE:
<223> OTHER INFORMATION: IL15 polypeptide

<400> SEQUENCE: 59

Gly Ile His Val Phe Ile Leu Gly Cys Phe Ser Ala Gly Leu Pro Lys
1               5                   10                  15

Thr Glu Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser
    130

<210> SEQ ID NO 60
<211> LENGTH: 175
<212> TYPE: PRT
<213> ORGANISM: artificial sequence
<220> FEATURE:
<223> OTHER INFORMATION: sIL15ra polypeptide

<400> SEQUENCE: 60

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 61
<211> LENGTH: 606
<212> TYPE: PRT

<213> ORGANISM: artificial sequence
<220> FEATURE:
<223> OTHER INFORMATION: soluble gp130

<400> SEQUENCE: 61

```
Met Leu Thr Leu Gln Thr Trp Leu Val Gln Ala Leu Phe Ile Phe Leu
 1               5                  10                  15

Thr Thr Glu Ser Thr Gly Glu Leu Leu Asp Pro Cys Gly Tyr Ile Ser
             20                  25                  30

Pro Glu Ser Pro Val Val Gln Leu His Ser Asn Phe Thr Ala Val Cys
         35                  40                  45

Val Leu Lys Glu Lys Cys Met Asp Tyr Phe His Val Asn Ala Asn Tyr
 50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
```

```
                385                 390                 395                 400
        Thr Val Arg Asn Leu Val Gly Lys Ser Asp Ala Ala Val Leu Thr Ile
                        405                 410                 415

Pro Ala Cys Asp Phe Gln Ala Thr His Pro Val Met Asp Leu Lys Ala
                        420                 425                 430

Phe Pro Lys Asp Asn Met Leu Trp Val Glu Trp Thr Thr Pro Arg Glu
                        435                 440                 445

Ser Val Lys Lys Tyr Ile Leu Glu Trp Cys Val Leu Ser Asp Lys Ala
                        450                 455                 460

Pro Cys Ile Thr Asp Trp Gln Gln Glu Asp Gly Thr Val His Arg Thr
        465                 470                 475                 480

Tyr Leu Arg Gly Asn Leu Ala Glu Ser Lys Cys Tyr Leu Ile Thr Val
                        485                 490                 495

Thr Pro Val Tyr Ala Asp Gly Pro Gly Ser Pro Glu Ser Ile Lys Ala
                        500                 505                 510

Tyr Leu Lys Gln Ala Pro Pro Ser Lys Gly Pro Thr Val Arg Thr Lys
                        515                 520                 525

Lys Val Gly Lys Asn Glu Ala Val Leu Glu Trp Asp Gln Leu Pro Val
                        530                 535                 540

Asp Val Gln Asn Gly Phe Ile Arg Asn Tyr Thr Ile Phe Tyr Arg Thr
        545                 550                 555                 560

Ile Ile Gly Asn Glu Thr Ala Val Asn Val Asp Ser Ser His Thr Glu
                        565                 570                 575

Tyr Thr Leu Ser Ser Leu Thr Ser Asp Thr Leu Tyr Met Val Arg Met
                        580                 585                 590

Ala Ala Tyr Thr Asp Glu Gly Gly Lys Asp Gly Pro Glu Phe
                        595                 600                 605

<210> SEQ ID NO 62
<211> LENGTH: 836
<212> TYPE: PRT
<213> ORGANISM: artificial sequence
<220> FEATURE:
<223> OTHER INFORMATION: soluble gp130 fused to a Fc

<400> SEQUENCE: 62

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
```

```
145                 150                 155                 160
Lys Ser Glu Trp Ala Thr His Lys Phe Ala Asp Cys Lys Ala Lys Arg
                165                 170                 175
Asp Thr Pro Thr Ser Cys Thr Val Asp Tyr Ser Thr Val Tyr Phe Val
                180                 185                 190
Asn Ile Glu Val Trp Val Glu Glu Asn Ala Leu Gly Lys Val Thr
                195                 200                 205
Ser Asp His Ile Asn Phe Asp Pro Val Tyr Lys Val Lys Pro Asn Pro
210                 215                 220
Pro His Asn Leu Ser Val Ile Asn Ser Glu Glu Leu Ser Ser Ile Leu
225                 230                 235                 240
Lys Leu Thr Trp Thr Asn Pro Ser Ile Lys Ser Val Ile Ile Leu Lys
                245                 250                 255
Tyr Asn Ile Gln Tyr Arg Thr Lys Asp Ala Ser Thr Trp Ser Gln Ile
                260                 265                 270
Pro Pro Glu Asp Thr Ala Ser Thr Arg Ser Ser Phe Thr Val Gln Asp
                275                 280                 285
Leu Lys Pro Phe Thr Glu Tyr Val Phe Arg Ile Arg Cys Met Lys Glu
                290                 295                 300
Asp Gly Lys Gly Tyr Trp Ser Asp Trp Ser Glu Glu Ala Ser Gly Ile
305                 310                 315                 320
Thr Tyr Glu Asp Arg Pro Ser Lys Ala Pro Ser Phe Trp Tyr Lys Ile
                325                 330                 335
Asp Pro Ser His Thr Gln Gly Tyr Arg Thr Val Gln Leu Val Trp Lys
                340                 345                 350
Thr Leu Pro Pro Phe Glu Ala Asn Gly Lys Ile Leu Asp Tyr Glu Val
                355                 360                 365
Thr Leu Thr Arg Trp Lys Ser His Leu Gln Asn Tyr Thr Val Asn Ala
                370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
                405                 410                 415
Pro Ala Cys Asp Phe Gln Ala Thr His Pro Val Met Asp Leu Lys Ala
                420                 425                 430
Phe Pro Lys Asp Asn Met Leu Trp Val Glu Trp Thr Thr Pro Arg Glu
                435                 440                 445
Ser Val Lys Lys Tyr Ile Leu Glu Trp Cys Val Leu Ser Asp Lys Ala
                450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                485                 490                 495
Thr Pro Val Tyr Ala Asp Gly Pro Gly Ser Pro Glu Ser Ile Lys Ala
                500                 505                 510
Tyr Leu Lys Gln Ala Pro Pro Ser Lys Gly Pro Thr Val Arg Thr Lys
                515                 520                 525
Lys Val Gly Lys Asn Glu Ala Val Leu Glu Trp Asp Gln Leu Pro Val
530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                565                 570                 575
```

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Arg Ser
        595                 600                 605

Cys Asp Lys Thr His Thr Cys Pro Pro Cys Pro Ala Pro Glu Ala Glu
    610                 615                 620

Gly Gly Pro Ser Val Phe Leu Phe Pro Pro Lys Pro Lys Asp Thr Leu
625                 630                 635                 640

Met Ile Ser Arg Thr Pro Glu Val Thr Cys Val Val Asp Val Ser
                645                 650                 655

His Glu Asp Pro Glu Val Lys Phe Asn Trp Tyr Val Asp Gly Val Glu
            660                 665                 670

Val His Asn Ala Lys Thr Lys Pro Arg Glu Glu Gln Tyr Asn Ser Thr
        675                 680                 685

Tyr Arg Val Val Ser Val Leu Thr Val Leu His Gln Asp Trp Leu Asn
    690                 695                 700

Gly Lys Glu Tyr Lys Cys Lys Val Ser Asn Lys Ala Leu Pro Ala Pro
705                 710                 715                 720

Ile Glu Lys Thr Ile Ser Lys Ala Lys Gly Gln Pro Arg Glu Pro Gln
                725                 730                 735

Val Tyr Thr Leu Pro Pro Ser Arg Glu Glu Met Thr Lys Asn Gln Val
            740                 745                 750

Ser Leu Thr Cys Leu Val Lys Gly Phe Tyr Pro Ser Asp Ile Ala Val
        755                 760                 765

Glu Trp Glu Ser Asn Gly Gln Pro Glu Asn Asn Tyr Lys Thr Thr Pro
    770                 775                 780

Pro Val Leu Asp Ser Asp Gly Ser Phe Phe Leu Tyr Ser Lys Leu Thr
785                 790                 795                 800

Val Asp Lys Ser Arg Trp Gln Gln Gly Asn Val Phe Ser Cys Ser Val
                805                 810                 815

Met His Glu Ala Leu His Asn His Tyr Thr Gln Lys Ser Leu Ser Leu
            820                 825                 830

Ser Pro Gly Lys
        835

<210> SEQ ID NO 63
<211> LENGTH: 7711
<212> TYPE: DNA
<213> ORGANISM: artificial sequence
<220> FEATURE:
<223> OTHER INFORMATION: Matrice TRAC locus_CubiCAR CD22 pCLS30056 full
      sequence

<400> SEQUENCE: 63 gtggcactt tcggggaaat gtgcgcggaa cccctatttg tttattttc taaatacatt      60 caaatatgta tccgctcatg agacaataac cctgataaat gcttcaataa tattgaaaaa    120
ggaagagtat gagtattcaa catttccgtg tcgcccttat cccttttt gcggcatttt     180 gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480

```
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtggttctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct aacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgttctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatggt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggagag cgcccaatac gcaaaccgcc tctccccgcg cgttggccga ttcattaatg   1980
cagctggcac gacaggtttc ccgactggaa agcgggcagt gagcgcaacg caattaatgt   2040
gagttagctc actcattagg caccccaggc tttacacttt atgcttccgg ctcgtatgtt   2100
gtgtggaatt gtgagcggat aacaatttca cacaggaaac agctatgacc atgattacgc   2160
caagcgcgtc aattaaccct cactaaaggg aacaaaagct gttaattaat tgctgggcct   2220
ttttcccatg cctgccttta ctctgccaga gttatattgc tggggttttg aagaagatcc   2280
tattaaataa aagaataagc agtattatta agtagccctg catttcaggt ttccttgagt   2340
ggcaggccag gcctggccgt gaacgttcac tgaaatcatg gcctcttggc caagattgat   2400
agcttgtgcc tgtccctgag tcccagtcca tcacgagcag ctggtttcta agatgctatt   2460
tcccgtataa agcatgagac cgtgacttgc cagccccaca gagccccgcc cttgtccatc   2520
actggcatct ggactccagc ctgggttggg gcaaagaggg aaatgagatc atgtcctaac   2580
cctgatcctc ttgtcccaca gatatccagt accctacga cgtgcccgac tacgcctccg   2640
gtgagggcag aggaagtctt ctaacatgcg gtgacgtgga ggagaatccg ggccccggat   2700
ccgctctgcc cgtcaccgct ctgctgctgc cactggcact gctgctgcac gctgctaggc   2760
ccggaggggg aggcagctgc ccctacagca accccagcct gtgcagcgga ggcggcggca   2820
gcggcggagg gggtagccag gtgcagctgc agcagagcgg ccctggcctg gtgaagccaa   2880
```

-continued

```
gccagacact gtccctgacc tgcgccatca gcggcgattc cgtgagctcc aactccgccg   2940
cctggaattg gatcaggcag tccccttctc ggggcctgga gtggctggga aggacatact   3000
atcggtctaa gtggtacaac gattatgccg tgtctgtgaa gagcagaatc acaatcaacc   3060
ctgacacctc caagaatcag ttctctctgc agctgaatag cgtgacacca gaggacaccg   3120
ccgtgtacta ttgcgccagg gaggtgaccg gcgacctgga ggatgccttt gacatctggg   3180
gccagggcac aatggtgacc gtgagctccg gaggcggcgg atctggcgga ggaggaagtg   3240
ggggcggcgg gagtgatatc cagatgacac agtccccatc ctctctgagc gcctccgtgg   3300
gcgacagagt gacaatcacc tgtagggcct cccagaccat ctggtcttac ctgaactggt   3360
atcagcagag gcccggcaag gcccctaatc tgctgatcta cgcagcaagc tccctgcaga   3420
gcggagtgcc atccagattc tctggcaggg gctccggcac agacttcacc ctgaccatct   3480
ctagcctgca ggccgaggac ttcgccacct actattgcca gcagtcttat agcatccccc   3540
agacatttgg ccagggcacc aagctggaga tcaagtcgga tcccggaagc ggaggggag   3600 gcagctgccc ctacagcaac cccagcctgt gcagcggagg cggcggcagc gagctgccca   3660
cccagggcac cttctccaac gtgtccacca acgtgagccc agccaagccc accaccaccg   3720
cctgtcctta ttccaatcct tccctgtgtg ctcccaccac aaccccgct ccaaggcccc   3780 ctaccccgc accaactatt gcctcccagc cactctcact gcggcctgag gcctgtcggc   3840
ccgctgctgg aggcgcagtg catacaaggg gcctcgattt cgcctgcgat atttacatct   3900
gggcacccct cgccggcacc tgcggggtgc ttctcctctc cctggtgatt accctgtatt   3960
gcagacgggg ccggaagaag ctcctctaca tttttaagca gcctttcatg cggccagtgc   4020
agacaaccca agaggaggat gggtgttcct gcagattccc tgaggaagag gaaggcgggt   4080
gcgagctgag agtgaagttc tccaggagcg cagatgcccc cgcctatcaa cagggccaga   4140
accagctcta caacgagctt aacctcggga ggcgcgaaga atacgacgtg ttggataaga   4200
gaagggggcg ggaccccgag atgggaggaa agccccggag gaagaaccct caggagggcc   4260
tgtacaacga gctgcagaag gataagatgg ccgaggccta ctcagagatc gggatgaagg   4320
gggagcggcg ccgcggggaag gggcacgatg ggctctacca ggggctgagc acagccacaa   4380
aggacacata cgacgccttg cacatgcagg cccttccacc ccgggaatag tctagagggc   4440
ccgtttaaac ccgctgatca gcctcgactg tgccttctag ttgccagcca tctgttgttt   4500
gccccctccc cgtgccttcc ttgaccctgg aaggtgccac tcccactgtc ctttcctaat   4560
aaaatgagga aattgcatcg cattgtctga gtaggtgtca ttctattctg ggggtgggg   4620 tggggcagga cagcaagggg gaggattggg aagacaatag caggcatgct ggggatgcgg   4680
tgggctctat gactagtggc gaattccgt gtaccagctg agagactcta aatccagtga   4740
caagtctgtc tgcctattca ccgattttga ttctcaaaca aatgtgtcac aaagtaagga   4800
ttctgatgtg tatatcacag acaaaactgt gctagacatg aggtctatgg acttcaagag   4860
caacagtgct gtggcctgga gcaacaaatc tgactttgca tgtgcaaacg ccttcaacaa   4920
cagcattatt ccagaagaca ccttcttccc cagcccaggt aagggcagct ttggtgcctt   4980
cgcaggctgt ttccttgctt caggaatggc caggttctgc ccagagctct ggtcaatgat   5040 gtctaaaaact cctctgattg gtggtctcgg ccttatccat tgccaccaaa ccctctttt   5100 tactaagcga tcgctccggt gcccgtcagt gggcagagcg cacatcgccc acagtccccg   5160
agaagttggg gggaggggtc ggcaattgaa cgggtgccta gagaaggtgg cgcggggtaa   5220
```

```
actgggaaag tgatgtcgtg tactggctcc gccttttcc cgagggtggg ggagaaccgt    5280
atataagtgc agtagtcgcc gtgaacgttc tttttcgcaa cgggtttgcc gccagaacac    5340
agctgaagct tcgaggggct cgcatctctc cttcacgcgc ccgccgccct acctgaggcc    5400
gccatccacg ccgttgagt cgcgttctgc cgcctcccgc ctgtggtgcc tcctgaactg    5460
cgtccgccgt ctaggtaagt ttaaagctca ggtcgagacc gggcctttgt ccggcgctcc    5520
cttggagcct acctagactc agccggctct ccacgctttg cctgaccctg cttgctcaac    5580
tctacgtctt tgtttcgttt tctgttctgc gccgttacag atccaagctg tgaccggcgc    5640
ctacctgaga tcaccggcgc caccatggct tcttaccctg gacaccagca tgcttctgcc    5700
tttgaccagg ctgccagatc caggggccac tccaacagga gaactgccct aagacccaga    5760
agacagcagg aagccactga ggtgaggcct gagcagaaga tgccaaccct gctgagggtg    5820
tacattgatg gacctcatgg catgggcaag accaccacca ctcaactgct ggtggcactg    5880
ggctccaggg atgacattgt gtatgtgcct gagccaatga cctactggag agtgctagga    5940
gcctctgaga ccattgccaa catctacacc acccagcaca ggctggacca gggagaaatc    6000
tctgctggag atgctgctgt ggtgatgacc tctgcccaga tcacaatggg aatgccctat    6060
gctgtgactg atgctgttct ggctcctcac attggaggag aggctggctc ttctcatgcc    6120
cctccacctg ccctgaccct gatctttgac agacacccca ttgcagccct gctgtgctac    6180
ccagcagcaa ggtacctcat gggctccatg accccacagg ctgtgctggc ttttgtggcc    6240
ctgatccctc caaccctccc tggcaccaac attgttctgg gagcactgcc tgaagacaga    6300
cacattgaca ggctggcaaa gaggcagaga cctggagaga gactggacct ggccatgctg    6360
gctgcaatca gaagggtgta tggactgctg gcaaacactg tgagataccc ccagtgtgga    6420
ggctcttgga gagaggactg gggacagctc tctggaacag cagtgccccc tcaaggagct    6480
gagccccagt ccaatgctgg tccaagaccc cacattgggg acaccctgtt cacctgttc    6540
agagcccctg agctgctggc tcccaatgga gacctgtaca atgtgtttgc ctgggctctg    6600
gatgttctag ccaagaggct gaggtccatg catgtgttca tcctggacta tgaccagtcc    6660
cctgctggat gcagagatgc tctgctgcaa ctaacctctg gcatggtgca gacccatgtg    6720
accacccctg gcagcatccc caccatctgt gacctagcca gaacctttgc cagggagatg    6780
ggagaggcca actaaggcgc gccactcgag cgctagctgg ccagacatga taagatacat    6840
tgatgagttt ggacaaacca caactagaat gcagtgaaaa aaatgcttta tttgtgaaat    6900
ttgtgatgct attgctttat ttgtaaccat tataagctgc aataaacaag ttaacaacaa    6960
caattgcatt cattttatgt ttcaggttca gggggaggtg tgggaggttt tttaaagcaa    7020
gtaaaacctc tacaaatgtg gtatggaagg cgcgcccaat tcgccctata gtgagtcgta    7080
ttacgtcgcg ctcactggcc gtcgttttac aacgtcgtga ctgggaaaac cctggcgtta    7140
cccaacttaa tcgccttgca gcacatcccc ctttcgccag ctggcgtaat agcgaagagg    7200
cccgcaccga aacgccttc ccaacagttg cgcagcctga atggcgaatg ggagcgccct    7260
gtagcggcgc attaagcgcg gcgggtgtgg tggttacgcg cagcgtgacc gctacacttg    7320
ccagcgccct agcgcccgct cctttcgctt tcttcccttc ctttctcgcc acgttcgccg    7380
gctttccccg tcaagctcta aatcgggggc tccctttagg gttccgattt agtgctttac    7440
ggcacctcga ccccaaaaaa cttgattagg gtgatggttg gcctgtagtg gccatagcc    7500
ctgatagacg gtttttcgcc ctttgacgtt ggagtccacg ttctttaata gtggactctt    7560
gttccaaact ggaacaacac tcaaccctat ctcggtctat tcttttgatt tataagggat    7620
```

<210> SEQ ID NO 64
<211> LENGTH: 7502
<212> TYPE: DNA
<213> ORGANISM: artificial sequence
<220> FEATURE:
<223> OTHER INFORMATION: Matrice CD25 locus_IL15_2A_sIL15Ra pCLS30519
full sequence

<400> SEQUENCE: 64

```
tttgccgatt tcggcctatt ggttaaaaaa tgagctgatt taacaaaaat ttaacgcgaa    7680
ttttaacaaa atattaacgc ttacaattta g                                   7711 gtttattatt cctgttccac agctattgtc tgccatataa aaacttaggc caggcacagt      60
ggctcacacc tgtaatccca gcactttgga aggccgaggc aggcagatca caaggtcagg     120
agttcgagac cagcctggcc aacatagcaa accccatctc tactaaaaaa tacaaaaatt     180
agccaggcat ggtggcgtgt gcactggttt agagtgagga ccacatttttt ttggtgccgt    240
gttacacata tgaccgtgac tttgttacac cactacagga ggaagagtag aagaacaatc     300
ggttctggcg tgaaacagac tttgaatttt gaccttctca agttggcggg agacgtggag     360
tccaacccag ggcccggtac cgggtccgcc accatggact ggacctggat tctgttcctc     420
gtggctgctg ctacaagagt gcacagcggc attcatgtct cattttggg ctgtttcagt     480
gcagggcttc ctaaaacaga agccaactgg gtgaatgtaa taagtgattt gaaaaaaatt     540
gaagatctta ttcaatctat gcatattgat gctactttat atacggaaag tgatgttcac     600
cccagttgca aagtaacagc aatgaagtgc tttctcttgg agttacaagt tatttcactt     660
gagtccggag atgcaagtat tcatgataca gtagaaaatc tgatcatcct agcaaacaac     720
agtttgtctt ctaatgggaa tgtaacagaa tctggatgca aagaatgtga ggaactggag     780
gaaaaaaata ttaagaaatt tttgcagagt tttgtacata ttgtccaaat gttcatcaac     840
acttctggaa gcggagctac taacttcagc ctgctgaagc aggctggaga cgtggaggag     900
aaccctggac ctgggaccgg ctctgcaacc atggattgga cgtggatcct gtttctcgtg     960
gcagctgcca aagagttca gtatcacg tgccctcccc ccatgtccgt ggaacacgca    1020
gacatctggg tcaagagcta cagcttgtac tccagggagc ggtacatttg taactctggt    1080
ttcaagcgta aagccggcac gtccagcctg acggagtgcg tgttgaacaa ggccacgaat    1140
gtcgcccact ggacaacccc cagtctcaaa tgcattagag accctgccct ggttcaccaa    1200
aggccagcgc caccctccac agtaacgacg gcagggtgac ccccacagcc agagagcctc    1260
tccccttctg gaaaagagcc cgcagcttca tctcccagct caaacaacac agcggccaca    1320
acagcagcta ttgtcccggg ctcccagctg atgccttcaa aatcaccttc cacaggaacc    1380
acagagataa gcagtcatga gtcctcccac ggcacccccct ctcagacaac agccaagaac    1440
tgggaactca gcatccgcct cccaccag ccgccaggtg tgtatccaca gggccacagc    1500
gacaccactg agggcagagg cagcctgctg acctgcggcg acgtcgagga accccggg    1560
cccatggggg caggtgccac cggccgcgcc atggacgggc gcgcctgct gctgttgctg    1620
cttctggggg tgtcccttgg aggtgccaag gaggcatgcc ccacaggcct gtacacacac    1680
agcggtgagt gctgcaaagc ctgcaacctg ggcgagggtg tggcccagcc ttgtggagcc    1740
aaccagaccg tgtgtgagcc ctgcctggac agcgtgacgt tctccgacgt ggtgagcgcg    1800
accgagccgt gcaagccgtg caccgagtgc gtgggctcc agagcatgtc ggcgccgtgc    1860
gtggaggccg atgacgccgt gtgccgctgc gcctacggct actaccagga tgagacgact    1920
```

-continued

```
gggcgctgcg aggcgtgccg cgtgtgcgag gcgggctcgg gcctcgtgtt ctcctgccag    1980
gacaagcaga acaccgtgtg cgaggagtgc cccgacggca cgtattccga cgaggccaac    2040
cacgtggacc cgtgcctgcc ctgcaccgtg tgcgaggaca ccgagcgcca gctccgcgag    2100
tgcacacgct gggccgacgc cgagtgcgag gagatccctg gccgttggat tacacggtcc    2160
acacccccag agggctcgga cagcacagcc cccagcaccc aggagcctga ggcacctcca    2220
gaacaagacc tcatagccag cacggtggca ggtgtggtga ccacagtgat gggcagctcc    2280
cagcccgtgg tgacccgagg caccaccgac aacctcatcc ctgtctattg ctccatcctg    2340
gctgctgtgg ttgtgggtct tgtggcctac atagccttca agaggtgaaa aaccaaaaga    2400
acaagaattt cttggtaaga agccgggaac agacaacaga agtcatgaag cccaagtgaa    2460
atcaaaggtg ctaaatggtc gcccaggaga catccgttgt gcttgcctgc gttttggaag    2520
ctctgaagtc acatcacagg acacggggca gtggcaacct tgtctctatg ccagctcagt    2580
cccatcagag agcgagcgct acccacttct aaatagcaat ttcgccgttg aagaggaagg    2640
gcaaaaccac tagaactctc catcttattt tcatgtatat gtgttcatgc gatcgctccg    2700
gtgcccgtca gtgggcagag cgcacatcgc ccacagtccc cgagaagttg ggggaggggg    2760
tcggcaattg aacgggtgcc tagagaaggt ggcgcggggt aaactgggaa agtgatgtcg    2820
tgtactggct ccgccttttt cccgagggtg ggggagaacc gtatataagt gcagtagtcg    2880
ccgtgaacgt tcttttttcgc aacgggtttg ccgccagaac acagctgaag cttcgagggg    2940
ctcgcatctc tccttcacgc gcccgccgcc ctacctgagg ccgccatcca cgccggttga    3000
gtcgcgttct gccgcctccc gcctgtggtg cctcctgaac tgcgtccgcc gtctaggtaa    3060
gtttaaagct caggtcgaga ccgggccttt gtccggcgct cccttggagc ctacctagac    3120
tcagccggct ctccacgctt tgcctgaccc tgcttgctca actctacgtc tttgtttcgt    3180
tttctgttct gcgccgttac agatccaagc tgtgaccggc gcctacctga gatcaccggc    3240
gccaccatgg cttcttaccc tggacaccag catgcttctg cctttgacca ggctgccaga    3300
tccaggggcc actccaacag gagaactgcc ctaagaccca gaagacagca ggaagccact    3360
gaggtgaggc ctgagcagaa gatgccaacc ctgctgaggg tgtacattga tggacctcat    3420
ggcatgggca agaccaccac cactcaactg ctggtggcac tgggctccag ggatgacatt    3480
gtgtatgtgc ctgagccaat gacctactgg agagtgctag gagcctctga gaccattgcc    3540
aacatctaca ccacccagca caggctggac cagggagaaa tctctgctgg agatgctgct    3600
gtggtgatga cctctgccca gatcacaatg ggaatgccct atgctgtgac tgatgctgtt    3660
ctggctcctc acattggagg agaggctggc tcttctcatg cccctccacc tgccctgacc    3720
ctgatctttg acagacaccc cattgcagcc ctgctgtgct acccagcagc aaggtacctc    3780
atgggctcca tgaccccaca ggctgtgctg gcttttgtgg ccctgatccc tccaaccctc    3840
cctggcacca acattgttct gggagcactg cctgaagaca gacacattga caggctggca    3900
aagaggcaga gacctggaga gagactggac ctggccatgc tggctgcaat cagaagggtg    3960
tatggactgc tggcaaacac tgtgagatac ctccagtgtg gaggctcttg agagagggac    4020
tggggacagc tctctggaac agcagtgccc cctcaaggag ctgagcccca gtccaatgct    4080
ggtccaagac cccacattgg ggacaccctg ttcaccctgt tcagagcccc tgagctgctg    4140
gctcccaatg gagacctgta caatgtgttt gcctgggctc tggatgttct agccaagagg    4200
ctgaggtcca tgcatgtgtt catcctggac tatgaccagt cccctgctgg atgcagagat    4260
```

```
gctctgctgc aactaacctc tggcatggtg cagacccatg tgaccacccc tggcagcatc    4320
cccaccatct gtgacctagc cagaaccttt gccaggagga tgggagaggc caactaaggc    4380
gcgccactcg agcgctagct ggccagacat gataagatac attgatgagt ttggacaaac    4440
cacaactaga atgcagtgaa aaaaatgctt tatttgtgaa atttgtgatg ctattgcttt    4500
atttgtaacc attataagct gcaataaaca agttaacaac aacaattgca ttcattttat    4560
gtttcaggtt cagggggagg tgtgggaggt tttttaaagc aagtaaaacc tctacaaatg    4620
tggtatggaa ggcgcgccca attcgcccta gtgagtcg tattacgtcg cgctcactgg     4680
ccgtcgtttt acaacgtcgt gactgggaaa accctggcgt tacccaactt aatcgccttg    4740
cagcacatcc cccttttcgcc agctggcgta atagcgaaga ggcccgcacc gaaacgccct    4800
tcccaacagt tgcgcagcct gaatggcgaa tgggagcgcc ctgtagcggc gcattaagcg    4860
cggcgggtgt ggtggttacg cgcagcgtga ccgctacact tgccagcgcc ctagcgcccg    4920
ctcctttcgc tttcttccct cctttctcg ccacgttcgc cggctttccc cgtcaagctc     4980
taaatcgggg gctcccttta gggttccgat ttagtgcttt acggcacctc gaccccaaaa    5040
aacttgatta gggtgatggt tggcctgtag tgggccatag ccctgataga cggttttttcg    5100 ccctttgacg ttggagtcca cgttctttaa tagtggactc ttgttccaaa ctggaacaac    5160
actcaaccct atctcggtct attctttga tttataaggg attttgccga tttcggccta    5220
ttggttaaaa aatgagctga tttaacaaaa atttaacgcg aattttaaca aaatattaac    5280
gcttacaatt taggtggcac ttttcgggga aatgtgcgcg gaacccctat ttgtttattt    5340
ttctaaatac attcaaatat gtatccgctc atgagacaat aaccctgata aatgcttcaa    5400
taatattgaa aaaggaagag tatgagtatt caacatttcc gtgtcgccct tattcccttt    5460
tttgcggcat tttgccttcc tgttttgct caccccagaaa cgctggtgaa agtaaaagat    5520
gctgaagatc agttgggtgc acgagtgggt tacatcgaac tggatctcaa cagcggtaag    5580
atccttgaga gttttcgccc cgaagaacgt tttccaatga tgagcacttt taaagttctg    5640
ctatgtggcg cggtattatc ccgtattgac gccgggcaag agcaactcgg tcgccgcata    5700
cactattctc agaatgactt ggttgagtac tcaccagtca cagaaaagca tcttacggat    5760
ggcatgacag taagagaatt atgcagtgct gccataacca tgagtgataa cactgcggcc    5820
aacttacttc tgacaacgat cggaggaccg aaggagctaa ccgcttttttt gcacaacatg    5880 ggggatcatg taactcgcct tgatcgttgg gaaccggagc tgaatgaagc cataccaaac    5940
gacgagcgtg acaccacgat gcctgtagca atggcaacaa cgttgcgcaa actattaact    6000
ggcgaactac ttactctagc ttcccggcaa caattaatag actggatgga ggcggataaa    6060
gttgcaggac cacttctgcg ctcggccctt ccggctggct ggtttattgc tgataaatct    6120
ggagccggtg agcgtggttc tcgcggtatc attgcagcac tggggccaga tggtaagccc    6180
tcccgtatcg tagttatcta cacgacgggg agtcaggcaa ctatggatga acgaaataga    6240
cagatcgctg agataggtgc ctcactgatt aagcattggt aactgtcaga ccaagtttac    6300
tcatatatac tttagattga tttaaaactt cattttaat ttaaaaggat ctaggtgaag    6360
atcctttttg ataatctcat gaccaaaatc ccttaacgtg agttttcgtt ccactgagcg    6420 tcagacccg tagaaaagat caaaggatct tcttgagatc cttttttct gcgcgtaatc     6480 tgctgcttgc aaacaaaaaa accaccgcta ccagcggtgg tttgtttgcc ggatcaagag    6540
ctaccaactc tttttccgaa ggtaactggc ttcagcagag cgcagatacc aaatactgtt    6600
cttctagtgt agccgtagtt aggccaccac ttcaagaact ctgtagcacc gcctacatac    6660
```

```
ctcgctctgc taatcctgtt accagtggct gctgccagtg gcgataagtc gtgtcttacc    6720
gggttggact caagacgata gttaccggat aaggcgcagc ggtcgggctg aacgggggqt    6780 tcgtgcacac agcccagctt ggagcgaacg acctacaccg aactgagata cctacagcgt    6840
gagctatgag aaagcgccac gcttcccgaa gggagaaagg cggacaggta tccggtaagc    6900
ggcagggtcg aacaggaga gcgcacgagg gagcttccag ggggaaacgc ctggtatctt    6960
tatagtcctg tcgggtttcg ccacctctga cttgagcgtc gatttttgtg atgctcgtca    7020 gggggcgga gcctatggaa aaacgccagc aacgcggcct ttttacggtt cctggccttt    7080
tgctggcctt tgctcacat ggtctttcct gcgttatccc ctgattctgt ggataaccgt    7140
attaccgcct ttgagtgagc tgataccgct cgccgcagcc gaacgaccga gcgcagcgag    7200
tcagtgagcg aggaagcgga gagcgcccaa tacgcaaacc gcctctcccc gcgcgttggc    7260
cgattcatta atgcagctgg cacgacaggt ttcccgactg gaaagcgggc agtgagcgca    7320
acgcaattaa tgtgagttag ctcactcatt aggcacccca ggctttacac tttatgcttc    7380
cggctcgtat gttgtgtgga attgtgagcg ataacaatt tcacacagga aacagctatg    7440
accatgatta cgccaagcgc gtcaattaac cctcactaaa gggaacaaaa gctgttaatt    7500
aa                                                                   7502

<210> SEQ ID NO 65
<211> LENGTH: 7778
<212> TYPE: DNA
<213> ORGANISM: artificial sequence
<220> FEATURE:
<223> OTHER INFORMATION: Matrice PD1 locus_IL15_2A_sIL15Ra pCLS30513
      full sequence

<400> SEQUENCE: 65
gactccccag acaggccctg aaccccccc accttctccc cagccctgct cgtggtgacc      60 gaagggaca cgccaccttt cacctgcagc ttctccaaca tcggagag cttcgtgcta      120 aactggtacc gcatgagccc cagcaaccag acggacaagc tggccgcctt ccccgaggac     180
cgcagccagc ccggccagga ctgccgcttc cgtgtcacac aactgcccaa cgggcgtgac     240
ttccacatga gcgtggtcag ggcccggcgc aatgacagcg gcacctacct ctgtggggcc     300
ggttctggcg tgaaacagac tttgaatttt gaccttctca agttgggcgg agacgtggag     360
tccaacccag ggcccggtac cggtccgcc accatggact ggacctggat tctgttcctc     420
gtggctgctg ctacaagagt gcacagcggc attcatgtct tcattttggg ctgtttcagt     480
gcagggcttc ctaaaacaga agccaactgg gtgaatgtaa taagtgattt gaaaaaaatt     540
gaagatctta ttcaatctat gcatattgat gctactttat atacggaaag tgatgttcac     600
cccagttgca aagtaacagc aatgaagtgc tttctcttgg agttacaagt tatttcactt     660
gagtccggag atgcaagtat tcatgataca gtagaaaatc tgatcatcct agcaaacaac     720
agtttgtctt ctaatgggaa tgtaacagaa tctggatgca aagaatgtga ggaactggag     780
gaaaaaaata ttaaagaatt tttgcagagt tttgtacata ttgtccaaat gttcatcaac     840
acttctggaa gcggagctac taacttcagc ctgctgaagc aggctggaga cgtggaggag     900
aaccctggac ctgggaccgg ctctgcaacc atggattgga cgtggatcct gtttctcgtg     960
gcagctgcca caagagttca cagtatcacg tgcccctccc ccatgtccgt ggaacacgca    1020
gacatctggg tcaagagcta cagcttgtac tccaggggag gtacatttg taactctggt    1080 ttcaagcgta aagccggcac gtccagcctg acggagtgcg tgttgaacaa ggccacgaat    1140
```

```
gtcgcccact ggacaacccc cagtctcaaa tgcattagag accctgccct ggttcaccaa    1200
aggccagcgc caccctccac agtaacgacg gcaggggtga ccccacagcc agagagcctc    1260
tccccttctg gaaaagagcc cgcagcttca tctcccagct caaacaacac agcggccaca    1320
acagcagcta ttgtcccggg ctcccagctg atgccttcaa aatcaccttc cacaggaacc    1380
acagagataa gcagtcatga gtcctcccac ggcaccccct ctcagacaac agccaagaac    1440
tgggaactca cagcatccgc ctcccaccag ccgccaggtg tgtatccaca gggccacagc    1500
gacaccactg agggcagagg cagcctgctg acctgcggcg acgtcgagga gaaccccggg    1560
cccatggggg caggtgccac cggccgcgcc atggacgggc gcgcctgct gctgttgctg      1620 cttctggggg tgtcccttgg aggtgccaag gaggcatgcc ccacaggcct gtacacacac    1680
agcggtgagt gctgcaaagc ctgcaacctg gcgagggtg tggcccagcc ttgtggagcc      1740
aaccagaccg tgtgtgagcc ctgcctggac agcgtgacgt tctccgacgt ggtgagcgcg    1800
accgagccgt gcaagccgtg caccgagtgc gtggggctcc agagcatgtc ggcgccgtgc    1860
gtggaggccg atgacgccgt gtgccgctgc gcctacggct actaccagga tgagacgact    1920
gggcgctgcg aggcgtgccg cgtgtgcgag gcgggctcgg gcctcgtgtt ctcctgccag    1980
gacaagcaga acaccgtgtg cgaggagtgc cccgacggca cgtattccga cgaggccaac    2040
cacgtggacc cgtgcctgcc ctgcaccgtg tgcgaggaca ccgagcgcca gctccgcgag    2100
tgcacacgct gggccgacgc cgagtgcgag gagatccctg gccgttggat tacacggtcc    2160
acacccccag agggctcgga cagcacagcc cccagcaccc aggagcctga ggcacctcca    2220
gaacaagacc tcatagccag cacggtggca ggtgtggtga ccacagtgat gggcagctcc    2280
cagcccgtgg tgacccgagg caccaccgac aacctcatcc ctgtctattg ctccatcctg    2340
gctgctgtgg ttgtgggtct tgtggcctac atagccttca gaggtgatc tagagggccc    2400 gtttaaaccc gctgatcagc ctcgactgtg ccttctagtt gccagccatc tgttgtttgc    2460 ccctccccg tgccttcctt gaccctggaa ggtgccactc ccactgtcct ttcctaataa    2520
aatgaggaaa ttgcatcgca ttgtctgagt aggtgtcatt ctattctggg gggtggggtg    2580
gggcaggaca gcaaggggga ggattgggaa gacaatagca ggcatgctgg ggatgcggtg    2640
ggctctatga ctagtggcga attcggcgca gatcaaagag agcctgcggg cagagctcag    2700
ggtgacaggt gcggcctcgg aggccccggg gcaggggtga gctgagccgg tcctggggtg    2760
ggtgtcccct cctgcacagg atcaggagct ccagggtcgt agggcaggga cccccagct     2820 ccagtccagg gctctgtcct gcacctgggg aatggtgacc ggcatctctg tcctctagct    2880
ctggaagcac cccagcccct ctagtctgcc ctcaccctg accctgaccc tccaccctga     2940
ccccgtccta acccctgacc tttggcgatc gctccggtgc ccgtcagtgg gcagagcgca    3000
catcgcccac agtccccgag aagttggggg gaggggtcgg caattgaacg ggtgcctaga    3060
gaaggtggcg cggggtaaac tgggaaagtg atgtcgtgta ctggctccgc ctttttcccg    3120
agggtggggg agaaccgtat ataagtgcag tagtcgccgt gaacgttctt tttcgcaacg    3180
ggtttgccgc cagaacacag ctgaagcttc gaggggctcg catctctcct tcacgcgccc    3240
gccgccctac ctgaggccgc catccacgcc ggttgagtcg cgttctgccg cctcccgcct    3300
gtggtgcctc ctgaactgcg tccgccgtct aggtaagttt aaagctcagg tcgagaccgg    3360
gcctttgtcc ggcgctccct ggagcctac ctagactcag ccggctctcc acgctttgcc     3420
tgaccctgct tgctcaactc tacgtctttg tttcgttttc tgttctgcgc cgttacagat    3480
```

```
ccaagctgtg accggcgcct acctgagatc accggcgcca ccatggcttc ttaccctgga   3540
caccagcatg cttctgcctt tgaccaggct gccagatcca ggggccactc caacaggaga   3600
actgccctaa gacccagaag acagcaggaa gccactgagg tgaggcctga gcagaagatg   3660
ccaaccctgc tgagggtgta cattgatgga cctcatggca tgggcaagac caccaccact   3720
caactgctgg tggcactggg ctccagggat gacattgtgt atgtgcctga gccaatgacc   3780
tactggagag tgctaggagc ctctgagacc attgccaaca tctacaccac ccagcacagg   3840
ctggaccagg gagaaatctc tgctggagat gctgctgtgg tgatgacctc tgcccagatc   3900
acaatgggaa tgccctatgc tgtgactgat gctgttctgg ctcctcacat tggaggagag   3960
gctggctctt ctcatgcccc tccacctgcc ctgaccctga tctttgacag acaccccatt   4020
gcagccctgc tgtgctaccc agcagcaagg tacctcatgg gctccatgac cccacaggct   4080
gtgctggctt ttgtggccct gatccctcca accctccctg gcaccaacat tgttctggga   4140
gcactgcctg aagacagaca cattgacagg ctggcaaaga ggcagagacc tggagagaga   4200
ctggacctgg ccatgctggc tgcaatcaga agggtgtatg gactgctggc aaacactgtg   4260
agatacctcc agtgtggagg ctcttggaga gaggactggg gacagctctc tggaacagca   4320
gtgcccccctc aaggagctga gccccagtcc aatgctggtc caagacccca cattggggac   4380
accctgttca ccctgttcag agccctgag ctgctggctc caatggaga cctgtacaat   4440
gtgtttgcct gggctctgga tgttctagcc aagaggctga ggtccatgca tgtgttcatc   4500
ctggactatg accagtcccc tgctggatgc agagatgctc tgctgcaact aacctctggc   4560
atggtgcaga cccatgtgac caccccctggc agcatcccca ccatctgtga cctagccaga   4620
accttttgcca gggagatggg agaggccaac taaggcgcgc cactcgagcg ctagctggcc   4680
agacatgata agatacattg atgagtttgg acaaaccaca actagaatgc agtgaaaaaa   4740
atgctttatt tgtgaaattt gtgatgctat tgctttattt gtaaccatta taagctgcaa   4800
taaacaagtt aacaacaaca attgcattca ttttatgttt caggttcagg ggaggtgtg   4860
ggaggttttt taaagcaagt aaaacctcta caaatgtggt atggaaggcg cgcccaattc   4920
gccctatagt gagtcgtatt acgtcgcgct cactggccgt cgttttacaa cgtcgtgact   4980
gggaaaaccc tggcgttacc caacttaatc gccttgcagc acatccccct ttcgccagct   5040
ggcgtaatag cgaagaggcc cgcaccgaaa cgccctttcc cacagttgcg cagcctgaat   5100
ggcgaatggg agcgccctgt agcggcgcat taagcgcggc gggtgtggtg gttacgcgca   5160
gcgtgaccgc tacacttgcc agcgccctag cgcccgctcc tttcgctttc ttcccttcct   5220
ttctcgccac gttcgccggc tttccccgtc aagctctaaa tcggggctc cctttagggt   5280
tccgatttag tgctttacgg cacctcgacc ccaaaaaact tgattagggt gatggttggc   5340
ctgtagtggg ccatagccct gatagacggt ttttcgccct ttgacgttgg agtccacgtt   5400
ctttaatagt ggactcttgt tccaaactgg aacaacactc aaccctatct cggtctattc   5460
ttttgattta agggattt tgccgatttc ggcctattgg ttaaaaaatg agctgattta   5520
acaaaaattt aacgcgaatt ttaacaaat attaacgctt acaatttagg tggcacttt   5580
cggggaaatg tgcgcggaac ccctatttgt ttatttttct aaatacattc aaatatgtat   5640
ccgctcatga caataaacc ctgataaatg cttcaataat attgaaaaag gaagagtatg   5700
agtattcaac atttccgtgt cgcccttatt ccctttttg cggcattttg ccttcctgtt   5760
tttgctcacc cagaaacgct ggtgaaagta aaagatgctg aagatcagtt gggtgcacga   5820
gtgggttaca tcgaactgga tctcaacagc ggtaagatcc ttgagagttt tcgccccgaa   5880
```

```
gaacgttttc caatgatgag cacttttaaa gttctgctat gtggcgcggt attatcccgt    5940
attgacgccg ggcaagagca actcggtcgc cgcatacact attctcagaa tgacttggtt    6000
gagtactcac cagtcacaga aaagcatctt acggatggca tgacagtaag agaattatgc    6060
agtgctgcca taaccatgag tgataacact gcggccaact tacttctgac aacgatcgga    6120
ggaccgaagg agctaaccgc ttttttgcac aacatggggg atcatgtaac tcgccttgat    6180
cgttgggaac cggagctgaa tgaagccata ccaaacgacg agcgtgacac cacgatgcct    6240
gtagcaatgg caacaacgtt gcgcaaacta ttaactggcg aactacttac tctagcttcc    6300
cggcaacaat taatagactg gatggaggcg gataaagttg caggaccact tctgcgctcg    6360
gcccttccgg ctggctggtt tattgctgat aaatctggag ccggtgagcg tggttctcgc    6420
ggtatcattg cagcactggg gccagatggt aagccctccc gtatcgtagt tatctacacg    6480
acggggagtc aggcaactat ggatgaacga atatagacaga tcgctgagat aggtgcctca    6540
ctgattaagc attggtaact gtcagaccaa gtttactcat atatacttta gattgattta    6600
aaacttcatt tttaatttaa aaggatctag gtgaagatcc ttttttgataa tctcatgacc    6660 aaaatccctt aacgtgagtt ttcgttccac tgagcgtcag accccgtaga aaagatcaaa    6720
ggatcttctt gagatccttt tttctgcgc gtaatctgct gcttgcaaac aaaaaaacca    6780
ccgctaccag cggtggtttg tttgccggat caagagctac caactctttt tccgaaggta    6840
actggcttca gcagagcgca gataccaaat actgttcttc tagtgtagcc gtagttaggc    6900
caccacttca agaactctgt agcaccgcct acatacctcg ctctgctaat cctgttacca    6960
gtggctgctg ccagtggcga taagtcgtgt cttaccgggt tggactcaag acgatagtta    7020
ccggataagg cgcagcggtc gggctgaacg gggggttcgt gcacacagcc cagcttggag    7080
cgaacgacct acaccgaact gagataccta cagcgtgagc tatgagaaag cgccacgctt    7140
cccgaaggga gaaaggcgga caggtatccg gtaagcggca gggtcggaac aggagagcgc    7200
acgagggagc ttccagggg aaacgcctgg tatctttata gtcctgtcgg gtttcgccac    7260
ctctgacttg agcgtcgatt tttgtgatgc tcgtcagggg ggcggagcct atggaaaaac    7320
gccagcaacg cggcctttt acggttcctg gccttttgct ggccttttgc tcacatggtc    7380
tttcctgcgt tatcccctga ttctgtggat aaccgtatta ccgcctttga gtgagctgat    7440
accgctcgcc gcagccgaac gaccgagcgc agcgagtcag tgagcgagga agcggagagc    7500
gcccaatacg caaaccgcct ctccccgcgc gttggccgat tcattaatgc agctggcacg    7560
acaggtttcc cgactggaaa gcgggcagtg agcgcaacgc aattaatgtg agttagctca    7620
ctcattaggc accccaggct ttacacttta tgcttccggc tcgtatgttg tgtggaattg    7680
tgagcggata acaatttcac acaggaaaca gctatgacca tgattacgcc aagcgcgtca    7740
attaaccctc actaaaggga caaaagctg ttaattaa                            7778
```

<210> SEQ ID NO 66  
<211> LENGTH: 8177  
<212> TYPE: DNA  
<213> ORGANISM: artificial sequence  
<220> FEATURE:  
<223> OTHER INFORMATION: Matrice CD25 locus_IL12a_2A_IL12b pCLS30520  
      full sequence

<400> SEQUENCE: 66

```
gtttattatt cctgttccac agctattgtc tgccatataa aaacttaggc caggcacagt     60
ggctcacacc tgtaatccca gcactttgga aggccgaggc aggcagatca caaggtcagg    120
```

```
agttcgagac cagcctggcc aacatagcaa acccccatct ctactaaaaa tacaaaaatt      180
agccaggcat ggtggcgtgt gcactggttt agagtgagga ccacatttt ttggtgccgt       240 gttacacata tgaccgtgac tttgttacac cactacagga ggaagagtag aagaacaatc     300
ggttctggcg tgaaacagac tttgaatttt gaccttctca agttggcggg agacgtggag     360
tccaacccag ggcccatgtg gccccctggg tcagcctccc agccaccgcc ctcacctgcc     420
gcggccacag gtctgcatcc agcggctcgc cctgtgtccc tgcagtgccg gctcagcatg     480
tgtccagcgc gcagcctcct ccttgtggct accctggtcc tcctggacca cctcagtttg     540
gccagaaacc tccccgtggc cactccagac ccaggaatgt tcccatgcct tcaccactcc     600
caaaacctgc tgagggccgt cagcaacatg ctccagaagg ccagacaaac tctagaattt     660 taccccttgca cttctgaaga gattgatcat gaagatatca caaagataa aaccagcaca     720 gtggaggcct gtttaccatt ggaattaacc aagaatgaga gttgcctaaa ttccagagag     780
acctctttca taactaatgg gagttgcctg gcctccagaa agacctcttt tatgatggcc     840
ctgtgcctta gtagtattta tgaagacttg aagatgtacc aggtggagtt caagaccatg     900
aatgcaaagc ttctgatgga tcctaagagg cagatctttc tagatcaaaa catgctggca     960
gttattgatg agctgatgca ggccctgaat ttcaacagtg agactgtgcc acaaaaatcc    1020
tcccttgaag aaccggattt ttataaaact aaaatcaagc tctgcatact tcttcatgct    1080
ttcagaattc gggcagtgac tattgataga gtgatgagct atctgaatgc ttccggaagc    1140
ggagctacta acttcagcct gctgaagcag gctggagacg tggaggagaa ccctggacct    1200
atgtgtcacc agcagttggt catctcttgg tttttccctgg tttttctggc atctccctc    1260 gtggccatat gggaactgaa gaaagatgtt tatgtcgtag aattggattg gtatccggat    1320
gcccctggag aaatggtggt cctcacctgt gacacccctg aagaagatgg tatcacctgg    1380 acttggacc agagcagtga ggtcttaggc tctggcaaaa ccctgaccat ccaagtcaaa    1440
gagtttggag atgctggcca gtacacctgt cacaaaggag gcgaggttct aagccattcg    1500
ctcctgctgc ttcacaaaaa ggaagatgga atttggtcca ctgatatttt aaaggaccag    1560
aaagaaccca aaataagac ctttctaaga tgcgaggcca agaattattc tggacgtttc    1620
acctgctggt ggctgacgac aatcagtact gatttgacat tcagtgtcaa aagcagcaga    1680
ggctcttctg acccccaagg ggtgacgtgc ggagctgcta cactctctgc agagagagtc    1740
agaggggaca caaggagta tgagtactca gtggagtgcc aggaggacag tgcctgccca    1800
gctgctgagg agagtctgcc cattgaggtc atggtggatg ccgttcacaa gctcaagtat    1860
gaaaactaca ccagcagctt cttcatcagg gacatcatca acctgaccc acccaagaac    1920 ttgcagctga agccattaaa gaattctcgg caggtggagg tcagctggga gtaccctgac    1980
acctggagta ctccacattc ctacttctcc ctgacattct gcgttcaggt ccagggcaag    2040
agcaagagag aaaagaaaga tagagtcttc acgacaagaa cctcagccac ggtcatctgc    2100
cgcaaaaatg ccagcattag cgtgcgggcc caggaccgct actatagctc atcttggagc    2160
gaatgggcat ctgtgccctg cagtgagggc agaggcagcc tgctgacctg cggcgacgtc    2220
gaggagaacc ccgggcccat gggggcaggt gccaccggcc gcgccatgga cgggccgcgc    2280
ctgctgctgt tgctgcttct gggggtgtcc cttggaggtg ccaaggaggc atgccccaca    2340
ggcctgtaca cacacagcgg tgagtgctgc aaagcctgca acctgggcga gggtgtggcc    2400
cagccttgtg gagccaacca gaccgtgtgt gagccctgcc tggacagcgt gacgttctcc    2460
```

```
gacgtggtga gcgcgaccga gccgtgcaag ccgtgcaccg agtgcgtggg gctccagagc    2520
atgtcggcgc cgtgcgtgga ggccgatgac gccgtgtgcc gctgcgccta cggctactac    2580
caggatgaga cgactgggcg ctgcgaggcg tgccgcgtgt gcgaggcggg ctcgggcctc    2640
gtgttctcct gccaggacaa gcagaacacc gtgtgcgagg agtgccccga cggcacgtat    2700
tccgacgagg ccaaccacgt ggacccgtgc ctgccctgca ccgtgtgcga ggacaccgag    2760
cgccagctcc gcgagtgcac acgctgggcc gacgccgagt gcgaggagat ccctggccgt    2820
tggattacac ggtccacacc cccagagggc tcggacagca cagcccccag cacccaggag    2880
cctgaggcac ctccagaaca agacctcata gccagcacgg tggcaggtgt ggtgaccaca    2940
gtgatgggca gctcccagcc cgtggtgacc cgaggcacca ccgacaacct catccctgtc    3000
tattgctcca tcctggctgc tgtggttgtg ggtcttgtgg cctacatagc cttcaagagg    3060
tgaaaaacca aagaacaag aatttcttgg taagaagccg ggaacagaca acagaagtca    3120
tgaagcccaa gtgaaatcaa aggtgctaaa tggtcgccca ggagacatcc gttgtgcttg    3180
cctgcgtttt ggaagctctg aagtcacatc acaggacacg gggcagtggc aaccttgtct    3240
ctatgccagc tcagtcccat cagagagcga gcgctaccca cttctaaata gcaatttcgc    3300
cgttgaagag gaagggcaaa accactagaa ctctccatct tattttcatg tatatgtgtt    3360
catgcgatcg ctccggtgcc cgtcagtggg cagagcgcac atcgcccaca gtccccgaga    3420
agttgggggg agggtcggc aattgaacgg gtgcctagaa aaggtggcgc ggggtaaact    3480
gggaaagtga tgtcgtgtac tggctccgcc ttttccccga gggtggggga aaccgtata    3540
taagtgcagt agtcgccgtg aacgttcttt ttcgcaacgg gtttgccgcc agaacacagc    3600
tgaagcttcg aggggctcgc atctctcctt cacgcgcccg ccgccctacc tgaggccgcc    3660
atccacgccg gttgagtcgc gttctgccgc ctcccgcctg tggtgcctcc tgaactgcgt    3720
ccgccgtcta ggtaagttta aagctcaggt cgagaccggg cctttgtccg gcgctccctt    3780
ggagcctacc tagactcagc cggctctcca cgctttgcct gacccctgctt gctcaactct    3840
acgtctttgt ttcgtttttct gttctgcgcc gttacagatc caagctgtga ccggcgccta    3900
cctgagatca ccggcgccac catggcttct taccctggac accagcatgc ttctgccttt    3960
gaccaggctg ccagatccag gggccactcc aacaggagaa ctgccctaag acccagaaga    4020
cagcaggaag ccactgaggt gaggcctgag cagaagatgc caaccctgct gagggtgtac    4080
attgatggac ctcatggcat gggcaagacc accaccactc aactgctggt ggcactgggc    4140
tccagggatg acattgtgta tgtgcctgag ccaatgacct actggagagt gctaggagcc    4200
tctgagacca ttgccaacat ctacaccacc cagcacaggc tggaccaggg agaaatctct    4260
gctggagatg ctgctgtggt gatgacctct gcccagatca caatgggaat gcccatgct    4320
gtgactgatg ctgttctggc tcctcacatt ggaggagagg ctggctcttc tcatgccct     4380
ccacctgccc tgacctgat cttgacaga cacccccatttg cagccctgct gtgctaccca    4440
gcagcaaggt acctcatggg ctccatgacc ccacaggctg tgctggcttt tgtggccctg    4500
atccctccaa ccctccctgg caccaacatt gttctgggag cactgcctga agacagacac    4560
attgacaggc tggcaaagag gcagagacct ggagagagac tggacctggc catgctggct    4620
gcaatcagaa gggtgtatgg actgctggca aacactgtga gatacctcca gtgtggaggc    4680
tcttggagag aggactgggg acagctctct ggaacagcag tgcccctca aggagctgag    4740
ccccagtcca atgctggtcc aagacccac attggggaca cctgttcac cctgttcaga    4800
gcccctgagc tgctggctcc caatggagac ctgtacaatg tgtttgcctg ggctctggat    4860
```

```
gttctagcca agaggctgag gtccatgcat gtgttcatcc tggactatga ccagtcccct    4920
gctggatgca gagatgctct gctgcaacta acctctggca tggtgcagac ccatgtgacc    4980
acccctggca gcatccccac catctgtgac ctagccagaa cctttgccag ggagatggga    5040
gaggccaact aaggcgcgcc actcgagcgc tagctggcca gacatgataa gatacattga    5100
tgagtttgga caaccacaa ctagaatgca gtgaaaaaaa tgctttattt gtgaaatttg    5160
tgatgctatt gctttatttg taaccattat aagctgcaat aaacaagtta caacaacaa    5220 ttgcattcat tttatgtttc aggttcaggg ggaggtgtgg gaggttttt aaagcaagta    5280 aaacctctac aaatgtggta tggaaggcgc gcccaattcg ccctatagtg agtcgtatta    5340
cgtcgcgctc actggccgtc gttttacaac gtcgtgactg ggaaaaccct ggcgttaccc    5400
aacttaatcg ccttgcagca catccccctt tcgccagctg gcgtaatagc gaagaggccc    5460
gcaccgaaac gcccttccca acagttgcgc agcctgaatg gcgaatggga gcgcctgta    5520 gcggcgcatt aagcgcggcg ggtgtggtgg ttacgcgcag cgtgaccgct acacttgcca    5580
gcgccctagc gcccgctcct ttcgctttct tcccttcctt tctcgccacg ttcgccggct    5640
ttccccgtca gctctaaat cggggctcc ctttagggtt ccgatttagt gctttacggc    5700
acctcgaccc caaaaaactt gattagggtg atggttggcc tgtagtgggc catagccctg    5760
atagacggtt tttcgccctt tgacgttgga gtccacgttc tttaatagtg gactcttgtt    5820
ccaaactgga acaacactca accctatctc ggtctattct tttgatttat aagggatttt    5880
gccgatttcg gcctattggt taaaaaatga gctgatttaa caaaaattta acgcgaattt    5940
taacaaaata ttaacgctta caatttaggt ggcactttc ggggaaatgt gcgcggaacc    6000
cctatttgtt tattttcta aatacattca aatatgtatc cgctcatgag acaataaccc    6060
tgataaatgc ttcaataata ttgaaaagg aagagtatga gtattcaaca tttccgtgtc    6120
gcccttattc ccttttttgc ggcattttgc cttcctgttt ttgctcaccc agaaacgctg    6180
gtgaaagtaa aagatgctga agatcagttg ggtgcacgag tgggttacat cgaactggat    6240
ctcaacagcg gtaagatcct tgagagtttt cgccccgaag aacgttttcc aatgatgagc    6300
acttttaaag ttctgctatg tggcgcggta ttatcccgta ttgacgccgg gcaagagcaa    6360
ctcggtcgcc gcatacacta ttctcagaat gacttggttg agtactcacc agtcacagaa    6420
aagcatctta cggatggcat gacagtaaga gaattatgca gtgctgccat aaccatgagt    6480
gataacactg cggccaactt acttctgaca acgatcggag gaccgaagga gctaaccgct    6540
tttttgcaca acatggggga tcatgtaact cgccttgatc gttgggaacc ggagctgaat    6600
gaagccatac caaacgacga gcgtgacacc acgatgcctg tagcaatggc aacaacgttg    6660
cgcaaactat taactggcga actacttact ctagcttccc ggcaacaatt aatagactgg    6720
atggaggcgg ataaagttgc aggaccactt ctgcgctcgg cccttccggc tggctggttt    6780
attgctgata aatctggagc cggtgagcgt ggttctcgcg gtatcattgc agcactgggg    6840
ccagatggta agccctcccg tatcgtagtt atctacacga cggggagtca ggcaactatg    6900
gatgaacgaa atagacagat cgctgagata ggtgcctcac tgattaagca ttggtaactg    6960
tcagaccaag tttactcata tatactttag attgatttaa aacttcattt ttaatttaaa    7020
aggatctagg tgaagatcct ttttgataat ctcatgacca aaatccctta acgtgagttt    7080
tcgttccact gagcgtcaga ccccgtagaa aagatcaaag gatcttcttg agatcctttt    7140
tttctgcgcg taatctgctg cttgcaaaca aaaaaaccac cgctaccagc ggtggtttgt    7200
```

```
ttgccggatc aagagctacc aactctttt ccgaaggtaa ctggcttcag cagagcgcag    7260
ataccaaata ctgttcttct agtgtagccg tagttaggcc accacttcaa gaactctgta    7320
gcaccgccta catacctcgc tctgctaatc ctgttaccag tggctgctgc cagtggcgat    7380
aagtcgtgtc ttaccggtt ggactcaaga cgatagttac cggataaggc gcagcggtcg    7440
ggctgaacgg ggggttcgtg cacacagccc agcttggagc gaacgaccta caccgaactg    7500
agatacctac agcgtgagct atgagaaagc gccacgcttc ccgaagggag aaaggcggac    7560
aggtatccgg taagcggcag ggtcggaaca ggagagcgca cgagggagct tccagggggga    7620
aacgcctggt atctttatag tcctgtcggg tttcgccacc tctgacttga gcgtcgattt    7680
ttgtgatgct cgtcaggggg gcggagccta tggaaaaacg ccagcaacgc ggccttttta    7740
cggttcctgg ccttttgctg gcctttgct cacatggtct ttcctgcgtt atcccctgat    7800
tctgtggata accgtattac cgcctttgag tgagctgata ccgctcgccg cagccgaacg    7860
accgagcgca gcgagtcagt gagcgaggaa gcggagagcg cccaatacgc aaaccgcctc    7920
tccccgcgcg ttggccgatt cattaatgca gctggcacga caggtttccc gactggaaag    7980
cgggcagtga gcgcaacgca attaatgtga gttagctcac tcattaggca ccccaggctt    8040
tacactttat gcttccggct cgtatgttgt gtggaattgt gagcggataa caatttcaca    8100
caggaaacag ctatgaccat gattacgcca agcgcgtcaa ttaaccctca ctaaagggaa    8160
caaaagctgt taattaa                                                  8177
```

<210> SEQ ID NO 67
<211> LENGTH: 6349
<212> TYPE: DNA
<213> ORGANISM: artificial sequence
<220> FEATURE:
<223> OTHER INFORMATION: Matrice PD1 locus_IL12a_2A_IL12b pCLS30511 full sequence

<400> SEQUENCE: 67

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acctcgcgaa     420
tgcatctaga tgactcccca gacaggccct ggaaccccc cacctctcc ccagccctgc     480
tcgtggtgac cgaaggggac aacgccacct tcacctgcag cttctccaac acatcggaga     540
gcttcgtgct aaactggtac cgcatgagcc ccagcaacca gacggacaag ctggccgcct     600
tccccgagga ccgcagccag cccggccagg actgccgctt ccgtgtcaca caactgccca     660
acggcgtga cttccacatg agcgtggtca gggcccggcg caatgacagc ggcacctacc     720
tctgtgggc cggttctggc gtgaaacaga ctttgaattt tgaccttctc aagttggcgg     780
gagacgtgga gtccaaccca gggccccatgt ggccccctgg gtcagcctcc cagccaccgc     840
cctcacctgc gcggccaca ggtctgcatc cagcggctcg ccctgtgtcc ctgcagtgcc     900
ggctcagcat gtgtccagcg cgcagcctcc tccttgtggc tacccctgtc ctcctggacc     960
acctcagttt ggccagaaac ctccccgtgg ccactccaga cccaggaatg ttcccatgcc    1020
```

| | |
|---|---|
| ttcaccactc ccaaaacctg ctgagggccg tcagcaacat gctccagaag gccagacaaa | 1080 |
| ctctagaatt ttacccttgc acttctgaag agattgatca tgaagatatc acaaaagata | 1140 |
| aaaccagcac agtggaggcc tgtttaccat tggaattaac caagaatgag agttgcctaa | 1200 |
| attccagaga gacctctttc ataactaatg ggagttgcct ggcctccaga aagacctctt | 1260 |
| ttatgatggc cctgtgcctt agtagtattt atgaagactt gaagatgtac caggtggagt | 1320 |
| tcaagaccat gaatgcaaag cttctgatgg atcctaagag gcagatcttt ctagatcaaa | 1380 |
| acatgctggc agttattgat gagctgatgc aggccctgaa tttcaacagt gagactgtgc | 1440 |
| cacaaaaatc ctcccttgaa gaaccggatt tttataaaac taaaatcaag ctctgcatac | 1500 |
| ttcttcatgc tttcagaatt cgggcagtga ctattgatag agtgatgagc tatctgaatg | 1560 |
| cttccggaag cggagctact aacttcagcc tgctgaagca ggctggagac gtggaggaga | 1620 |
| accctggacc tatgtgtcac cagcagttgg tcatctcttg gttttccctg gttttctgg | 1680 |
| catctcccct cgtggccata tgggaactga agaaagatgt ttatgtcgta gaattggatt | 1740 |
| ggtatccgga tgcccctgga gaaatggtgg tcctcacctg tgacacccct gaagaagatg | 1800 |
| gtatcacctg gaccttggac cagagcagtg aggtcttagg ctctggcaaa accctgacca | 1860 |
| tccaagtcaa agagtttgga gatgctggcc agtacacctg tcacaaagga ggcgaggttc | 1920 |
| taagccattc gctcctgctg cttcacaaaa aggaagatgg aatttggtcc actgatattt | 1980 |
| taaaggacca gaaagaaccc aaaaataaga cctttctaag atgcgaggcc aagaattatt | 2040 |
| ctggacgttt cacctgctgg tggctgacga caatcagtac tgatttgaca ttcagtgtca | 2100 |
| aaagcagcag aggctcttct gaccccccaag gggtgacgtg cggagctgct acactctctg | 2160 |
| cagagagagt cagaggggac aacaaggagt atgagtactc agtggagtgc caggaggaca | 2220 |
| gtgcctgccc agctgctgag gagagtctgc ccattgaggt catggtggat gccgttcaca | 2280 |
| agctcaagta tgaaaactac accagcagct tcttcatcag ggacatcatc aaacctgacc | 2340 |
| cacccaagaa cttgcagctg aagccattaa agaattctcg gcaggtggag gtcagctggg | 2400 |
| agtaccctga cacctggagt actccacatt cctacttctc cctgacattc tgcgttcagg | 2460 |
| tccagggcaa gagcaagaga gaaaagaaag atagagtctt cacggacaag acctcagcca | 2520 |
| cggtcatctg ccgcaaaaat gccagcatta gcgtgcgggc ccaggaccgc tactatagct | 2580 |
| catcttggag cgaatgggca tctgtgccct gcagtgaggg cagaggcagc ctgctgacct | 2640 |
| gcggcgacgt cgaggagaac cccgggccca tgggggcagg tgccaccggc cgcgccatgg | 2700 |
| acgggccgcg cctgctgctg ttgctgcttc tgggggtgtc ccttggaggt gccaaggagg | 2760 |
| catgccccac aggcctgtac acacacagcg gtgagtgctg caaagcctgc aacctgggcg | 2820 |
| agggtgtggc ccagccttgt ggagccaacc agaccgtgtg tgagccctgc ctggacagcg | 2880 |
| tgacgttctc cgacgtggtg agcgcgaccg agccgtgcaa gccgtgcacc gagtgcgtgg | 2940 |
| ggctccagag catgtcggcg ccgtgcgtgg aggccgatga cgccgtgtgc cgctgcgcct | 3000 |
| acggctacta ccaggatgag acgactgggc gctgcgaggc gtgccgcgtg tgcgaggcgg | 3060 |
| gctcgggcct cgtgttctcc tgccaggaca gcagaacac cgtgtgcgag gagtgccccg | 3120 |
| acggcacgta ttccgacgag gccaaccacg tggacccgtg cctgccctgc accgtgtgcg | 3180 |
| aggacaccga gcgccagctc cgcgagtgca cacgctgggc cgacgccgag tgcgaggaga | 3240 |
| tccctggccg ttggattaca cggtccacac cccagagggg ctcggacagc acagccccca | 3300 |
| gcacccagga gcctgaggca cctccagaac aagacctcat agccagcacg gtggcaggtg | 3360 |
| tggtgaccac agtgatgggc agctcccagc ccgtggtgac ccgaggcacc accgacaacc | 3420 |

```
tcatccctgt ctattgctcc atcctggctg ctgtggttgt gggtcttgtg gcctacatag   3480
ccttcaagag gtgatctaga gggcccgttt aaacccgctg atcagcctcg actgtgcctt   3540
ctagttgcca gccatctgtt gtttgccccc ccccgtgcc ttccttgacc ctggaaggtg   3600
ccactcccac tgtcctttcc taataaaatg aggaaattgc atcgcattgt ctgagtaggt   3660
gtcattctat tctgggggt ggggtggggc aggacagcaa gggggaggat tgggaagaca    3720
atagcaggca tgctggggat gcggtgggct ctatgactag tggcgaattc ggcgcagatc   3780
aaagagagcc tgcgggcaga gctcaggtg acaggtgcgg cctcggaggc cccggggcag    3840
gggtgagctg agccggtcct ggggtgggtg tcccctcctg cacaggatca ggagctccag   3900
ggtcgtaggg cagggacccc ccagctccag tccagggctc tgtcctgcac ctggggaatg   3960
gtgaccggca tctctgtcct ctagctctgg aagcacccca gccctctag tctgccctca    4020 cccctgaccc tgaccctcca ccctgacccc gtcctaaccc ctgacctttg atcggatccc   4080
gggcccgtcg actgcagagg cctgcatgca agcttggcgt aatcatggtc atagctgttt   4140
cctgtgtgaa attgttatcc gctcacaatt ccacacaaca tacgagccgg aagcataaag   4200
tgtaaagcct ggggtgccta atgagtgagc taactcacat taattgcgtt gcgctcactg   4260
cccgctttcc agtcgggaaa cctgtcgtgc cagctgcatt aatgaatcgg ccaacgcgcg   4320
gggagaggcg gtttgcgtat tgggcgctct tccgcttcct cgctcactga ctcgctgcgc   4380
tcggtcgttc ggctgcggcg agcggtatca gctcactcaa aggcggtaat acggttatcc   4440
acagaatcag gggataacgc aggaaagaac atgtgagcaa aaggccagca aaaggccagg   4500
aaccgtaaaa aggccgcgtt gctggcgttt ttccataggc tccgcccccc tgacgagcat   4560
cacaaaaatc gacgctcaag tcagaggtgg cgaaacccga caggactata agataccag    4620 gcgtttcccc ctggaagctc cctcgtgcgc tctcctgttc cgaccctgcc gcttaccgga   4680
tacctgtccg cctttctccc ttcgggaagc gtggcgcttt ctcatagctc acgctgtagg   4740
tatctcagtt cggtgtaggt cgttcgctcc aagctgggct gtgtgcacga accccccgtt   4800
cagcccgacc gctgcgcctt atccggtaac tatcgtcttg agtccaaccc ggtaagacac   4860
gacttatcgc cactggcagc agccactggt aacaggatta gcagagcgag gtatgtaggc   4920
ggtgctacag agttcttgaa gtggtggcct aactacggct acactagaag aacagtattt   4980
ggtatctgcg ctctgctgaa gccagttacc ttcggaaaaa gagttggtag ctcttgatcc   5040
ggcaaacaaa ccaccgctgg tagcggtggt ttttttgttt gcaagcagca gattacgcgc   5100
agaaaaaaag gatctcaaga agatcctttg atcttttcta cggggtctga cgctcagtgg   5160
aacgaaaact cacgttaagg gattttggtc atgagattat caaaaaggat cttcacctag   5220
atccttttaa attaaaaatg aagttttaaa tcaatctaaa gtatatatga gtaaacttgg   5280
tctgacagtt accaatgctt aatcagtgag gcacctatct cagcgatctg tctatttcgt   5340
tcatccatag ttgcctgact ccccgtcgtg tagataacta cgatacggga gggcttacca   5400
tctggcccca gtgctgcaat gataccgcga gacccacgct caccggctcc agatttatca   5460
gcaataaacc agccagccgg aagggccgag cgcagaagtg gtcctgcaac tttatccgcc   5520
tccatccagt ctattaattg ttgccgggaa gctagagtaa gtagttcgcc agttaatagt   5580
ttgcgcaacg ttgttgccat tgctacaggc atcgtggtgt cacgctcgtc gtttggtatg   5640
gcttcattca gctccggttc ccaacgatca aggcgagtta catgatcccc catgttgtgc   5700
aaaaaagcgg ttagctcctt cggtcctccg atcgttgtca gaagtaagtt ggccgcagtg   5760
```

| | |
|---|---|
| ttatcactca tggttatggc agcactgcat aattctctta ctgtcatgcc atccgtaaga | 5820 |
| tgcttttctg tgactggtga gtactcaacc aagtcattct gagaatagtg tatgcggcga | 5880 |
| ccgagttgct cttgcccggc gtcaatacgg gataataccg cgccacatag cagaacttta | 5940 |
| aaagtgctca tcattggaaa acgttcttcg gggcgaaaac tctcaaggat cttaccgctg | 6000 |
| ttgagatcca gttcgatgta acccactcgt gcacccaact gatcttcagc atcttttact | 6060 |
| ttcaccagcg tttctgggtg agcaaaaaca ggaaggcaaa atgccgcaaa aaagggaata | 6120 |
| agggcgacac ggaaatgttg aatactcata ctcttccttt ttcaatatta ttgaagcatt | 6180 |
| tatcagggtt attgtctcat gagcggatac atatttgaat gtatttagaa aaataaacaa | 6240 |
| ataggggttc cgcgcacatt tccccgaaaa gtgccacctg acgtctaaga aaccattatt | 6300 |
| atcatgacat aacctataaa aataggcgt atcacgaggc cctttcgtc | 6349 |

<210> SEQ ID NO 68
<211> LENGTH: 2489
<212> TYPE: DNA
<213> ORGANISM: artificial sequence
<220> FEATURE:
<223> OTHER INFORMATION: HLAE trimer matrix (VMAPRTLFL peptide) inserted
      at the B2m locus

<400> SEQUENCE: 68

| | |
|---|---|
| cacttagcat ctctggggcc agtctgcaaa gcgagggggc agccttaatg tgcctccagc | 60 |
| ctgaagtcct agaatgagcg cccggtgtcc caagctgggg cgcgcacccc agatcggagg | 120 |
| gcgccgatgt acagacagca aactcaccca gtcagtgca tgccttctta aacatcacga | 180 |
| gactctaaga aaaggaaact gaaaacggga aagtccctct ctctaacctg gcactgcgtc | 240 |
| gctggcttgg agacaggtga cggtccctgc gggccttgtc ctgattggct gggcacgcgt | 300 |
| ttaatataag tggaggcgtc gcgctggcgg gcattcctga agctgacagc attcgggccg | 360 |
| agatgtctcg ctccgtggcc ttagctgtgc tcgcgctact ctctcttagc ggcctcgaag | 420 |
| ctgttatggc tccgcggact ttattcttag gtggtggcgg atccggtggt ggcggttctg | 480 |
| gtggtggcgg ctccatccag cgtacgccca aaattcaagt ctacagccga catcctgcag | 540 |
| agaacggcaa atctaatttc ctgaactgct atgtatcagg ctttcaccct agcgatatag | 600 |
| aagtggacct gctgaaaaac ggagagagga tagaaaaggt cgaacacagc gacctctcct | 660 |
| tttccaagga ctggagcttt tatcttctgt attatactga atttacaccc acggaaaaag | 720 |
| atgagtatgc gtgccgagta aaccacgtca cgctgtcaca gcccaaaata gtaaaatggg | 780 |
| atcgcgacat gggtggtggc ggttctggtg gtggcggtag tggcggcgga ggaagcggtg | 840 |
| gtggcggttc cggatctcac tccttgaagt atttccacac ttccgtgtcc cggcccggcc | 900 |
| gcggggagcc ccgcttcatc tctgtgggct acgtggacga cacccagttc gtgcgcttcg | 960 |
| acaacgacgc cgcgagtccg aggatggtgc cgcgggcgcc gtggatggag caggaggggt | 1020 |
| cagagtattg ggaccgggag acacggagcg ccagggacac cgcacagatt ttccgagtga | 1080 |
| acctgcggac gctgcgcggc tactacaatc agagcgaggc cgggtctcac accctgcagt | 1140 |
| ggatgcatgg ctgcgagctg gggcccgaca ggcgcttcct ccgcgggtat gaacagttcg | 1200 |
| cctacgacgg caaggattat ctcaccctga atgaggacct gcgctcctgg accgcggtgg | 1260 |
| acacggcggc tcagatctcc gagcaaaagt caaatgatgc ctctgaggcg gagcaccaga | 1320 |
| gagcctacct ggaagacaca tgcgtggagt ggctccacaa atacctggag aaggggaagg | 1380 |
| agacgctgct tcacctggag ccccaaaga cacacgtgac tcaccacccc atctctgacc | 1440 |

```
atgaggccac cctgaggtgc tgggctctgg gcttctaccc tgcggagatc acactgacct    1500
ggcagcagga tggggagggc catacccagg acacggagct cgtggagacc aggcctgcag    1560
gggatggaac cttccagaag tgggcagctg tggtggtgcc ttctggagag gagcagagat    1620
acacgtgcca tgtgcagcat gagggctac ccgagcccgt caccctgaga tggaagccgg    1680
cttcccagcc caccatcccc atcgtgggca tcattgctgg cctggttctc cttggatctg    1740
tggtctctgg agctgtggtt gctgctgtga tatggaggaa gaagagctca ggtgaaaag    1800 gagggagcta ctataaggct gagtggagcg acagtgccca ggggtctgag tctcacagct    1860
tgtaactgtg ccttctagtt gccagccatc tgttgtttgc ccctcccccg tgccttcctt    1920
gaccctggaa ggtgccactc ccactgtcct ttcctaataa aatgaggaaa ttgcatcgca    1980
ttgtctgagt aggtgtcatt ctattctggg gggtggggtg gggcaggaca gcaaggggga    2040
ggattgggaa gacaatagca ggcatgctgg ggatgcggtg ggctctatgt ctctttctgg    2100
cctggaggct atccagcgtg agtctctcct accctcccgc tctggtcctt cctctcccgc    2160
tctgcaccct ctgtggccct cgctgtgctc tctcgctccg tgacttccct tctccaagtt    2220
ctccttggtg gcccgccgtg gggctagtcc agggctggat ctcggggaag cggcggggtg    2280
gcctgggagt ggggaagggg gtgcgcaccc gggacgcgcg ctacttgccc ctttcggcgg    2340
ggagcagggg agacctttgg cctacggcga cgggagggtc gggacaaagt ttagggcgtc    2400
gataagcgtc agagcgccga ggttggggga gggtttctct ccgctctttt cgcggggcct    2460
ctggctcccc cagcgcagct ggagtgggg                                      2489

<210> SEQ ID NO 69
<211> LENGTH: 2289
<212> TYPE: DNA
<213> ORGANISM: artificial sequence
<220> FEATURE:
<223> OTHER INFORMATION: HLAE trimer matrix (VMAPRTLFL peptide)

<400> SEQUENCE: 69
cgcgcacccc agatcggagg gcgccgatgt acagacagca aactcaccca gtctagtgca     60
tgccttctta aacatcacga gactctaaga aaaggaaact gaaaacggga aagtccctct    120
ctctaacctg gcactgcgtc gctggcttgg agacaggtga cggtccctgc gggccttgtc    180
ctgattggct gggcacgcgt ttaatataag tggaggcgtc gcgctggcgg gcattcctga    240
agctgacagc attcgggccg agatgtctcg ctccgtggcc ttagctgtgc tcgcgctact    300
ctctcttagc ggcctcgaag ctgttatggc tccgcggact ttattcttag gtggtggcgg    360
atccggtggt ggcggttctg gtggtggcgg ctccatccag cgtacgccca aaattcaagt    420
ctacagccga catcctgcag agaacggcaa atctaatttc ctgaactgct atgtatcagg    480 cttttcaccct agcgatatag aagtggacct gctgaaaaac ggagagagga tagaaaaggt    540
cgaacacagc gacctctcct tttccaagga ctggagcttt tatcttctgt attatactga    600
atttacaccc acggaaaaag atgagtatgc gtgccgagta aaccacgtca cgctgtcaca    660
gcccaaaata gtaaaatggg atcgcgacat gggtggtggc ggttctggtg gtggcggtag    720
tggcggcgga ggaagcggtg gtgcggttc cggatctcac tccttgaagt atttccacac    780
ttccgtgtcc cggcccggcc gcggggagcc ccgcttcatc tctgtgggct acgtggacga    840
cacccagttc gtgcgcttcg acaacgacgc cgcgagtccg aggatggtgc cgcgggcgcc    900
gtggatggag caggagggt cagagtattg ggaccgggag acacgagcg ccaggacac     960 cgcacagatt ttccgagtga acctgcggac gctgcgcggc tactacaatc agagcgaggc   1020
```

```
cgggtctcac accctgcagt ggatgcatgg ctgcgagctg ggccccgaca ggcgcttcct    1080
ccgcgggtat gaacagttcg cctacgacgg caaggattat ctcaccctga atgaggacct    1140
gcgctcctgg accgcggtgg acacggcggc tcagatctcc gagcaaaagt caaatgatgc    1200
ctctgaggcg gagcaccaga gagcctacct ggaagacaca tgcgtggagt ggctccacaa    1260
atacctggag aaggggaagg agacgctgct tcacctggag cccccaaaga cacacgtgac    1320
tcaccacccc atctctgacc atgaggccac cctgaggtgc tgggtctgg gcttctaccc     1380
tgcggagatc acactgacct ggcagcagga tggggagggc catacccagg acacggagct    1440
cgtggagacc aggcctgcag gggatggaac cttccagaag tgggcagctg tggtggtgcc    1500
ttctggagag gagcagagat acacgtgcca tgtgcagcat gaggggctac ccgagcccgt    1560
caccctgaga tggaagccgg cttcccagcc caccatcccc atcgtgggca tcattgctgg    1620
cctggttctc cttggatctg tggtctctgg agctgtggtt gctgctgtga tatggaggaa    1680
gaagagctca ggtggaaaag gagggagcta ctataaggct gagtggagcg acagtgccca    1740
ggggtctgag tctcacagct tgtaactgtg ccttctagtt gccagccatc tgttgtttgc    1800
ccctcccccg tgccttcctt gaccctgaa ggtgccactc ccactgtcct ttcctaataa     1860
aatgaggaaa ttgcatcgca ttgtctgagt aggtgtcatt ctattctggg gggtggggtg    1920
gggcaggaca gcaaggggga ggattgggaa gacaatagca ggcatgctgg ggatgcggtg    1980
ggctctatgt ctctttctgg cctggaggct atccagcgtg agtctctcct accctcccgc    2040
tctggtcctt cctctcccgc tctgcaccct cgtgtgccct cgctgtgctc tctcgctccg    2100
tgacttccct tctccaagtt ctccttggtg gcccgccgtg gggctagtcc agggctggat    2160
ctcggggaag cggcggggtg gcctgggagt ggggaagggg gtgcgcaccc gggacgcgcg    2220
ctacttgccc ctttcggcgg ggagcagggg agacctttgg cctacggcga cgggagggtc    2280
gggacaaag                                                            2289

<210> SEQ ID NO 70
<211> LENGTH: 2489
<212> TYPE: DNA
<213> ORGANISM: artificial sequence
<220> FEATURE:
<223> OTHER INFORMATION: HLAE trimer matrix (VMAPRTLIL peptide) inserted
      at the B2m locus

<400> SEQUENCE: 70
cacttagcat ctctggggcc agtctgcaaa gcgaggggc agccttaatg tgcctccagc       60
ctgaagtcct agaatgagcg cccggtgtcc caagctgggg cgcgcacccc agatcggagg     120
gcgccgatgt acagacagca aactcaccca gtcagtgca tgccttctta aacatcacga     180
gactctaaga aaggaaact gaaaacggga aagtccctct ctctaacctg gcactgcgtc     240
gctggcttgg agacaggtga cggtccctgc gggccttgtc ctgattggct gggcacgcgt     300
ttaatataag tggaggcgtc gcgctggcgg gcattcctga agctgacagc attcgggccg    360
agatgtctcg ctccgtggcc ttagctgtgc tcgcgctact ctctcttagc ggcctcgaag    420
ctgttatggc tccgcggact ttaattttag gtggtggcgg atccggtggt ggcggttctg    480
gtggtggcgg ctccatccag cgtacgccca aaattcaagt ctacagccga catcctgcag    540
agaacggcaa atctaatttc ctgaactgct atgtatcagg ctttcaccct agcgatatag    600
aagtggacct gctgaaaaac ggagagagga tagaaaaggt cgaacacagc gacctctcct    660
tttccaagga ctggagcttt tatcttctgt attatactga atttacaccc acggaaaaag    720
```

```
atgagtatgc gtgccgagta aaccacgtca cgctgtcaca gcccaaaata gtaaaatggg    780
atcgcgacat gggtggtggc ggttctggtg gtggcggtag tggcggcgga ggaagcggtg    840
gtggcggttc cggatctcac tccttgaagt atttccacac ttccgtgtcc cggcccggcc    900
gcggggagcc ccgcttcatc tctgtgggct acgtggacga cacccagttc gtgcgcttcg    960
acaacgacgc cgcgagtccg aggatggtgc cgcgggcgcc gtggatggag caggaggggt   1020
cagagtattg ggaccgggag acacggagcg ccagggacac cgcacagatt ttccgagtga   1080
acctgcggac gctgcgcggc tactacaatc agagcgaggc cgggtctcac accctgcagt   1140
ggatgcatgc tgcgagctg gggcccgaca gcgcttcct ccgcgggtat gaacagttcg     1200
cctacgacgg caaggattat ctcaccctga atgaggacct gcgctcctgg accgcggtgg   1260
acacggcggc tcagatctcc gagcaaaagt caaatgatgc ctctgaggcg agcaccaga    1320 gagcctacct ggaagacaca tgcgtggagt ggctccacaa atacctggag aaggggaagg   1380
agacgctgct tcacctggag cccccaaaga cacacgtgac tcaccacccc atctctgacc   1440
atgaggccac cctgaggtgc tgggctctgg gcttctaccc tgcggagatc acactgacct   1500
ggcagcagga tggggaggc catacccagg acacggagc cgtggagacc aggcctgcag    1560
gggatggaac cttccagaag tgggcagctg tggtggtgcc ttctggagag gagcagagat   1620
acacgtgcca tgtgcagcat gaggggctac ccgagcccgt caccctgaga tggaagccgg   1680
cttcccagcc caccatcccc atcgtgggca tcattgctgg cctggttctc cttggatctg   1740
tggtctctgg agctgtggtt gctgctgtga tatggaggaa gaaagagctca ggtgaaaag   1800 gagggagcta ctataaggct gagtggagcg acagtgccca ggggtctgag tctcacagct   1860
tgtaactgtg ccttctagtt gccagccatc tgttgtttgc ccctcccccg tgccttcctt   1920
gaccctggaa ggtgccactc ccactgtcct ttcctaataa aatgaggaaa ttgcatcgca   1980
ttgtctgagt aggtgtcatt ctattctggg ggtggggtg gggcaggaca gcaagggga    2040 ggattgggaa gacaatagca ggcatgctgg ggatgcggtg ggctctatgt ctctttctgg   2100
cctggaggct atccagcgtg agtctctcct accctcccgc tctggtcctt cctctcccgc   2160
tctgcaccct ctgtggccct cgctgtgctc tctcgctccg tgacttccct tctccaagtt   2220
ctccttggtg gcccgccgtg gggctagtcc agggctggat ctcggggaag cggcggggtg   2280
gcctgggagt ggggaagggg gtgcgcaccc gggacgcgcg ctacttgccc cttcggcgg   2340 ggagcagggg agacctttgg cctacggcga cgggagggtc gggacaaagt ttagggcgtc   2400
gataagcgtc agagcgccga ggttggggga gggtttctct tccgctcttt cgcggggcct   2460
ctggctcccc cagcgcagct ggagtgggg                                     2489
```

<210> SEQ ID NO 71  
<211> LENGTH: 2289  
<212> TYPE: DNA  
<213> ORGANISM: artificial sequence  
<220> FEATURE:  
<223> OTHER INFORMATION: HLAE trimer matrix (VMAPRTLIL peptide)

<400> SEQUENCE: 71

```
cgcgcacccc agatcggagg gcgccgatgt acagacagca aactcaccca gtctagtgca     60
tgccttctta aacatcacga gactctaaga aaaggaaact gaaaacggga aagtccctct    120
ctctaacctg gcactgcgtc gctggcttgg agacaggtga cggtccctgc gggccttgtc    180
ctgattggct gggcacgcgt ttaatataag tggaggcgtc gcgctggcgg gcattcctga    240
```

```
agctgacagc attcgggccg agatgtctcg ctccgtggcc ttagctgtgc tcgcgctact    300
ctctcttagc ggcctcgaag ctgttatggc tccgcggact ttaattttag gtggtggcgg    360
atccggtggt ggcggttctg gtggtggcgg ctccatccag cgtacgccca aaattcaagt    420
ctacagccga catcctgcag agaacggcaa atctaatttc ctgaactgct atgtatcagg    480
cttccaccct agcgatatag aagtggacct gctgaaaaac ggagagagga tagaaaaggt    540
cgaacacagc gacctctcct tttccaagga ctggagcttt tatcttctgt attatactga    600
atttacaccc acggaaaaag atgagtatgc gtgccgagta aaccacgtca cgctgtcaca    660
gcccaaaata gtaaaatggg atcgcgacat gggtggtggc ggttctggtg gtggcggtag    720
tggcggcgga ggaagcggtg gtggcggttc cggatctcac tccttgaagt atttccacac    780
ttccgtgtcc cggcccggcc gcggggagcc ccgcttcatc tctgtgggct acgtggacga    840
cacccagttc gtgcgcttcg acaacgacgc cgcgagtccg aggatggtgc gcgggcgcc     900
gtggatggag caggagggggt cagagtattg ggaccgggag acacggagcg ccagggacac    960
cgcacagatt ttccgagtga acctgcgac gctgcgcggc tactacaatc agagcgaggc    1020
cgggtctcac accctgcagt ggatgcatgg ctgcgagctg gggcccgaca ggcgcttcct    1080
ccgcgggtat gaacagttcg cctacgacgg caaggattat ctcaccctga atgaggacct    1140
gcgctcctgg accgcggtgg acaccgcggc tcagatctcc gagcaaaagt caaatgatgc    1200
ctctgaggcg gagcaccaga gagcctacct ggaagacaca tgcgtggagt ggctccacaa    1260
atacctggag aaggggaagg agacgctgct tcacctggag cccccaaaga cacacgtgac    1320
tcaccacccc atctctgacc atgaggccac cctgaggtgc tgggctctgg gcttctaccc    1380
tgcggagatc acactgacct ggcagcagga tggggagggc catacccagg acacggagct    1440
cgtggagacc aggcctgcag gggatggaac cttccagaag tgggcagctg tggtggtgcc    1500
ttctggagag gagcagagat acacgtgcca tgtgcagcat gaggggctac ccgagcccgt    1560
caccctgaga tggaagccgg cttcccagcc caccatcccc atcgtgggca tcattgctgg    1620
cctggttctc cttggatctg tggtctctgg agctgtggtt gctgctgtga tatggaggaa    1680
gaagagctca ggtggaaaag gagggagcta ctataaggct gagtggagcg acagtgccca    1740
ggggtctgag tctcacagct tgtaactgtg ccttctagtt gccagccatc tgttgtttgc    1800
ccctcccccg tgccttcctt gaccctggaa ggtgccactc ccactgtcct ttcctaataa    1860
aatgaggaaa ttgcatcgca ttgtctgagt aggtgtcatt ctattctggg gggtggggtg    1920
gggcaggaca gcaaggggga ggattgggaa gacaatagca ggcatgctgg ggatgcggtg    1980
ggctctatgt ctctttctgg cctggaggct atccagcgtg agtctctcct accctcccgc    2040
tctggtcctt cctctcccgc tctgcaccct ctgtggccct cgctgtgctc tctcgctccg    2100
tgacttccct tctccaagtt ctccttggtg gcccgccgtg gggctagtcc agggctggat    2160
ctcggggaag cggcgggtg gcctgggagt ggggaagggg gtgcgcaccc gggacgcgcg    2220
ctacttgccc ctttcggcgg ggagcagggg agacctttgg cctacggcga cgggagggtc    2280
gggacaaag                                                            2289

<210> SEQ ID NO 72
<211> LENGTH: 2531
<212> TYPE: DNA
<213> ORGANISM: artificial sequence
<220> FEATURE:
<223> OTHER INFORMATION: UL18Trimer matrix _Actine peptide inserted at
      the B2m locus
```

```
<400> SEQUENCE: 72
cacttagcat ctctgggcc agtctgcaaa gcgagggggc agccttaatg tgcctccagc      60
ctgaagtcct agaatgagcg cccggtgtcc caagctgggg cgcgcacccc agatcggagg    120
gcgccgatgt acagacagca aactcaccca gtctagtgca tgccttctta aacatcacga    180
gactctaaga aaggaaact gaaaacggga aagtccctct ctctaacctg gcactgcgtc    240
gctggcttgg agacaggtga cggtccctgc gggccttgtc ctgattggct gggcacgcgt    300
ttaatataag tggaggcgtc gcgctggcgg gcattcctga agctgacagc attcgggccg    360
agatgtctcg ctccgtggcc ttagctgtgc tcgcgctact ctctcttagc ggcctcgaag    420
ctgccctgcc ccacgccatt ttgcggctcg gtggtggcgg atccggtggt ggcggttctg    480
gtggtggcgg ctccatccag cgtacgccca aaattcaagt ctacagccga catcctgcag    540
agaacggcaa atctaatttc ctgaactgct atgtatcagg ctttcaccct agcgatatag    600
aagtggacct gctgaaaaac ggagagagga tagaaaaggt cgaacacagc gacctctcct    660
tttccaagga ctggagcttt tatcttctgt attatactga atttacaccc acggaaaaag    720
atgagtatgc gtgccgagta aaccacgtca cgctgtcaca gcccaaaata gtaaatgggg    780
atcgcgacat gggtggtggc ggttctggtg gtggcggtag tggcggcgga ggaagcggtg    840
gtggcggttc cggatctatg cacgtgctga gatacggata taccggcatc ttcgacgata    900
catcccatat gactctgacc gtggtcggga tttttgacgg acagcacttc tttacatacc    960
atgtgaacag ctccgataag gcttctagtc gagcaaatgg caccatctca tggatggcca   1020
acgtgagcgc agcctacccc acatatctgg acggagaacg cgctaaaggc gatctgatct   1080
tcaatcagac cgagcagaac ctgctggagc tggaaattgc tctggggtac aggtctcaga   1140
gtgtcctgac atggactcac gaatgtaata ccacagagaa cggagcttc gtggcaggat   1200 atgagggctt tgggtgggac ggagaaacac tgatggagct gaaggataat ctgactctgt   1260
ggaccggccc taactacgaa atcagctggc tgaagcagaa caagacttac atcgacggaa   1320
agatcaaaaa catcagcgag ggcgatacta ccatccagcg caattacctg aagggcaact   1380
gcacccagtg gagcgtgatc tactctgggt tccagacacc tgtcactcac ccagtggtca   1440 aaggggagt gcgaaaccag aatgacaacc gggccgaggc cttctgtaca tcctacggct   1500
tctttcccgg ggagatcaat attactttta tccattacgg caacaaggcc cccgacgatt   1560
ctgagcctca gtgcaatccc ctgctgccta ccttcgatgg cacatttcac cagggtgct   1620 acgtcgctat cttctgcaat cagaactata cttgccgggt gacccatggg aactggactg   1680
tggaaatccc aatttcagtc accagccccg acgattcaag ctccggagag gtgccagatc   1740
accccaccgc aaataagaga tacaacacca tgacaatctc tagtgtgctg ctggccctgc   1800
tgctgtgcgc actgctgttc gcttttctgc attacttcac aactctgaag cagtatctgc   1860
ggaacctggc atttgcctgg cggtacagaa agtgagatc aagctgactg tgccttctag   1920
ttgccagcca tctgttgttt gcccctcccc cgtgccttcc ttgaccctgg aaggtgccac   1980
tcccactgtc ctttcctaat aaaatgagga aattgcatcg cattgtctga gtaggtgtca   2040
ttctattctg gggggtgggg tggggcagga cagcaagggg gaggattggg aagacaatag   2100
caggcatgct ggggatgcgg tgggctctat gtctctttct ggcctggagg ctatccagcg   2160
tgagtctctc ctaccctccc gctctggtcc ttcctctccc gctctgcacc ctctgtggcc   2220
ctcgctgtgc tctctcgctc cgtgacttcc cttctccaag ttctccttgg tggcccgccg   2280
tggggctagt ccaggctgg atctcgggga agcggcgggg tggcctggga gtggggaagg   2340
```

```
gggtgcgcac ccgggacgcg cgctacttgc cccttcggc gggggagcagg ggagacettt    2400 ggcctacggc gacgggaggg tcgggacaaa gtttagggcg tcgataagcg tcagagcgcc    2460
gaggttgggg gagggtttct cttccgctct ttcgcggggc ctctggctcc cccagcgcag    2520
ctggagtggg g                                                        2531
```

<210> SEQ ID NO 73
<211> LENGTH: 2331
<212> TYPE: DNA
<213> ORGANISM: artificial sequence
<220> FEATURE:
<223> OTHER INFORMATION: UL18Trimer matrix _Actine peptide

<400> SEQUENCE: 73

```
cgcgcacccc agatcggagg gcgccgatgt acagacagca aactcaccca gtctagtgca      60
tgccttctta acatcacga gactctaaga aaaggaaact gaaaacggga aagtccctct      120
ctctaacctg gcactgcgtc gctggcttgg agacaggtga cggtccctgc gggccttgtc     180
ctgattggct gggcacgcgt ttaatataag tggaggcgtc gcgctggcgg gcattcctga    240
agctgacagc attcgggccg agatgtctcg ctccgtggcc ttagctgtgc tcgcgctact    300
ctctcttagc ggcctcgaag ctgccctgcc ccacgccatt ttgcggctcg gtggtggcgg    360
atccggtggt ggcggttctg gtggtggcgg ctccatccag cgtacgccca aaattcaagt    420
ctacagccga catcctgcag agaacggcaa atctaatttc ctgaactgct atgtatcagg    480 cttttcaccct agcgatatag aagtggacct gctgaaaaac ggagagagga tagaaaaggt    540
cgaacacagc gacctctcct tttccaagga ctggagcttt tatcttctgt attatactga    600
atttacaccc acggaaaaag atgagtatgc gtgccgagta aaccacgtca cgctgtcaca    660
gcccaaaata gtaaaatggg atcgcgacat gggtggtggc ggttctggtg gtggcggtag    720
tggcggcgga ggaagcggtg gtggcggttc cggatctatg cacgtgctga gatacggata    780
taccggcatc ttcgacgata catcccatat gactctgacc gtggtcggga ttttgacgg     840 acagcacttc tttacatacc atgtgaacag ctccgataag gcttctagtc gagcaaatgg    900
caccatctca tggatggcca acgtgagcgc agcctacccc acatatctgg acggagaacg    960
cgctaaaggc gatctgatct tcaatcagac cgagcagaac ctgctggagc tggaaattgc    1020
tctggggtac aggtctcaga gtgtcctgac atggactcac gaatgtaata ccacagagaa    1080
cgggagcttc gtggcaggat atgagggctt tgggtgggac ggagaaacac tgatggagct    1140
gaaggataat ctgactctgt ggaccggccc taactacgaa atcagctggc tgaagcagaa    1200
caagacttac atcgacggaa agatcaaaaa catcagcgag gcgatacta ccatccagcg     1260 caattacctg aagggcaact gcacccagtg gagcgtgatc tactctgggt tccagacacc    1320
tgtcactcac ccagtggtca aaggggagt gcgaaaccag aatgacaacc gggccgaggc    1380
cttctgtaca tcctacggct tctttcccgg ggagatcaat attactttta tccattacgg    1440
caacaaggcc cccgacgatt ctgagcctca gtgcaatccc ctgctgccta ccttcgatgg    1500
cacatttcac cagggtgct acgtcgctat cttctgcaat cagaactata cttgccgggt    1560
gacccatggg aactggactg tggaaatccc aatttcagtc accagccccg acgattcaag    1620
ctccggagag gtgccagatc accccaccgc aaataagaga tacaacacca tgacaatctc    1680
tagtgtgctg ctgcccctgc tgctgtgcgc actgctgttc gctttttctgc attacttcac    1740 aactctgaag cagtatctgc ggaacctggc atttgcctgg cggtacagaa aagtgagatc    1800
```

| aagctgactg tgccttctag ttgccagcca tctgttgttt gcccctcccc cgtgccttcc | 1860 |
| ttgaccctgg aaggtgccac tcccactgtc ctttcctaat aaaatgagga aattgcatcg | 1920 |
| cattgtctga gtaggtgtca ttctattctg ggggtgggg tggggcagga cagcaagggg | 1980 |
| gaggattggg aagacaatag caggcatgct ggggatgcgg tgggctctat gtctctttct | 2040 |
| ggcctggagg ctatccagcg tgagtctctc ctaccctccc gctctggtcc ttcctctccc | 2100 |
| gctctgcacc ctctgtggcc ctcgctgtgc tctctcgctc cgtgacttcc cttctccaag | 2160 |
| ttctccttgg tggcccgccg tggggctagt ccagggctgg atctcgggga agcggcgggg | 2220 |
| tggcctggga gtggggaagg gggtgcgcac ccgggacgcg cgctacttgc ccctttcggc | 2280 |
| ggggagcagg ggagaccttt ggcctacggc gacgggaggg tcgggacaaa g | 2331 |

<210> SEQ ID NO 74
<211> LENGTH: 2531
<212> TYPE: DNA
<213> ORGANISM: artificial sequence
<220> FEATURE:
<223> OTHER INFORMATION: UL18Trimer matrix _HLACw peptide inserted at the B2m locus

<400> SEQUENCE: 74

| cacttagcat ctctggggcc agtctgcaaa gcgagggggc agccttaatg tgcctccagc | 60 |
| ctgaagtcct agaatgagcg cccggtgtcc caagctgggg cgcgcacccc agatcggagg | 120 |
| gcgccgatgt acagacagca aactcaccca gtctagtgca tgccttctta aacatcacga | 180 |
| gactctaaga aaaggaaact gaaaacggga aagtccctct ctctaacctg gcactgcgtc | 240 |
| gctggcttgg agacaggtga cggtccctgc gggccttgtc ctgattggct gggcacgcgt | 300 |
| ttaatataag tggaggcgtc gcgctggcgg gcattcctga agctgacagc attcgggccg | 360 |
| agatgtctcg ctccgtggcc ttagctgtgc tcgcgctact ctctcttagc ggcctcgaag | 420 |
| ctgttatggc tccgcggact ttaattttag gtggtggcgg atccggtggt ggcggttctg | 480 |
| gtggtggcgg ctccatccag cgtacgccca aaattcaagt ctacagccga catcctgcag | 540 |
| agaacggcaa atctaatttc ctgaactgct atgtatcagg cttthaccct agcgatatag | 600 |
| aagtggacct gctgaaaaac ggagagagga tagaaaaggt cgaacacagc gacctctcct | 660 |
| tttccaagga ctggagcttt tatcttctgt attatactga atttacaccc acggaaaaag | 720 |
| atgagtatgc gtgccgagta aaccacgtca cgctgtcaca gcccaaaata gtaaaatggg | 780 |
| atcgcgacat gggtggtggc ggttctggtg gtggcggtag tggcggcgga ggaagcggtg | 840 |
| gtggcggttc cggatctatg cacgtgctga gatacggata taccggcatc ttcgacgata | 900 |
| catcccatat gactctgacc gtggtcggga ttttgacgg acagcacttc tttacatacc | 960 |
| atgtgaacag ctccgataag gcttctagtc gagcaaatgg caccatctca tggatggcca | 1020 |
| acgtgagcgc agcctacccc acatatctgg acggagaacg cgctaaaggc gatctgatct | 1080 |
| tcaatcagac cgagcagaac ctgctggagc tggaaattgc tctggggtac aggtctcaga | 1140 |
| gtgtcctgac atggactcac gaatgtaata ccacagaaga cgggagcttc gtggcaggat | 1200 |
| atgagggctt tggtgggac ggagaaacac tgatggagct gaaggataat ctgactctgt | 1260 |
| ggaccggccc taactacgaa atcagctggc tgaagcagaa caagacttac atcgacggaa | 1320 |
| agatcaaaaa catcagcgag ggcgatacta ccatccagcg caattacctg aagggcaact | 1380 |
| gcacccagtg gagcgtgatc tactctgggt tccagacacc tgtcactcac ccagtggtca | 1440 |
| aaggggagt gcgaaaccag aatgacaacc gggccgaggc cttctgtaca tcctacggct | 1500 |

| tctttcccgg ggagatcaat attactttta tccattacgg caacaaggcc cccgacgatt | 1560 |
| ctgagcctca gtgcaatccc ctgctgccta ccttcgatgg cacatttcac caggggtgct | 1620 |
| acgtcgctat cttctgcaat cagaactata cttgccgggt gacccatggg aactggactg | 1680 |
| tggaaatccc aatttcagtc accagccccg acgattcaag ctccggagag gtgccagatc | 1740 |
| accccaccgc aaataagaga tacaacacca tgacaatctc tagtgtgctg ctggccctgc | 1800 |
| tgctgtgcgc actgctgttc gcttttctgc attacttcac aactctgaag cagtatctgc | 1860 |
| ggaacctggc atttgcctgg cggtacagaa aagtgagatc aagctgactg tgccttctag | 1920 |
| ttgccagcca tctgttgttt gcccctcccc cgtgccttcc ttgaccctgg aaggtgccac | 1980 |
| tcccactgtc ctttcctaat aaaatgagga aattgcatcg cattgtctga gtaggtgtca | 2040 |
| ttctattctg gggggtgggg tggggcagga cagcaagggg gaggattggg aagacaatag | 2100 |
| caggcatgct ggggatgcgg tgggctctat gtctctttct ggcctggagg ctatccagcg | 2160 |
| tgagtctctc ctaccctccc gctctggtcc ttcctctccc gctctgcacc ctctgtggcc | 2220 |
| ctcgctgtgc tctctcgctc cgtgacttcc cttctccaag ttctccttgg tggcccgccg | 2280 |
| tggggctagt ccagggctgg atctcgggga agcggcgggg tggcctggga gtggggaagg | 2340 |
| gggtgcgcac ccgggacgcg cgctacttgc ccctttcggc gggagcagg ggagaccttt | 2400 |
| ggcctacggc gacgggaggg tcgggacaaa gtttagggcg tcgataagcg tcagagcgcc | 2460 |
| gaggttgggg gagggtttct cttccgctct ttcgcggggc ctctggctcc cccagcgcag | 2520 |
| ctggagtggg g | 2531 |

<210> SEQ ID NO 75
<211> LENGTH: 2331
<212> TYPE: DNA
<213> ORGANISM: artificial sequence
<220> FEATURE:
<223> OTHER INFORMATION: UL18Trimer matrix _HLACw peptide

<400> SEQUENCE: 75

| cgcgcacccc agatcggagg gcgccgatgt acagacagca aactcaccca gtctagtgca | 60 |
| tgccttctta aacatcacga gactctaaga aaaggaaact gaaaacggga aagtccctct | 120 |
| ctctaacctg gcactgcgtc gctggcttgg agacaggtga cggtccctgc gggccttgtc | 180 |
| ctgattggct gggcacgcgt ttaatataag tggaggcgtc gcgctggcgg gcattcctga | 240 |
| agctgacagc attcgggccg agatgtctcg ctccgtggcc ttagctgtgc tcgcgctact | 300 |
| ctctcttagc ggcctcgaag ctgttatggc tccgcggact ttaattttag gtggtggcgg | 360 |
| atccggtggt ggcggttctg gtggtggcgg ctccatccag cgtacgccca aaattcaagt | 420 |
| ctacagccga catcctgcag agaacggcaa atctaatttc ctgaactgct atgtatcagg | 480 |
| ctttcacccct agcgatatag aagtggacct gctgaaaaac ggagagagga tagaaaaggt | 540 |
| cgaacacagc gacctctcct tttccaagga ctggagcttt tatcttctgt attatactga | 600 |
| atttacaccc acggaaaaag atgagtatgc gtgccgagta aaccacgtca cgctgtcaca | 660 |
| gcccaaaata gtaaaatggg atcgcgacat gggtggtggc ggttctggtg gtggcggtag | 720 |
| tggcggcgga ggaagcggtg gtggcggttc cggatctatg cacgtgctga gatacggata | 780 |
| taccggcatc ttcgacgata catcccatat gactctgacc gtggtcggga ttttttgacgg | 840 |
| acagcacttc tttacatacc atgtgaacag ctccgataag gcttctagtc gagcaaatgg | 900 |
| caccatctca tggatggcca acgtgagcgc agcctacccc acatatctgg acggagaacg | 960 |
| cgctaaaggc gatctgatct tcaatcagac cgagcagaac ctgctggagc tggaaattgc | 1020 |

```
tctggggtac aggtctcaga gtgtcctgac atggactcac gaatgtaata ccacagagaa    1080
cgggagcttc gtggcaggat atgagggctt tgggtgggac ggagaaacac tgatggagct    1140
gaaggataat ctgactctgt ggaccggccc taactacgaa atcagctggc tgaagcagaa    1200
caagacttac atcgacggaa agatcaaaaa catcagcgag ggcgatacta ccatccagcg    1260
caattacctg aagggcaact gcacccagtg gagcgtgatc tactctgggt tccagacacc    1320
tgtcactcac ccagtggtca aaggggagt gcgaaaccag aatgacaacc gggccgaggc    1380
cttctgtaca tcctacggct tctttcccgg ggagatcaat attacttta tccattacgg    1440 caacaaggcc cccgacgatt ctgagcctca gtgcaatccc ctgctgccta ccttcgatgg    1500
cacatttcac caggggtgct acgtcgctat cttctgcaat cagaactata cttgccgggt    1560
gacccatggg aactggactg tggaaatccc aatttcagtc accagccccg acgattcaag    1620
ctccggagag gtgccagatc accccaccgc aaataagaga tacaacacca tgacaatctc    1680
tagtgtgctg ctgccctgc tgctgtgcgc actgctgttc gcttttctgc attacttcac    1740
aactctgaag cagtatctgc ggaacctggc atttgcctgg cggtacagaa aagtgagatc    1800
aagctgactg tgccttctag ttgccagcca tctgttgttt gccctcccc cgtgccttcc    1860 ttgaccctgg aaggtgccac tcccactgtc ctttcctaat aaaatgagga aattgcatcg    1920
cattgtctga gtaggtgtca ttctattctg ggggtgggg tggggcagga cagcaagggg    1980
gaggattggg aagacaatag caggcatgct ggggatgcgg tgggctctat gtctctttct    2040
ggcctggagg ctatccagcg tgagtctctc ctaccctccc gctctggtcc ttcctctccc    2100
gctctgcacc ctctgtggcc ctcgctgtgc tctctcgctc cgtgacttcc cttctccaag    2160
ttctccttgg tgggccgccg tggggctagt ccagggctgg atctcgggga agcggcgggg    2220
tggcctggga gtggggaagg gggtgcgcac ccgggacgcg cgctacttgc cccttttcggc    2280 ggggagcagg ggagaccttt ggcctacggc gacgggaggg tcgggacaaa g             2331
```

<210> SEQ ID NO 76
<211> LENGTH: 2531
<212> TYPE: DNA
<213> ORGANISM: artificial sequence
<220> FEATURE:
<223> OTHER INFORMATION: UL18Trimer matrix _HLAG peptide inserted at the B2m locus

<400> SEQUENCE: 76

```
cacttagcat ctctggggcc agtctgcaaa gcgaggggc agccttaatg tgcctccagc      60
ctgaagtcct agaatgagcg cccggtgtcc caagctgggg cgcgcacccc agatcggagg    120
gcgccgatgt acagacagca aactcaccca gtcagtgca tgccttctta aacatcacga    180
gactctaaga aaaggaaact gaaaacggga aagtccctct ctctaacctg gcactgcgtc    240
gctggcttgg agacaggtga cggtccctgc gggccttgtc ctgattggct ggcacgcgt    300 ttaatataag tggaggcgtc gcgctggcgg gcattcctga agctgacagc attcgggccg    360
agatgtctcg ctccgtggcc ttagctgtgc tcgcgctact ctctcttagc ggcctcgaag    420
ctgttatggc tccgcggact ttattcttag gtggtggcgg atccgtggt ggcggttctg    480 gtggtggcgg ctccatccag cgtacgccca aaattcaagt ctacagccga catcctgcag    540
agaacggcaa atctaatttc ctgaactgct atgtatcagg ctttcaccct agcgatatag    600
aagtggacct gctgaaaaac ggagagagga tagaaaaggt cgaacacagc gacctctcct    660
tttccaagga ctggagcttt tatcttctgt attatactga atttacaccc acggaaaaag    720
```

```
atgagtatgc gtgccgagta aaccacgtca cgctgtcaca gcccaaaata gtaaaatggg    780
atcgcgacat gggtggtggc ggttctggtg gtggcggtag tggcggcgga ggaagcggtg    840
gtggcggttc cggatctatg cacgtgctga gatacggata taccggcatc ttcgacgata    900
catcccatat gactctgacc gtggtcggga ttttgacgg acagcacttc tttacatacc    960
atgtgaacag ctccgataag gcttctagtc gagcaaatgg caccatctca tggatggcca   1020
acgtgagcgc agcctacccc acatatctgg acgagaacg cgctaaaggc gatctgatct   1080
tcaatcagac cgagcagaac ctgctggagc tggaaattgc tctggggtac aggtctcaga   1140
gtgtcctgac atggactcac gaatgtaata ccacagagaa cgggagcttc gtggcaggat   1200
atgagggctt tgggtgggac ggagaaacac tgatggagct gaaggataat ctgactctgt   1260
ggaccggccc taactacgaa atcagctggc tgaagcagaa caagacttac atcgacggaa   1320
agatcaaaaa catcagcgag ggcgatacta ccatccagcg caattacctg aagggcaact   1380
gcacccagtg gagcgtgatc tactctgggt tccagacacc tgtcactcac ccagtggtca   1440
aaggggagt gcgaaaccag aatgacaacc gggccgaggc cttctgtaca tcctacggct   1500
tctttcccgg ggagatcaat attactttta tccattacgg caacaaggcc ccgacgatt   1560
ctgagcctca gtgcaatccc ctgctgccta ccttcgatgg cacatttcac cagggggtgct   1620
acgtcgctat cttctgcaat cagaactata cttgccgggt gacccatggg aactggactg   1680
tggaaatccc aattcagtc accagcccg acgattcaag ctccggagag gtgccagatc   1740
accccaccgc aaataagaga tacaacacca tgacaatctc tagtgtgctg ctggccctgc   1800
tgctgtgcgc actgctgttc gcttttctgc attacttcac aactctgaag cagtatctgc   1860
ggaacctggc atttgcctgg cggtacagaa aagtgagatc aagctgactg tgccttctag   1920
ttgccagcca tctgttgttt gcccctcccc cgtgccttcc ttgaccctgg aaggtgccac   1980
tcccactgtc cttcctaat aaaatgagga aattgcatcg cattgtctga gtaggtgtca   2040
ttctattctg gggggtgggg tgggcagga cagcaagggg gaggattggg aagacaatag   2100
caggcatgct ggggatgcgg tgggctctat gtctctttct ggcctggagg ctatccagcg   2160
tgagtctctc ctaccctccc gctctggtcc ttcctctccc gctctgcacc ctctgtggcc   2220
ctcgctgtgc tctctcgctc cgtgacttcc cttctccaag ttctccttgg tggcccgccg   2280
tggggctagt ccagggctgg atctcgggga agcggcgggg tggcctggga gtggggaagg   2340
gggtgcgcac ccgggacgcg cgctacttgc ccctttcggc ggggagcagg ggagaccttt   2400
ggcctacggc gacgggaggg tcgggacaaa gtttagggcg tcgataagcg tcagagcgcc   2460
gaggttgggg gagggtttct cttccgctct ttcgcggggc ctctggctcc cccagcgcag   2520
ctggagtggg g                                                        2531
```

<210> SEQ ID NO 77
<211> LENGTH: 2331
<212> TYPE: DNA
<213> ORGANISM: artificial sequence
<220> FEATURE:
<223> OTHER INFORMATION: UL18Trimer matrix _HLAG peptide

<400> SEQUENCE: 77

```
cgcgcacccc agatcggagg gcgccgatgt acagacagca aactcaccca gtctagtgca     60
tgccttctta aacatcacga gactctaaga aaaggaaact gaaacggga aagtccctct    120
ctctaacctg gcactgcgtc gctggcttgg agacaggtga cggtccctgc gggccttgtc    180
```

```
ctgattggct gggcacgcgt ttaatataag tggaggcgtc gcgctggcgg gcattcctga    240
agctgacagc attcgggccg agatgtctcg ctccgtggcc ttagctgtgc tcgcgctact    300
ctctcttagc ggcctcgaag ctgttatggc tccgcggact ttattcttag gtggtggcgg    360
atccggtggt ggcggttctg gtggtggcgg ctccatccag cgtacgccca aaattcaagt    420
ctacagccga catcctgcag agaacggcaa atctaatttc ctgaactgct atgtatcagg    480
cttttcaccct agcgatatag aagtggacct gctgaaaaac ggagagagga tagaaaaggt    540
cgaacacagc gacctctcct tttccaagga ctggagcttt tatcttctgt attatactga    600
atttacaccc acgaaaaaag atgagtatgc gtgccgagta aaccacgtca cgctgtcaca    660
gcccaaaata gtaaaatggg atcgcgacat gggtggtggc ggttctggtg gtggcggtag    720
tggcggcgga ggaagcggtg gtggcggttc cggatctatg cacgtgctga gatacggata    780
taccggcatc ttcgacgata catcccatat gactctgacc gtggtcggga ttttttgacgg    840
acagcacttc tttacatacc atgtgaacag ctccgataag gcttctagtc gagcaaatgg    900
caccatctca tggatggcca acgtgagcgc agcctacccc acatatctgg acggagaacg    960
cgctaaaggc gatctgatct tcaatcagac cgagcagaac ctgctggagc tggaaattgc   1020
tctggggtac aggtctcaga gtgtcctgac atggactcac gaatgtaata ccacagagaa   1080
cgggagcttc gtggcaggat atgagggctt tgggtgggac ggagaaacac tgatggagct   1140
gaaggataat ctgactctgt ggaccggccc taactacgaa atcagctggc tgaagcagaa   1200
caagacttac atcgacggaa agatcaaaaa catcagcgag ggcgatacta ccatccagcg   1260
caattacctg aagggcaact gcacccagtg gagcgtgatc tactctgggt tccagacacc   1320
tgtcactcac ccagtggtca aaggggagt gcgaaaccag aatgacaacc gggccgaggc   1380
cttctgtaca tcctacggct tctttcccgg ggagatcaat attactttta tccattacgg   1440
caacaaggcc cccgacgatt ctgagcctca gtgcaatccc ctgctgccta ccttcgatgg   1500
cacatttcac caggggtgct acgtcgctat cttctgcaat cagaactata cttgccgggt   1560
gacccatggg aactggactg tggaaatccc aatttcagtc accagccccg acgattcaag   1620
ctccggagag gtgccagatc accccaccgc aaataagaga tacaacacca tgacaatctc   1680
tagtgtgctg ctggccctgc tgctgtgcgc actgctgttc gcttttctgc attacttcac   1740
aactctgaag cagtatctgc ggaacctggc atttgcctgg cggtacagaa aagtgagatc   1800
aagctgactg tgccttctag ttgccagcca tctgttgttt gcccctcccc cgtgccttcc   1860
ttgaccctgg aaggtgccac tcccactgtc ctttcctaat aaaatgagga aattgcatcg   1920
cattgtctga gtaggtgtca ttctattctg ggggtgggg tgggcagga cagcaagggg   1980
gaggattggg aagacaatag caggcatgct ggggatgcgg tggctctat gtctcttct    2040
ggcctggagg ctatccagcg tgagtctctc ctaccctccc gctctggtcc ttcctctccc   2100
gctctgcacc ctctgtggcc ctcgctgtgc tctctcgctc cgtgacttcc cttctccaag   2160
ttctccttgg tggcccgccg tggggctagt ccagggctgg atctcgggga agcggcgggg   2220
tggcctggga gtgggaagg gggtgcgcac ccgggacgcg cgctacttgc cccttttcggc   2280
ggggagcagg ggagaccttt ggcctacggc gacgggaggg tcgggacaaa g            2331
```

<210> SEQ ID NO 78
<211> LENGTH: 47
<212> TYPE: DNA
<213> ORGANISM: artificial sequence
<220> FEATURE:
<223> OTHER INFORMATION: TALEN target B2m1

<400> SEQUENCE: 78
tccgtggcct tagctgtgct cgcgctactc tctctttctg gcctgga                           47

<210> SEQ ID NO 79
<211> LENGTH: 47
<212> TYPE: DNA
<213> ORGANISM: artificial sequence
<220> FEATURE:
<223> OTHER INFORMATION: TALEN target B2m2

<400> SEQUENCE: 79
ttagctgtgc tcgcgctact ctctctttct ggcctggagg ctatcca                           47

<210> SEQ ID NO 80
<211> LENGTH: 936
<212> TYPE: PRT
<213> ORGANISM: artificial sequence
<220> FEATURE:
<223> OTHER INFORMATION: pCLS31134 right TALEN B2m1

<400> SEQUENCE: 80

```
Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Glu Lys Ile Lys Pro Lys Val Arg Ser Thr Val
                35                  40                  45

Ala Gln His His Glu Ala Leu Val Gly His Gly Phe Thr His Ala His
                50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
                115                 120                 125

Thr Gly Gln Leu Leu Lys Ile Ala Lys Arg Gly Gly Val Thr Ala Val
                130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser His Asp Gly Gly Lys
                165                 170                 175

Gln Ala Leu Glu Thr Val Gln Arg Leu Leu Pro Val Leu Cys Gln Ala
                180                 185                 190

His Gly Leu Thr Pro Glu Gln Val Val Ala Ile Ala Ser His Asp Gly
                195                 200                 205

Gly Lys Gln Ala Leu Glu Thr Val Gln Arg Leu Leu Pro Val Leu Cys
                210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
                260                 265                 270

Ser Asn Gly Gly Gly Lys Gln Ala Leu Glu Thr Val Gln Arg Leu Leu
```

```
            275                 280                 285
Pro Val Leu Cys Gln Ala His Gly Leu Thr Pro Gln Gln Val Val Ala
    290                 295                 300
Ile Ala Ser Asn Asn Gly Gly Lys Gln Ala Leu Glu Thr Val Gln Arg
305                 310                 315                 320
Leu Leu Pro Val Leu Cys Gln Ala His Gly Leu Thr Pro Gln Gln Val
                325                 330                 335
Val Ala Ile Ala Ser Asn Asn Gly Gly Lys Gln Ala Leu Glu Thr Val
            340                 345                 350
Gln Arg Leu Leu Pro Val Leu Cys Gln Ala His Gly Leu Thr Pro Glu
        355                 360                 365
Gln Val Val Ala Ile Ala Ser His Asp Gly Gly Lys Gln Ala Leu Glu
    370                 375                 380
Thr Val Gln Arg Leu Leu Pro Val Leu Cys Gln Ala His Gly Leu Thr
385                 390                 395                 400
Pro Glu Gln Val Val Ala Ile Ala Ser His Asp Gly Gly Lys Gln Ala
                405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser Asn Gly Gly Lys
        435                 440                 445
Gln Ala Leu Glu Thr Val Gln Arg Leu Leu Pro Val Leu Cys Gln Ala
    450                 455                 460
His Gly Leu Thr Pro Gln Gln Val Val Ala Ile Ala Ser Asn Gly Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Glu Gln Val Val Ala Ile Ala Ser Asn
            500                 505                 510
Ile Gly Gly Lys Gln Ala Leu Glu Thr Val Gln Ala Leu Leu Pro Val
        515                 520                 525
Leu Cys Gln Ala His Gly Leu Thr Pro Gln Gln Val Val Ala Ile Ala
    530                 535                 540
Ser Asn Asn Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
                565                 570                 575
Ile Ala Ser His Asp Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser Asn Gly Gly Lys Gln Ala Leu Glu Thr Val
    610                 615                 620
Gln Arg Leu Leu Pro Val Leu Cys Gln Ala His Gly Leu Thr Pro Gln
625                 630                 635                 640
Gln Val Val Ala Ile Ala Ser Asn Asn Gly Gly Lys Gln Ala Leu Glu
                645                 650                 655
Thr Val Gln Arg Leu Leu Pro Val Leu Cys Gln Ala His Gly Leu Thr
            660                 665                 670
Pro Gln Gln Val Val Ala Ile Ala Ser Asn Gly Gly Gly Arg Pro Ala
        675                 680                 685
Leu Glu Ser Ile Val Ala Gln Leu Ser Arg Pro Asp Pro Ala Leu Ala
    690                 695                 700
```

```
Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
                820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
            915                 920                 925

Gly Glu Ile Asn Phe Ala Ala Asp
    930                 935

<210> SEQ ID NO 81
<211> LENGTH: 936
<212> TYPE: PRT
<213> ORGANISM: artificial sequence
<220> FEATURE:
<223> OTHER INFORMATION: pCLS31135 left TALEN B2m1

<400> SEQUENCE: 81

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125
```

```
Thr Gly Gln Leu Leu Lys Ile Ala Lys Arg Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Glu Gln Val Val Ala Ile Ala Ser His Asp Gly Gly Lys
                165                 170                 175

Gln Ala Leu Glu Thr Val Gln Arg Leu Leu Pro Val Leu Cys Gln Ala
                180                 185                 190

His Gly Leu Thr Pro Glu Gln Val Val Ala Ile Ala Ser His Asp Gly
            195                 200                 205

Gly Lys Gln Ala Leu Glu Thr Val Gln Arg Leu Leu Pro Val Leu Cys
210                 215                 220

Gln Ala His Gly Leu Thr Pro Glu Gln Val Val Ala Ile Ala Ser Asn
225                 230                 235                 240

Ile Gly Gly Lys Gln Ala Leu Glu Thr Val Gln Ala Leu Leu Pro Val
                245                 250                 255

Leu Cys Gln Ala His Gly Leu Thr Pro Gln Gln Val Val Ala Ile Ala
                260                 265                 270

Ser Asn Asn Gly Gly Lys Gln Ala Leu Glu Thr Val Gln Arg Leu Leu
            275                 280                 285

Pro Val Leu Cys Gln Ala His Gly Leu Thr Pro Gln Gln Val Val Ala
290                 295                 300

Ile Ala Ser Asn Asn Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Glu
            355                 360                 365

Gln Val Val Ala Ile Ala Ser His Asp Gly Gly Lys Gln Ala Leu Glu
        370                 375                 380

Thr Val Gln Arg Leu Leu Pro Val Leu Cys Gln Ala His Gly Leu Thr
385                 390                 395                 400

Pro Glu Gln Val Val Ala Ile Ala Ser Asn Ile Gly Gly Lys Gln Ala
                405                 410                 415

Leu Glu Thr Val Gln Ala Leu Leu Pro Val Leu Cys Gln Ala His Gly
                420                 425                 430

Leu Thr Pro Gln Gln Val Val Ala Ile Ala Ser Asn Asn Gly Gly Lys
            435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser Asn Ile Gly
465                 470                 475                 480

Gly Lys Gln Ala Leu Glu Thr Val Gln Ala Leu Leu Pro Val Leu Cys
                485                 490                 495

Gln Ala His Gly Leu Thr Pro Glu Gln Val Val Ala Ile Ala Ser Asn
                500                 505                 510

Ile Gly Gly Lys Gln Ala Leu Glu Thr Val Gln Ala Leu Leu Pro Val
            515                 520                 525

Leu Cys Gln Ala His Gly Leu Thr Pro Glu Gln Val Val Ala Ile Ala
530                 535                 540
```

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
            565                 570                 575

Ile Ala Ser Asn Asn Gly Gly Lys Gln Ala Leu Glu Thr Val Gln Arg
        580                 585                 590

Leu Leu Pro Val Leu Cys Gln Ala His Gly Leu Thr Pro Glu Gln Val
    595                 600                 605

Val Ala Ile Ala Ser Asn Ile Gly Gly Lys Gln Ala Leu Glu Thr Val
610                 615                 620

Gln Ala Leu Leu Pro Val Leu Cys Gln Ala His Gly Leu Thr Pro Gln
625                 630                 635                 640

Gln Val Val Ala Ile Ala Ser Asn Asn Gly Gly Lys Gln Ala Leu Glu
            645                 650                 655

Thr Val Gln Arg Leu Leu Pro Val Leu Cys Gln Ala His Gly Leu Thr
        660                 665                 670

Pro Gln Gln Val Val Ala Ile Ala Ser Asn Gly Gly Arg Pro Ala
    675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
    755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
            805                 810                 815

Gly Val Ile Val Asp Thr Lys Ala Tyr Ser Gly Gly Tyr Asn Leu Pro
        820                 825                 830

Ile Gly Gln Ala Asp Glu Met Gln Arg Tyr Val Glu Glu Asn Gln Thr
    835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
            885                 890                 895

Gly Ala Val Leu Ser Val Glu Glu Leu Leu Ile Gly Gly Glu Met Ile
        900                 905                 910

Lys Ala Gly Thr Leu Thr Leu Glu Glu Val Arg Arg Lys Phe Asn Asn
    915                 920                 925

Gly Glu Ile Asn Phe Ala Ala Asp
930                 935

<210> SEQ ID NO 82
<211> LENGTH: 936
<212> TYPE: PRT

<213> ORGANISM: artificial sequence
<220> FEATURE:
<223> OTHER INFORMATION: pCLS31136 right TALEN B2m2

<400> SEQUENCE: 82

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Ile Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Gly Gly Gly Lys Gln Ala Leu Glu Thr Val Gln Arg
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
            340                 345                 350

Gln Arg Leu Leu Pro Val Leu Cys Gln Ala His Gly Leu Thr Pro Gln
        355                 360                 365

Gln Val Val Ala Ile Ala Ser Asn Gly Gly Lys Gln Ala Leu Glu
    370                 375                 380

Thr Val Gln Arg Leu Leu Pro Val Leu Cys Gln Ala His Gly Leu Thr

```
                385                 390                 395                 400
Pro Gln Val Val Ala Ile Ala Ser Asn Asn Gly Gly Lys Gln Ala
                    405                 410                 415
Leu Glu Thr Val Gln Arg Leu Leu Pro Val Leu Cys Gln Ala His Gly
                    420                 425                 430
Leu Thr Pro Glu Gln Val Val Ala Ile Ala Ser His Asp Gly Gly Lys
                    435                 440                 445
Gln Ala Leu Glu Thr Val Gln Arg Leu Leu Pro Val Leu Cys Gln Ala
        450                 455                 460
His Gly Leu Thr Pro Gln Gln Val Val Ala Ile Ala Ser Asn Gly Gly
465                 470                 475                 480
Gly Lys Gln Ala Leu Glu Thr Val Gln Arg Leu Leu Pro Val Leu Cys
                        485                 490                 495
Gln Ala His Gly Leu Thr Pro Glu Gln Val Val Ala Ile Ala Ser His
                    500                 505                 510
Asp Gly Gly Lys Gln Ala Leu Glu Thr Val Gln Arg Leu Leu Pro Val
        515                 520                 525
Leu Cys Gln Ala His Gly Leu Thr Pro Gln Gln Val Val Ala Ile Ala
    530                 535                 540
Ser Asn Asn Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
                565                 570                 575
Ile Ala Ser His Asp Gly Gly Lys Gln Ala Leu Glu Thr Val Gln Arg
            580                 585                 590
Leu Leu Pro Val Leu Cys Gln Ala His Gly Leu Thr Pro Gln Gln Val
                595                 600                 605
Val Ala Ile Ala Ser Asn Asn Gly Gly Lys Gln Ala Leu Glu Thr Val
            610                 615                 620
Gln Arg Leu Leu Pro Val Leu Cys Gln Ala His Gly Leu Thr Pro Glu
625                 630                 635                 640
Gln Val Val Ala Ile Ala Ser His Asp Gly Gly Lys Gln Ala Leu Glu
                    645                 650                 655
Thr Val Gln Arg Leu Leu Pro Val Leu Cys Gln Ala His Gly Leu Thr
                        660                 665                 670
Pro Gln Gln Val Val Ala Ile Ala Ser Asn Gly Gly Gly Arg Pro Ala
            675                 680                 685
Leu Glu Ser Ile Val Ala Gln Leu Ser Arg Pro Asp Pro Ala Leu Ala
    690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
                740                 745                 750
His Lys Leu Lys Tyr Val Pro His Glu Tyr Ile Glu Leu Ile Glu Ile
                755                 760                 765
Ala Arg Asn Ser Thr Gln Asp Arg Ile Leu Glu Met Lys Val Met Glu
            770                 775                 780
Phe Phe Met Lys Val Tyr Gly Tyr Arg Gly Lys His Leu Gly Gly Ser
785                 790                 795                 800
Arg Lys Pro Asp Gly Ala Ile Tyr Thr Val Gly Ser Pro Ile Asp Tyr
                805                 810                 815
```

```
Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Asn Gln Thr
            835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
                900                 905                 910

Lys Ala Gly Thr Leu Thr Leu Glu Glu Val Arg Arg Lys Phe Asn Asn
                915                 920                 925

Gly Glu Ile Asn Phe Ala Ala Asp
    930                 935

<210> SEQ ID NO 83
<211> LENGTH: 936
<212> TYPE: PRT
<213> ORGANISM: artificial sequence
<220> FEATURE:
<223> OTHER INFORMATION: pCLS31137 left TALEN B2m2

<400> SEQUENCE: 83

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Gln Glu Lys Ile Lys Pro Lys Val Arg Ser Thr Val
            35                  40                  45

Ala Gln His His Glu Ala Leu Val Gly His Gly Phe Thr His Ala His
        50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Gln Gln Val Val Ala Ile Ala Ser Asn Asn Gly
        195                 200                 205

Gly Lys Gln Ala Leu Glu Thr Val Gln Arg Leu Leu Pro Val Leu Cys
    210                 215                 220

Gln Ala His Gly Leu Thr Pro Glu Gln Val Val Ala Ile Ala Ser Asn
225                 230                 235                 240
```

```
Ile Gly Gly Lys Gln Ala Leu Glu Thr Val Gln Ala Leu Leu Pro Val
            245                 250                 255

Leu Cys Gln Ala His Gly Leu Thr Pro Gln Gln Val Val Ala Ile Ala
            260                 265                 270

Ser Asn Gly Gly Lys Gln Ala Leu Glu Thr Val Gln Arg Leu Leu
            275                 280                 285

Pro Val Leu Cys Gln Ala His Gly Leu Thr Pro Glu Gln Val Val Ala
            290                 295                 300

Ile Ala Ser Asn Ile Gly Gly Lys Gln Ala Leu Glu Thr Val Gln Ala
305                 310                 315                 320

Leu Leu Pro Val Leu Cys Gln Ala His Gly Leu Thr Pro Gln Gln Val
                325                 330                 335

Val Ala Ile Ala Ser Asn Asn Gly Gly Lys Gln Ala Leu Glu Thr Val
            340                 345                 350

Gln Arg Leu Leu Pro Val Leu Cys Gln Ala His Gly Leu Thr Pro Glu
            355                 360                 365

Gln Val Val Ala Ile Ala Ser His Asp Gly Gly Lys Gln Ala Leu Glu
        370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Gly Gly Lys
            435                 440                 445

Gln Ala Leu Glu Thr Val Gln Arg Leu Leu Pro Val Leu Cys Gln Ala
        450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser His
            500                 505                 510

Asp Gly Gly Lys Gln Ala Leu Glu Thr Val Gln Arg Leu Leu Pro Val
            515                 520                 525

Leu Cys Gln Ala His Gly Leu Thr Pro Glu Gln Val Val Ala Ile Ala
        530                 535                 540

Ser Asn Ile Gly Gly Lys Gln Ala Leu Glu Thr Val Gln Ala Leu Leu
545                 550                 555                 560

Pro Val Leu Cys Gln Ala His Gly Leu Thr Pro Gln Gln Val Val Ala
                565                 570                 575

Ile Ala Ser Asn Asn Gly Gly Lys Gln Ala Leu Glu Thr Val Gln Arg
            580                 585                 590

Leu Leu Pro Val Leu Cys Gln Ala His Gly Leu Thr Pro Gln Gln Val
            595                 600                 605

Val Ala Ile Ala Ser Asn Asn Gly Gly Lys Gln Ala Leu Glu Thr Val
            610                 615                 620

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
                645                 650                 655
```

```
Thr Val Gln Arg Leu Leu Pro Val Leu Cys Gln Ala His Gly Leu Thr
            660                 665                 670

Pro Gln Gln Val Val Ala Ile Ala Ser Asn Gly Gly Arg Pro Ala
        675                 680                 685

Leu Glu Ser Ile Val Ala Gln Leu Ser Arg Pro Asp Pro Ala Leu Ala
    690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
    770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Asn Gln Thr
        835                 840                 845

Arg Asn Lys His Ile Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
    930                 935

<210> SEQ ID NO 84
<211> LENGTH: 338
<212> TYPE: PRT
<213> ORGANISM: artificial sequence
<220> FEATURE:
<223> OTHER INFORMATION: HLAG1

<400> SEQUENCE: 84

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80
```

```
Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 85
<211> LENGTH: 246
<212> TYPE: PRT
<213> ORGANISM: artificial sequence
<220> FEATURE:
<223> OTHER INFORMATION: HLAG2

<400> SEQUENCE: 85

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
```

```
                     100                 105                 110
Glu Ala Lys Pro Pro Lys Thr His Val Thr His His Pro Val Phe Asp
            115                 120                 125

Tyr Glu Ala Thr Leu Arg Cys Trp Ala Leu Gly Phe Tyr Pro Ala Glu
        130                 135                 140

Ile Ile Leu Thr Trp Gln Arg Asp Gly Glu Asp Gln Thr Gln Asp Val
145                 150                 155                 160

Glu Leu Val Glu Thr Arg Pro Ala Gly Asp Gly Thr Phe Gln Lys Trp
                165                 170                 175

Ala Ala Val Val Val Pro Ser Gly Glu Glu Gln Arg Tyr Thr Cys His
            180                 185                 190

Val Gln His Glu Gly Leu Pro Glu Pro Leu Met Leu Arg Trp Lys Gln
        195                 200                 205

Ser Ser Leu Pro Thr Ile Pro Ile Met Gly Ile Val Ala Gly Leu Val
    210                 215                 220

Val Leu Ala Ala Val Thr Gly Ala Ala Val Ala Ala Val Leu Trp
225                 230                 235                 240

Arg Lys Lys Ser Ser Asp
                245

<210> SEQ ID NO 86
<211> LENGTH: 154
<212> TYPE: PRT
<213> ORGANISM: artificial sequence
<220> FEATURE:
<223> OTHER INFORMATION: HLAG3

<400> SEQUENCE: 86

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Lys Gln Ser Ser Leu Pro Thr Ile Pro Ile Met Gly Ile Val
        115                 120                 125

Ala Gly Leu Val Val Leu Ala Ala Val Thr Gly Ala Ala Val Ala
    130                 135                 140

Ala Val Leu Trp Arg Lys Lys Ser Ser Asp
145                 150

<210> SEQ ID NO 87
<211> LENGTH: 246
<212> TYPE: PRT
<213> ORGANISM: artificial sequence
<220> FEATURE:
<223> OTHER INFORMATION: HLAG4

<400> SEQUENCE: 87
```

```
Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
                100                 105                 110

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
        130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
                180                 185                 190

His Arg Tyr Leu Glu Asn Gly Lys Glu Met Leu Gln Arg Ala Lys Gln
            195                 200                 205

Ser Ser Leu Pro Thr Ile Pro Ile Met Gly Ile Val Ala Gly Leu Val
        210                 215                 220

Val Leu Ala Ala Val Val Thr Gly Ala Ala Val Ala Ala Val Leu Trp
225                 230                 235                 240

Arg Lys Lys Ser Ser Asp
                245

<210> SEQ ID NO 88
<211> LENGTH: 319
<212> TYPE: PRT
<213> ORGANISM: artificial sequence
<220> FEATURE:
<223> OTHER INFORMATION: HLAG5

<400> SEQUENCE: 88

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
                100                 105                 110
```

Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
            165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
            210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
            245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
275                 280                 285

Gly Leu Pro Glu Pro Leu Met Leu Arg Trp Ser Lys Glu Gly Asp Gly
            290                 295                 300

Gly Ile Met Ser Val Arg Glu Ser Arg Ser Leu Ser Glu Asp Leu
305                 310                 315

<210> SEQ ID NO 89
<211> LENGTH: 227
<212> TYPE: PRT
<213> ORGANISM: artificial sequence
<220> FEATURE:
<223> OTHER INFORMATION: HLAG6

<400> SEQUENCE: 89

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
            85                  90                  95

Thr Asp Arg Met Asn Leu Gln Thr Leu Arg Gly Tyr Tyr Asn Gln Ser
            100                 105                 110

Glu Ala Lys Pro Pro Lys Thr His Val Thr His His Pro Val Phe Asp
            115                 120                 125

Tyr Glu Ala Thr Leu Arg Cys Trp Ala Leu Gly Phe Tyr Pro Ala Glu
            130                 135                 140

Ile Ile Leu Thr Trp Gln Arg Asp Gly Glu Asp Gln Thr Gln Asp Val
145                 150                 155                 160

```
Glu Leu Val Glu Thr Arg Pro Ala Gly Asp Gly Thr Phe Gln Lys Trp
                165                 170                 175
Ala Ala Val Val Val Pro Ser Gly Glu Glu Gln Arg Tyr Thr Cys His
            180                 185                 190
Val Gln His Glu Gly Leu Pro Glu Pro Leu Met Leu Arg Trp Ser Lys
        195                 200                 205
Glu Gly Asp Gly Gly Ile Met Ser Val Arg Glu Ser Arg Ser Leu Ser
    210                 215                 220
Glu Asp Leu
225

<210> SEQ ID NO 90
<211> LENGTH: 116
<212> TYPE: PRT
<213> ORGANISM: artificial sequence
<220> FEATURE:
<223> OTHER INFORMATION: HLAG7

<400> SEQUENCE: 90

Met Val Val Met Ala Pro Arg Thr Leu Phe Leu Leu Leu Ser Gly Ala
1               5                   10                  15
Leu Thr Leu Thr Glu Thr Trp Ala Gly Ser His Ser Met Arg Tyr Phe
            20                  25                  30
Ser Ala Ala Val Ser Arg Pro Gly Arg Gly Glu Pro Arg Phe Ile Ala
        35                  40                  45
Met Gly Tyr Val Asp Asp Thr Gln Phe Val Arg Phe Asp Ser Asp Ser
    50                  55                  60
Ala Cys Pro Arg Met Glu Pro Arg Ala Pro Trp Val Glu Gln Glu Gly
65                  70                  75                  80
Pro Glu Tyr Trp Glu Glu Glu Thr Arg Asn Thr Lys Ala His Ala Gln
                85                  90                  95
Thr Asp Arg Met Asn Leu Gln Thr Leu Arg Gly Tyr Tyr Asn Gln Ser
            100                 105                 110
Glu Ala Ser Glu
        115

<210> SEQ ID NO 91
<211> LENGTH: 9
<212> TYPE: PRT
<213> ORGANISM: artificial sequence
<220> FEATURE:
<223> OTHER INFORMATION: G peptide

<400> SEQUENCE: 91

Val Met Ala Pro Arg Thr Leu Ile Leu
1               5

<210> SEQ ID NO 92
<211> LENGTH: 9
<212> TYPE: PRT
<213> ORGANISM: artificial sequence
<220> FEATURE:
<223> OTHER INFORMATION: G peptide

<400> SEQUENCE: 92

Val Met Ala Pro Arg Thr Leu Leu Leu
1               5

<210> SEQ ID NO 93
<211> LENGTH: 9
<212> TYPE: PRT
```

```
<213> ORGANISM: artificial sequence
<220> FEATURE:
<223> OTHER INFORMATION: G peptide

<400> SEQUENCE: 93

Val Met Ala Pro Arg Thr Leu Val Leu
1               5

<210> SEQ ID NO 94
<211> LENGTH: 9
<212> TYPE: PRT
<213> ORGANISM: artificial sequence
<220> FEATURE:
<223> OTHER INFORMATION: G peptide

<400> SEQUENCE: 94

Ala Met Ala Pro Arg Thr Leu Ile Leu
1               5

<210> SEQ ID NO 95
<211> LENGTH: 9
<212> TYPE: PRT
<213> ORGANISM: artificial sequence
<220> FEATURE:
<223> OTHER INFORMATION: G peptide

<400> SEQUENCE: 95

Val Met Ala Pro Arg Ser Leu Ile Leu
1               5

<210> SEQ ID NO 96
<211> LENGTH: 9
<212> TYPE: PRT
<213> ORGANISM: artificial sequence
<220> FEATURE:
<223> OTHER INFORMATION: G peptide

<400> SEQUENCE: 96

Val Met Ala Pro Arg Ser Leu Leu Leu
1               5

<210> SEQ ID NO 97
<211> LENGTH: 9
<212> TYPE: PRT
<213> ORGANISM: artificial sequence
<220> FEATURE:
<223> OTHER INFORMATION: G peptide

<400> SEQUENCE: 97

Val Met Ala Pro Arg Thr Leu Phe Leu
1               5

<210> SEQ ID NO 98
<211> LENGTH: 9
<212> TYPE: PRT
<213> ORGANISM: artificial sequence
<220> FEATURE:
<223> OTHER INFORMATION: G peptide

<400> SEQUENCE: 98

Val Met Ala Pro Arg Ile Leu Ile Leu
1               5

<210> SEQ ID NO 99
<211> LENGTH: 10
<212> TYPE: PRT
<213> ORGANISM: artificial sequence
```

```
<220> FEATURE:
<223> OTHER INFORMATION: G peptide

<400> SEQUENCE: 99

Tyr Leu Leu Pro Arg Arg Gly Pro Arg Leu
1               5                   10

<210> SEQ ID NO 100
<211> LENGTH: 9
<212> TYPE: PRT
<213> ORGANISM: artificial sequence
<220> FEATURE:
<223> OTHER INFORMATION: G peptide

<400> SEQUENCE: 100

Ala Leu Pro His Ala Ile Leu Arg Leu
1               5
```